US012673982B2

(12) United States Patent
Veerapathran et al.

(10) Patent No.: US 12,673,982 B2
(45) Date of Patent: Jul. 7, 2026

(54) ENGINEERED ARTIFICIAL ANTIGEN PRESENTING CELLS FOR TUMOR INFILTRATING LYMPHOCYTE EXPANSION

(71) Applicant: Iovance Biotherapeutics, Inc., San Carlos, CA (US)

(72) Inventors: Anand Veerapathran, Tampa, FL (US); Aishwarya Gokuldass, Chennai (IN); Brian Rabinovich, Winchester, MA (US); Michael T. Lotze, Pittsburgh, PA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 1458 days.

(21) Appl. No.: 17/229,127

(22) Filed: Apr. 13, 2021

(65) Prior Publication Data
US 2022/0315893 A1    Oct. 6, 2022

Related U.S. Application Data

(63) Continuation of application No. 16/526,353, filed on Jul. 30, 2019, now Pat. No. 11,667,890, which is a
(Continued)

(51) Int. Cl.
*C07K 14/705* (2006.01)
*A61K 39/00* (2006.01)
(Continued)

(52) U.S. Cl.
CPC ........ *C07K 14/70575* (2013.01); *A61K 40/11* (2025.01); *A61K 40/42* (2025.01);
(Continued)

(58) Field of Classification Search
None
See application file for complete search history.

(56) References Cited

U.S. PATENT DOCUMENTS

| | | | |
|---|---|---|---|
| 4,370,338 A | 1/1983 | Mizoule | |
| 4,766,106 A | 8/1988 | Katre et al. | |

(Continued)

FOREIGN PATENT DOCUMENTS

| | | | |
|---|---|---|---|
| CN | 106244538 A | 12/2016 | |
| CN | 106591232 A | 4/2017 | |

(Continued)

OTHER PUBLICATIONS

Bruce L Levine, Global Manufacturing of CAR T Cell Therapy, 2017, Molecular Therapy Methods & Clinical Development, Review, 92-101 (Year: 2017).*

(Continued)

*Primary Examiner* — Tracy Vivlemore
*Assistant Examiner* — Hanna Marie Thueson
(74) *Attorney, Agent, or Firm* — Lei Xu

(57) ABSTRACT

In some embodiments, compositions and methods re¬lating to isolated artificial antigen presenting cells (aAPCs) are dis¬closed, including aAPCs comprising a myeloid cell transduced with one or more viral vectors, such as a MOLM-14 or a EM-3 myeloid cell, wherein the myeloid cell endogenously expresses HLA-A/B/C, ICOS-L, and CD58, and wherein the one or more viral vectors com¬prise a nucleic acid encoding CD86 and a nucleic acid encoding 4-1BBL and/or OX40L and transduce the myeloid cell to express CD86 and 4-1BBL and/or OX40L proteins. In some embodiments, methods of expanding tumor infiltrating lym-phocytes (TILs) with aAPCs and methods of treating cancers using TILs after expansion with aAPCs are also disclosed.

23 Claims, 98 Drawing Sheets

Specification includes a Sequence Listing.

Related U.S. Application Data continuation of application No. 15/800,967, filed on Nov. 1, 2017, now Pat. No. 10,415,015, which is a continuation of application No. PCT/US2017/059271, filed on Oct. 31, 2017.

(60) Provisional application No. 62/481,831, filed on Apr. 5, 2017, provisional application No. 62/475,053, filed on Mar. 22, 2017, provisional application No. 62/438,600, filed on Dec. 23, 2016, provisional application No. 62/415,274, filed on Oct. 31, 2016.

(51) Int. Cl.

| | |
|---|---|
| *A61K 40/11* | (2025.01) |
| *A61K 40/42* | (2025.01) |
| *A61P 35/00* | (2006.01) |
| *C07K 16/42* | (2006.01) |
| *C12N 5/078* | (2010.01) |
| *C12N 5/0781* | (2010.01) |
| *C12N 5/0784* | (2010.01) |

(52) U.S. Cl.

CPC ........ *A61P 35/00* (2018.01); *C07K 14/70532* (2013.01); *C07K 16/4283* (2013.01); *C12N 5/0635* (2013.01); *C12N 5/0639* (2013.01); *C12N 5/065* (2013.01); *A61K 2039/515* (2013.01); *C07K 2317/622* (2013.01); *C12N 2501/06* (2013.01); *C12N 2501/2302* (2013.01); *C12N 2501/25* (2013.01); *C12N 2501/51* (2013.01); *C12N 2501/515* (2013.01); *C12N 2501/998* (2013.01); *C12N 2502/11* (2013.01); *C12N 2502/99* (2013.01)

(56) References Cited

U.S. PATENT DOCUMENTS

| | | | |
|---|---|---|---|
| 4,820,516 A | | 4/1989 | Sawyer et al. |
| 4,902,502 A | | 2/1990 | Nitecki et al. |
| 5,089,261 A | | 2/1992 | Nitecki et al. |
| 5,126,132 A | | 6/1992 | Rosenberg |
| 5,177,017 A | | 1/1993 | Lin et al. |
| 5,206,344 A | | 4/1993 | Katre et al. |
| 5,279,833 A | | 1/1994 | Rose |
| 5,422,261 A | | 6/1995 | Lee et al. |
| 5,443,983 A | | 8/1995 | Ochoa et al. |
| 5,593,875 A | | 1/1997 | Wurm et al. |
| 5,593,877 A | | 1/1997 | King |
| 5,601,819 A | | 2/1997 | Wong et al. |
| 5,648,260 A | | 7/1997 | Winter et al. |
| 5,674,704 A | * | 10/1997 | Goodwin ............. C07K 14/715 |
| | | | 435/320.1 |
| 5,714,350 A | | 2/1998 | Co et al. |
| 5,739,277 A | | 4/1998 | Presta et al. |
| 5,766,902 A | | 6/1998 | Craig et al. |
| 5,783,433 A | | 7/1998 | Frenz et al. |
| 5,824,778 A | | 10/1998 | Ishikawa et al. |
| 5,827,642 A | | 10/1998 | Riddell et al. |
| 5,834,250 A | | 11/1998 | Wells et al. |
| 5,869,046 A | | 2/1999 | Presta et al. |
| 5,877,293 A | | 3/1999 | Adair et al. |
| 5,886,152 A | | 3/1999 | Nakatani et al. |
| 5,908,635 A | | 6/1999 | Thierry |
| 5,928,893 A | | 7/1999 | Kang et al. |
| 5,942,607 A | * | 8/1999 | Freeman ............. C07K 16/2827 |
| | | | 536/23.5 |
| 5,962,320 A | | 10/1999 | Robinson |
| 5,989,888 A | | 11/1999 | Dwulet et al. |
| 6,025,337 A | | 2/2000 | Truong et al. |
| 6,040,177 A | | 3/2000 | Riddell et al. |
| 6,054,297 A | | 4/2000 | Carter et al. |
| 6,056,938 A | | 5/2000 | Unger et al. |
| 6,096,871 A | | 8/2000 | Presta et al. |
| 6,110,490 A | | 8/2000 | Thierry |
| 6,121,022 A | | 9/2000 | Presta et al. |
| 6,123,938 A | | 9/2000 | Stern et al. |
| 6,194,551 B1 | | 2/2001 | Dusogie et al. |
| 6,210,669 B1 | | 4/2001 | Aruffo et al. |
| 6,242,195 B1 | | 6/2001 | Idusogie et al. |
| 6,277,375 B1 | | 8/2001 | Ward |
| 6,303,121 B1 | | 10/2001 | Kwon |
| 6,312,700 B1 | | 11/2001 | Starr |
| 6,350,861 B1 | | 2/2002 | Co et al. |
| 6,352,694 B1 | | 3/2002 | June et al. |
| 6,362,325 B1 | | 3/2002 | Kwon |
| 6,391,607 B1 | | 5/2002 | Lazarus et al. |
| 6,410,517 B1 | | 6/2002 | Truong et al. |
| 6,475,994 B2 | | 11/2002 | Tomalia et al. |
| 6,489,458 B2 | | 12/2002 | Hackett et al. |
| 6,528,624 B1 | | 3/2003 | Idusogie et al. |
| 6,534,055 B1 | | 3/2003 | June et al. |
| 6,534,484 B1 | | 3/2003 | Wheeler et al. |
| 6,538,124 B1 | | 3/2003 | Idusogie et al. |
| 6,569,997 B1 | | 5/2003 | Kwon |
| 6,627,442 B1 | | 9/2003 | Humeau et al. |
| 6,706,289 B2 | | 3/2004 | Lewis et al. |
| 6,737,056 B1 | | 5/2004 | Presta |
| 6,821,505 B2 | | 11/2004 | Ward |
| 6,867,041 B2 | | 3/2005 | Berenson et al. |
| 6,887,466 B2 | | 5/2005 | June et al. |
| 6,887,673 B2 | | 5/2005 | Kunkel et al. |
| 6,905,680 B2 | | 6/2005 | June et al. |
| 6,905,681 B1 | | 6/2005 | June et al. |
| 6,905,685 B2 | | 6/2005 | Kwon |
| 6,974,863 B2 | | 12/2005 | Kwon |
| 6,998,253 B1 | | 2/2006 | Presta et al. |
| 7,070,995 B2 | | 7/2006 | Jensen |
| 7,083,784 B2 | | 8/2006 | Dall'Acqua et al. |
| 7,118,742 B2 | | 10/2006 | Ware |
| 7,144,575 B2 | | 12/2006 | June et al. |
| 7,175,843 B2 | | 2/2007 | June et al. |
| 7,189,705 B2 | | 3/2007 | Lam et al. |
| 7,214,493 B2 | | 5/2007 | Kunkel et al. |
| 7,232,566 B2 | | 6/2007 | June et al. |
| 7,288,638 B2 | | 10/2007 | Jure-Kunkel et al. |
| 7,297,526 B2 | | 11/2007 | Shak |
| 7,407,785 B2 | | 8/2008 | Lazarus et al. |
| 7,446,190 B2 | | 11/2008 | Sadelain et al. |
| 7,479,269 B2 | | 1/2009 | June et al. |
| 7,504,101 B2 | | 3/2009 | Weinberg |
| 7,550,140 B2 | | 6/2009 | Bakker et al. |
| 7,569,664 B2 | | 8/2009 | Jakobsen et al. |
| 7,572,631 B2 | | 8/2009 | Berenson et al. |
| 7,622,444 B2 | | 11/2009 | Weinberg |
| 7,638,325 B2 | | 12/2009 | June et al. |
| 7,687,070 B2 | | 3/2010 | Gebeyehu et al. |
| 7,696,175 B2 | | 4/2010 | Epstein et al. |
| 7,754,482 B2 | | 7/2010 | Riley et al. |
| 7,767,429 B2 | | 8/2010 | Bookbinder et al. |
| 7,812,135 B2 | | 10/2010 | Smith et al. |
| 7,943,743 B2 | | 5/2011 | Korman et al. |
| 7,951,365 B2 | | 5/2011 | Winqvist et al. |
| 7,960,515 B2 | | 6/2011 | Min et al. |
| 7,961,515 B2 | | 6/2011 | Kato et al. |
| 8,007,785 B2 | | 8/2011 | Winqvist et al. |
| 8,008,449 B2 | | 8/2011 | Korman et al. |
| 8,133,983 B2 | | 3/2012 | Bakker et al. |
| 8,168,757 B2 | | 5/2012 | Finnefrock et al. |
| 8,202,517 B2 | | 6/2012 | Bookbinder et al. |
| 8,206,702 B2 | | 6/2012 | Winqvist et al. |
| 8,211,424 B2 | | 7/2012 | Winqvist et al. |
| 8,211,425 B2 | | 7/2012 | Winqvist et al. |
| 8,217,149 B2 | | 7/2012 | Irving et al. |
| 8,236,930 B2 | | 8/2012 | Min et al. |
| 8,287,856 B2 | | 10/2012 | Li et al. |
| 8,337,850 B2 | | 12/2012 | Ahrens et al. |
| 8,354,509 B2 | | 1/2013 | Carven et al. |
| 8,367,804 B2 | | 2/2013 | Boulter et al. |
| 8,388,967 B2 | | 3/2013 | Smith et al. |
| 8,399,645 B2 | | 3/2013 | Campana et al. |
| 8,431,124 B2 | | 4/2013 | Bookbinder et al. |
| 8,431,380 B2 | | 4/2013 | Bookbinder et al. |

(56)        References Cited

U.S. PATENT DOCUMENTS

| | | | |
|---|---|---|---|
| 8,450,460 B2 | 5/2013 | Hill et al. |
| 8,580,247 B2 | 11/2013 | Li et al. |
| 8,617,884 B2 | 12/2013 | Berenson et al. |
| 8,686,119 B2 | 4/2014 | Rotem-Yehudar et al. |
| 8,709,424 B2 | 4/2014 | Schebye et al. |
| 8,722,400 B2 | 5/2014 | Riley et al. |
| 8,735,553 B1 | 5/2014 | Li et al. |
| 8,779,108 B2 | 7/2014 | Queva et al. |
| 8,809,050 B2 | 8/2014 | Vera et al. |
| 8,821,867 B2 | 9/2014 | Ahrens et al. |
| 8,907,053 B2 | 12/2014 | Sasikumar et al. |
| 8,916,381 B1 | 12/2014 | June et al. |
| 8,921,519 B2 | 12/2014 | Hill et al. |
| 8,956,860 B2 | 2/2015 | Vera et al. |
| 8,962,804 B2 | 2/2015 | Williams et al. |
| 9,006,399 B2 | 4/2015 | Liu et al. |
| 9,028,823 B2 | 5/2015 | Smith et al. |
| 9,028,824 B2 | 5/2015 | Min et al. |
| 9,044,442 B2 | 6/2015 | Sasikumar et al. |
| 9,096,642 B2 | 8/2015 | Sasikumar et al. |
| 9,163,085 B2 | 10/2015 | Liu et al. |
| 9,211,316 B2 | 12/2015 | Montano |
| 9,328,156 B2 | 5/2016 | June et al. |
| 9,340,599 B2 | 5/2016 | Hill et al. |
| 9,359,420 B2 | 6/2016 | Hill et al. |
| 9,468,678 B2 | 10/2016 | Ahrens et al. |
| 9,476,028 B2 | 10/2016 | Karlsson-Parra et al. |
| 9,528,088 B2 | 12/2016 | Berenson et al. |
| 9,555,105 B2 | 1/2017 | Riley et al. |
| 9,687,510 B2 | 6/2017 | Borrello et al. |
| 9,790,267 B2 * | 10/2017 | Kaplan ................ C07K 16/303 |
| 10,172,887 B2 | 1/2019 | Borrello et al. |
| 2004/0110704 A1 | 6/2004 | Yamaune et al. |
| 2005/0095244 A1 | 5/2005 | Jure-Kunkel et al. |
| 2005/0106717 A1 | 5/2005 | Wilson et al. |
| 2005/0177518 A1 | 8/2005 | Michener |
| 2006/0034810 A1 | 2/2006 | Riley et al. |
| 2009/0028857 A1 | 1/2009 | Li et al. |
| 2010/0136030 A1 | 6/2010 | Salah-Eddine et al. |
| 2010/0203056 A1 | 8/2010 | Irving et al. |
| 2010/0266617 A1 | 10/2010 | Carven et al. |
| 2010/0285013 A1 | 11/2010 | Li et al. |
| 2011/0008369 A1 | 1/2011 | Finnefrock et al. |
| 2011/0027218 A1 | 2/2011 | Hill et al. |
| 2011/0052530 A1 | 3/2011 | Dudley et al. |
| 2011/0111494 A1 | 5/2011 | Hill et al. |
| 2011/0136228 A1 | 6/2011 | Vera et al. |
| 2011/0274685 A1 | 11/2011 | Keler et al. |
| 2012/0015888 A1 | 1/2012 | Rosenberg et al. |
| 2012/0189639 A1 | 7/2012 | Schebye et al. |
| 2012/0213771 A1 | 8/2012 | Keler et al. |
| 2012/0244133 A1 | 9/2012 | Rosenberg et al. |
| 2013/0022600 A1 | 1/2013 | Li et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0102075 A1 | 4/2013 | Vera et al. |
| 2013/0108641 A1 | 5/2013 | Baurin et al. |
| 2013/0108651 A1 | 5/2013 | Carven et al. |
| 2013/0109843 A1 | 5/2013 | Carven et al. |
| 2013/0115617 A1 | 5/2013 | Wilson |
| 2014/0065135 A1 | 3/2014 | Irving et al. |
| 2014/0112942 A1 | 4/2014 | Van Eenennaam et al. |
| 2014/0227237 A1 | 8/2014 | June et al. |
| 2014/0294898 A1 | 10/2014 | Miller et al. |
| 2014/0328791 A1 | 11/2014 | Bossard et al. |
| 2014/0341917 A1 | 11/2014 | Nastri et al. |
| 2014/0348841 A1 | 11/2014 | Schebye et al. |
| 2014/0377284 A1 | 12/2014 | Simons et al. |
| 2014/0377739 A1 | 12/2014 | Welch et al. |
| 2015/0064204 A1 | 3/2015 | Beers et al. |
| 2015/0073024 A1 | 3/2015 | Sasikumar et al. |
| 2015/0073042 A1 | 3/2015 | Sasikumar et al. |
| 2015/0087581 A1 | 3/2015 | Sasikumar et al. |

| | | | | |
|---|---|---|---|---|
| 2015/0110734 A1 | 4/2015 | Hill et al. | |
| 2015/0119923 A1 | 4/2015 | Liberatore et al. | |
| 2015/0125419 A1 | 5/2015 | Hill et al. | |
| 2015/0125491 A1 | 5/2015 | Sasikumar et al. | |
| 2015/0126709 A1 | 5/2015 | Hill et al. | |
| 2015/0126710 A1 | 5/2015 | Hill et al. | |
| 2015/0132217 A1 * | 5/2015 | Chang ................ A61K 39/3955 |
| | | | 424/85.5 |
| 2015/0132288 A1 | 5/2015 | Simons et al. | |
| 2015/0152385 A1 * | 6/2015 | Sanchez-Schmitz ... A61P 17/00 |
| | | | 435/372 |
| 2015/0175966 A1 | 6/2015 | Vera et al. | |
| 2015/0190506 A1 | 7/2015 | Cheung et al. | |
| 2015/0320798 A1 | 11/2015 | Borrello et al. | |
| 2016/0010058 A1 | 1/2016 | Gros et al. | |
| 2016/0051698 A1 | 2/2016 | Schneck et al. | |
| 2016/0144018 A1 | 5/2016 | Hinrichs et al. | |
| 2016/0176941 A1 | 6/2016 | Hill et al. | |
| 2016/0208216 A1 | 7/2016 | Vera et al. | |
| 2016/0272695 A1 | 9/2016 | Hill et al. | |
| 2017/0114321 A1 | 4/2017 | Berenson et al. | |
| 2017/0152478 A1 | 6/2017 | Rosenberg et al. | |
| 2017/0160269 A1 | 6/2017 | Linnemann et al. | |
| 2017/0258838 A1 | 9/2017 | Borrello et al. | |
| 2018/0148690 A1 | 5/2018 | Gros et al. | |
| 2018/0187150 A1 | 7/2018 | De Larichaudy | |
| 2019/0000070 A1 | 1/2019 | De Larichaudy | |
| 2019/0062706 A1 | 2/2019 | Almaasbak et al. | |
| 2019/0136186 A1 | 5/2019 | Germeroth et al. | |

FOREIGN PATENT DOCUMENTS

| | | | |
|---|---|---|---|
| CN | 107384867 A | 11/2017 |
| EP | 0154316 | 11/1985 |
| EP | 0401384 | 6/1990 |
| EP | 0404097 | 9/1996 |
| EP | 1176195 | 1/2002 |
| EP | 0672141 | 5/2003 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |
| WO | 88/07089 | 9/1988 |
| WO | 93/11161 | 6/1993 |
| WO | 1994/26290 | 11/1994 |
| WO | 95/12673 | 5/1995 |
| WO | 95/21925 | 8/1995 |
| WO | 95/27735 | 10/1995 |
| WO | 1995027735 | 10/1995 |
| WO | 96/14339 | 5/1996 |
| WO | 98/05787 | 2/1998 |
| WO | 98/10088 | 3/1998 |
| WO | 98/23289 | 6/1998 |
| WO | 99/42585 | 8/1999 |
| WO | 99/51642 | 10/1999 |
| WO | 99/54342 | 10/1999 |
| WO | 99/58572 | 11/1999 |
| WO | 00/09560 | 2/2000 |
| WO | 00/32767 | 6/2000 |
| WO | 00/42072 | 7/2000 |
| WO | 2001/88097 | 11/2001 |
| WO | 02/44215 | 6/2002 |
| WO | 02/060919 | 8/2002 |
| WO | 03/035835 | 5/2003 |
| WO | 03/057171 | 7/2003 |
| WO | 03/074569 | 9/2003 |
| WO | 2004/016750 | 2/2004 |
| WO | 2004/029207 | 4/2004 |
| WO | 2004/035752 | 4/2004 |
| WO | 2004/063351 | 7/2004 |
| WO | 2004/074455 | 9/2004 |
| WO | 2004/099249 | 11/2004 |
| WO | 2005/040217 | 5/2005 |
| WO | 2005/070963 | 8/2005 |
| WO | 2005/077981 | 8/2005 |
| WO | 2005/092925 | 10/2005 |
| WO | 2005/103077 | 11/2005 |

(56)                    References Cited

FOREIGN PATENT DOCUMENTS

| WO | 2005/123780 | 12/2005 | | |
| WO | 2006/019447 | 2/2006 | | |
| WO | 2006/047350 | 5/2006 | | |
| WO | 2006/085967 | 8/2006 | | |
| WO | 2006/121810 | 11/2006 | | |
| WO | 2008/025516 | 3/2008 | | |
| WO | 2008/156712 | 12/2008 | | |
| WO | 2009/007120 | 1/2009 | | |
| WO | 2010/003766 | 1/2010 | | |
| WO | 2010/010051 | 1/2010 | | |
| WO | 2010/042433 | 4/2010 | | |
| WO | 2010/0126766 | 4/2010 | | |
| WO | 2010/078966 | 7/2010 | | |
| WO | 2011/028683 | 3/2011 | | |
| WO | 2011072088 | 6/2011 | | |
| WO | 2012/004367 | 1/2012 | | |
| WO | 2012/027328 | 3/2012 | | |
| WO | 2012/032433 | 3/2012 | | |
| WO | 2012065086 | 5/2012 | | |
| WO | 2012129201 | 9/2012 | | |
| WO | 2012/177788 | 12/2012 | | |
| WO | 2013/028231 | 2/2013 | | |
| WO | 2013/038191 | 3/2013 | | |
| WO | 2013/039954 | 3/2013 | | |
| WO | 2013173835 | 11/2013 | | |
| WO | 2013188427 | 12/2013 | | |
| WO | 2014/148895 | 9/2014 | | |
| WO | 2014210036 | 12/2014 | | |
| WO | 2015/026684 | 2/2015 | | |
| WO | 2015/031667 | 3/2015 | | |
| WO | 2015/033301 | 3/2015 | | |
| WO | 2015/036927 | 3/2015 | | |
| WO | 2015/119923 | 8/2015 | | |
| WO | 2016/145085 | 9/2015 | | |
| WO | 2015/164816 | 10/2015 | | |
| WO | 2015/189356 | 12/2015 | | |
| WO | 2015/189357 | 12/2015 | | |
| WO | 2015189356 | A1 | 12/2015 | |
| WO | 2016/108244 | 7/2016 | | |
| WO | 2017048614 | A1 | 3/2017 | |
| WO | 2018005712 | A1 | 1/2018 | |
| WO | WO-2018081789 | A1 * | 5/2018 | ............ A61K 35/17 |
| WO | 2018102761 | A1 | 6/2018 | |
| WO | 2018170188 | A2 | 9/2018 | |
| WO | WO-2020205662 | A1 * | 10/2020 | ............ A61K 40/11 |
| WO | WO-2021061832 | A1 * | 4/2021 | ......... C12N 15/907 |

OTHER PUBLICATIONS

Doublas J Norman, The Role of OKT3 in Clinical Transplantation, 1991, Pediatr Nephrol, vol. 5, 130-136 (Year: 1991).*

Ben-Avi et al., Establishment of adoptive cell therapy with tumor infiltrating lymphocytes for non-small cell lung cancer patients, 2018, Cancer Immunology, Immunotherapy, vol. 67, p. 1221-1230 (Year: 2018).*

Forget et al., The beneficial effects of a gas-permeable flask for expansion of Tumor-Infiltrating lymphocytes as reflected in their mitochondrial function and respiration capacity, 2016, OncoImmunology. vol. 5, p. 1-7 (Year: 2016).*

Axelsson et al., "Cryopreserved peripheral blood mononuclear cells are suitable for the assessment of immunological markers in type 1 diabetic children", Cryobiology, Aug. 2008, 57, 201-208.

Bierer et al., "Cyclosporin A and FK506: molecular mechanisms of immunosuppression and probes for transplantation of biology", Current Opinion in Immunology, 1993, 57, 763-773.

Bird et al., "Single-Chain Antigen-Binding Proteins", Reports, Oct. 1988, 423-426.

Boshart et al., "A Very Strong Enhancer is located upstream of an immediate early gene cytomegalovirus", Cell, Jun. 1995, 41, 521-530.

Cawthon, "Telomere measurements by quantitative PCR", Nucleic Acids, Mar. 2002, 30(10), 6 pages.

Eton et al., "A Phase II Study of "Decrescendo" Interleukin-2 plus Interferon-a-2a in Patients with Progressive Metastatic Melanoma after chemotherapy", Cancer, Apr. 2000, 88(7), 1703-1709.

Goff et al., "Tumor Infiltrating Lymphocyte Therapy for Metastatic Melanoma: Analysis of Tumors Resected for TIL", J. Immunother, Oct. 2010, 33(8), 840-847.

Goff et al., "Randomized, Prospective Evaluation Comparing Intensity of Lymphodepletion before adoptive transfer of tumor-infiltrating lymphocytes for patients with metastatic melanoma", Journal of Clinical Oncology, Jul. 2016, 34(20), 71 pages.

Gossen et al., "Transcriptional Activation by Tetracyclines in Mammalian Cells", Science, Jun. 1995, 268, 1766-1769.

Gribskov et al., "Sigma Factors from *E. coli*, B subtilis, phage SP01, and phage T4 homologous proteins", Nucleic Acids Research, Mar. 1986, 14(16), 19 pages.

Grussenmeyer et al., "Complexes of Polyoma virus medium T antigen and cellular proteins", Proc Natl. Acad. Sci., USA Dec. 1985, 82, 7952-7954.

Harvey et al., "Inducible Control of Gene Expression: Prospects for Gene Therapy", Current Opinion in Chemical Biology, 1998, 2, 512-518.

Holliger, et al., "Diabodies: Small bivalent and biospecific antibody fragments", Proc. Natl. Acad. Sci. USA, Jul. 1993, 90, 6444-6448.

Houot et al., "Therapeutic effect of CD137 immunomodulation in lymphoma and its enhancement by Treg depletion", Blood, Oct. 2009, 114(16), 3431-3438.

Huston et al., "Protein engineering of antibody binding sites: recovery of specific activity in an anti-digoxin single-chain Fv analogue produced in *Escherichia coli*", Proc. Natl. Acad. Sci., USA, Aug. 1988, 85, 5879-5883.

Jones et al., "Lentiviral Vector Design for Optimal T Cell Receptor Gene Expression in the transduction of peripheral blood lymphocytes and tumor-infiltrating lymphocytes", Human Gene Therapy, Jun. 2009, 20, 630-640.

Katzen, "Gateway Recombinational cloning: a biological operating system" Expert Opin. Drug Discov. 2007, 2(4), 571-589.

Kohrt et al., "CD137 stimulation enhances the antilymphoma activity of anti-CD20 antibodies", Blood, Feb. 2011, 117(8), 2423-2432.

Lee et al., "4-1BB Signaling Activates the T Cell Factor 1 Effector /B-Catenin Pathway with Delayed Kinetics via ERK Signaling and Delayed PI3K/AKT Activation to Promote the Proliferation of CD8+ T Cells", PLOS, Jul. 2013, 11 pages.

Lee et al., "Tumor-Infiltrating Lymphocytes in Melanoma", Curr Oncol Rep. Aug. 2012, 14, 468-474.

Liu et al., "Calcineurin is a Common Target of Cyclophilin-Cyclosporin A and FKBp-FK506 Complexes", Cell, Aug. 1991, 66, 807-815.

Lynch, "The Promise of 4-1-BB (CD137_-mediated immunomodulation and immunotherapy of Cancer", Immunological Reviews, 2008, 277-286.

Magari et al., "Pharmacological Control of a Humanized Gene Therapy System Implanted into Nude Mice", J. Clin. Invest. Dec. 1997, 100(11), 2865-2872.

Nilsson et al., "Immobilization and Purification of Enzymes with Staphyloccal Protein A Gene Fusions", The EMBO Journal , 1985, 4(4), 1075-1080.

Nilsson et al., "Expression and Purification of Recombinant Insulin-Like growth factors from *Escherichia coli*", Methods In Enzymology, 1991, 198, 14 pages.

No et al., "Ecdysone-inducible gene expression in mammalian cells and transgeneic Mice", Proc Natl. Acad. Sci. USA, Apr. 1996, 93, 3346-3351.

O'Day et al., "Advantages of Concurrent Biochemotherapy Modified by Decrescendo Interleukin-2, Granulocyte Colony-Stimulating Factor, and Tamoxifen for Patients with Metastatic Melanoma", Journal of Oncology, Sep. 1999, 17(9), 2752-2761.

Poljak, "Production and Structure of Diabodies", Structure, Dec. 1994, 2, 1121-1123.

Rosenberg et al., "Use of Tumor-Infiltrating Lymphocytes and Interleukin-2 in the Immunotherapy of Patients with Metastatic Melanoma", The New England Journal of Medicine, Dec. 1988, 5 pages.

(56)                    References Cited

OTHER PUBLICATIONS

Sabbagh et al., "ERK-Dependent Bim Modulation Downstream of 4-1BB-TRAF1 Signaling Axis is a Crital Mediator of CD8 T Cell Survival in Vivo", The Journal of Immunology, 2008, 8093-8101.
Sallusto et al., "Central Memory and Effector Memory T Cell Subsets: Function, Generation, and Maintenance", Annu. Rev. Immunol., 2004, 22, 745-763.
Scharping et al., "The Turmor Microenvironment Represses T Cell Mitochondrial Biogenesis to Drive Intratumoral T Cell Metabolic Insufficiency and Dysfunction", Immunity, Aug. 2016, 45, 374-388.
Smith et al., "Single-Step Purification of Polypeptides Expressed in Escherichia coli as fusions with glutathione S-Transferase", Gene, Mar. 1988, 67, 31-40.
Smith et al., "Comparison of Biosequences" Advances in Applied Mathematics, 1981, 2, 482-489.
Steinke et al., "Th2 Cytokines and asthma Interleukin-4: Its role in the parthenogenesis of asthma, and targeting it for asthma treatment with interleukin-4 receptor antagonists", Respir Res, Feb. 2001, 2, 66-70.
Swartz et al., "Tumor Microenvironment Complexity: Emerging Roles in Cancer Therapy", American Association for Cancer Research, May 2012, 72(10), 2473-2480.
Turtle, "Artificial Antigen-Presenting Cells for Use in Adoptive Immunotherapy", The Cancer Journal, Jul.-Aug. 2010, 16(4), 374-381.
Vinay et al., "Dual Immunoregulatory pathways of 4-1BB Signaling", J. Mol Med., Feb. 2006, 84, 726-736.
Wang et at., "Positive and Negative regulation of gene expression in eukaryotic cells with an inducible transcriptional regulator", Gene Therapy, 1997, 4, 432-441.
Wang et al., "Ligand-Inducible and liver specific target gene expression in transgenic mice", Nature Biotechnology, Mar. 1997, 15, 239-243.
Wang et al., "Development of a Hypoxia-inducible cytosine deaminase expression vector for gene-directed prodrug cancer therapy", Cancer Gene Therapy, Jan. 2005, 12, 276-283.
Wang et al., "In Vitro Characterization of the Anti-PD-1 Antibody Nivolumab, BMS-936558, and in Vivo Toxicology in Non-Human primates", Cancer Immunol. Res., Sep. 2014, 2(9), 846-856.
Watts, "TNF/TNFR Family Members in Costimulation of T Cell Responses", Annu. Rev. Immunol. 2005, 23, 23-68.
Weber et al., "Safety, Efficacy, and Biomarkers of Nivolumab with Vaccine in Ipilimumab-Refractory or Naive-Melanoma", Journal of Clinical Oncology, Dec. 2013, 31(34), 10 pages.
Weinberg et al., "Engagement of the OX-40 Receptor in Vivo Enhances Antitumor Immunity", The Journal of Immunology, 2000, 2160-2169.
Yang et al., "Naive T-Cells in myelodysplastic syndrome display intrinsic human telomerase reverse transcriptase (hTERT) Deficiency", Leukemia, 2013, 27, 897-906.
Yi et al., "T-Cell exhaustion: Characteristics, causes and conversion", Immunology, 2010, 129, 474-481.
Pini et al Design and use of a phage display library. Human antibodies with subnanomolar affinity against a marker of angiogenesis eluted from a two-dimensional gel J. Biol. Chem. 273:21769-21776(1998).
Ngo, in The Protein Folding Problem and Tertiary Structure Prediction, Merz et al. (eds.), Birkhauser Boston: Boston, MA, pp. 433 and 492-495, 1994.
Radvanyi, et al., "Specific Lymphocyte Subsets Predict Response to Adoptive Cell Therapy Using Expanded Autologous Tumor-Infiltrating Lymphocytes in Metastatic Melanoma Patients"; Clin Cancer Res 2012, 18, 6758-6770.
Gruijl, et al., "IL-21 promotes the expansion of CD27+CD28+tumor infiltrating lymphocytes with high cytotoxic potential and low collateral expansionof regulatory T cells"; J. Transl. Med. 2013, 11, 37.
Maciejowski et al., "Telomeres in cancer: tumour suppression and genome instability"; Nat Rev Mol Cell Biol. Mar. 2017; 18(3):175-186.

De Lange T, Shiue L, Myers RM, Cox DR, Naylor SL, Killery AM, Varmus HE. "Structure and variability of human chromosome ends"; Mol Cell Biol. 1990;10:518-527.
Santegoets, S. J., "IL-21 promotes the expansion of CD27+CD28+ tumor infiltrating lymphocytes with high cytotoxic potential and low collateral expansion of regulatory T cells"; J Transl Med., 2013, 11:37 (https://nwww.ncbi.hlm.nih.gov/pmc/articles/PMC3626 797/).
Musin, "The problem of the twenty-five spheres"; (2003). Russ. Math Surv. 58(4): 794-795.
Batzer, "Enhanced evolutionary PCR using oligonucleotides with inosine at the 3'-terminus"; Nucleic Acids Research, vol. 19, 18, 5081.
Sethuraman et al., "Successful expansion and characterization of tumor infiltrating lymphocytes (TILs) from non-melanoma tumors"; Journal for ImmunoTherapy of Cancer, vol. 4, Supp. 1, 2016, p. 41-42.
Richards et al., "Flow Cytometry Assessment of Residual Melanoma Cells in Tumor-Infiltrating Lymphocyte Cultures"; Cytometry A 2012; 81:374-81.
Dudley ME, Wunderlich Jr, Shelton TE, et al., "Generation of Tumor-Infiltrating Lymphocyte Cultures for Use In Adoptive Transfer Therapy for Melanoma Patients"; 2003, J. Immunother., 26, 332-342.
Goff et al., "Randomized, Prospective Evaluation Comparing Intensityof Lymphodepletion Before Adoptive Transfer of Tumor-Infiltrating Lymphocytes for Patients With Metastatic Melanoma"; J. Clin Oncol. Jul. 10, 2016; 34(2) 2389-97.
Thomas, et al., "Targeting human CD27 with an agonist antibody stimulates T-cell activation and antitumor immunity"; Oncolummunology 2014, 3, e27255.
Jung, et al., "Bypassing glycosylation: engineering aglycosylated full-length IgG antibodies for human therapy"; Cur. Opin. Biotechnology 2011, 22, 858-867.
Roth, et al., "Immune Response against Tumors"; Adv. Immunol. 1994, 57, 281-351.
Fearon, et al., "Induction in a Murine Tumor of Immunogenic Tumor Variants by Transfection with a Foreign Gene"; Cancer Res. 1988, 48, 2975-2980.
Keir, et al., "PD-1 and Its Ligands in Tolerance and Immunity"; Annu. Rev. Immunol. 2008, 26, 677-704.
Topalian, et al., "Safety, Activity, and Immune Correlates of Anti-PD-1 Antibody in Cancer"; N. Eng. J. Med. 2012, 366, 2443-54.
Page, et al., "Immune Modulation in Cancer with Antibodies"; Ann. Rev. Med., 2014, 65, 185-202.
Fuerst, "Metastatic Melanoma: Immunotherapy with Pembrolizumab Induces Durable Responses"; Oncology Times, 2014, 36, 35-56.
Robert, et al., " Anti-programmed-death-receptor-1 treatment with pembrolizumab in ipilimumab-refractory advanced melanoma: a randomised dose-comparison cohort of a phase 1 trial"; Lancet, 2014, 384, 1109-17.
Thomas, et al., "Immunotherapy for non-small-cell lung cancer"; Exp. Opin. Biol. Ther., 2014, 14, 1061-1064.
Brahmer, et al. "Clinical activity and biomarkers of MEDI4736, an anti-PD-L1 antibody, in patients with NSCLC"; Journal of Clinical Oncology 32, No. 15-suppl (May 2014) 8021-8021.
McDermott, et al., "Durable benefit and the potential for long-term survival with immunotherapy in advanced melanoma"; Cancer Treatment Rev., 2014, 40, 1056-64.
Chacon, et al., "Manipulating the Tumor Microenvironment Ex Vivo for Enhanced Expansion of Tumor-Infiltrating Lymphocytes for Adoptive Cell Therapy"; Clin. Cancer Res. 2015, 21, 611-21.
Joseph, et al., "Impact of Clinical and Pathologic Features on Tumor-Infiltrating Lymphocyte Expansion from Surgically Excised Melanoma Metastases for Adoptive T-cell Therapy"; Clin. Cancer Res. 2011, 17, 4882-91.
Tran, et al., "T-Cell Transfer Therapy Targeting Mutant KRAS in Cancer"; N. Engl. J. Med. 2016, 375, 2255-62.
Tran, et al., "Cancer Immunotherapy Based on Mutation-Specific CD4+ T Cells in a Patient with Epithelial Cancer"; Science 2014, 344, 641-45.
Paulsen, et al., "Modulation of CD4+ T-cell activation by CD95 co-stimulation"; Cell Death Differ. 2011, 18, 619-31.

(56)         References Cited

OTHER PUBLICATIONS

Monnier, et al., "In Vivo Applications of Single Chain Fv (Variable Domain) (scFv) FragmentsAntibodies"; 2013, 2, 193-208.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):OF1-OF9 (2013).

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Robbins, et al., "Cutting Edge: Persistence of Transferred Lymphocyte Clonotypes Correlates with Cancer Regression In Patients Receiving Cell Transfer Therapy"; J. Immunol 2004; 173, 7125-7130.

Shen et al., "Persistence of Tumor Infiltrating Lymphocytes in Adoptive Immunotherapy Correlates With Telomere Length"; J. Immunother, 30, 123-129 (2007).

Zhou, et al., "Persistence of Multiple Tumor-Specific T-Cell Clones Is Associated with Complete Tumor Regression In a Melanoma Patient Receiving Adoptive Cell Transfer Therapy"; J. Immunother, 28, 53-62 (2005).

Eil R, Vodnala SK, et al., "Ionic immune suppression within the tumour microenvironment limits T cell effector function"; Nature, 2016; 537, 539-543.

Feske, et al., "Ion Channels in Innate and Adaptive Immunity"; Annu. Rev. Immunol. 2015, 33, 291-353.

Di, et al., "Inhibition of the K+ channel KCa3.1 ameliorates T cell-mediated colitis"; Proc. Natl Acad. Sci. USA 2010, 107, 1541-46.

Sankaranarayanan, et al., "Naphtho[1,2-d]thiazol-2-ylamine (SKA-31), a New Activatorof KCa2 and KCa3.1 Potassium Channels, Potentiates the Endothelium-Derived Hyperpolarizing Factor Responseand Lowers Blood Pressure"; Mol. Pharmacol. 2009, 75, 281-95.

Strobaek, et al., "Activation of human IK and SK Ca2+-activated K+ channels by NS309 (6,7-dichloro-1H-indole-2,3- dione 3-oxime)"; Biochim. Biophys. Acta 2004, 1665, 1-5.

Abeagbo, "1-Ethyl-2-benzimidazolinone stimulates endothelial K channels and Ca nitric oxide formation in rat mesenteric vessels"; Eur. J. Pharmacol. 1999, 379, 151-59.

Devor, et al., "Modulation of Cl-secretion by benzimidazolones. I. Direct activation of a Ca2+-dependent K+ channel"; Am. J. Physiol. 1996, 271, L775-L784.

Singh, et al., "Benzimidazolone Activators of Chloride Secretion: Potential Therapeutics for Cystic Fibrosis and Chronic Obstructive Pulmonary Disease"; J. Pharmacol. Exp. Ther. 2001, 296, 600-611.

Grunnet, et al., "Pharmacological modulation of SK3 channels"; Neuropharmacology 2001, 40, 879-887.

Coleman, et al., "New Positive Ca21-Activated K1 Channel Gating Modulators with Selectivity for KCa3.1 s"; Mol. Pharmacol. 2014, 86, 342-57.

Hinrichs et al.; "Exploiting the curative potential of adoptive T-cell therapy for cancer"; Immunol Rev. Jan. 2014; 257 (1):56-71.

Somerville et al., "Clinical scale rapid expansion of lymphocytes for adoptive cell transfer therapy in the WAVE® bioreactor"; J Transl Med. Apr. 4, 2012;0-69.

Campbell, et al., "CCR7 Expression and Memory T Cell Diversity in Humans"; J. Immunol. 2001, 166, 877-84.

Huang et al., "Survival, Persistence, and Progressive Differentiation of Adoptively Transferred Tumor-Reactive T Cells Associated with Tumor Regression"; J. Immunother, 28(3), 258-267 (2005).

Fantozzi, "Mouse models of breast cancer metastasis"; Breast Cancer Res. 2006, 8, 212.

Gattinoni, et al., "Adoptive immunotherapy for cancer: building on success", Nat. Rev. Immunol. May 2006, 6(5), 383-393.

Dudley, et al., "Cancer Regression and Autoimmunity in Patients After Clonal Repopulation with Antitumor Lymphocytes", Science, Oct. 2002, 298, 850-54.

Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley, et al., "Adoptive Cell Therapy for Patients with Metastatic Melanoma: Evaluation of Intensive Myeloablative Chemoradiation Preparative Regimens" , J. Clin. Oncol., Nov. 2008, 26(32), 5233-39.

Riddell, et al., "Restoration of Viral Immunity in Immunodeficient Humans by the Adoptive Transfer of T Cell Clones", Science, Jul. 1992, 257, 238-41.

Dudley, et al., "Generation of Tumor-Infiltrating Lymphocyte Cultures for USe in Adoptive Transfer Therapy for Melanoma Patients", J. Immunother., 2003, 26(4), 332-42.

Butler et al., "Human cell-based artificial antigen-presenting cells for cancer immunotherapy", Immunol. Rev. Jan. 2014, 257(1), 191-209.

Friedman, et al., "Augmented Lymphocyte expansion from solid tumors with engineered cells for costimulatory enhancement", J. Immunother. Nov. 2011, 34(9), 651-661.

Ye, et al., "Engineered Artificial antigen presenting cells facilitate direct and efficient expansion of tumor infiltrating lymphocytes", J. Translat. Med. 2011, 9(131), 13 pages.

Forget, et al., "Activation and propagation of tumor infiltrating lymphocytes on clinical-grade designer antigen presenting cells for adoptive immunotherapy of melanmoa", J Immunother. 2014, 37(9), 448-60.

Maus, et al., Ex Vivo expansion of polyclonal and antigen-specific cytotoxic T lymphocytes by artificial APCs expressing ligands for the T-cell receptor, CD28 abd 4-1BB Nat. Biotechnol. 2002, 20, 143-148.

Suhoski, et al., "Engineering Artificial Antigen-presenting cells to express a diverse array of co-stimulatory molecules", Mol. Ther., May 2007, 15(5), 981-988.

Matsuo et al., Two acute monocytic leukemia (AML-M5a) cells lines, (MOLM-13 and MOLM-14) with interclonal phenotypic heterogeneity showing MLL-AF9 fusion resulting from an occult chromosome insertion, ins(11;9)(q23; p22p23) Leukemia 1997, 11, 1469-77.

Konopka, et al., "Cell lines and clinical isolates derived from PH1-positive chronic myelogenous leukemia patients express c-abl proteins with a common structural alteration", Proc. Nat'l Acad. Sci. USA, Mar. 1985, 82, 1810-4.

International Search Report for PCT/US2017/059271 dated Feb. 3, 2018, 9 pages.

Written Opinion for PCT/US2017/059271 dated Feb. 3, 2018, 13 pages.

Burks, et al., "In vitro scanning saturation mutagenesis of an antibody binding pocket", Proc. Natl. Acad. Sci. USA Janaury 1997, 94, 412-417.

Gordon et al., "Gene Therapy using Retroviral Vectors", Curr. Op. Biotechnol., 1994, 5, 611-616.

Miller, et al., "Use of Retroviral Vectors for Gene Transfer and Expression", Meth. Enzymol., 1993, 217, 581-599.

Nelson, "IL-2, Regulatory T Cells and Tolerance", J. Immunol., Feb. 2004, 172, 3983-88.

Malek, "The Biology of Interleukin-2", Annu. Rev. Immunol. 2008, 26, 453-79.

Fry et al., "Interleukin-7: from bench to clinic", Blood, Jan. 2002, 99(11), 3892-904.

Fehniger et al., "Interleukin 15: biology and relevance to human disease", Blood, Jan. 2001, 97(1), 14-32.

Spolski et al., "Interleukin-21: a double-edged sword with therapeutic potential",, Nat. Rev. Drug. Disc., May 2014, 13, 379-95.

Levine, et al., "Gene Transfer in humans using a conditionally replicating lentiviral vector" Proc. Nat 'l, Acad. Sci., Nov. 2006, 103, 17372-77.

Zufferey, et al., "Multiply attenuated leniviral vector achieves efficient gene delivery in vivo", Nat. Biotechnol., Jul. 1997, 15, 871-75.

(56)          References Cited

OTHER PUBLICATIONS

Dull, et al.,"A Third-Generation Lentivirus Vector with a Conditional Packaging System", J. Virology, Nov. 1998, 72(11), 8463-71.
Cepko et al., "Transduction of Genes Using Retrovirus Vectors", Cur. Prot. Mol. Biol. 1996, 9.9.1-9.9.16.
Hackett, et al., "A Transposon and Transposase System for Human Application", Mol. Therapy, Jan. 2010, 18(4), 674-83.
Tsong, "Electroporation of Cell Membranes", Biophys. J., Aug. 1991, 60, 297-306.
Graham et al., "A New Technique for the Assay of Infectivity of Human Adenovirus 5 DNA", Virology, Jan. 1973, 52, 456-467.
Wigler, et al. "DNA-meditated transfer of the adenine phosphoribosyltransferase locus into mammalian cells", Proc. Natl. Acad. Sci., Mar. 1979, 76, 1373-1376.
Chen et al., "High-Efficiency Transformation of Mammalian Cells by Plasmid DNA", Mol. Cell. Biol., Aug. 1987, 7(8), 2745-2752.
Rose, et al., "A New Cationic Liposome Reagent Mediating Nearly Quantitative Transfection of Animal Cells", Biotechniques, 1991, 10(4), 520-525.
Felgner, et al., "Lipofection: A Highly efficient, lipid-mediated DNA-transfection procedure", Proc. Natl. Acad. Sci. USA, Nov. 1987, 84, 7413-7417.
Jin, et al., "Simplified Method of the Growth of Human Tumor Infiltrating Lymphocytes (TIL) in Gas-Permeable Flasks to Nos. Needed for Patient Treatment", J. Immunotherapy, Apr. 2012, 35(3), 283-292.
Mullany, et al, "Minireview: Animal Models and Mechanisms of Ovarian Cancer Development", Endocrinology, Apr. 2012, 153(4), 1585-92.
Fong, et al., "Ovarian Cancer mouse models: a summary of current models and their limitations", J. Ovarian Res. Sep. 2009, 2(12), 8 pages.
Herreros-Villanueva, et al., "Mouse models of pancreatic Cancer", World J. Gastroenterol., Mar. 2012, 18(12), 1286-1294.
Fantozzi et al., "Mouse Models of breast cancer metastasis", Breast Cancer Res., Jul. 2006, 8(212), 11 pages.
Damsky, et al., "Mouse Melanoma models and cells lines", Pigment Cell & Melanoma Res. 2010, 23, 853-859.
Meuwissen, et al., "Mouse models for human lung cancer", Genes & Development, 2005, 19, 643-664.
Kim, "Animal Models of Cancer in the head and neck region", Clin. Exp. Otorhinolaryngol., Jun. 2009, 2(2), 55-60.
Raskind W. H. et al., "Correlation between cytogenetic and molecular findings in human chronic myelogenous leukemia ines EM-2 and EM-3", Cancer Genetics and Cytogenetics, Elsevier Science Publishing, New York, NY, US, vol. 25, No. 2, Apr. 1, 1987, pp. 271-284.
Gajewski T. F. et al., "The P815 Mastocytoma Tumor Model", Curr. Protoc. Immunol., Chapter 20, Unit 20.4, May 31, 2001.
Deniger D. C. et a., "Activating and Propagating Polyclonal Gamma Delta T Cells with Broad Specificity for Malignancies", Clinical Cancer Research, vol. 20, No. 22, Nov. 15, 2014, pp. 5708-5719.
Sadehghi, et al., "Rapid expansion of T cells: Effects of culture and cryopreservation and importance of short-term cell recovery" Acta Oncologica 2013, 52, 978-986.
Tsoukas et al., "Activation of resting T lymphocytes by anti-CD3 (T3) antibodies in the absence of monocytes", J. Immunol. 1985, 135, 1719.
Tran et al., "Minimally Cultured tumor-infiltrating lymphocytes display optimal characteristics for adoptive cell therapy", 2008, J. Immunother., Oct. 2008 31(8), 742-751.
Chang et al., "Emerging concepts in immunotherapt T-cell metabolism as a therapeutic target", Nat. Immunol., Apr. 2016, 17(4), 364-368.
U.S. National Institutes of Health, "A Study of Varlilumab and Atezolizuamb in Patients with Advanced Cancer", U.S. National Library of Medicine, Sep. 2015, clinicaltrials.gov identifier NCT02543645, 6 pages.
U.S. National Institutes of Health, A Study of Varlilumab (Anti-CD27) and Ipilimumab and CDX-1401 in Patients with Unresectable Stage III or IV Melanoma, U.S. National Library of Medicine, Apr. 2015, clinicaltrials.gov identifier NCT02413827, 6 pages.
U.S. National Institutes of Health, "A Study of Varlilumab (Anti-CD27) and Sunitinib in Patients with Metastatic Clear Cell Renal Cell Carcinoma", U.S. National Library of Medicine, Mar. 2015, clinicaltrials.gov identifier NCT2386111, 6 pages.
U.S. National Institutes of Health, "A Dose of Escalation and Cohort Expansion of Anti-CD27 (Varlilumab) and Anti- PD-1 (Nivolumab) in Advanced Refractory Solid Tumors", U.S. National Library of Medicine, Jan. 2015, clinicaltrials.gov identifier NCT02335918, 6 pages.
U.S. National Institutes of Health, Combination Study of Urelumab and Rituximsb in Patients with b-cell Non-Hodgkins Lymphoma, U.S. National Library of Medicine, Jan. 2015, clinicaltrials.gov identifier NCT01775631, 6 pages.
U.S. National Institutes of Health, Combination Study of Urelumab and Cetuximab in Patients with Advanced/ Metastatic Colorectal Cancer or Advanced/Metastatic Head and Neck Cancer, U.S. National Library of Medicine, Apr. 2014, clinicaltrials.gov identifier NCT02110082, 6 pages.
U.S. National Institutes of Health, "An Investigational Immunotherapy Study to Determine the Safety of Urelumab given in Combination with Nivoluamb in Solid Tumors and B-Cell Non-Hodgkins Lymphoma", U.S. National Library of Medicine, Oct. 2014, clinicaltrials. gov identifier NCT02253992, 7 pages.
U.S. National Institutes of Health, Safety Tolerability, Pharmacokinetics, and Immunoregulatory Study of Urelumab ) BMS-663513) in Subjects with Advanced / Metastatic Solid Tumors and Relapsed/ Refractory B-Cell Non-Hodgkin's Lymphoma National Library of Medicine, Nov. 2011, clinicaltrials.gov identifier NCT01471210, 8 pages.
Segal, et al., "Results from an Integrated Safety Analysis of Urelumab, an Agonist Anti CD-137 Monoclonal Antibody", Clin. Cancer Res., Apr. 2017, 23(8), 1929-1936.
Samaik et al., "Developmental Therapeutics", J Clin Oncology, May 27, 2017, 35(155), 6 pages.
Curti, et al., "OX40 is a Potent Immune-Stimulating Target in Late-Stage Cancer Patients", Cancer Res., Dec. 2013, 73(24), 7189-98.
Oshima, et al., "Characterization of Murine CD70 by Molecular cloning and mAb", Int. Immunol. Jan. 1998, 10(4), 517-26.
Claus, et al., "CD27 Signaling Increases the Frequency of Regulatory T Cells and Promotes Tumor Growth", Cancer Res. Jul. 2012, 72(14), 3664-76.
Aulwurm, et al., "Immune Stimulatory effects of CD70 override CD70—mediated immune cell apoptosis in rodent glioma models and confer long-lasting antiglimoa immunity in vivo", Int. J. Cancer 2006, 118, 1728-35.
He, et al., "Agonist Anti-Human CD27 Monoclonal Antibody induces T Cell Activation and Tumor Immunity in human CD27—Transgenic Mice", J. Immunol. 2013, 191, 4174-83.
Nocentini and Riccardi, "GITR: A multifaceted regulator of immunity belonging to the tumor necrosis factor receptor superfamily", Eur. J. Immunol., Feb. 2005, 35, 1016-1022.
Ko, et al., "Treatment of Advanced Tumors with Agonistic anti-GITR mAb and its effects on tumor-infiltrating foxp3+CD4+ regulatory T cells", J. Exp. Med., Oct. 2005, 202(7), 885-91.
Shimizu, et al., "Stimulation of CD25+CD4 regulatory T cells through GITR breaks immunological self-tolerance", Nature Immunology, Jan. 2002, 3, 135-142.
Cohen, et al., "Agonist Antibody Enhances Vaccine-induced CD8+ T-Cell Responses and Tumor Immunity", Cancer Res., May 2006, 66(9), 4904-12.
Azuma, "Role of the Glucocorticoid-Induced TNFR-Related Protein (GITR)-GITR Ligand Pathway in Innate and Adaptive Immunity", Crit. Rev. Immunol. 2010, 30(6), 547-57.
Schaer, et al., "Modulation of GITR for Cancer Immunotherapy", Curr. Opin. Immunol. 2012, 24, 217-224.
Montgomery, et al., "Herpes Simplex Virus-1 Entry into Cells Mediated by a novel member of the TNF/NGF Receptor Family", Cell, Nov. 1996, 87, 427-36.

(56) References Cited

OTHER PUBLICATIONS

Mauri, et al., "LIGHT, a New Member of the TNF Superfamily, and Lymphotoxin a Are ligands for Herpesvirus Entry mediator", Immunity, Jan. 1998, 8, 21-30.

Tamada, et al., "Reciprocal Expression of the TNF Family Receptor Herpes Virus Entry Mediator and its ligand LIGHT on activated T Cells: LIGHT down-regulates its own receptor", J. Immunol. 2000, 165, 4397-404.

Harrop, et al., "Herpesvirus entry mediator ligand (HVEM-L), a novel ligand for HVEM/TR2, Stimulates Proliferation of T Cells and Inhibits HT29 Cell Growth", J. Biol. Chem., Oct. 1998, 273(42), 27548-56.

Linch et al., "OX40 agonists and combination immunotherapy: putting the pedal to the metal", Front. Oncol., Feb. 2015, 34, 1-14.

Ward, et al., "Binding activities of a repertoire of a single immunoglobulin variable domains secreted from *Escherichia coli*", Nature, Oct. 1989, 341, 544-546.

Jones, et al., "replacing the complementarity—determining regions in a human antibody with those from a mouse", Nature, May 1986, 321, 522-525.

Riechmann, et al., "Reshaping human antibodies for therapy", Nature, Mar. 1988, 332, 323-329.

Presta, "Antibody engineering", Curr. Op. Struct. Biol. 1992, 2, 593-596.

Yamane-Ohnuki, et al., "Establishment of FUT8 knockout Chinese hamster ovary cells: an ideal host cell line for producing completely defucosylated antibodies wth enhanced antibody-dependent cellular cytotoxicity", Biotechnol. Bioeng., Mar. 2004, 87, 614-622.

Shields, et al., "Lack of fucose on Human IgG1 N-Linked Oligosaccharide improves binding to human FcγRIII and antibody-dependent cellular toxicity", J. Biol. Chem., Jul. 2002, 277(30), 26733-26740.

Umana, et al., "Engineered glycoforms of an antineuro-blastoma IgG1 with Optimized antibody-dependent cellular cytotoxic activity", Nat. Biotech., Feb. 1999, 17, 176-180.

Tarentino, et al., "The Isolation and Structure of the Core Oligosaccharide Sequences of IgM" Biochem. 1975, 14(25), 5516-5523.

Muranski, et al., "Increased intensity lymphodepletion and adoptive immunotherapy—how far can we go?", Nat. Clin. Pract. Oncol., Dec. 2006, 3, 668-681.

Gassner, et al., "Fludarabine modulates composition and function of the T Cell pool in patients with chronic lymphocytic leukaemia", Cancer. Immunol. Immunother., 2011, 60, 75-85.

Brummell, et al., "Probing the Combining Site of an Anti-Carbohydrate antibody by saturation—mutagenesis: Role of the heavy-chain CDR3 Residues", Biochemistry 1993, 32(4), 1180-1187.

Kobayashi, et al., "Tryptophan H33 plays an important role in pyrimidine (6-4) pyrimidone photoproduct binding by a high-affinity antibody", Protein Engineering, 1999, 12(10), 879-884 (1999).

Sano et al., "Xenograft models of head and neck cancers", Head Neck Oncol., Aug. 2009, 1(32), 6 pages.

Batzer, et al., "Enhanced evolutionary PCR using olignucleotides with inosine at the 3'-terminus", Nucleic Acid Res. Jul. 1991, 19(18), 1 page.

Ohtsuka, et al., "An Alternative approach to Deoxyoligonucleotides as hybridization probes by insertion of deoxyinosine at ambiguous codon positions", J. Biol. Chem. 1985, 260(5), 2605-2608.

Rossolini, et al., "Use of deoxyinosine-containing primers vs degenerate primers for polymerase chain reaction based on ambiguous sequence information", Mol. Cell. Probes 1994, 8, 91-98.

Gieffers et al., "APG350 induces Superior Clustering of TRAIL receptors and shows therapeutic antitumor efficacy Independent of Cross-linking via Fcγ receptors", Mol. Cancer Therapeutics, Dec. 2013, 12(12), 2735-47.

Fisher, et al., "Targeting of 4-1BB by monoclonal antibody PF-05082566 enhances T-Cell function and promotes anti-tumor activity", Cancer Immunolog. & Immunother. 2012, 61, 1721-33.

Jin et al. "Simplified Method of the Growth of Human Tumor Infiltrating Lymphocytes in Gas-Permeable Flasks to Numbers needed for patient treatment", J Immunother., Apr. 2012, 35(3), 283-92.

U.S. National Institutes of Health, "A study of PF-05082566 in combination with Mogamulizumab in Patients with Advanced Solid Tumors", U.S. National Library of Medicine, May 2015, clinicaltrials.gov identifier NCT02444793, 8 pages.

U.S. National Institutes of Health, "A Study of PF-05082566 as a Single Agent and in Combination with Rituximab", U.S. National Library of Medicine, Mar. 2011, clinicaltrials.gov identifier NCT001307267, 6 pages.

U.S. National Institutes of Health, Study of OX40 Agonist PF-04518600 Alone and in Combination with 4-1BB Agonist PF-05082566, U.S. National Library of Medicine, Dec. 2014, clinicaltrials.gov identifier NCT02315066, 6 pages.

U.S. National Institutes of Health, A Study of CDX-1127 (Varlilumab) in Patients with Select Solid Tumor Types or Hematologic Cancer, U.S. National Library of Medicine, Oct. 2011, clinicaltrials.gov identifier NCT01460134, 7 pages.

Donia et al., "Simplified protocol for clinical-grade tumor-infiltrating lymphocyte manufacturing with use of the Wave bioreactor"; Cythotherapy, Aug. 2014; 16(8):1117-20.

Henning et al., "Measurement of T-Cell Telomere Length UNIT 7.47 Using Amplified-Signal FISH Staining and Flow Cytometry Curr Protoc Cytom."; Jan. 5, 2017; 79:7.1-47.10.

Kelesidis et al. "Assessment of Telomere Length, UNIT 7.26 Phenotype, and DNA Conten"; Curr Protoc Cytom. Jan. 5, 2017; 79:7.26.1-7.26.23.

Gardner et al., "Gender and telomere length: Systematic review and meta-analysis"; Exp Gerontol. Mar. 201451:15-27.

Carbonari et al., "Correlation between terminal restriction fragments and flow-FISH measures in samples over wide range telomere lengths"; Cell Prolif. Feb. 2014;47(1):20-7.

Rufer et al.; "Telomere length dynamics in human lymphocyte subpopulations measured by flow cytometry"; Nat Biotechnol. Aug. 1998; 16(8):743-7.

Li et al., "MART-1-Specific Melanoma Tumor-Infiltrating Lymphocytes Maintaining CD28 Expression Have Improved Survival and Expansion Capability Following Antigenic Restimulation In Vitro"; J. Immunol. Jan. 1, 2010;184(1):452-65.

Rosenberg et al., "Adoptive cell therapy for the treatment of patients with metastatic melanoma"; Curr Opin Immunol. Apr. 2009;21(2)233-40.

Shen et al., "Persistence of Tumor Infiltrating Lymphocytes in AdoptiveImmunotherapy Correlates With Telomere Length"; J Immunother. Jan. 2007;30(1):123-9.

Zhou et al.; "Persistence of Multiple Tumor-Specific T-Cell Clones Is Associated with Complete Tumor Regression In a Melanoma Patient Receiving Adoptive Cell Transfer Therapy"; J. Immunol. Nov. 15, 2005;175(10):7046-52.

Erdel et al.; "Telomere Recognition and Assembly Mechanism of Mammalian Shelterin"; Cell Rep Jan. 3, 2017;18(1):41-53.

Cardenas et al., "A Xenopus egg factor with DNA-binding properties characteristic of terminus-specific telomeric proteins"; Genes Dev. May 1993;7(5):883-94.

De Lange; "Activation of telomerase in a human tumor"; Proc Natl Acad Sci USA Apr. 12, 1994;91(8):2882-5.

De Lange; "Structure and Variability of Human Chromosome Ends"; Mol Cell Biol. Feb. 1990; 10(2):518-27.

Buck et al., "T cell metabolism drives immunity"; JEM 212: 1345-1360; 2015.

Tran, KQ, Zhou, J., Durflinger KH, et al., "Minimally Cultured Tumor-infiltrating Lymphocytes Display Optimal Characteristics for Adoptive Cell Therapy"; 2008, J. Immunother., 31, 742-751.

Chandran et al., "Treatment of metastatic uveal melanoma with adoptive transfer of tumour-infiltrating lymphocytes: a single-centre, two-stage, single-arm, phase 2 study"; Lancet Oncol, doi: 10.1016/S1470-2045(17)30251-6 (2017).

Stevanovic et al., "Complete Regression of Metastatic Cervical Cancer After Treatment With Human Papillomavirus—Targeted Tumor-Infiltrating T Cells"; J Clin Oncol 33, doi: 10.1200/jco.2014. 58.9093 (2015).

(56) References Cited

OTHER PUBLICATIONS

Dayhoff, "Atlas of Protein Sequences and Structure", M.O. Dayhoff ed., 5 suppl., 3, 353-358, National Biomedical Research Foundation, Washington D.C. USA.

* cited by examiner

TIL: High APC ratio

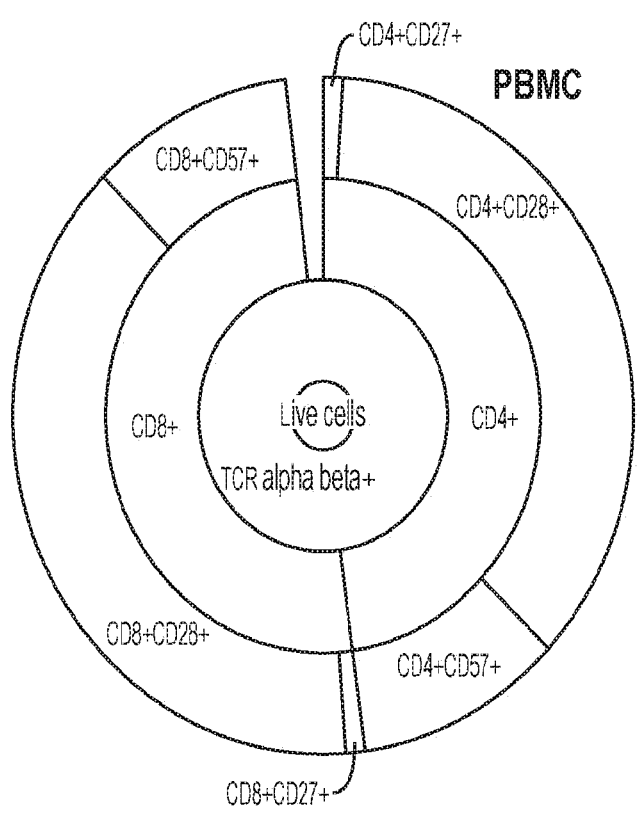
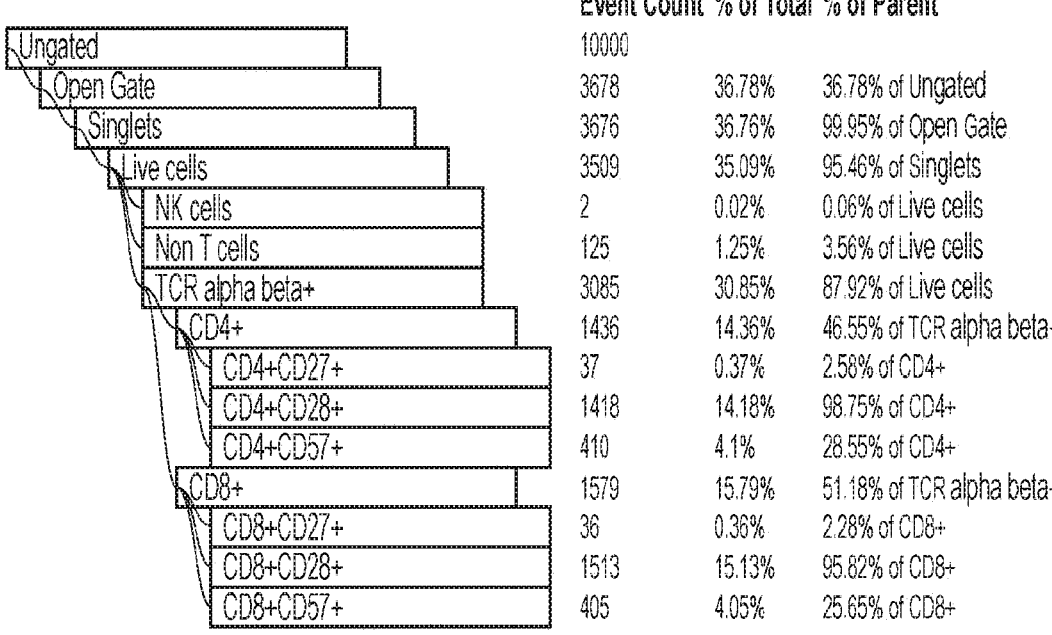
| | Event Count | % of Total | % of Parent |
|---|---|---|---|
| Ungated | 10000 | | |
| Open Gate | 3678 | 36.78% | 36.78% of Ungated |
| Singlets | 3676 | 36.76% | 99.95% of Open Gate |
| Live cells | 3509 | 35.09% | 95.46% of Singlets |
| NK cells | 2 | 0.02% | 0.06% of Live cells |
| Non T cells | 125 | 1.25% | 3.56% of Live cells |
| TCR alpha beta+ | 3085 | 30.85% | 87.92% of Live cells |
| CD4+ | 1436 | 14.36% | 46.55% of TCR alpha beta+ |
| CD4+CD27+ | 37 | 0.37% | 2.58% of CD4+ |
| CD4+CD28+ | 1418 | 14.18% | 98.75% of CD4+ |
| CD4+CD57+ | 410 | 4.1% | 28.55% of CD4+ |
| CD8+ | 1579 | 15.79% | 51.18% of TCR alpha beta+ |
| CD8+CD27+ | 36 | 0.36% | 2.28% of CD8+ |
| CD8+CD28+ | 1513 | 15.13% | 95.82% of CD8+ |
| CD8+CD57+ | 405 | 4.05% | 25.65% of CD8+ |
FIG. 22

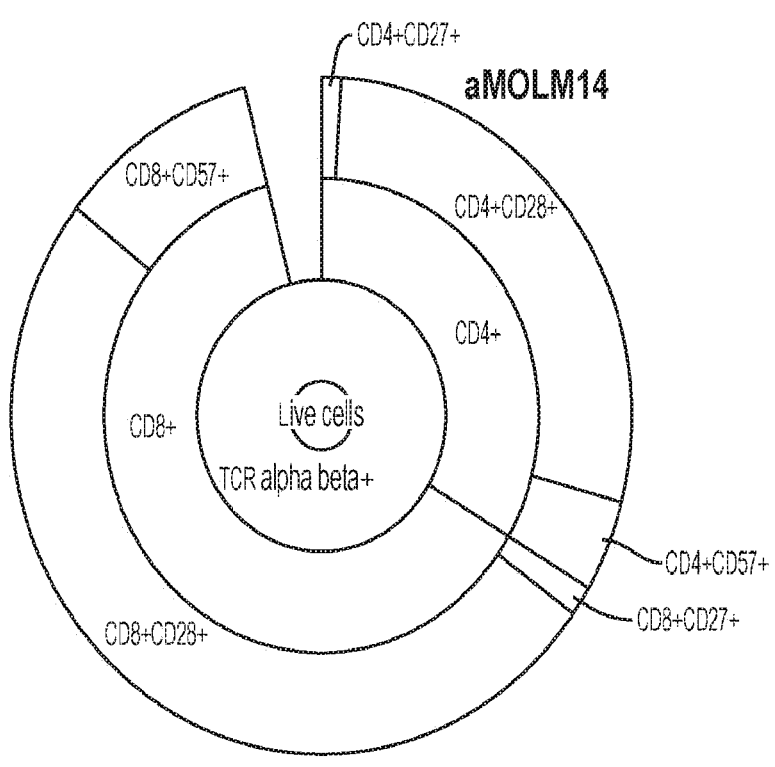
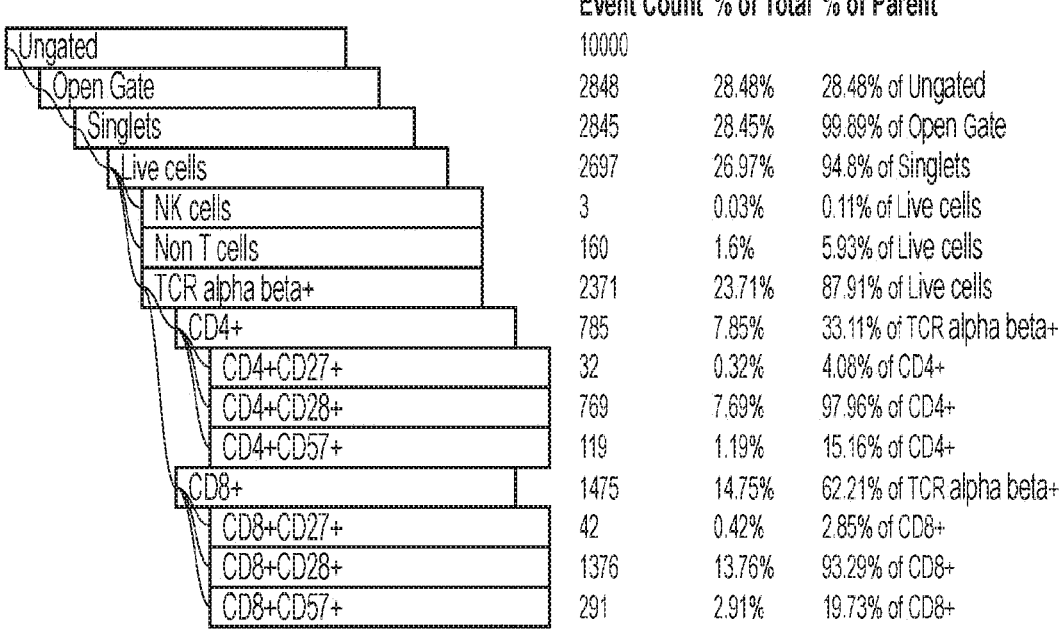
| | Event Count | % of Total | % of Parent |
|---|---|---|---|
| Ungated | 10000 | | |
| Open Gate | 2848 | 28.48% | 28.48% of Ungated |
| Singlets | 2845 | 28.45% | 99.89% of Open Gate |
| Live cells | 2697 | 26.97% | 94.8% of Singlets |
| NK cells | 3 | 0.03% | 0.11% of Live cells |
| Non T cells | 160 | 1.6% | 5.93% of Live cells |
| TCR alpha beta+ | 2371 | 23.71% | 87.91% of Live cells |
| CD4+ | 785 | 7.85% | 33.11% of TCR alpha beta+ |
| CD4+CD27+ | 32 | 0.32% | 4.08% of CD4+ |
| CD4+CD28+ | 769 | 7.69% | 97.96% of CD4+ |
| CD4+CD57+ | 119 | 1.19% | 15.16% of CD4+ |
| CD8+ | 1475 | 14.75% | 62.21% of TCR alpha beta+ |
| CD8+CD27+ | 42 | 0.42% | 2.85% of CD8+ |
| CD8+CD28+ | 1376 | 13.76% | 93.29% of CD8+ |
| CD8+CD57+ | 291 | 2.91% | 19.73% of CD8+ |
FIG. 23

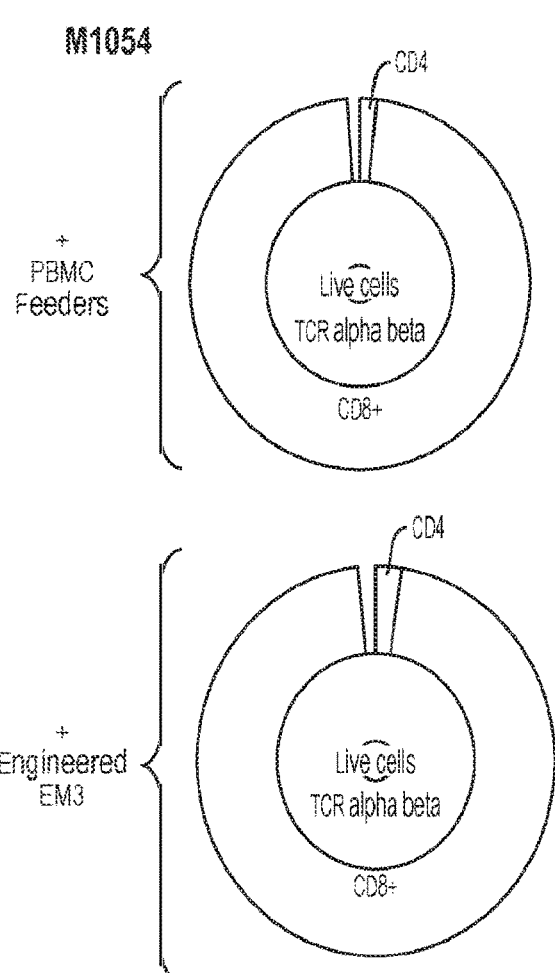

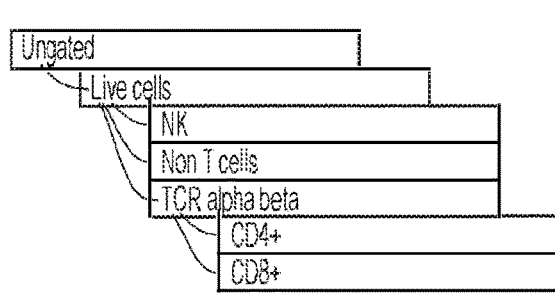

| | Event Count | % of Total | % of Parent |
|---|---|---|---|
| Ungated | 30000 | | |
| Live cells | 21976 | 73.25% | 73.25% of Ungated |
| NK | 58 | 0.19% | 0.26% of Live cells |
| Non T cells | 369 | 1.23% | 1.68% of Live cells |
| TCR alpha beta | 21077 | 70.26% | 95.91% of Live cells |
| CD4+ | 368 | 1.23% | 1.75% of TCR alpha beta |
| CD8+ | 20554 | 68.51% | 97.52% of TCR alpha beta |

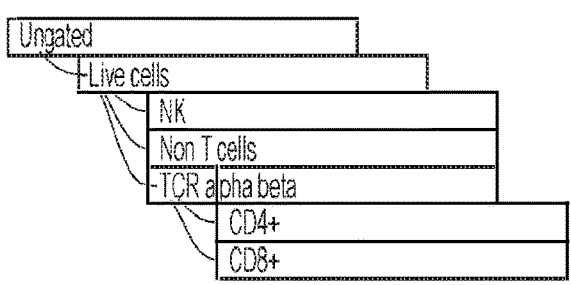

| | Event Count | % of Total | % of Parent |
|---|---|---|---|
| Ungated | 30000 | | |
| Live cells | 22173 | 73.91% | 73.91% of Ungated |
| NK | 1 | 0% | 0% of Live cells |
| Non T cells | 230 | 0.77% | 1.04% of Live cells |
| TCR alpha beta | 21709 | 72.36% | 97.91% of Live cells |
| CD4+ | 532 | 1.77% | 2.45% of TCR alpha beta |
| CD8+ | 20863 | 69.54% | 96.1% of TCR alpha beta |

FIG. 45
M1055
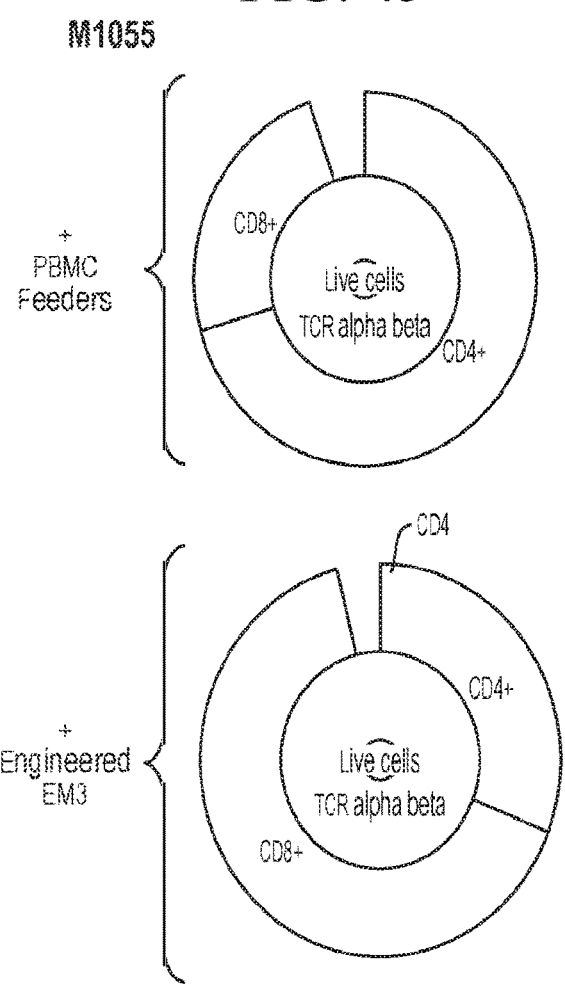
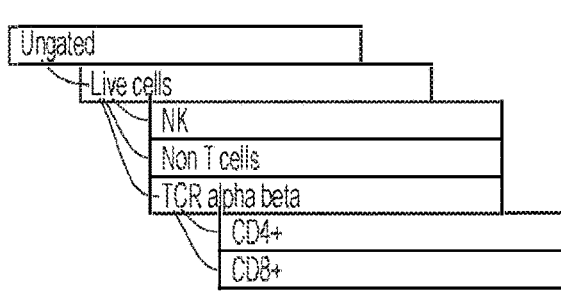
|  | Event Count | % of Total | % of Parent |
|---|---|---|---|
| Ungated | 30000 |  |  |
| Live cells | 20353 | 67.84% | 67.84% of Ungated |
| NK | 0 |  |  |
| Non T cells | 43 | 0.14% | 0.21% of Live cells |
| TCR alpha beta | 20226 | 67.42% | 99.38% of Live cells |
| CD4+ | 14211 | 47.37% | 70.26% of TCR alpha beta |
| CD8+ | 4956 | 16.52% | 24.5% of TCR alpha beta |
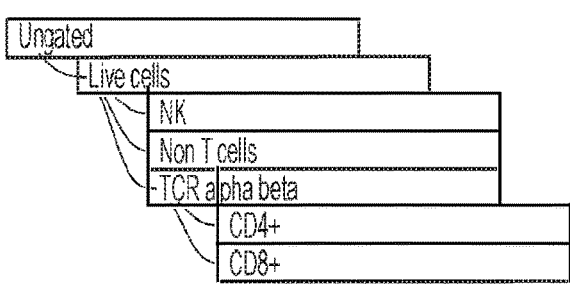
|  | Event Count | % of Total | % of Parent |
|---|---|---|---|
| Ungated | 30000 |  |  |
| Live cells | 16288 | 54.29% | 54.29% of Ungated |
| NK | 0 |  |  |
| Non T cells | 11 | 0.04% | 0.07% of Live cells |
| TCR alpha beta | 16262 | 54.21% | 99.84% of Live cells |
| CD4+ | 5014 | 16.71% | 30.83% of TCR alpha beta |
| CD8+ | 10668 | 35.56% | 65.6% of TCR alpha beta |

IFN-γ Release by TIL co-cultured with P815-Fl-Clone G6
(in presence of α-CD3)

Ratio TIL:P815

Induction of LAMP1 in TIL cocultured with P815-FI-Clone G6

M1053T

M1030T

M1053T

M1030T

M1053T

M1030T

Enzymatic TNFα M1053T

Enzymatic TNFα M1030T aEM3 7C12
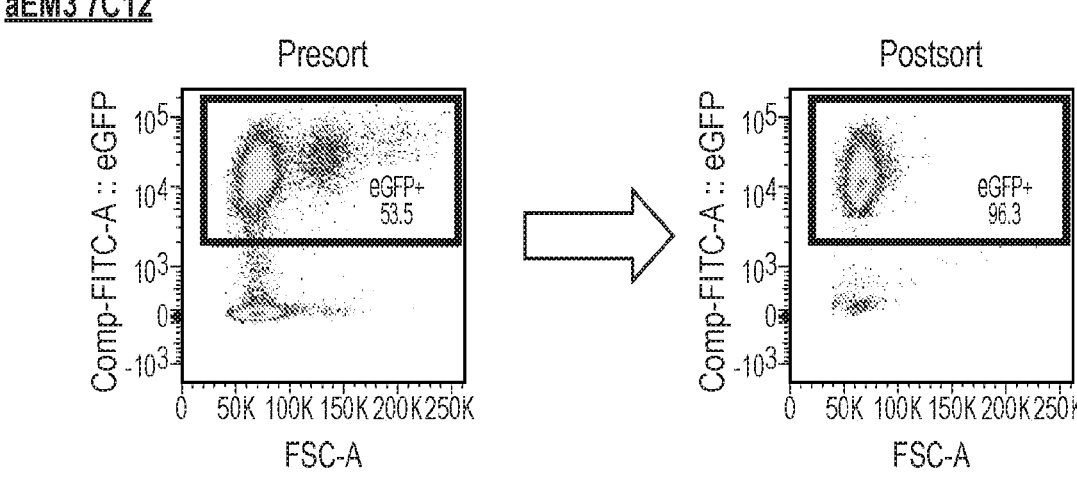
aEM3 8B5
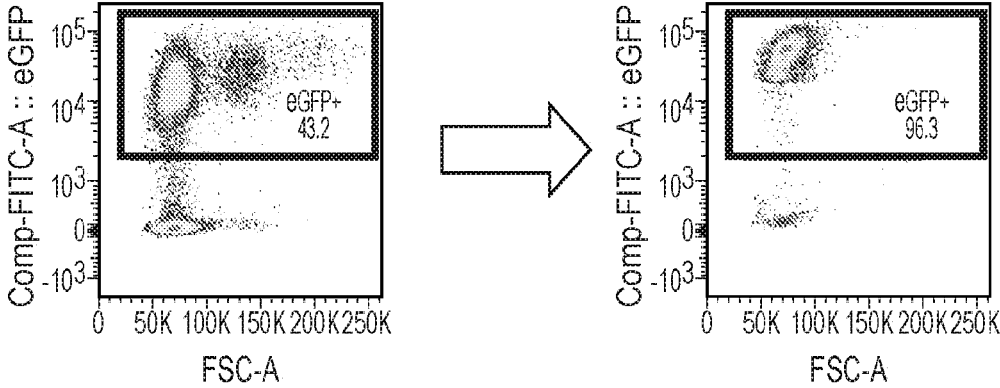
Flow Panel:
1. DAPI
2. eGFP
FIG. 80

* For D11, none of the counts Vs. CM1 were statistically relevant based on student 't' test

* p>0.05, Calculated by student 't' test pLenti-C-Myc-DDK OX40L
6924 bp

SEQUENCE LISTING

<160> NUMBER OF SEQ ID NOS: 43

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
```

-continued

```
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
                35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
                100                 105                 110

Thr Val Ser Ile Phe Pro Pro Ser Ser Glu Gln Leu Thr Ser Gly Gly
                115                 120                 125

Ala Ser Val Val Cys Phe Leu Asn Asn Phe Tyr Pro Lys Asp Ile Asn
```

```
         130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
                195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2

<400> SEQUENCE: 3

Met Ala Pro Thr Ser Ser Ser Thr Lys Lys Thr Gln Leu Gln Leu Glu
1                   5                   10                  15

His Leu Leu Leu Asp Leu Gln Met Ile Leu Asn Gly Ile Asn Asn Tyr
                20                  25                  30

Lys Asn Pro Lys Leu Thr Arg Met Leu Thr Phe Lys Phe Tyr Met Pro
                35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
                100                 105                 110

Ala Thr Ile Val Glu Phe Leu Asn Arg Trp Ile Thr Phe Cys Gln Ser
                115                 120                 125

Ile Ile Ser Thr Leu Thr
    130

<210> SEQ ID NO 4
<211> LENGTH: 132
<212> TYPE: PRT
<213> ORGANISM: Artificial Sequence
<220> FEATURE:
<223> OTHER INFORMATION: aldesleukin

<400> SEQUENCE: 4

Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80
```

-continued

```
Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 5
<211> LENGTH: 153
<212> TYPE: PRT
<213> ORGANISM: Artificial Sequence
<220> FEATURE:
<223> OTHER INFORMATION: recombinant human IL-7

<400> SEQUENCE: 5

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
            85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 6
<211> LENGTH: 115
<212> TYPE: PRT
<213> ORGANISM: Artificial Sequence
<220> FEATURE:
<223> OTHER INFORMATION: recombinant human IL-15

<400> SEQUENCE: 6

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
            85                  90                  95
```

-continued

```
Ile Lys Glu Phe Leu Gln Ser Phe Val His Ile Val Gln Met Phe Ile
            100                 105                 110

Asn Thr Ser
        115

<210> SEQ ID NO 7
<211> LENGTH: 132
<212> TYPE: PRT
<213> ORGANISM: Artificial Sequence
<220> FEATURE:
<223> OTHER INFORMATION: IL-21

<400> SEQUENCE: 7

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
        35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
        130

<210> SEQ ID NO 8
<211> LENGTH: 323
<212> TYPE: PRT
<213> ORGANISM: Artificial Sequence
<220> FEATURE:
<223> OTHER INFORMATION: human CD86

<400> SEQUENCE: 8

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
```

-continued

```
            130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
                180                 185                 190

Val Ser Ile Ser Leu Ser Val Ser Phe Pro Asp Val Thr Ser Asn Met
            195                 200                 205

Thr Ile Phe Cys Ile Leu Glu Thr Asp Lys Thr Arg Leu Leu Ser Ser
        210                 215                 220

Pro Phe Ser Ile Glu Leu Glu Asp Pro Gln Pro Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Lys Arg Pro Arg Asn
                260                 265                 270

Ser Tyr Lys Cys Gly Thr Asn Thr Met Glu Arg Glu Glu Ser Glu Gln
            275                 280                 285

Thr Lys Lys Arg Glu Lys Ile His Ile Pro Glu Arg Ser Asp Glu Ala
        290                 295                 300

Gln Arg Val Phe Lys Ser Ser Lys Thr Ser Ser Cys Asp Lys Ser Asp
305                 310                 315                 320

Thr Cys Phe
```

<210> SEQ ID NO 9
<211> LENGTH: 254
<212> TYPE: PRT
<213> ORGANISM: Artificial Sequence
<220> FEATURE:
<223> OTHER INFORMATION: human 4-1BBL

<400> SEQUENCE: 9

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175
```

-continued

```
Ala Ala Leu Ala Leu Thr Val Asp Leu Pro Pro Ala Ser Ser Glu Ala
            180                 185             190

Arg Asn Ser Ala Phe Gly Phe Gln Gly Arg Leu Leu His Leu Ser Ala
            195                 200             205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

```
<210> SEQ ID NO 10
<211> LENGTH: 183
<212> TYPE: PRT
<213> ORGANISM: Artificial Sequence
<220> FEATURE:
<223> OTHER INFORMATION: human OX40L

<400> SEQUENCE: 10
```

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
        130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

```
<210> SEQ ID NO 11
<211> LENGTH: 220
<212> TYPE: PRT
<213> ORGANISM: Artificial Sequence
<220> FEATURE:
<223> OTHER INFORMATION: human CD28

<400> SEQUENCE: 11
```

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
```

-continued

```
              35                    40                    45

Arg Glu Phe Arg Ala Ser Leu His Lys Gly Leu Asp Ser Ala Val Glu
     50                    55                    60

Val Cys Val Val Tyr Gly Asn Tyr Ser Gln Gln Leu Gln Val Tyr Ser
65                    70                    75                    80

Lys Thr Gly Phe Asn Cys Asp Gly Lys Leu Gly Asn Glu Ser Val Thr
               85                    90                    95

Phe Tyr Leu Gln Asn Leu Tyr Val Asn Gln Thr Asp Ile Tyr Phe Cys
               100                   105                   110

Lys Ile Glu Val Met Tyr Pro Pro Tyr Leu Asp Asn Glu Lys Ser
               115                   120                   125

Asn Gly Thr Ile Ile His Val Lys Gly Lys His Leu Cys Pro Ser Pro
     130                   135                   140

Leu Phe Pro Gly Pro Ser Lys Pro Phe Trp Val Leu Val Val Val Gly
145                   150                   155                   160

Gly Val Leu Ala Cys Tyr Ser Leu Leu Val Thr Val Ala Phe Ile Ile
               165                   170                   175

Phe Trp Val Arg Ser Lys Arg Ser Arg Leu Leu His Ser Asp Tyr Met
               180                   185                   190

Asn Met Thr Pro Arg Arg Pro Gly Pro Thr Arg Lys His Tyr Gln Pro
               195                   200                   205

Tyr Ala Pro Pro Arg Asp Phe Ala Ala Tyr Arg Ser
     210                   215                   220
```

<210> SEQ ID NO 12
<211> LENGTH: 223
<212> TYPE: PRT
<213> ORGANISM: Artificial Sequence
<220> FEATURE:
<223> OTHER INFORMATION: human CTLA-4

<400> SEQUENCE: 12

```
Met Ala Cys Leu Gly Phe Gln Arg His Lys Ala Gln Leu Asn Leu Ala
1                5                    10                   15

Thr Arg Thr Trp Pro Cys Thr Leu Leu Phe Phe Leu Leu Phe Ile Pro
               20                   25                   30

Val Phe Cys Lys Ala Met His Val Ala Gln Pro Ala Val Val Leu Ala
               35                   40                   45

Ser Ser Arg Gly Ile Ala Ser Phe Val Cys Glu Tyr Ala Ser Pro Gly
     50                   55                   60

Lys Ala Thr Glu Val Arg Val Thr Val Leu Arg Gln Ala Asp Ser Gln
65                   70                   75                   80

Val Thr Glu Val Cys Ala Ala Thr Tyr Met Met Gly Asn Glu Leu Thr
               85                   90                   95

Phe Leu Asp Asp Ser Ile Cys Thr Gly Thr Ser Ser Gly Asn Gln Val
               100                  105                  110

Asn Leu Thr Ile Gln Gly Leu Arg Ala Met Asp Thr Gly Leu Tyr Ile
               115                  120                  125

Cys Lys Val Glu Leu Met Tyr Pro Pro Pro Tyr Tyr Leu Gly Ile Gly
     130                  135                  140

Asn Gly Thr Gln Ile Tyr Val Ile Asp Pro Glu Pro Cys Pro Asp Ser
145                  150                  155                  160

Asp Phe Leu Leu Trp Ile Leu Ala Ala Val Ser Ser Gly Leu Phe Phe
               165                  170                  175

Tyr Ser Phe Leu Leu Thr Ala Val Ser Leu Ser Lys Met Leu Lys Lys
```

```
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
        210                 215                 220

<210> SEQ ID NO 13
<211> LENGTH: 255
<212> TYPE: PRT
<213> ORGANISM: Artificial Sequence
<220> FEATURE:
<223> OTHER INFORMATION: human 4-1BB

<400> SEQUENCE: 13

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 14
<211> LENGTH: 277
<212> TYPE: PRT
<213> ORGANISM: Artificial Sequence
<220> FEATURE:
<223> OTHER INFORMATION: human OX40

<400> SEQUENCE: 14

Met Cys Val Gly Ala Arg Arg Leu Gly Arg Gly Pro Cys Ala Ala Leu
1               5                   10                  15
```

-continued

```
Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
            50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
            245                 250                 255

Gly Ser Phe Arg Thr Pro Ile Gln Glu Glu Gln Ala Asp Ala His Ser
        260                 265                 270

Thr Leu Ala Lys Ile
        275
```

<210> SEQ ID NO 15
<211> LENGTH: 7569
<212> TYPE: DNA
<213> ORGANISM: Artificial Sequence
<220> FEATURE:
<223> OTHER INFORMATION: pLV430G human 4-1BBL vector

<400> SEQUENCE: 15

```
cgataaccct aattcgatag catatgcttc ccgttgggta acatatgcta ttgaattagg      60
gttagtctgg atagtatata ctactacccg ggaagcatat gctacccgtt tagggttcac     120
cggtgatgcc ggccacgatg cgtccggcgt agaggatcta atgtgagtta gctcactcat     180
taggcacccc aggctttaca ctttatgctt ccggctcgta tgttgtgtgg aattgtgagc     240
ggataacaat ttcacacagg aaacagctat gaccatgatt acgccaagcg cgcaattaac     300
cctcactaaa gggaacaaaa gctggagctg caagcttaat gtagtcttat gcaatactct     360
tgtagtcttg caacatggta acgatgagtt agcaacatgc cttacaagga gagaaaaagc     420
accgtgcatg ccgattggtg gaagtaaggt ggtacgatcg tgccttatta ggaaggcaac     480
agacgggtct gacatggatt ggacgaacca ctgaattgcc gcattgcaga gatattgtat     540
```

-continued

```
ttaagtgcct agctcgatac ataaacgggt ctctctggtt agaccagatc tgagcctggg      600
agctctctgg ctaactaggg aacccactgc ttaagcctca ataaagcttg ccttgagtgc      660
ttcaagtagt gtgtgcccgt ctgttgtgtg actctggtaa ctagagatcc ctcagaccct      720
tttagtcagt gtggaaaatc tctagcagtg gcgcccgaac agggacttga aagcgaaagg      780
gaaaccagag gagctctctc gacgcaggac tcggcttgct gaagcgcgca cggcaagagg      840
cgaggggcgg cgactggtga gtacgccaaa aattttgact agcggaggct agaaggagag      900
agatgggtgc gagagcgtca gtattaagcg ggggagaatt agatcgcgat gggaaaaaat      960
tcggttaagg ccagggggaa agaaaaaata taaattaaaa catatagtat gggcaagcag     1020
ggagctagaa cgattcgcag ttaatcctgg cctgttagaa acatcagaag gctgtagaca     1080
aatactggga cagctacaac catcccttca gacaggatca gaagaactta gatcattata     1140
taatacagta gcaaccctct attgtgtgca tcaaaggata gagataaaag acaccaagga     1200
agctttagac aagatagagg aagagcaaaa caaaagtaag accaccgcac agcaagcggc     1260
cgctgatctt cagacctgga ggaggagata tgagggacaa ttggagaagt gaattatata     1320
aatataaagt agtaaaaatt gaaccattag gagtagcacc caccaaggca aagagaagag     1380
tggtgcagag agaaaaaaga gcagtgggaa taggagcttt gttccttggg ttcttgggag     1440
cagcaggaag cactatgggc gcagcgtcaa tgacgctgac ggtacaggcc agacaattat     1500
tgtctggtat agtgcagcag cagaacaatt gctgagggc tattgaggcg caacagcatc     1560
tgttgcaact cacagtctgg ggcatcaagc agctccaggc aagaatcctg gctgtggaaa     1620
gatacctaaa ggatcaacag ctcctgggga tttggggttg ctctggaaaa ctcatttgca     1680
ccactgctgt gccttggaat gctagttgga gtaataaatc tctggaacag atttggaatc     1740
acacgacctg gatggagtgg gacagagaaa ttaacaatta cacaagctta atacactcct     1800
taattgaaga atcgcaaaac cagcaagaaa agaatgaaca agaattattg gaattagata     1860
aatgggcaag tttgtggaat tggtttaaca taacaaattg gctgtggtat ataaaattat     1920
tcataatgat agtaggaggc ttggtaggtt taagaatagt ttttgctgta ctttctatag     1980
tgaatagagt taggcaggga tattcaccat tatcgtttca gacccacctc ccaacccga     2040 ggggacccga caggcccgaa ggaatagaag aagaaggtgg agagagagac agagacagat     2100
ccattcgatt agtgaacgga tctcgacggt atcggtttta aaagaaaagg ggggattggg     2160
gggtacagtg caggggaaag aatagtagac ataatagcaa cagacataca aactaaagaa     2220
ttacaaaaac aaattacaaa aattcaaaat tttatcgatt ttatttagtc tccagaaaaa     2280 gggggggaatg aaagacccca cctgtaggtt tggcaagcta gcttaagtaa cgccattttg     2340
caaggcatgg aaaatacata actgagaata gagaagttca gatcaaggtt aggaacagag     2400
agacagcaga atatgggcca aacaggatat ctgtggtaag cagttcctgc cccggctcag     2460
ggccaagaac agatggtccc cagatgcggt cccgccctca gcagtttcta gagaaccatc     2520
agatgtttcc agggtgcccc aaggacctga aatgaccctg tgccttattt gaactaacca     2580
atcagttcgc ttctcgcttc tgttcgcgcg cttctgctcc ccgagctcaa taaaagagcc     2640
cacaacccct cactcggcgc gccagtcctc cgatagactg cgtcgcccgg gtaccgatat     2700
caacaagttt gtacaaaaaa gcaggcttcg ccaccatgga atacgcctct gatgccagcc     2760
tggaccccga agctccttgg cctcctgccc ctagagccag agcctgtaga gtgctgcctt     2820
gggctctggt ggctggcctt ctccttctgc tgctgctggc cgctgcctgc gctgtgtttc     2880
tggcttgtcc ttgggccgtg tcaggcgcca gagcttctcc tggatctgcc gccagcccca     2940
```

-continued

```
gactgagaga gggacctgag ctgagccccg atgatcctgc cggactgctg gatctgagac      3000
agggcatgtt cgcccagctg gtggcccaga acgtgctgct gatcgatggc cccctgagct      3060
ggtacagcga tcctggactg gctggcgtgt cactgacagg cggcctgagc tacaaagagg      3120
acaccaaaga actggtggtg gccaaggccg gcgtgtacta cgtgttcttt cagctggaac      3180
tgcggagagt ggtggccggc gaaggatccg gctctgtgtc tctggcactg catctgcagc      3240
ccctgagatc tgctgcaggc gctgctgcac tggccctgac agtggacctg cctccagcct      3300
ctagcgaggc cagaaactcc gcattcgggt ttcaaggcag actgctgcac ctgtctgccg      3360
gccagagact gggagtgcat ctgcacacag aggccagagc cagacacgcc tggcagctga      3420
cacagggcgc tacagtgctg ggcctgttca gagtgacccc cgaaattcca gccggcctgc      3480
ccagccctag aagcgagtag gacccagctt tcttgtacaa agtggtgatt cgagttaatt      3540
aagctagcct agtgccattt gttcagtggt tcgtagggct ttcccccact gtttggcttt      3600
cagttatatg gatgatgtgg tattgggggc caagtctgta cagcatcttg agtccctttt      3660
taccgctgtt accaattttc ttttgtcttt gggtatacat ttaaacccta acaaaacaaa      3720
gagatggggt tactctctaa attttatggg ttatgtcatt ggatgttatg ggtccttgcc      3780
acaagaacac atcatacaaa aaatcaaaga atgttttaga aaacttccta ttaacaggcc      3840
tattgattgg aaagtatgtc aacgaattgt gggtcttttg ggttttgctg cccctttttac      3900 acaatgtggt tatcctgcgt tgatgccttt gtatgcatgt attcaatcta agcaggcttt      3960
cactttctcg ccaacttaca aggcctttct gtgtaaacaa tacctgaacc tttacccgt      4020 tgcccggcaa cggccaggtc tgtgccaagt gtttgctgac gcaaccccca ctggctgggg      4080
cttggtcatg ggccatcagc gcatgcgtgg aaccttttcg gctcctctgc cgatccatac      4140
tgcggaactc ctagccgctt gttttgctcg cagcaggtct ggagcaaaca ttatcgggac      4200
tgataactct gttgtcctat cccgcaaata tacatcgttt ccatggctgc taggctgtgc      4260
tgccaactgg atcctgcgcg ggacgtcctt tgtttacgtc ccgtcggcgc tgaatcctgc      4320
ggacgaccct tctcggggtc gcttgggact ctctcgtccc cttctccgtc tgccgttccg      4380
accgaccacg gggcgcacct ctctttacgc ggactccccg tctgtgcctt ctcatctgcc      4440
ggaccgtgtg cacttcgctt cacctctgca cgtcgcatgg agaccaccgt gaacgcccac      4500
caaatattgc ccaaggtctt acataagagg actcttggac tctcagcaat gtcaacgacc      4560
gaccttgagg catacttcaa agactgtttg tttaaagact gggaggagtt gggggaggag      4620
attaggttaa aggtctttgt actaggaggc tgtaggcata aattggtctg cgcaccagca      4680
ccatggcgca atcactagag cggggtacct ttaagaccaa tgacttacaa ggcagctgta      4740
gatcttagcc acttttttaaa agaaaagggg ggactggaag ggctaattca ctcccaacga      4800
agacaagatc tgctttttgc ttgtactggg tctctctggt tagaccagat ctgagcctgg      4860
gagctctctg gctaactagg gaacccactg cttaagcctc aataaagctt gccttgagtg      4920
cttcaagtag tgtgtgcccg tctgttgtgt gactctggta actagagatc cctcagaccc      4980
ttttagtcag tgtggaaaat ctctagcagt agtagttcat gtcatcttat tattcagtat      5040
ttataacttg caaagaaatg aatatcagag agtgagagga acttgtttat tgcagcttat      5100
aatggttaca aataaagcaa tagcatcaca aatttcacaa ataaagcatt ttttttcactg      5160 cattctagtt gtggtttgtc caaactcatc aatgtatctt atcatgtctg gctctagcta      5220
tcccgcccct aactccgccc atcccgcccc taactccgcc cagttccgcc cattctccgc      5280
```

-continued

```
cccatggctg actaattttt tttatttatg cagaggccga ggccggatcc cttgagtggc    5340
tttcatcctg gagcagactt tgcagtctgt ggactgcaac acaacattgc ctttatgtgt    5400
aactcttggc tgaagctctt acaccaatgc tgggggacat gtacctccca ggggcccagg    5460
aagactacgg gaggctacac caacgtcaat cagagggggcc tgtgtagcta ccgataagcg    5520
gaccctcaag agggcattag caatagtgtt tataaggccc ccttgttaat tcttgaagac    5580
gaaagggcct cgtgatacgc ctattttttat aggttaatgt catgataata atggtttctt    5640
agacgtcagg tggcacttttt cggggaaatg tgcgcggaac ccctatttgt ttatttttct    5700
aaatacattc aaatatgtat ccgctcatga dacaataacc ctgataaatg cttcaataat    5760
attgaaaaag gaagagtatg agtattcaac atttccgtgt cgcccttatt ccctttttttg    5820 cggcattttg ccttcctgtt tttgctcacc cagaaacgct ggtgaaagta aaagatgctg    5880
aagatcagtt gggtgcacga gtgggttaca tcgaactgga tctcaacagc ggtaagatcc    5940
ttgagagttt tcgccccgaa gaacgttttc caatgatgag cactttttaaa gttctgctat    6000 gtggcgcggt attatcccgt gttgacgccg ggcaagagca actcggtcgc cgcatacact    6060
attctcagaa tgacttggtt gagtactcac cagtcacaga aaagcatctt acggatggca    6120
tgacagtaag agaattatgc agtgctgcca taaccatgag tgataacact gcggccaact    6180
tacttctgac aacgatcgga ggaccgaagg agctaaccgc ttttttgcac aacatggggg    6240
atcatgtaac tcgccttgat cgttgggaac cggagctgaa tgaagccata ccaaacgacg    6300
agcgtgacac cacgatgcct gcagcaatgg caacaacgtt gcgcaaacta ttaactggcg    6360
aactacttac tctagcttcc cggcaacaat taatagactg gatggaggcg gataaagttg    6420
caggaccact tctgcgctcg gcccttccgg ctggctggtt tattgctgat aaatctggag    6480
ccggtgagcg tgggtctcgc ggtatcattg cagcactggg gccagatggt aagccctccc    6540
gtatcgtagt tatctacacg acggggagtc aggcaactat ggatgaacga aatagacaga    6600
tcgctgagat aggtgcctca ctgattaagc attggtaact gtcagaccaa gtttactcat    6660
atatacttta gattgattta aaacttcatt tttaatttaa aaggatctag gtgaagatcc    6720 ttttttgataa tctcatgacc aaaatccctt aacgtgagtt ttcgttccac tgagcgtcag    6780
accccgtaga aaagatcaaa ggatcttctt gagatccttt ttttctgcgc gtaatctgct    6840
gcttgcaaac aaaaaaacca ccgctaccag cggtggtttg tttgccggat caagagctac    6900
caactctttt tccgaaggta actggcttca gcagagcgca gataccaaat actgtccttc    6960
tagtgtagcc gtagttaggc caccacttca agaactctgt agcaccgcct acatacctcg    7020
ctctgctaat cctgttacca gtggctgctg ccagtggcga taagtcgtgt cttaccgggt    7080
tggactcaag acgatagtta ccggataagg cgcagcggtc gggctgaacg gggggttcgt    7140
gcacacagcc cagcttggag cgaacgacct acaccgaact gagatacta cagcgtgagc    7200 attgagaaag cgccacgctt cccgaaggga gaaaggcgga caggtatccg gtaagcggca    7260
gggtcggaac aggagagcgc acgagggagc ttccaggggg aaacgcctgg tatctttata    7320
gtcctgtcgg gtttcgccac ctctgacttg agcgtcgatt tttgtgatgc tcgtcagggg    7380
ggcggagcct atgaaaaaac gccagcaacg cggcctttttt acggttcctg gccttttgct    7440
ggcctttttg aagctgtccc tgatggtcgt catctacctg cctggacagc atggcctgca    7500
acgcgggcat cccgatgccg ccggaagcga gaagaatcat aatggggaag gccatccagc    7560
ctcgcgtcg                                                             7569
```

<210> SEQ ID NO 16
<211> LENGTH: 765
<212> TYPE: DNA
<213> ORGANISM: Artificial Sequence
<220> FEATURE:
<223> OTHER INFORMATION: 4-1BBL CoOP

<400> SEQUENCE: 16
atggaatacg cctctgatgc cagcctggac cccgaagctc cttggcctcc tgcccctaga      60
gccagagcct gtagagtgct gccttgggct ctggtggctg gccttctcct tctgctgctg     120
ctggccgctg cctgcgctgt gtttctggct tgtccttggg ccgtgtcagg cgccagagct     180
tctcctggat ctgccgccag ccccagactg agagagggac ctgagctgag ccccgatgat     240
cctgccggac tgctggatct gagacagggc atgttcgccc agctggtggc ccagaacgtg     300
ctgctgatcg atggcccccct gagctggtac agcgatcctg actggctggg cgtgtcactg     360
acaggcggcc tgagctacaa agaggacacc aaagaactgg tggtggccaa ggccggcgtg     420
tactacgtgt ctttcagct ggaactgcgg agagtggtgg ccggcgaagg atccggctct     480
gtgtctctgg cactgcatct gcagcccctg agatctgctg caggcgctgc tgcactggcc     540
ctgacagtgg acctgcctcc agcctctagc gaggccagaa actccgcatt cgggtttcaa     600
ggcagactgc tgcacctgtc tgccggccag agactgggag tgcatctgca cacagaggcc     660
agagccagac acgcctggca gctgacacag ggcgctacag tgctgggcct gttcagagtg     720
acccccgaaa ttccagccgg cctgcccagc cctagaagcg agtag                     765

<210> SEQ ID NO 17
<211> LENGTH: 832
<212> TYPE: DNA
<213> ORGANISM: Artificial Sequence
<220> FEATURE:
<223> OTHER INFORMATION: 4-1BBL PRCP

<400> SEQUENCE: 17
ggggacaagt ttgtacaaaa aagcaggctt cgccaccatg gaatacgcct ctgatgccag      60
cctggacccc gaagctcctt ggcctcctgc ccctagagcc agagcctgta gagtgctgcc     120
ttgggctctg gtggctggcc ttctccttct gctgctgctg gccgctgcct gcgctgtgtt     180
tctggcttgt ccttgggccg tgtcaggcgc cagagcttct cctggatctg ccgccagccc     240
cagactgaga gagggacctg agctgagccc cgatgatcct gccggactgc tggatctgag     300
acagggcatg ttcgcccagc tggtggccca gaacgtgctg ctgatcgatg gcccccctgag     360 ctggtacagc gatcctggac tggctggcgt gtcactgaca ggcggcctga gctacaaaga     420
ggacaccaaa gaactggtgg tggccaaggc cggcgtgtac tacgtgttct ttcagctgga     480
actgcggaga gtggtggccg gcgaaggatc cggctctgtg tctctggcac tgcatctgca     540
gcccctgaga tctgctgcag gcgctgctgc actggccctg acagtggacc tgcctccagc     600
ctctagcgag gccagaaact ccgcattcgg gtttcaaggc agactgctgc acctgtctgc     660
cggccagaga ctgggagtgc atctgcacac agaggccaga gccagacacg cctggcagct     720
gacacagggc gctacagtgc tgggcctgtt cagagtgacc cccgaaattc agccggcct      780 gcccagccct agaagcgagt aggacccagc tttcttgtac aaagtggtcc cc             832

<210> SEQ ID NO 18
<211> LENGTH: 7776
<212> TYPE: DNA
<213> ORGANISM: Artificial Sequence
<220> FEATURE:

<223> OTHER INFORMATION: pLV430G human CD86 vector

<400> SEQUENCE: 18

```
cgataacccct aattcgatag catatgcttc ccgttgggta acatatgcta ttgaattagg      60
gttagtctgg atagtatata ctactacccg ggaagcatat gctacccgtt tagggttcac     120
cggtgatgcc ggccacgatg cgtccggcgt agaggatcta atgtgagtta gctcactcat     180
taggcacccc aggctttaca ctttatgctt ccggctcgta tgttgtgtgg aattgtgagc     240
ggataacaat ttcacacagg aaacagctat gaccatgatt acgccaagcg cgcaattaac     300
cctcactaaa gggaacaaaa gctggagctg caagcttaat gtagtcttat gcaatactct     360
tgtagtcttg caacatggta acgatgagtt agcaacatgc cttacaagga gagaaaaagc     420
accgtgcatg ccgattggtg gaagtaaggt ggtacgatcg tgccttatta ggaaggcaac     480
agacgggtct gacatggatt ggacgaacca ctgaattgcc gcattgcaga gatattgtat     540
ttaagtgcct agctcgatac ataaacgggt ctctctggtt agaccagatc tgagcctggg     600
agctctctgg ctaactaggg aacccactgc ttaagcctca ataaagcttg ccttgagtgc     660
ttcaagtagt gtgtgcccgt ctgttgtgtg actctggtaa ctagagatcc ctcagaccct     720
tttagtcagt gtggaaaatc tctagcagtg gcgcccgaac agggacttga aagcgaaagg     780
gaaaccagag gagctctctc gacgcaggac tcggcttgct gaagcgcgca cggcaagagg     840
cgaggggcgg cgactggtga gtacgccaaa aattttgact agcggaggct agaaggagag     900
agatgggtgc gagagcgtca gtattaagcg ggggagaatt agatcgcgat gggaaaaaat     960
tcggttaagg ccaggggga agaaaaaata taaattaaaa catatagtat gggcaagcag    1020
ggagctagaa cgattcgcag ttaatcctgg cctgttagaa acatcagaag gctgtagaca    1080
aatactggga cagctacaac catcccttca gacaggatca gaagaactta gatcattata    1140
taatacagta gcaaccctct attgtgtgca tcaaaggata gagataaaag acaccaagga    1200
agctttagac aagatagagg aagagcaaaa caaaagtaag accaccgcac agcaagcggc    1260
cgctgatctt cagacctgga ggaggagata tgagggacaa ttggagaagt gaattatata    1320
aatataaagt agtaaaaatt gaaccattag gagtagcacc caccaaggca agagaagag     1380 tggtgcagag agaaaaaaga gcagtgggaa taggagcttt gttccttggg ttcttgggag    1440
cagcaggaag cactatgggc gcagcgtcaa tgacgctgac ggtacaggcc agacaattat    1500
tgtctggtat agtgcagcag cagaacaatt tgctgagggc tattgaggcg caacagcatc    1560
tgttgcaact cacagtctgg ggcatcaagc agctccaggc aagaatcctg ctgtggaaa     1620 gatacctaaa ggatcaacag ctcctgggga tttggggttg ctctggaaaa ctcatttgca    1680
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaacccga     2040 ggggacccga caggcccgaa ggaatagaag aagaaggtgg agagagagac agagacagat    2100
ccattcgatt agtgaacgga tctcgacggt atcggtttta aagaaaaggg gggattgggg    2160
gggtacagtg caggggaaag aatagtagac ataatagcaa cagacataca aactaaagaa    2220
ttacaaaaac aaaattacaa aattcaaaat tttatcgatt ttatttagtc tccagaaaaa    2280
```

-continued

```
gggggaatg aaagacccca cctgtaggtt tggcaagcta gcttaagtaa cgccatttg    2340 caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttcgcgcg cttctgctcc ccgagctcaa taaaagagcc    2640
cacaacccct cactcggcgc gccagtcctc cgatagactg cgtcgcccgg gtaccgatat    2700
caacaagttt gtacaaaaaa gcaggcttcg ccaccatggg cctgagcaac atcctgttcg    2760
tgatggcctt cctgctgtcc ggagccgccc tctgaagat ccaggcctac ttcaacgaga    2820
ccgccgacct gccctgccag ttcgccaaca gccagaacca gagcctgagc gaactggtgg    2880
tgttctggca ggaccaggaa aacctggtcc tgaacgaggt gtacctgggc aaagaaaagt    2940
tcgacagcgt gcacagcaag tacatgggcc ggaccagctt cgacagcgac agctggaccc    3000
tgcggctgca caacctgcag atcaaggaca agggcctgta ccagtgcatc atccaccaca    3060
agaaacccac cggcatgatc agaatccacc agatgaacag cgagctgtcc gtgctggcca    3120
acttcagcca gcccgagatc gtgcccatca gcaacatcac cgagaacgtg tacatcaacc    3180
tgacctgcag cagcatccac ggctacccg agcccaagaa aatgagcgtg ctgctgcgga    3240
ccaagaacag caccatcgag tacgacggcg tgatgcagaa aagccaggac aacgtgaccg    3300
agctgtacga cgtgagcatc agcctgagcg tgagcttccc cgacgtgacc agcaacatga    3360
ccatcttttg catcctggaa accgacaaga cccggctgct gtccagcccc ttcagcatcg    3420
agctggaaga tcccagccc cctcccgacc acatcccctg gatcaccgcc gtgctgccca    3480
ccgtgatcat ctgcgtgatg gtgttctgcc tgatcctgtg gaagtggaag aagaagaagc    3540
ggcctaggaa cagctacaag tgcggcacca acaccatgga acgggaggaa agcgagcaga    3600
ccaagaagcg ggagaagatc cacatccccg agcggagcga cgaggcccag cgggtgttca    3660
agagcagcaa gaccagcagc tgcgacaaga gcgacacctg cttctaggac ccagcttttct    3720 tgtacaaagt ggtgattcga gttaattaag ctagcctagt gccatttgtt cagtggttcg    3780
tagggctttc ccccactgtt tggctttcag ttatatggat gatgtggtat tggggggccaa    3840 gtctgtacag catcttgagt cccttttac cgctgttacc aattttcttt tgtctttggg    3900 tatacatttta aaccctaaca aaacaaagag atggggttac tctctaaatt ttatgggtta    3960
tgtcattgga tgttatgggt ccttgccaca agaacacatc atacaaaaaa tcaaagaatg    4020
ttttagaaaa cttcctatta acaggcctat tgattggaaa gtatgtcaac gaattgtggg    4080
tcttttgggt tttgctgccc ctttacaca atgtggttat cctgcgttga tgcctttgta    4140
tgcatgtatt caatctaagc aggctttcac tttctcgcca acttacaagg cctttctgtg    4200
taaacaatac ctgaacctt accccgttgc ccggcaacgg ccaggtctgt gccaagtgtt    4260
tgctgacgca accccactg gctggggctt ggtcatgggc catcagcgca tgcgtggaac    4320
cttttcggct cctctgccga tccatactgc ggaactccta gccgcttgtt ttgctcgcag    4380
caggtctgga gcaaacatta tcgggactga taactctgtt gtcctatccc gcaaatatac    4440
atcgtttcca tggctgctag gctgtgctgc caactggatc ctgcgcggga cgtcctttgt    4500
ttacgtcccg tcgcgctga atcctgcgga cgacccttct cggggtcgct tgggactctc    4560
tcgtcccctt ctccgtctgc cgttccgacc gaccacgggg cgcacctctc tttacgcgga    4620
```

-continued

```
ctccccgtct gtgccttctc atctgccgga ccgtgtgcac ttcgcttcac ctctgcacgt    4680
cgcatggaga ccaccgtgaa cgcccaccaa atattgccca aggtcttaca taagaggact    4740
cttggactct cagcaatgtc aacgaccgac cttgaggcat acttcaaaga ctgtttgttt    4800
aaagactggg aggagttggg ggaggagatt aggttaaagg tctttgtact aggaggctgt    4860
aggcataaat tggtctgcgc accagcacca tggcgcaatc actagagcgg ggtaccttta    4920
agaccaatga cttacaaggc agctgtagat cttagccact ttttaaaaga aaaggggga    4980 ctggaagggc taattcactc ccaacgaaga caagatctgc tttttgcttg tactgggtct    5040
ctctggttag accagatctg agcctgggag ctctctggct aactagggaa cccactgctt    5100
aagcctcaat aaagcttgcc ttgagtgctt caagtagtgt gtgcccgtct gttgtgtgac    5160
tctggtaact agagatccct cagacccttt tagtcagtgt ggaaaatctc tagcagtagt    5220
agttcatgtc atcttattat tcagtattta taacttgcaa agaaatgaat atcagagagt    5280
gagaggaact tgtttattgc agcttataat ggttacaaat aaagcaatag catcacaaat    5340
ttcacaaata aagcattttt ttcactgcat tctagttgtg gtttgtccaa actcatcaat    5400
gtatcttatc atgtctggct ctagctatcc cgcccctaac tccgcccatc ccgcccctaa    5460
ctccgcccag ttccgcccat tctccgcccc atggctgact aatttttttt atttatgcag    5520
aggccgaggc cggatccctt gagtggcttt catcctggag cagactttgc agtctgtgga    5580
ctgcaacaca acattgcctt tatgtgtaac tcttggctga agctcttaca ccaatgctgg    5640
gggacatgta cctcccaggg gcccaggaag actacgggag gctacaccaa cgtcaatcag    5700
aggggcctgt gtagctaccg ataagcggac cctcaagagg gcattagcaa tagtgtttat    5760
aaggccccct tgttaattct tgaagacgaa agggcctcgt gatacgccta ttttttatagg    5820 ttaatgtcat gataataatg gtttcttaga cgtcaggtgg cacttttcgg ggaaatgtgc    5880
gcggaacccc tatttgttta tttttctaaa tacattcaaa tatgtatccg ctcatgagac    5940
aataaccctg ataaatgctt caataatatt gaaaaaggaa gagtatgagt attcaacatt    6000
tccgtgtcgc ccttattccc ttttttgcgg cattttgcct tcctgttttt gctcacccag    6060
aaacgctggg gaaagtaaaa gatgctgaag atcagttggg tgcacgagtg ggttacatcg    6120
aactggatct caacagcggt aagatccttg agagttttcg ccccgaagaa cgttttccaa    6180
tgatgagcac ttttaaagtt ctgctatgtg gcgcggtatt atcccgtgtt gacgccgggc    6240
aagagcaact cggtcgccgc atacactatt ctcagaatga cttggttgag tactcaccag    6300
tcacagaaaa gcatcttacg gatggcatga cagtaagaga attatgcagt gctgccataa    6360
ccatgagtga taacactgcg gccaacttac ttctgacaac gatcggagga ccgaaggagc    6420
taaccgcttt tttgcacaac atgggggatc atgtaactcg ccttgatcgt tgggaaccgg    6480
agctgaatga agccatacca aacgacgagc gtgacaccac gatgcctgca gcaatggcaa    6540
caacgttgcg caaactatta actggcgaac tacttactct agcttcccgg caacaattaa    6600
tagactggat ggaggcggat aaagttgcag gaccacttct gcgctcggcc cttccggctg    6660
gctggtttat tgctgataaa tctggagccg gtgagcgtgg gtctcgcggt atcattgcag    6720
cactggggcc agatggtaag ccctcccgta tcgtagttat ctacacgacg gggagtcagg    6780
caactatgga tgaacgaaat agacagatcg ctgagatagg tgcctcactg attaagcatt    6840
ggtaactgtc agaccaagtt tactcatata ctttttagat tgatttaaaa cttcattttt    6900
aatttaaaag gatctaggtg aagatccttt ttgataatct catgaccaaa atcccttaac    6960
gtgagttttc gttccactga gcgtcagacc ccgtagaaaa gatcaaagga tcttcttgag    7020
```

```
atcctttttt tctgcgcgta atctgctgct tgcaaacaaa aaaaccaccg ctaccagcgg      7080
tggtttgttt gccggatcaa gagctaccaa ctcttttttcc gaaggtaact ggcttcagca      7140
gagcgcagat accaaatact gtccttctag tgtagccgta gttaggccac cacttcaaga      7200
actctgtagc accgcctaca tacctcgctc tgctaatcct gttaccagtg gctgctgcca      7260
gtggcgataa gtcgtgtctt accgggttgg actcaagacg atagttaccg gataaggcgc      7320
agcggtcggg ctgaacgggg ggttcgtgca cacagcccag cttggagcga acgacctaca      7380
ccgaactgag atacctacag cgtgagcatt gagaaagcgc cacgcttccc gaagggagaa      7440
aggcggacag gtatccggta agcggcaggg tcggaacagg agagcgcacg agggagcttc      7500 caggggggaaa cgcctggtat ctttatagtc ctgtcgggtt tcgccacctc tgacttgagc      7560
gtcgattttt gtgatgctcg tcaggggggc ggagcctatg gaaaaacgcc agcaacgcgg      7620 ccttttttacg gttcctggcc ttttgctggc cttttttgaag ctgtccctga tggtcgtcat      7680
ctacctgcct ggacagcatg gcctgcaacg cgggcatccc gatgccgccg gaagcgagaa      7740
gaatcataat ggggaaggcc atccagcctc gcgtcg                               7776
```

```
<210> SEQ ID NO 19
<211> LENGTH: 969
<212> TYPE: DNA
<213> ORGANISM: Artificial Sequence
<220> FEATURE:
<223> OTHER INFORMATION: CD86 CoOP

<400> SEQUENCE: 19
```

```
atgggcctga gcaacatcct gttcgtgatg gccttcctgc tgtccggagc cgcccctctg       60
aagatccagg cctacttcaa cgagaccgcc gacctgccct gccagttcgc caacagccag      120
aaccagagcc tgagcgaact ggtggtgttc tggcaggacc aggaaaacct ggtcctgaac      180
gaggtgtacc tgggcaaaga aaagttcgac agcgtgcaca gcaagtacat gggccggacc      240
agcttcgaca gcgacagctg gaccctgcgg ctgcacaacc tgcagatcaa ggacaagggc      300
ctgtaccagt gcatcatcca ccacaagaaa cccaccggca tgatcagaat ccaccagatg      360
aacagcgagc tgtccgtgct ggccaacttc agccagcccg atcgtgcc catcagcaac      420 atcaccgaga cgtgtacat caacctgacc tgcagcagca tccacggcta ccccgagccc      480
aagaaaatga gcgtgctgct gcggaccaag aacagcacca tcgagtacga cggcgtgatg      540
cagaaaagcc aggacaacgt gaccgagctg tacgacgtga gcatcagcct gagcgtgagc      600
ttccccgacg tgaccagcaa catgaccatc ttttgcatcc tggaaaccga caagacccgg      660
ctgctgtcca gcccccttcag catcgagctg gaagatcccc agccccctcc cgaccacatc      720
ccctggatca ccgccgtgct gcccaccgtg atcatctgcg tgatggtgtt ctgcctgatc      780
ctgtggaagt ggaagaagaa gaagcggcct aggaacagct acaagtgcgg caccaacacc      840
atggaacggg aggaaagcga gcagaccaag aagcgggaga agatccacat ccccgagcgg      900
agcgacgagg cccagcgggt gttcaagagc agcaagacca gcagctgcga caagagcgac      960
acctgcttc                                                            969
```

```
<210> SEQ ID NO 20
<211> LENGTH: 1039
<212> TYPE: DNA
<213> ORGANISM: Artificial Sequence
<220> FEATURE:
<223> OTHER INFORMATION: CD86 PCRP
```

-continued

```
<400> SEQUENCE: 20
ggggacaagt ttgtacaaaa aagcaggctt cgccaccatg ggcctgagca acatcctgtt      60
cgtgatggcc ttcctgctgt ccggagccgc ccctctgaag atccaggcct acttcaacga     120
gaccgccgac ctgccctgcc agttcgccaa cagccagaac cagagcctga gcgaactggt     180
ggtgttctgg caggaccagg aaaacctggt cctgaacgag gtgtacctgg gcaaagaaaa     240
gttcgacagc gtgcacagca agtacatggg ccggaccagc ttcgacagcg acagctggac     300
cctgcggctg cacaacctgc agatcaagga caagggcctg taccagtgca tcatccacca     360
caagaaaccc accggcatga tcagaatcca ccagatgaac agcgagctgt ccgtgctggc     420
caacttcagc cagcccgaga tcgtgcccat cagcaacatc accgagaacg tgtacatcaa     480
cctgacctgc agcagcatcc acggctaccc cgagcccaag aaaatgagcg tgctgctgcg     540
gaccaagaac agcaccatcg agtacgacgg cgtgatgcag aaaagccagg acaacgtgac     600
cgagctgtac gacgtgagca tcagcctgag cgtgagcttc cccgacgtga ccagcaacat     660
gaccatcttt tgcatcctgg aaaccgacaa gacccggctg ctgtccagcc ccttcagcat     720
cgagctggaa gatccccagc cccctcccga ccacatcccc tggatcaccg ccgtgctgcc     780
caccgtgatc atctgcgtga tggtgttctg cctgatcctg tggaagtgga agaagaagaa     840
gcggcctagg aacagctaca agtgcggcac caacaccatg gaacgggagg aaagcgagca     900
gaccaagaag cgggagaaga tccacatccc cgagcggagc gacgaggccc agcgggtgtt     960
caagagcagc aagaccagca gctgcgacaa gagcgacacc tgcttctagg acccagcttt    1020
cttgtacaaa gtggtcccc                                                 1039

<210> SEQ ID NO 21
<211> LENGTH: 3526
<212> TYPE: DNA
<213> ORGANISM: Artificial Sequence
<220> FEATURE:
<223> OTHER INFORMATION: pDONR221 CD86 vector

<400> SEQUENCE: 21
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta ggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacacattg atgagcaatg cttttttata atgccaagt ttgtacaaaa     660 aagcaggctt cgccaccatg ggcctgagca acatcctgtt cgtgatggcc ttcctgctgt     720
ccggagccgc ccctctgaag atccaggcct acttcaacga gaccgccgac ctgccctgcc     780
agttcgccaa cagccagaac cagagcctga gcgaactggt ggtgttctgg caggaccagg     840
aaaacctggt cctgaacgag gtgtacctgg gcaaagaaaa gttcgacagc gtgcacagca     900
agtacatggg ccggaccagc ttcgacagcg acagctggac cctgcggctg cacaacctgc     960
```

-continued

```
agatcaagga caagggcctg taccagtgca tcatccacca caagaaaccc accggcatga   1020
tcagaatcca ccagatgaac agcgagctgt ccgtgctggc caacttcagc cagcccgaga   1080
tcgtgcccat cagcaacatc accgagaacg tgtacatcaa cctgacctgc agcagcatcc   1140
acggctaccc cgagcccaag aaaatgagcg tgctgctgcg gaccaagaac agcaccatcg   1200
agtacgacgg cgtgatgcag aaaagccagg acaacgtgac cgagctgtac gacgtgagca   1260
tcagcctgag cgtgagcttc cccgacgtga ccagcaacat gaccatcttt tgcatcctgg   1320
aaaccgacaa gacccggctg ctgtccagcc ccttcagcat cgagctggaa gatccccagc   1380
cccctcccga ccacatcccc tggatcaccg ccgtgctgcc caccgtgatc atctgcgtga   1440
tggtgttctg cctgatcctg tggaagtgga agaagaagaa gcggcctagg aacagctaca   1500
agtgcggcac caacaccatg gaacgggagg aaagcgagca gaccaagaag cgggagaaga   1560
tccacatccc cgagcggagc gacgaggccc agcgggtgtt caagagcagc aagaccagca   1620
gctgcgacaa gagcgacacc tgcttctagg acccagcttt cttgtacaaa gtggtcatta   1680
taagaaagca ttgcttatca atttgttgca acgaacaggt cactatcagt caaaataaaa   1740
tcattatttg ccatccagct gatatcccct atagtgagtc gtattacatg gtcatagctg   1800
tttcctggca gctctggccc gtgtctcaaa atctctgatg ttacattgca caagataaaa   1860
taatatcatc atgaacaata aaactgtctg cttacataaa cagtaataca aggggtgtta   1920
tgagccatat tcaacgggaa acgtcgaggc cgcgattaaa ttccaacatg gatgctgatt   1980
tatatgggta taaatgggct cgcgataatg tcgggcaatc aggtgcgaca atctatcgct   2040
tgtatgggaa gcccgatgcg ccagagttgt ttctgaaaca tggcaaaggt agcgttgcca   2100
atgatgttac agatgagatg gtcagactaa actggctgac ggaatttatg cctcttccga   2160
ccatcaagca tttttatccg tactcctgatg atgcatggtt actcaccact gcgatccccg   2220
gaaaaacagc attccaggta ttagaagaat atcctgattc aggtgaaaat attgttgatg   2280
cgctggcagt gttcctgcgc cggttgcatt cgattcctgt ttgtaattgt ccttttaaca   2340
gcgatcgcgt atttcgtctc gctcaggcgc aatcacgaat gaataacggt ttggttgatg   2400
cgagtgattt tgatgacgag cgtaatggct ggcctgttga acaagtctgg aaagaaatgc   2460
ataaactttt gccattctca ccggattcag tcgtcactca tggtgatttc tcacttgata   2520
accttatttt tgacgagggg aaattaatag gttgtattga tgttggacga gtcggaatcg   2580
cagaccgata ccaggatctt gccatcctat ggaactgcct cggtgagttt tctccttcat   2640
tacagaaacg gctttttcaa aaatatggta ttgataatcc tgatatgaat aaattgcagt   2700
ttcatttgat gctcgatgag ttttttctaat cagaattggt taattggttg taacactggc   2760
agagcattac gctgacttga cgggacggcg caagctcatg accaaaatcc cttaacgtga   2820
gttacgcgtc gttccactga cgcgtcagacc ccgtagaaaa gatcaaagga tcttcttgag   2880
atcctttttt tctgcgcgta atctgctgct tgcaaacaaa aaaaccaccg ctaccagcgg   2940
tggtttgttt gccggatcaa gagctaccaa ctctttttcc gaaggtaact ggcttcagca   3000
gagcgcagat accaaatact gttcttctag tgtagccgta gttaggccac cacttcaaga   3060
actctgtagc accgcctaca tacctcgctc tgctaatcct gttaccagtg gctgctgcca   3120
gtggcgataa gtcgtgtctt accgggttgg actcaagacg atagttaccg gataaggcgc   3180
agcggtcggg ctgaacgggg ggttcgtgca cacagcccag cttggagcga acgacctaca   3240
ccgaactgag atacctacag cgtgagctat gagaaagcgc cacgcttccc gaagggagaa   3300
```

-continued

```
aggcggacag gtatccggta agcggcaggg tcggaacagg agagcgcacg agggagcttc    3360 caggggaaa cgcctggtat ctttatagtc ctgtcgggtt tcgccacctc tgacttgagc    3420 gtcgatttt gtgatgctcg tcagggggc ggagcctatg gaaaaacgcc agcaacgcgg     3480 ccttttacg gttcctggcc ttttgctggc cttttgctca catgtt                   3526
```

```
<210> SEQ ID NO 22
<211> LENGTH: 3319
<212> TYPE: DNA
<213> ORGANISM: Artificial Sequence
<220> FEATURE:
<223> OTHER INFORMATION: pDONR221 4-1BBL vector

<400> SEQUENCE: 22
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca ataatgatt ttattttgac tgatagtgac      600
ctgttcgttg caacacattg atgagcaatg cttttttata atgcacaagt ttgtacaaaa     660
aagcaggctt cgccaccatg gaatacgcct ctgatgccag cctggacccc gaagctcctt     720
ggcctcctgc ccctagagcc agagcctgta gagtgctgcc ttgggctctg gtggctggcc     780
ttctccttct gctgctgctg gccgctgcct gcgctgtgtt tctggcttgt ccttgggccg     840
tgtcaggcgc cagagcttct cctggatctg ccgccagccc cagactgaga gagggacctg     900
agctgagccc cgatgatcct gccggactgc tggatctgag acagggcatg ttcgcccagc     960
tggtggccca gaacgtgctg ctgatcgatg ccccctgag ctggtacagc gatcctggac      1020
tggctggcgt gtcactgaca ggcggcctga gctacaaaga ggacaccaaa gaactggtgg    1080
tggccaaggc cggcgtgtac tacgtgttct ttcagctgga actgcggaga gtggtggccg    1140
gcgaaggatc cggctctgtg tctctggcac tgcatctgca gccctgaga tctgctgcag      1200 gcgctgctgc actggccctg acagtggacc tgcctccagc ctctagcgag gccagaaact    1260
ccgcattcgg gtttcaaggc agactgctgc acctgtctgc cggccagaga ctgggagtgc    1320
atctgcacac agaggccaga gccagacacg cctggcagct gacacagggc gctacagtgc    1380
tgggcctgtt cagagtgacc cccgaaattc agccggcct gcccagccct agaagcgagt      1440
aggacccagc tttcttgtac aaagtggtca ttataagaaa gcattgctta tcaatttgtt    1500
gcaacgaaca ggtcactatc agtcaaaata aaatcattat ttgccatcca gctgatatcc    1560
cctatagtga tcgtattac atggtcatag ctgtttcctg gcagctctgg cccgtgtctc      1620
aaaatctctg atgttacatt gcacaagata aaataatatc atcatgaaca ataaaactgt    1680
ctgcttacat aaacagtaat acaaggggtg ttatgagcca tattcaacgg gaaacgtcga    1740
ggccgcgatt aaattccaac atggatgctg atttatatgg gtataaatgg ctcgcgata     1800 atgtcgggca atcaggtgcg acaatctatc gcttgtatgg gaagcccgat gcgccagagt    1860
```

-continued

```
tgtttctgaa acatggcaaa ggtagcgttg ccaatgatgt tacagatgag atggtcagac      1920
taaactggct gacggaattt atgcctcttc cgaccatcaa gcattttatc cgtactcctg      1980
atgatgcatg gttactcacc actgcgatcc ccggaaaaac agcattccag gtattagaag      2040
aatatcctga ttcaggtgaa aatattgttg atgcgctggc agtgttcctg cgccggttgc      2100
attcgattcc tgtttgtaat tgtcctttta acagcgatcg cgtatttcgt ctcgctcagg      2160
cgcaatcacg aatgaataac ggtttggttg atgcgagtga ttttgatgac gagcgtaatg      2220
gctggcctgt tgaacaagtc tggaaagaaa tgcataaact tttgccattc tcaccggatt      2280
cagtcgtcac tcatggtgat ttctcacttg ataaccttat ttttgacgag gggaaattaa      2340
taggttgtat tgatgttgga cgagtcggaa tcgcagaccg ataccaggat cttgccatcc      2400
tatggaactg cctcggtgag ttttctcctt cattacagaa acggcttttt caaaaatatg      2460
gtattgataa tcctgatatg aataaattgc agtttcattt gatgctcgat gagtttttct      2520
aatcagaatt ggttaattgg ttgtaacact ggcagagcat tacgctgact tgacgggacg      2580
gcgcaagctc atgaccaaaa tcccttaacg tgagttacgc gtcgttccac tgagcgtcag      2640
accccgtaga aaagatcaaa ggatcttctt gagatccttt ttttctgcgc gtaatctgct      2700
gcttgcaaac aaaaaaacca ccgctaccag cggtggtttg tttgccggat caagagctac      2760
caactctttt tccgaaggta actggcttca gcagagcgca gataccaaat actgttcttc      2820
tagtgtagcc gtagttaggc caccacttca agaactctgt agcaccgcct acatacctcg      2880
ctctgctaat cctgttacca gtggctgctg ccagtggcga taagtcgtgt cttaccgggt      2940
tggactcaag acgatagtta ccggataagg cgcagcggtc gggctgaacg gggggttcgt      3000
gcacacagcc cagcttggag cgaacgacct acaccgaact gagatacCta cagcgtgagc      3060
tatgagaaag cgccacgctt cccgaaggga gaaaggcgga caggtatccg gtaagcggca      3120
gggtcggaac aggagagcgc acgagggagc ttccaggggg aaacgcctgg tatctttata      3180
gtcctgtcgg gtttcgccac ctctgacttg agcgtcgatt tttgtgatgc tcgtcagggg      3240
ggcggagcct atggaaaaac gccagcaacg cggccttttt acggttcctg gccttttgct      3300
ggccttttgc tcacatgtt                                                   3319
```

<210> SEQ ID NO 23
<211> LENGTH: 8449
<212> TYPE: DNA
<213> ORGANISM: Artificial Sequence
<220> FEATURE:
<223> OTHER INFORMATION: pLV430G vector

<400> SEQUENCE: 23

```
cgataaccct aattcgatag catatgcttc ccgttgggta acatatgcta ttgaattagg       60
gttagtctgg atagtatata ctactacccg ggaagcatat gctacccgtt tagggttcac      120
cggtgatgcc ggccacgatg cgtccggcgt agaggatcta atgtgagtta gctcactcat      180
taggcacccc aggctttaca ctttatgctt ccggctcgta tgttgtgtgg aattgtgagc      240
ggataacaat ttcacacagg aaacagctat gaccatgatt acgccaagcg cgcaattaac      300
cctcactaaa gggaacaaaa gctggagctg caagcttaat gtagtcttat gcaatactct      360
tgtagtcttg caacatggta acgatgagtt agcaacatgc cttacaagga gagaaaaagc      420
accgtgcatg ccgattggtg gaagtaaggt ggtacgatcg tgccttatta ggaaggcaac      480
agacgggtct gacatggatt ggacgaacca ctgaattgcc gcattgcaga gatattgtat      540
```

```
ttaagtgcct agctcgatac ataaacgggt ctctctggtt agaccagatc tgagcctggg     600
agctctctgg ctaactaggg aacccactgc ttaagcctca ataaagcttg ccttgagtgc     660
ttcaagtagt gtgtgcccgt ctgttgtgtg actctggtaa ctagagatcc ctcagaccct     720
tttagtcagt gtggaaaatc tctagcagtg gcgcccgaac agggacttga aagcgaaagg     780
gaaaccagag gagctctctc gacgcaggac tcggcttgct gaagcgcgca cggcaagagg     840
cgaggggcgg cgactggtga gtacgccaaa aattttgact agcggaggct agaaggagag     900
agatgggtgc gagagcgtca gtattaagcg ggggagaatt agatcgcgat gggaaaaaat     960
tcggttaagg ccagggggaa agaaaaaata taaattaaaa catatagtat gggcaagcag    1020
ggagctagaa cgattcgcag ttaatcctgg cctgttagaa acatcagaag gctgtagaca    1080
aatactggga cagctacaac catcccttca gacaggatca gaagaactta gatcattata    1140
taatacagta gcaaccctct attgtgtgca tcaaaggata gagataaaag acaccaagga    1200
agctttagac aagatagagg aagagcaaaa caaaagtaag accaccgcac agcaagcggc    1260
cgctgatctt cagacctgga ggaggagata tgagggacaa ttggagaagt gaattatata    1320
aatataaagt agtaaaaatt gaaccattag gagtagcacc caccaaggca aagagaagag    1380
tggtgcagag agaaaaaaga gcagtgggaa taggagcttt gttccttggg ttcttgggag    1440
cagcaggaag cactatgggc gcagcgtcaa tgacgctgac ggtacaggcc agacaattat    1500
tgtctggtat agtgcagcag cagaacaatt tgctgagggc tattgaggcg caacagcatc    1560
tgttgcaact cacagtctgg ggcatcaagc agctccaggc aagaatcctg gctgtggaaa    1620
gatacctaaa ggatcaacag ctcctgggga tttggggttg ctctggaaaa ctcatttgca    1680
ccactgctgt gccttggaat gctagttgga gtaataaatc tctggaacag atttggaatc    1740
acacgacctg gatggagtgg gacagagaaa ttaacaatta cacaagctta atacactcct    1800
taattgaaga atcgcaaaac cagcaagaaa agaatgaaca agaattattg gaattagata    1860
aatgggcaag tttgtggaat tggtttaaca taacaaattg gctgtggtat ataaaattat    1920
tcataatgat agtaggaggc ttggtaggtt taagaatagt ttttgctgta ctttctatag    1980
tgaatagagt taggcaggga tattcaccat tatcgtttca gacccacctc ccaaccccga    2040
ggggacccga caggcccgaa ggaatagaag aagaaggtgg agagagagac agagacagat    2100
ccattcgatt agtgaacgga tctcgacggt atcggtttta aaagaaaagg ggggattggg    2160
gggtacagtg caggggaaag aatagtagac ataatagcaa cagacataca aactaaagaa    2220
ttacaaaaac aaattacaaa aattcaaaat tttatcgatt ttatttagtc tccagaaaaa    2280 gggggggaatg aaagaccocca cctgtaggtt tggcaagcta gcttaagtaa cgccattttg    2340
caaggcatgg aaaatacata actgagaata gagaagttca gatcaaggtt aggaacagag    2400
agacagcaga atatgggcca aacaggatat ctgtggtaag cagttcctgc cccggctcag    2460
ggccaagaac agatggtccc cagatgcggt cccgccctca gcagtttcta gagaaccatc    2520
agatgtttcc agggtgcccc aaggacctga aatgaccctg tgccttattt gaactaacca    2580
atcagttcgc ttctcgcttc tgttccgcgc cttctgctcc ccgagctcaa taaaagagcc    2640
cacaacccct cactcggcgc gccagtcctc cgatagactg cgtcgcccgg gtaccgatat    2700
cacaagtttg tacaaaaaag ctgaacgaga aacgtaaaat gatataaata tcaatatatt    2760
aaattagatt ttgcataaaa aacagactac ataatactgt aaaacacaac atatccagtc    2820
actatggcgg ccgcattagg caccccaggc tttacacttt atgcttccgg ctcgtataat    2880
gtgtggattt tgagttagga tccgtcgaga ttttcaggag ctaaggaagc taaaatggag    2940
```

-continued

```
aaaaaaatca ctggatatac caccgttgat atatcccaat ggcatcgtaa agaacatttt      3000
gaggcatttc agtcagttgc tcaatgtacc tataaccaga ccgttcagct ggatattacg      3060
gcctttttaa agaccgtaaa gaaaaataag cacaagtttt atccggcctt tattcacatt      3120
cttgcccgcc tgatgaatgc tcatccggaa ttccgtatgg caatgaaaga cggtgagctg      3180
gtgatatggg atagtgttca cccttgttac accgttttcc atgagcaaac tgaaacgttt      3240
tcatcgctct ggagtgaata ccacgacgat ttccggcagt ttctacacat atattcgcaa      3300
gatgtggcgt gttacggtga aaacctggcc tatttcccta aagggtttat tgagaatatg      3360
tttttcgtct cagccaatcc ctgggtgagt ttcaccagtt ttgatttaaa cgtggccaat      3420
atggacaact tcttcgcccc cgttttcacc atgggcaaat attatacgca aggcgacaag      3480
gtgctgatgc cgctggcgat tcaggttcat catgccgttt gtgatggctt ccatgtcggc      3540
agaatgctta atgaattaca acagtactgc gatgagtggc agggcggggc gtaaacgcgt      3600
ggatccggct tactaaaagc cagataacag tatgcgtatt tgcgcgctga tttttgcggt      3660
ataagaatat atactgatat gtatacccga agtatgtcaa aaagaggtat gctatgaagc      3720
agcgtattac agtgacagtt gacacgcgaca gctatcagtt gctcaaggca tatatgatgt      3780
caatatctcc ggtctggtaa gcacaaccat gcagaatgaa gcccgtcgtc tgcgtgccga      3840
acgctggaaa gcggaaaatc aggaagggat ggctgaggtc gcccggttta ttgaaatgaa      3900
cggctctttt gctgacgaga acaggggctg gtgaaatgca gtttaaggtt tacacctata      3960
aaagagagag ccgttatcgt ctgtttgtgg atgtacagag tgatattatt gacacgcccg      4020
ggcgacggat ggtgatcccc ctggccagtg cacgtctgct gtcagataaa gtctcccgtg      4080
aactttaccc ggtggtgcat atcggggatg aaagctggcg catgatgacc accgatatgg      4140
ccagtgtgcc ggtctccgtt atcggggaag aagtggctga tctcagccac cgcgaaaatg      4200
acatcaaaaa cgccattaac ctgatgttct gggggaatata aatgtcaggc tcccttatac      4260
acagccagtc tgcaggtcga ccatagtgac tggatatgtt gtgtttttaca gtattatgta      4320 gtctgtttt tatgcaaaat ctaatttaat atattgatat ttatatcatt ttacgtttct      4380
cgttcagctt tcttgtacaa agtggtgatt cgagttaatt aagctagcct agtgccattt      4440
gttcagtggt tcgtagggct ttcccccact gtttggcttt cagttatatg gatgatgtgg      4500
tattgggggc caagtctgta cagcatcttg agtccctttt taccgctgtt accaattttc      4560
ttttgtcttt gggtatacat ttaaacccta acaaaacaaa gagatggggt tactctctaa      4620
attttatggg ttatgtcatt ggatgttatg ggtccttgcc acaagaacac atcatacaaa      4680
aaatcaaaga atgttttaga aaacttccta ttaacaggcc tattgattgg aaagtatgtc      4740
aacgaattgt gggtcttttg ggttttgctg ccccttttac acaatgtggt tatcctgcgt      4800
tgatgccttt gtatgcatgt attcaatcta agcaggcttt cactttctcg ccaacttaca      4860
aggcctttct gtgtaaacaa tacctgaacc tttaccccgt tgcccggcaa cggccaggtc      4920
tgtgccaagt gtttgctgac gcaacccca ctggctgggg cttggtcatg ggccatcagc      4980
gcatgcgtgg aacctttttcg gctcctctgc cgatccatac tgcggaactc ctagccgctt      5040
gttttgctcg cagcaggtct ggagcaaaca ttatcggggac tgataactct gttgtcctat      5100
cccgcaaata tacatcgttt ccatggctgc taggctgtgc tgccaactgg atcctgcgcg      5160
ggacgtcctt tgtttacgtc ccgtcggcgc tgaatcctgc ggacgaccct tctcggggtc      5220
gcttgggact ctctcgtccc cttctccgtc tgccgttccg accgaccacg gggcgcacct      5280
```

-continued

```
ctctttacgc ggactccccg tctgtgcctt ctcatctgcc ggaccgtgtg cacttcgctt     5340
cacctctgca cgtcgcatgg agaccaccgt gaacgcccac caaatattgc ccaaggtctt     5400
acataagagg actcttggac tctcagcaat gtcaacgacc gaccttgagg catacttcaa     5460
agactgtttg tttaaagact gggaggagtt gggggaggag attaggttaa aggtctttgt     5520
actaggaggc tgtaggcata aattggtctg cgcaccagca ccatggcgca atcactagag     5580
cggggtacct ttaagaccaa tgacttacaa ggcagctgta gatcttagcc acttttttaaa    5640 agaaaagggg ggactggaag ggctaattca ctcccaacga agacaagatc tgcttttttgc    5700 ttgtactggg tctctctggt tagaccagat ctgagcctgg gagctctctg gctaactagg     5760
gaacccactg cttaagcctc aataaagctt gccttgagtg cttcaagtag tgtgtgcccg     5820
tctgttgtgt gactctggta actagagatc cctcagaccc ttttagtcag tgtggaaaat     5880
ctctagcagt agtagttcat gtcatcttat tattcagtat ttataacttg caaagaaatg     5940
aatatcagag agtgagagga acttgtttat tgcagcttat aatggttaca aataaagcaa     6000
tagcatcaca aatttcacaa ataaagcatt ttttttcactg cattctagtt gtggtttgtc     6060
caaactcatc aatgtatctt atcatgtctg gctctagcta tcccgcccct aactccgccc     6120
atcccgcccc taactccgcc cagttccgcc cattctccgc cccatggctg actattttt      6180 tttatttatg cagaggccga ggccggatcc cttgagtggc tttcatcctg gagcagactt     6240
tgcagtctgt ggactgcaac acaacattgc ctttatgtgt aactcttggc tgaagctctt     6300
acaccaatgc tggggggacat gtacctccca ggggcccagg aagactacgg gaggctacac    6360
caacgtcaat cagagggggcc tgtgtagcta ccgataagcg gaccctcaag agggcattag     6420
caatagtgtt tataaggccc ccttgttaat tcttgaagac gaaagggcct cgtgatacgc     6480 ctattttttat aggttaatgt catgataata atggtttctt agacgtcagg tggcactttt    6540
cggggaaatg tgcgcggaac ccctatttgt ttattttttct aaatacattc aaatatgtat    6600
ccgctcatga caataaacc ctgataaatg cttcaataat attgaaaaag gaagagtatg      6660
agtattcaac atttccgtgt cgcccttatt cccttttttg cggcatttttg ccttcctgtt    6720 tttgctcacc cagaaacgct ggtgaaagta aaagatgctg aagatcagtt gggtgcacga     6780
gtgggttaca tcgaactgga tctcaacagc ggtaagatcc ttgagagttt cgccccgaa      6840 gaacgttttc caatgatgag cacttttaaa gttctgctat gtggcgcggt attatcccgt      6900
gttgacgccg ggcaagagca actcggtcgc cgcatacact attctcagaa tgacttggtt     6960
gagtactcac cagtcacaga aaagcatctt acggatggca tgacagtaag agaattatgc     7020
agtgctgcca taaccatgag tgataacact gcggccaact tacttctgac aacgatcgga     7080
ggaccgaagg agctaaccgc ttttttgcac aacatggggg atcatgtaac tcgccttgat     7140
cgttgggaac cggagctgaa tgaagccata ccaaacgacg agcgtgacac cacgatgcct     7200
gcagcaatgg caacaacgtt gcgcaaacta ttaactggcg aactacttac tctagcttcc     7260
cggcaacaat taatagactg gatggaggcg gataaagttg caggaccact tctgcgctcg     7320
gcccttccgg ctggctggtt tattgctgat aaatctggag ccggtgagcg tgggtctcgc     7380
ggtatcattg cagcactggg gccagatggt aagccctccc gtatcgtagt tatctacacg     7440
acggggagtc aggcaactat ggatgaacga aatagacaga tcgctgagat aggtgcctca     7500
ctgattaagc attggtaact gtcagaccaa gtttactcat atatacttta gattgattta     7560
aaacttcatt tttaatttaa aaggatctag gtgaagatcc tttttgataa tctcatgacc     7620
aaaatccctt aacgtgagtt ttcgttccac tgagcgtcag accccgtaga aaagatcaaa     7680
```

-continued

```
ggatcttctt gagatccttt ttttctgcgc gtaatctgct gcttgcaaac aaaaaaacca    7740
ccgctaccag cggtggtttg tttgccggat caagagctac caactctttt tccgaaggta    7800
actggcttca gcagagcgca gataccaaat actgtccttc tagtgtagcc gtagttaggc    7860
caccacttca agaactctgt agcaccgcct acatacctcg ctctgctaat cctgttacca    7920
gtggctgctg ccagtggcga taagtcgtgt cttaccgggt tggactcaag acgatagtta    7980
ccggataagg cgcagcggtc gggctgaacg gggggttcgt gcacacagcc cagcttggag    8040
cgaacgacct acaccgaact gagataccta cagcgtgagc attgagaaag cgccacgctt    8100
cccgaaggga gaaaggcgga caggtatccg gtaagcggca gggtcggaac aggagagcgc    8160
acgagggagc ttccaggggg aaacgcctgg tatctttata gtcctgtcgg gtttcgccac    8220
ctctgacttg agcgtcgatt tttgtgatgc tcgtcagggg ggcggagcct atggaaaaac    8280
gccagcaacg cggccttttt acggttcctg gccttttgct ggcctttttg aagctgtccc    8340
tgatggtcgt catctacctg cctggacagc atggcctgca acgcgggcat cccgatgccg    8400
ccggaagcga gaagaatcat aatggggaag gccatccagc ctcgcgtcg                8449
```

<210> SEQ ID NO 24
<211> LENGTH: 4761
<212> TYPE: DNA
<213> ORGANISM: Artificial Sequence
<220> FEATURE:
<223> OTHER INFORMATION: pDONR221 vector

<400> SEQUENCE: 24

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa      540 aacgacggcc agtcttaagc tcgggcccca ataatgatt ttattttgac tgatagtgac      600
ctgttcgttg caacacattg atgagcaatg ctttttttata atgccaactt tgtacaaaaa     660
agctgaacga gaaacgtaaa atgatataaa tatcaatata ttaaattaga ttttgcataa     720
aaaacagact acataatact gtaaaacaca acatatccag tcactatgaa tcaactactt     780
agatggtatt agtgacctgt agtcgaccga cagccttcca aatgttcttc gggtgatgct     840
gccaacttag tcgaccgaca gccttccaaa tgttcttctc aaacggaatc gtcgtatcca     900
gcctactcgc tattgtcctc aatgccgtat aaatcataa aagaaataa gaaaagagg       960 tgcgagcctc ttttttgtgt gacaaaataa aacatctac ctattcatat acgctagtgt     1020
catagtcctg aaaatcatct gcatcaagaa caatttcaca actcttatac ttttctctta    1080
caagtcgttc ggcttcatct ggattttcag cctctatact tactaaacgt gataaagttt    1140
ctgtaatttc tactgtatcg acctgcagac tggctgtgta taagggagcc tgacatttat    1200
attccccaga acatcaggtt aatggcgttt ttgatgtcat tttcgcggtg gctgagatca    1260
```

-continued

```
gccacttctt  ccccgataac  ggagaccggc  acactggcca  tatcggtggt  catcatgcgc   1320
cagctttcat  ccccgatatg  caccaccggg  taaagttcac  gggagacttt  atctgacagc   1380
agacgtgcac  tggccagggg  gatcaccatc  cgtcgcccgg  gcgtgtcaat  aatatcactc   1440
tgtacatcca  caaacagacg  ataacggctc  tctcttttat  aggtgtaaac  cttaaactgc   1500
atttcaccag  cccctgttct  cgtcagcaaa  agagccgttc  atttcaataa  accgggcgac   1560
ctcagccatc  ccttcctgat  tttccgcttt  ccagcgttcg  gcacgcagac  gacgggcttc   1620
attctgcatg  gttgtgctta  ccagaccgga  gatattgaca  tcatatatgc  cttgagcaac   1680
tgatagctgt  cgctgtcaac  tgtcactgta  atacgctgct  tcatagcata  cctcttttg    1740 acatacttcg  ggtatacata  tcagtatata  ttcttatacc  gcaaaaatca  gcgcgcaaat   1800
acgcatactg  ttatctggct  tttagtaagc  cggatccacg  cggcgtttac  gccccgccct   1860
gccactcatc  gcagtactgt  tgtaattcat  taagcattct  gccgacatgg  aagccatcac   1920
agacggcatg  atgaacctga  atcgccagcg  gcatcagcac  cttgtcgcct  tgcgtataat   1980
atttgcccat  ggtgaaaacg  ggggcgaaga  agttgtccat  attggccacg  tttaaatcaa   2040
aactggtgaa  actcacccag  ggattggctg  agacgaaaaa  catattctca  ataaaccctt   2100
tagggaaata  ggccaggttt  tcaccgtaac  acgccacatc  ttgcgaatat  atgtgtagaa   2160
actgccggaa  atcgtcgtgg  tattcactcc  agagcgatga  aaacgtttca  gtttgctcat   2220
ggaaaacggt  gtaacaaggg  tgaacactat  cccatatcac  cagctcaccg  tctttcattg   2280
ccatacggaa  ttccggatga  gcattcatca  ggcgggcaag  aatgtgaata  aaggccggat   2340
aaaacttgtg  cttattttc   tttacggtct  ttaaaaaggc  cgtaatatcc  agctgaacgg   2400
tctggttata  ggtacattga  gcaactgact  gaaatgcctc  aaaatgttct  ttacgatgcc   2460
attgggatat  atcaacggtg  gtatatccag  tgattttttt  ctccatttta  gcttccttag   2520
ctcctgaaaa  tctcgataac  tcaaaaaata  cgcccggtag  tgatcttatt  tcattatggt   2580
gaaagttgga  acctcttacg  tgccgatcaa  cgtctcattt  tcgccaaaag  ttggcccagg   2640
gcttcccggt  atcaacaggg  acaccaggat  ttatttattc  tgcgaagtga  tcttccgtca   2700
caggtattta  ttcggcgcaa  agtgcgtcgg  gtgatgctgc  caacttagtc  gactacaggt   2760
cactaatacc  atctaagtag  ttgattcata  gtgactggat  atgttgtgtt  ttacagtatt   2820
atgtagtctg  ttttttatgc  aaaatctaat  ttaatatatt  gatatttata  tcattttacg   2880
tttctcgttc  agctttcttg  tacaaagttg  gcattataag  aaagcattgc  ttatcaattt   2940
gttgcaacga  acaggtcact  atcagtcaaa  ataaaatcat  tatttgccat  ccagctgata   3000
tcccctatag  tgagtcgtat  tacatggtca  tagctgtttc  ctggcagctc  tggcccgtgt   3060
ctcaaaatct  ctgatgttac  attgcacaag  ataaaataat  atcatcatga  acaataaaac   3120
tgtctgctta  cataaacagt  aatacaaggg  gtgttatgag  ccatattcaa  cgggaaacgt   3180
cgaggccgcg  attaaattcc  aacatggatg  ctgatttata  tgggtataaa  tgggctcgcg   3240
ataatgtcgg  gcaatcaggt  gcgacaatct  atcgcttgta  tgggaagccc  gatgcgccag   3300
agttgtttct  gaaacatggc  aaaggtagcg  ttgccaatga  tgttacagat  gagatggtca   3360
gactaaactg  gctgacggaa  tttatgcctc  ttccgaccat  caagcatttt  atccgtactc   3420
ctgatgatgc  atggttactc  accactgcga  tccccggaaa  aacagcattc  caggtattag   3480
aagaatatcc  tgattcaggt  gaaaatattg  ttgatgcgct  ggcagtgttc  ctgcgccggt   3540
tgcattcgat  tcctgtttgt  aattgtcctt  ttaacagcga  tcgcgtattt  cgtctcgctc   3600
aggcgcaatc  acgaatgaat  aacggtttgg  ttgatgcgag  tgattttgat  gacgagcgta   3660
```
atggctggcc tgttgaacaa gtctggaaag aaatgcataa actttttgcca ttctcaccgg    3720 attcagtcgt cactcatggt gatttctcac ttgataacct tattttttgac gagggggaaat    3780 taataggttg tattgatgtt ggacgagtcg gaatcgcaga ccgataccag gatcttgcca    3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
acggcgcaag ctcatgacca aaatccctta acgtgagtta cgcgtcgttc cactgagcgt    4080 cagacccccgt agaaaagatc aaaggatctt cttgagatcc tttttttctg cgcgtaatct    4140
gctgcttgca aacaaaaaaa ccaccgctac cagcggtggt ttgtttgccg gatcaagagc    4200
taccaactct ttttccgaag gtaactggct tcagcagagc gcagatacca atactgttc     4260 ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg attttttgtga tgctcgtcag    4680 gggggcggag cctatggaaa aacgccagca acgcggcctt tttacggttc ctggccttt    4740 gctggccttt tgctcacatg t    4761

<210> SEQ ID NO 25
<211> LENGTH: 10703
<212> TYPE: DNA
<213> ORGANISM: Artificial Sequence
<220> FEATURE:
<223> OTHER INFORMATION: psPAX2 plasmid

<400> SEQUENCE: 25
aaaaggatct tcacctagat ccttttaaat taaaaatgaa gttttaaatc aatctaaagt     60
atatatgagt aaacttggtc tgacagttac caatgcttaa tcagtgaggc acctatctca    120
gcgatctgtc tatttcgttc atccatagtt gcctgactcc ccgtcgtgta gataactacg    180
atacgggagg gcttaccatc tggccccagt gctgcaatga taccgcgaga cccacgctca    240
ccggctccag atttatcagc aataaaccag ccagccggaa gggccgagcg cagaagtggt    300
cctgcaactt tatccgcctc catccagtct attaattgtt gccgggaagc tagagtaagt    360
agttcgccag ttaatagttt cgcaacgtt gttgccattg ctacaggcat cgtggtgtca    420
cgctcgtcgt ttggtatggc ttcattcagc tccggttccc aacgatcaag gcgagttaca    480
tgatccccca tgttgtgcaa aaaagcggtt agctccttcg gtcctccgat cgttgtcaga    540
agtaagttgg ccgcagtgtt atcactcatg gttatggcag cactgcataa ttctcttact    600
gtcatgccat ccgtaagatg cttttctgtg actggtgagt actcaaccaa gtcattctga    660
gaatagtgta tgcggcgacc gagttgctct tgcccggcgt caatacggga taataccgcg    720
ccacatagca gaactttaaa agtgctcatc attggaaaac gttcttcggg gcgaaaactc    780
tcaaggatct taccgctgtt gagatccagt tcgatgtaac ccactcgtgc acccaactga    840
tcttcagcat cttttacttt caccagcgtt tctgggtgag caaaaacagg aaggcaaaat    900

-continued

```
gccgcaaaaa agggaataag ggcgacacgg aaatgttgaa tactcatact cttccttttt      960
caatattatt gaagcattta tcagggttat tgtctcatga gcggatacat atttgaatgt     1020
atttagaaaa ataaacaaat aggggttccg cgcacatttc cccgaaaagt gccacctggt     1080
cgacattgat tattgactag ttattaatag taatcaatta cggggtcatt agttcatagc     1140
ccatatatgg agttccgcgt tacataactt acggtaaatg gcccgcctgg ctgaccgccc     1200
aacgaccccc gcccattgac gtcaataatg acgtatgttc ccatagtaac gccaataggg     1260
actttccatt gacgtcaatg ggtggactat ttacggtaaa ctgcccactt ggcagtacat     1320
caagtgtatc atatgccaag tacgccccct attgacgtca atgacggtaa atggcccgcc     1380
tggcattatg cccagtacat gaccttatgg gactttccta cttggcagta catctacgta     1440
ttagtcatcg ctattaccat gggtcgaggt gagccccacg ttctgcttca ctctccccat     1500 ctccccccccc tccccacccc caattttgta tttatttatt ttttaattat tttgtgcagc     1560
gatgggggcg ggggggggg gggcgcgcgc caggcggggc ggggcggggc gagggcgggg     1620
gcggggcgag gcggagaggt gcggcggcag ccaatcagag cggcgcgctc cgaaagtttc     1680
cttttatggc gaggcggcgg cggcggcggc cctataaaaa gcgaagcgcg cggcgggcgg     1740
gagtcgctgc gttgccttcg ccccgtgccc cgctccgcgc cgcctcgcgc cgcccgcccc     1800
ggctctgact gaccgcgtta ctcccacagg tgagcgggcg ggacggccct tctcctccgg     1860
gctgtaatta gcgcttggtt taatgacggc tcgtttcttt tctgtggctg cgtgaaagcc     1920
ttaaagggct ccgggagggc cctttgtgcg gggggagcg gctcggggg tgcgtgcgtg     1980 tgtgtgtgcg tggggagcgc cgcgtgcggc ccgcgctgcc cggcggctgt gagcgctgcg     2040
ggcgcggcgc ggggctttgt gcgctccgcg tgtgcgcgag gggagcgcgg ccggggccgg     2100
tgccccgcgg tgcgggggg ctgcgagggg aacaaaggct gcgtgcgggg tgtgtgcgtg     2160
ggggggtgag cagggggtgt gggcgcggcg gtcgggctgt aaccccccc tgcacccccc     2220 tccccgagtt gctgagcacg gcccggcttc gggtgcgggg ctccgtgcgg ggcgtggcgc     2280
ggggctcgcc gtgccgggcg gggggtggcg gcaggtgggg gtgccgggcg gggcggggcc     2340
gcctcgggcc ggggagggct cggggaggg gcgcggcggc cccggagcgc cggcggctgt     2400
cgaggcgcgg cgagccgcag ccattgcctt ttatggtaat cgtgcgagag ggcgcaggga     2460
cttcctttgt cccaaatctg gcggagccga aatctgggag gcgccgccgc accccctcta     2520
gcgggcgcgg gcgaagcggt gcggcgccgg caggaaggaa atgggcgggg agggccttcg     2580
tgcgtcgccg cgccgccgtc cccttctcca tctccagcct cggggctgcc gcaggggac     2640 ggctgccttc gggggggacg gggcagggcg gggttcggct tctggcgtgt gaccggcggc     2700
tctagagcct ctgctaacca tgttcatgcc ttcttctttt tcctacagct cctgggcaac     2760
gtgctggtta ttgtgctgtc tcatcatttt ggcaaagaat tcgggccggc cgcgttgacg     2820
cgcacggcaa gaggcgaggg gcggcgactg tgagagatg ggtgcgagag cgtcagtatt     2880 aagcgggga gaattagatc gatgggaaaa aattcggtta aggccagggg gaaagaaaaa     2940
atataaatta aaacatatag tatgggcaag cagggagcta gaacgattcg cagttaatcc     3000
tggcctgtta gaaacatcag aaggctgtag acaaatactg ggacagctac aaccatccct     3060
tcagacagga tcagaagaac ttagatcatt atataataca gtagcaaccc tctattgtgt     3120
gcatcaaagg atagagataa aagacaccaa ggaagcttta gacaagatag aggaagagca     3180
aaacaaaagt aagaaaaaag cacagcaagc agcagctgac acaggacaca gcaatcaggt     3240
cagccaaaat tacccctatag tgcagaacat ccaggggcaa atggtacatc aggccatatc     3300
```

-continued

```
acctagaact ttaaatgcat gggtaaaagt agtagaagag aaggctttca gcccagaagt    3360
gatacccatg tttttcagcat tatcagaagg agccaccca caagatttaa acaccatgct    3420
aaacacagtg gggggacatc aagcagccat gcaaatgtta aaagagacca tcaatgagga    3480
agctgcagaa tgggatagag tgcatccagt gcatgcaggg cctattgcac caggccagat    3540
gagagaacca aggggaagtg acatagcagg aactactagt acccttcagg aacaaatagg    3600
atggatgaca cataatccac ctatcccagt aggagaaatc tataaaagat ggataatcct    3660
gggattaaat aaaatagtaa gaatgtatag ccctaccagc attctggaca taagacaagg    3720
accaaaggaa ccctttagag actatgtaga ccgattctat aaaactctaa gagccgagca    3780
agcttcacaa gaggtaaaaa attggatgac agaaaccttg ttggtccaaa atgcgaaccc    3840
agattgtaag actattttaa aagcattggg accaggagcg acactagaag aaatgatgac    3900
agcatgtcag ggagtggggg gacccggcca taaagcaaga gttttggctg aagcaatgag    3960
ccaagtaaca aatccagcta ccataatgat acagaaaggc aattttagga accaaagaaa    4020
gactgttaag tgtttcaatt gtggcaaaga aagggcacata gccaaaaatt gcagggcccc    4080
taggaaaaag ggctgttgga aatgtggaaa ggaaggacac caaatgaaag attgtactga    4140
gagacaggct aattttttag ggaagatctg gccttcccac aagggaaggc cagggaattt    4200
tcttcagagc agaccagagc caacagcccc accagaagag agcttcaggt ttggggaaga    4260
gacaacaact ccctctcaga agcaggagcc gatagacaag gaactgtatc ctttagcttc    4320
cctcagatca ctctttggca gcgacccctc gtcacaataa agatagggggg caattaaag    4380 gaagctctat tagatacagg agcagatgat acagtattag aagaaatgaa tttgccagga    4440
agatggaaac caaaaatgat aggggggaatt ggaggtttta tcaaagtagg acagtatgat    4500
cagatactca tagaaatctg cggacataaa gctataggta cagtattagt aggacctaca    4560
cctgtcaaca taattggaag aaatctgttg actcagattg gctgcacttt aaattttccc    4620
attagtccta ttgagactgt accagtaaaa ttaaagccag gaatggatgg cccaaaagtt    4680
aaacaatggc cattgacaga agaaaaaata aaagcattag tagaaatttg tacagaaatg    4740
gaaaaggaag gaaaaatttc aaaaattggg cctgaaaatc catacaatac tccagtattt    4800
gccataaaga aaaaagacag tactaaatgg agaaaattag tagatttcag agaacttaat    4860
aagagaactc aagatttctg ggaagttcaa ttaggaatac cacatcctgc agggttaaaa    4920
cagaaaaaat cagtaacagt actggatgtg ggcgatgcat attttttcagt tcccttagat    4980 aaagacttca ggaagtatac tgcatttacc atacctagta taaacaatga gacaccaggg    5040
attagatatc agtacaatgt gcttccacag ggatggaaag gatcaccagc aatattccag    5100
tgtagcatga caaaaatctt agagcctttt agaaaacaaa atccagacat agtcatctat    5160
caatacatgg atgatttgta tgtaggatct gacttagaaa tagggcagca tagaacaaaa    5220
atagaggaac tgagacaaca tctgttgagg tggggattta ccacaccaga caaaaaacat    5280
cagaaagaac ctccattcct ttggatgggt tatgaactcc atcctgataa atggacagta    5340
cagcctatag tgctgccaga aaaggacagc tggactgtca atgacataca gaaattagtg    5400
ggaaaattga attgggcaag tcagatttat gcagggatta agtaaggca attatgtaaa    5460 cttcttaggg gaaccaaagc actaacagaa gtagtaccac taacagaaga agcagagcta    5520
gaactggcag aaaacaggga gattctaaaa gaaccggtac atggagtgta ttatgaccca    5580
tcaaaagact taatagcaga aatacagaag caggggcaag gccaatggac atatcaaatt    5640
```

-continued

```
tatcaagagc catttaaaaa tctgaaaaca ggaaaatatg caagaatgaa gggtgcccac      5700
actaatgatg tgaaacaatt aacagaggca gtacaaaaaa tagccacaga aagcatagta      5760
atatggggaa agactcctaa atttaaatta cccatacaaa aggaaacatg ggaagcatgg      5820
tggacagagt attggcaagc cacctggatt cctgagtggg agtttgtcaa tacccctccc      5880
ttagtgaagt tatggtacca gttagagaaa gaacccataa taggagcaga aactttctat      5940
gtagatgggg cagccaatag ggaaactaaa ttaggaaaag caggatatgt aactgacaga      6000
ggaagacaaa aagttgtccc cctaacggac acaacaaatc agaagactga gttacaagca      6060
attcatctag ctttgcagga ttcgggatta gaagtaaaca tagtgacaga ctcacaatat      6120
gcattgggaa tcattcaagc acaaccagat aagagtgaat cagagttagt cagtcaaata      6180
atagagcagt taataaaaaa ggaaaaagtc tacctggcat gggtaccagc acacaaagga      6240
attggaggaa atgaacaagt agatgggttg gtcagtgctg gaatcaggaa agtactattt      6300
ttagatggaa tagataaggc ccaagaagaa catgagaaat atcacagtaa ttggagagca      6360
atggctagtg attttaacct accacctgta gtagcaaaag aaatagtagc cagctgtgat      6420
aaatgtcagc taaaagggga agccatgcat ggacaagtag actgtagccc aggaatatgg      6480
cagctagatt gtacacattt agaaggaaaa gttatcttgg tagcagttca tgtagccagt      6540
ggatatatag aagcagaagt aattccagca gagacagggc aagaaacagc atacttcctc      6600
ttaaaattag caggaagatg gccagtaaaa acagtacata cagacaatgg cagcaatttc      6660
accagtacta cagttaaggc cgcctgttgg tgggcgggga tcaagcagga atttggcatt      6720
ccctacaatc cccaaagtca aggagtaata gaatctatga ataaagaatt aaagaaaatt      6780
ataggacagg taagagatca ggctgaacat cttaagacag cagtacaaat ggcagtattc      6840
atccacaatt ttaaaagaaa aggggggatt ggggggtaca gtgcagggga agaatagta      6900 gacataatag caacagacat acaaactaaa gaattacaaa aacaaattac aaaaattcaa      6960
aattttcggg tttattacag ggacagcaga gatccagttt ggaaaggacc agcaaagctc      7020
ctctggaaag gtgaaggggc agtagtaata caagataata gtgacataaa agtagtgcca      7080
agaagaaaag caaagatcat cagggattat ggaaaacaga tggcaggtga tgattgtgtg      7140
gcaagtagac aggatgagga ttaacacatg gaattctgca acaactgctg tttatccatt      7200
tcagaattgg gtgtcgacat agcagaatag gcgttactcg acagaggaga gcaagaaatg      7260
gagccagtag atcctagact agagccctgg aagcatccag gaagtcagcc taaaactgct      7320
tgtaccaatt gctattgtaa aaagtgttgc tttcattgcc aagtttgttt catgacaaaa      7380
gccttaggca tctcctatgg caggaagaag cggagacagc gacgaagagc tcatcagaac      7440
agtcagactc atcaagcttc tctatcaaag cagtaagtag tacatgtaat gcaacctata      7500
atagtagcaa tagtagcatt agtagtagca ataataatag caatagttgt gtggtccata      7560
gtaatcatag aatataggaa aatggccgct gatcttcaga cctggaggag gagatatgag      7620
ggacaattgg agaagtgaat tatataaata taaagtagta aaaattgaac cattaggagt      7680
agcacccacc aaggcaaaga gaagagtggt gcagagagaa aaaagagcag tgggaatagg      7740
agctttgttc cttgggttct tgggagcagc aggaagcact atgggcgcag cctcaatgac      7800
gctgacggta caggccagac aattattgtc tggtatagtg cagcagcaga caaatttgct      7860
gagggctatt gaggcgcaac agcatctgtt gcaactcaca gtctggggca tcaagcagct      7920
ccaagcaaga atcctagctg tggaaagata cctaaaggat caacagctcc tagggatttg      7980
gggttgctct ggaaaactca tttgcaccac tgctgtgcct tggaatgcta gttggagtaa      8040
```

```
taaatctctg gaacagatct ggaatcacac gacctggatg gagtgggaca gagaaattaa    8100
caattacaca agcttaatac actccttaat tgaagaatcg caaaaccagc aagaaaagaa    8160
tgaacaagaa ttattggaat tagataaatg ggcaagtttg tggaattggt ttaacataac    8220
aaattggctg tggtatataa aattattcat aatgatagta ggaggcttgg taggtttaag    8280
aatagttttt gctgtacttt ctatagtgaa tagagttagg cagggatatt caccattatc    8340
gtttcagacc cacctcccaa tcccgagggg acccgacagg cccgaaggaa tagaagaaga    8400
aggtggagag agagacagag acagatccat tcgattagtg aacggatcct tggcacttat    8460
ctgggacgat ctgcggagcc tgtgcctctt cagctaccac cgcttgagag acttactctt    8520
gattgtaacg aggattgtgg aacttctggg acgcaggggg tgggaagccc tcaaatattg    8580
gtggaatctc ctacaatatt ggagtcagga gctaaagaat agtgctgtta gcttgctcaa    8640
tgccacagcc atagcagtag ctgagggggac agatagggtt atagaagtag tacaaggagc    8700
ttgtagagct attcgccaca tacctagaag aataagacag ggcttggaaa ggattttgct    8760
ataagctcga aacaaccggt acctctagaa ctatagctag cagatctttt tccctctgcc    8820
aaaaattatg gggacatcat gaagcccctt gagcatctga cttctggcta ataaaggaaa    8880
tttattttca ttgcaatagt gtgttggaat ttttttgtgtc tctcactcgg aaggacatat    8940
gggagggcaa atcatttaaa acatcagaat gagtatttgg tttagagttt ggcaacatat    9000
gccatatgct ggctgccatg aacaaaggtg gctataaaga ggtcatcagt atatgaaaca    9060
gccccctgct gtccattcct tattccatag aaaagccttg acttgaggtt agatttttt     9120 tatattttgt tttgtgttat ttttttcttt aacatcccta aaattttcct tacatgtttt    9180
actagccaga tttttcctcc tctcctgact actcccagtc atagctgtcc ctcttctctt    9240
atgaagatcc ctcgacctgc agcccaagct tggcgtaatc atggtcatag ctgtttcctg    9300
tgtgaaattg ttatccgctc acaattccac acaacatacg agccggaagc ataaagtgta    9360
aagcctgggg tgcctaatga gtgagctaac tcacattaat tgcgttgcgc tcactgcccg    9420
ctttccagtc gggaaacctg tcgtgccagc ggatccgcat ctcaattagt cagcaaccat    9480
agtcccgccc ctaactccgc ccatcccgcc cctaactccg cccagttccg cccattctcc    9540
gccccatggc tgactaattt ttttttattta tgcagaggcc gaggccgcct cggcctctga    9600
gctattccag aagtagtgag gaggcttttt tggaggccta ggcttttgca aaaagctaac    9660
ttgtttattg cagcttataa tggttacaaa taaagcaata gcatcacaaa tttcacaaat    9720
aaagcatttt tttcactgca ttctagttgt ggtttgtcca aactcatcaa tgtatcttat    9780
catgtctgga tccgctgcat taatgaatcg gccaacgcgc ggggagaggc ggtttgcgta    9840
ttgggcgctc ttccgcttcc tcgctcactg actcgctgcg ctcggtcgtt cggctgcggc    9900
gagcggtatc agctcactca aaggcggtaa tacggttatc cacagaatca ggggataacg    9960
caggaaagaa catgtgagca aaaggccagc aaaaggccag gaaccgtaaa aaggccgcgt   10020
tgctggcgtt tttccatagg ctccgccccc ctgacgagca tcacaaaaat cgacgctcaa   10080
gtcagaggtg cgaaacccg acaggactat aaagatacca ggcgtttccc cctggaagct    10140
ccctcgtgcg ctctcctgtt ccgaccctgc cgcttaccgg atacctgtcc gcctttctcc    10200
cttcgggaag cgtggcgctt tctcaatgct cacgctgtag gtatctcagt tcggtgtagg    10260
tcgttcgctc caagctgggc tgtgtgcacg aaccccccgt tcagcccgac cgctgcgcct    10320
tatccggtaa ctatcgtctt gagtccaacc cggtaagaca cgacttatcg ccactggcag    10380
```

-continued

```
cagccactgg taacaggatt agcagagcga ggtatgtagg cggtgctaca gagttcttga    10440
agtggtggcc taactacggc tacactagaa ggacagtatt tggtatctgc gctctgctga    10500
agccagttac cttcggaaaa agagttggta gctcttgatc cggcaaacaa accaccgctg    10560
gtagcggtgg ttttttttgtt tgcaagcagc agattacgcg cagaaaaaaa ggatctcaag    10620
aagatccttt gatcttttct acggggtctg acgctcagtg gaacgaaaac tcacgttaag    10680
ggattttggt catgagatta tca                                             10703

<210> SEQ ID NO 26
<211> LENGTH: 7298
<212> TYPE: DNA
<213> ORGANISM: Artificial Sequence
<220> FEATURE:
<223> OTHER INFORMATION: pCIGO-VSV.G plasmid

<400> SEQUENCE: 26
gtcgacggat cgggagatca attccggcac ctgtcctacg agttgcatga taaagaagac       60
agtcataagt gcggcgacga tagtcatgcc ccgcgcccac cggaaggagc tgactgggtt      120
gaaggctctc aagggcatcg gtcgatgcag gaaaaggaca agcagcgaaa attcacgccc      180
ccttgggagg tggcggcata tgcaaaggat agcactccca ctctactact gggtatcata      240
tgctgactgt atatgcatga ggatagcata tgctacccgg atacagatta ggatagcata      300
tactacccag atatagatta ggatagcata tgctacccag atatagatta ggatagccta      360
tgctacccag atataaatta ggatagcata tactacccag atatagatta ggatagcata      420
tgctacccag atatagatta ggatagccta tgctacccag atatagatta ggatagcata      480
tgctacccag atatagatta ggatagcata tgctatccag atatttgggt agtatatgct      540
acccagatat aaattaggat agcatatact accctaatct ctattaggat agcatatgct      600
acccggatac agattaggat agcatatact acccagatat agattaggat agcatatgct      660
acccagatat agattaggat agcctatgct acccagatat aaattaggat agcatatact      720
acccagatat agattaggat agcatatgct acccagatat agattaggat agcctatgct      780
acccagatat agattaggat agcatatgct atccagatat ttgggtagta tatgctaccc      840
atggcaacat tagcccaccg tgctctcagc gacctcgtga atatgaggac caacaaccct      900
gtgcttggcg ctcaggcgca agtgtgtgta atttgtcctc cagatcgcag caatcgcgcc      960
cctatcttgg cccgcccacc tacttatgca ggtattcccc ggggtgccat tagtggtttt    1020
gtgggcaagt ggtttgaccg cagtggttag cggggttaca atcagccaag ttattacacc    1080
cttattttac agtccaaaac cgcagggcgg cgtgtggggg ctgacgcgtg cccccactcc    1140
acaatttcaa aaaaagagt ggccacttgt ctttgtttat gggccccatt ggcgtggagc    1200
cccgtttaat tttcgggggt gttagagaca accagtggag tccgctgctg tcggcgtcca    1260
ctctctttcc ccttgttaca aatagagtgt aacaacatgg ttcacctgtc ttggtccctg    1320
cctgggacac atcttaataa ccccagtatc atattgcact aggattatgt gttgcccata    1380
gccataaatt cgtgtgagat ggacatccag tctttacggc ttgtccccac cccatggatt    1440
tctattgtta aagatattca gaatgtttca ttcctacact agtatttatt gcccaagggg    1500
tttgtgaggg ttatattggt gtcatagcac aatgccacca ctgaaccccc cgtccaaatt    1560
ttattctggg ggcgtcacct gaaaccttgt tttcgagcac ctcacataca ccttactgtt    1620
cacaactcag cagttattct attagctaaa cgaaggagaa tgaagaagca ggcgaagatt    1680
caggagagtt cactgcccgc tccttgatct tcagccactg cccttgtgac taaaatggtt    1740
```

```
cactaccctc gtggaatcct gaccccatgt aaataaaacc gtgacagctc atggggtggg      1800
agatatcgct gttccttagg acccttttac taaccctaat tcgatagcat atgcttcccg      1860
ttgggtaaca tatgctattg aattaggggt agtctggata gtatatacta ctacccggga      1920
agcatatgct acccgtttag ggttaacaag ggggccttat aaacactatt gctaatgccc      1980
tcttgagggt ccgcttatcg gtagctacac aggcccctct gattgacgtt ggtgtagcct      2040
cccgtagtct tcctgggccc ctgggaggta catgtccccc agcattggtg taagagcttc      2100
agccaagagt tacacataaa ggcaatgttg tgttgcagtc cacagactgc aaagtctgct      2160
ccaggatgaa agccactcaa gggatcttca atattggcca ttagccatat tattcattgg      2220
ttatatagca taaatcaata ttggctattg gccattgcat acgttgtatc tatatcataa      2280
tatgtacatt tatattggct catgtccaat atgaccgcca tgttggcatt gattattgac      2340
tagttattaa tagtaatcaa ttacggggtc attagttcat agcccatata tggagttccg      2400
cgttacataa cttacggtaa atggcccgcc tggctgaccg cccaacgacc cccgcccatt      2460
gacgtcaata atgacgtatg ttcccatagt aacgccaata gggactttcc attgacgtca      2520
atgggtggag tatttacggt aaactgccca cttggcagta catcaagtgt atcatatgcc      2580
aagtccgccc cctattgacg tcaatgacgg taaatggccc gcctggcatt atgcccagta      2640
catgacctta cgggactttc ctacttggca gtacatctac gtattagtca tcgctattac      2700
catggtgatg cggttttggc agtacaccaa tgggcgtgga tagcggtttg actcacgggg      2760
atttccaagt ctccacccca ttgacgtcaa tgggagtttg ttttggcacc aaaatcaacg      2820
ggactttcca aaatgtcgta ataaccccgc cccgttgacg caaatgggcg gtaggcgtgt      2880
acggtgggag gtctatataa gcagagctcg tttagtgaac cgtcagatca ctagaagctt      2940
tattgcggta gtttatcaca gttaaattgc taacgcagtc agtgcttctg acacaacagt      3000
ctcgaactta agctgcagaa gttggtcgtg aggcactggg caggtaagta tcaaggttac      3060
aagacaggtt taaggagacc aatagaaact gggcttgtcg agacagagaa gactcttgcg      3120
tttctgatag gcacctattg gtcttactga catccacttt gcctttctct ccacaggtgt      3180
ccactcccag ttcaattaca gctcttaagg ctagagtact aatacgact cactataggc      3240 tagcggtacc gagctcggat ccactagtaa cggccgccag tgtgctggaa ttcaacagag      3300
atcgatctgt ttccttgaca ctatgaagtg ccttttgtac ttagcctttt tattcattgg      3360
ggtgaattgc aagttcacca tagttttttcc acacaaccaa aaaggaaact ggaaaaatgt      3420
tccttctaat taccattatt gcccgtcaag ctcagattta aattggcata atgacttaat      3480
aggcacagcc atacaagtca aaatgcccaa gagtcacaag gctattcaag cagacggttg      3540
gatgtgtcat gcttccaaat gggtcactac ttgtgatttc cgctggtatg gaccgaagta      3600
tataacacag tccatccgat ccttcactcc atctgtagaa caatgcaagg aaagcattga      3660
acaaacgaaa caaggaactt ggctgaatcc aggcttccct cctcaaagtt gtggatatgc      3720
aactgtgacg gatgccgaag cagtgattgt ccaggtgact cctcaccatg tgctggttga      3780
tgaatacaca ggagaatggg ttgattcaca gttcatcaac ggaaaatgca gcaattacat      3840
atgccccact gtccataact ctacaacctg gcattctgac tataaggtca aagggctatg      3900
tgattctaac ctcatttcca tggacatcac cttcttctca gaggacggag agctatcatc      3960
cctgggaaag gagggcacag ggttcagaag taactacttt gcttatgaaa ctggaggcaa      4020
ggcctgcaaa atgcaatact gcaagcattg gggagtcaga ctcccatcag gtgtctggtt      4080
```

-continued

```
cgagatggct gataaggatc tctttgctgc agccagattc cctgaatgcc cagaagggtc    4140
aagtatctct gctccatctc agacctcagt ggatgtaagt ctaattcagg acgttgagag    4200
gatcttggat tattccctct gccaagaaac ctggagcaaa atcagagcgg gtcttccaat    4260
ctctccagtg gatctcagct atcttgctcc taaaaaccca ggaaccggtc ctgctttcac    4320
cataatcaat ggtaccctaa aatactttga gaccagatac atcagagtcg atattgctgc    4380
tccaatcctc tcaagaatgg tcggaatgat cagtggaact accacagaaa gggaactgtg    4440
ggatgactgg gcaccatatg aagacgtgga aattggaccc aatggagttc tgaggaccag    4500
ttcaggatat aagtttcctt tatacatgat tggacatggt atgttggact ccgatcttca    4560
tcttagctca aaggctcagg tgttcgaaca tcctcacatt caagacgctg cttcgcaact    4620
tcctgatgat gagagtttat ttttttggtga tactgggcta tccaaaaatc caatcgagct    4680
tgtagaaggt tggttcagta gttggaaaag ctctattgcc tctttttttct ttatcatagg    4740 gttaatcatt ggactattct tggttctccg agttggtatc catctttgca ttaaattaaa    4800
gcacaccaag aaaagacaga tttatacaga catagagatg aaccgacttg gaaagtaact    4860
caaatcctgc acaacagatt cttcatgttt ggaccaaatc aacttgtgat accatgctca    4920
aagaggcctc aattatattt gagtttttaa tttttatgga attctgcaga tatccatcac    4980
actggcggcc gctcgagcat gcatctagag ggccctattc tatagtgtca cctaaatgct    5040
agagctcgct gatcagcctc gactgtgcct tctagttgcc agccatctgt tgtttgcccc    5100
tcccccgtgc cttccttgac cctggaaggt gccactccca ctgtcctttc ctaataaaat    5160
gaggaaattg catcgcattg tctgagtagg tgtcattcta ttctgggggg tggggtgggg    5220
caggacagca aggggggagga ttgggaagac aatagcaggc atgctgggga tgcggtgggc    5280
tctatggctt ctgaggcgga aagaaccagc tgcattaatg aatcggccaa cgcgcgggga    5340
gaggcggttt gcgtattggg cgctcttccg cttcctcgct cactgactcg ctgcgctcgg    5400
tcgttcggct gcggcgagcg gtatcagctc actcaaaggc ggtaatacgg ttatccacag    5460
aatcagggga taacgcagga agaacatgt gagcaaaagg ccagcaaaag gccaggaacc    5520
gtaaaaaggc cgcgttgctg gcgtttttcc ataggctccg cccccctgac gagcatcaca    5580
aaaatcgacg ctcaagtcag aggtggcgaa acccgacagg actataaaga taccaggcgt    5640
ttccccctgg aagctccctc gtgcgctctc ctgttccgac cctgccgctt accggatacc    5700
tgtccgcctt tctcccttcg ggaagcgtgg cgctttctca atgctcacgc tgtaggtatc    5760
tcagttcggt gtaggtcgtt cgctccaagc tgggctgtgt gcacgaaccc cccgttcagc    5820
ccgaccgctg cgccttatcc ggtaactatc gtcttgagtc caacccggta agacacgact    5880
tatcgccact ggcagcagcc actggtaaca ggattagcag agcgaggtat gtaggcggtg    5940
ctacagagtt cttgaagtgg tggcctaact acggctacac tagaaggaca gtatttggta    6000
tctgcgctct gctgaagcca gttaccttcg gaaaaagagt tggtagctct tgatccggca    6060
aacaaaccac cgctggtagc ggtggttttt ttgtttgcaa gcagcagatt acgcgcagaa    6120
aaaaaggatc tcaagaagat cctttgatct tttctacggg gtctgacgct cagtggaacg    6180
aaaactcacg ttaagggatt ttggtcatga gattatcaaa aaggatcttc acctagatcc    6240
ttttaaatta aaaatgaagt tttaaatcaa tctaaagtat atatgagtaa acttggtctg    6300
acagttacca atgcttaatc agtgaggcac ctatctcagc gatctgtcta tttcgttcat    6360
ccatagttgc ctgactcccc gtcgtgtaga taactacgat acgggagggc ttaccatctg    6420
gccccagtgc tgcaatgata ccgcgagacc cacgctcacc ggctccagat ttatcagcaa    6480
```

```
taaaccagcc agccggaagg gccgagcgca gaagtggtcc tgcaacttta tccgcctcca    6540
tccagtctat taattgttgc cgggaagcta gagtaagtag ttcgccagtt aatagtttgc    6600
gcaacgttgt tgccattgct acaggcatcg tggtgtcacg ctcgtcgttt ggtatggctt    6660
cattcagctc cggttcccaa cgatcaaggc gagttacatg atcccccatg ttgtgcaaaa    6720
aagcggttag ctccttcggt cctccgatcg ttgtcagaag taagttggcc gcagtgttat    6780
cactcatggt tatggcagca ctgcataatt ctcttactgt catgccatcc gtaagatgct    6840
tttctgtgac tggtgagtac tcaaccaagt cattctgaga atagtgtatg cggcgaccga    6900
gttgctcttg cccggcgtca atacgggata ataccgcgcc acatagcaga actttaaaag    6960
tgctcatcat tggaaaacgt tcttcggggc gaaaactctc aaggatctta ccgctgttga    7020
gatccagttc gatgtaaccc actcgtgcac ccaactgatc ttcagcatct tttactttca    7080
ccagcgtttc tgggtgagca aaaacaggaa ggcaaaatgc cgcaaaaaag ggaataaggg    7140
cgacacggaa atgttgaata ctcatactct tcctttttca atattattga agcatttatc    7200
agggttattg tctcatgagc ggatacatat ttgaatgtat ttagaaaaat aaacaaatag    7260
gggttccgcg cacatttccc cgaaaagtgc cacctgac                            7298
```

```
<210> SEQ ID NO 27
<211> LENGTH: 231
<212> TYPE: PRT
<213> ORGANISM: Artificial Sequence
<220> FEATURE:
<223> OTHER INFORMATION: mFC-7C12 scFv

<400> SEQUENCE: 27

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Asn Phe Asn Asp Gln
            20                  25                  30

Tyr Met Ser Trp Ile Arg Gln Ala Pro Gly Lys Gly Leu Glu Trp Val
        35                  40                  45

Ser Phe Ile Ser Gly Ser Gly Gly Thr Thr Tyr Tyr Thr Asp Ser Val
    50                  55                  60

Lys Gly Arg Phe Thr Ile Ser Arg Asp Asn Thr Lys Asp Ser Leu Tyr
65                  70                  75                  80

Leu Gln Met Asn Ser Leu Thr Val Glu Asp Thr Ala Val Tyr Tyr Cys
                85                  90                  95

Ala Arg Gly Gly Asn Tyr Tyr Thr Ser Val Gly Arg Gly Thr Leu Val
            100                 105                 110

Thr Val Ser Ala Gly Gly Gly Gly Ser Gly Ala Pro Asp Ile Gln Met
        115                 120                 125

Thr Gln Ser Pro Gly Thr Leu Ser Leu Ser Pro Gly Glu Arg Ala Ile
    130                 135                 140

Leu Ser Cys Arg Ala Ser Gln Ser Val Ser Gly Tyr Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Ser Leu Arg Pro Glu Asp Ile Gly
        195                 200                 205

Thr Tyr Tyr Cys Lys Gln Tyr Ile Asn Ala Pro Phe Thr Phe Gly Gly
```

```
     210             215             220

Gly Thr Lys Val Glu Ile Lys
225                 230

<210> SEQ ID NO 28
<211> LENGTH: 243
<212> TYPE: PRT
<213> ORGANISM: Artificial Sequence
<220> FEATURE:
<223> OTHER INFORMATION: mFC-8B3 scFv

<400> SEQUENCE: 28

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Pro Tyr Asn Gly Asn Thr Asp Tyr Ala Gln Lys Val
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Gly Gly Gly Thr Trp Tyr Ser Asp Leu Trp Gly Arg Gly Thr
            100                 105                 110

Leu Val Thr Val Ser Ala Gly Gly Gly Ser Gly Gly Gly Gly Ser
        115                 120                 125

Gly Gly Gly Gly Ser Gly Ala Pro Glu Ile Val Leu Thr Gln Ser Pro
    130                 135                 140

Ser Thr Leu Ser Ala Ser Val Gly Asp Arg Val Ser Ile Thr Cys Arg
145                 150                 155                 160

Ala Ser Gln Ser Ile Gly Gly Ser Leu Ala Trp Tyr Gln Gln Lys Pro
                165                 170                 175

Gly Lys Ala Pro Lys Leu Leu Ile Ser Glu Ala Ser Thr Leu Glu Arg
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Val Ala Thr Tyr Tyr Cys
    210                 215                 220

Gln Lys Tyr Asn Ser Val Pro Leu Thr Phe Gly Pro Gly Thr Lys Val
225                 230                 235                 240

Glu Ile Lys

<210> SEQ ID NO 29
<211> LENGTH: 693
<212> TYPE: DNA
<213> ORGANISM: Artificial Sequence
<220> FEATURE:
<223> OTHER INFORMATION: mFC-7C12 scFv

<400> SEQUENCE: 29
caggtgcagc tggtgcagtc tggggggaggc ttggtcaagc ctggagggtc cctgagactc      60
tcctgtgcag cctctggatt caatttcaat gaccagtaca tgagttggat ccgccaggct     120
ccagggaagg ggctggagtg ggtttcattc attagtggta gtggtggtac cacatactac     180
acagactctg tgaagggccg gttcaccatc tccagggaca caccaagga ctcattgtat      240
```

-continued

```
ttgcaaatga acagcctgac agtcgaggac acggccgtgt actactgtgc gagaggaggg      300
aattattata cttcggtggg ccggggcacc ctggtcaccg tctcggccgg tggcggcgga      360
tctggcgcgc cagacatcca gatgacccag tctccaggca ccctgtcttt gtctccaggg      420
gaaagagcca tcctctcctg cagggccagt cagagtgtta gcggctacct agcctggtat      480
caacagaaac ctggccaggc tcccaggctc ctcatctatg gtgcatccag cagggccact      540
ggcatcccag acaggttcag tggcagtggg tctgggacag acttcactct caccatcagc      600
agcctgcggc ctgaagatat tggaacatat tactgtaaac agtacattaa tgccccattc      660
actttcggcg gcgggaccaa ggtggagatc aaa                                  693
```

<210> SEQ ID NO 30
<211> LENGTH: 729
<212> TYPE: DNA
<213> ORGANISM: Artificial Sequence
<220> FEATURE:
<223> OTHER INFORMATION: mFC-8B3 scFv

<400> SEQUENCE: 30

```
caggtacagc tgcagcagtc aggggctgag gtgaagaagc ctgggtcctc ggtgaaggtc       60
tcctgcaagg cttctggagg caccttcagc agctatgcta tcagctgggt gcgacaggcc      120
cctggacaag gcttgagtg gatgggatgg atcagccctt acaatggtaa cacagattat      180
gcacagaagg tccagggcag agtcaccttg accacagaca catccacgag cacagcctac      240
atggagctga ggagcctgag atccgacgac acggccgtgt attactgtgc gacaggtggc      300
gggacctggt actccgatct ctggggccgt ggcaccctgg tcaccgtctc ggccggtggc      360
ggtggcagcg gcggtggtgg gtccggtggc ggcggatctg gcgcgccaga aattgtgctg      420
actcagtctc cctccaccct gtctgcatct gtaggagaca gagtcagcat cacttgccgg      480
gccagtcaga gtattggtgg gtcgttggcc tggtatcaac aaaagccagg gaaagcccct      540
aagctcctga tctctgaggc gtctacttta gagaggggcg tcccatcaag attcagcggc      600
agtggatctg ggacagattt cactctcacc atcagcagcc tgcagcctga agatgttgca      660
acttattact gtcaaaaata taacagtgtc ccgctcactt tcggccctgg gaccaaggtg      720
gagatcaaa                                                           729
```

<210> SEQ ID NO 31
<211> LENGTH: 9862
<212> TYPE: DNA
<213> ORGANISM: Artificial Sequence
<220> FEATURE:
<223> OTHER INFORMATION: destination vector pLV4301G

<400> SEQUENCE: 31

```
cgataaccct aattcgatag catatgcttc ccgttgggta acatatgcta ttgaattagg       60
gttagtctgg atagtatata ctactacccg gaagcatat gctacccgtt tagggttcac      120
cggtgatgcc ggccacgatg cgtccggcgt agaggatcta atgtgagtta gctcactcat      180
taggcacccc aggctttaca ctttatgctt ccggctcgta tgttgtgtgg aattgtgagc      240
ggataacaat ttcacacagg aaacagctat gaccatgatt acgccaagcg cgcaattaac      300
cctcactaaa gggaacaaaa gctggagctg caagcttaat gtagtcttat gcaatactct      360
tgtagtcttg caacatggta acgatgagtt agcaacatgc cttacaagga gagaaaaagc      420
accgtgcatg ccgattggtg gaagtaaggt ggtacgatcg tgccttatta ggaaggcaac      480
```

-continued

```
agacgggtct gacatggatt ggacgaacca ctgaattgcc gcattgcaga gatattgtat      540
ttaagtgcct agctcgatac ataaacgggt ctctctggtt agaccagatc tgagcctggg      600
agctctctgg ctaactaggg aacccactgc ttaagcctca ataaagcttg ccttgagtgc      660
ttcaagtagt gtgtgcccgt ctgttgtgtg actctggtaa ctagagatcc ctcagaccct      720
tttagtcagt gtggaaaatc tctagcagtg gcgcccgaac agggacttga aagcgaaagg      780
gaaaccagag gagctctctc gacgcaggac tcggcttgct gaagcgcgca cggcaagagg      840
cgaggggcgg cgactggtga gtacgccaaa aattttgact agcggaggct agaaggagag      900
agatgggtgc gagagcgtca gtattaagcg ggggagaatt agatcgcgat gggaaaaaat      960
tcggttaagg ccagggggaa agaaaaaata taaattaaaa catatagtat gggcaagcag     1020
ggagctagaa cgattcgcag ttaatcctgg cctgttagaa acatcagaag gctgtagaca     1080
aatactggga cagctacaac catcccttca gacaggatca gaagaactta gatcattata     1140
taatacagta gcaaccctct attgtgtgca tcaaaggata gagataaaag acaccaagga     1200
agctttagac aagatagagg aagagcaaaa caaaagtaag accaccgcac agcaagcggc     1260
cgctgatctt cagacctgga ggaggagata tgagggacaa ttggagaagt gaattatata     1320
aatataaagt agtaaaaatt gaaccattag gagtagcacc caccaaggca aagagaagag     1380
tggtgcagag agaaaaaaga gcagtgggaa taggagcttt gttccttggg ttcttgggag     1440
cagcaggaag cactatgggc gcagcgtcaa tgacgctgac ggtacaggcc agacaattat     1500
tgtctggtat agtgcagcag cagaacaatt tgctgagggc tattgaggcg caacagcatc     1560
tgttgcaact cacagtctgg ggcatcaagc agctccaggc aagaatcctg gctgtggaaa     1620
gatacctaaa ggatcaacag ctcctgggga tttggggttg ctctggaaaa ctcatttgca     1680
ccactgctgt gccttggaat gctagttgga gtaataaatc tctggaacag atttggaatc     1740
acacgacctg gatggagtgg gacagagaaa ttaacaatta cacaagctta atacactcct     1800
taattgaaga atcgcaaaac cagcaagaaa agaatgaaca agaattattg gaattagata     1860
aatgggcaag tttgtggaat tggtttaaca taacaaattg gctgtggtat ataaaattat     1920
tcataatgat agtaggaggc ttggtaggtt taagaatagt ttttgctgta ctttctatag     1980
tgaatagagt taggcaggga tattcaccat tatcgtttca gacccacctc ccaaccccga     2040
ggggacccga caggcccgaa ggaatagaag aagaaggtgg agagagagac agagacagat     2100
ccattcgatt agtgaacgga tctcgacggt atcggtttta aaagaaaagg ggggattggg     2160
gggtacagtg caggggaaag aatagtagac ataatagcaa cagacataca aactaaagaa     2220
ttacaaaaac aaattacaaa aattcaaaat tttatcgatt ttatttagtc tccagaaaaa     2280 gggggaatg aaagacccca cctgtaggtt tggcaagcta gcttaagtaa cgccattttg     2340
caaggcatgg aaaatacata actgagaata gagaagttca gatcaaggtt aggaacagag     2400
agacagcaga atatgggcca aacaggatat ctgtggtaag cagttcctgc cccggctcag     2460
ggccaagaac agatggtccc cagatgcggt cccgccctca gcagtttcta gagaaccatc     2520
agatgtttcc agggtgcccc aaggacctga atgaccctg tgccttattt gaactaacca     2580
atcagttcgc ttctcgcttc tgttcgcgcg cttctgctcc ccgagctcaa taaaagagcc     2640
cacaacccct cactcggcgc gccagtcctc cgatagactg cgtcgcccgg gtaccgatat     2700
cacaagtttg tacaaaaaag ctgaacgaga acgtaaaat gatataaata tcaatatatt     2760
aaattagatt ttgcataaaa aacagactac ataatactgt aaaacacaac atatccagtc     2820
actatggcgg ccgcattagg cacccaggc tttcacttttat gcttccgg ctcgtataat     2880
```

```
gtgtggattt tgagttagga tccgtcgaga ttttcaggag ctaaggaagc taaaatggag    2940
aaaaaaatca ctggatatac caccgttgat atatcccaat ggcatcgtaa agaacatttt    3000
gaggcatttc agtcagttgc tcaatgtacc tataaccaga ccgttcagct ggatattacg    3060
gcctttttaa agaccgtaaa gaaaaataag cacaagtttt atccggcctt tattcacatt    3120
cttgcccgcc tgatgaatgc tcatccggaa ttccgtatgg caatgaaaga cggtgagctg    3180
gtgatatggg atagtgttca cccttgttac accgttttcc atgagcaaac tgaaacgttt    3240
tcatcgctct ggagtgaata ccacgacgat ttccggcagt ttctacacat atattcgcaa    3300
gatgtggcgt gttacggtga aaacctggcc tatttcccta aagggtttat tgagaatatg    3360
tttttcgtct cagccaatcc ctgggtgagt ttcaccagtt ttgatttaaa cgtggccaat    3420
atggacaact tcttcgcccc cgttttcacc atgggcaaat attatacgca aggcgacaag    3480
gtgctgatgc cgctggcgat tcaggttcat catgccgttt gtgatggctt ccatgtcggc    3540
agaatgctta atgaattaca acagtactgc gatgagtggc agggcggggc gtaaatggat    3600
ccggcttact aaaagccaga taacagtatg cgtatttgcg cgctgatttt tgcggtataa    3660
gaatatatac tgatatgtat acccgaagta tgtcaaaaag aggtatgcta tgaagcagcg    3720
tattacagtg acagttgaca gcgacagcta tcagttgctc aaggcatata tgatgtcaat    3780
atctccggtc tggtaagcac aaccatgcag aatgaagccc gtcgtctgcg tgccgaacgc    3840
tggaaagcgg aaaatcagga agggatggct gaggtcgccc ggtttattga aatgaacggc    3900
tcttttgctg acgagaacag gggctggtga aatgcagttt aaggtttaca cctataaaag    3960
agagagccgt tatcgtctgt ttgtggatgt acagagtgat attattgaca cgcccgggcg    4020
acggatggtg atccccctgg ccagtgcacg tctgctgtca gataaagtct cccgtgaact    4080
ttacccggtg gtgcatatcg gggatgaaag ctggcgcatg atgaccaccg atatggccag    4140
tgtgccggtc tccgttatcg gggaagaagt ggctgatctc agccaccgcg aaaatgacat    4200
caaaaacgcc attaacctga tgttctgggg aatataaatg tcaggctccc ttatacacag    4260
ccagtctgca ggtcgaccat agtgactgga tatgttgtgt tttacagtat tatgtagtct    4320
gttttttatg caaaatctaa tttaatatat tgatatttat atcattttac gtttctcgtt    4380
cagctttctt gtacaaagtg gtgattcgag ttaattaagt taacgaattc ccccctctc    4440 cctcccccc cctaacgtt actggccgaa gccgcttgga ataaggccgg tgtgcgtttg    4500
tctatatgtt attttccacc atattgccgt cttttggcaa tgtgagggcc cggaaacctg    4560
gccctgtctt cttgacgagc attcctaggg gtctttcccc tctcgccaaa ggaatgcaag    4620
gtctgttgaa tgtcgtgaag gaagcagttc ctctggaagc ttcttgaaga caaacaacgt    4680
ctgtagcgac cctttgcagg cagcggaacc ccccacctgg cgacaggtgc ctctgcggcc    4740
aaaagccacg tgtataagat acacctgcaa aggcggcaca accccagtgc cacgttgtga    4800
gttggatagt tgtggaaaga tcaaatggc tctcctcaag cgtattcaac aaggggctga    4860
aggatgccca gaaggtaccc cattgtatgg gatctgatct ggggcctcgg tgcacatgct    4920
ttacatgtgt ttagtcgagg ttaaaaaacg tctaggcccc ccgaaccacg gggacgtggt    4980
tttcctttga aaaacacgat gataatatgg ccacaaccat gggaggcgga agcggcggag    5040
gctcccctcg aggcaccatg gtgagcaagg gcgaggagct gttcaccggg gtggtgccca    5100
tcctggtcga gctggacggc gacgtaaacg gccacaagtt cagcgtgtcc ggcgagggcg    5160
agggcgatgc cacctacggc aagctgaccc tgaagttcat ctgcaccacc ggcaagctgc    5220
```

-continued

```
ccgtgccctg gcccaccctc gtgaccaccc tgacctacgg cgtgcagtgc ttcagccgct    5280
accccgacca catgaagcag cacgacttct tcaagtccgc catgcccgaa ggctacgtcc    5340
aggagcgcac catcttcttc aaggacgacg gcaactacaa gacccgcgcc gaggtgaagt    5400
tcgagggcga caccctggtg aaccgcatcg agctgaaggg catcgacttc aaggaggacg    5460
gcaacatcct ggggcacaag ctggagtaca actacaacag ccacaacgtc tatatcatgg    5520
ccgacaagca gaagaacggc atcaaggtga acttcaagat ccgccacaac atcgaggacg    5580
gcagcgtgca gctcgccgac cactaccagc agaacacccc catcggcgac ggccccgtgc    5640
tgctgcccga caaccactac ctgagcaccc agtccgccct gagcaaagac cccaacgaga    5700
agcgcgatca catggtcctg ctggagttcg tgaccgccgc cgggatcact ctcggcatgg    5760
acgagctgta caagtaacgc gtcccgggtc tagagctagc ggtaccatgc attacgtagt    5820
cgacgactta attaagctag cctagtgcca tttgttcagt ggttcgtagg gctttccccc    5880
actgtttggc tttcagttat atggatgatg tggtattggg ggccaagtct gtacagcatc    5940
ttgagtccct ttttaccgct gttaccaatt ttcttttgtc tttgggtata catttaaacc    6000
ctaacaaaac aaagagatgg ggttactctc taaattttat gggttatgtc attggatgtt    6060
atgggtcctt gccacaagaa cacatcatac aaaaaatcaa agaatgtttt agaaaacttc    6120
ctattaacag gcctattgat tggaaagtat gtcaacgaat tgtgggtctt ttgggttttg    6180
ctgccccttt tacacaatgt ggttatcctg cgttgatgcc tttgtatgca tgtattcaat    6240
ctaagcaggc tttcactttc tcgccaactt acaaggcctt tctgtgtaaa caatacctga    6300
acctttaccc cgttgcccgg caacggccag gtctgtgcca agtgtttgct gacgcaaccc    6360
ccactggctg gggcttggtc atgggccatc agcgcatgcg tggaaccttt tcggctcctc    6420
tgccgatcca tactgcggaa ctcctagccg cttgttttgc tcgcagcagg tctggagcaa    6480
acattatcgg gactgataac tctgttgtcc tatcccgcaa atatacatcg tttccatggc    6540
tgctaggctg tgctgccaac tggatcctgc gcgggacgtc ctttgtttac gtcccgtcgg    6600
cgctgaatcc tgcggacgac ccttctcggg gtcgcttggg actctctcgt ccccttctcc    6660
gtctgccgtt ccgaccgacc acggggcgca cctctcttta cgcggactcc ccgtctgtgc    6720
cttctcatct gccggaccgt gtgcacttcg cttcacctct gcacgtcgca tggagaccac    6780
cgtgaacgcc caccaaatat tgcccaaggt cttacataag aggactcttg gactctcagc    6840
aatgtcaacg accgaccttg aggcatactt caaagactgt ttgtttaaag actgggagga    6900
gttgggggag gagattaggt taaaggtctt tgtactagga ggctgtaggc ataaattggt    6960
ctgcgcacca gcaccatggc gcaatcacta gagcggggta cctttaagac caatgactta    7020
caaggcagct gtagatctta gccactttt aaaagaaaag gggggactgg aagggctaat    7080
tcactcccaa cgaagacaag atctgctttt tgcttgtact gggtctctct ggttagacca    7140
gatctgagcc tgggagctct ctggctaact agggaaccca ctgcttaagc ctcaataaag    7200
cttgccttga gtgcttcaag tagtgtgtgc ccgtctgttg tgtgactctg gtaactagag    7260
atccctcaga cccttttagt cagtgtggaa aatctctagc agtagtagtt catgtcatct    7320
tattattcag tatttataac ttgcaaagaa atgaatatca gagagtgaga ggaacttgtt    7380
tattgcagct tataatggtt acaaataaag caatagcatc acaaatttca caaataaagc    7440
atttttttca ctgcattcta gttgtggttt gtccaaactc atcaatgtat cttatcatgt    7500
ctggctctag ctatcccgcc cctaactccg cccatcccgc ccctaactcc gcccagttcc    7560
gcccattctc cgccccatgg ctgactaatt ttttttattt atgcagaggc cgaggccgga    7620
```

-continued

```
tcccttgagt ggctttcatc ctggagcaga cttttgcagtc tgtggactgc aacacaacat   7680
tgcctttatg tgtaactctt ggctgaagct cttacaccaa tgctggggga catgtacctc   7740 ccagggccc aggaagacta cgggaggcta caccaacgtc aatcagaggg gcctgtgtag   7800
ctaccgataa gcggaccctc aagagggcat tagcaatagt gtttataagg ccccttgtt   7860 aattcttgaa gacgaaaggg cctcgtgata cgcctatttt tataggttaa tgtcatgata   7920
ataatggttt cttagacgtc aggtggcact tttcggggaa atgtgcgcgg aacccctatt   7980
tgtttatttt tctaaataca ttcaaatatg tatccgctca tgagacaata accctgataa   8040
atgcttcaat aatattgaaa aaggaagagt atgagtattc aacatttccg tgtcgccctt   8100
attccctttt ttgcggcatt ttgccttcct gttttttgctc acccagaaac gctggtgaaa   8160
gtaaaagatg ctgaagatca gttgggtgca cgagtgggtt acatcgaact ggatctcaac   8220
agcggtaaga tccttgagag ttttcgcccc gaagaacgtt ttccaatgat gagcactttt   8280
aaagttctgc tatgtggcgc ggtattatcc cgtgttgacg ccgggcaaga gcaactcggt   8340
cgccgcatac actattctca gaatgacttg gttgagtact caccagtcac agaaaagcat   8400
cttacggatg gcatgacagt aagagaatta tgcagtgctg ccataaccat gagtgataac   8460
actgcggcca acttacttct gacaacgatc ggaggaccga aggagctaac cgcttttttg   8520
cacaacatgg gggatcatgt aactcgcctt gatcgttggg aaccggagct gaatgaagcc   8580
ataccaaacg acgagcgtga caccacgatg cctgcagcaa tggcaacaac gttgcgcaaa   8640
ctattaactg gcgaactact tactctagct tcccggcaac aattaatag a ctggatggag   8700 gcggataaag ttgcaggacc acttctgcgc tcggcccttc cggctggctg gtttattgct   8760
gataaatctg gagccggtga gcgtgggtct cgcggtatca ttgcagcact ggggccagat   8820
ggtaagccct cccgtatcgt agttatctac acgacgggga gtcaggcaac tatggatgaa   8880
cgaaatagac agatcgctga gataggtgcc tcactgatta agcattggta actgtcagac   8940
caagtttact catatatact ttagattgat ttaaaacttc attttttaatt taaaaggatc   9000 taggtgaaga tcctttttga taatctcatg accaaaatcc cttaacgtga gttttcgttc   9060
cactgagcgt cagacccgt a gaaaagatc aaaggatctt cttgagatcc ttttttttctg   9120 cgcgtaatct gctgcttgca acaaaaaaa ccaccgctac cagcggtggt ttgtttgccg   9180
gatcaagagc taccaactct ttttccgaag gtaactggct tcagcagagc gcagatacca   9240
aatactgtcc ttctagtgta gccgtagtta ggccaccact tcaagaactc tgtagcaccg   9300
cctacatacc tcgctctgct aatcctgtta ccagtggctg ctgccagtgg cgataagtcg   9360
tgtcttaccg ggttggactc aagacgatag ttaccggata aggcgcagcg gtcgggctga   9420
acggggggtt cgtgcacaca gcccagcttg gagcgaacga cctacaccga actgagatac   9480
ctacagcgtg agcattgaga aagcgccacg cttcccgaag ggagaaaggc ggacaggtat   9540
ccggtaagcg gcagggtcgg aacaggagag cgcacgaggg agcttccagg gggaaacgcc   9600
tggtatcttt atagtcctgt cgggtttcgc cacctctgac ttgagcgtcg attttttgtga   9660 tgctcgtcag ggggggcggag cctatggaaa aacgccagca acgcggcctt tttacggttc   9720
ctggcctttt gctggccttt ttgaagctgt ccctgatggt cgtcatctac ctgcctggac   9780
agcatggcct gcaacgcggg catcccgatg ccgccggaag cgagaagaat cataatgggg   9840
aaggccatcc agcctcgcgt cg                                              9862
```

<210> SEQ ID NO 32

<211> LENGTH: 3334
<212> TYPE: DNA
<213> ORGANISM: Artificial Sequence
<220> FEATURE:
<223> OTHER INFORMATION: donor vector 1, pMK 7c12 anti mFC scFV CoOp
       ECORV SacII L1R5

<400> SEQUENCE: 32

```
ctaaattgta agcgttaata ttttgttaaa attcgcgtta aattttttgtt aaatcagctc        60 attttttaac caataggccg aaatcggcaa aatccctttat aaatcaaaag aatagaccga       120 gataggggttg agtggccgct acagggcgct cccattcgcc attcaggctg cgcaactgtt       180
gggaagggcg tttcggtgcg ggcctcttcg ctattacgcc agctggcgaa aggggggatgt      240 gctgcaaggc gattaagttg ggtaacgcca gggtttttcc agtcacgacg ttgtaaaacg       300
acggccagtg agcgcgacgt aatacgactc actatagggc gaattgaagg aaggccgtca       360
aggccgcata aataatgatt ttattttgac tgatagtgac ctgttcgttg caacaaattg       420
atgagcaatg cttttttata atgccaactt tgtacaaaaa agctgaacga tatcgccacc       480
atgggcagca cagccattct ggccctgctg ctggcagtgc tgcagggcgt gtcagctcag       540
gtgcagctgg tgcagtctgg cggcggactc gtgaaacctg gcggcagcct gagactgagc       600
tgtgccgcca gcggcttcaa cttcaacgac cagtacatga gctggatccg gcaggcccct       660
ggcaagggac tggaatgggt gtccttcatc agcggcagcg gcggcaccac ctactacacc       720
gatagcgtga agggccggtt caccatcagc cgggacaaca ccaaggacag cctgtacctg       780
cagatgaaca gcctgaccgt ggaagatacc gccgtgtact actgcgccag aggcggcaat       840
tactacacca gcgtgggcag aggcaccctc gtgacagtgt ctgctggcgg aggcggatca       900
ggcggcggag gatcaggggg aggcggaagc ggagcacccg atatccagat gacacagagc       960
cccggcaccc tgtctctgag ccctggcgaa agagccatcc tgagctgcag agccagccag      1020
agcgtgtccg gatacctggc ttggtatcag cagaagcccg gccaggcccc cagactgctg      1080
atctatggcg ccagcagcag agccacaggc atccccgata gattcagcgg ctctggcagc      1140
ggcaccgact tcaccctgac aatcagctcc ctgcggcccg aggacatcgg cacctactat      1200
tgcaagcagt acatcaacgc cccccttcacc ttcggcggag gcaccaaggt ggaaatcaag     1260
ccgcgggcca cttttgtata caaaagtgga acgagaaacg taaaatgata taaatatcaa      1320
tatattaaat tagattttgc ataaaaaaca gactacataa tactgtaaaa cacaacatat      1380
ccagtcacta tgaatcaact acttagatgg tattagtgac ctgtactggg cctcatgggc      1440 cttccttttca ctgcccgctt tccagtcggg aaacctgtcg tgccagctgc attaacatgg     1500
tcatagctgt ttccttgcgt attgggcgct ctccgcttcc tcgctcactg actcgctgcg      1560
ctcggtcgtt cgggtaaagc ctggggtgcc taatgagcaa aaggccagca aaaggccagg      1620
aaccgtaaaa aggccgcgtt gctggcgttt ttccataggc tccgcccccc tgacgagcat      1680
cacaaaaatc gacgctcaag tcagaggtgg cgaaacccga caggactata aagataccag      1740
gcgtttcccc ctggaagctc cctcgtgcgc tctcctgttc cgaccctgcc gcttaccgga      1800
tacctgtccg cctttctccc ttcgggaagc gtggcgcttt ctcatagctc acgctgtagg      1860
tatctcagtt cggtgtaggt cgttcgctcc aagctgggct gtgtgcacga accccccgtt      1920
cagcccgacc gctgcgcctt atccggtaac tatcgtcttg agtccaaccc ggtaagacac      1980
gacttatcgc cactggcagc agccactggt aacaggatta gcagagcgag gtatgtaggc      2040
ggtgctacag agttcttgaa gtggtggcct aactacggct acactagaag aacagtattt      2100
```

```
ggtatctgcg ctctgctgaa gccagttacc ttcggaaaaa gagttggtag ctcttgatcc    2160
ggcaaacaaa ccaccgctgg tagcggtggt ttttttgttt gcaagcagca gattacgcgc    2220
agaaaaaaag gatctcaaga agatcctttg atcttttcta cggggtctga cgctcagtgg    2280
aacgaaaact cacgttaagg gattttggtc atgagattat caaaaaggat cttcacctag    2340
atccttttaa attaaaaatg aagttttaaa tcaatctaaa gtatatatga gtaaacttgg    2400
tctgacagtt attagaaaaa ttcatccagc agacgataaa acgcaatacg ctggctatcc    2460
ggtgccgcaa tgccatacag caccagaaaa cgatccgccc attcgccgcc cagttcttcc    2520
gcaatatcac gggtggccag cgcaatatcc tgataacgat ccgccacgcc cagacggccg    2580
caatcaataa agccgctaaa acggccattt tccaccataa tgttcggcag gcacgcatca    2640
ccatgggtca ccaccagatc ttcgccatcc ggcatgctcg ctttcagacg cgcaaacagc    2700
tctgccggtg ccaggccctg atgttcttca tccagatcat cctgatccac caggcccgct    2760
tccatacggg tacgcgcacg ttcaatacga tgtttcgcct gatgatcaaa cggacaggtc    2820
gccgggtcca gggtatgcag acgacgcatg gcatccgcca taatgctcac ttttttctgcc   2880 ggcgccagat ggctagacag cagatcctga cccggcactt cgcccagcag cagccaatca    2940
cggcccgctt cggtcaccac atccagcacc gccgcacacg gaacaccggt ggtggccagc    3000
cagctcagac gcgccgcttc atcctgcagc tcgttcagcg caccgctcag atcggttttc    3060
acaaacagca ccgacgacc ctgcgcgctc agacgaaaca ccgccgcatc agagcagcca     3120
atggtctgct gcgcccaatc atagccaaac agacgttcca cccacgctgc cgggctaccc    3180
gcatgcaggc catcctgttc aatcatactc ttcctttttc aatattattg aagcatttat    3240
cagggttatt gtctcatgag cggatacata tttgaatgta tttagaaaaa taaacaaata    3300
ggggttccgc gcacatttcc ccgaaaagtg ccac                                3334
```

```
<210> SEQ ID NO 33
<211> LENGTH: 2779
<212> TYPE: DNA
<213> ORGANISM: Artificial Sequence
<220> FEATURE:
<223> OTHER INFORMATION: donor vector 2, pMK hCD8a scaffold TN L5 L2

<400> SEQUENCE: 33
ctaaattgta agcgttaata tttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actatagggc gaattgaagg aaggccgtca     360
aggccgcata ataatgatt ttattttgac tgatagtgac ctgttcgttg caacaaattg      420
atgagcaatg cttttttata atgcccaact ttgtatacaa aagtggcccg cggacaacaa      480 ccctgcccc cagacctcct accccagccc ctacaattgc agccagcct ctgagcctga       540 ggcccgaggc ttgtagacct gctgctggcg gagccgtgca caccagagga ctggatttcg     600
cctgcgacat ctacatctgg gccctctgg ccggcacatg tggcgtgctg ctgctgagcc      660
tcgtgatcac cctgtactgc ggctccacca gcggctccgg caagcccggc tctggcgagg     720
gctccaccag cggcgactac aaggacgacg atgacaagta ataggatatc ggttcagctt     780
tcttgtacaa agttggcatt ataagaaagc attgcttatc aatttgttgc aacgaacagg     840
```

```
tcactatcag tcaaaataaa atcattattt ctgggcctca tgggccttcc tttcactgcc      900
cgctttccag tcgggaaacc tgtcgtgcca gctgcattaa catggtcata gctgtttcct      960
tgcgtattgg gcgctctccg cttcctcgct cactgactcg ctgcgctcgg tcgttcgggt     1020
aaagcctggg gtgcctaatg agcaaaaggc cagcaaaagg ccaggaaccg taaaaaggcc     1080
gcgttgctgg cgtttttcca taggctccgc cccctgacg agcatcacaa aaatcgacgc      1140
tcaagtcaga ggtggcgaaa cccgacagga ctataaagat accaggcgtt ccccctgga     1200 agctccctcg tgcgctctcc tgttccgacc ctgccgctta ccggatacct gtccgccttt     1260
ctcccttcgg gaagcgtggc gctttctcat agctcacgct gtaggtatct cagttcggtg     1320
taggtcgttc gctccaagct gggctgtgtg cacgaacccc ccgttcagcc cgaccgctgc     1380
gccttatccg gtaactatcg tcttgagtcc aacccggtaa gacacgactt atcgccactg     1440
gcagcagcca ctggtaacag gattagcaga gcgaggtatg taggcggtgc tacagagttc     1500
ttgaagtggt ggcctaacta cggctacact agaagaacag tatttggtat ctgcgctctg     1560
ctgaagccag ttaccttcgg aaaaagagtt ggtagctctt gatccggcaa acaaaccacc     1620
gctggtagcg gtggtttttt tgtttgcaag cagcagatta cgcgcagaaa aaaggatct     1680 caagaagatc ctttgatctt ttctacgggg tctgacgctc agtggaacga aaactcacgt     1740
taagggattt tggtcatgag attatcaaaa aggatcttca cctagatcct tttaaattaa     1800
aaatgaagtt ttaaatcaat ctaaagtata tatgagtaaa cttggtctga cagttattag     1860
aaaaattcat ccagcagacg ataaaacgca atacgctggc tatccggtgc cgcaatgcca     1920
tacagcacca gaaaacgatc cgcccattcg ccgcccagtt cttccgcaat atcacgggtg     1980
gccagcgcaa tatcctgata cgatccgcc acgcccagac ggccgcaatc aataaagccg     2040
ctaaaacggc cattttccac cataatgttc ggcaggcacg catcaccatg ggtcaccacc     2100
agatcttcgc catccggcat gctcgctttc agacgcgcaa acagctctgc cggtgccagg     2160
ccctgatgtt cttcatccag atcatcctga tccaccaggc ccgcttccat acgggtacgc     2220
gcacgttcaa tacgatgttt cgcctgatga tcaaacggac aggtcgccgg gtccagggta     2280
tgcagacgac gcatggcatc cgccataatg ctcacttttt ctgccggcgc cagatggcta     2340
gacagcagat cctgacccgg cacttcgccc agcagcagcc aatcacggcc cgcttcggtc     2400
accacatcca gcaccgccgc acacggaaca ccggtggtgg ccagccagct cagacgcgcc     2460
gcttcatcct gcagctcgtt cagcgcaccg ctcagatcgg ttttcacaaa cagcaccgga     2520
cgaccctgcg cgctcagacg aaacaccgcc gcatcagagc agccaatggt ctgctgcgcc     2580
caatcatagc caaacagacg ttccacccac gctgccgggc tacccgcatg caggccatcc     2640
tgttcaatca tactcttcct ttttcaatat tattgaagca tttatcaggg ttattgtctc     2700
atgagcggat acatatttga atgtatttag aaaaataaac aaataggggt tccgcgcaca     2760
tttccccgaa aagtgccac                                                   2779
```

<210> SEQ ID NO 34
<211> LENGTH: 9338
<212> TYPE: DNA
<213> ORGANISM: Artificial Sequence
<220> FEATURE:
<223> OTHER INFORMATION: Final vector used for lentiviral production,
    pLV4301G 7C12 scFV mIgG hCD8 flag

<400> SEQUENCE: 34

```
cgataaccct aattcgatag catatgcttc ccgttgggta acatatgcta ttgaattagg      60
```

-continued

```
gttagtctgg atagtatata ctactacccg ggaagcatat gctacccgtt tagggttcac    120
cggtgatgcc ggccacgatg cgtccggcgt agaggatcta atgtgagtta gctcactcat    180
taggcacccc aggctttaca ctttatgctt ccggctcgta tgttgtgtgg aattgtgagc    240
ggataacaat ttcacacagg aaacagctat gaccatgatt acgccaagcg cgcaattaac    300
cctcactaaa gggaacaaaa gctggagctg caagcttaat gtagtcttat gcaatactct    360
tgtagtcttg caacatggta acgatgagtt agcaacatgc cttacaagga gagaaaaagc    420
accgtgcatg ccgattggtg gaagtaaggt ggtacgatcg tgccttatta ggaaggcaac    480
agacgggtct gacatggatt ggacgaacca ctgaattgcc gcattgcaga gatattgtat    540
ttaagtgcct agctcgatac ataaacgggt ctctctggtt agaccagatc tgagcctggg    600
agctctctgg ctaactaggg aacccactgc ttaagcctca ataaagcttg ccttgagtgc    660
ttcaagtagt gtgtgcccgt ctgttgtgtg actctggtaa ctagagatcc ctcagaccct    720
tttagtcagt gtggaaaatc tctagcagtg gcgcccgaac agggacttga aagcgaaagg    780
gaaaccagag gagctctctc gacgcaggac tcggcttgct gaagcgcgca cggcaagagg    840
cgaggggcgg cgactggtga gtacgccaaa aattttgact agcggaggct agaaggagag    900
agatgggtgc gagagcgtca gtattaagcg ggggagaatt agatcgcgat gggaaaaaat    960
tcggttaagg ccaggggaa agaaaaaata taaattaaaa catatagtat gggcaagcag   1020
ggagctagaa cgattcgcag ttaatcctgg cctgttagaa acatcagaag gctgtagaca   1080
aatactggga cagctacaac catcccttca gacaggatca gaagaactta gatcattata   1140
taatacagta gcaaccctct attgtgtgca tcaaaggata gagataaaag acaccaagga   1200
agctttagac aagatagagg aagagcaaaa caaaagtaag accaccgcac agcaagcggc   1260
cgctgatctt cagacctgga ggaggagata tgagggacaa ttggagaagt gaattatata   1320
aatataaagt agtaaaaatt gaaccattag gagtagcacc caccaaggca aagagaagag   1380
tggtgcagag agaaaaaaga gcagtgggaa taggagcttt gttccttggg ttcttgggag   1440
cagcaggaag cactatgggc gcagcgtcaa tgacgctgac ggtacaggcc agacaattat   1500
tgtctggtat agtgcagcag cagaacaatt gctgagggc tattgaggcg caacagcatc   1560
tgttgcaact cacagtctgg ggcatcaagc agctccaggc aagaatcctg gctgtggaaa   1620
gatacctaaa ggatcaacag ctcctgggga tttggggttg ctctggaaaa ctcatttgca   1680
ccactgctgt gccttggaat gctagttgga gtaataaatc tctggaacag atttggaatc   1740
acacgacctg gatggagtgg gacagagaaa ttaacaatta cacaagctta atacactcct   1800
taattgaaga atcgcaaaac cagcaagaaa agaatgaaca agaattattg gaattagata   1860
aatgggcaag tttgtggaat tggtttaaca taacaaattg gctgtggtat ataaaattat   1920
tcataatgat agtaggaggc ttggtaggtt taagaatagt ttttgctgta ctttctatag   1980
tgaatagagt taggcaggga tattcaccat tatcgtttca gacccacctc ccaacccga   2040 ggggacccga caggcccgaa ggaatagaag aagaaggtgg agagagagac agagacagat   2100
ccattcgatt agtgaacgga tctcgacggt atcggtttta aaagaaaagg ggggattggg   2160
gggtacagtg caggggaaag aatagtagac ataatagcaa cagacataca aactaaagaa   2220
ttacaaaaac aaaattacaa aattcaaaat tttatcgatt ttatttagtc tccagaaaaa   2280 gggggggaatg aaagacccca cctgtaggtt tggcaagcta gcttaagtaa cgccattttg   2340
caaggcatgg aaaatacata actgagaata gagaagttca gatcaaggtt aggaacagag   2400
```

-continued

```
agacagcaga atatgggcca aacaggatat ctgtggtaag cagttcctgc cccggctcag   2460
ggccaagaac agatggtccc cagatgcggt cccgccctca gcagtttcta gagaaccatc   2520
agatgtttcc agggtgcccc aaggacctga aatgaccctg tgccttattt gaactaacca   2580
atcagttcgc ttctcgcttc tgttcgcgcg cttctgctcc ccgagctcaa taaaagagcc   2640
cacaacccct cactcggcgc gccagtcctc cgatagactg cgtcgcccgg gtaccgatat   2700
caccaacttt gtacaaaaaa gctgaacgat atcgccacca tgggcagcac agccattctg   2760
gccctgctgc tggcagtgct gcagggcgtg tcagctcagg tgcagctggt gcagtctggc   2820
ggcggactcg tgaaacctgg cggcagcctg agactgagct gtgccgccag cggcttcaac   2880
ttcaacgacc agtacatgag ctggatccgg caggcccctg gcaagggact ggaatgggtg   2940
tccttcatca gcggcagcgg cggcaccacc tactacaccg atagcgtgaa gggccggttc   3000
accatcagcc gggacaacac caaggacagc ctgtacctgc agatgaacag cctgaccgtg   3060
gaagataccg ccgtgtacta ctgcgccaga ggcggcaatt actacaccag cgtgggcaga   3120
ggcaccctcg tgacagtgtc tgctggcgga ggcggatcag gcggcggagg tcagggggga   3180
ggcggaagcg gagcacccga tatccagatg acacagagcc ccggcaccct gtctctgagc   3240
cctggcgaaa gagccatcct gagctgcaga gccagccaga gcgtgtccgg atacctggct   3300
tggtatcagc agaagcccgg ccaggccccc agactgctga tctatggcgc cagcagcaga   3360
gccacaggca tccccgatag attcagcggc tctggcagcg gcaccgactt caccctgaca   3420
atcagctccc tgcggcccga ggacatcggc acctactatt gcaagcagta catcaacgcc   3480
cccttcacct tcggcggagg caccaaggtg gaaatcaagc gcgggccaa ctttgtatac   3540 aaaagtggcc cgcggacaac aacccctgcc cccagacctc ctaccccagc ccctacaatt   3600
gccagccagc ctctgagcct gaggcccgag gcttgtagac ctgctgctgg cggagccgtg   3660
cacaccagag gactggattt cgcctgcgac atctacatct gggcccctct ggccggcaca   3720
tgtggcgtgc tgctgctgag cctcgtgatc accctgtact cggctccac cagcggctcc   3780 ggcaagcccg ctctggcga gggctccacc agcggcgact acaaggacga cgatgacaag   3840
taataggata tcggttcagc tttcttgtac aaagttggga ttcgagttaa ttaagttaac   3900
gaattccccc cctctccctc ccccccccct aacgttactg gccgaagccg cttggaataa   3960
ggccggtgtg cgtttgtcta tatgttattt tccaccatat tgccgtcttt tggcaatgtg   4020
agggcccgga aacctggccc tgtcttcttg acgagcattc ctaggggtct ttcccctctc   4080
gccaaaggaa tgcaaggtct gttgaatgtc gtgaaggaag cagttcctct ggaagcttct   4140
tgaagacaaa caacgtctgt agcgacccttt tgcaggcagc ggaaccccccc acctggcgac   4200 aggtgcctct gcggccaaaa gccacgtgta taagatacac ctgcaaaggc ggcacaaccc   4260
cagtgccacg ttgtgagttg gatagttgtg gaaagagtca aatggctctc ctcaagcgta   4320
ttcaacaagg gctgaagga tgcccagaag gtaccccatt gtatgggatc tgatctgggg   4380
cctcggtgca catgctttac atgtgtttag tcgaggttaa aaaacgtcta ggccccccga   4440
accacgggga cgtggttttc ctttgaaaaa cacgatgata atatggccac aaccatggga   4500
ggcggaagcg gcggaggctc ccctcgaggc accatggtga gcaagggcga ggagctgttc   4560
accggggtgg tgcccatcct ggtcgagctg gacggcgacg taaacggcca caagttcagc   4620
gtgtccggcg agggcgaggg cgatgccacc tacggcaagc tgaccctgaa gttcatctgc   4680
accaccggca agctgcccgt gccctggccc accctcgtga ccaccctgac ctacggcgtg   4740
cagtgcttca gccgctaccc cgaccacatg aagcagcacg acttcttcaa gtccgccatg   4800
```

-continued

```
cccgaaggct acgtccagga gcgcaccatc ttcttcaagg acgacggcaa ctacaagacc    4860
cgcgccgagg tgaagttcga gggcgacacc ctggtgaacc gcatcgagct gaagggcatc    4920
gacttcaagg aggacggcaa catcctgggg cacaagctgg agtacaacta caacagccac    4980
aacgtctata tcatggccga caagcagaag aacggcatca aggtgaactt caagatccgc    5040
cacaacatcg aggacggcag cgtgcagctc gccgaccact accagcagaa cacccccatc    5100
ggcgacggcc ccgtgctgct gcccgacaac cactacctga gcacccagtc cgccctgagc    5160
aaagacccca acgagaagcg cgatcacatg gtcctgctgg agttcgtgac cgccgccggg    5220
atcactctcg gcatggacga gctgtacaag taacgcgtcc cgggtctaga gctagcggta    5280
ccatgcatta cgtagtcgac gacttaatta agctagccta gtgccatttg ttcagtggtt    5340
cgtagggctt tcccccactg tttggctttc agttatatgg atgatgtggt attggggggcc    5400 aagtctgtac agcatcttga gtcccttttt accgctgtta ccaatttttct tttgtctttg    5460 ggtatacatt taaaccctaa caaaacaaag agatgggggtt actctctaaa ttttatgggt    5520
tatgtcattg gatgttatgg gtccttgcca caagaacaca tcatacaaaa aatcaaagaa    5580 tgtttttagaa aacttcctat taacaggcct attgattgga aagtatgtca acgaattgtg    5640
ggtcttttgg gttttgctgc ccctttttaca caatgtggtt atcctgcgtt gatgcctttg    5700
tatgcatgta ttcaatctaa gcaggctttc actttctcgc caacttacaa ggcctttctg    5760
tgtaaacaat acctgaacct ttaccccgtt gcccggcaac ggccaggtct gtgccaagtg    5820
tttgctgacg caaccccccac tggctggggc ttggtcatgg gccatcagcg catgcgtgga    5880
accttttcgg ctcctctgcc gatccatact gcggaactcc tagccgcttg ttttgctcgc    5940
agcaggtctg gagcaaacat tatcgggact gataactctg ttgtcctatc ccgcaaatat    6000
acatcgtttc catggctgct aggctgtgct gccaactgga tcctgcgcgg gacgtccttt    6060
gtttacgtcc cgtcggcgct gaatcctgcg gacgacccctt ctcggggtcg cttgggactc    6120
tctcgtcccc ttctccgtct gccgttccga ccgaccacgg ggcgcacctc tctttacgcg    6180
gactccccgt ctgtgccttc tcatctgccg gaccgtgtgc acttcgcttc acctctgcac    6240
gtcgcatgga gaccaccgtg aacgcccacc aaatattgcc caaggtctta cataagagga    6300
ctcttggact ctcagcaatg tcaacgaccg accttgaggc atacttcaaa gactgtttgt    6360
ttaaagactg ggaggagttg ggggaggaga ttaggttaaa ggtctttgta ctaggaggct    6420
gtaggcataa attggtctgc gcaccagcac catggcgcaa tcactagagc ggggtacctt    6480
taagaccaat gacttacaag gcagctgtag atcttagcca cttttttaaaa gaaaaggggg    6540 gactggaagg gctaattcac tcccaacgaa gacaagatct gctttttgct tgtactgggt    6600
ctctctggtt agaccagatc tgagcctggg agctctctgg ctaactaggg aacccactgc    6660
ttaagcctca ataaagcttg ccttgagtgc ttcaagtagt gtgtgcccgt ctgttgtgtg    6720
actctggtaa ctagagatcc ctcagaccct tttagtcagt gtggaaaatc tctagcagta    6780
gtagttcatg tcatcttatt attcagtatt tataacttgc aaagaaatga atatcagaga    6840
gtgagaggaa cttgtttatt gcagcttata atggttacaa ataaagcaat agcatcacaa    6900
atttcacaaa taaagcattt ttttcactgc attctagttg tggtttgtcc aaactcatca    6960
atgtatctta tcatgtctgg ctctagctat cccgccccta actccgccca tcccgcccct    7020
aactccgccc agttccgccc attctccgcc ccatggctga ctaatttttt ttatttatgc    7080
agaggccgag gccggatccc ttgagtggct ttcatcctgg agcagacttt gcagtctgtg    7140
```

```
gactgcaaca caacattgcc tttatgtgta actcttggct gaagctctta caccaatgct    7200
gggggacatg tacctcccag gggcccagga agactacggg aggctacacc aacgtcaatc    7260 agagggcct gtgtagctac cgataagcgg accctcaaga gggcattagc aatagtgttt     7320
ataaggcccc cttgttaatt cttgaagacg aaagggcctc gtgatacgcc tattttttata   7380 ggttaatgtc atgataataa tggtttctta gacgtcaggt ggcactttc ggggaaatgt      7440 gcgcggaacc cctatttgtt tattttttcta aatacattca aatatgtatc cgctcatgag    7500
acaataaccc tgataaatgc ttcaataata ttgaaaaagg aagagtatga gtattcaaca    7560
tttccgtgtc gcccttattc ccttttttgc ggcattttgc cttcctgttt ttgctcaccc     7620
agaaacgctg gtgaaagtaa aagatgctga agatcagttg ggtgcacgag tgggttacat     7680
cgaactggat ctcaacagcg gtaagatcct tgagagtttt cgccccgaag aacgttttcc     7740
aatgatgagc acttttaaag ttctgctatg tggcgcggta ttatcccgtg ttgacgccgg     7800
gcaagagcaa ctcggtcgcc gcatacacta ttctcagaat gacttggttg agtactcacc     7860
agtcacagaa aagcatctta cggatggcat gacagtaaga gaattatgca gtgctgccat     7920
aaccatgagt gataacactg cggccaactt acttctgaca acgatcggag gaccgaagga     7980
gctaaccgct ttttttgcaca acatggggga tcatgtaact cgccttgatc gttgggaacc     8040
ggagctgaat gaagccatac caaacgacga gcgtgacacc acgatgcctg cagcaatggc     8100
aacaacgttg cgcaaactat taactggcga actacttact ctagcttccc ggcaacaatt     8160
aatagactgg atggaggcgg ataaagttgc aggaccactt ctgcgctcgg cccttccggc     8220
tggctggttt attgctgata atctggagc cggtgagcgt gggtctcgcg gtatcattgc      8280
agcactgggg ccagatggta agccctcccg tatcgtagtt atctacacga cggggagtca     8340
ggcaactatg gatgaacgaa atagacagat cgctgagata ggtgcctcac tgattaagca     8400
ttggtaactg tcagaccaag tttactcata tatactttag attgatttaa aacttcattt     8460
ttaatttaaa aggatctagg tgaagatcct ttttgataat ctcatgacca aaatcccttta    8520 acgtgagttt tcgttccact gagcgtcaga ccccgtagaa aagatcaaag gatcttcttg     8580
agatcctttt tttctgcgcg taatctgctg cttgcaaaca aaaaaaccac cgctaccagc     8640
ggtggtttgt ttgccggatc aagagctacc aactcttttt ccgaaggtaa ctggcttcag     8700
cagagcgcag ataccaaata ctgtccttct agtgtagccg tagttaggcc accacttcaa     8760
gaactctgta gcaccgccta catacctcgc tctgctaatc ctgttaccag tggctgctgc     8820
cagtggcgat aagtcgtgtc ttaccgggtt ggactcaaga cgatagttac cggataaggc     8880
gcagcggtcg ggctgaacgg ggggttcgtg cacacagccc agcttggagc gaacgaccta     8940
caccgaactg agatacctac agcgtgagca ttgagaaagc gccacgcttc cgaagggag       9000 aaaggcggac aggtatccgg taagcggcag ggtcggaaca ggagagcgca cgagggagct     9060
tccaggggga aacgcctggt atctttatag tcctgtcggg tttcgccacc tctgacttga     9120
gcgtcgattt ttgtgatgct cgtcaggggg cggagcctta tggaaaaacg ccagcaacgc     9180
ggccttttta cggttcctgg ccttttgctg gcctttttga gctgtccct gatggtcgtc       9240 atctacctgc ctggacagca tggcctgcaa cgcgggcatc ccgatgccgc cggaagcgag     9300
aagaatcata tgggggaagg ccatccagcc tcgcgtcg                             9338
```

<210> SEQ ID NO 35
<211> LENGTH: 9862
<212> TYPE: DNA
<213> ORGANISM: Artificial Sequence

```
<220> FEATURE:
<223> OTHER INFORMATION: destination vector, pLV4301G

<400> SEQUENCE: 35
cgataaccct aattcgatag catatgcttc ccgttgggta acatatgcta ttgaattagg       60
gttagtctgg atagtatata ctactacccg ggaagcatat gctacccgtt tagggttcac      120
cggtgatgcc ggccacgatg cgtccggcgt agaggatcta atgtgagtta gctcactcat      180
taggcacccc aggctttaca ctttatgctt ccggctcgta tgttgtgtgg aattgtgagc      240
ggataacaat ttcacacagg aaacagctat gaccatgatt acgccaagcg cgcaattaac      300
cctcactaaa gggaacaaaa gctggagctg caagcttaat gtagtcttat gcaatactct      360
tgtagtcttg caacatggta acgatgagtt agcaacatgc cttacaagga gagaaaaagc      420
accgtgcatg ccgattggtg gaagtaaggt ggtacgatcg tgccttatta ggaaggcaac      480
agacgggtct gacatggatt ggacgaacca ctgaattgcc gcattgcaga gatattgtat      540
ttaagtgcct agctcgatac ataaacgggt ctctctggtt agaccagatc tgagcctggg      600
agctctctgg ctaactaggg aacccactgc ttaagcctca ataaagcttg ccttgagtgc      660
ttcaagtagt gtgtgcccgt ctgttgtgtg actctggtaa ctagagatcc ctcagaccct      720
tttagtcagt gtggaaaatc tctagcagtg gcgcccgaac agggacttga aagcgaaagg      780
gaaaccagag gagctctctc gacgcaggac tcggcttgct gaagcgcgca cggcaagagg      840
cgaggggcgg cgactggtga gtacgccaaa aattttgact agcggaggct agaaggagag      900
agatgggtgc gagagcgtca gtattaagcg ggggagaatt agatcgcgat gggaaaaaat      960
tcggttaagg ccagggggaa agaaaaaata taaattaaaa catatagtat gggcaagcag     1020
ggagctagaa cgattcgcag ttaatcctgg cctgttagaa acatcagaag gctgtagaca     1080
aatactggga cagctacaac catcccttca gacaggatca gaagaactta gatcattata     1140
taatacagta gcaaccctct attgtgtgca tcaaaggata gagataaaag acaccaagga     1200
agctttagac aagatagagg aagagcaaaa caaaagtaag accaccgcac agcaagcggc     1260
cgctgatctt cagacctgga ggaggagata tgagggacaa ttggagaagt gaattatata     1320
aatataaagt agtaaaaatt gaaccattag gagtagcacc caccaaggca agagaagag      1380 tggtgcagag agaaaaaaga gcagtgggaa taggagcttt gttccttggg ttcttgggag     1440
cagcaggaag cactatgggc gcagcgtcaa tgacgctgac ggtacaggcc agacaattat     1500
tgtctggtat agtgcagcag cagaacaatt gctgagggc tattgaggcg caacagcatc      1560
tgttgcaact cacagtctgg ggcatcaagc agctccaggc aagaatcctg gctgtggaaa     1620
gatacctaaa ggatcaacag ctcctgggga tttgggttg ctctggaaaa ctcatttgca      1680
ccactgctgt gccttggaat gctagttgga gtaataaatc tctggaacag atttggaatc     1740
acacgacctg gatggagtgg gacagagaaa ttaacaatta cacaagctta atacactcct     1800
taattgaaga atcgcaaaac cagcaagaaa agaatgaaca agaattattg gaattagata     1860
aatgggcaag tttgtggaat tggtttaaca taacaaattg gctgtggtat ataaaattat     1920
tcataatgat agtaggaggc ttggtaggtt taagaatagt ttttgctgta ctttctatag     1980
tgaatagagt taggcaggga tattcaccat tatcgtttca gacccacctc ccaaccccga     2040
ggggacccga caggcccgaa ggaatagaag aagaaggtgg agagagagac agagacagat     2100
ccattcgatt agtgaacgga tctcgacggt atcggtttta aagaaaaagg ggggattggg     2160
gggtacagtg caggggaaag aatagtagac ataatagcaa cagacataca aactaaagaa     2220
```

-continued

```
ttacaaaaac aaattacaaa aattcaaaat tttatcgatt ttatttagtc tccagaaaaa   2280 gggggggaatg aaagaccca cctgtaggtt tggcaagcta gcttaagtaa cgccattttg   2340
caaggcatgg aaaatacata actgagaata gagaagttca gatcaaggtt aggaacagag   2400
agacagcaga atatgggcca aacaggatat ctgtggtaag cagttcctgc cccggctcag   2460
ggccaagaac agatggtccc cagatgcggt cccgccctca gcagtttcta gagaaccatc   2520
agatgtttcc agggtgcccc aaggacctga aatgaccctg tgccttattt gaactaacca   2580
atcagttcgc ttctcgcttc tgttcgcgcg cttctgctcc ccgagctcaa taaaagagcc   2640
cacaacccct cactcggcgc gccagtcctc cgatagactg cgtcgcccgg gtaccgatat   2700
cacaagtttg tacaaaaaag ctgaacgaga aacgtaaaat gatataaata tcaatatatt   2760
aaattagatt ttgcataaaa aacagactac ataatactgt aaaacacaac atatccagtc   2820
actatggcgg ccgcattagg cacccaggc tttacacttt atgcttccgg ctcgtataat   2880
gtgtggattt tgagttagga tccgtcgaga ttttcaggag ctaaggaagc taaaatggag   2940
aaaaaaatca ctggatatac caccgttgat atatcccaat ggcatcgtaa agaacatttt   3000
gaggcatttc agtcagttgc tcaatgtacc tataaccaga ccgttcagct ggatattacg   3060
gcctttttaa agaccgtaaa gaaaaataag cacaagtttt atccggcctt tattcacatt   3120
cttgcccgcc tgatgaatgc tcatccggaa ttccgtatgg caatgaaaga cggtgagctg   3180
gtgatatggg atagtgttca cccttgttac accgttttcc atgagcaaac tgaaacgttt   3240
tcatcgctct ggagtgaata ccacgacgat ttccggcagt ttctacacat atattcgcaa   3300
gatgtggcgt gttacggtga aaacctggcc tatttcccta aagggtttat tgagaatatg   3360
tttttcgtct cagccaatcc ctgggtgagt ttcaccagtt ttgatttaaa cgtggccaat   3420
atggacaact tcttcgcccc cgttttcacc atgggcaaat attatacgca aggcgacaag   3480
gtgctgatgc cgctggcgat tcaggttcat catgccgttt gtgatggctt ccatgtcggc   3540
agaatgctta atgaattaca acagtactgc gatgagtggc agggcggggc gtaaatggat   3600
ccggcttact aaaagccaga taacagtatg cgtatttgcg cgctgatttt gcggtataa   3660 gaatatatac tgatatgtat acccgaagta tgtcaaaaag aggtatgcta tgaagcagcg   3720
tattacagtg acagttgaca gcgacagcta tcagttgctc aaggcatata tgatgtcaat   3780
atctccggtc tggtaagcac aaccatgcag aatgaagccc gtcgtctgcg tgccgaacgc   3840
tggaaagcgg aaaatcagga agggatggct gaggtcgccc ggtttattga aatgaacggc   3900
tcttttgctg acgagaacag gggctggtga aatgcagttt aaggtttaca cctataaaag   3960
agagagccgt tatcgtctgt ttgtggatgt acagagtgat attattgaca cgcccgggcg   4020
acggatggtc atcccctgg ccagtgcacg tctgctgtca gataaagtct cccgtgaact   4080
ttacccggtg gtgcatatcg gggatgaaag ctggcgcatg atgaccaccg atatggccag   4140
tgtgccggtc tccgttatcg gggaagaagt ggctgatctc agccaccgcg aaaatgacat   4200
caaaaacgcc attaacctga tgttctgggg aatataaatg tcaggctccc ttatacacag   4260
ccagtctgca ggtcgaccat agtgactgga tatgttgtgt tttacagtat tatgtagtct   4320
gttttttatg caaaatctaa tttaatatat tgatatttat atcattttac gtttctcgtt   4380
cagctttctt gtacaaagtg gtgattcgag ttaattaagt taacgaattc cccccctctc   4440 cctcccccc ccctaacgtt actggccgaa gccgcttgga ataaggccgg tgtgcgtttg   4500
tctatatgtt attttccacc atattgccgt cttttggcaa tgtgagggcc cggaaacctg   4560
gccctgtctt cttgacgagc attcctaggg gtctttcccc tctcgccaaa ggaatgcaag   4620
```

```
gtctgttgaa tgtcgtgaag gaagcagttc ctctggaagc ttcttgaaga caaacaacgt    4680
ctgtagcgac cctttgcagg cagcggaacc ccccacctgg cgacaggtgc ctctgcggcc    4740
aaaagccacg tgtataagat acacctgcaa aggcggcaca accccagtgc cacgttgtga    4800
gttggatagt tgtggaaaga gtcaaatggc tctcctcaag cgtattcaac aaggggctga    4860
aggatgccca gaaggtaccc cattgtatgg gatctgatct ggggcctcgg tgcacatgct    4920
ttacatgtgt ttagtcgagg ttaaaaaacg tctaggcccc ccgaaccacg gggacgtggt    4980
tttcctttga aaaacacgat gataatatgg ccacaaccat gggaggcgga agcggcggag    5040
gctcccctcg aggcaccatg gtgagcaagg gcgaggagct gttcaccggg gtggtgccca    5100
tcctggtcga gctggacggc gacgtaaacg gccacaagtt cagcgtgtcc ggcgagggcg    5160
agggcgatgc cacctacggc aagctgaccc tgaagttcat ctgcaccacc ggcaagctgc    5220
ccgtgccctg gcccaccctc gtgaccaccc tgacctacgg cgtgcagtgc ttcagccgct    5280
accccgacca catgaagcag cacgacttct tcaagtccgc catgcccgaa ggctacgtcc    5340
aggagcgcac catcttcttc aaggacgacg gcaactacaa gacccgcgcc gaggtgaagt    5400
tcgagggcga caccctggtg aaccgcatcg agctgaaggg catcgacttc aaggaggacg    5460
gcaacatcct ggggcacaag ctggagtaca actacaacag ccacaacgtc tatatcatgg    5520
ccgacaagca gaagaacggc atcaaggtga acttcaagat ccgccacaac atcgaggacg    5580
gcagcgtgca gctcgccgac cactaccagc agaacacccc catcggcgac ggccccgtgc    5640
tgctgcccga caaccactac ctgagcaccc agtccgccct gagcaaagac cccaacgaga    5700
agcgcgatca catggtcctg ctggagttcg tgaccgccgc cgggatcact ctcggcatgg    5760
acgagctgta caagtaacgc gtcccgggtc tagagctagc ggtaccatgc attacgtagt    5820
cgacgactta attaagctag cctagtgcca tttgttcagt ggttcgtagg gctttccccc    5880
actgtttggc tttcagttat atggatgatg tggtattggg ggccaagtct gtacagcatc    5940
ttgagtccct ttttaccgct gttaccaatt ttcttttgtc tttgggtata catttaaacc    6000
ctaacaaaac aaagagatgg ggttactctc taaattttat gggttatgtc attggatgtt    6060
atgggtcctt gccacaagaa cacatcatac aaaaaatcaa agaatgtttt agaaaacttc    6120
ctattaacag gcctattgat tggaaagtat gtcaacgaat tgtgggtctt ttgggttttg    6180
ctgccccttt tacacaatgt ggttatcctg cgttgatgcc tttgtatgca tgtattcaat    6240
ctaagcaggc tttcactttc tcgccaactt acaaggcctt tctgtgtaaa caatacctga    6300
acctttaccc cgttgcccgg caacggccag gtctgtgcca agtgtttgct gacgcaaccc    6360
ccactggctg gggcttggtc atgggccatc agcgcatgcg tggaaccttt tcggctcctc    6420
tgccgatcca tactgcggaa ctcctagccg cttgttttgc tcgcagcagg tctggagcaa    6480
acattatcgg gactgataac tctgttgtcc tatcccgcaa atatacatcg tttccatggc    6540
tgctaggctg tgctgccaac tggatcctgc gcgggacgtc ctttgtttac gtcccgtcgg    6600
cgctgaatcc tgcggacgac ccttctcggg gtcgcttggg actctctcgt ccccttctcc    6660
gtctgccgtt ccgaccgacc acggggcgca cctctcttta cgcggactcc ccgtctgtgc    6720
cttctcatct gccggaccgt gtgcacttcg cttcacctct gcacgtcgca tggagaccac    6780
cgtgaacgcc caccaaatat tgcccaaggt cttacataag aggactcttg gactctcagc    6840
aatgtcaacg accgaccttg aggcatactt caaagactgt ttgtttaaag actgggagga    6900
gttgggggag gagattaggt taaaggtctt tgtactagga ggctgtaggc ataaattggt    6960
```

```
ctgcgcacca gcaccatggc gcaatcacta gagcggggta cctttaagac caatgactta      7020
caaggcagct gtagatctta gccacttttt aaaagaaaag gggggactgg aagggctaat      7080
tcactcccaa cgaagacaag atctgctttt tgcttgtact gggtctctct ggttagacca      7140
gatctgagcc tgggagctct ctggctaact agggaaccca ctgcttaagc ctcaataaag      7200
cttgccttga gtgcttcaag tagtgtgtgc ccgtctgttg tgtgactctg gtaactagag      7260
atccctcaga cccttttagt cagtgtggaa aatctctagc agtagtagtt catgtcatct      7320
tattattcag tatttataac ttgcaaagaa atgaatatca gagagtgaga ggaacttgtt      7380
tattgcagct tataatggtt acaaataaag caatagcatc acaaatttca caaataaagc      7440
atttttttca ctgcattcta gttgtggttt gtccaaactc atcaatgtat cttatcatgt      7500
ctggctctag ctatcccgcc cctaactccg cccatcccgc ccctaactcc gcccagttcc      7560
gcccattctc cgccccatgg ctgactaatt ttttttattt atgcagaggc cgaggccgga      7620
tcccttgagt ggctttcatc ctggagcaga cttttgcagtc tgtggactgc aacacaacat      7680
tgcctttatg tgtaactctt ggctgaagct cttacaccaa tgctggggga catgtacctc      7740
ccaggggccc aggaagacta cgggaggcta caccaacgtc aatcagaggg gcctgtgtag      7800
ctaccgataa gcggaccctc aagagggcat tagcaatagt gtttataagg ccccttgtt      7860 aattcttgaa gacgaaaggg cctcgtgata cgcctatttt tataggttaa tgtcatgata      7920
ataatggttt cttagacgtc aggtggcact tttcggggaa atgtgcgcgg aacccctatt      7980
tgtttatttt tctaaataca ttcaaatatg tatccgctca tgagacaata accctgataa      8040
atgcttcaat aatattgaaa aaggaagagt atgagtattc aacatttccg tgtcgccctt      8100
attccctttt ttgcggcatt ttgccttcct gtttttgctc acccagaaac gctggtgaaa      8160
gtaaaagatg ctgaagatca gttgggtgca cgagtgggtt acatcgaact ggatctcaac      8220
agcggtaaga tccttgagag ttttcgcccc gaagaacgtt ttccaatgat gagcactttt      8280
aaagttctgc tatgtggcgc ggtattatcc cgtgttgacg ccgggcaaga gcaactcggt      8340
cgccgcatac actattctca gaatgacttg gttgagtact caccagtcac agaaaagcat      8400
cttacggatg gcatgacagt aagagaatta tgcagtgctg ccataaccat gagtgataac      8460
actgcggcca acttacttct gacaacgatc ggaggaccga aggagctaac cgcttttttg      8520
cacaacatgg gggatcatgt aactcgcctt gatcgttggg aaccggagct gaatgaagcc      8580
ataccaaacg acgagcgtga caccacgatg cctgcagcaa tggcaacaac gttgcgcaaa      8640
ctattaactg gcgaactact tactctagct tcccggcaac aattaataga ctggatggag      8700
gcggataaag ttgcaggacc acttctgcgc tcggcccttc cggctggctg gtttattgct      8760
gataaatctg gagccggtga gcgtgggtct cgcggtatca ttgcagcact ggggccagat      8820
ggtaagccct cccgtatcgt agttatctac acgacgggga gtcaggcaac tatggatgaa      8880
cgaaatagac agatcgctga gataggtgcc tcactgatta agcattggta actgtcagac      8940
caagtttact catatatact ttagattgat ttaaaacttc atttttaatt taaaaggatc      9000
taggtgaaga tcctttttga taatctcatg accaaaatcc cttaacgtga gttttcgttc      9060
cactgagcgc cagaccccgt agaaaagatc aaaggatctt cttgagatcc ttttttttctg      9120 cgcgtaatct gctgcttgca acaaaaaaa ccaccgctac cagcggtggt ttgtttgccg      9180
gatcaagagc taccaactct ttttccgaag gtaactggct tcagcagagc gcagatacca      9240
aatactgtcc ttctagtgta gccgtagtta ggccaccact tcaagaactc tgtagcaccg      9300
cctacatacc tcgctctgct aatcctgtta ccagtggctg ctgccagtgg cgataagtcg      9360
```

```
tgtcttaccg ggttggactc aagacgatag ttaccggata aggcgcagcg gtcgggctga    9420 acgggggggtt cgtgcacaca gcccagcttg gagcgaacga cctacaccga actgagatac    9480
ctacagcgtg agcattgaga aagcgccacg cttcccgaag ggagaaaggc ggacaggtat    9540
ccggtaagcg gcagggtcgg aacaggagag cgcacgaggg agcttccagg gggaaacgcc    9600
tggtatcttt atagtcctgt cgggtttcgc cacctctgac ttgagcgtcg attttttgtga    9660 tgctcgtcag ggggggcggag cctatggaaa aacgccagca acgcggcctt tttacggttc    9720
ctggcctttt gctggccttt ttgaagctgt ccctgatggt cgtcatctac ctgcctggac    9780
agcatggcct gcaacgcggg catcccgatg ccgccggaag cgagaagaat cataatgggg    9840
aaggccatcc agcctcgcgt cg                                             9862
```

<210> SEQ ID NO 36
<211> LENGTH: 3340
<212> TYPE: DNA
<213> ORGANISM: Artificial Sequence
<220> FEATURE:
<223> OTHER INFORMATION: donor vector 1, pMK 8B3 anti mFC scFV CoOp
     ECORV SacII L1R5

<400> SEQUENCE: 36

```
ctaaattgta agcgttaata ttttgttaaa attcgcgtta aatttttgtt aaatcagctc      60 atttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt     240 gctgcaaggc gattaagttg ggtaacgcca gggttttccc agtcacgacg ttgtaaaacg     300
acggccagtg agcgcgacgt aatacgactc actatagggc gaattgaagg aaggccgtca     360
aggccgcata aataatgatt ttattttgac tgatagtgac ctgttcgttg caacaaattg     420
atgagcaatg ctttttttata atgccaactt tgtacaaaaa agctgaacga tatcgccacc     480
atgggcagca cagccattct ggccctgctg ctggcagtgc tgcagggcgt gtcagctcag     540
gtgcagctgc agcagtctgg cgccgaagtg aagaaacccg gcagcagcgt gaaggtgtcc     600
tgcaaggcta gcggcggcac cttcagcagc tacgccattt cttgggtgcg ccaggcccct     660
ggacagggcc tggaatggat gggctggatc agcccctaca acggcaacac cgactacgcc     720
cagaaagtgc agggcagagt gaccctgacc accgacacca gcacctccac cgcctacatg     780
gaactgcgga gcctgagaag cgacgacacc gccgtgtact actgtgccac aggcggcgga     840
acctggtaca gcgatctgtg gggcagaggc accctcgtga cagtgtctgc tggcggcgga     900
ggatctggcg gaggcggaag tggcggggga ggaagcggag cacctgagat cgtgctgacc     960
cagagcccta gcacactgag cgccagcgtg ggcgacagag tgtccatcac ctgtagagcc    1020
agccagagca tcggaggcag cctggcctgg tatcagcaga agcctggcaa ggcccccaag    1080
ctgctgatct ctgaggccag caccctggaa agaggcgtgc cagcagatt ttccggcagc    1140 ggctctggca ccgacttcac cctgacaatc agcagcctgc agcccgagga cgtggccacc    1200
tactactgcc agaagtacaa cagcgtgccc ctgaccttcg ccctggcac caaggtggaa    1260 atcaagccgc gggccaactt tgtatacaaa agtggaacga gaaacgtaaa atgatataaa    1320
tatcaatata ttaaattaga ttttgcataa aaaacagact acataatact gtaaaacaca    1380
acatatccag tcactatgaa tcaactactt agatggtatt agtgacctgt actgggcctc    1440
atgggccttc ctttcactgc ccgctttcca gtcgggaaac ctgtcgtgcc agctgcatta    1500
```

-continued

```
acatggtcat agctgtttcc ttgcgtattg ggcgctctcc gcttcctcgc tcactgactc    1560
gctgcgctcg gtcgttcggg taaagcctgg ggtgcctaat gagcaaaagg ccagcaaaag    1620
gccaggaacc gtaaaaaggc cgcgttgctg gcgtttttcc ataggctccg cccccctgac    1680
gagcatcaca aaaatcgacg ctcaagtcag aggtggcgaa acccgacagg actataaaga    1740
taccaggcgt ttccccctgg aagctccctc gtgcgctctc ctgttccgac cctgccgctt    1800
accggatacc tgtccgcctt tctcccttcg ggaagcgtgg cgctttctca tagctcacgc    1860
tgtaggtatc tcagttcggt gtaggtcgtt cgctccaagc tgggctgtgt gcacgaaccc    1920
cccgttcagc ccgaccgctg cgccttatcc ggtaactatc gtcttgagtc caacccggta    1980
agacacgact tatcgccact ggcagcagcc actggtaaca ggattagcag agcgaggtat    2040
gtaggcggtg ctacagagtt cttgaagtgg tggcctaact acggctacac tagaagaaca    2100
gtatttggta tctgcgctct gctgaagcca gttaccttcg gaaaaagagt tggtagctct    2160
tgatccggca aacaaaccac cgctggtagc ggtggttttt ttgtttgcaa gcagcagatt    2220
acgcgcagaa aaaaggatc tcaagaagat cctttgatct tttctacggg gtctgacgct    2280
cagtggaacg aaaactcacg ttaagggatt ttggtcatga gattatcaaa aaggatcttc    2340
acctagatcc ttttaaatta aaaatgaagt tttaaatcaa tctaaagtat atatgagtaa    2400
acttggtctg acagttatta gaaaaattca tccagcagac gataaaacgc aatacgctgg    2460
ctatccggtg ccgcaatgcc atacagcacc agaaaacgat ccgcccattc gccgcccagt    2520
tcttccgcaa tatcacgggt ggccagcgca atatcctgat aacgatccgc cacgcccaga    2580
cggccgcaat caataaagcc gctaaaacgg ccattttcca ccataatgtt cggcaggcac    2640
gcatcaccat gggtcaccac cagatcttcg ccatccggca tgctcgcttt cagacgcgca    2700
aacagctctg ccggtgccag gccctgatgt tcttcatcca gatcatcctg atccaccagg    2760
cccgcttcca tacgggtacg cgcacgttca atacgatgtt tcgcctgatg atcaaacgga    2820
caggtcgccg ggtccagggt atgcagacga cgcatggcat ccgccataat gctcactttt    2880
tctgccggcg ccagatggct agacagcaga tcctgacccg gcacttcgcc cagcagcagc    2940
caatcacggc ccgcttcggt caccacatcc agcaccgccg cacacggaac accggtggtg    3000
gccagccagc tcagacgcgc cgcttcatcc tgcagctcgt tcagcgcacc gctcagatcg    3060
gttttcacaa acagcaccgg acgaccctgc gcgctcagac gaaacaccgc cgcatcagag    3120
cagccaatgg tctgctgcgc ccaatcatag ccaaacagac gttccaccca cgctgccggg    3180
ctacccgcat gcaggccatc ctgttcaatc atactcttcc tttttcaata ttattgaagc    3240
atttatcagg gttattgtct catgagcgga tacatatttg aatgtattta gaaaaataaa    3300
caaatagggg ttccgcgcac atttccccga aaagtgccac                          3340
```

<210> SEQ ID NO 37
<211> LENGTH: 2779
<212> TYPE: DNA
<213> ORGANISM: Artificial Sequence
<220> FEATURE:
<223> OTHER INFORMATION: donor vector 2, pMK hCD8a scaffold TN L5 L2

<400> SEQUENCE: 37

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acaggcgct cccattcgcc attcaggctg cgcaactgtt     180
```

-continued

```
gggaagggcg tttcggtgcg ggcctcttcg ctattacgcc agctggcgaa aggggatgt      240 gctgcaaggc gattaagttg ggtaacgcca gggtttccc agtcacgacg ttgtaaaacg       300
acggccagtg agcgcgacgt aatacgactc actatagggc gaattgaagg aaggccgtca      360
aggccgcata aataatgatt ttattttgac tgatagtgac ctgttcgttg caacaaattg      420
atgagcaatg cttttttata atgcccaact ttgtatacaa aagtggcccg cggacaacaa      480
cccctgcccc cagacctcct accccagccc ctacaattgc cagccagcct ctgagcctga      540
ggcccgaggc ttgtagacct gctgctggcg gagccgtgca caccagagga ctggatttcg      600
cctgcgacat ctacatctgg gcccctctgg ccggcacatg tggcgtgctg ctgctgagcc      660
tcgtgatcac cctgtactgc ggctccacca gcggctccgg caagcccggc tctggcgagg      720
gctccaccag cggcgactac aaggacgacg atgacaagta ataggatatc ggttcagctt      780
tcttgtacaa agttggcatt ataagaaagc attgcttatc aatttgttgc aacgaacagg      840
tcactatcag tcaaaataaa atcattattt ctgggcctca tgggccttcc tttcactgcc      900
cgctttccag tcgggaaacc tgtcgtgcca gctgcattaa catggtcata gctgtttcct      960
tgcgtattgg cgctctccg cttcctcgct cactgactcg ctgcgctcgg tcgttcgggt      1020
aaagcctggg gtgcctaatg agcaaaaggc cagcaaaagg ccaggaaccg taaaaaggcc      1080
gcgttgctgg cgtttttcca taggctccgc cccctgacg agcatcacaa aaatcgacgc      1140
tcaagtcaga ggtggcgaaa cccgacagga ctataaagat accaggcgtt tccccctgga      1200
agctccctcg tgcgctctcc tgttccgacc ctgccgctta ccggatacct gtccgccttt      1260
ctcccttcgg gaagcgtggc gctttctcat agctcacgct gtaggtatct cagttcggtg      1320
taggtcgttc gctccaagct gggctgtgtg cacgaacccc ccgttcagcc cgaccgctgc      1380
gccttatccg gtaactatcg tcttgagtcc aacccggtaa gacacgactt atcgccactg      1440
gcagcagcca ctggtaacag gattagcaga gcgaggtatg taggcggtgc tacagagttc      1500
ttgaagtggt ggcctaacta cggctacact agaagaacag tatttggtat ctgcgctctg      1560
ctgaagccag ttaccttcgg aaaaagagtt ggtagctctt gatccggcaa acaaaccacc      1620
gctggtagcg gtggtttttt tgtttgcaag cagcagatta cgcgcagaaa aaaggatct      1680 caagaagatc ctttgatctt ttctacgggg tctgacgctc agtggaacga aaactcacgt      1740
taagggattt tggtcatgag attatcaaaa aggatcttca cctagatcct tttaaattaa      1800
aaatgaagtt ttaaatcaat ctaaagtata tatgagtaaa cttggtctga cagttattag      1860
aaaaattcat ccagcagacg ataaaacgca atacgctggc tatccggtgc cgcaatgcca      1920
tacagcacca gaaaacgatc cgcccattcg ccgcccagtt cttccgcaat atcacgggtg      1980
gccagcgcaa tatcctgata acgatccgcc acgcccagac ggccgcaatc aataaagccg      2040
ctaaaacggc cattttccac cataatgttc ggcaggcacg catcaccatg ggtcaccacc      2100
agatcttcgc catccggcat gctcgctttc agacgcgcaa acagctctgc cggtgccagg      2160
ccctgatgtt cttcatccag atcatcctga tccaccaggc ccgcttccat acgggtacgc      2220
gcacgttcaa tacgatgttt cgcctgatga tcaaacggac aggtcgccgg gtccagggta      2280
tgcagacgac gcatggcatc cgccataatg ctcactttttt ctgccggcgc cagatggcta      2340
gacagcagat cctgacccgg cacttcgccc agcagcagcc aatcacggcc cgcttcggtc      2400
accacatcca gcaccgccgc acacggaaca ccggtggtgg ccagccagct cagacgcgcc      2460
gcttcatcct gcagctcgtt cagcgcaccg ctcagatcgg ttttcacaaa cagcaccgga      2520
cgaccctgcg cgctcagacg aaacaccgcc gcatcagagc agccaatggt ctgctgcgcc      2580
```

-continued

```
caatcatagc caaacagacg ttccacccac gctgccgggc tacccgcatg caggccatcc    2640
tgttcaatca tactcttcct tttttcaatat tattgaagca tttatcaggg ttattgtctc    2700
atgagcggat acatatttga atgtatttag aaaaataaac aaataggggt tccgcgcaca    2760
tttccccgaa aagtgccac                                                 2779

<210> SEQ ID NO 38
<211> LENGTH: 9344
<212> TYPE: DNA
<213> ORGANISM: Artificial Sequence
<220> FEATURE:
<223> OTHER INFORMATION: Final vector used for lentiviral production,
      pLV4301G 8B3 scFV mIgG hCD8 flag

<400> SEQUENCE: 38 cgataacccct aattcgatag catatgcttc ccgttgggta acatatgcta ttgaattagg     60
gttagtctgg atagtatata ctactacccg ggaagcatat gctacccgtt tagggttcac    120
cggtgatgcc ggccacgatg cgtccggcgt agaggatcta atgtgagtta gctcactcat    180
taggcacccc aggctttaca ctttatgctt ccggctcgta tgttgtgtgg aattgtgagc    240
ggataacaat ttcacacagg aaacagctat gaccatgatt acgccaagcg cgcaattaac    300
cctcactaaa gggaacaaaa gctggagctg caagcttaat gtagtcttat gcaatactct    360
tgtagtcttg caacatggta acgatgagtt agcaacatgc cttacaagga gagaaaaagc    420
accgtgcatg ccgattggtg gaagtaaggt ggtacgatcg tgccttatta ggaaggcaac    480
agacgggtct gacatggatt ggacgaacca ctgaattgcc gcattgcaga gatattgtat    540
ttaagtgcct agctcgatac ataaacgggt ctctctggtt agaccagatc tgagcctggg    600
agctctctgg ctaactaggg aacccactgc ttaagcctca ataaagcttg ccttgagtgc    660
ttcaagtagt gtgtgcccgt ctgttgtgtg actctggtaa ctagagatcc ctcagaccct    720
tttagtcagt gtggaaaatc tctagcagtg gcgcccgaac agggacttga aagcgaaagg    780
gaaaccagag gagctctctc gacgcaggac tcggcttgct gaagcgcgca cggcaagagg    840
cgaggggcgg cgactggtga gtacgccaaa aattttgact agcggaggct agaaggagag    900
agatgggtgc gagagcgtca gtattaagcg ggggagaatt agatcgcgat gggaaaaaat    960
tcggttaagg ccagggggaa agaaaaaata taaattaaaa catatagtat gggcaagcag   1020
ggagctagaa cgattcgcag ttaatcctgg cctgttagaa acatcagaag gctgtagaca   1080
aatactggga cagctacaac catcccttca gacaggatca gaagaactta gatcattata   1140
taatacagta gcaaccctct attgtgtgca tcaaaggata gagataaaag acaccaagga   1200
agctttagac aagatagagg aagagcaaaa caaaagtaag accaccgcac agcaagcggc   1260
cgctgatctt cagacctgga ggaggagata tgagggacaa ttggagaagt gaattatata   1320
aatataaagt agtaaaaatt gaaccattag gagtagcacc caccaaggca agagaagag   1380 tggtgcagag agaaaaaaga gcagtgggaa taggagcttt gttccttggg ttcttgggag   1440
cagcaggaag cactatgggc gcagcgtcaa tgacgctgac ggtacaggcc agacaattat   1500
tgtctggtat agtgcagcag cagaacaatt tgctgagggc tattgaggcg caacagcatc   1560
tgttgcaact cacagtctgg ggcatcaagc agctccaggc aagaatcctg gctgtggaaa   1620
gatacctaaa ggatcaacag ctcctgggga tttgggggttg ctctggaaaa ctcatttgca   1680
ccactgctgt gccttggaat gctagttgga gtaataaatc tctggaacag atttggaatc   1740
acacgacctg gatggagtgg gacagagaaa ttaacaatta cacaagctta atacactcct   1800
```

-continued

```
taattgaaga atcgcaaaac cagcaagaaa agaatgaaca agaattattg gaattagata   1860
aatgggcaag tttgtggaat tggtttaaca taacaaattg gctgtggtat ataaaattat   1920
tcataatgat agtaggaggc ttggtaggtt taagaatagt ttttgctgta ctttctatag   1980
tgaatagagt taggcaggga tattcaccat tatcgtttca gacccacctc ccaacccga    2040 ggggacccga caggcccgaa ggaatagaag aagaaggtgg agagagagac agagacagat   2100
ccattcgatt agtgaacgga tctcgacggt atcggtttta aaagaaaagg ggggattggg   2160
gggtacagtg caggggaaag aatagtagac ataatagcaa cagacataca aactaaagaa   2220
ttacaaaaac aaattacaaa aattcaaaat tttatcgatt ttatttagtc tccagaaaaa   2280 gggggggaatg aaagacccca cctgtaggtt tggcaagcta gcttaagtaa cgccattttg   2340
caaggcatgg aaaatacata actgagaata gagaagttca gatcaaggtt aggaacagag   2400
agacagcaga atatgggcca aacaggatat ctgtggtaag cagttcctgc cccggctcag   2460
ggccaagaac agatggtccc cagatgcggt cccgccctca gcagtttcta gagaaccatc   2520
agatgtttcc agggtgcccc aaggacctga aatgaccctg tgccttattt gaactaacca   2580
atcagttcgc ttctcgcttc tgttcgcgcg cttctgctcc ccgagctcaa taaaagagcc   2640
cacaacccct cactcggcgc gccagtcctc cgatagactg cgtcgcccgg gtaccgatat   2700
caccaacttt gtacaaaaaa gctgaacgat atcgccacca tgggcagcac agccattctg   2760
gccctgctgc tggcagtgct gcaggcgtg tcagctcagg tgcagctgca gcagtctggc   2820
gccgaagtga agaaacccgg cagcagcgtg aaggtgtcct gcaaggctag cggcggcacc   2880
ttcagcagct acgccatttc ttgggtgcgc caggcccctg gacagggcct ggaatggatg   2940
ggctggatca gcccctacaa cggcaacacc gactacgccc agaaagtgca gggcagagtg   3000
accctgacca ccgacaccag cacctccacc gcctacatgg aactgcggag cctgagaagc   3060
gacgacaccg ccgtgtacta ctgtgccaca ggcggcggaa cctggtacag cgatctgtgg   3120
ggcagaggca ccctcgtgac agtgtctgct ggcggcggag gatctggcgg aggcggaagt   3180
ggcgggggag gaagcggagc acctgagatc gtgctgaccc agagccctag cacactgagc   3240
gccagcgtgg gcgacagagt gtccatcacc tgtagagcca gccagagcat cggaggcagc   3300
ctggcctggt atcagcagaa gcctggcaag gcccccaagc tgctgatctc tgaggccagc   3360
accctggaaa gaggcgtgcc cagcagattt tccggcagcg gctctggcac cgacttcacc   3420
ctgacaatca gcagcctgca gcccgaggac gtggccacct actactgcca gaagtacaac   3480
agcgtgcccc tgaccttcgg ccctggcacc aaggtggaaa tcaagccgcg ggccaacttt   3540
gtatacaaaa gtggcccgcg gacaacaacc cctgcccca gacctcctac cccagcccct   3600
acaattgcca gccagcctct gagcctgagg cccgaggctt gtagacctgc tgctggcgga   3660
gccgtgcaca ccagaggact ggatttcgcc tgcgacatct acatctgggc ccctctggcc   3720
ggcacatgtg gcgtgctgct gctgagcctc gtgatcaccc tgtactgcgg ctccaccagc   3780
ggctccggca gcccggctc tggcgagggc tccaccagcg gcgactacaa ggacgacgat   3840
gacaagtaat aggatatcgg ttcagctttc ttgtacaaag ttgggattcg agttaattaa   3900
gttaacgaat ccccccctc tccctcccccc ccccctaacg ttactggccg aagccgcttg   3960
gaataaggcc ggtgtgcgtt tgtctatatg ttattttcca ccatattgcc gtcttttggc   4020
aatgtgaggg cccggaaacc tggccctgtc ttcttgacga gcattcctag gggtctttcc   4080
cctctcgcca aaggaatgca aggtctgttg aatgtcgtga aggaagcagt tcctctggaa   4140
```

-continued

```
gcttcttgaa gacaaacaac gtctgtagcg acccttttgca ggcagcggaa ccccccacct    4200
ggcgacaggt gcctctgcgg ccaaaagcca cgtgtataag atacacctgc aaaggcggca    4260 caacccccagt gccacgttgt gagttggata gttgtggaaa gagtcaaatg gctctcctca    4320
agcgtattca acaaggggct gaaggatgcc cagaaggtac cccattgtat gggatctgat    4380
ctggggcctc ggtgcacatg ctttacatgt gtttagtcga ggttaaaaaa cgtctaggcc    4440
ccccgaacca cggggacgtg gttttccttt gaaaaacacg atgataatat ggccacaacc    4500
atgggaggcg gaagcggcgg aggctcccct cgaggcacca tggtgagcaa gggcgaggag    4560
ctgttcaccg gggtggtgcc catcctggtc gagctggacg gcgacgtaaa cggccacaag    4620
ttcagcgtgt ccggcgaggg cgagggcgat gccacctacg gcaagctgac cctgaagttc    4680
atctgcacca ccggcaagct gcccgtgccc tggcccaccc tcgtgaccac cctgacctac    4740
ggcgtgcagt gcttcagccg ctaccccgac cacatgaagc agcacgactt cttcaagtcc    4800
gccatgcccg aaggctacgt ccaggagcgc accatcttct tcaaggacga cggcaactac    4860
aagacccgcg ccgaggtgaa gttcgagggc gacaccctgg tgaaccgcat cgagctgaag    4920
ggcatcgact tcaaggagga cggcaacatc ctggggcaca agctggagta caactacaac    4980
agccacaacg tctatatcat ggccgacaag cagaagaacg gcatcaaggt gaacttcaag    5040
atccgccaca acatcgagga cggcagcgtg cagctcgccg accactacca gcagaacacc    5100
cccatcggcg acggccccgt gctgctgccc gacaaccact acctgagcac ccagtccgcc    5160
ctgagcaaag accccaacga gaagcgcgat cacatggtcc tgctggagtt cgtgaccgcc    5220
gccgggatca ctctcggcat ggacgagctg tacaagtaac gcgtcccggg tctagagcta    5280
gcggtaccat gcattacgta gtcgacgact taattaagct agcctagtgc catttgttca    5340
gtggttcgta gggctttccc ccactgtttg gctttcagtt atatggatga tgtggtattg    5400
ggggccaagt ctgtacagca tcttgagtcc cttttttaccg ctgttaccaa ttttcttttg    5460
tctttgggta tacatttaaa ccctaacaaa acaaagagat ggggttactc tctaaatttt    5520
atgggttatg tcattggatg ttatgggtcc ttgccacaag aacacatcat acaaaaaatc    5580
aaagaatgtt ttagaaaact tcctattaac aggcctattg attggaaagt atgtcaacga    5640
attgtgggtc tttttgggttt tgctgcccct tttacacaat gtggttatcc tgcgttgatg    5700
cctttgtatg catgtattca atctaagcag gctttcactt tctcgccaac ttacaaggcc    5760
tttctgtgta aacaatacct gaacctttac cccgttgccc ggcaacggcc aggtctgtgc    5820
caagtgtttg ctgacgcaac ccccactggc tggggcttgg tcatgggcca tcagcgcatg    5880
cgtggaacct tttcggctcc tctgccgatc catactgcgg aactcctagc cgcttgtttt    5940
gctcgcagca ggtctggagc aaacattatc gggactgata actctgttgt cctatcccgc    6000
aaatatacat cgtttccatg ctgctaggc tgtgctgcca actggatcct gcgcgggacg    6060
tcctttgttt acgtcccgtc ggcgctgaat cctgcggacg acccttctcg gggtcgcttg    6120
ggactctctc gtccccttct ccgtctgccg ttccgaccga ccacgggcg cacctctctt    6180 tacgcggact ccccgtctgt gccttctcat ctgccggacc gtgtgcactt cgcttcacct    6240
ctgcacgtcg catggagacc accgtgaacg cccaccaaat attgcccaag gtcttacata    6300
agaggactct tggactctca gcaatgtcaa cgaccgacct tgaggcatac ttcaaagact    6360
gtttgtttaa agactgggag gagttggggg aggagattag gttaaaggtc tttgtactag    6420
gaggctgtag gcataaattg gtctgcgcac cagcaccatg gcgcaatcac tagagcgggg    6480
tacctttaag accaatgact tacaaggcag ctgtagatct tagccacttt ttaaaagaaa    6540
```

-continued

```
aggggggact ggaagggcta attcactccc aacgaagaca agatctgctt tttgcttgta   6600
ctgggtctct ctggttagac cagatctgag cctgggagct ctctggctaa ctagggaacc   6660
cactgcttaa gcctcaataa agcttgcctt gagtgcttca agtagtgtgt gcccgtctgt   6720
tgtgtgactc tggtaactag agatccctca gaccctttta gtcagtgtgg aaaatctcta   6780
gcagtagtag ttcatgtcat cttattattc agtatttata acttgcaaag aaatgaatat   6840
cagagagtga gaggaacttg tttattgcag cttataatgg ttacaaataa agcaatagca   6900
tcacaaattt cacaaataaa gcattttttt cactgcattc tagttgtggt ttgtccaaac   6960
tcatcaatgt atcttatcat gtctggctct agctatcccg cccctaactc cgcccatccc   7020
gcccctaact ccgcccagtt ccgcccattc tccgccccat ggctgactaa ttttttttat   7080
ttatgcagag gccgaggccg gatcccttga gtggctttca tcctggagca gactttgcag   7140
tctgtggact gcaacacaac attgccttta tgtgtaactc ttggctgaag ctcttacacc   7200
aatgctgggg gacatgtacc tcccaggggc ccaggaagac tacgggaggc tacaccaacg   7260
tcaatcagag gggcctgtgt agctaccgat aagcggaccc tcaagagggc attagcaata   7320
gtgtttataa ggcccccttg ttaattcttg aagacgaaag ggcctcgtga tacgcctatt   7380
tttataggtt aatgtcatga taataatggt ttcttagacg tcaggtggca cttttcgggg   7440
aaatgtgcgc ggaacccta tttgtttatt tttctaaata cattcaaata tgtatccgct   7500
catgagacaa taaccctgat aaatgcttca ataatattga aaaaggaaga gtatgagtat   7560
tcaacatttc cgtgtcgccc ttattccctt ttttgcggca ttttgccttc ctgtttttgc   7620
tcacccagaa acgctggtga aagtaaaaga tgctgaagat cagttgggtg cacgagtggg   7680
ttacatcgaa ctggatctca acagcggtaa gatccttgag agttttcgcc ccgaagaacg   7740
ttttccaatg atgagcactt ttaaagttct gctatgtggc gcggtattat cccgtgttga   7800
cgccgggcaa gagcaactcg gtcgccgcat acactattct cagaatgact tggttgagta   7860
ctcaccagtc acagaaaagc atcttacgga tggcatgaca gtaagagaat tatgcagtgc   7920
tgccataacc atgagtgata acactgcggc caacttactt ctgacaacga tcggaggacc   7980
gaaggagcta accgcttttt tgcacaacat ggggggatcat gtaactcgcc ttgatcgttg   8040
ggaaccggag ctgaatgaag ccataccaaa cgacgagcgt gacaccacga tgcctgcagc   8100
aatggcaaca acgttgcgca aactattaac tggcgaacta cttactctag cttcccggca   8160
acaattaata gactggatgg aggcggataa agttgcagga ccacttctgc gctcggccct   8220
tccggctggc tggtttattg ctgataaatc tggagccggt gagcgtgggt ctcgcggtat   8280
cattgcagca ctggggccag atggtaagcc ctcccgtatc gtagttatct acacgacggg   8340
gagtcaggca actatggatg aacgaaatag acagatcgct gagataggtg cctcactgat   8400
taagcattgg taactgtcag accaagttta ctcatatata ctttagattg atttaaaact   8460
tcatttttaa tttaaaagga tctaggtgaa gatccttttt gataatctca tgaccaaaat   8520
cccttaacgt gagttttcgt tccactgagc gtcagacccc gtagaaaaga tcaaaggatc   8580
ttcttgagat cctttttttc tgcgcgtaat ctgctgcttg caaacaaaaa aaccaccgct   8640
accagcggtg gtttgtttgc cggatcaaga gctaccaact ctttttccga aggtaactgg   8700
cttcagcaga gcgcagatac caaatactgt ccttctagtg tagccgtagt taggccacca   8760
cttcaagaac tctgtagcac cgcctacata cctcgctctg ctaatcctgt taccagtggc   8820
tgctgccagt ggcgataagt cgtgtcttac cgggttggac tcaagacgat agttaccgga   8880
```

```
taaggcgcag cggtcgggct gaacggggggg ttcgtgcaca cagcccagct tggagcgaac   8940
gacctacacc gaactgagat acctacagcg tgagcattga gaaagcgcca cgcttcccga   9000
agggagaaag gcggacaggt atccggtaag cggcagggtc ggaacaggag agcgcacgag   9060
ggagcttcca gggggaaacg cctggtatct ttatagtcct gtcgggtttc gccacctctg   9120
acttgagcgt cgatttttgt gatgctcgtc agggggggcgg agcctatgga aaaacgccag   9180
caacgcggcc tttttacggt tcctggcctt ttgctggcct ttttgaagct gtccctgatg   9240
gtcgtcatct acctgcctgg acagcatggc ctgcaacgcg ggcatcccga tgccgccgga   9300
agcgagaaga atcataatgg ggaaggccat ccagcctcgc gtcg            9344
```

```
<210> SEQ ID NO 39
<211> LENGTH: 6924
<212> TYPE: DNA
<213> ORGANISM: Artificial Sequence
<220> FEATURE:
<223> OTHER INFORMATION: pLenti-C-Myc-DDK OX40L

<400> SEQUENCE: 39
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat cgcgttgaca    240
ttgattattg actagttatt aatagtaatc aattacgggg tcattagttc atagcccata    300
tatggagttc cgcgttacat aacttacggt aaatggcccg cctggctgac cgcccaacga    360
cccccgccca ttgacgtcaa taatgacgta tgttcccata gtaacgccaa tagggacttt    420
ccattgacgt caatgggtgg agtatttacg gtaaactgcc cacttggcag tacatcaagt    480
gtatcatatg ccaagtacgc cccctattga cgtcaatgac ggtaaatggc ccgcctggca    540
ttatgcccag tacatgacct tatgggactt tcctacttgg cagtacatct acgtattagt    600
catcgctatt accatggtga tgcggttttg gcagtacatc aatgggcgtg atagcggtt    660 tgactcacgg ggatttccaa gtctccaccc cattgacgtc aatgggagtt tgttttggca    720
ccaaaatcaa cgggactttc caaaatgtcg taacaactcc gccccattga cgcaaatggg    780
cggtaggcgt gtacggtggg aggtctatat aagcagcgcg ttttgcctgt actgggtctc    840
tctggttaga ccagatctga gcctgggagc tctctggcta actagggaac ccactgctta    900
agcctcaata aagcttgcct tgagtgcttc aagtagtgtg tgcccgtctg ttgtgtgact    960
ctggtaacta gagatccctc agacccttt agtcagtgtg gaaaatctct agcagtggcg   1020
cccgaacagg gacttgaaag cgaaagggaa accagaggag ctctctcgac gcaggactcg   1080
gcttgctgaa gcgcgcacgg caagaggcga ggggcggcga ctggtgagta cgccaaaaat   1140
tttgactagc ggaggctaga aggagagaga tgggtgcgag agcgtcagta ttaagcgggg   1200
gagaattaga tcgcgatggg aaaaaattcg gttaaggcca ggggaaaga aaaaatataa   1260 attaaaacat atagtatggg caagcaggga gctagaacga ttcgcagtta atcctggcct   1320
gttagaaaca tcagaaggct gtagacaaat actgggacag ctacaaccat cccttcagac   1380
aggatcagaa gaacttagat cattatataa tacagtagca accctctatt gtgtgcatca   1440
aaggatagag ataaaagaca ccaaggaagc tttagacaag atagaggaag agcaaaacaa   1500
aagtaagacc accgcacagc aagcggccgg ccgctgatct tcagacctgg aggaggagat   1560
atgagggaca attggagaag tgaattatat aaatataaag tagtaaaaat tgaaccatta   1620
```

-continued

```
ggagtagcac ccaccaaggc aaagagaaga gtggtgcaga gagaaaaaag agcagtggga     1680
ataggagctt tgttccttgg gttcttggga gcagcaggaa gcactatggg cgcagcgtca     1740
atgacgctga cggtacaggc cagacaatta ttgtctggta tagtgcagca gcagaacaat     1800
ttgctgaggg ctattgaggc gcaacagcat ctgttgcaac tcacagtctg gggcatcaag     1860
cagctccagg caagaatcct ggctgtggaa agatacctaa aggatcaaca gctcctgggg     1920 atttgggggtt gctctggaaa actcatttgc accactgctg tgccttggaa tgctagttgg     1980
agtaataaat ctctggaaca gatttggaat cacacgacct ggatggagtg ggacagagaa     2040
attaacaatt acacaagctt aatacactcc ttaattgaag aatcgcaaaa ccagcaagaa     2100
aagaatgaac aagaattatt ggaattagat aaatgggcaa gtttgtggaa ttggtttaac     2160
ataacaaatt ggctgtggta tataaaatta ttcataatga tagtaggagg cttggtaggt     2220
ttaagaatag tttttgctgt actttctata gtgaatagag ttaggcaggg atattcacca     2280
ttatcgtttc agacccacct cccaaccccg aggggacccg acaggcccga aggaatagaa     2340
gaagaaggtg gagagagaga cagagacaga tccattcgat tagtgaacgg atcggcactg     2400
cgtgcgccaa ttctgcagac aaatggcagt attcatccac aattttaaaa gaaaaggggg     2460 gattggggggg tacagtgcag gggaaagaat agtagacata atagcaacag acatacaaac     2520
taaagaatta caaaaacaaa ttacaaaaat tcaaaatttt cgggtttatt acagggacag     2580
cagagatcca gtttggttag taccgggccc gctctagaca tgtccaatat gaccgccatg     2640
ttgacattga ttattgacta gttattaata gtaatcaatt acgggggtcat tagttcatag     2700 cccatatatg gagttccgcg ttacataact tacggtaaat ggcccgcctg gctgaccgcc     2760
caacgacccc cgcccattga cgtcaataat gacgtatgtt cccatagtaa cgccaatagg     2820
gactttccat tgacgtcaat gggtggagta tttacggtaa actgcccact ggcagtaca     2880 tcaagtgtat catatgccaa gtccgccccc tattgacgtc aatgacggta aatggcccgc     2940
ctggcattat gcccagtaca tgaccttacg ggactttcct acttggcagt acatctacgt     3000
attagtcatc gctattacca tggtgatgcg gttttggcag tacaccaatg ggcgtggata     3060
gcggtttgac tcacggggat ttccaagtct ccaccccatt gacgtcaatg ggagtttgtt     3120
ttggcaccaa aatcaacggg actttccaaa atgtcgtaat aaccccgccc cgttgacgca     3180
aatgggcggt aggcgtgtac ggtgggaggt ctatataagc agagctcgtt tagtgaaccg     3240
tcagaatttt gtaatacgac tcactatagg gcggccggga attcgtcgac tggatccggt     3300
accgaggaga tctgccgccg cgatcgccat ggaaagggtc caacccctgg aagagaatgt     3360
gggaaatgca gccaggccaa gattcgagag gaacaagcta ttgctggtgg cctctgtaat     3420
tcagggactg gggctgctcc tgtgcttcac ctacatctgc ctgcacttct ctgctcttca     3480
ggtatcacat cggtatcctc gaattcaaag tatcaaagta caatttaccg aatataagaa     3540
ggagaaaggt ttcatcctca cttcccaaaa ggaggatgaa atcatgaagg tgcagaacaa     3600
ctcagtcatc atcaactgtg atgggttta tctcatctcc ctgaagggct acttctccca     3660
ggaagtcaac attagccttc attaccagaa ggatgaggag cccctcttcc aactgaagaa     3720
ggtcaggtct gtcaactcct tgatggtggc ctctctgact tacaaagaca aagtctactt     3780
gaatgtgacc actgacaata cctccctgga tgacttccat gtgaatggcg gagaactgat     3840
tcttatccat caaaatcctg gtgaattctg tgtccttacg cgtacgcggc cgctcgagca     3900
gaaactcatc tcagaagagg atctggcagc aaatgatatc ctggattaca aggatgacga     3960
```

-continued

```
cgataaggtt taaacggccg gccgcggtct gtacaagtag gattcgtcga gggacctaat      4020
aacttcgtat agcatacatt atacgaagtt atacatgttt aagggttccg gttccactag      4080
gtacaattcg atatcaagct tatcgataat caacctctgg attacaaaat ttgtgaaaga      4140
ttgactggta ttcttaacta tgttgctcct tttacgctat gtggatacgc tgctttaatg      4200
cctttgtatc atgctattgc ttcccgtatg gctttcattt tctcctcctt gtataaatcc      4260
tggttgctgt ctctttatga ggagttgtgg cccgttgtca ggcaacgtgg cgtggtgtgc      4320
actgtgtttg ctgacgcaac ccccactggt tggggcattg ccaccacctg tcagctcctt      4380
tccgggactt tcgctttccc cctccctatt gccacggcgg aactcatcgc cgcctgcctt      4440
gcccgctgct ggacaggggc tcggctgttg ggcactgaca attccgtggt gttgtcgggg      4500
aaatcatcgt cctttccttg gctgctcgcc tgtgttgcca cctggattct gcgcgggacg      4560
tccttctgct acgtcccttc ggccctcaat ccagcggacc ttccttcccg cggcctgctg      4620
ccggctctgc ggcctcttcc gcgtcttcgc cttcgccctc agacgagtcg gatctccctt      4680
tgggccgcct ccccgcatcg ataccgtcga cctcgatcga gacctagaaa aacatggagc      4740
aatcacaagt agcaatacag cagctaccaa tgctgattgt gcctggctag aagcacaaga      4800
ggaggaggag gtgggttttc cagtcacacc tcaggtacct ttaagaccaa tgacttacaa      4860
ggcagctgta gatcttagcc actttttaaa agaaaagggg ggactggaag ggctaattca      4920
ctcccaacga agacaagata tccttgatct gtggatctac cacacacaag gctacttccc      4980
tgattggcag aactacacac cagggccagg gatcagatat ccactgacct ttggatggtg      5040
ctacaagcta gtaccagttg agcaagagaa ggtagaagaa gccaatgaag gagagaacac      5100
ccgcttgtta caccctgtga gcctgcatgg gatggatgac ccggagagag aagtattaga      5160
gtggaggttt gacagccgcc tagcatttca tcacatggcc cgagagctgc atccggactg      5220
tactgggtct ctctggttag accagatctg agcctgggag ctctctggct aactagggaa      5280
cccactgctt aagcctcaat aaagcttgcc ttgagtgctt caagtagtgt gtgcccgtct      5340
gttgtgtgac tctggtaact agagatccct cagacccttt tagtcagtgt ggaaaatctc      5400
tagcagcatg tgagcaaaag gccagcaaaa ggccaggaac cgtaaaaagg ccgcgttgct      5460
ggcgtttttc cataggctcc gcccccctga cgagcatcac aaaaatcgac gctcaagtca      5520
gaggtggcga aacccgacag gactataaag ataccaggcg tttccccctg gaagctccct      5580
cgtgcgctct cctgttccga ccctgccgct taccggatac ctgtccgcct ttctcccttc      5640
gggaagcgtg cgctttctc atagctcacg ctgtaggtat ctcagttcgg tgtaggtcgt      5700
tcgctccaag ctgggctgtg tgcacgaacc ccccgttcag cccgaccgct cgccttatc      5760 cggtaactat cgtcttgagt ccaacccggt aagacacgac ttatcgccac tggcagcagc      5820
cactggtaac aggattagca gagcgaggta tgtaggcggt gctacagagt tcttgaagtg      5880
gtggcctaac tacggctaca ctagaagaac agtatttggt atctgcgctc tgctgaagcc      5940
agttaccttc ggaaaaagag ttggtagctc ttgatccggc aaacaaacca ccgctggtag      6000
cggtggtttt tttgtttgca agcagcagat tacgcgcaga aaaaaaggat ctcaagaaga      6060
tcctttgatc ttttctacgg ggtctgacgc tcagtggaac gaaaactcac gttaagggat      6120
tttggtcatg attacgcccc gccctgccac tcatcgcagt actgttgtaa ttcattaagc      6180
attctgccga catggaagcc atcacaaacg gcatgatgaa cctgaatcgc cagcggcatc      6240
agcaccttgt cgccttgcgt ataatatttg cccatggtga aaacgggggc gaagaagttg      6300
tccatattgg ccacgtttaa atcaaaactg gtgaaactca cccagggatt ggctgagacg      6360
```

-continued

```
aaaaacatat tctcaataaa ccctttaggg aaataggcca ggttttcacc gtaacacgcc    6420
acatcttgcg aatatatgtg tagaaactgc cggaaatcgt cgtggtattc actccagagc    6480
gatgaaaacg tttcagtttg ctcatggaaa acggtgtaac aagggtgaac actatcccat    6540
atcaccagct caccgtcttt cattgccata cggaactccg gatgagcatt catcaggcgg    6600
gcaagaatgt gaataaaggc cggataaaac ttgtgcttat ttttctttac ggtctttaaa    6660
aaggccgtaa tatccagctg aacggtctgg ttataggtac attgagcaac tgactgaaat    6720
gcctcaaaat gttctttacg atgccattgg gatatatcaa cggtggtata tccagtgatt    6780 ttttctcca tactcttcct ttttcaatat tattgaagca tttatcaggg ttattgtctc    6840
atgagcggat acatatttga atgtatttag aaaaataaac aaataggggt cccgcgcaca    6900
tttccccgaa aagtgccacc tgac    6924
```

```
<210> SEQ ID NO 40
<211> LENGTH: 39
<212> TYPE: DNA
<213> ORGANISM: Artificial Sequence
<220> FEATURE:
<223> OTHER INFORMATION: Tel-1b primer

<400> SEQUENCE: 40
cggtttgttt gggtttgggt ttgggtttgg gtttgggtt                               39

<210> SEQ ID NO 41
<211> LENGTH: 39
<212> TYPE: DNA
<213> ORGANISM: Artificial Sequence
<220> FEATURE:
<223> OTHER INFORMATION: Tel-2b primer

<400> SEQUENCE: 41
ggcttgcctt acccttaccc ttacccttac ccttaccct                               39

<210> SEQ ID NO 42
<211> LENGTH: 27
<212> TYPE: DNA
<213> ORGANISM: Artificial Sequence
<220> FEATURE:
<223> OTHER INFORMATION: hgb1 primer

<400> SEQUENCE: 42
gcttctgaca caactgtgtt cactagc                                            27

<210> SEQ ID NO 43
<211> LENGTH: 23
<212> TYPE: DNA
<213> ORGANISM: Artificial Sequence
<220> FEATURE:
<223> OTHER INFORMATION: hgb2 primer

<400> SEQUENCE: 43
caccaacttc atccacgttc acc                                                23
```

1

ENGINEERED ARTIFICIAL ANTIGEN PRESENTING CELLS FOR TUMOR INFILTRATING LYMPHOCYTE EXPANSION

CROSS-REFERENCE TO RELATED APPLICATIONS

This application is a continuation of U.S. patent application Ser. No. 16/526,353, filed on Jul. 30, 2019, which is a continuation of U.S. patent application Ser. No. 15/800,967, filed Nov. 1, 2017, which is a continuation of International Application No. PCT/US17/59271, filed Oct. 31, 2017, which claims the benefit of priority to U.S. Provisional Application No. 62/481,831, filed Apr. 5, 2017, U.S. Provisional Application No. 62/475,053, filed Mar. 22, 2017, U.S. Provisional Application No. 62/438,600, filed Dec. 23, 2016, and U.S. Provisional Application No. 62/415,274, filed Oct. 31, 2016, the entireties of which are incorporated herein by reference.

FIELD OF THE INVENTION

Engineered artificial antigen presenting cells (aAPCs) for expansion of tumor infiltrating lymphocytes are disclosed.

BACKGROUND OF THE INVENTION

Treatment of bulky, refractory cancers using adoptive autologous transfer of tumor infiltrating lymphocytes (TILs) represents a powerful approach to therapy for patients with poor prognoses. Gattinoni, et al, *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al, *Science* 2002, 298, 850-54; Dudley, et al, *J. Clin. Oncol.* 2005, 23, 2346-57; Dudley, et al, *J. Clin. Oncol.* 2008, 26, 5233-39; Riddell, et al, *Science* 1992, 257, 238-41; Dudley, et al, *J. Immunother.* 2003, 26, 332-42. However, although REP can result in a 1,000-fold expansion of TILs over a 14-day period, it requires a large excess {e.g., 200-fold) of irradiated allogeneic peripheral blood mononuclear cells (PBMCs), often from multiple donors, as feeder cells, as well as anti-CD3 antibody (OKT-3) and high doses of IL-2. Dudley, et al, *J. Immunother.* 2003, 26, 332-42. Despite their high performance, PBMCs have multiple drawbacks, including the large numbers of allogeneic PBMCs required, the need to obtain PBMCs by leukapheresis from multiple healthy donors, the resulting interdonor variability in PBMC viability after cryopreservation and variable TIL expansion results, the risk of undetected viral pathogens causing downstream patient infections, and the extensive and costly laboratory testing of each individual donor cell product to confirm sterility and quality (including viral contaminant testing) and to test expansion properties.

Unfortunately, aAPCs developed for use in the expansion of TILs have suffered from poor performance when compared to PBMCs, including alterations of the phenotypic properties of the input TILs, as well as poor expansion performance and/or high variability in expansion results. Because of the large number of potential cells that might be adapted for use as aAPCs and the unpredictability of identifying suitable candidates, the focus of aAPC development for polyclonal TILs to date has been solely on the well-established K562 cell line. Butler and Hirano, *Immunol. Rev.* 2014, 257, 191-209. For example, K562 cells modified to express 4-1BBL (CD137L) were tested in pre-REP culture (but not in REP culture) to determine enhancement of TIL expansion from tumor digest, but PBMCs were still required to be used in conjunction with K562 cells to obtain TIL expansion. Friedman, et al., *J. Immunother.* 2011, 34, 651-661. Other engineered K562 cells modified to express CD64, CD86, and 4-1BBL were tested and achieved TIL expansion that was at best comparable to PBMCs, and most likely less than PBMCs, and also suffered from skewing of the polyclonal TIL phenotype to a less favorable $CD8^+/CD4^+$ T cell ratio. Ye, et al., *J. Translat. Med.* 2011, 9, 131. Recently, K562 cells modified to express CD86, 4-1BBL (CD137L), high affinity Fc receptor (CD64) and membrane-bound IL-15 have also been shown to propagate TIL (post-REP) at equivalent numbers compared to PBMC feeders, but with the additional complexity of membrane-bound IL-15. Forget, et al., *J. Immunother.* 2014, 37, 448-60. Other systems developed have lacked critical costimulatory molecules, have led to unfavorable T cell phenotypic skewing, or have required additional interleukins (such as IL-21). Butler and Hirano, *Immunol. Rev.* 2014, 257, 191-209. Overall, K562 modified aAPCs have not been shown to provide for consistent expansion of TILs with acceptable variability while also performing better than PBMCs in other measures including overall expansion cell counts. Alternative aAPCs besides K562 cells have been successful in other cell expansion methods, but have not achieved the same performance as PBMCs with the unique polyclonal subset of cells that make up TILs. Maus, et al, *Nat. Biotechnol.* 2002, 20, 143-148; Suhoski, et al., *Mol. Ther.* 2007, 15, 981-988.

The MOLM-14 human leukemia cell line was established from the peripheral blood of a patient with relapsed acute monocytic leukemia, and initial phenotypic characterization indicated the presence of at least the following markers: CD4, CD9, CD1 1a, CD13, CD14, CD15, CD32, CD33, CD64, CD65, CD87, CD92, CD93, CD1 16, CD1 18, and CD155. Matsuo, et al., *Leukemia* 1997, 11, 1469-77. Additional phenotypic characterization of MOLM-14 found higher levels of HLA-AB/C, CD64, CD80, ICOS-L, CD58, and lower levels of CD86. MOLM-14 cells and the closely-related MOLM-13 cells have not been previously reported as useful aAPCs for the expansion of cells for tumor immunotherapy applications.

The EM-3 human cell line was established from the bone marrow of a patient with Philadelphia chromosome-positive CML. Konopka, et al., *Proc. Nat'l Acad. Sci. USA* 1985, 82, 1810-4. EM-3 cells and the closely-related EM-2 cell line have not been previously reported as useful aAPCs for the expansion of cells for tumor immunotherapy applications. Phenotypic characterization for EM-3 cells indicates the presence of at least the following markers: CD13, CD15, and CD33.

The present invention provides the unexpected finding that engineered myeloid lineage cells, including MOLM-13, MOLM-14, EM-3, and EM-2 cells, transduced with additional costimulatory molecules, including CD86 (B7-2), 4-1BBL (CD137L), and OX40L (CD134L), provide for superior and highly efficient expansions of TILs in large numbers with minimal variability, reduced cost, and no reliance on human blood samples as a source of PBMCs, with the benefit of using an aAPC which can be produced efficiently from a master cell bank. CD86 and 4-1BBL are costimulatory molecules that provide costimulatory signals for T cell activation. The MOLM-14, MOLM-13, EM-3, and/or EM-2 cells transduced with additional costimulatory molecules are useful, for example, in the expansion of TILs for use in cancer immunotherapy and other therapies.

SUMMARY OF THE INVENTION

In an embodiment, the invention provides an artificial antigen presenting cell (aAPC) comprising a myeloid cell transduced with one or more vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein.

In an embodiment, each of the CD86 protein and the 4-1BBL protein are human proteins.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC can stimulate and expand a tumor infiltrating lymphocyte (TIL) contacted with the aAPC.

It will be apparent that in certain embodiments of the invention, the nucleic acid molecule encoding CD86 may be comprised in a different viral vector to the nucleic acid molecule encoding 4-1BBL or the same viral vector.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC expands a population of TILs by at least 50-fold over a period of 7 days in a cell culture medium comprising IL-2 at a concentration of about 3000 IU/mL and OKT-3 antibody at a concentration of about 30 ng/mL.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the aAPC can stimulate and expand a T cell contacted with the aAPC.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell endogenously expresses HLA-A/B/C, ICOS-L, and CD58.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is essentially devoid of membrane-bound IL-15.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a MOLM-14 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a MOLM-13 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a EM-3 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the myeloid cell is a EM-2 cell.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the CD86 protein comprises an amino acid sequence as set forth in SEQ ID NO:8, or an amino acid sequence comprising one or more conservative amino acid substitutions thereof, and the 4-1BBL protein comprises SEQ ID NO:9, or an amino acid sequence comprising one or more conservative amino acid substitutions thereof.

In an embodiment, the invention provides an aAPC comprising a myeloid cell transduced with one or more viral vectors, wherein the one or more viral vectors comprise a nucleic acid molecule encoding CD86 and a nucleic acid molecule encoding 4-1BBL, and wherein the myeloid cell expresses a CD86 protein and a 4-1BBL protein, wherein the nucleic acid molecule encoding CD86 comprises a nucleic acid sequence as set forth in SEQ ID NO: 16 and the nucleic acid molecule encoding 4-1BBL comprises a nucleic acid sequence as set forth in SEQ ID NO: 19.

In an embodiment, the invention provides a method of expanding tumor infiltrating lymphocytes (TILs), the method comprising the step of contacting a population of TILs with an aAPC comprising a myeloid cell transduced with one or more viral vectors, wherein the one or more viral vectors comprise a nucleic acid molecule encoding CD86 and a nucleic acid molecule encoding 4-1BBL, wherein the myeloid cell expresses a CD86 protein and a 4-1BBL protein, and wherein the population of TILs is expanded. In an embodiment, the method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the cell culture medium further comprises IL-2 at an initial concentration of about 3000 IU/mL and OKT-3 antibody at an initial concentration of about 30 ng/mL.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the population of APCs expands the population of TILs by at least 50-fold over a period of 7 days in a cell culture medium.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the myeloid cell endogenously expresses HLA-A/B/C, ICOS-L, and CD58.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the myeloid cell is a MOLM-14 cell.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the myeloid cell is a MOLM-13 cell.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the myeloid cell is a EM-3 cell.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the myeloid cell is a EM-2 cell.

In an embodiment, the foregoing method is an in vitro or an ex vivo method.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid molecule encoding CD86 and a nucleic acid molecule encoding 4-1BBL, and wherein the myeloid cell expresses a CD86 protein and a 4-1BBL protein, and (b) contacting the population of TILs with the population of aAPCs in a cell culture medium, wherein the CD86 protein comprises an amino acid sequence as set forth in SEQ ID NO:8, or comprises an amino acid sequence comprising one or more conservative amino acid substitutions thereof, and the 4-1BBL protein comprises an amino acid sequence as set forth in SEQ ID NO:9, or comprises an amino acid sequence comprising one or conservative amino acid substitutions thereof.

7

8

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the nucleic acid encoding CD86 comprises a nucleic acid sequence as set forth in SEQ ID NO: 16 and the nucleic acid encoding 4-1BBL comprises a nucleic acid sequence as set forth in SEQ ID NO: 19.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the expansion is performed using a gas permeable container.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is between 1 to 200 and 1 to 400.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is about 1 to 300.

In an embodiment, the invention provides a method of expanding tumor infiltrating lymphocytes (TILs), the method comprising contacting a population of TILs comprising a population of TILs with a myeloid artificial antigen presenting cell (aAPC), wherein the myeloid aAPC comprises at least two co-stimulatory ligands that specifically bind with at least two co-stimulatory molecules on the TILs, wherein binding of the co-stimulatory molecules with the co-stimulatory ligand induces proliferation of the TILs, thereby specifically expanding TILs, and wherein the at least two co-stimulatory ligands comprise CD86 and 4-1BBL. In an embodiment, the foregoing method is an in vitro or ex vivo method.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-A/B/C, ICOS-L, and CD58, and wherein the myeloid aAPCs are transduced to express a CD86 protein and a 4-1BBL protein.

In an embodiment, the invention provides a population of tumor infiltrating lymphocytes (TILs) for use in treating cancer, wherein the TILs are a second population of TILs and are obtainable from a method comprising the steps of:

(a) performing a rapid expansion of a first population of TILs using a population of myeloid artificial antigen presenting cells (myeloid aAPCs) in a cell culture medium to obtain the second population of TILs, wherein the TILs are/have been obtained from a tumor resected from a patient, and wherein the second population of TILs is at least 50-fold greater in number than the first population of TILs after 7 days from the start of the rapid expansion; and wherein the myeloid aAPCs endogenously expresses HLA-AB/C, ICOS-L, and CD58, and wherein the myeloid aAPCs are transduced to express a CD86 protein and a 4-1BBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-AB/C, ICOS-L, and CD58, wherein the myeloid aAPCs are transduced to express a CD86 protein and a 4-1BBL protein, wherein the myeloid aAPCs comprise MOLM-14 cells transduced with one or more viral vectors, and wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a population of tumor infiltrating cells (TILs) for use in treating a cancer, wherein the population of TILs is a second population of TILs and is obtainable by a process comprising:

(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, wherein the second population of TILs is at least 50-fold greater in number than the first population of TILs after 7 days from the start of the rapid expansion;

wherein the myeloid aAPCs endogenously expresses HLA-AB/C, ICOS-L, and CD58, wherein the myeloid aAPCs are transduced to express a CD86 protein and a 4-lBBL protein, wherein the myeloid aAPCs comprise MOLM-14 cells transduced with one or more viral vectors, and wherein the one or more viral vectors comprise a nucleic acid encoding CD86 and a nucleic acid encoding 4-lBBL, and wherein the MOLM-14 cells express a CD86 protein and a 4-lBBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-AB/C, ICOS-L, and CD58, wherein the myeloid aAPCs are transduced to express a CD86 protein and a 4-lBBL protein, wherein the myeloid aAPCs comprise EM-3 cells transduced with one or more viral vectors, and wherein the one or more viral vectors comprise a nucleic acid encoding CD86 and a nucleic acid encoding 4-lBBL, and wherein the EM-3 cells express a CD86 protein and a 4-1BBL protein.

In an embodiment, the invention provides a population of tumor infiltrating lymphocytes (TILs) for use in treating a cancer, the population of TILs being a second population of TILs and obtainable by a process comprising:

(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and wherein the myeloid aAPCs endogenously expresses HLA-AB/C, ICOS-L, and CD58, wherein the myeloid aAPCs are transduced to express a CD86 protein and a 4-lBBL protein, wherein the myeloid aAPCs comprise EM-3 cells transduced with one or more viral vectors, and wherein the one or more viral vectors comprise a nucleic acid encoding CD86 and a nucleic acid encoding 4-lBBL, and wherein the EM-3 cells express a CD86 protein and a 4-1BBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-AB/C, ICOS-L, and CD58, wherein the myeloid aAPCs are transduced to express a CD86 protein and a 4-lBBL protein, and wherein the rapid expansion is performed over a period not greater than 14 days.

In an embodiment, the invention provides a population of tumor infiltrating lymphocytes (TILs) for use in treating a cancer, wherein the population of TILs is a second population and is obtainable by a method comprising the steps of:

(a) performing a rapid expansion of the first population of TILs using a population of myeloid artificial antigen presenting cells (myeloid aAPCs) in a cell culture medium to obtain the second population of TILs, wherein the second population of TILs is at least 50-fold greater in number than the first population of TILs after 7 days from the start of the rapid expansion, wherein the myeloid aAPCs endogenously express HLA-AB/C, ICOS-L and CD58, wherein the myeloid aAPCs are transduced to express a CD86 protein and a 4-lBBL protein, and wherein the rapid expansion is performed over a period not greater than 14 days.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-AB/C, ICOS-L, and CD58, wherein the myeloid aAPCs are transduced to express a CD86 protein and a 4-lBBL protein, and wherein the cell culture medium further comprises IL-2 at an initial concentration of about 3000 IU/mL and OKT-3 antibody at an initial concentration of about 30 ng/mL.

In an embodiment, the invention provides a population of tumor infiltrating lymphocytes (TILs) for use in treating a cancer, the population of TILs being a second population of TILs and obtainable by a process comprising:

(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and wherein the myeloid aAPCs endogenously express HLA-A/B/C, ICOS-L, and CD58, wherein the myeloid aAPCs are transduced to express a CD86 protein and a 4-lBBL protein, and wherein the cell culture medium further comprises IL-2 at an initial concentration of about 3000 IU/mL and OKT-3 antibody at an initial concentration of about 30 ng/mL.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-lBBL protein, and wherein the expansion is performed using a gas permeable container.

In an embodiment, the invention provides a population of tumor infiltrating lymphocytes (TILs) for use in treating a cancer, the population of TILs being a second population of TILs and obtainable by a process comprising:

(a) performing a rapid expansion of a first population of TILs using a population of myeloid artificial antigen presenting cells (myeloid aAPCs) in a cell culture medium to obtain the second population of TILs, wherein the first population of TILs are/have been obtained from a tumor resected from a patient, and wherein the second population of TILs is at least 50-fold greater in number than the first population of TILs after 7 days from the start of the rapid expansion; and wherein the myeloid aAPCs endogenously express HLA-AB/C, ICOS-L, and CD58, wherein the myeloid aAPCs are transduced to express a CD86 protein and a 4-lBBL protein, and wherein the expansion is performed using a gas permeable container.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-AB/C, ICOS-L, and CD58, wherein the myeloid aAPCs are transduced to express a CD86 protein and a 4-lBBL protein, and wherein the ratio of the second population of TILs to the population of aAPCs is between 1 to 200 and 1 to 400.

In an embodiment, the invention provides a population of tumor infiltrating cells (TILs) for use in treating a cancer, the population of TILs being a second population of TILs and obtainable by a process comprising the steps of:

(a) performing a rapid expansion of a first population of TILs using a population of myeloid artificial antigen presenting cells (myeloid aAPCs) in a cell culture medium to obtain the second population of TILs, wherein the first population of TILs is/has been obtained from a tumor resected from a patient, and wherein the second population of TILs is at least 50-fold greater in number than the first population of TILs after 7 days from the start of the rapid expansion; and wherein the myeloid aAPCs endogenously expresses HLA-A/B/C, ICOS-L, and CD58, wherein the myeloid aAPCs are transduced to express a CD86 protein and a 4-lBBL protein, and wherein the ratio of the second population of TILs to the population of aAPCs is between 1 to 200 and 1 to 400. In certain embodiments, the ratio of the second population of TILs to the population of aAPCs is about 1 to 300.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-lBBL protein, and wherein the ratio of the second population of TILs to the population of aAPCs is about 1 to 300.

In an embodiment, the invention provides a method of treating a cancer with a population of tumor infiltrating lymphocytes (TILs) comprising the steps of:

(a) obtaining a first population of TILs from a tumor resected from a patient;

(b) performing a rapid expansion of the first population of TILs using a population of myeloid artificial antigen presenting cells (myeloid aAPCs) in a cell culture medium to obtain a second population of TILs, wherein the second population of TILs is at least 50-fold greater in number than the first population of TILs after 7 days from the start of the rapid expansion; and (c) administering a therapeutically effective portion of the second population of TILs to a patient with the cancer; wherein the myeloid aAPCs endogenously expresses HLA-A/B/C, ICOS-L, and CD58, wherein the myeloid aAPCs are transduced to express a CD86 protein and a 4-lBBL protein, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a population of tumor infiltrating lymphocytes (TILs) for use in treating a cancer, the population of TILs being a second population of TILs and obtainable by a method comprising the steps of:

(a) performing a rapid expansion of a first population of TILs using a population of myeloid artificial antigen presenting cells (myeloid aAPCs) in a cell culture medium to obtain the second population of TILs, wherein the first population of TILs is/has been obtained from a tumor resected from a patient, and wherein the second population of TILs is at least 50-fold greater in number than the first population of TILs after 7 days from the start of the rapid expansion; and wherein the myeloid aAPCs endogenously expresses HLA-A/B/C, ICOS-L, and CD58, wherein the myeloid aAPCs are transduced to express a CD86 protein and a 4-1BBL protein, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a population of tumor infiltrating lymphocytes (TILs) for use in treating a cancer, wherein the population of TILs is a third population of TILs and obtainable by a method comprising the steps of:

(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;

(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3.

In an embodiment, the myeloid aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the myeloid cells comprise MOLM-13 cells transduced with one or more viral vectors, wherein the one or more viral vectors comprise a nucleic acid encoding CD86 and a nucleic acid encoding 4-1BBL, and wherein the MOLM-13 cells express a CD86 protein and a 4-1BBL protein. In certain embodiments, the myeloid cells comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein. In certain embodiments, the myeloid cells comprise EM-2 cells transduced with one or more viral vectors, wherein the one or more viral vectors comprise a nucleic acid encoding CD86 and a nucleic acid encoding 4-1BBL, and wherein the EM-2 cells express a CD86 protein and a 4-lBBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) treating the patient with a non-myeloablative lymphodepletion regimen, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days;

(e) administering a therapeutically effective portion of the third population of TILs to a patient with the cancer; and (f) treating the patient with a high-dose IL-2 regimen, wherein the high-dose IL-2 regimen comprises 600,000 or 720,000 IU/kg of aldesleukin administered as a 15-minute bolus intravenous infusion every eight hours until tolerance;

wherein the myeloid aAPCs comprise MOLM-14 cells transduced with one or more viral vectors, wherein the one or more viral vectors comprise a nucleic acid encoding CD86 and a nucleic acid encoding 4-lBBL, and wherein the MOLM-14 cells express a CD86 protein and a 4-lBBL protein.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) treating the patient with a non-myeloablative lymphodepletion regimen, wherein the non-myeloablative lymphodepletion regimen comprises the steps of administration of cyclophosphamide at a dose of 60 mg/m$^2$/day for two days followed by administration of fludarabine at a dose of 25 mg/m$^2$/day for five days;

(e) administering a therapeutically effective portion of the third population of TILs to a patient with the cancer; and (f) treating the patient with a high-dose IL-2 regimen, wherein the high-dose IL-2 regimen comprises 600,000 or 720,000 IU/kg of aldesleukin administered as a 15-minute bolus intravenous infusion every eight hours until tolerance;

wherein the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the invention provides a population of tumor infiltrating lymphocytes (TILs) for use in treating a cancer, wherein the population of TILs are a third population of TILs and obtainable by a method comprising the steps of:

(a) an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3;

and further wherein the population of TILs is for administration to a patient in combination with a non-myeloablative lymphodepletion regimen, wherein the non-myeloablative lymphodepletion regimen comprises cyclophosphamide which is for administration at a dose of 60 mg/m$^2$/day for two days followed by fludarabine which is for administration at a dose of 25 mg/m$^2$/day for five days and further wherein the population of TILs is for administration in combination with a high-dose IL-2 regimen, wherein the high-dose IL-2 regimen comprises 600,000 or 720,000 IU/kg of aldesleukin for administration as a 15-minute bolus intravenous infusion every eight hours until tolerance. In certain embodiments, the population of TILs is for administration prior to the high-dose IL-2 regimen and subsequent to the non-myeloablative lymphodepletion regimen.

In certain embodiments, the myeloid aAPCs comprise MOLM-14 cells transduced with one or more viral vectors, wherein the one or more viral vectors comprise a nucleic acid encoding CD86 and a nucleic acid encoding 4-lBBL, and wherein the MOLM-14 cells express a CD86 protein and a 4-lBBL protein. the myeloid aAPCs comprise MOLM-13 cells transduced with one or more viral vectors, wherein the one or more viral vectors comprise a nucleic acid encoding CD86 and a nucleic acid encoding 4-lBBL, and wherein the MOLM-13 cells express a CD86 protein and a 4-lBBL protein. In certain embodiments, the myeloid aAPCs comprise EM-3 cells transduced with one or more viral vectors, wherein the one or more viral vectors comprise a nucleic acid encoding CD86 and a nucleic acid encoding 4-1BBL, and wherein the EM-3 cells express a CD86 protein and a 4-1BBL protein.

In an embodiment, the population of TILs is for use in the treating of a cancer selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises JL-2 and OKT-3; and (d) administering a therapeutically effective portion of the third population of TILs to a patient with the cancer, wherein IL-2 is present at an initial concentration of about 3000 IU/mL and OKT-3 antibody is present at an initial concentration of about 30 ng/mL in the second cell culture medium.

In an embodiment, the invention provides a population of tumor infiltrating lymphocytes (TILs) for use in treating a cancer, wherein the population of TILs is a third population of TILs and is obtainable by a method comprising the steps:

(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein IL-2 is present at an initial concentration of about 3000 IU/mL and OKT-3 antibody is present at an initial concentration of about 30 ng/mL in the second cell culture medium.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and (d) administering a therapeutically effective portion of the third population of TILs to a patient with the cancer, wherein the rapid expansion is performed over a period not greater than 14 days.

In an embodiment, the invention provides a population of tumor infiltrating lymphocytes (TILs) for use in treating a cancer, wherein the population of TILs is a third population of TILs and is obtainable by a method comprising the steps:

(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2; and (b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein the rapid expansion is performed over a period not greater than 14 days.

In embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and (d) administering a therapeutically effective portion of the third population of TILs to a patient with the cancer, wherein the initial expansion is performed using a gas permeable container.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; and (d) administering a therapeutically effective portion of the third population of TILs to a patient with the cancer, wherein the rapid expansion is performed using a gas permeable container.

In an embodiment, the invention provides a population of tumor infiltrating lymphocytes (TILs) for use in treating a cancer, wherein the population of TILs is a third population of TILs and is obtainable by a method comprising the steps:

(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;

(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3; wherein the initial expansion and/or the rapid expansion is performed using a gas-permeable container.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the ratio of the second population of TILs to the population of aAPCs in the rapid expansion is between 1 to 80 and 1 to 400.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the ratio of the second population of TILs to the population of aAPCs in the rapid expansion is about 1 to 300.

In an embodiment, the invention provides a population of tumor infiltrating lymphocytes (TILs) for use in treating a cancer, wherein the population of TILs is a third population of TILs and is obtainable by a method comprising the steps:

(a) performing an initial expansion of a first population of TILs in a first cell culture medium to obtain a second population of TILs, wherein the first population of TILs is/has been obtained from a tumor resected from a patient, and wherein the second population of TILs is at least 5-fold greater in number than the first population of TILs, and wherein the first cell culture medium comprises IL-2;

(b) performing a rapid expansion of the second population of TILs using a population of myeloid artificial antigen presenting cells (aAPCs) in a second cell culture medium to obtain the third population of TILs, wherein the third population of TILs is at least 50-fold greater in number than the second population of TILs after 7 days from the start of the rapid expansion; and wherein the second cell culture medium comprises IL-2 and OKT-3, and wherein the ratio of the second population of TILs to the population of aAPCs in the rapid expansion is between 1 to 80 and 1 to 400.

In an embodiment, the the ratio of the second population of TILs to the population of aAPCs in the rapid expansion is about 1 to 300.

In an embodiment, the invention provides a method of treating a cancer with a population of tumor infiltrating lymphocytes (TILs) comprising the steps of:

(a) obtaining a first population of TILs from a tumor resected from a patient;

(b) performing an initial expansion of the first population of TILs in a first cell culture medium to obtain a second population of TILs, wherein the second population of TILs is at least 5-fold greater in number than the first population of TILs, and wherein the first cell culture medium comprises IL-2;

(c) performing a rapid expansion of the second population of TILs using a population of myeloid artificial antigen presenting cells (aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3;

(d) administering a therapeutically effective portion of the third population of TILs to a patient with the cancer, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma.

In an embodiment, the invention provides a kit for specifically inducing proliferation of a tumor infiltrating lymphocyte expressing a known co-stimulatory molecule, the kit comprising an effective amount of an aAPC, wherein said aAPC comprises a MOLM-14 cell or a EM-3 cell transduced using a lentiviral vector (LV), wherein the LV comprises a nucleic acid encoding at least one co-stimulatory ligand that specifically binds said known co-stimulatory molecule, wherein binding of the known co-stimulatory molecule with said co-stimulatory ligand stimulates and expands said T cell, the kit further comprising an applicator and an instructional material for the use of said kit.

In an embodiment, the invention provides a method for assessing the potency of tumor infiltrating lymphocytes (TILs) comprising the steps of:

(a) providing a plurality of mouse mastocytoma P815 cells expressing the endogenous CD 16 Fc receptor, wherein the P815 cells are transduced with a lentiviral vector based on enhanced green fluorescent protein (GFP) and Firefly Luciferase;

(b) co-culturing the plurality of P815 cells TILs with and without OKT-3 to assess T cell receptor (TCR) activation (specific killing) or lymphokine activated killing (LAK, non-specific killing), respectively;

(c) incubating for four hours;

(d) adding Luciferin and incubating for 5 minutes;

(e) reading bioluminescence intensity using a luminometer; and (f) and calculating percent cytotoxicity and survival.

BRIEF DESCRIPTION OF THE DRAWINGS

The foregoing summary, as well as the following detailed description of the invention, will be better understood when read in conjunction with the appended drawings.

FIG. 22 illustrates a sunburst visualization showing fine distribution of Live, T cell receptor (TCR) α/β, CD4, CD8, CD27, CD28, and CD57 TILs expanded with PBMC feeders.

FIG. 23 illustrates a sunburst visualization showing fine distribution of Live, TCR α/β, CD4, CD8, CD27, CD28, and CD57 TILs expanded with aMOLM14 aAPCs.

FIG. 44 illustrates a sunburst visualization to show fine distribution of Live, TCR α/β, CD4+, and CD8+ TILs expanded with aEM3 aAPCs or PBMC feeders (TIL batch M1054).

FIG. 45 illustrates the sunburst visualization to show fine distribution of Live, TCR α/β, CD4+, and CD8+ TILs expanded with aEM3 aAPCs or PBMC feeders (TIL batch M1055).

FIG. 80 illustrates the results of a flow panel analysis used to determine the purity of aEM3 cells.

FIG. 82 illustrates that TIL may advantageously expanded (pre-REP) with serum free media (i.e., CTS Optmizer) to provide increased cell numbers as compared to CM1.

FIG. 86 illustrates the total cell counts for experiment one and FIG. 87 illustrates the total cell counts for experiment two.

BRIEF DESCRIPTION OF THE SEQUENCE LISTING

Figure 1:
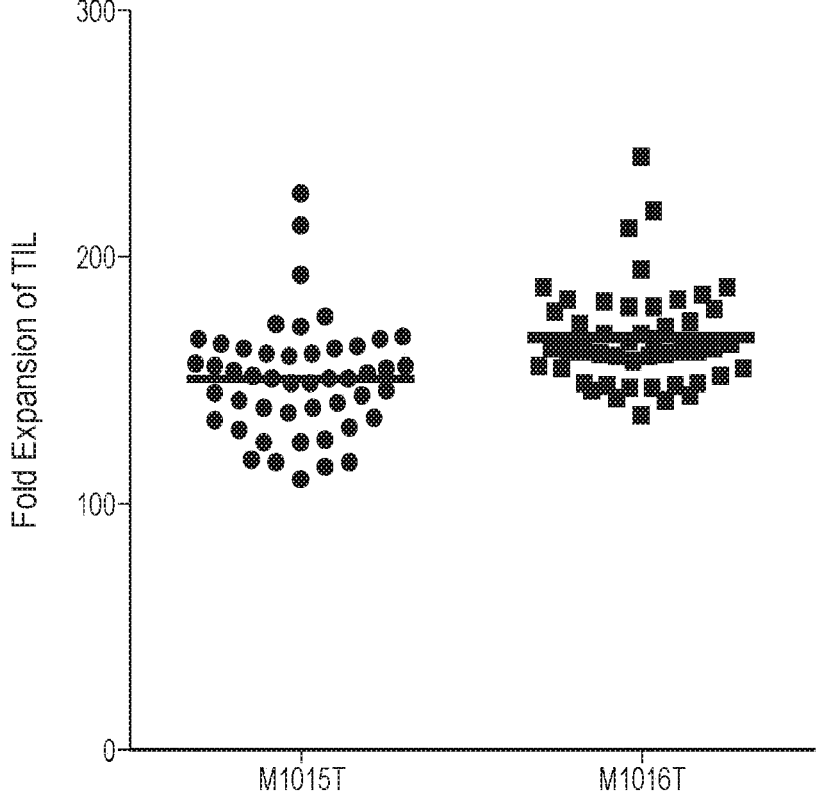
FIG. 1 illustrates the results of rapid expansion of TILs using irradiated allogeneic PBMC feeder cells. Each TIL line (M1015T and M1016T) ($1.3 \times 10^5$ cells) was co-cultured with 46 different irradiated feeders ($1.3 \times 10^7$ cells), IL-2 (3000 IU/mL) and OKT-3 (30 ng/mL) in a T25 flask for 7 days. The fold expansion value for TILs was calculated on Day 7. The figure shows the number of fold expansions for two TIL lines in separate stimulation experiments, with 46 different feeder lots tested, and highlights the variability of expansion results using PBMC feeder cells.

SEQ ID NO: 1 is an amino acid sequence for the heavy chain of muromonab.

SEQ ID NO:2 is an amino acid sequence for the light chain of muromonab.

SEQ ID NO:3 is an amino acid sequence for recombinant human IL-2.

SEQ ID NO:4 is an amino acid sequence for aldesleukin.

SEQ ID NO:5 is an amino acid sequence for recombinant human IL-7.

SEQ ID NO:6 is an amino acid sequence for recombinant human IL-15.

SEQ ID NO:7 is an amino acid sequence for recombinant IL-21.

SEQ ID NO:8 is the amino acid sequence of human CD86.

SEQ ID NO:9 is the amino acid sequence of human 4-1BBL (CD137L).

SEQ ID NO: 10 is the amino acid sequence of human OX40L (CD134L).

SEQ ID NO: 11 is the amino acid sequence of human CD28.

SEQ ID NO: 12 is the amino acid sequence of human CTLA-4.

SEQ ID NO: 13 is the amino acid sequence of human 4-1BB (CD137).

SEQ ID NO: 14 is the amino acid sequence of human OX40 (CD134).

SEQ ID NO: 15 is a nucleotide sequence for the pLV430G 4-1BBL empty vector.

SEQ ID NO: 16 is a nucleotide sequence for the 4-1BBL CoOP portion of the pLV430G human 4-1BBL vector.

SEQ ID NO: 17 is a nucleotide sequence for the 4-1BBL PCRP.

SEQ ID NO: 18 is a nucleotide sequence for the pLV430G hCD86 empty vector.

SEQ ID NO: 19 is a nucleotide sequence for the hCD86 CoOP portion of the pLV430G human hCD86 vector.

SEQ ID NO:20 is a nucleotide sequence for the hCD86 CoOP B1 B2 PCRP portion of the pLV430G human hCD86 vector.

SEQ ID NO:21 is a nucleotide sequence for the pDONR221 hCD86 vector.

SEQ ID NO:22 is a nucleotide sequence for the pDONR221 4-1BBL vector.

SEQ ID NO:23 is a nucleotide sequence for the pLV430G vector.

SEQ ID NO:24 is a nucleotide sequence for the pDONR22 1 vector.

SEQ ID NO:25 is a nucleotide sequence for the psPAX2 helper plasmid for lentiviral production.

SEQ ID NO:26 is a nucleotide sequence for the pCIGO-VSV.G helper plasmid for lentiviral production.

SEQ ID NO:27 is the amino acid sequence of the mFc-7C12 scFv clone.

SEQ ID NO:28 is the amino acid sequence of the mFc-8B3 scFv clone.

SEQ ID NO:29 is a nucleotide sequence for the mFC-7C12 scFv.

SEQ ID NO:30 is a nucleotide sequence for the mFC-8B3 scFv.

SEQ ID NO:31 is a nucleotide sequence for the destination vector pLV4301G.

SEQ ID NO:32 is a nucleotide sequence for the donor vector 1, pMK 7c 12 anti mFC scFv CoOp ECORV SacII L1R5.

SEQ ID NO:33 is a nucleotide sequence for the donor vector 2, pMK hCD8a scaffold TN L5 L2.

SEQ ID NO:34 is a nucleotide sequence for the final vector used for lentiviral production, pLV4301G 7C12 scFv mIgG hCD8 flag.

SEQ ID NO:35 is a nucleotide sequence for the destination vector, pLV4301G.

SEQ ID NO:36 is a nucleotide sequence for the donor vector 1, pMK 8B3 anti mFC scFv CoOp ECORV SacII L1R5.

SEQ ID NO:37 is a nucleotide sequence for the donor vector 2, pMK hCD8a scaffold TN L5 L2.

SEQ ID NO:38 is a nucleotide sequence for the final vector used for lentiviral production, pLV4301G 8B3 scFv mIgG hCD8 flag.

SEQ ID NO:39 is a nucleotide sequence for pLenti-C-Myc-DDK OX40L vector for lentiviral production.

SEQ ID NO:40 is a nucleotide sequence for Tel-1b primer used for quantitative polymerase chain reaction measurements of telomere length.

SEQ ID NO:41 is a nucleotide sequence for Tel-2b primer used for quantitative polymerase chain reaction measurements of telomere length.

SEQ ID NO:42 is a nucleotide sequence for Tel-1b primer used for quantitative polymerase chain reaction measurements of telomere length.

SEQ ID NO:43 is a nucleotide sequence for Tel-1b primer used for quantitative polymerase chain reaction measurements of telomere length.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "antigen" refers to a substance that induces an immune response. In some embodiments, an antigen is a molecule capable of being bound by an antibody or a T cell receptor (TCR) if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Thl and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to herein as "freshly harvested" or "a first population of TILs"), and "secondary TILs" are any TIL cell populations that have been expanded or proliferated as discussed herein, including, but not limited to bulk TILs and expanded TILs ("REP TILs" or "post-REP TILs", or "second population of TILs" or "third population of TILs" where appropriate).

TILs can generally be defined either biochemically, using cell surface markers, or functionally, by their ability to infiltrate tumors and effect treatment. TILs can be generally categorized by expressing one or more of the following biomarkers: CD4, CD8, TCR $\alpha\beta$, CD27, CD28, CD56, CCR7, CD45Ra, CD95, PD-1, and CD25. Additionally, and alternatively, TILs can be functionally defined by their ability to infiltrate solid tumors upon reintroduction into a patient.

By "cryopreserved TILs" herein is meant that TILs are treated and stored in the range of about $-150°$ C. to $-60°$ C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

By "population of cells" (including TILs) herein is meant a number of cells that share common traits.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD 127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7$^{lo}$) and are heterogeneous or low for CD62L expression (CD62L$^{lo}$). The surface phenotype of central memory T cells also includes TCR, CD3, CD 127 (IL-7R), and IL-15R. Transcription factors for central memory T cells include BLIMPL Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

The term "conservative amino acid substitutions" means amino acid sequence modifications which do not abrogate the binding of an antibody to an antigen or a protein to its ligand. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (Ile, Leu, Val, Met); and Class VI (Phe, Tyr, Tip). For example, substitution of an Asp for another class III residue such as Asn, Gin, or Glu, is a conservative substitution. Thus, a predicted nonessential amino acid residue in a 4-1BBL or CD86 protein is preferably replaced with another amino acid residue from the same class. Methods of identifying amino acid conservative substitutions which do not eliminate antigen or ligand binding are well-known in the art (see, e.g., Brummell, et al, *Biochemistry* 1993, 32, 1180-1 187; Kobayashi, et al., *Protein Eng.* 1999, 12, 879-884 (1999); and Burks, et al, *Proc. Natl. Acad. Sci. USA* 1997, 94, 412-417).

The term "retrovirus" refers to RNA viruses that utilize reverse transcriptase during their replication cycle, wherein retroviral genomic RNA is converted into double-stranded DNA by reverse transcriptase. The double-stranded DNA form is integrated into the chromosome of the infected cell (a "provirus"). The provirus serves as a template for RNA polymerase II and directs the expression of RNA molecules which encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. Several genera included within the family Retroviridae, including Cisternavirus A, Oncovirus A, Oncovirus B, Oncovirus C, Oncovirus D, Lentivirus, Gammaretrovirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. Because they are integrated into the host DNA, they are capable of transmitting sequences of host DNA from cell to cell. Example gammaretroviral vectors include those derived from the amphotropic Moloney murine leukemia virus (MLV-A), which use cell surface phosphate transporter receptors for entry and then permanently integrate into proliferating cell chromosomes. The amphotropic MLV vector system has been well established and is a popular tool for gene delivery (See, e.g., Gordon and Anderson, *Curr. Op. Biotechnol.*, 1994, 5, 611-616 and Miller, et al., *Meth. Enzymol*, 1993, 217, 581-599, the disclosures of which are incorporated herein by reference.

The term "lentivirus" refers to a genus that includes HIV (human immunodeficiency virus; including HIV type 1, and HIV type 2), visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T cells).

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3s. Other anti-CD3 antibodies include, for example, otelixizumab, teplizumab, and visilizumab.

The term "OKT-3" (also referred to herein as "OKT3") refers to a monoclonal antibody or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotec GmbH, Bergisch Gladbach, Germany) and muromonab or variants, conservative amino acid substitutions, glycoforms, or biosimilars thereof. The amino acid sequences of the heavy and light chains of muromonab are given in Table 1 (SEQ ID NO: 1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

mulations of IL-2 suitable for use in the invention are described in U.S. Pat. No. 6,706,289, the disclosure of which is incorporated by reference herein.

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the

TABLE 1

Amino acid sequences of muromonab.

| Identifier (Description) | Sequence (One-Letter Amino Acid Symbols) | | | | | | |
|---|---|---|---|---|---|---|---|
| SEQ ID NO: 1 (Muromonab heavy chain) | QVQLQQSGAE | LARPGASVKM | SCKASGYTFT | RYTMHWVKQR | PGQGLEWIGY | INPSRGYTNY | 60 |
| | NQKFKDKATL | TTDKSSSTAY | MQLSSLTSED | SAVYYCARYY | DDHYCLDYWG | QGTTLTVSSA | 120 |
| | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVWDVS | HEDPEVKFNW | YVDGVEVHNA | KTKPREEQYN | 300 |
| | STYRWSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 (Muromonab light chain) | QIVLTQSPAI | MSASPGEKVT | MTCSASSSVS | YMNWYQQKSG | TSPKRWIYDT | SKLASGVPAH | 60 |
| | FRGSGSGTSY | SLTISGMEAE | DAATYYCQQW | SSNPFTFGSG | TKLEINRADT | APTVSIFPPS | 120 |
| | SEQLTSGGAS | WCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELL-GRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 Al, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. For-invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-7 recombinant protein, Cat. No. Gibco PHC0071). The amino acid sequence of recombinant human IL-7 suitable for use in the invention is given in Table 2 (SEQ ID NO:5).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:6).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4[+] T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:7).

EM-3 cells indicates the presence of at least the following markers: CD13, CD15, and CD33. The EM-3 cell line is deposited at DSMZ under Accession No. ACC134 whilst the closely related EM-2 cell line is deposited at DSMZ under Accession No. ACC135. As used herein the term "EM-3 cell" refers to a EM-3 cell and/or a cell derived from the deposited EM-3 parental cell line.

As used herein, the term "a CD86 protein" may refer to a protein comprising an amino acid sequence as set forth in

TABLE 2

Amino acid sequences of interleukins.

| Identifier (Description) | Sequence (One-Letter Amino Acid Symbols) | | | | | | |
|---|---|---|---|---|---|---|---|
| SEQ ID NO: 3 (recombinant human IL-2 (rhIL-2)) | MAPTSSSTKK EEELKPLEEV RWITFCQSII | TQLQLEHLLL LNLAQSKNFH STLT | DLQMILNGIN LRPRDLISNI | NYKNPELTRM NVIVLELKGS | LTFKFYMPKK ETTFMCEYAD | ATELKHLQCL ETATIVEFLN | 60 120 134 |
| SEQ ID NO: 4 (aldesleukin) | PTSSSTKKTQ ELKPLEEVLN ITFSQSIIST | LQLEHLLLDL LAQSKNFHLR LT | QMILNGINNY PRDLISNINV | KNPELTRMLT IVLELEGSET | FKFYMPKKAT TFMCEYADET | ELKHLQCLEE ATIVEFLNRW | 60 120 132 |
| SEQ ID NO: 5 (recombinant human IL-7 (rhIL-7)) | MDCDIEGEDG ARKLRQFLKM KEQKKLNDLC | KQYESVLMVS NSTGDFDLHL FLKRLLQEIK | IDQLLDSMKE LEVSEGTTIL TCWNKILMGT | IGSNCLNNEF LNCTGQVKGR KEH | NFFKRHICDA KPAALGEAQP | NKEGMFLFRA TKSLEENKSL | 60 120 153 |
| SEQ ID NO: 6 (recombinant human IL-15 (rhIL-15)) | MNWVNVISDL HDTVENLIIL | KKIEDLIQSM ANNSLSSNGN | HIDATLYTES VTESGCKECE | DVHPSCKVTA ELEEKNIKEF | MKCFLLELQV LQSFVHIVQM | ISLESGDASI FINTS | 60 115 |
| SEQ ID NO: 7 (recombinant human IL-21 (rhIL-21)) | MQDRHMIRMR NNERIINVSI HLSSRTHGSE | QLIDIVDQLK KKLKRKPPST DS | NYVNDLVPEF NAGRRQKHRL | LPAPEDVETN TCPSCDSYEK | CEWSAFSCFQ KPPKEFLERF | KAQLKSANTG KSLLQHMIHQ | 60 120 132 |

The term "myeloid cell" as used herein refers to cells of the myeloid lineage or derived therefrom. The myeloid lineage includes a number of morphologically, pheriotypically, and functionally distinct cell types including different subsets of granulocytes (neutrophils, eosinophils, and basophils), monocytes, macrophages, erythrocytes, megakaryocytes, and mast cells. In certain embodiments, the myeloid ceil is a cell derived from a cell line of myeloid lineage.

"MOLM-14" refers to a human leukemia cell line which was established from the peripheral blood of a patient with relapsed acute monocytic leukemia, and initial phenotypic characterization indicated the presence of at least the following markers: CD4, CD9, CD1 1a, CD13, CD14, CD15, CD32, CD33, CD64, CD65, CD87, CD92, CD93, CD1 16, CD1 18, and CD155. Matsuo, et a/., *Leukemia* 1997, 11, 1469-77. Additional phenotypic characterization of MOLM-14 found higher levels of HLA-A/B/C, CD64, CD80, ICOS-L, CD58, and lower levels of CD86. The MOLM-14 cell line is deposited at DSMZ under Accession No. ACC777. The closely related MOLM-13 cell line is deposited at DSMZ under Accession No. ACC554. As used herein the term "MOLM-14 cell" refers to a MOLM-14 cell and/or a cell derived from the deposited MOLM-14 parental cell line. As used herein the term "MOLM-13 cell" refers to a MOLM-13 cell and/or a cell derived from the deposited MOLM-13 parental cell line.

"EM-3" refers to a human cell line was established from the bone marrow of a patient with Philadelphia chromosome-positive CML. Konopka, et al, *Proc. Nat'l Acad. Sci. USA* 1985, 82, 1810-4. Phenotypic characterization for SEQ ID NO:8 or a protein comprising an amino acid sequence having at least 90% sequence identity to the amino acid sequence depicted in SEQ ID NO: 8, e.g., 91%, 92%, 93%, 94%, 95%, 96%, 97%, 98% or 99%.

As used herein, the term "4-1BBL" or "CD137L" may refer to a protein comprising an amino acid sequence as set forth in SEQ ID NO:9 or a protein comprising an amino acid sequence having at least 90% sequence identity to the amino acid sequence depicted in SEQ ID NO:9, e.g., 91%, 92%, 93%, 94%, 95%, 96%, 97%, 98% or 99%.

As used herein, the term "OX40L" or "CD137L" may refer to a protein comprising an amino acid sequence as set forth in SEQ ID NO: 10 or a protein comprising an amino acid sequence having at least 90% sequence identity to the amino acid sequence depicted in SEQ ID NO: 10, e.g., 91%, 92%, 93%, 94%, 95%, 96%, 97%, 98% or 99%.

The term "biosimilar" means a biological product, including a monoclonal antibody or fusion protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

As used herein, the term "variant" encompasses but is not limited to proteins, antibodies or fusion proteins which comprise an amino acid sequence which differs from the amino acid sequence of a reference protein or antibody by way of one or more substitutions, deletions and/or additions at certain positions within or adjacent to the amino acid sequence of the reference protein or antibody. The variant may comprise one or more conservative substitutions in its amino acid sequence as compared to the amino acid sequence of a reference protein or antibody. Conservative substitutions may involve, e.g., the substitution of similarly charged or uncharged amino acids. The variant retains the ability to specifically bind to the antigen of the reference protein or antibody. The term "variant" also includes pegylated antibodies or proteins.

"Pegylation" refers to a modified antibody, or a fragment thereof, or protein that typically is reacted with polyethylene glycol (PEG), such as a reactive ester or aldehyde derivative of PEG, under conditions in which one or more PEG groups become attached to the antibody, antibody fragment, or protein. Pegylation may, for example, increase the biological (e.g., serum) half life of the antibody or protein. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Ci-Cio) alkoxy- or aryloxy-polyethylene glycol or polyethylene glycol-maleimide. The antibody or protein to be pegylated may be an aglycosylated antibody. Methods for pegylation are known in the art and can be applied to the antibodies and proteins described herein, as described for example in European Patent Nos. EP 01543 16 and EP 0401384.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of excludes any element, step or material other than those specified in the claim and, in the latter instance, impurities ordinary associated with the specified material(s). The term "consisting essentially of limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

Artificial Antigen Presenting Cells

In an embodiment, the invention includes an isolated artificial antigen presenting cell (aAPC) comprising a cell that expresses HLA-A/B/C, CD64, CD80, ICOS-L, and CD58, and is modified to express one or more costimulatory molecules. In an embodiment, the invention includes an aAPC comprising a MOLM-14 cell that is modified to express one or more costimulatory molecules. In an embodiment, the invention includes an aAPC comprising a MOLM-13 cell that is modified to express one or more costimulatory molecules.

In an embodiment, the invention includes an aAPC comprising a MOLM-14 cell that endogenously expresses HLA-A/B/C, CD64, CD80, ICOS-L, and CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the MOLM-14 cell.

In an embodiment, the invention includes an aAPC comprising a MOLM-14 cell transduced with one or more viral vectors, wherein the one or more viral vectors comprise a nucleic acid encoding CD86 and a nucleic acid encoding 4-1BBL, and wherein the MOLM-14 cell expresses CD86 and 4-1BBL. In an embodiment, the invention includes an aAPC comprising a MOLM-13 cell transduced with one or more viral vectors, wherein the one or more viral vectors comprise a nucleic acid encoding CD86 and a nucleic acid encoding 4-1BBL, and wherein the MOLM-13 cell expresses CD86 and 4-1BBL. In an embodiment, the invention includes a method of preparing any of the foregoing embodiments of aAPCs.

In an embodiment, the invention includes an aAPC comprising a MOLM-14 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-13 cell modified to express a CD86 protein comprising an amino acid sequence as set forth in SEQ ID NO: 8, and conservative amino acid substitutions thereof, and a 4-1BBL protein comprising an amino acid sequence as set forth in SEQ ID NO:9, and conservative amino acid substitutions thereof, wherein the CD86 protein and the 4-1BBL protein are expressed on the surface of the MOLM-13 cell. In an embodiment, the invention includes a method of preparing any of the foregoing embodiments of aAPCs.

In an embodiment, the invention includes an aAPC comprising a MOLM-14 cell modified to express a CD86 protein comprising a sequence with greater than 99% identity to an amino acid sequence as set forth in SEQ ID NO: 8 and a 4-1BBL protein comprising a sequence with greater than 99% identity to an amino acid sequence as set forth in SEQ ID NO: 9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 98% identity to an amino acid sequence as set forth in SEQ ID NO: 8 and a 4-1BBL protein comprising a sequence with greater than 98% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 97% identity to an amino acid sequence as set forth in SEQ ID NO: 8 and a 4-1BBL protein comprising a sequence with greater than 97% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 96% identity to an amino acid sequence as set forth in SEQ ID NO:8 and a 4-1BBL protein comprising a sequence with greater than 96% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 95% identity to an amino acid sequence as set forth in SEQ ID NO: 8 and a 4-1BBL protein comprising a sequence with greater than 95% identity to an amino acid sequence as set forth in SEQ ID NO:9, wherein the CD86 protein and the 4-1BBL protein are expressed on the surface of the MOLM-14 cell. In an embodiment, the invention includes an aAPC comprising a MOLM-14 cell modified to express a CD86 protein comprising a sequence with greater than 90% identity to an amino acid sequence as set forth in SEQ ID NO: 8 and a 4-1BBL protein comprising a sequence with greater than 90% identity to an amino acid sequence as set forth in SEQ ID NO:9, wherein the CD86 protein and the 4-1BBL protein are expressed on the surface of the MOLM-14 cell. In an embodiment, the invention includes a method of preparing any of the foregoing embodiments of aAPCs.

In an embodiment, the invention includes an aAPC comprising a MOLM-13 cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-lBBL protein are expressed on the surface of the MOLM-13 cell. In an embodiment, the invention includes an aAPC comprising a MOLM-13 cell modified to express a CD86 protein comprising an amino acid sequence as set forth in SEQ ID NO: 8, and conservative amino acid substitutions thereof, and a 4-lBBL protein comprising an amino acid sequence as set forth in SEQ ID NO:9, and conservative amino acid substitutions thereof, wherein the CD86 protein and the 4-lBBL protein are expressed on the surface of the MOLM-13 cell. In an embodiment, the invention includes a method of preparing any of the foregoing embodiments of aAPCs.

In an embodiment, the invention includes an aAPC comprising a MOLM-13 cell modified to express a CD86 protein comprising a sequence with greater than 99% identity to an amino acid sequence as set forth in SEQ ID NO: 8 and a 4-lBBL protein comprising a sequence with greater than 99% identity to an amino acid sequence as set forth in SEQ ID NO: 9, wherein the CD86 protein and the 4-lBBL protein are expressed on the surface of the MOLM-13 cell. In an embodiment, the invention includes an aAPC comprising a MOLM-13 cell modified to express a CD86 protein comprising a sequence with greater than 98% identity to an amino acid sequence as set forth in SEQ ID NO: 8 and a 4-lBBL protein comprising a sequence with greater than 98% identity to an amino acid sequence as set forth in SEQ ID NO:9, wherein the CD86 protein and the 4-lBBL protein are expressed on the surface of the MOLM-13 cell. In an embodiment, the invention includes an aAPC comprising a MOLM-13 cell modified to express a CD86 protein comprising a sequence with greater than 97% identity to an amino acid sequence as set forth in SEQ ID NO: 8 and a 4-lBBL protein comprising a sequence with greater than 97% identity to an amino acid sequence as set forth in SEQ ID NO:9, wherein the CD86 protein and the 4-lBBL protein are expressed on the surface of the MOLM-13 cell. In an embodiment, the invention includes an aAPC comprising a MOLM-13 cell modified to express a CD86 protein comprising a sequence with greater than 96% identity to an amino acid sequence as set forth in SEQ ID NO:8 and a 4-lBBL protein comprising a sequence with greater than 96% identity to an amino acid sequence as set forth in SEQ ID NO:9, wherein the CD86 protein and the 4-lBBL protein are expressed on the surface of the MOLM-13 cell. In an embodiment, the invention includes an aAPC comprising a MOLM-13 cell modified to express a CD86 protein comprising a sequence with greater than 95% identity to an amino acid sequence as set forth in SEQ ID NO: 8 and a 4-lBBL protein comprising a sequence with greater than 95% identity to an amino acid sequence as set forth in SEQ ID NO:9, wherein the CD86 protein and the 4-lBBL protein are expressed on the surface of the MOLM-13 cell. In an embodiment, the invention includes an aAPC comprising a MOLM-13 cell modified to express a CD86 protein comprising a sequence with greater than 90% identity to an amino acid sequence as set forth in SEQ ID NO: 8 and a 4-1BBL protein comprising a sequence with greater than 90% identity to an amino acid sequence as set forth in SEQ ID NO:9, wherein the CD86 protein and the 4-lBBL protein are expressed on the surface of the MOLM-13 cell. In an embodiment, the invention includes a method of preparing any of the foregoing embodiments of aAPCs.

In an embodiment, the invention includes an aAPC comprising a MOLM-14 cell transduced with one or more viral vectors, wherein the one or more viral vectors comprise a nucleic acid encoding CD86 and a nucleic acid encoding OX40L, and wherein the MOLM-14 cell expresses CD86 and OX40L. In an embodiment, the invention includes an aAPC comprising a MOLM-13 cell transduced with one or more viral vectors, wherein the one or more viral vectors comprise a nucleic acid encoding CD86 and a nucleic acid encoding OX40L, and wherein the MOLM-13 cell expresses CD86 and OX40L. In an embodiment, the invention includes a method of preparing any of the foregoing embodiments of aAPCs.

In an embodiment, the invention includes an aAPC comprising a MOLM-14 cell modified to express a CD86 protein comprising an amino acid sequence as set forth in SEQ ID NO:8 and a OX40L protein comprising an amino acid sequence as set forth in SEQ ID NO: 10, wherein the CD86 protein and the OX40L protein are expressed on the surface of the MOLM-14 cell. In an embodiment, the invention includes an aAPC comprising a MOLM-13 cell modified to express a CD86 protein comprising an amino acid sequence as set forth in SEQ ID NO: 8, and conservative amino acid substitutions thereof, and a OX40L protein comprising an amino acid sequence as set forth in SEQ ID NO: 10, and conservative amino acid substitutions thereof, wherein the CD86 protein and the OX40L protein are expressed on the surface of the MOLM-13 cell. In an embodiment, the invention includes a method of preparing any of the foregoing embodiments of aAPCs.

In an embodiment, the invention includes an aAPC comprising a MOLM-14 cell modified to express a CD86 protein comprising a sequence with greater than 99% identity to an amino acid sequence as set forth in SEQ ID NO: 8 and a OX40L protein comprising a sequence with greater than 99% identity to an amino acid sequence as set forth in SEQ ID NO: 10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 98% identity to an amino acid sequence as set forth in SEQ ID NO: 8 and a OX40L protein comprising a sequence with greater than 98% identity to an amino acid sequence as set forth in SEQ ID NO: 10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 97% identity to an amino acid sequence as set forth in SEQ ID NO: 8 and a OX40L protein comprising a sequence with greater than 97% identity to an amino acid sequence as set forth in SEQ ID NO: 10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 96% identity to an amino acid sequence as set forth in SEQ ID NO:8 and a OX40L protein comprising a sequence with greater than 96% identity to an amino acid sequence as set forth in SEQ ID NO: 10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 95% identity to an amino acid sequence as set forth in SEQ ID NO: 8 and a OX40L protein comprising a sequence with greater than 95% identity to an amino acid sequence as set forth in SEQ ID NO: 10, wherein the CD86 protein and the OX40L protein are expressed on the surface of the MOLM-14 cell. In an embodiment, the invention includes an aAPC comprising a MOLM-14 cell modified to express a CD86 protein comprising a sequence with greater than 90% identity to an amino acid sequence as set forth in SEQ ID NO: 8 and a OX40L protein comprising a sequence with greater than 90% identity to an amino acid sequence as set forth in SEQ ID NO: 10, wherein the CD86 protein and the OX40L protein are expressed on the surface of the MOLM-14 cell. In an embodiment, the invention includes a method of preparing any of the foregoing embodiments of aAPCs.

In any of the foregoing embodiments, it will be understood that an aAPC comprising a MOLM-14 or MOLM-13 cell may be modified to express both OX40L and 4-1BBL.

The sequences for human CD86, human 4-1BBL (CD137L), and human OX40L (CD134L) are given in Table 3.

amino acid sequence as set forth in SEQ ID NO: 13 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 97% identity to an amino acid sequence as set forth in SEQ ID NO: 13 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 96% identity to an

TABLE 3

Amino acid sequences for human CD86, human 4-1BBL, and human OX40L.

| Identifier (Description) | Sequence (One-Letter Amino Acid Symbols) | | | | | |
|---|---|---|---|---|---|---|
| SEQ ID NO: 8 (human CD86) | MGLSNILFVM | AFLLSGAAPL | KIQAYFNETA | DLPCQFANSQ | NQSLSELWF WQDQENLVLN | 60 |
| | EVYLGKEKFD | SVHSKYMGRT | SFDSDSWTLR | LHNLQIKDKG | LYQCIIHHKK PTGMIRIHQM | 120 |
| | NSELSVLANF | SQPEIVPISN | ITENVYINLT | CSSIHGYPEP | KKMSVLLRTK NSTIEYDGIM | 180 |
| | QKSQDNVTEL | YDVSISLSVS | FPDVTSNMTI | FCILETDKTR | LLSSPFSIEL EDPQPPPDHI | 240 |
| | PWITAVLPTV | IICVMVFCLI | LWKWKKKKRP | RNSYKCGTNT | MEREESEQTK KREKIHIPER | 300 |
| | SDEAQRVFKS | SKTSSCDKSD | TCF | | | 323 |
| SEQ ID NO: 9 (human 4-1BBL, CD137) | MEYASDASLD | PEAPWPPAPA | ARACRVLPWA | LVAGLLLLLL | LAAACAVFLA CPWAVSGARA | 60 |
| | SPGSAASPRL | REGPELSPDD | PAGLLDLRQG | MFAQLVAQNV | LLIDGPLSWY SDPGLAGVSL | 120 |
| | TGGLSYKEDT | KELWAKAGV | YYVFFQLELR | RWAGEGSGS | VSLALHLQPL RSAAGAAALA | 180 |
| | LTVDLPPASS | EARNSAFGFQ | GRLLHLSAGQ | RLGVHLHTEA | RARHAWQLTQ GATVLGLFRV | 240 |
| | TPEIPAGLPS | PRSE | | | | 254 |
| SEQ ID NO: 10 (human OX40L, CD134L) | MERVQPLEEN | VGNAARPRFE | RNKLLLVASV | IQGLGLLLCF | TYICLHFSAL QVSHRYPRIQ | 60 |
| | SIKVQFTEYK | KEKGFILTSQ | KEDEIMKVQN | NSVIINCDGF | YLISLKGYFS QEWISLHYQ | 120 |
| | KDEEPLFQLK | KVRSWSLMV | ASLTYKDKVY | LNVTTDNTSL | DDFHWGGEL ILIHQNPGEF | 180 |
| | CVL | | | | | 183 |

In an embodiment, the invention includes an aAPC comprising a MOLM-14 cell modified to express a first protein that binds to a second protein comprising an amino acid sequence as set forth in SEQ ID NO: 13, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes an aAPC comprising a MOLM-13 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising a MOLM-14 cell modified to express a first protein that binds to a second protein comprising a sequence with greater than 99% identity to an amino acid sequence as set forth in SEQ ID NO: 13 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 98% identity to an amino acid sequence as set forth in SEQ ID NO: 13 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 95% identity to an amino acid sequence as set forth in SEQ ID NO: 13 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 90% identity to an amino acid sequence as set forth in SEQ ID NO: 13 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising a MOLM-13 cell modified to express a first protein that binds to a second protein comprising a sequence with greater than 99% identity to an amino acid sequence as set forth in SEQ ID NO: 13 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 98% identity to an amino acid sequence as set forth in SEQ ID NO: 13 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 97% identity to an amino acid sequence as set forth in SEQ ID NO: 13 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 96% identity to an amino acid sequence as set forth in SEQ ID NO: 13 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 95% identity to an amino acid sequence as set forth in SEQ ID NO: 13 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 90% identity to an amino acid sequence as set forth in SEQ ID NO: 13 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising a MOLM-14 cell modified to express a first protein that binds to a second protein comprising an amino acid sequence as set forth in SEQ ID NO: 14, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes an aAPC comprising a MOLM-13 cell modified to express a first protein that binds to a second protein comprising an amino acid sequence as set forth in SEQ ID NO: 14, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising a MOLM-14 cell modified to express a first protein that binds to a second protein comprising a sequence with greater than 99% identity to an amino acid sequence as set forth in SEQ ID NO: 14 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 98% identity to an amino acid sequence as set forth in SEQ ID NO: 14 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 97% identity to an amino acid sequence as set forth in SEQ ID NO: 14 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 96% identity to an amino acid sequence as set forth in SEQ ID NO: 14 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 95% identity to an amino acid sequence as set forth in SEQ ID NO: 14 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising a MOLM-14 cell modified to express a first protein that binds to a second protein comprising a sequence with greater than 90% identity to an amino acid sequence as set forth in SEQ ID NO: 14 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising a MOLM-13 cell modified to express a first protein that binds to a second protein comprising a sequence with greater than 99% identity to an amino acid sequence as set forth in SEQ ID NO: 14 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 98% identity to an amino acid sequence as set forth in SEQ ID NO: 14 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 97% identity to an amino acid sequence as set forth in SEQ ID NO: 14 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 96% identity to an amino acid sequence as set forth in SEQ ID NO: 14 and a third protein that binds to a fourth protein comprising a sequence with greater than 96% identity to an amino acid sequence as set forth in SEQ ID NO: 11 or SEQ ID NO: 12.

In an embodiment, the invention includes an aAPC comprising a MOLM-13 cell modified to express a first protein that binds to a second protein comprising a sequence with greater than 95% identity to an amino acid sequence as set forth in SEQ ID NO: 14 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising a MOLM-13 cell modified to express a first protein that binds to a second protein comprising a sequence with greater than 90% identity to an amino acid sequence as set forth in SEQ ID NO: 14 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

The sequences for the ligands to which human CD86 binds (CD28 and CTLA-4), the ligand to which human 4-1BBL binds (4-1BB), and the ligand to which human OX40L binds (OX40) are given in Table 4.

In an embodiment, the invention includes an aAPC comprising an EM-3 cell transduced with one or more viral vectors, wherein the one or more viral vectors comprise a nucleic acid encoding CD86 and a nucleic acid encoding 4-1BBL, and wherein the EM-3 cell expresses CD86 and 4-1BBL. In an embodiment, the invention includes a method of preparing any of the foregoing embodiments of aAPCs.

In an embodiment, the invention includes an aAPC comprising an EM-3 cell modified to express a CD86 protein comprising an amino acid sequence as set forth in SEQ ID NO: 8 and a 4-1BBL protein comprising an amino acid sequence as set forth in SEQ ID NO:9, wherein the CD86 protein and the 4-1BBL protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a CD86 protein comprising a sequence with greater than 99% identity to an amino acid sequence as set forth in SEQ ID NO:8 and a 4-1BBL protein comprising a sequence with greater than

TABLE 4

Amino acid sequences for human CD28, human CTLA-4, human 4-IBB, and human OX40.

| Identifier (Description) | Sequence (One-Letter Amino Acid Symbols) | | | | | |
|---|---|---|---|---|---|---|
| SEQ ID NO: 11 (human CD28) | MLRLLLALNL | FPSIQVTGNK | ILVKQSPMLV | AYDNAVNLSC | KYSYNLFSRE | FRASLHKGLD | 60 |
| | SAVEVCVVYG | NYSQQLQVYS | KTGENCDGKL | GNESVTFYLQ | NLYVNQTDIY | FCKIEVMYPP | 120 |
| | PYLDNEKSNG | TIIHVKGKHL | CPSPLFPGPS | KPFWVLVVVG | GVLACYSLLV | TVAFIIFWVR | 180 |
| | SKRSRLLHSD | YMNMTPRRPG | PTRKHYQPYA | PPRDFAAYRS | | | 220 |
| SEQ ID NO: 12 (human CTLA-4) | MACLGFQRHK | AQLNLATRTW | PCTLLFFLLF | IPVECKAMHV | AQPAVVLASS | RGIASFVCEY | 60 |
| | ASPGKATEVR | VTVLRQADSQ | VTEVCAATYM | MGNELTFLDD | SICTGTSSGN | QVNLTIQGLR | 120 |
| | AMDTGLYICK | VELMYPPPYY | LGIGNGTQIY | VIDPEPCPDS | DFLLWILAAV | SSGLFFYSFL | 180 |
| | LTAVSLSKML | KKRSPLTTGV | YVKMPPTEPE | CEKQFQPYFI | PIN | | 223 |
| SEQ ID NO: 13 (human 4-1BB) | MGNSCYNIVA | TLLLVLNFER | TRSLQDPCSN | CPAGTFCDNN | RNQICSPCPP | NSFSSAGGQR | 60 |
| | TCDICRQCKG | VERTRKECSS | TSNAECDCTP | GFHCLGAGCS | MCEQDCKQGQ | ELTKKGCKDC | 120 |
| | CFGTENDQKR | GICRPWTNCS | LDGKSVLVNG | THERDVVCGP | SPADLSPGAS | SVTPPAPARE | 180 |
| | PGHSPQIISF | FLALTSTALL | FLLFFLTLRF | SVVKRGRKKL | LYIFKQPFMR | PVQTTQEEDG | 240 |
| | CSCRFPEEEE | GGCEL | | | | | 255 |
| SEQ ID NO: 14 (human OX40) | MCVGARRLGR | GPCAALLLLG | LGLSTVTGLH | CVGDTYPSND | RCCHECRPGN | GMVSRCSRSQ | 60 |
| | NTVCRPCGPG | FYNDVVSSKP | CKPCTWCNLR | SGSERKQLCT | ATQDTVCRCR | AGTQPLDSYK | 120 |
| | PGVDCAPCPP | GHFSPGDNQA | CKPWTNCTLA | GKHTLQPASN | SSDAICEDRD | PPATQPQETQ | 180 |
| | GPPARPITVQ | PTEAWPRTSQ | GPSTRPVEVP | GGRAVAAILG | LGLVLGLLGP | LAILLALYLL | 240 |
| | RRDQRLPPDA | HKPPGGGSFR | TPIQEEQADA | HSTLAKI | | | 277 |

In an embodiment, the invention includes an isolated artificial antigen presenting cell (aAPC) comprising a cell that expresses HLA-A/B/C, ICOS-L, and CD58, and is modified to express one or more costimulatory molecules, wherein the aAPC is derived from an EM-3 parental cell line. In an embodiment, the invention includes an aAPC comprising an EM-3 cell that is modified to express one or more costimulatory molecules. In an embodiment, the invention includes an aAPC comprising an EM-2 cell that is modified to express one or more costimulatory molecules.

In an embodiment, the invention includes an aAPC comprising an EM-3 cell that expresses HLA-A/B/C, ICOS-L, and CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the EM-3 cell.

99% identity to an amino acid sequence as set forth in SEQ ID NO: 9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 97% identity to an amino acid sequence as set forth in SEQ ID NO:8 and a 4-1BBL protein comprising a sequence with greater than 97% identity to an amino acid sequence as set forth in SEQ ID NO:9, wherein the CD86 protein and the 4-1BBL protein are expressed on the surface of the EM-3 cell. In an embodiment, the invention includes an aAPC comprising a EM-3 cell modified to express a CD86 protein comprising a sequence with greater than 96% identity to an amino acid sequence as set forth in SEQ ID NO: 8 and a 4-1BBL protein comprising a sequence with greater than 96% identity to an amino acid sequence as set forth in SEQ ID NO:9, wherein the CD86 protein and the 4-lBBL protein are expressed on the surface of the EM-3 cell. In an embodiment, the invention includes an aAPC comprising a EM-3 cell modified to express a CD86 protein comprising a sequence with greater than 95% identity to an amino acid sequence as set forth in SEQ ID NO:8 and a 4-lBBL protein comprising a sequence with greater than 95% identity to an amino acid sequence as set forth in SEQ ID NO:9, wherein the CD86 protein and the 4-lBBL protein are expressed on the surface of the EM-3 cell. In an embodiment, the invention includes an aAPC comprising a EM-3 cell modified to express a CD86 protein comprising a sequence with greater than 90% identity to an amino acid sequence as set forth in SEQ ID NO: 8 and a 4-lBBL protein comprising a sequence with greater than 90% identity to an amino acid sequence as set forth in SEQ ID NO: 9, wherein the CD86 protein and the 4-lBBL protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising an EM-3 cell modified to express a first protein that binds to a second protein comprising a sequence with greater than 99% identity to an amino acid sequence as set forth in SEQ ID NO: 13 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 98% identity to an amino acid sequence as set forth in SEQ ID NO: 13 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising an EM-3 modified to express a first protein that binds to a second protein comprising a sequence with greater than 97% identity to an amino acid sequence as set forth in SEQ ID NO: 13 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 96% identity to an amino acid sequence as set forth in SEQ ID NO: 13 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 95% identity to an amino acid sequence as set forth in SEQ ID NO: 13 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 90% identity to an amino acid sequence as set forth in SEQ ID NO: 13 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising an EM-3 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-2 cell modified to express a CD86 protein comprising an amino acid sequence as set forth in SEQ ID NO: 8 and a 4-1BBL protein comprising an amino acid sequence as set forth in SEQ ID NO:9, wherein the CD86 protein and the 4-1BBL protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a CD86 protein comprising a sequence with greater than 99% identity to an amino acid sequence as set forth in SEQ ID NO:8 and a 4-1BBL protein comprising a sequence with greater than 99% identity to an amino acid sequence as set forth in SEQ ID NO: 9, wherein the CD86 protein and the 4-1BBL protein are expressed on the surface of the EM-2 cell. In an embodiment, the invention includes an aAPC comprising a EM-2 cell modified to express a CD86 protein comprising a sequence with greater than 98% identity to an amino acid sequence as set forth in SEQ ID NO:8 and a 4-1BBL protein comprising a sequence with greater than 98% identity to an amino acid sequence as set forth in SEQ ID NO:9, wherein the CD86 protein and the 4-lBBL protein are expressed on the surface of the EM-2 cell. In an embodiment, the invention includes an aAPC comprising a EM-2 cell modified to express a CD86 protein comprising a sequence with greater than 97% identity to an amino acid sequence as set forth in SEQ ID NO:8 and a 4-lBBL protein comprising a sequence with greater than 97% identity to an amino acid sequence as set forth in SEQ ID NO:9, wherein the CD86 protein and the 4-lBBL protein are expressed on the surface of the EM-2 cell. In an embodiment, the invention includes an aAPC comprising a EM-2 cell modified to express a CD86 protein comprising a sequence with greater than 96% identity to an amino acid sequence as set forth in SEQ ID NO: 8 and a 4-1BBL protein comprising a sequence with greater than 96% identity to an amino acid sequence as set forth in SEQ ID NO:9, wherein the CD86 protein and the 4-lBBL protein are expressed on the surface of the EM-2 cell. In an embodiment, the invention includes an aAPC comprising a EM-2 cell modified to express a CD86 protein comprising a sequence with greater than 95% identity to an amino acid sequence as set forth in SEQ ID NO:8 and a 4-lBBL protein comprising a sequence with greater than 95% identity to an amino acid sequence as set forth in SEQ ID NO:9, wherein the CD86 protein and the 4-lBBL protein are expressed on the surface of the EM-2 cell. In an embodiment, the invention includes an aAPC comprising a EM-2 cell modified to express a CD86 protein comprising a sequence with greater than 90% identity to an amino acid sequence as set forth in SEQ ID NO: 8 and a 4-lBBL protein comprising a sequence with greater than 90% identity to an amino acid sequence as set forth in SEQ ID NO: 9, wherein the CD86 protein and the 4-lBBL protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a first protein that binds to a second protein comprising an amino acid sequence as set forth in SEQ ID NO:13, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising an EM-2 cell modified to express a first protein that binds to a second protein comprising a sequence with greater than 99% identity to an amino acid sequence as set forth in SEQ ID NO: 13 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 98% identity to an amino acid sequence as set forth in SEQ ID NO: 13 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising an EM-2 modified to express a first protein that binds to a second protein comprising a sequence with greater than 97% identity to an amino acid sequence as set forth in SEQ ID NO: 13 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 96% identity to an amino acid sequence as set forth in SEQ ID NO: 13 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 95% identity to an amino acid sequence as set forth in SEQ ID NO: 13 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 90% identity to an amino acid sequence as set forth in SEQ ID NO: 13 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising an EM-2 cell modified to express a single chain fragment variable (scFv) binding domain, such as clones 7C12 and 8B3 described herein, to bind the Fc domain of a monoclonal antibody, such as OKT-3, providing an additional proliferative signal.

Figure 96:
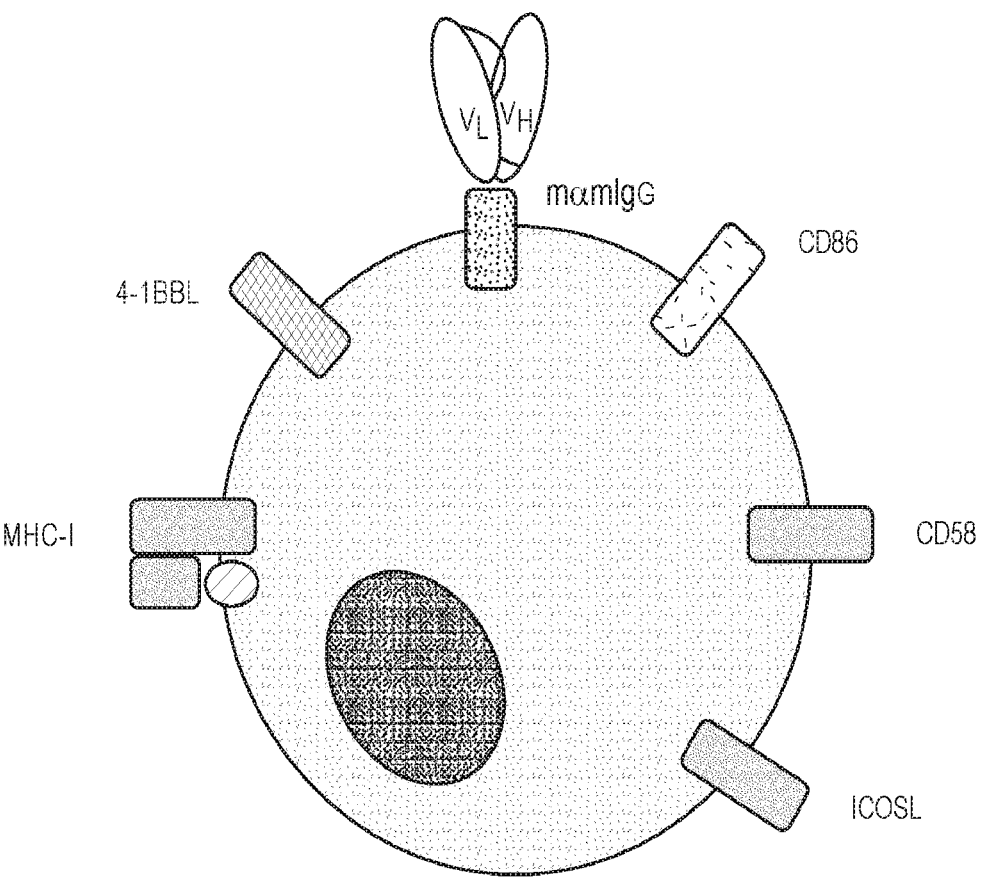
FIG. 96 illustrates a schematic diagram of an embodiment of an aAPC of the present invention.
Figure 97:
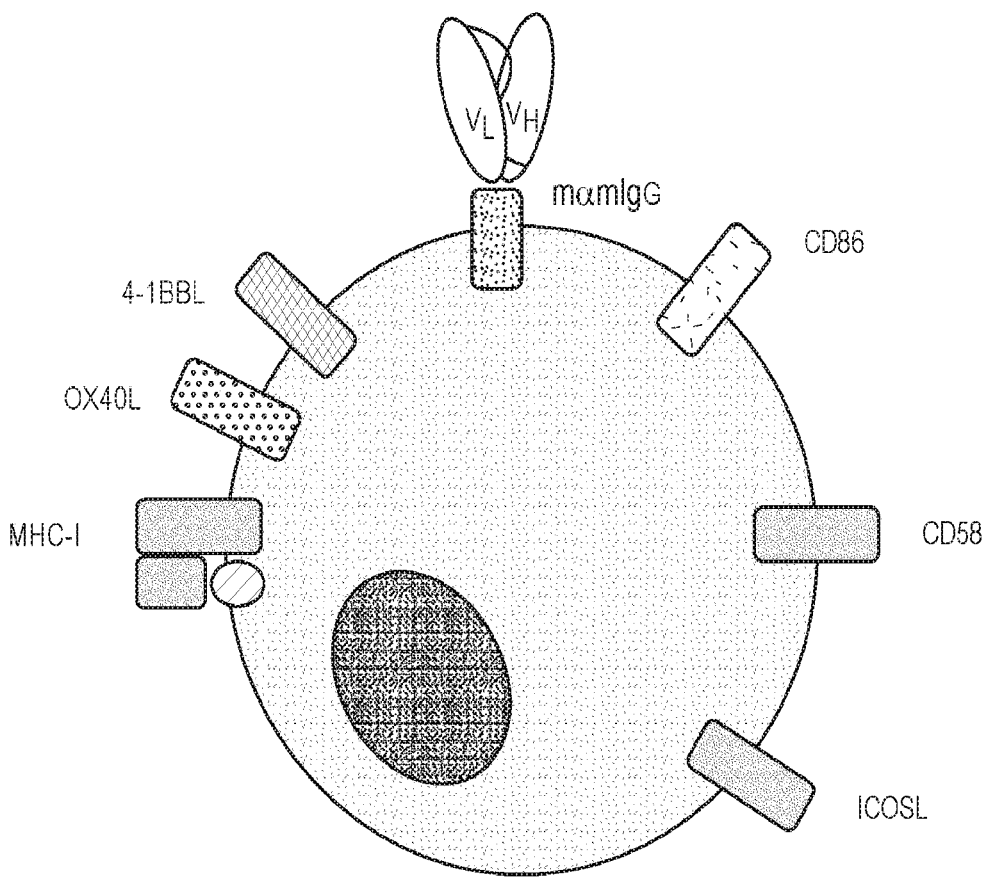
FIG. 97 illustrates a schematic diagram of an embodiment of an aAPC of the present invention.
Figure 98:
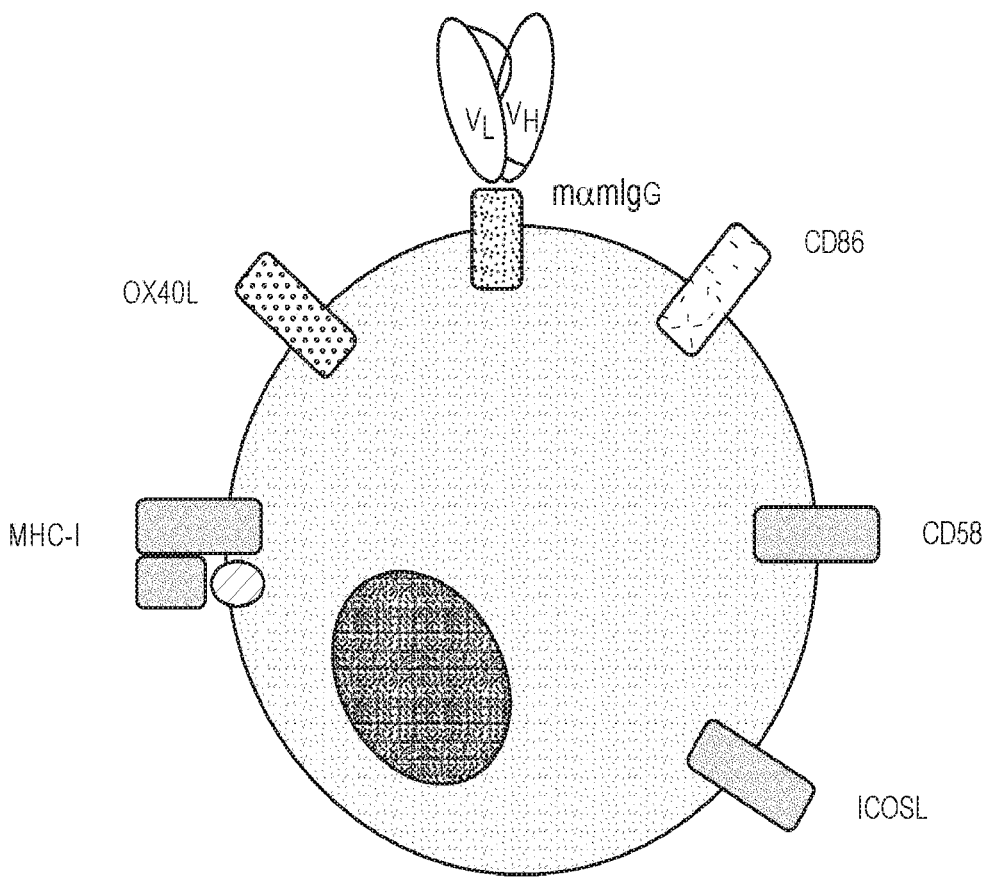
FIG. 98 illustrates a schematic diagram of an embodiment of an aAPC of the present invention.

In an embodiment, the invention includes an aAPC comprising an EM-3 or an EM-2 cell modified as depicted in FIG. 96. In an embodiment, the invention includes an aAPC comprising an EM-3 or an EM-2 cell modified as depicted in FIG. 97. In an embodiment, the invention includes an aAPC comprising an EM-3 or an EM-2 cell modified as depicted in FIG. 98.

In an embodiment, the invention includes an aAPC comprising an EM-3 cell that expresses ULA-A/B/C, ICOS-L, and CD58, wherein the cell is modified to express a CD86 protein comprising an amino acid sequence as set forth in SEQ ID NO:8, and conservative amino acid substitutions thereof, and a OX40L protein comprising an amino acid sequence as set forth in SEQ ID NO: 10, and conservative amino acid substitutions thereof, and wherein the CD86 protein and the OX40L protein are expressed on the surface of the EM-3 cell.

In an embodiment, the invention includes an aAPC comprising an EM-3 cell transduced with one or more viral vectors, wherein the one or more viral vectors comprise a nucleic acid encoding CD86 and a nucleic acid encoding OX40L, and wherein the EM-3 cell expresses CD86 and OX40L. In an embodiment, the invention includes a method of preparing any of the foregoing embodiments of aAPCs.

In an embodiment, the invention includes an aAPC comprising an EM-3 cell modified to express a CD86 protein comprising an amino acid sequence as set forth in SEQ ID NO: 8 and a OX40L protein comprising an amino acid sequence as set forth in SEQ ID NO: 10, wherein the CD86 protein and the OX40L protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a CD86 protein comprising a sequence with greater than 99% identity to an amino acid sequence as set forth in SEQ ID NO:8 and a OX40L protein comprising a sequence with greater than 99% identity to an amino acid sequence as set forth in SEQ ID NO: 10, wherein the CD86 protein and the OX40L protein are expressed on the surface of the EM-3 cell. In an embodiment, the invention includes an aAPC comprising a EM-3 cell modified to express a CD86 protein comprising a sequence with greater than 98% identity to an amino acid sequence as set forth in SEQ ID NO:8 and a OX40L protein comprising a sequence with greater than 98% identity to an amino acid sequence as set forth in SEQ ID NO: 10, wherein the CD86 protein and the OX40L protein are expressed on the surface of the EM-3 cell. In an embodiment, the invention includes an aAPC comprising a EM-3 cell modified to express a CD86 protein comprising a sequence with greater than 97% identity to an amino acid sequence as set forth in SEQ ID NO:8 and a OX40L protein comprising a sequence with greater than 97% identity to an amino acid sequence as set forth in SEQ ID NO: 10, wherein the CD86 protein and the OX40L protein are expressed on the surface of the EM-3 cell. In an embodiment, the invention includes an aAPC comprising a EM-3 cell modified to express a CD86 protein comprising a sequence with greater than 96% identity to an amino acid sequence as set forth in SEQ ID NO: 8 and a OX40L protein comprising a sequence with greater than 96% identity to an amino acid sequence as set forth in SEQ ID NO: 10, wherein the CD86 protein and the OX40L protein are expressed on the surface of the EM-3 cell. In an embodiment, the invention includes an aAPC comprising a EM-3 cell modified to express a CD86 protein comprising a sequence with greater than 95% identity to an amino acid sequence as set forth in SEQ ID NO:8 and a OX40L protein comprising a sequence with greater than 95% identity to an amino acid sequence as set forth in SEQ ID NO: 10, wherein the CD86 protein and the OX40L protein are expressed on the surface of the EM-3 cell. In an embodiment, the invention includes an aAPC comprising a EM-3 cell modified to express a CD86 protein comprising a sequence with greater than 90% identity to an amino acid sequence as set forth in SEQ ID NO:8 and a OX40L protein comprising a sequence with greater than 90% identity to an amino acid sequence as set forth in SEQ ID NO: 10, wherein the CD86 protein and the OX40L protein are expressed on the surface of the EM-3 cell. In an embodiment, the invention includes a method of preparing any of the foregoing embodiments of aAPCs.

In an embodiment, the invention includes an aAPC comprising an EM-3 cell modified to express a first protein that binds to a second protein comprising an amino acid sequence as set forth in SEQ ID NO: 14, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising an EM-3 cell modified to express a first protein that binds to a second protein comprising a sequence with greater than 99% identity to an amino acid sequence as set forth in SEQ ID NO: 14 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 98% identity to an amino acid sequence as set forth in SEQ ID NO: 14 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising an EM-3 modified to express a first protein that binds to a second protein comprising a sequence with greater than 97% identity to an amino acid sequence as set forth in SEQ ID NO: 14 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 96% identity to an amino acid sequence as set forth in SEQ ID NO: 14 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising an EM-3 cell modified to express a first protein that binds to a second protein comprising a sequence with greater than 95% identity to an amino acid sequence as set forth in SEQ ID NO: 14 and a third protein that binds to a fourth protein comprising a sequence with greater than 95% identity to an amino acid sequence as set forth in SEQ ID NO: 11 or SEQ ID NO: 12.

In an embodiment, the invention includes an aAPC comprising an EM-3 cell modified to express a first protein that binds to a second protein comprising a sequence with greater than 90% identity to an amino acid sequence as set forth in SEQ ID NO: 14 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising an EM-3 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-2 cell modified to express a CD86 protein comprising an amino acid sequence as set forth in SEQ ID NO: 8 and a OX40L protein comprising an amino acid sequence as set forth in SEQ ID NO: 10, wherein the CD86 protein and the OX40L protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a CD86 protein comprising a sequence with greater than 99% identity to an amino acid sequence as set forth in SEQ ID NO:8 and a OX40L protein comprising a sequence with greater than 99% identity to an amino acid sequence as set forth in SEQ ID NO: 10, wherein the CD86 protein and the OX40L protein are expressed on the surface of the EM-2 cell. In an embodiment, the invention includes an aAPC comprising a EM-2 cell modified to express a CD86 protein comprising a sequence with greater than 98% identity to an amino acid sequence as set forth in SEQ ID NO:8 and a OX40L protein comprising a sequence with greater than 98% identity to an amino acid sequence as set forth in SEQ ID NO: 10, wherein the CD86 protein and the OX40L protein are expressed on the surface of the EM-2 cell. In an embodiment, the invention includes an aAPC comprising a EM-2 cell modified to express a CD86 protein comprising a sequence with greater than 97% identity to an amino acid sequence as set forth in SEQ ID NO:8 and a OX40L protein comprising a sequence with greater than 97% identity to an amino acid sequence as set forth in SEQ ID NO: 10, wherein the CD86 protein and the OX40L protein are expressed on the surface of the EM-2 cell. In an embodiment, the invention includes an aAPC comprising a EM-2 cell modified to express a CD86 protein comprising a sequence with greater than 96% identity to an amino acid sequence as set forth in SEQ ID NO: 8 and a OX40L protein comprising a sequence with greater than 96% identity to an amino acid sequence as set forth in SEQ ID NO: 10, wherein the CD86 protein and the OX40L protein are expressed on the surface of the EM-2 cell. In an embodiment, the invention includes an aAPC comprising a EM-2 cell modified to express a CD86 protein comprising a sequence with greater than 95% identity to an amino acid sequence as set forth in SEQ ID NO:8 and a OX40L protein comprising a sequence with greater than 95% identity to an amino acid sequence as set forth in SEQ ID NO: 10, wherein the CD86 protein and the OX40L protein are expressed on the surface of the EM-2 cell. In an embodiment, the invention includes an aAPC comprising a EM-2 cell modified to express a CD86 protein comprising a sequence with greater than 90% identity to an amino acid sequence as set forth in SEQ ID NO:8 and a OX40L protein comprising a sequence with greater than 90% identity to an amino acid sequence as set forth in SEQ ID NO: 10, wherein the CD86 protein and the OX40L protein are expressed on the surface of the EM-2 cell. In an embodiment, the invention includes a method of preparing any of the foregoing embodiments of aAPCs.

In an embodiment, the invention includes an aAPC comprising an EM-2 cell modified to express a first protein that binds to a second protein comprising an amino acid sequence as set forth in SEQ ID NO: 14, and conservative amino acid substitutions thereof, and a third protein that binds to a fourth protein comprising an amino acid sequence as set forth in SEQ ID NO: 11 or SEQ ID NO: 12, and conservative amino acid substitutions thereof. In an embodiment, the invention includes a method of preparing any of the foregoing embodiments of aAPCs.

In an embodiment, the invention includes an aAPC comprising an EM-2 cell modified to express a first protein that binds to a second protein comprising a sequence with greater than 99% identity to an amino acid sequence as set forth in SEQ ID NO: 14 and a third protein that binds to a fourth protein comprising a sequence with greater than 99% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 98% identity to an amino acid sequence as set forth in SEQ ID NO: 14 and a third protein that binds to a fourth protein comprising a sequence with greater than 98% identity to an amino acid sequence as set forth in SEQ ID NO: 11 or SEQ ID NO: 12. In an embodiment, the invention includes an aAPC comprising an EM-2 modified to express a first protein that binds to a second protein comprising a sequence with greater than 97% identity to an amino acid sequence as set forth in SEQ ID NO: 14 and a third protein that binds to a fourth protein comprising a sequence with greater than 97% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 96% identity to an amino acid sequence as set forth in SEQ ID NO: 14 and a third protein that binds to a fourth protein comprising a sequence with greater than 96% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 95% identity to an amino acid sequence as set forth in SEQ ID NO: 14 and a third protein that binds to a fourth protein comprising a sequence with greater than 95% identity to an amino acid sequence as set forth in SEQ ID NO: 11 or SEQ ID NO: 12. In an embodiment, the invention includes an aAPC comprising an EM-2 cell modified to express a first protein that binds to a second protein comprising a sequence with greater than 90% identity to an amino acid sequence as set forth in SEQ ID NO: 14 and a third protein that binds to a fourth protein comprising a sequence with greater than 90% identity to an amino acid sequence as set forth in SEQ ID NO: 11 or SEQ ID NO: 12. In an embodiment, the invention includes a method of preparing any of the foregoing embodiments of aAPCs.

In an embodiment, the invention includes an aAPC comprising an EM-2 cell modified to express a single chain fragment variable (scFv) binding domain, such as clones 7C12 and 8B3 described herein, to bind the Fc domain of a monoclonal antibody, such as OKT-3, providing an additional proliferative signal.

In an embodiment, the invention includes an aAPC comprising an EM-3 or an EM-2 cell modified as depicted in FIG. 96. In an embodiment, the invention includes an aAPC comprising an EM-3 or an EM-2 cell modified as depicted in FIG. 97. In an embodiment, the invention includes an aAPC comprising an EM-3 or an EM-2 cell modified as depicted in FIG. 98.

In any of the foregoing embodiments, it is understood that an aAPC comprising an EM-3 or EM-2 cell may be modified to express both OX40L and 4-1BBL.

In an embodiment, the invention includes an isolated artificial antigen presenting cell (aAPC) comprising a cell that expresses CD58, and is modified to express one or more costimulatory molecules, wherein the aAPC is derived from a K562-lineage parental cell line. In an embodiment, the invention includes an aAPC comprising a K562-lineage cell that is modified to express one or more costimulatory molecules. In an embodiment, the K562 lineage parental cell line is deposited under accession no. ATCC CCL-243 and also at European Collection of Authenticated Cell Cultures (ECACCECACC 89121407).

In an embodiment, the invention includes an aAPC comprising a K562-lineage cell that expresses CD58, wherein the cell is modified to express a CD86 protein comprising an amino acid sequence as set forth in SEQ ID NO:8, and conservative amino acid substitutions thereof, and a 4-1BBL protein comprising an amino acid sequence as set forth in SEQ ID NO:9, and conservative amino acid substitutions thereof, and wherein the CD86 protein and the 4-1BBL protein are expressed on the surface of the K562-lineage cell.

In an embodiment, the invention includes an aAPC comprising a K562-lineage cell transduced with one or more viral vectors, wherein the one or more viral vectors comprise a nucleic acid encoding CD86 and a nucleic acid encoding 4-1BBL, and wherein the K562-lineage cell expresses CD86 and 4-1BBL. In an embodiment, the invention includes a method of preparing any of the foregoing embodiments of aAPCs.

In an embodiment, the invention includes an aAPC comprising a K562-lineage cell modified to express a CD86 protein comprising an amino acid sequence as set forth in SEQ ID NO:8 and a 4-1BBL protein comprising an amino acid sequence as set forth in SEQ ID NO:9, wherein the CD86 protein and the 4-1BBL protein are expressed on the surface of the K562-lineage cell. In an embodiment, the invention includes a method of preparing any of the foregoing embodiments of aAPCs.

In an embodiment, the invention includes an aAPC comprising a K562-lineage cell modified to express a CD86 protein comprising a sequence with greater than 99% identity to an amino acid sequence as set forth in SEQ ID NO: 8 and a 4-1BBL protein comprising a sequence with greater than 99% identity to an amino acid sequence as set forth in SEQ ID NO: 9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 98% identity to an amino acid sequence as set forth in SEQ ID NO: 8 and a 4-1BBL protein comprising a sequence with greater than 98% identity to an amino acid sequence as set forth in SEQ ID NO: 9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 97% identity to an amino acid sequence as set forth in SEQ ID NO: 8 and a 4-1BBL protein comprising a sequence with greater than 97% identity to an amino acid sequence as set forth in SEQ ID NO: 9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 96% identity to an amino acid sequence as set forth in SEQ ID NO: 8 and a 4-1BBL protein comprising a sequence with greater than 96% identity to an amino acid sequence as set forth in SEQ ID NO: 9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 95% identity to an amino acid sequence as set forth in SEQ ID NO: 8 and a 4-1BBL protein comprising a sequence with greater than 95% identity to an amino acid sequence as set forth in SEQ ID NO: 9, wherein the CD86 protein and the 4-1BBL protein are expressed on the surface of the K562-lineage cell. In an embodiment, the invention includes an aAPC comprising a K562-lineage cell modified to express a CD86 protein comprising a sequence with greater than 90% identity to an amino acid sequence as set forth in SEQ ID NO: 8 and a 4-1BBL protein comprising a sequence with greater than 90% identity to an amino acid sequence as set forth in SEQ ID NO: 9, wherein the CD86 protein and the 4-1BBL protein are expressed on the surface of the K562-lineage cell. In an embodiment, the invention includes a method of preparing any of the foregoing embodiments of aAPCs.

In an embodiment, the invention includes an aAPC comprising a K562-lineage cell modified to express a first protein that binds to a second protein comprising an amino acid sequence as set forth in SEQ ID NO: 11, and conservative amino acid substitutions thereof, and a third protein that binds to a fourth protein comprising an amino acid sequence as set forth in SEQ ID NO: 12 or SEQ ID NO: 13, and conservative amino acid substitutions thereof. In an embodiment, the invention includes a method of preparing any of the foregoing embodiments of aAPCs.

In an embodiment, the invention includes an aAPC comprising a K562-lineage cell modified to express a first protein that binds to a second protein comprising a sequence with greater than 99% identity to an amino acid sequence as set forth in SEQ ID NO: 11 and a third protein that binds to a fourth protein comprising a sequence with greater than 99% identity to an amino acid sequence as set forth in SEQ ID NO: 12 or SEQ ID NO: 13. In an embodiment, the invention includes an aAPC comprising a K562-lineage cell modified to express a first protein that binds to a second protein comprising a sequence with greater than 98% identity to an amino acid sequence as set forth in SEQ ID NO: 11 and a third protein that binds to a fourth protein comprising a sequence with greater than 98% identity to an amino acid sequence as set forth in SEQ ID NO: 12 or SEQ ID NO: 13. In an embodiment, the invention includes an aAPC comprising a K562-lineage modified to express a first protein that binds to a second protein comprising a sequence with greater than 97% identity to an amino acid sequence as set forth in SEQ ID NO: 11 and a third protein that binds to a fourth protein comprising a sequence with greater than 97% identity to an amino acid sequence as set forth in SEQ ID NO: 12 or SEQ ID NO: 13. In an embodiment, the invention includes an aAPC comprising a K562-lineage cell modified to express a first protein that binds to a second protein comprising a sequence with greater than 96% identity to an amino acid sequence as set forth in SEQ ID NO: 11 and a third protein that binds to a fourth protein comprising a sequence with greater than 96% identity to an amino acid sequence as set forth in SEQ ID NO: 12 or SEQ ID NO: 13. In an embodiment, the invention includes an aAPC comprising a K562-lineage cell modified to express a first protein that binds to a second protein comprising a sequence with greater than 95% identity to an amino acid sequence as set forth in SEQ ID NO: 11 and a third protein that binds to a fourth protein comprising a sequence with greater than 95% identity to an amino acid sequence as set forth in SEQ ID NO: 12 or SEQ ID NO: 13. In an embodiment, the invention includes an aAPC comprising a K562-lineage cell modified to express a first protein that binds to a second protein comprising a sequence with greater than 90% identity to an amino acid sequence as set forth in SEQ ID NO: 11 and a third protein that binds to a fourth protein comprising a sequence with greater than 90% identity to an amino acid sequence as set forth in SEQ ID NO: 12 or SEQ ID NO: 13. In an embodiment, the invention includes a method of preparing any of the foregoing embodiments of aAPCs.

In an embodiment, the invention includes an aAPC comprising an K562-lineage cell modified to express a single chain fragment variable (scFv) binding domain, such as clones 7C12 and 8B3 described herein, to bind the Fc domain of a monoclonal antibody, such as OKT-3, providing an additional proliferative signal.

Methods of Preparing Artificial Antigen Presenting Cells

In an embodiment, a method of preparing an aAPC includes the step of stable incorporation of genes for production of CD86 and 4-1BBL. In an embodiment, a method of preparing an aAPC includes the step of retroviral transduction. In an embodiment, a method of preparing an aAPC includes the step of lentiviral transduction. Lentiviral transduction systems are known in the art and are described, e.g., in Levine, et al., *Proc. Nat'l Acad. Sci.* 2006, 103, 17372-77; Zufferey, et al, *Nat. Biotechnol.* 1997, 15, 871-75; Dull, et al., *J. Virology* 1998, 72, 8463-71, and U.S. Pat. No. 6,627, 442, the disclosures of each of which are incorporated by reference herein. In an embodiment, a method of preparing an aAPC includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of preparing an aAPC includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mPvNA {e.g., an mRNA comprising a cap and poly-A tail). Suitable transposon-mediated gene transfer systems, including the salmonid-type Tcl-like transposase (SB or Sleeping Beauty transposase), such as SB 10, SB 11, and SB1OOx, and engineered enzymes with increased enzymatic activity, are described in, e.g., Hackett, et al, *Mol. Therapy* 2010, 18, 674-83 and U.S. Pat. No. 6,489,458, the disclosures of each of which are incorporated by reference herein.

Examples of viruses modified and applied to such techniques include adenoviruses, adeno-associated viruses, herpes simplex viruses, and retroviruses. Generally, nucleic acid molecules of interest may be cloned into a viral genome. Upon replication and packaging of the viral genome, the resultant viral particle is capable of delivering the nucleic acid of interest into a cell via the viral entry mechanism.

Of particular interest is the use of modified retroviruses to introduce genetic material into cells to treat genetic defects and other diseases.

The present invention provides highly efficient methods, and compositions related thereto, for the stable transduction of cells with viral vectors and viral particles. By "stable transduction," it is meant where an integrated form of the viral vector has been inserted into the chromosomal DNA of the transduced cell. The methods comprise exposing the cells to be transduced to contact with at least one molecule that binds the cell surface. This contacting step may occur prior to, during, or after the cells are exposed to the viral vector or viral particle. Hereinafter, the term "viral vector" will be used to denote any form of a nucleic acid derived from a virus and used to transfer genetic material into a cell via transduction. The term encompasses viral vector nucleic acids, such as DNA and RNA, encapsidated forms of these nucleic acids, and viral particles in which the viral vector nucleic acids have been packaged.

Additional examples of cell surface binding molecules include polypeptides, nucleic acids, carbohydrates, lipids, and ions, all optionally complexed with other substances. Preferably, the molecules bind factors found on the surfaces of blood cells, such as CD1a, CD1b, CD1c, CD1d, CD2, CD3γ, CD3δ, CD3∈, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79a, CD79B, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD114, CD115, CD116, CD117, CD118, CD119, CD120a, CD120b, CD121a, CD121b, CD122, CD123, CDw124, CD125, CD126, CDw127, CDw128a, CDw128b, CDw130, CDw131, CD 132, CD133, CD134, CD135, CD 136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ. Small letters (e.g. "a" or "b") indicate complex CD molecules composed of multiple gene products or belonging to families of structurally related proteins. The notation "w" refers to putative CD molecules that have not yet been fully confirmed. A more complete listing of CD molecules is found in Kishimoto, T. (ed). Current information on CD molecules is also found in Shaw, S. (ed)., Protein Reviews on the Web: An International WWW Resource/Journal at http://www.b-si.vt.edu/immunology.

More preferred are molecules that bind factors found on the Surfaces of lymphocytes, T cells and leukocytes, Such as CD2, CD3γ, CD3δ, CD3∈, CD5, CD6, CD7, CD8α, CD8β, CD9, CD11a, CD18, CD25, CD26, CD27, CD28, CD29, CD30, CD37, CD3δ, CD39, CD43, CD44, CD45R, CD46, CD48, CD49a, CD49b, CD49c, CD49d, CD49e, CD49f, CD50, CD53, CD54, CD56, CD57, CD58, CD59, CDw60, CD62L, CD68, CD69, CDw70, CD71, CD73, CDw75, CDw76, CD84, CD85, CD86, CD87, CD89, CD90, CD94, CD96, CD97, CD98, CD99, CD100, CD101, CD103, CD107a, CD107b, CDw108, CDw109, CD118, CD119, CD120b, CD121a, CD122, CDw124, CDw127, CDw128a, CDw130, CD132, CD134, CDw137, CD140a, CD140b, CD143, CD146, CD148, CD152, CD153, CD154, CD155, CD161, CD162, CD165, CD166, and TCRζ.

Of course any cell can be used in the practice of the invention. Preferably, the cell to be transduced is a eukaryotic cell. More preferably, the cell is a primary cell. Cell lines, however, may also be transduced with the methods of the invention and, in many cases, more easily transduced. In one preferred embodiment, the cell to be transduced is a primary lymphocyte (such as a T lymphocyte) or a macrophage (such as a monocytic macrophage), or is a precursor to either of these cells, such as a hematopoietic stem cell. Other preferred cells for transduction in general are cells of the hematopoietic system, or, more generally, cells formed by hematopoiesis as well as the stem cells from which they form and cells associated with blood cell function. Such cells include granulocytes and lymphocytes formed by hematopoiesis as well as the progenitor pluripotent, lymphoid, and myeloid stem cells. Cells associated with blood cell function include cells that aid in the functioning of immune system cells, such as antigen presenting cells like dendritic cells, endothelial cells, monocytes, and Langerhans cells. In a preferred embodiment, the cells are T lymphocytes (or T cells), such as those expressing CD4 and CD8 markers.

In particularly preferred embodiments, the cell is a primary CD4+ T lymphocyte or a primary CD34+ hematopoietic stem cell. However, and given that the viral vectors for use in the invention may be pseudotyped with Vesicular Stomatitis Virus envelope G protein (as discussed below), any cell can be transduced via the methods of the present invention.

Preferably, the cell is of a eukaryotic, multicellular species (e.g., as opposed to a unicellular yeast cell), and, even more preferably, is of mammalian origin, e.g., a human cell.

Such a "larger collection of cells" can comprise, for instance, a cell culture (either mixed or pure).

Additional applications of the invention in cancer therapy are numerous, and one skilled in the art would be able to use the invention set out herein for the treatment of many types of cancers without undue experimentation. Furthermore, in Vivo uses are not restricted to disease states and can be used to transduce normal cells. For example, the invention may be used to transduce hematopoietic stem cells in vivo in the bone marrow. Any combination of antibodies or other cell surface binding molecules, such as FLT-3 ligand, TPO and Kit ligand, or functional analogs thereof, or stromal cells expressing the cell surface binding molecule, could be added with vector upon direct injection into the bone marrow for high efficiency bone marrow transduction.

Transduction of mainly a cell type of interest can be accomplished by the choice of cell surface moiety to be bound. Thus in a mixed population of blood cells, for example, transduction of cells expressing CD3, Such as certain T cells, will be enhanced when CD3 specific anti bodies are used to interact with the cells. This will occur in preference over other cell types in the population, such as granulocytes and monocytes that do not express CD3.

The invention also encompasses the transduction of purified or isolated cell types if desired. The use of a purified or isolated cell type provides additional advantages Such as higher efficiencies of transduction due to higher vector concentrations relative to the cell to be transduced.

The present invention includes viral vectors, and compositions comprising them, for use in the disclosed methods. The vectors are preferably retroviral (family Retroviridae) vectors, and more preferably lentiviral vectors. Other retro viral vectors, such as oncoviral and murine retroviral vectors, may also be used. Additional vectors may be derived from other DNA viruses or viruses that can convert their genomes into DNA during some point of their lifecycle. Preferably the viruses are from the families Adenoviridae, Parvoviridae Hepandaviridae (including the hepatitis delta virus and the hepatitis E virus which is not normally classified in the Hepandaviridae), Papoviridae (including the polyomavirinae and the papillomavirinae), Herpesviridae, and Poxviridae.

Additional viruses of the family Retroviridae (i.e., a retrovirus), are of the genus or subfamily Oncovirinae, Spumavirinae, Spumavirus, Lentivirinae, and Lentivirus. An RNA virus of the subfamily Oncovirinae is desirably a human T-lymphotropic virus type 1 or 2 (i.e., HTLV-1 or HTLV-2) or bovine leukemia virus (BLV), an avian leukosissarcoma virus (e.g., Rous Sarcoma virus (RSV), avian myeloblastosis virus (AMV), avian erythroblastosis virus (AEV), and Rous-associated virus (RAV; RAV-0 to RAV-50), a mammalian C-type virus (e.g., Moloney murine leukemia virus (Mul V), Harvey murine sarcoma virus (HaMSV), Abelson murine leukemia virus (A-MuLV), AKR-Mul V, feline leukemia virus (FeLV), simian sarcoma virus, reticuloendotheliosis virus (REV), Spleen necrosis virus (SNV)), a B-type virus (e.g., mouse mammary tumor virus (MMTV)), and a D-type virus (e.g., Mason-Pfizer monkey virus (MPMV) and "SAIDS" viruses).

An RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human Immunodeficiency virus" are used herein to refer to these HIV viruses, and HIV-related and-associated viruses, generically. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), and a caprine arthritisencephalitis virus (CAEV).

A particularly preferred lentiviral vector is one derived from HIV, most preferably HI-1, HIV-2, or chimeric combinations thereof. Of course different serotypes of retroviruses, especially HIV, may be used singly or in any combination to prepare vectors for use in the present invention. Preferred vectors of the invention contains cis acting elements that are present in the wild-type virus, but not present in a "basic" lentiviral vector. A "basic" lentiviral vector contains minimally, LTRS and packaging sequences in the 5' leader and gag encoding Sequences, but can also optionally contain the RRE element to facilitate nuclear export of vector RNA in a Rev dependent manner. A preferred vector additionally contains nucleotide aequences that enhance the efficiency of transduction into cells.

An example of such a vector is pN2cGFP, a vector that contains the complete sequences of gag and pol. Another example is a vector that contain sequences from about position 4551 to position 5096 in pol (reference positions from the pNL4-3 sequence, Accession number M19921, HIVNL43 9709 bp, kindly provided by C. E. Buckler, NIAID, NIH, Bethesda, MD). However any cis-acting sequence from the wt-HIV that can improve vector transduction efficiency may be used. Other examples of vectors capable of efficient transduction via the present invention are cr2HIV constructs as described in U.S. Pat. No. 5,885,806.

Additional examples of Viral vector constructs that may be used in the present invention are found in U.S. Pat. No. 5,885,806, which is hereby incorporated by reference as if fully set forth. The constructs in U.S. Pat. No. 5,885,806 are merely examples that do not limit the scope of vectors that efficiently transduce cells. Instead, the constructs provide additional guidance to the skilled artisan that a viral vector for use with the present invention may contain minimal sequences from the wild-type virus or contain sequences up to almost the entire genome of wild-type virus, yet exclude an essential nucleic acid sequence required for replication and/or production of disease. Methods for determining precisely the sequences required for efficient transduction of cells are routine and well known in the art. For example, a systematic incorporation of viral sequences back into a "basic" vector or deleting sequences from vectors that contain virtually the entire HIV genome, such as cr2HIVs, is routine and well known in the art.

Furthermore, placing sequences from other viral back bones into viral vectors of interest, such as the cytomegalovirus (CMV), is also well known in the art. Regardless of the actual viral vector used, various accessory proteins encoded by, and sequences present in, the viral genetic material may be left in the vector or helper genomes if these proteins or sequences increase transduction efficiency in certain cell types. Numerous routine screens are available to determine whether certain genetic material increases transduction efficiency by incorporating the sequence in either the vector or helper genomes. A preferred embodiment of the invention is to not include accessory proteins in either the vector or helper genomes. But this preference does not exclude embodiments of the invention where accessory proteins and other sequences are left in either the vector or a helper genome to increase transduction efficiency.

The viral vector for use in the transduction methods of the invention can also comprise and express one or more nucleic acid sequences under the control of a promoter present in the virus or under the control of a heterologous promoter introduced into the vector. The promoters may further contain insulatory elements, such as erythroid DNAse hypersensitive sites, so as to flank the operon for tightly controlled gene expression. Preferred promoters include the HIV-LTR, CMV promoter, PGK, U1, EBER transcriptional units from Epstein Barr Virus, tRNA, U6 and U7. While Pol II promoters are preferred, Pol III promoters may also be used. Tissue specific promoters are also preferred embodiments. For example, the beta globin Locus Control Region enhancer and the alpha & beta globin promoters can provide tissue specific expression in erythrocytes and erythroid cells. Another further preferred embodiment is to use cis-acting sequences that are associated with the promoters. For example, The U1 gene may be used to enhance antisense gene expression where non-promoter sequences are used to target the antisense or ribozymes molecule to a target spliced RNA as set out in U.S. Pat. No. 5,814,500, which is hereby incorporated by reference.

Such sequences and gene products are preferably biologically active agents capable of producing a biological effect in a cell.

In one preferred embodiment, the agent is a cell surface molecule.

In the methods of the invention, the cells to be transduced are exposed to contact with the at least one molecule that binds the cell surface before, after, or simultaneously with application of the viral vector. For example, the cells can be cultured in media with CD3 and CD28 antibodies (coated onto the surface of the culture dish or immobilized on beads present in the culture) before, after, or in the presence of the viral vector to be transduced. Preferably, the cells are exposed to immobilized CD3 and/or CD28 only after or only upon initial contact with the viral vector. Under these conditions, the cells are not exposed to cell surface binding molecule(s) prior to actual transduction with the viral vector. In embodiments where contact with a cell surface binding molecule occurs after exposure of the cells to a viral vector (transduction), the contact preferably occurs within three days of transduction, more preferably within one to two days after transduction.

Incubation of the cells with the viral vector may be for different lengths of time, depending on the conditions and materials used. Factors that influence the incubation time include the cell, vector and MOI (multiplicity of infection) used, the molecule(s) and amounts used to bind the cell surface, whether and how said molecule(s) are immobilized or solubilized, and the level of transduction efficiency desired. Preferably, the incubation is for about eight to about 72 hours, more preferably for about 12 to about 48 hours. In a particularly preferred embodiment, the incubation is for about 24 hours and is optionally repeated once.

Contact between the cells to be transduced and a viral vector occurs at least once, but it may occur more than once, depending upon the cell type. For example, high efficiency transduction of CD34 positive stem cells have been accomplished with multiple transductions with vector. A preferred method of the invention is to Simultaneously introduce a viral vector in combination with a cell surface binding molecule (e.g. CD3 and/or CD28 antibodies or a FLT-3 ligand, TPO or Kit ligand) and avoid changing the medium for between about one and about eight days after transduction. More preferably, the medium is not changed for three days post transduction. Transduction can proceed for as long as the conditions permit without the process being significantly detrimental to the cells or the organism containing them. Additional examples of cell surface binding proteins for such use include those described hereinabove.

Similarly, the MOI used is from about 1 to about 400, preferably less than 500. Generally, the preferred MOI is from about 2 to about 50. More preferably, the MOI is from about 10 to about 30, although ranges of from about 1 to about 10, about 20, about 30, or about 40 are also contemplated. Most preferred is an MOI of about 20. Furthermore, the copy number of viral vector per cell should be at least one. However, many copies of the vector per cell may also be used with the above described methods. The preferred range of copies per cell is from about 1 to about 100. The more preferred copy number is the minimum copy number that provides a therapeutic, prophylactic or biological impact resulting from vector transduction or the most efficient transduction.

For therapeutic or prophylactic applications, a more preferred copy number is the maximum copy number that is tolerated by the cell without being significantly detrimental to the cell or the organism containing it. Both the minimum and maximum copy number per cell will vary depending upon the cell to be transduced as well as other cells that may be present. The optimum copy number is readily determined by those skilled in the art using routine methods. For example, cells are transduced at increasing increments of concentration or multiplicities of infection. The cells are then analyzed for copy number, therapeutic or biological impact and for detrimental effects on the transduced cells or a host containing them (e.g. safety and toxicity).

After incubation with the viral vector in vitro, the cells may be cultured in the presence of the cell surface binding molecule(s) for various times before the cells are analyzed for the efficiency of transduction or otherwise used. Alternatively, the cells may be cultured under any conditions that result in cell growth and proliferation, Such as incubation with interleukin-2 (IL-2) or incubation with the cell surface binding molecule(s) followed by IL-2.

The efficiency of transduction observed with the present invention is from about 75-100%. Preferably, the efficiency is at least about 75 to 90%. More preferred embodiments of the invention are where transduction efficiency is at least about 90 to 100%. Most preferred embodiments have transduction efficiencies of at least 91, 92,93, 94, 95, 96, 97,98, 99 and 100%. In addition to the above, the transduced cells may be used in research or for treatment or prevention of disease conditions in living subjects.

Therapeutic uses for the transduced cells include the introduction of the cells into a living organism. For example, unstimulated primary T cells isolated from an individual infected with, or at risk of being infected with HIV, may be first transduced by a vector, like that described in U.S. Pat. No. 5,885,806, using the present methods and followed by injection of the transduced cells back into the individual.

The present invention is directed to methods, and compositions related thereto, for the stable transduction of cells with viral vectors to efficiencies of greater than about 75%. Stably transduced cells may be distinguished from transiently transduced, or pseudotransduced cells, after about seven to ten days, or optionally after about 14 days, post transduction. The methods relate to the fact that contact of the cells to be transduced with at least one molecule that binds the cell surface increases the efficiency of stable transduction.

The methods of the invention comprise the step of transduction with a viral vector in combination with contact with a cell surface binding molecule. As noted above, the contact may occur before, after or at the same time as transduction with the vector. The invention is broadly applicable to any cell, and the use of any cell surface binding molecule. Cells for use with the present methods include unstimulated primary cells, which are freshly isolated from an in vivo source as well as cell lines, which may have been previously cultured for various times in the presence of factors which maintain them in a proliferating state.

In the case of primary cells, they are first obtained from an in vivo source followed optionally by selection for particular cell types. For example, if primary CD4+ and/or CD8+ T cells are to be used, peripheral blood (PB) or cord blood ("CB" from an umbilical source) samples are first obtained followed by enrichment for CD4+ and/or CD8+cell types. Standard magnetic beads positive selection, plastic adherence negative selection, and/or other art recognized standard techniques may be used to isolate CD4+ and/or CD8+cells away from contaminating PB cells. Purity of the isolated cell types may be determined by immunophenotyping and flow cytometry using standard techniques.

After isolation, the primary cells may be used in the present methods to be transduced with Viral vectors at efficiencies of greater than 75%. The invention is most advantageously used with primary lymphocytes, Such as T cells, transduced with an HIV-1 based vector capable of expressing heterologous genetic material of interest. Another preferred use is with primary hematopoietic stem cells, such as CD34 positive cells. In cases where the heterologous genetic material is or encodes a therapeutic or prophylactic product for use in vivo to treat or prevent a disease, the transduced primary cell can be introduced back into an in vivo environment, such as a patient. As such, the invention contemplates the use of the transfected cells in gene therapy to treat, or prevent, a disease by combating a genetic defect or targeting a viral infection.

For the transduction of primary cells in a mixed population, the above isolation/purification steps would not be used. Instead, the cell to be transduced would be targeted by selection of at least one appropriate cell surface molecule or moiety found on that cell type and the preparation of one or more molecules capable of binding said moiety. The cell surface moiety may be a receptor, marker, or other recognizable epitope on the surface of the targeted cells. Once selected, molecules that interact with the moiety, such as specific antibodies, may be prepared for use in the present invention.

For example, CD4+ and/or CD8+ cells can either be first purified and then transduced by the methods of the invention with the use of immobilized CD3 and CD28 antibodies or alternatively be transduced as part of a mixed population, like peripheral blood cells (PBCs) or peripheral blood mononuclear cells (PBMNCs), by use of the same antibodies. Hematopoietic stem cells in total white blood cell populations, which may be difficult to purify or isolate, may be transduced in the mixed populations by use of immobilized CD34 antibodies.

The cell surface binding molecules of the invention may target and bind any moiety found on the surface of the cell to be transduced. Preferably, the moieties are found as part of receptors, markers, or other proteinaceous or nonproteinaceous factors on the cell Surface. The moieties include epitopes recognized by the cell surface binding molecule. These epitopes include those comprising a polypeptide sequence, a carbohydrate, a lipid, a nucleic acid, an ion and combinations thereof.

Examples of cell surface binding molecules include an antibody or an antigen binding fragment thereof and a ligand or binding domain for a cell surface receptor. The cell surface binding molecule may itself be a polypeptide, a nucleic acid, a carbohydrate, a lipid, or an ion. Preferably, the molecule is an antibody or a fragment thereof, such as a $F_{ab}$, or $F_v$ fragment. More preferably, the molecule is not used in a soluble form but is rather immobilized on a solid medium, such a bead, with which the cells to be transduced may be cultured, or the surface of a tissue culture dish, bag or plate, upon which the cells to be transduced may be cultured. In a preferred embodiment for the transduction of CD4+ or CD8+ cells, monoclonal antibodies that recognize CD3 and/or CD28 may be used in a cell culture bag in the presence of a viral vector.

The present invention includes compositions comprising a cell surface binding molecule for use as part of the disclosed methods. An exemplary composition comprises the molecule and a viral vector to be transduced, optionally in the presence of the cells to be transduced. The viral vectors may be derived from any source, but are preferably retroviral vectors. More preferably, they are lentiviral vectors. A particularly preferred lentiviral vector is one derived from a Human Immunodeficiency Virus (HIV), most preferably HIV-1, HIV-2, or chimeric combinations thereof. Of course different viral vectors may be simultaneously transduced into the same cell by use of the present methods. For example, one vector can be a replication deficient or conditionally replicating retroviral vector while a second vector can be a packaging construct that permits the first vector to be replicated/packaged and propagated. When various viral accessory proteins are to be encoded by a viral vector, they may be present in any one of the vectors being transduced into the cell. Alternatively, the viral accessory proteins may be present in the transduction process via their presence in the viral particles used for transduction. Such viral particles may have an effective amount of the accessory proteins co-packaged to result in an increase in transduction efficiency. In a preferred embodiment, the viral vector does not encode one or more of the accessory proteins.

A viral vector for use in the transduction methods of the invention can also comprise and express one or more nucleic acid sequences under the control of a promoter. In one embodiment of the invention, a nucleic acid sequence encodes a gene product that, upon expression, would alleviate or correct a genetic deficiency in the cell to be transduced. In another embodiment, the nucleic acid sequence encodes or constitutes a genetic antiviral agent that can prevent or treat viral infection. By "genetic antiviral agent", it is meant any substance that is encoded or constituted by genetic material. Examples of such agents are provided in U.S. Pat. No. 5,885,806. They include agents that function by inhibiting viral proteins, such as reverse transcriptase or proteases, competing with viral factors for binding or target sites, or targeting viral targets directly for degradation, Such as in the case of ribozymes and antisense constructs. Other examples of genetic antiviral agents include antisense, RNA decoys, transdominant mutants, interferons, toxins, nucleic acids that modulate or modify RNA splicing, immunogens, and ribozymes, such as "hammerhead" and external guide sequence (EGS) mediated forms thereof.

The cells to be transduced may be exposed to contact with the viral vector either before, after or simultaneously with contact with the cell surface binding molecule. Thus the cells can be first exposed to the vector for a period of time followed by introduction of the cell surface binding molecule. Such cells may be newly isolated or prepared primary cells that have not been intentionally stimulated to enter the cell cycle. Alternatively, the cells can be first exposed to the cell surface binding molecule for a period of time followed by contact with the viral vector. After contact with the vector, excess vector is preferably not removed and the cells cultured under conditions conducive to cell growth and/or proliferation. Such conditions may be in the presence of the cell surface binding molecule or other stimulatory/activating factors, such as cytokines and lymphokines in the case of T cells. Alternatively, excess vector may be removed after contact with the cell and before further culturing.

Another embodiment of the invention is to culture the cells in the presence of both viral vector and cell surface binding molecule simultaneously. Such cells are preferably not previously stimulated. After a period of time, the cells are cultured under growth or proliferation inducing conditions such as the continued presence of the cell surface binding molecule or other stimulatory/activating factors. Alternatively, excess vector may be removed before further culturing.

Incubation of the cells to be transduced with the viral vector may be for different lengths of time, depending on the conditions and materials used. Factors that influence the incubation time include the cell, vector and MOI (multiplicity of infection) used, the molecule(s) and amounts used to bind the cell surface, whether and how said molecule(s) are immobilized, and the level of transduction efficiency desired. In a preferred embodiment of the invention, the cells are T lymphocytes, the vector HIV based, the MOI is about 20, the cell Surface binding molecules are CD3 and CD28 antibodies immobilized on beads, and the resultant efficiency at least 93%. As would be evident to the skilled person in the art, some of the above factors are directly correlated while others are inversely correlated. For example, a decrease in the MOI will likely decrease the level of efficiency while efficiency can likely be maintained if an increased amount of cell surface binding molecules is used.

The length of incubation viral vector and the cells to be transformed is preferably for 24 hours and optionally repeated once for lymphocytes and up to four times for hematopoietic stem cells. Similarly, and in embodiments where the cells are incubated with the cell surface binding molecule before introduction of the viral vector, the incubation may be for about 12 hours to about 96 hours. Preferably, incubation with a cell surface binding molecule occurs simultaneously with contact of the cells with the viral vector. Under such circumstances, the cell surface binding molecules may be left in contact with the cells when the vector is introduced. Alternatively, excess cell surface binding molecules may be first removed from the culture before introduction of the vector to the cells.

After contact with the vector, the cells are cultured under conditions conducive to their growth or proliferation. Preferably, the conditions are continued culturing in the presence of the cell surface binding molecules. Alternatively, the cells are initially cultured with the cell surface binding molecule followed by substitution with media containing another factor conducive to cell growth, such as interleukin-2. Yet another embodiment would be to remove both the excess cell surface binding molecule and the excess vector followed by culturing in the presence of a factor conducive to growth or proliferation as well as enhancing further vector transduction. Such factors include mitogens such as phytohemagglutinin (PHA) and cytokines, growth factors, activators, cell surface receptors, cell surface molecules, soluble factors, or combinations thereof, as well as active fragments of such molecules, alone or in combination with another protein or factor, or combinations thereof.

Examples of additional factors include epidermal growth factor (EGF), transforming growth factor alpha (TGF-alpha), angiotensin, transforming growth factor beta (TGF-beta), GDF, bone morphogenic protein (BMP), fibroblast growth factor (FGF acidic and basic), vascular endothelial growth factor (VEGF), PIGF, human growth hormone (HGH), bovine growth hormone (BGH), heregulins, amphiregulin, Ach receptor inducing activity (ARIA), RANTES (regulated on activation, normal T expressed and secreted), angiogenins, hepatocyte growth factor, tumor necrosis factor beta (TNF-beta), tumor necrosis factor alpha (TNF-alpha), angiopoietins 1 or 2, insulin, insulin growth factors I or II (IGF-I or IGF-2), ephrins, leptins, interleukins 1, 2, 3, 4, 5, 6, 7, 8, 9, 10, 11, 12, 13, 14, or 15 (IL-1, IL-2, IL-3, IL-4, L-5, IL-6, IL-7, IL-8, IL-9, IL-10, IL-11, IL-12, IL-13, IL-14, or IL-15), G-CSF (granulocyte colony stimulating factor), GM-CSF (granulocyte-macrophage colony stimulating factor), M-CSF (macrophage colony stimulating factor), LIF (leukemia inhibitory factor), angiostatin, oncostatin, erythropoietin (EPO), interferon alpha (including subtypes), interferons beta, gamma, and omega, chemokines, macrophage inflammatory protein-I alpha or beta (MIP-1 alpha or beta), monocyte chemotactic protein-1 or-2 (MCP-1 or 2), GRO beta, MWF (macrophage migration inhibitory factor), MGSA (melanoma growth stimulatory activity), alpha inhibin HGF, PD-ECGF, bFGF, lymphotoxin, Mullerian inhibiting substance, FAS ligand, osteogenic protein, pleiotrophin/midkine, ciliary neurotrophic factor, androgen induced growth factor, autocrine motility factor, hedgehog protein, estrogen, progesterone, androgen, glucocorticoid receptor, RAR/RXR, thyroid receptor, TRAP/CD40, EDF (erythroid differentiating factor), Fic (growth factor inducible chemokine), IL-1RA, SDF, NGR or RGD ligand, NGF, thymosine-alpha1, OSM, chemokine receptors, Stem cell factor (SCF), or combinations thereof. As evident to one skilled in the art, the choice of culture conditions will depend on knowledge in the art concerning the cells transduced as well as the subsequent intended use of the cells. For example, the combination of IL-3, IL-6 and stem cell factor would not be a choice for transduced cells that are to be used in human transplantation. Similarly, the choice of culture conditions would preferably not be to the detriment of cell viability or transduction efficiency.

Preferably, the post transduction incubation is for a period of about four hours, or for about one to about seven to ten days. More preferably from about 16 to about 20 hours or for about four, about five or about six days. About fourteen days of post-transduction incubation is also contemplated.

The efficiency of transduction observed with the present invention is from about 75-100%. Preferably, the efficiency is at least about 75 to 90%. More preferred embodiments of the invention are where transduction efficiency is at least about 90 to 95%. The most preferred embodiments have transduction efficiencies of at least 91, 92,93, 94, 95, 96, 97, 98, 99 and 100%.

In addition to the above, the transduced cells may be used in research or for treatment of disease conditions in living subjects. Particularly preferred as part of the invention are therapeutic uses for the transduced cells to produce gene products of interest or for direct introduction into a living organism as part of gene therapy. For example, and as exemplified below, primary T cells can be isolated and transduced with a viral vector.

In another embodiment, the T cells are transduced with genes or nucleic acids capable of conditionally killing the T cell upon introduction into a host organism. This has applications in allogenic bone marrow transplantation to prevent graft versus host disease by killing T cells with a pro-drug approach.

Alternatively, the primary cells can be deficient in a gene product, and the deficiency correctable by the transduced viral vector. Such cells would be reintroduced into the living subject after transduction with the vector.

Thus, both in vitro and ex vivo applications of the invention are contemplated. For transfers into a living subject, the transduced cells are preferably in a biologically acceptable solution or pharmaceutically acceptable formulation. Such a transfer may be made intravenously, intraperitoneally or by other injection and non-injection methods known in the art. The dosages to be administered will vary depending on a variety of factors, but may be readily determined by the skilled practitioner. There are numerous applications of the present invention, with known or well designed payloads in the viral vector, where the benefits conferred by the transduced genetic material will outweigh any risk of negative effects.

In an embodiment, a method of preparing an aAPC includes the step of stable incorporation of genes for transient production of CD86 and 4-1BBL. In an embodiment, a method of preparing an aAPC includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of preparing an aAPC includes the step of calcium phosphate transfection. Calcium phosphate transfection methods (calcium phosphate DNA precipitation, cell surface coating, and endocytosis) are known in the art and are described in Graham and van der Eb, Virology 1973, 52, 456-467; Wigler, et al, *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of preparing an aAPC includes the step of liposomal transfection. Liposomal transfection methods, such as methods that employ a 1:1 (w/w) liposome formulation of the cationic lipid/V-[1-(2,3-dioleyloxy)propyl]-«, «,«-trimethylammonium chloride (DOTMA) and dioleoyl phophotidylethanolamine (DOPE) in filtered water, are known in the art and are described in Rose, et al, *Biotechniques* 1991, 10, 520-525 and Feigner, et al, *Proc. Natl. Acad. Sci. USA,* 1987, 84, I 413-'l 41'l and in U.S. Pat. Nos. 5,279,833; 5,908,635; 6,056,938; 6,110,490; 6,534,484; and 7,687,070, the disclosures of each of which are incorporated by reference herein. In an embodiment, a method of preparing an aAPC includes the step of transfection using methods described in U.S. Pat. Nos. 5,766,902; 6,025,337; 6,410,517; 6,475,994; and 7,189,705; the disclosures of each of which are incorporated by reference herein.

In an embodiment, the aAPC is transduced by first using the Gateway cloning method (commercially available from ThermoFisher, Inc.) to prepare vector for lentiviral transduction, followed by lentiviral transduction using the vector and one or more associated helper plasmids, as is also described elsewhere herein. In the Gateway cloning method, a gene is selected (such as CD86) and is then provided with primers and amplified using PCR technology with the help of an attB tagged primer pair. The PCR fragment is then combined with a donor vector (pDONR, such as pDONR221) that includes attP sites to provide an entry clone, using the BP reaction. An integration reaction between the attB and the attP sites combines the PCR fragment with the donor vector. The resulting entry clone contains the gene of interest flanked by attL sites. The LR reaction is then used to combine the entry clone with a destination vector to produce an expression vector. In the LR reaction, a recombination reaction is used to link the entry clone with the destination vector (such as pLV430G) using the attL and attR sites and a clonase enzyme. The attL sites are already found in the entry clone, while the destination vector includes the attR sites. The LR reaction is carried out to transfer the sequence of interest into one or more destination vectors in simultaneous reactions.

In some embodiments, the aAPCs described herein may be grown and maintained under serum-based media and/or serum free media. According to an exemplary method, aAPCs may be cultured in 24 well plates at a cell density of about $1\times10^6$ cells per well for 3 to 5 days. The cells may then be isolated and/or washed by centrifugation and resuspended in media or cryopreserved in an appropriate cryopreservation media (e.g., CryoStor 10 (BioLife Solutions)) and stored in a –80° C. freezer.

In some embodiments, the aAPCs described herein may be grown in the presence of serum-based media. In some embodiments, the aAPCs described herein by may be grown in the presence of serum-based media that includes human serum (hSerum) containing media (e.g., cDMEM with 10% hSerum). In some embodiments, the aAPCs grown in the presence of serum-based media may be selected from the group consisting of aMOLM-13 cells, aMOLM-14 cells, and aEM3 cells.

In some embodiments, the aAPCs described herein may be grown in the presence of serum free media. In some embodiments, the serum free media may be selected from the group consisting of CTS Optmizer (ThermoFisher), Xvivo-20 (Lonza), Prime T Cell CDM (Irvine), XFSM (MesenCult), and the like. In some embodiments, the aAPCs grown in the presence of serum free media may be selected from the group consisting of aMOLM-13 cells, aMOLM-14 cells, and aEM3 cells.

Methods of Expanding Tumor Infiltrating Lymphocytes and T Cells

In an embodiment, the invention includes a method of expanding tumor infiltrating lymphocytes (TILs), the method comprising contacting a population of TILs comprising at least one TIL with an aAPC described herein, wherein said aAPC comprises at least one co-stimulatory ligand that specifically binds with a co-stimulatory molecule expressed on the cellular surface of the TILs, wherein binding of said co-stimulatory molecule with said co-stimulatory ligand induces proliferation of the TILs, thereby specifically expanding TILs.

In an embodiment, the invention provides a method of expanding a population of tumor infiltrating lymphocytes (TILs) using any of the aAPCs of the present disclosure, the method comprising the steps as described in Jin, et al., *J. Immunotherapy* 2012, 35, 283-292, the disclosure of which is incorporated by reference herein. For example, the tumor may be placed in enzyme media and mechanically dissociated for approximately 1 minute. The mixture may then be incubated for 30 minutes at 37° C. in 5% $CO_2$ and then mechanically disrupted again for approximately 1 minute. After incubation for 30 minutes at 37° C. in 5% $CO_2$, the tumor may be mechanically disrupted a third time for approximately 1 minute. If after the third mechanical disruption, large pieces of tissue are present, 1 or 2 additional mechanical dissociations may be applied to the sample, with or without 30 additional minutes of incubation at 37° C. in 5% $CO_2$. At the end of the final incubation, if the cell suspension contains a large number of red blood cells or dead cells, a density gradient separation using Ficoll may be performed to remove these cells. TIL cultures were initiated in 24-well plates (Costar 24-well cell culture cluster, flat bottom; Corning Incorporated, Corning, NY), each well may be seeded with $1\times10^6$ tumor digest cells or one tumor fragment approximately 1 to 8 $mm^3$ in size in 2 mL of complete medium (CM) with IL-2 (6000 IU/mL; Chiron Corp., Emeryville, CA). CM consists of RPMI 1640 with GlutaMAX, supplemented with 10% human AB serum, 25 mM Hepes, and 10 mg/mL gentamicin. Cultures may be initiated in gas-permeable flasks with a 40 mL capacity and a 10 $cm^2$ gas-permeable silicon bottom (G-Rex 10; Wilson Wolf Manufacturing, New Brighton, each flask may be loaded with 10-40×$10^6$ viable tumor digest cells or 5-30 tumor fragments in 10-40 mL of CM with IL-2. G-Rex 10 and 24-well plates may be incubated in a humidified incubator at 37° C. in 5% $CO_2$ and 5 days after culture initiation, half the media may be removed and replaced with fresh CM and IL-2 and after day 5, half the media may be changed every 2-3 days. Rapid expansion protocol (REP) of TILs may be performed using T-175 flasks and gas-permeable bags or gas-permeable G-Rex flasks, as described elsewhere herein, using the aAPCs of the present disclosure. For REP in T-175 flasks, $1\times10^6$ TILs may be suspended in 150 mL of media in each flask. The TIL may be cultured with aAPCs of the present disclosure at a ratio described herein, in a 1 to 1 mixture of CM and AIM-V medium (50/50 medium), supplemented with 3000 IU/mL of IL-2 and 30 ng/mL of anti-CD3 antibody (OKT-3). The T-175 flasks may be incubated at 37° C. in 5% $CO_2$. Half the media may be changed on day 5 using 50/50 medium with 3000 IU/mL of IL-2. On day 7, cells from 2 T-175 flasks may be combined in a 3 L bag and 300 mL of AIM-V with 5% human AB serum and 3000 IU/mL of IL-2 may be added to the 300 mL of TIL suspension. The number of cells in each bag may be counted every day or two days, and fresh media may be added to keep the cell count between 0.5 and $2.0\times10^6$ cells/mL. For REP in 500 mL capacity flasks with 100 cm² gas-permeable silicon bottoms (e.g., G-Rex 100, Wilson Wolf Manufacturing, as described elsewhere herein), $5\times10^6$ or $10\times10^6$ TILs may be cultured with aAPCs at a ratio described herein (e.g., 1 to 100) in 400 mL of 50/50 medium, supplemented with 3000 IU/mL of IL-2 and 30 ng/mL of anti-CD3 antibody (OKT-3). The G-Rel00 flasks may be incubated at 37° C. in 5% $CO_2$. On day five, 250 mL of supernatant may be removed and placed into centrifuge bottles and centrifuged at 1500 rpm (491 g) for 10 minutes. The obtained TIL pellets may be resuspended with 150 mL of fresh 50/50 medium with 3000 IU/mL of IL-2 and added back to the G-Rex 100 flasks. When TIL are expanded serially in G-Rex 100 flasks, on day seven the TIL in each G-Rex 100 are suspended in the 300 mL of media present in each flask and the cell suspension may be divided into three 100 mL aliquots that may be used to seed 3 G-Rel00 flasks. About 150 mL of AFM-V with 5% human AB serum and 3000 RJ/mL of IL-2 may then be added to each flask. G-Rex 100 flasks may then be incubated at 37° C. in 5% $CO_2$, and after four days, 150 mL of AFM-V with 3000 IU/mL of IL-2 may be added to each G-Rel00 flask. After this, the REP may be completed by harvesting cells on day 14 of culture.

As described herein, TILs may be expanded advantageously in the presence of serum free media. In some embodiments, the TIL expansion methods described herein may include the use of serum free media rather than serum-based media (e.g., complete media or CM1). In some embodiments, the TIL expansion methods described herein may use serum free media rather than serum-based media. In some embodiments, the serum free media may be selected from the group consisting of CTS Optmizer (ThermoFisher), Xvivo-20 (Lonza), Prime T Cell CDM (Irvine), and the like.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the cell culture medium further comprises IL-2 at an initial concentration of about 3000 IU/mL and OKT-3 antibody at an initial concentration of about 30 ng/mL.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the population of APCs expands the population of TILs by at least 50-fold over a period of 7 days in a cell culture medium.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the myeloid cell endogenously expresses HLA-A/B/C, ICOS-L, and CD58.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the myeloid cell is a MOLM-14 cell.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the myeloid cell is a MOLM-13 cell.

In an embodiment, the invention provides a method of expanding a population of tumor infiltrating lymphocytes (TILs), the method comprising the steps of:

(c) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (d) contacting the population of TILs with the population of aAPCs in a cell culture medium, wherein the myeloid cell is a EM-3 cell.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the CD86 protein comprises an amino acid sequence as set forth in SEQ ID NO:8, or conservative amino acid substitutions thereof, and the 4-1BBL protein comprises an amino acid sequence as set forth in SEQ ID NO:9, or conservative amino acid substitutions thereof.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the nucleic acid encoding CD86 comprises a nucleic acid sequence as set forth in SEQ ID NO: 19 and the nucleic acid encoding 4-1BBL comprises a nucleic acid sequence as set forth in SEQ ID NO: 16.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the expansion is performed using a gas permeable container.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is between 1 to 200 and 1 to 400.

In an embodiment, the invention provides a method of expanding a population of tumor infiltrating lymphocytes (TILs), the method comprising the steps of:

(a) transducing a myeloid cell with one or more viral vectors to obtain a population of artificial antigen presenting cells (aAPCs), wherein the one or more viral vectors comprise a nucleic acid encoding CD86 and a nucleic acid encoding 4-1BBL, and wherein the myeloid cell expresses a CD86 protein and a 4-1BBL protein, and (b) contacting the population of TILs with the population of aAPCs in a cell culture medium, wherein the ratio of the population of TILs to the population of aAPCs is about 1 to 300.

In an embodiment, the invention provides a method of expanding tumor infiltrating lymphocytes (TILs), the method comprising contacting a population of TILs comprising a population of TILs with a myeloid artificial antigen presenting cell (aAPC), wherein the myeloid aAPC comprises at least two co-stimulatory ligands that specifically bind with at least two co-stimulatory molecule on the TILs, wherein binding of the co-stimulatory molecules with the co-stimulatory ligand induces proliferation of the TILs, thereby specifically expanding TILs, and wherein the at least two co-stimulatory ligands comprise CD86 and 4-1BBL.

In any of the foregoing embodiments, the aAPC may further comprise OX40L in addition to 4-1BBL, or may comprise OX40L instead of 4-1BBL.

In an embodiment, a method of expanding or treating a cancer includes a step wherein TILs are obtained from a patient tumor sample. A patient tumor sample may be obtained using methods known in the art. For example, TILs may be cultured from enzymatic tumor digests and tumor fragments (about 1 to about 8 mm$^3$ in size) from sharp dissection. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In an embodiment, REP can be performed in a gas permeable container using the aAPCs of the present disclosure by any suitable method. For example, TILs can be rapidly expanded using non-specific T cell receptor stimulation in the presence of interleukin-2 (IL-2) or interleukin-15 (IL-15). The non-specific T cell receptor stimulus can include, for example, about 30 ng/mL of an anti-CD3 antibody, e.g. OKT-3, a monoclonal anti-CD3 antibody (commercially available from Ortho-McNeil, Raritan, NJ, USA or Miltenyi Biotech, Auburn, CA, USA) or UHCT-1 (commercially available from BioLegend, San Diego, CA, USA). TILs can be rapidly expanded by further stimulation of the TILs in vitro with one or more antigens, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2.

In an embodiment, a method for expanding TILs may include using about 5000 mL to about 25000 mL of cell culture medium, about 5000 mL to about 10000 mL of cell culture medium, or about 5800 mL to about 8700 mL of cell culture medium. In an embodiment, a method for expanding TILs may include using about 1000 mL to about 2000 mL of cell medium, about 2000 mL to about 3000 mL of cell culture medium, about 3000 mL to about 4000 mL of cell culture medium, about 4000 mL to about 5000 mL of cell culture medium, about 5000 mL to about 6000 mL of cell culture medium, about 6000 mL to about 7000 mL of cell culture medium, about 7000 mL to about 8000 mL of cell culture medium, about 8000 mL to about 9000 mL of cell culture medium, about 9000 mL to about 10000 mL of cell culture medium, about 10000 mL to about 15000 mL of cell culture medium, about 15000 mL to about 20000 mL of cell culture medium, or about 20000 mL to about 25000 mL of cell culture medium. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad, CA, USA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the rapid expansion is performed using a gas permeable container. Such embodiments allow for cell populations to expand from about $5 \times 10^5$ cells/cm$^2$ to between $10 \times 10^6$ and $30 \times 10^6$ cells/cm$^2$. In an embodiment, this expansion occurs without feeding. In an embodiment, this expansion occurs without feeding so long as medium resides at a height of about 10 cm in a gas-permeable flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739 A1, International Patent Application Publication No. WO 2014/210036 A1, U.S. Patent Application Publication No. US 2013/0115617 A1, International Publication No. WO 2013/188427 A1, U.S. Patent Application Publication No. US 2011/0136228 A1, U.S. Pat. No. 8,809,050, International Patent Application Publication No. WO 2011/072088 A2, U.S. Patent Application Publication No. US 2016/0208216 A1, U.S. Patent Application Publication No. US 2012/0244133 A1, International Patent Application Publication No. WO 2012/129201 A1, U.S. Patent Application Publication No. US 2013/0102075 A1, U.S. Pat. No. 8,956,860, International Patent Application Publication No. WO 2013/173835 A1, and U.S. Patent Application Publication No. US 2015/0175966 A1, the disclosures of which are incorporated herein by reference. Such processes are also described in Jin, et al., *J. Immunotherapy* 2012, 35, 283-292, the disclosure of which is incorporated by reference herein.

In an embodiment, the gas permeable container is a G-Rex 10 flask (Wilson Wolf Manufacturing Corporation, New Brighton, MN, USA). In an embodiment, the gas permeable container includes a 10 cm$^2$ gas permeable culture surface. In an embodiment, the gas permeable container includes a 40 mL cell culture medium capacity. In an embodiment, the gas permeable container provides 100 to 300 million TILs after 2 medium exchanges.

In an embodiment, the gas permeable container is a G-Rex 100 flask (Wilson Wolf Manufacturing Corporation, New Brighton, MN, USA). In an embodiment, the gas permeable container includes a 100 cm$^2$ gas permeable culture surface. In an embodiment, the gas permeable container includes a 450 mL cell culture medium capacity. In an embodiment, the gas permeable container provides 1 to 3 billion TILs after 2 medium exchanges.

In an embodiment, the gas permeable container is a G-Rex 100M flask (Wilson Wolf Manufacturing Corporation, New Brighton, MN, USA). In an embodiment, the gas permeable container includes a 100 cm$^2$ gas permeable culture surface. In an embodiment, the gas permeable container includes a 1000 mL cell culture medium capacity. In an embodiment, the gas permeable container provides 1 to 3 billion TILs without medium exchange.

In an embodiment, the gas permeable container is a G-Rex 100 L flask (Wilson Wolf Manufacturing Corporation, New Brighton, MN, USA). In an embodiment, the gas permeable container includes a 100 cm$^2$ gas permeable culture surface. In an embodiment, the gas permeable container includes a 2000 mL cell culture medium capacity. In an embodiment, the gas permeable container provides 1 to 3 billion TILs without medium exchange.

In an embodiment, the gas permeable container is a G-Rex 24 well plate (Wilson Wolf Manufacturing Corporation, New Brighton, MN, USA). In an embodiment, the gas permeable container includes a plate with wells, wherein each well includes a 2 cm$^2$ gas permeable culture surface. In an embodiment, the gas permeable container includes a plate with wells, wherein each well includes a 8 mL cell culture medium capacity. In an embodiment, the gas permeable container provides 20 to 60 million cells per well after 2 medium exchanges.

In an embodiment, the gas permeable container is a G-Rex 6 well plate (Wilson Wolf Manufacturing Corporation, New Brighton, MN, USA). In an embodiment, the gas permeable container includes a plate with wells, wherein each well includes a 10 cm$^2$ gas permeable culture surface. In an embodiment, the gas permeable container includes a plate with wells, wherein each well includes a 40 mL cell culture medium capacity. In an embodiment, the gas permeable container provides 100 to 300 million cells per well after 2 medium exchanges.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, the rapid expansion uses about $1 \times 10^9$ to about $1 \times 10^{11}$ aAPCs. In an embodiment, the rapid expansion uses about $1 \times 10^9$ aAPCs. In an embodiment, the rapid expansion uses about $1 \times 10^{10}$ aAPCs. In an embodiment, the rapid expansion uses about $1 \times 10^{11}$ aAPCs.

In an embodiment, the ratio of TILs to aAPCs (TIL:aAPC) is selected from the group consisting of 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, 1:225, 1:250, 1:275, 1:300, 1:350, 1:400, 1:450, and 1:500. In a preferred embodiment, the ratio of TILs to aAPCs (TIL:aAPC) is about 1:90. In a preferred embodiment, the ratio of TILs to aAPCs (TIL:aAPC) is about 1:95. In a preferred embodiment, the ratio of TILs to aAPCs (TIL:aAPC) is about 1:100. In a preferred embodiment, the ratio of TILs to aAPCs (TIL:aAPC) is about 1:105. In a preferred embodiment, the ratio of TILs to aAPCs (TIL:aAPC) is about 1:110.

In an embodiment, the ratio of TILs to aAPCs in the rapid expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to aAPCs in the rapid expansion is between 1 to 50 and 1 to 300. In an embodiment, the ratio of TILs to aAPCs in the rapid expansion is between 1 to 100 and 1 to 200.

In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises an OKT-3 antibody. In a preferred embodiment, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody.

In an embodiment, a rapid expansion process for TILs may be performed using T-175 flasks and gas permeable bags as previously described (Tran, et al., *J. Immunother.* 2008, 31, 742-51; Dudley, et al, *J. Immunother.* 2003, 26, 332-42) or gas permeable cultureware (G-Rex flasks, commercially available from Wilson Wolf Manufacturing Corporation, New Brighton, MN, USA). For TIL rapid expansion in T-175 flasks, $1 \times 10^6$ TILs suspended in 150 mL of media may be added to each T-175 flask. The TILs may be cultured with aAPCs at a ratio of 1 TIL to 100 aAPCs and the cells were cultured in a 1 to 1 mixture of CM and AFM-V medium, supplemented with 3000 IU (international units) per mL of IL-2 and 30 ng per ml of anti-CD3 antibody {e.g., OKT-3). The T-175 flasks may be incubated at 37° C. in 5% $CO_2$. Half the media may be exchanged on day 5 using 50/50 medium with 3000 IU per mL of IL-2. On day 7 cells from two T-175 flasks may be combined in a 3 liter bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, for TIL rapid expansions in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with aAPCs at a ratio of 1 to 100 in 400 mL of 50/50 medium, supplemented with 5% human AB serum, 3000 IU per mL of IL-2 and 30 ng per mL of anti-CD3 (OKT-3). The G-Rex 100 flasks may be incubated at 37° C. in 5% $CO_2$. On day 5, 250 mL of supernatant may be removed and placed into centrifuge bottles and centrifuged at 1500 rpm (revolutions per minute; 491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 R7 per mL of IL-2 may be added to each G-Rex 100 flask. The cells may be harvested on day 14 of culture.

In an embodiment, TILs may be prepared as follows. 2 $mm^3$ tumor fragments are cultured in complete media (CM) comprised of AIM-V medium (Invitrogen Life Technologies, Carlsbad, CA) supplemented with 2 mM glutamine (Mediatech, Inc. Manassas, VA), 100 U/mL penicillin (Invitrogen Life Technologies), 100 μg/mL streptomycin (Invitrogen Life Technologies), 5% heat-inactivated human AB serum (Valley Biomedical, Inc. Winchester, VA) and 600

IU/mL rhIL-2 (Chiron, Emeryville, CA). For enzymatic digestion of solid tumors, tumor specimens were diced into RPMI-1640, washed and centrifuged at 800 rpm for 5 minutes at 15-22° C., and resuspended in enzymatic digestion buffer (0.2 mg/mL Collagenase and 30 units/ml of DNase in RPMI-1640) followed by overnight rotation at room temperature. TILs established from fragments may be grown for 3-4 weeks in CM and expanded fresh or cryopreserved in heat-inactivated HAB serum with 10% dimethylsulfoxide (DMSO) and stored at –180° C. until the time of study. Tumor associated lymphocytes (TAL) obtained from ascites collections were seeded at $3 \times 10^6$ cells/well of a 24 well plate in CM. TIL growth was inspected about every other day using a low-power inverted microscope.

In an embodiment, TILs are expanded in gas-permeable containers. Gas-permeable containers have been used to expand TILs using PBMCs using methods, compositions, and devices known in the art, including those described in U.S. Patent Application Publication No. U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, about 10 L, about 11 L, about 12 L, about 13 L, about 14 L, about 15 L, about 16 L, about 17 L, about 18 L, about 19 L, about 20 L, about 25 L, and about 30 L. In an embodiment, the cell expansion system includes a gas permeable cell bag with a volume range selected from the group consisting of between 50 and 150 mL, between 150 and 250 mL, between 250 and 350 mL, between 350 and 450 mL, between 450 and 550 mL, between 550 and 650 mL, between 650 and 750 mL, between 750 and 850 mL, between 850 and 950 mL, and between 950 and 1050 mL. In an embodiment, the cell expansion system includes a gas permeable cell bag with a volume range selected from the group consisting of between 1 L and 2 L, between 2 L and 3 L, between 3 L and 4 L, between 4 L and 5 L, between 5 L and 6 L, between 6 L and 7 L, between 7 L and 8 L, between 8 L and 9 L, between 9 L and 10 L, between 10 L and 11 L, between 11 L and 12 L, between 12 L and 13 L, between 13 L and 14 L, between 14 L and 15 L, between 15 L and 16 L, between 16 L and 17 L, between 17 L and 18 L, between 18 L and 19 L, and between 19 L and 20 L. In an embodiment, the cell expansion system includes a gas permeable cell bag with a volume range selected from the group consisting of between 0.5 L and 5 L, between 5 L and 10 L, between 10 L and 15 L, between 15 L and 20 L, between 20 L and 25 L, and between 25 L and 30 L. In an embodiment, the cell expansion system utilizes a rocking time of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, and about 28 days. In an embodiment, the cell expansion system utilizes a rocking time of between 30 minutes and 1 hour, between 1 hour and 12 hours, between 12 hours and 1 day, between 1 day and 7 days, between 7 days and 14 days, between 14 days and 21 days, and between 21 days and 28 days. In an embodiment, the cell expansion system utilizes a rocking rate of about 2 rocks/minute, about 5 rocks/minute, about 10 rocks/minute, about 20 rocks/minute, about 30 rocks/minute, and about 40 rocks/minute. In an embodiment, the cell expansion system utilizes a rocking rate of between 2 rocks/minute and 5 rocks/minute, 5 rocks/minute and 10 rocks/minute, 10 rocks/minute and 20 rocks/minute, 20 rocks/minute and 30 rocks/minute, and 30 rocks/minute and 40 rocks/minute. In an embodiment, the cell expansion system utilizes a rocking angle of about 2°, about 3°, about 4°, about 5°, about 6°, about 7°, about 8°, about 9°, about 10°, about 11°, and about 12°. In an embodiment, the cell expansion system utilizes a rocking angle of between 2° and 3°, between 3° and 4°, between 4° and 5°, between 5° and 6°, between 6° and 7°, between 7° and 8°, between 8° and 9°, between 9° and 10°, between 10° and 11°, and between 11° and 12°.

In an embodiment, a method of expanding TILs using aAPCs further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

In an embodiment, the aAPCs of the present invention may be used to expand T cells. Any of the foregoing embodiments of the present invention described for the expansion of TILs may also be applied to the expansion of T cells. In an embodiment, the aAPCs of the present invention may be used to expand CD8$^+$ T cells. In an embodiment, the aAPCs of the present invention may be used to expand CD4$^+$ T cells. In an embodiment, the aAPCs of the present invention may be used to expand T cells transduced with a chimeric antigen receptor (CAR-T). In an embodiment, the aAPCs of the present invention may be used to expand T cells comprising a modified T cell receptor (TCR). The CAR-T cells may be targeted against any suitable antigen, including CD19, as described in the art, e.g., in U.S. Pat. Nos. 7,070,995; 7,446,190; 8,399,645; 8,916,381; and 9,328,156; the disclosures of which are incorporated by reference herein. The modified TCR cells may be targeted against any suitable antigen, including NY-ESO-1, TRP-1, TRP-2, tyrosinase cancer antigen, MAGE-A3, SSX-2, and VEGFR2, or antigenic portions thereof, as described in the art, e.g., in U.S. Pat. Nos. 8,367,804 and 7,569,664, the disclosures of which are incorporated by reference herein.

Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs. The TILs, populations and compositions thereof described herein may be for use in the treatment of a disease. In an embodiment, the TILs, populations and compositions described herein are for use in the treatment of a hyperproliferative disorder.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer, renal cancer, and renal cell carcinoma, pancreatic cancer, and glioblastoma. In some embodiments, the hyperproliferative disorder is a hematological malignancy. In some embodiments, the hematological malignancy is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of tumor infiltrating lymphocytes (TILs) comprising the steps of: (a) obtaining a first population of TILs from a tumor resected from a patient; (b) performing a rapid expansion of the first population of TILs using a population of artificial antigen presenting cells (aAPCs) in a cell culture medium to obtain a second population of TILs, wherein the second population of TILs is at least 50-fold greater in number than the first population of TILs; and (c) administering a therapeutically effective portion of the second population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days.

In an embodiment, the invention includes a method of treating a cancer with a population of tumor infiltrating lymphocytes (TILs) comprising the steps of: (a) obtaining a first population of TILs from a tumor resected from a patient; (b) performing an initial expansion of the first population of TILs using a first population of artificial antigen presenting cells (aAPCs) in a first cell culture medium to obtain a second population of TILs, wherein the second population of TILs is at least 10-fold greater in number than the first population of TILs, and wherein the first cell culture medium comprises IL-2; (c) performing a rapid expansion of the second population of TILs using a second population of aAPCs in a second cell culture medium to obtain a third population of TILs, wherein the third population of TILs is at least 50-fold greater in number than the first population of TILs; and wherein the second cell culture medium comprises IL-2 and OKT-3; (d) administering a therapeutically effective portion of the third population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days. In an embodiment, the initial expansion is performed using a gas permeable container.

In an embodiment, the invention includes a method of treating a cancer with a population of tumor infiltrating lymphocytes (TILs) comprising the steps of: (a) obtaining a first population of TILs from a tumor resected from a patient; (b) performing an initial expansion of the first population of TILs in a first cell culture medium to obtain a second population of TILs, wherein the second population of TILs is at least 10-fold greater in number than the first population of TILs, and wherein the first cell culture medium comprises IL-2; (c) performing a rapid expansion of the second population of TILs using a population of artificial antigen presenting cells (aAPCs) in a second cell culture medium to obtain a third population of TILs, wherein the third population of TILs is at least 50-fold greater in number than the first population of TILs; and wherein the second cell culture medium comprises IL-2 and OKT-3; (d) administering a therapeutically effective portion of the third population of TILs to a patient with the cancer. In an embodiment, the aAPCs comprise MOLM-14 cells transduced with one or more viral vectors, wherein the one or more viral vectors comprise a nucleic acid encoding CD86 and a nucleic acid encoding 4-1BBL, and wherein the MOLM-14 cells express a CD86 protein and a 4-1BBL protein. In an embodiment, the rapid expansion is performed over a period not greater than 14 days.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al, *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al, *Pigment Cell & Melanoma Res.* 2010, 23, 853-859. Models for determining efficacy of treatments for lung cancer are described, e.g., in Meuwissen, et al, *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, Head Neck Oncol. 2009, 1, 32.

Non-Myeloablative Lymphodepletion with Chemotherapy

In an embodiment, the invention includes a method of treating a cancer with a population of TILs, wherein a patient is pre-treated with non-myeloablative chemotherapy prior to an infusion of TILs according to the present disclosure. In an embodiment, the invention provides a population of TILs obtainable by a method described herein for use in treating a cancer, wherein the population of TILs is for treating a patient which is pre-treated with non-myeloablative chemotherapy. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the aAPC-expanded TILs of the invention.

In general, lymphodepletion is achieved using administration of fludarabine or cyclophosphamide (the active form being referred to as mafosfamide) and combinations thereof. Such methods are described in Gassner, et al, *Cancer Immunol. Immunother.* 2011, 60, 75-85, Muranski, et al, *Nat. Clin. Pract. Oncol,* 2006, 3, 668-681, Dudley, et al, *J. Clin. Oncol.* 2008, 26, 5233-5239, and Dudley, et al, *J. Clin. Oncol.* 2005, 23, 2346-2357, all of which are incorporated by reference herein in their entireties.

In some embodiments, the fludarabine is administered at a concentration of 0.5 μg/mL-10 μg/mL fludarabine. In some embodiments, the fludarabine is administered at a concentration of Ag/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 μg/ml-10 μg/ml by administration of cyclophosphamide. In some embodiments, mafosfamide, the active form of cyclophosphamide, is obtained at a concentration of 1 μg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m²/day, 150 mg/m²/day, 175 mg/m²/day, 200 mg/m²/day, 225 mg/m²/day, 250 mg/m²/day, 275 mg/m²/day, or 300 mg/m²/day. In some embodiments, the cyclophosphamide is administered intravenously (i.v.) In some embodiments, the cyclophosphamide treatment is administered for 2-7 days at 35 mg/kg/day. In some embodiments, the cyclophosphamide treatment is administered for 4-5 days at 250 mg/m²/day i.v. In some embodiments, the cyclophosphamide treatment is administered for 4 days at 250 mg/m²/day i.v.

In some embodiments, lymphodepletion is performed by administering the fludarabine and the cyclophosphamide are together to a patient. In some embodiments, fludarabine is administered at 25 mg/m²/day i.v. and cyclophosphamide is administered at 250 mg/m²/day i.v. over 4 days.

In an embodiment, the lymphodepletion is performed by administration of cyclophosphamide at a dose of 60 mg/m²/day for two days followed by administration of fludarabine at a dose of 25 mg/m²/day for five days.

Pharmaceutical Compositions, Dosages, and Dosing Regimens

In an embodiment, TILs expanded using aAPCs of the present disclosure are administered to a patient as a pharmaceutical composition. In an embodiment, the pharmaceutical composition is a suspension of TILs in a sterile buffer. TILs expanded using aAPCs of the present disclosure may be administered by any suitable route as known in the art. Preferably, the TILs are administered as a single infusion, such as an intra-arterial or intravenous infusion, which preferably lasts approximately 30 to 60 minutes. Other suitable routes of administration include intraperitoneal, intrathecal, and intralymphatic administration.

Any suitable dose of TILs can be administered. Preferably, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \chi 10^{10}$ to about $4.3 \chi 10^{10}$ of TILs are administered.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \chi 10^7$, $4 \chi 10^7$, $5 \chi 10^7$, $6 \chi 10^7$, $7 \chi 10^7$, $8 \chi 10^7$, $9 \chi 10^7$, $1 \chi 10^8$, $2 \chi 10^8$, $3 \chi 10^8$, $4 \chi 10^8$, $5 \chi 10^8$, $6 \chi 10^8$, $7 \chi 10^8$, $8 \chi 10^8$, $9 \chi 10^8$, $1 \chi 10^9$, $2 \chi 10^9$, $3 \chi 10^9$, $4 \chi 10^9$, $5 \chi 10^9$, $6 \chi 10^9$, $7 \chi 10^9$, $8 \chi 10^9$, $9 \chi 10^9$, $1 \chi 10^{10}$, $2 \chi 10^{10}$, $3 \chi 10^{10}$, $4 \chi 10^{10}$, $5 \chi 10^{10}$, $6 \chi 10^{10}$, $7 \chi 10^{10}$, $8 \chi 10^{10}$, $9 \chi 10^{10}$, $1 \chi 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \chi 10^{12}$, $2 \chi 10^{12}$, $3 \chi 10^{12}$, $4 \chi 10^{12}$, $5 \chi 10^{12}$, $6 \chi 10^{12}$, $7 \chi 10^{12}$, $8 \chi 10^{12}$, $9 \chi 10^{12}$, $1 \chi 10^{13}$, $2 \chi 10^{13}$, $3 \chi 10^{13}$, $4 \chi 10^{13}$, $5 \chi 10^{13}$, $6 \chi 10^{13}$, $7 \chi 10^{13}$, $8 \times 10^{13}$ and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \chi 10^7$ io $5 \chi 10^7$, $5 \times 10$ to $1 \times 10^8$, $1 \chi 10^8$ io $5 \chi 10^8$, $5 \times 10^8$ to $1 \times 10^9$, $1 \chi 10^9$ io $5 \chi 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \chi 10^{12}$, $1 \chi 10^{12}$ io $5 \chi 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001%) w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.0019 to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9%) to about 12%) or about 1%> to about 10%> w/w, w/v or v/v of the pharmaceutical composition.

In some embodiments, the concentration of the TILs provided in the pharmaceutical compositions of the invention is in the range from about 0.001%, to about 10%>, about 0.01%> to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of embodiments of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\chi10^6$, $2\times10^6$, $3\times10^6$, $4\times10^6$, $5\times10^6$, $6\times10^6$, $7\chi10^6$, $8\chi10^6$, $9\chi10^6$, $1\chi10^7$, $2\chi10^7$, $3\chi10^7$, $4\chi10^7$, $5\chi10^7$, $6\chi10^7$, $7\chi10^7$, $8\chi10^7$, $9\chi10^7$, $1\chi10^8$, $2\chi10^8$, $3\chi10^8$, $4\chi10^8$, $5\chi10^8$, $6\chi10^8$, $7\chi10^8$, $8\chi10^8$, $9\chi10^8$, $1\chi10^9$, $2\chi10^9$, $3\chi10^9$, $4\chi10^9$, $5\chi10^9$, $6\chi10^9$, $7\chi10^9$, $8\chi10^9$, $9\chi10^9$, $1\chi10^{10}$, $2\chi10^{10}$, $3\chi10^{10}$, $4\chi10^{10}$, $5\chi10^{10}$, $6\chi10^{10}$, $7\chi10^{10}$, $8\chi10^{10}$, $9\chi10^{10}$, $1\chi10^{11}$, $2\chi10^{11}$, $3\chi10^{11}$, $4\chi10^{11}$, $5\chi10^{11}$, $6\chi\ddot{i}\theta^{11}$, $7\chi10^{11}$, $8\chi10^{11}$, $9\times10^{11}$, $1\chi10^{12}$, $2\chi10^{12}$, $3\chi10^{12}$, $4\chi10^{12}$, $5\chi10^{12}$, $6\chi10^{12}$, $7\chi10^{12}$, $8\chi10^{12}$, $9\chi10^{12}$, $1\chi10^{13}$, $2\chi10^{13}$, $3\chi10^{13}$, $4\chi10^{13}$, $5\chi10^{13}$, $6\chi10^{13}$, $7\chi10^{13}$, $8\chi10^{13}$, and $9\chi10^{13}$. In some embodiments, an effective dosage of TILs is in the range of $1\times10^6$ to $5\times10^6$, $5\times10^6$ to $1\chi10^7$, $1\times10^7$ to $5\times10^7$, $5\times10^7$ to $1\chi10^8$, $1\times10^8$ to $5\times10^8$, $5\times10^8$ to $1\chi10^9$, $1\times10^9$ to $5\chi10^9$, $5\times10^9$ to $1\chi10^{10}$, $1\times10^{10}$ to $5\chi10^{10}$, $5\times10^{10}$ to $1\times10^{11}$, $5\times10^{11}$ to $1\chi10^{12}$, $1\chi10^{12}$ io $5\chi10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Variability in Expansion of Tumor Infiltrating Lymphocytes Using PBMC Feeder Cells The variability in TIL expansion obtained by use of PBMC feeder cells may be demonstrated by comparing the results of multiple TIL expansions on the same line of TILs obtained from a patient. FIG. 1 illustrates typical results of rapid expansion of TILs using irradiated allogeneic PBMC feeder cells (PBMC feeders). Two TIL lines labeled M1015T and M1016T ($1.3 \times 10^5$ cells) were co-cultured with 46 different irradiated feeder cell lots ($1.3 \times 10^7$), IL-2 (3000 IU/mL, recombinant human IL-2 (e.g., aldesleukin or equivalent), CellGenix, Inc., Portsmouth, M L USA) and OKT-3 (30 ng/mL, MACS GMP CD3 pure, Miltenyi Biotec GmbH, Bergisch Gladbach, Germany) in a T25 flask for 7 days. The fold expansion value for TILs was calculated on Day 7. The figure shows the number of fold expansions for the two TIL lines in separate stimulation experiments. For each TIL line, 46 different PBMC feeder lots were tested. The results range over more than 100-fold for each TIL line, and highlight the variability of expansion results using PBMC feeder cells. The aAPCs of the present invention offer reduced variability in expansion performance compared to PBMC feeders, as well as other advantages, as shown in the following examples.

Example 2—Selection of Myeloid Cells for aAPC Development

Phenotypic characterization was performed on various myeloid-lineage cell lines to identify potential candidates for further modification into aAPCs for TIL expansion. The results are summarized in Table 5. The MOLM-14 cell line exhibited endogenous expression of CD64, and was selected for further development. The EM-3 cell line was selected based on the observation of endogenous expression of ICOS-L (which was not observed for the EM-2 cell line, despite being taken from the same patient).

Example 3—Preparation of MOLM-14 Artificial Antigen Presenting Cells (aMOLM14 aAPCs)

MOLM-14 cells were obtained from Leibniz-Institut DSMZ-Deutsche Sammlung von Mikroorganismen and Zellkulturen GmbH. To develop MOLM-14 based aAPCs, MOLM-14 cells were engineered with the costimulatory molecules CD86 and 4-lBBL (CD137L). Human CD86 (hCD86) and human 4-lBBL (h4-lBBL) genes were cloned into commercially-available PLV430G and co-transfected with PDONR22 1 vectors (Invitrogen/Thermo Fisher Scientific, Carlsbad, CA, USA) using a lentiviral transduction method. The gateway cloning method was used as described in Katzen, *Expert Opin. Drug Disc.* 2007, 4, 571-589, to clone hCD86 and hCD137L genes onto the PLV430G and PDONR22 1 vectors. The 293 T cell line (human embryonic kidney cells transformed with large T antigen) was used for lentiviral production, transduced to MOLM-14 cells. The transfected cells were sorted (S3e Cell Sorter, Bio-Rad, Hercules, CA, USA) using APC-conjugated CD86 and PE-conjugated CD137L to isolate and enrich the cells. The enriched cells were checked for purity by flow cytometry.

Figure 2:
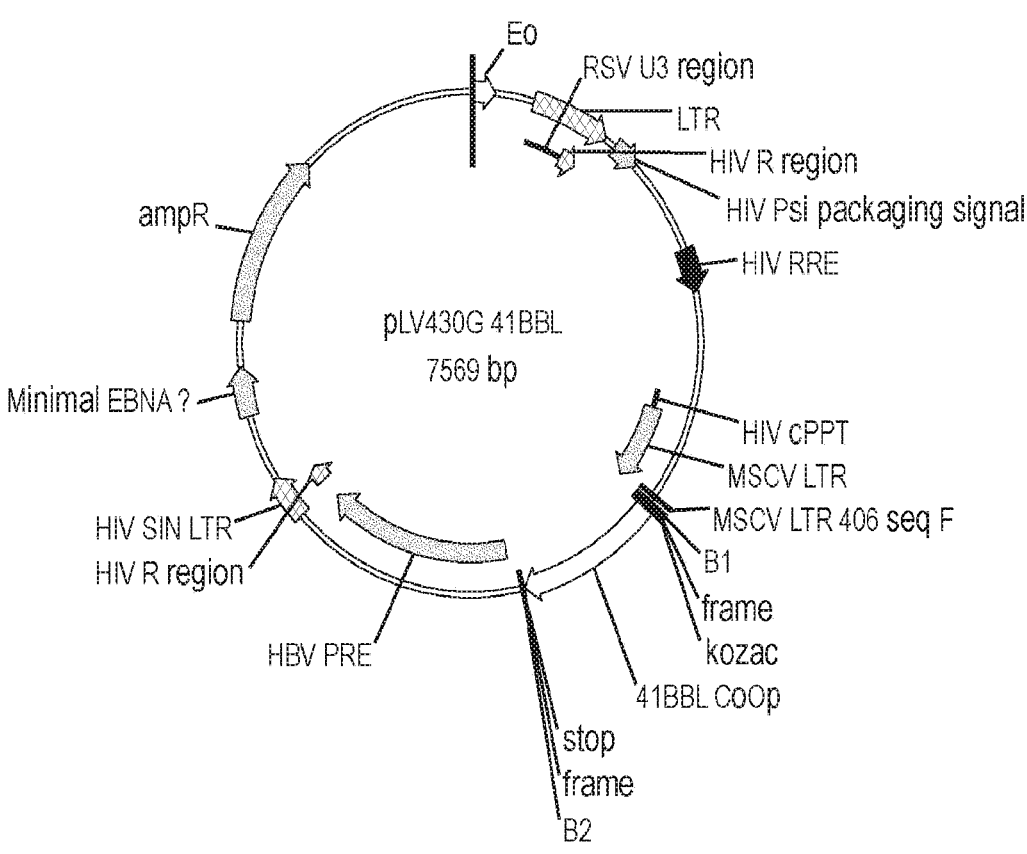
FIG. 2 illustrates a vector diagram of the pLV430G human 4-1BBL vector.
Figure 3:
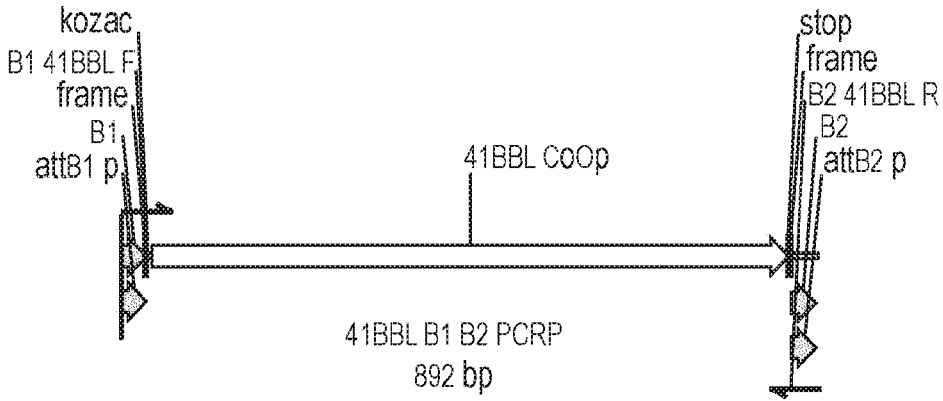
FIG. 3 illustrates a diagram of the 4-1BBL PCRP (polymerase chain reaction product) portion of the pLV430G human 4-1BBL vector.
Figure 4:
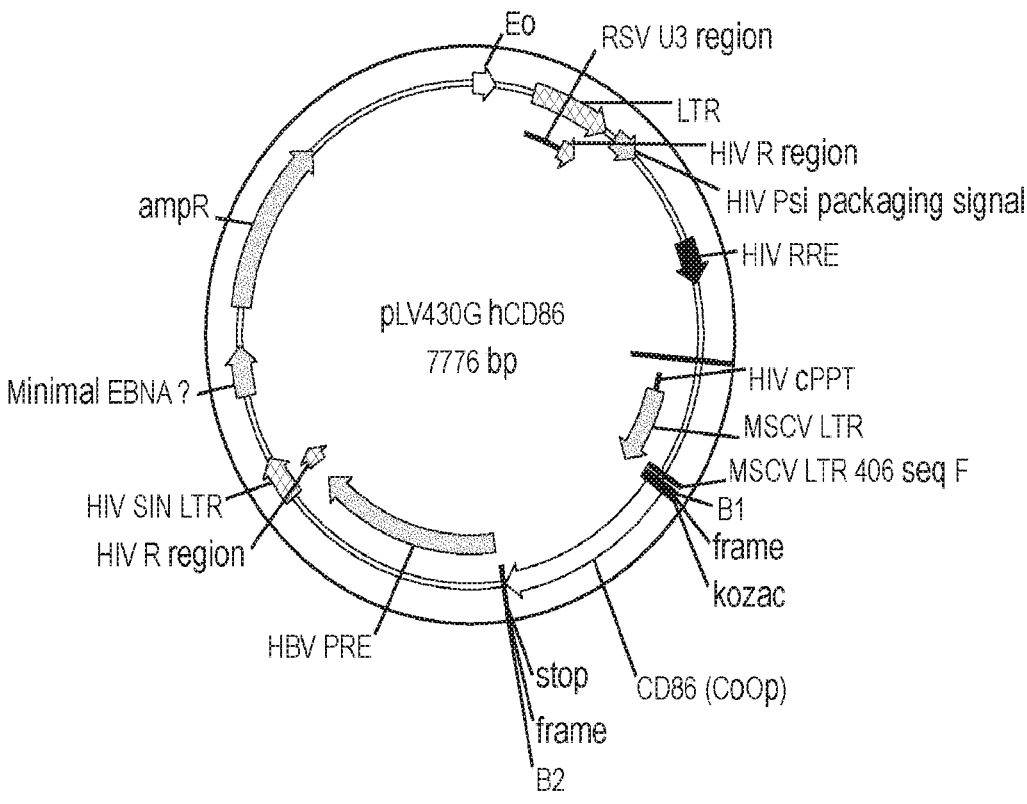
FIG. 4 illustrates a vector diagram of the pLV430G human CD86 vector.
Figure 5:
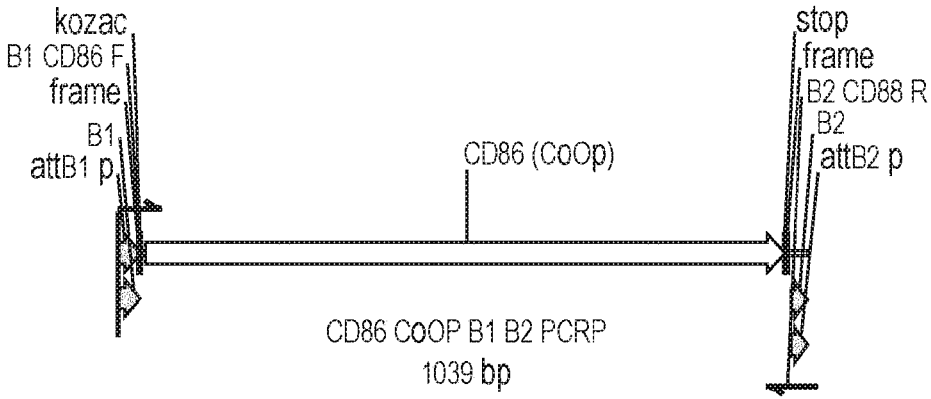
FIG. 5 illustrates a diagram of the CD86 PCRP portion of the pLV430G human CD86 vector.
Figure 6:
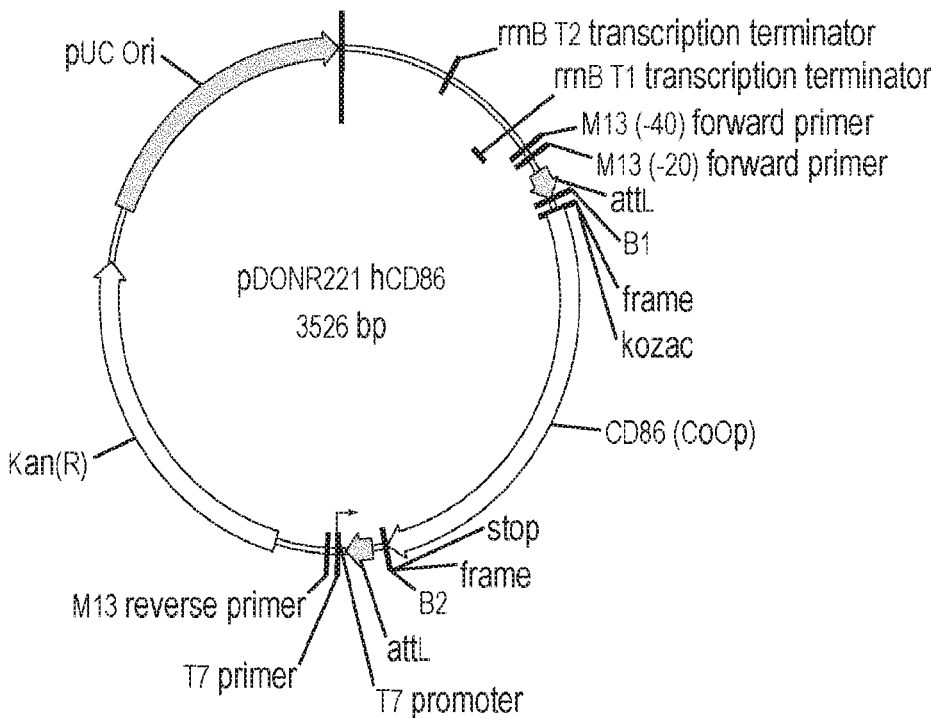
FIG. 6 illustrates a vector diagram of the pDONR221 human CD86 donor vector.
Figure 7:
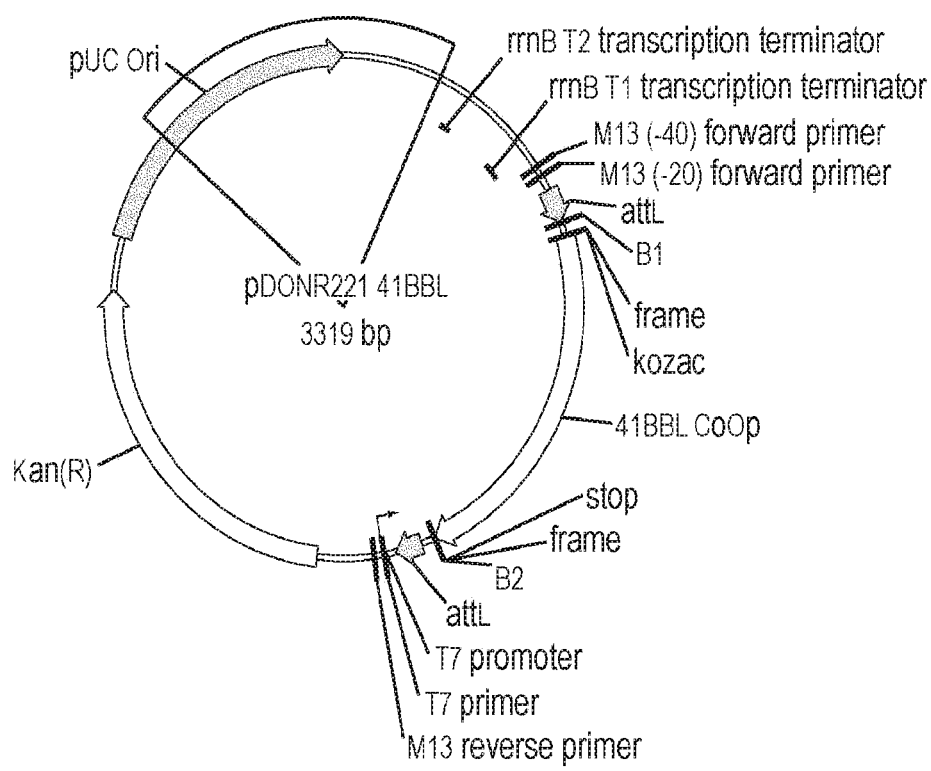
FIG. 7 illustrates a vector diagram of the pDONR22 1 human 4-1BBL donor vector.
Figure 8:
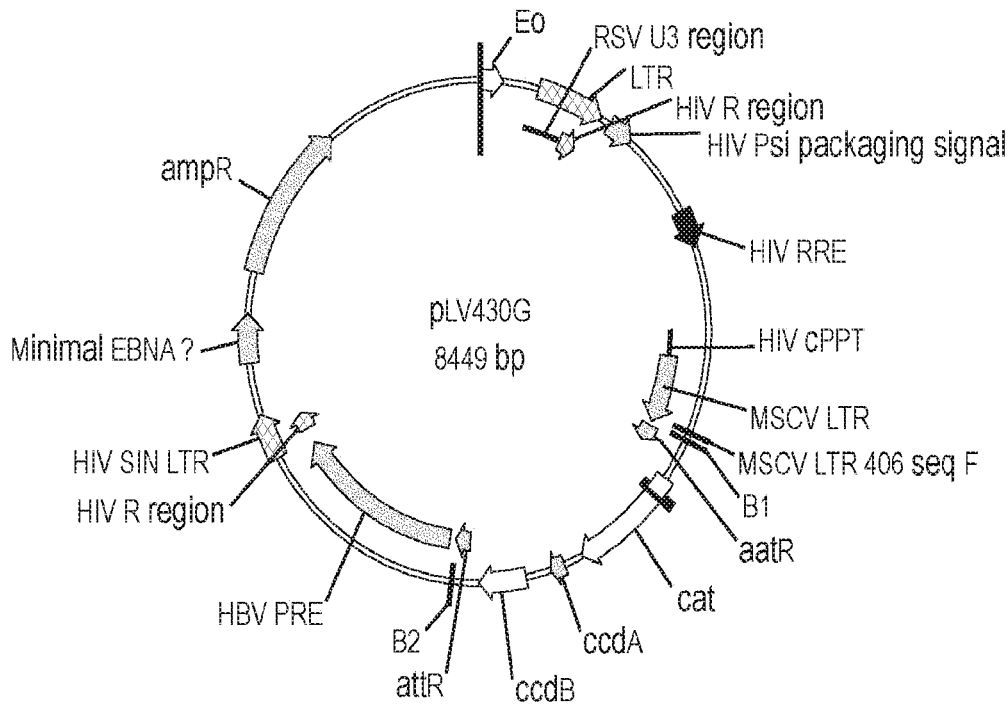
FIG. 8 illustrates a vector diagram of the pLV430G empty vector.
Figure 9:
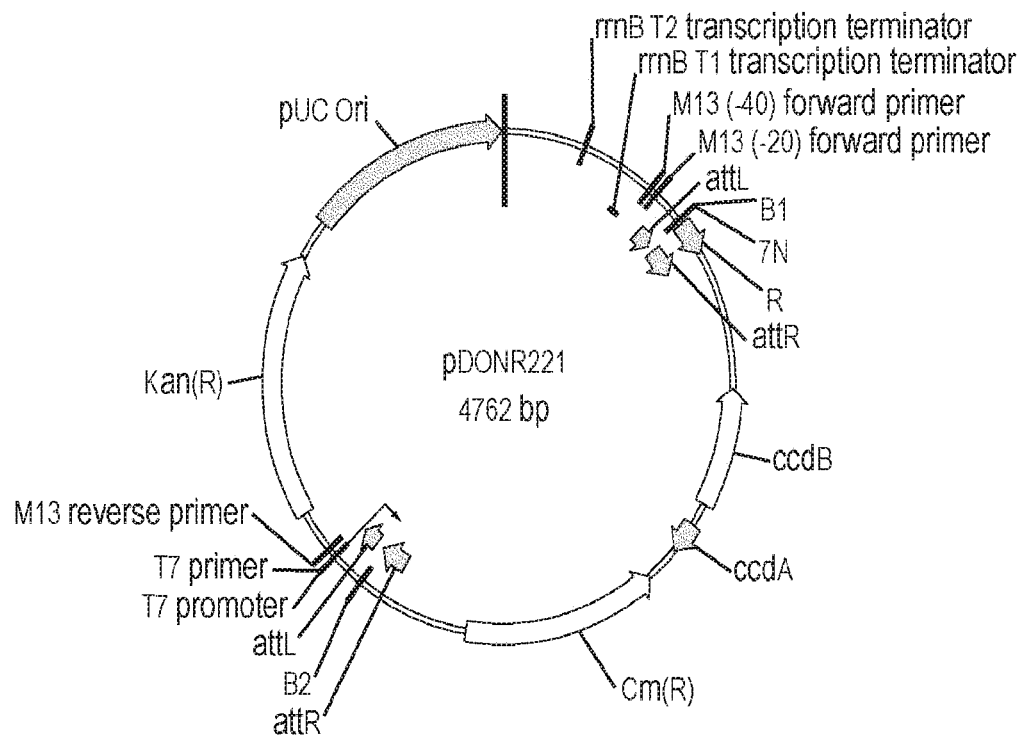
FIG. 9 illustrates a vector diagram of the pDONR221 empty vector.
Figure 10:
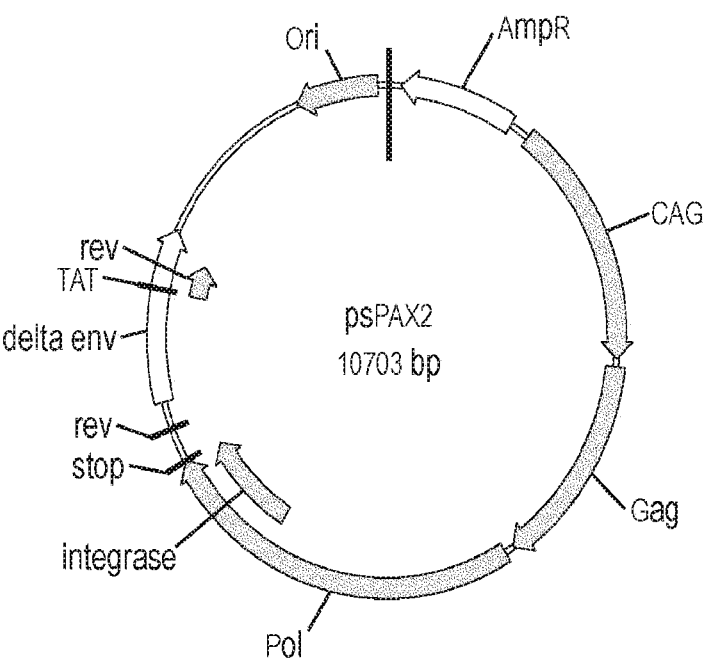
FIG. 10 illustrates a vector diagram of the psPAX2 helper plasmid for lentivirus production.
Figure 11:
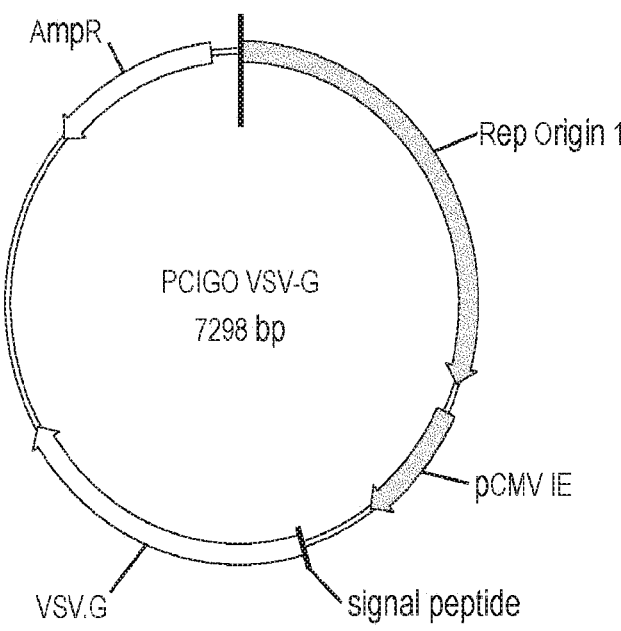
FIG. 11 illustrates a vector diagram of the pCIGO-VSV.G helper plasmid for lentivirus production.

The vectors and portions thereof used for cloning are depicted in FIG. 2 to FIG. 11, and the nucleotide sequences for each vector are given in Table 6. The pLV430G human 4-lBBL vector is illustrated in FIG. 2, with the polymerase chain reaction product (PCRP) portion shown in FIG. 3. The pLV430G human CD86 vector is illustrated in FIG. 4, with the PCRP portion shown in FIG. 5. The pDONR221 human CD86 donor and human 4-1BBL donor vectors are shown in FIG. 6 and FIG. 7, respectively. Diagrams of the empty pLV430G destination vector and empty pDONR221 donor vector for the Gateway cloning method are shown in FIG. 8 and FIG. 9, respectively. FIG. 10 and FIG. 11 illustrate vector diagrams of the psPAX2 and pCIGO-VSV.G helper plasmids used for lentivirus production.

TABLE 5

Summary of costimulatory molecules expressed endogenously on candidate cell lines for aAPCs. CML refers to chronic myeloid leukemia, and AML refers to acute myeloid leukemia. "Pop" refers to the population of cells observed to express the marker (1/2 pop = 50%).

| Cell line Origin | EM-2 Myeloid blast crisis, CML | EM-3 Myeloid blast crisis, CML | KG1-246 AML | KG1-8031 AML | K562 myeloid erythro-leukemia, CML | MOLM-14 AML |
|---|---|---|---|---|---|---|
| HLA-A/B/C | + | + | + | + | – | + |
| CD64 | – | – | – | – | – | + |
| CD80 | – | – | – | – | – | + |
| ICOS-L | – | + | – | – | – | + |
| 4-1BBL | – | – | – | – | – | – |
| PD-Ll | – | – | – | – | – | – |
| CD58 | + | + | + | + | + | + |
| CD86 | – | – | – | – | – | + (l/2 pop) |

TABLE 6

Nucleotide sequences for preparation of lentivirus for transduction of aAPCs.

| Identifier (Description) | Sequence | |
|---|---|---|
| SEQ ID NO: 15 (pLV430G human 4-1BBL vector) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg gggagaaatt agatcgcgat gggaaaaaat | 960 |
| | tcggttaagg ccagggggga agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt gctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aaagaaaagg ggggattggg | 2160 |
| | gggtacagtg caggggaaag aatagtagac cagcataca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacagcaga atatggccca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga atgaccctg tgccttattt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | caacaagttt gtacaaaaaa gcaggcttcg ccaccatgga atacgcctct gatgccagc | 2760 |
| | tggaccccga agctccttgg cctcctgccc ctagagccag agcctgtaga gtgctgcctt | 2820 |
| | gggctctggt ggctggcctt ctccttctgc tgctgctggc cgctgcctgc gctgtgtttc | 2880 |
| | tggccttgtcc ttgggccgtg tcaggccgcca gagcttctcc tggatctggc gccagcccca | 2940 |
| | gactgagaga gggacctgag ctgagcccccg atgatcctgc cggactgctg gatctgagac | 3000 |
| | agggcatgtt cgcccagctg gtggcccaga acgtgctgct gatcgatggc cccctgagct | 3060 |
| | ggtacagcga tcctggactg gctggcgtgt cactgacagg cggcctgagc tacaaagagg | 3120 |
| | acaccaaaga actggtggtg gccaaggccg gcgtgtacta cgtgttcttt cagctggaac | 3180 |
| | tgcggagagt ggtggccggc gaaggatccg gctctgtgtc tctggccactg cacctccagcct | 3240 |
| | ccctgagatc tgctgcaggc gctgctgcac tggcctgac agtggacctg cctccagcct | 3300 |
| | ctagcgaggc cagaaactcc gcattcgggt tcaaggcag actgctgcac ctgtctgccg | 3360 |
| | gccagagact gggagtgcat ctgcacacag aggccagagc cagacacgcc tggcagctga | 3420 |
| | cacagggcgc tacagtgctg ggcctgttca gagtgacccc cgaaattcca gccggctgc | 3480 |
| | ccagccctag aagcgagtag gacccagctt tcttgtacaa agtggtgatt cgagttaatt | 3540 |
| | aagctagcct agtgccattt gttcagtggt tcgtagggct ttcccccact gtttggcttt | 3600 |
| | cagttatatg gatgatgtgg tattgggggc caagtctgta cagcatcttg agtcccttt | 3660 |
| | taccgctgtt accaattttc ttttgtcttt gatgtatgt ttaaaccta acaaaacaaa | 3720 |
| | gagatggggt tactctctaa attttatggg ttatgtcatt ggatgttatg ggtccttgcc | 3780 |
| | acaagaacac atcatcaaaa aaatcaaaga atgttttaga aaacttccta ttaacaggcc | 3840 |
| | tattgattgg aaagtatgtc aacgaattgt gggtcttttg gttttgctg cccttttac | 3900 |
| | acaatgtggt tatcctgcgt tgatgccttt gtatgcatgt attcaatcta agcaggcttt | 3960 |
| | cacttttctcg ccaacttaca aggcctttct gtgtaaacaa tacctgaacc tttacccccgt | 4020 |
| | tgcccggcaa cggccaggtc tgtgccaagt gtttgctgac gcaacccca ctggctgggg | 4080 |
| | cttggtcatg ggccatcagc gcatgcgtgg aaccttttcg gctcctctgc cgatccatac | 4140 |
| | tgcggaactc ctagccgctt gtttttgctcg cagcaggtct ggagcaaaca ttatcgggac | 4200 |
| | tgataactct gttgtcctat cccgcaaata tacatcgttt ccatggctgc taggctgtgc | 4260 |
| | tgccaactgg atcctgcgcg gacgtccctt tgtttacgtc ccgtcggcgc tgaatcctgc | 4320 |
| | ggacgaccct tctcgggggtc gcttgggact ctctcgtccc cttctccgtc tgccgttccg | 4380 |
| | accgaccacg gggcgcacct ctctttacgc ggactccccg tctgtgcctt ctcatctgcc | 4440 |
| | ggaccgtgtg cacttcgctt cacctctgca cgtcgcatgg agaccaccgt gaacgccac | 4500 |

TABLE 6-continued

Nucleotide sequences for preparation of lentivirus for transduction of aAPCs.

| Identifier (Description) | Sequence | |
|---|---|---|
| | caaatattgc ccaaggtctt acataagagg actcttggac tctcagcaat gtcaacgacc | 4560 |
| | gaccttgagg catacttcaa agactgtttg tttaaagact gggaggagtt gggggaggag | 4620 |
| | attaggttaa aggtctttgt actaggaggc tgtaggcata aattggtctg cgcaccagca | 4680 |
| | ccatggcgca atcactagag cggggtacct ttaagaccaa tgacttacaa ggcagctgta | 4740 |
| | gatcttagcc acttttttaaa agaaaagggg ggactggaag ggctaattca ctcccaacga | 4800 |
| | agacaagatc tgcttttttgc ttgtactggg tctctctggt tagaccagat ctgagcctgg | 4860 |
| | gagctctctg gctaactagg gaacccactg cttaagcctc aataaagctt gccttgagtg | 4920 |
| | cttcaagtag tgtgtgcccg tctgttgtgt gactctggta actagagatc cctcagaccc | 4980 |
| | ttttagtcag tgtggaaaat ctctagcagt agtagttcat gtcatcttat tattcagtat | 5040 |
| | ttataacttg caaagaaatg aatatcagag agtgagagga acttgtttat tgcagcttat | 5100 |
| | aatggttaca aataaagcaa tagcatcaca aatttcacaa ataaagcatt ttttttcactg | 5160 |
| | cattctagtt gtggtttgtc caaactcatc aatgtatctt atcatgtctg gctctagcta | 5220 |
| | tccccgcccct aactccgccc atcccgcccc taactccgcc cagttccgcc cattctccgc | 5280 |
| | cccatggctg actaattttt tttatttatg cagaggccga ggccggatcc cttgagtggc | 5340 |
| | tttcatcctg gagcagactt tgcagtctgt ggactgcaac acaacattgc ctttatgtgt | 5400 |
| | aactcttggc tgaagctctt acaccaatgc tggggggacat gtacctccca ggggcccagg | 5460 |
| | aagactacgg gaggctacac caacgtcaat cagaggggcc tgtgtagcta ccgataagcg | 5520 |
| | gaccctcaag agggcattag caatagtgtt tataaggccc ccttgttaat tcttgaagac | 5580 |
| | gaaagggcct cgtgatacgc ctattttttat aggttaatgt catgataata atggtttctt | 5640 |
| | agacgtcagg tggcacttttt cggggaaatg tgcgcggaac ccctatttgt ttatttttct | 5700 |
| | aaatacattc aaatatgtat ccgctcatga gacaataacc ctgataaatg cttcaataat | 5760 |
| | attgaaaaag gaagagtatg agtattcaac atttccgtgt cgcccttatt cccttttttg | 5820 |
| | cggcattttg ccttcctgtt tttgctcacc cagaaacgct ggtgaaagta aaagatgctg | 5880 |
| | aagatcagtt gggtgcacga gtgggttaca tcgaactgga tctcaacagc ggtaagatcc | 5940 |
| | ttgagagttt tcgccccgaa gaacgttttc caatgatgag cactttttaaa gttctgctat | 6000 |
| | gtggcgcggt attatcccgt gttgacgccg ggcaagagca actcggtcgc cgcatacact | 6060 |
| | attctcagaa tgacttggtt gagtactcac cagtcacaga aaagcatctt acggatggca | 6120 |
| | tgacagtaag agaattatgc agtgctgcca taaccatgag tgataacact gcggccaact | 6180 |
| | tacttctgac aacgatcgga ggaccgaagg agctaaccgc tttttttgcac aacatgggg | 6240 |
| | atcatgtaac tcgccttgat cgttgggaac cggagctgaa tgaagccata ccaaacgacg | 6300 |
| | agcgtgacac cacgatgcct gcagcaatgg caacaacgtt gcgcaaacta ttaactggcg | 6360 |
| | aactacttac tctagcttcc cggcaacaat taatagactg gatggaggcg gataaagttg | 6420 |
| | caggaccact tctgcgctcg gcccttccgg ctggctggtt tattgctgat aaatctggag | 6480 |
| | ccggtgagcg tgggtctcgc ggtatcattg cagcactggg gccagatggt aagccctccc | 6540 |
| | gtatcgtagt tatctacacg acggggagtc aggcaactat ggatgaacga aatagacaga | 6600 |
| | tcgctgagat aggtgcctca ctgattaagc attggtaact gtcagaccaa gtttactcat | 6660 |
| | atatacttta gattgattta aaacttcatt tttaatttaa aaggatctag gtgaagatcc | 6720 |
| | tttttgataa tctcatgacc aaaatccctt aacgtgagtt ttcgttccac tgagcgtcag | 6780 |
| | accccgtaga aaagatcaaa ggatcttctt gagatccttt ttttctgcgc gtaatctgct | 6840 |
| | gcttgcaaac aaaaaaacca ccgctaccag cggtggtttg tttgccggat caagagctac | 6900 |
| | caactctttt tccgaaggta actggcttca gcagagcgca gataccaaat actgtccttc | 6960 |
| | tagtgtagcc gtagttaggc caccacttca agaactctgt agcaccgcct acatacctcg | 7020 |
| | ctctgctaat cctgttacca gtggctgctg ccagtggcga taagtcgtgt cttaccgggt | 7080 |
| | tggactcaag acgatagtta ccggataagg cgcagcggtc gggctgaacg ggggggttcgt | 7140 |
| | gcacacagcc cagcttggag cgaacgacct gagctacacc gaactgagat acctacagcg | 7200 |
| | attgagaaag cgccacgctt cccgaaggga gaaaggcgga caggtatccg gtaagcggca | 7260 |
| | gggtcggaac aggagagcgc acgagggagc ttccaggggg aaacgcctgg tatctttata | 7320 |
| | gtcctgtcgg gtttcgccac ctctgacttg agcgtcgatt tttgtgatgc tcgtcagggg | 7380 |
| | ggcggagcct atggaaaaac gccagcaacg cggcctttttt acggttcctg gccttttgct | 7440 |
| | ggccttttgc aagctgtccc tgatggtcgt catctacctg cctggacagc atggcctgca | 7500 |
| | acgcgggcat cccgatgccg ccggaagcga agaatcat aatgggggaag gccatccagc | 7560 |
| | ctcgcgtcg | 7569 |
| SEQ ID NO: 16 (4-1BBL CoOP) | atggaatacg cctctgatgc cagcctggac cccgaagctc cttggcctcc tgccctaga | 60 |
| | gccagagcct gtagagtgct gccttgggct ctggtggctg gccttctcct tctgctgctg | 120 |
| | ctggccgctg cctgcgctgt gtttctggct tgtccttggg ccgtgtcagg cgccagagct | 180 |
| | tctcctggat ctgccgccag ccccagactg agagagggac ctgagctgag ccccgatgat | 240 |
| | cctgccggac tgctggatct gagacaaggc agtttcgccc agctggtggc ccagaacgtg | 300 |
| | ctgctgatcg atggcccccct gagctggtac agcgatccct gactggctgg cgtgtcactg | 360 |
| | acaggcggcc tgagctacaa agaggacacc aaagaactgg tggtggccaa ggccggcgtg | 420 |
| | tactacgtgt tctttcagct ggaactgcgg agagtggtgg ccggcgaagg atccggctct | 480 |
| | gtgtctctgg cactgcatct gcagcccctg aggtcagcgctg caggcgctgc tgcactggcc | 540 |
| | ctgacagtgg acctgcctcc agcctctagc gaggccagaa actccgcatt cgggtttcaa | 600 |
| | ggcagactgc tgcacctgtc tgccggccag agactgggag tgcatctgca cacagaggcc | 660 |
| | agagccagac acgcctggca gctgacacag ggcgctacag tgctgggcct gttcagagtg | 720 |
| | accccgaaa ttccagccgg cctgcccagc cctagaagcg agtag | 765 |
| SEQ ID NO: 17 (4-1BBL FRCP) | ggggacaagt ttgtacaaaa aagcaggctt cgccaccatg gaatacgcct ctgatgccag | 60 |
| | cctggacccc gaagctcctt ggcctcctgc ccctagagcc agagcctgta gagtgctgcc | 120 |
| | ttgggctctg gtggctggcc ttctccttct gctgctgctg gccgctgcct gcgctgtgtt | 180 |
| | tctggcttgt ccttgggccg tgtcaggcgc cagagcttct cctggatctg ccgccagccc | 240 |
| | cagactgaga gagggacctg agctgagccc cgatgatcct gccggactgc tggatctgag | 300 |
| | acagggcatg ttcgcccagc tggtggccca gaacgtgctg ctgatcgatg gcccccctgag | 360 |
| | ctggtacagc gatccctgac tggctggcgt gtcactgaca ggcggcctga gctacaaaga | 420 |
| | ggacaccaaa gaactggtgg tggccaaggc cggcgtgtac tacgtgttct ttcagctgga | 480 |

TABLE 6-continued

Nucleotide sequences for preparation of lentivirus for transduction of aAPCs.

| Identifier (Description) | Sequence | |
|---|---|---|
| | actgcggaga gtggtggccg gcgaaggatc cggctctgtg tctctggcac tgcatctgca | 540 |
| | gccctgaga tctgctgcag gcgctgctgc actggccctg acagtggacc tgcctccagc | 600 |
| | ctctagcgag gccagaaact ccgcattcgg gtttcaaggc agactgctgc acctgtctgc | 660 |
| | cggccagaga ctgggagtgc atctgcacac agaggccaga gccagacacg cctggcagct | 720 |
| | gacacagggc gctacagtgc tgggcctgtt cagagtgacc cccgaaattc cagccggcct | 780 |
| | gcccagccct agaagcgagt aggacccagc tttcttgtac aaagtggtcc cc | 832 |
| SEQ ID NO: 18 (pLV430G human CD86 vector) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgagggcg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggaa agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccaccte ccaacccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaagg ggggattggg | 2160 |
| | gggtacagtg cagggggaaaa gaatagtagac ataatagcaa cagacataca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt ggcaagcta gcttaagtaa cgccattttg | 2340 |
| | caaggcatgg aaaatacata actgagaata gagaagttca gatcaaggtt aggaacagag | 2400 |
| | agacagcaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaaccct cactcggcgc gccagtcctc cgatagactg cgtcgcccgg gtaccgatat | 2700 |
| | caacaagttt gtacaaaaaa gcaggcttcg ccaccatggg cctgagcaac atcctgttcg | 2760 |
| | tgatggcctt cctgctgtcc ggagccgccc ctctgaagat ccaggcctac ttcaacgaga | 2820 |
| | ccgccgacct gccctgccag ttcgccaaca gccagaacca gagcctgagc gaactggtgg | 2880 |
| | tgttctggca ggaccaggaa aacctggtcc tgaacgaggt gtacctgggc aaagaaaagt | 2940 |
| | tcgacagcgt gcacagcaag tacatgggcc ggaccagctt cgacagcgac agctggaccc | 3000 |
| | tgcggctgca caacctgcag atcaaggaca ggcctgtca ccagtgcatc atccaccaca | 3060 |
| | agaatccacc cggcatgatc agaatccacc agatgaacag cgagctgtcc gtgctggcca | 3120 |
| | acttcagcca gcccgagatc gtgcccatca gcaacatcac cgagaacgtg tacatcaacc | 3180 |
| | tgacctgcag cagcatccac ggctaccccg agcccaagaa aatgagcgtg ctgctgcgga | 3240 |
| | ccaagaacag caccatcgag tacgacggcg tgatgcagaa aagccaggac aacgtgaccg | 3300 |
| | agctgtacga cgtgagcatc agcctgagcg tgagcttccc cgacgtgacc agcaacatga | 3360 |
| | ccatcttttg catcctggaa accgacaaga cccggctgct gtccagcccc ttcagcatcg | 3420 |
| | agctggaaga tcccagccc cctcccgacc acatcccctg gatcaccgcc gtgctgccca | 3480 |
| | ccgtgatcat ctgcgtgatg gtgttctgcc tgatcctgtg gaagtggaag aagaagaagc | 3540 |
| | ggcctaggaa cagctacaag tgcggcacca acaccatgga acgggaggaa agcgagcaga | 3600 |
| | ccaagaagcg ggagaagatc cacatccccg agcggagcga cgaggcccag cgggtgttca | 3660 |
| | agagcagcaa gaccagcagc tgcgacaaga gcgacacctg cttctaggac ccagctttct | 3720 |
| | tgtacaaagt ggtgattcga gttaattaag ctagccagt gccatttgtt cagtggttcg | 3780 |
| | tagggctttc ccccactgtt ggctttcag ttatatggat gatgtggtat tggggccaa | 3840 |
| | gtctacag catcttgagt cccttttac cgctgttacc aatttctttt gtctttggg | 3900 |
| | tatacattta aaccctaaca aaacaaagag atggggttac tctctaaatt ttatgggtta | 3960 |
| | tgtcattgga tgttatgggt ccttgccaca agaacacatc atacaaaaaa tcaaagaatg | 4020 |
| | ttttagaaaa cttcctatta acaggcctat tgattggaaa gtatgtcaac gaattgtggg | 4080 |

TABLE 6-continued

Nucleotide sequences for preparation of lentivirus for transduction of aAPCs.

| Identifier (Description) | Sequence | |
|---|---|---|
| | tcttttgggt tttgctgccc cttttacaca atgtggttat cctgcgttga tgcctttgta | 4140 |
| | tgcatgtatt caatctaagc aggctttcac tttctcgcca acttacaagg cctttctgtg | 4200 |
| | taaacaatac ctgaaccttt accccgttgc ccggcaacgg ccaggtctgt gccaagtgtt | 4260 |
| | tgctgacgca acccccactg gctgggggctt ggtcatgggc catcagcgca tgcgtggaac | 4320 |
| | cttttcggct cctctgccga tccatactgc ggaactccta gccgcttgtt ttgctcgcag | 4380 |
| | caggtctgga gcaaacatta tcgggactga taactctgtt gtcctatccc gcaaatatac | 4440 |
| | atcgtttcca tggctgctag gctgtgctgc caactggatc ctgcgcggga cgtcctttgt | 4500 |
| | ttacgtcccg tcggcgctga atcctgcgga cgacccttct cggggtcgct tgggactctc | 4560 |
| | tcgtcccctt ctccgtctgc cgttccgacc gaccacgggg cgcacctctc tttacgcgga | 4620 |
| | ctcccgtct gtgccttctc atctgccgga ccgtgtgcac ttcgcttcac ctctgcacgt | 4680 |
| | cgcatggaga ccaccgtgaa cgcccaccaa atattgccca aggtcttaca taagaggact | 4740 |
| | cttggactct cagcaatgtc aacgaccgac cttgaggcat acttcaaaga ctgtttgttt | 4800 |
| | aaagactggg aggagttggg ggaggagatt aggttaaagg tctttgtact aggaggctgt | 4860 |
| | aggcataaat tggtctgcgc accagcacca tggcgcaatc actagagcgg ggtacctta | 4920 |
| | agaccaatga cttacaaggc agctgtagat cttagccact tttaaaaga aaggggggga | 4980 |
| | ctggaagggc taattcactc ccaacgaaga caagatctgc tttttgcttg tactgggtct | 5040 |
| | ctctggttag accagatctg agcctgggag ctctctggct aactagggaa cccactgctt | 5100 |
| | aagcctcaat aaagcttgcc ttgagtgctt caagtagtgt gtgcccgtct gttgtgtgac | 5160 |
| | tctggtaact agagatccct cagacccttt tagtcagtgt ggaaaatctc tagcagtagt | 5220 |
| | agttcatgtc atcttattat tcagtattta taacttgcaa agaaatgaat atcagagagt | 5280 |
| | gagaggaact tgtttattgc agcttataat ggttacaaat aaagcaatag catcacaaat | 5340 |
| | ttcacaaata aagcattttt ttcactgcat tctagttgtg gtttgtccaa actcatcaat | 5400 |
| | gtatcttatc atgtctggct ctagctatcc cgcccctaac tccgcccatc ccgcccctaa | 5460 |
| | ctccgcccag ttccgcccat tctccgcccc atggctgact aattttttt atttatgcag | 5520 |
| | aggccgaggc cggatccctt gagtggcttt catcctggag cagactttgc agtctgtgga | 5580 |
| | ctgcaacaca acattgcctt tatgtgtaac tcttggctga agctcttaca ccaatgctgg | 5640 |
| | gggacatgta cctcccaggg gcccaggaag actacgggag gctacaccaa cgtcaatcag | 5700 |
| | agggggcctgt gtagctaccg ataagcggac cctcaagagg gcattagcaa tagtgtttat | 5760 |
| | aaggcccct tgttaattct tgaagacgaa agggcctcgt gatacgccta tttttatagg | 5820 |
| | ttaatgtcat gataataatg gtttcttaga cgtcaggtgg cactttttcgg ggaaatgtgc | 5880 |
| | gcggaacccc tatttgttta tttttctaaa tacattcaaa tatgtatccg ctcatgagac | 5940 |
| | aataaccctg ataaatgctt caataatatt gaaaaaggaa gagtatgagt attcaacatt | 6000 |
| | tccgtgtcgc ccttattccc tttttttgcgg cattttgcct tcctgttttt gctcacccag | 6060 |
| | aaacgctggt gaaagtaaaa gatgctgaag atcagttggg tgcacgagtg ggttacatcg | 6120 |
| | aactggatct caacagcggt aagatccttg agagttttcg ccccgaagaa cgttttccaa | 6180 |
| | tgatgagcac ttttaaagtt ctgctatgtg gcgcggtatt atcccgtgtt gacgccgggc | 6240 |
| | aagagcaact cggtcgccgc atacactatt ctcagaatga cttggttgag tactcaccag | 6300 |
| | tcacagaaaa gcatcttacg gatggcatga cagtaagaga attatgcagt gctgccataa | 6360 |
| | ccatgagtga taacactgcg gccaacttac ttctgacaac gatcggagga ccgaaggagc | 6420 |
| | taaccgcttt tttgcacaac atgggggatc atgtaactcg ccttgatcgt tgggaaccgg | 6480 |
| | agctgaatga agccatacca aacgacgagc gtgacaccac gatgcctgca gcaatggcaa | 6540 |
| | caacgttgcg caaactatta actggcgaac tacttactct agcttcccgg caacaattaa | 6600 |
| | tagactggat ggaggcggat aaagttgcag gaccacttct gcgctcggcc cttccggctg | 6660 |
| | gctggtttat tgctgataaa tctggagccg gtgagcgtgg gtctcgcggt atcattgcag | 6720 |
| | cactggggcc agatggtaag ccctcccgta tcgtagttat ctacacgacg gggagtcagg | 6780 |
| | caactatgga tgaacgaaat agacagatcg ctgagatagg tgcctcactg attaagcatt | 6840 |
| | ggtaactgtc agaccaagtt tactcatata tactttagat tgatttaaaa cttcattttt | 6900 |
| | aatttaaaag gatctaggtg aagatccttt ttgataatct catgaccaaa atcccttaac | 6960 |
| | gtgagttttc gttccactga gcgtcagacc ccgtagaaaa gatcaaagga tcttcttgag | 7020 |
| | atccttttt tctgcgcgta atctgctgct tgcaaacaaa aaaaccaccg ctaccagcgg | 7080 |
| | tggtttgttt gccggatcaa gagctaccaa ctctttttcc gaaggtaact ggcttcagca | 7140 |
| | gagcgcagat accaaatact gtccttctag tgtagccgta gttaggccac cacttcaaga | 7200 |
| | actctgtagc accgcctaca tacctcgctc tgctaatcct gttaccagtg gctgctgcca | 7260 |
| | gtggcgataa gtcgtgtctt accgggttgg actcaagacg atagttaccg gataaggcgc | 7320 |
| | agcggtcggg ctgaacgggg ggttcgtgca cacagcccag cttggagcga acgacctaca | 7380 |
| | ccgaactgag atacctacag cgtgagcatt gagaaagcgc cacgcttccc gaagggagaa | 7440 |
| | aggcggacag gtatccggta agcggcaggg tcggaacagg agagcgcacg agggagcttc | 7500 |
| | caggggggaaa cgcctggtat ctttatagtc ctgtcgggt tcgccacctc tgacttgagc | 7560 |
| | gtcgatttt gtgatgctcg tcaggggggc ggagcctatg gaaaaacgcc agcaacgcgg | 7620 |
| | cctttttacg gttcctggcc ttttgctggc cttttttgaaa ctgtccctga tggtcgtcat | 7680 |
| | ctacctgcct ggacagcatg gcctgcaacg cgggcatccc gatgccgccg gaagcgagaa | 7740 |
| | gaatcataat ggggaaggcc atccagcctc gcgtcg | 7776 |
| SEQ ID NO: 19 (CD86 CoOP) | atgggggcctga gcaaacatcct gttcgtgatg gccttcctgc tgtccggagc cgcccctctg | 60 |
| | aagatccagg cctacttcaa cgagaccgcc gacctgccct gccagttcgc caacagccag | 120 |
| | aaccagagcc tgagcgaact ggtggtgttc tggcaggacc aggaaaacct ggtcctgaac | 180 |
| | gaggtgtacc tgggcaaaga aaagttcgac agcgtgcaca gcaagtacat gggccggacc | 240 |
| | agcttcgaca cgcagcagctg gaccctgcgg ctgcacaacc tgcagatcaa ggacaagggc | 300 |
| | ctgtaccagt gcatcatcca ccacaagaaa cccaccggca tgatcagaat ccaccagatg | 360 |
| | aacagcgagc tgtccgtgct ggccaacttc agccagcccg agatcgtgcc catcagcaac | 420 |
| | atcaccgaga cgtgtacact caacctgacc tgcagcagca tccacggcta ccccgagccc | 480 |
| | aagaaaatga gcgtgctgct gcggaccaag aacagcacca tcgagtacga cggcgtgatg | 540 |
| | cagaaaagcc aggacaacgt gaccgagctg tacgacgtga gcatcagcct gagcgtgagc | 600 |
| | ttccccgacg tgaccagcaa catgaccatc ttttgcatcc tggaaaccca caagacccgg | 660 |
| | ctgctgtcca gcccccttcag catcgagctg gaagatcccc agccccctcc cgaccacatc | 720 |

TABLE 6-continued

Nucleotide sequences for preparation of lentivirus for transduction of aAPCs.

| Identifier (Description) | Sequence | |
|---|---|---|
| | ccctggatca ccgccgtgct gcccaccgtg atcatctgcg tgatggtgtt ctgcctgatc | 780 |
| | ctgtggaagt ggaagaagaa gaagcggcct aggaacagct acaagtgcgg caccaacacc | 840 |
| | atggaacggg aggaaagcga gcagaccaag aagcgggaga agatccacat ccccgagcgg | 900 |
| | agcgacgagg cccagcgggt gttcaagagc agcaagacca gcagctgcga caagagcgac | 960 |
| | acctgcttc | 969 |
| | | |
| SEQ ID NO: 20 (CD86 PCRP) | ggggacaagt ttgtacaaaa aagcaggctt cgccaccatg ggcctgagca acatcctgtt | 60 |
| | cgtgatggcc ttcctgctgt ccggagccgc ccctctgaag atccaggcct acttcaacga | 120 |
| | gaccgccgac ctgccctgcc agttcgccaa cagccagaac cagagcctga gcgaactggt | 180 |
| | ggtgttctgg caggaccagg aaaacctggt cctgaacgag gtgtacctgg gcaaagaaaa | 240 |
| | gttcgacagc gtgcacagca agtacatggg ccggaccagc ttcgacagcg acagctggac | 300 |
| | cctgcggctg cacaacctgc agatcaagga caagggcctg taccagtgca tcatccacca | 360 |
| | caagaaaccc accggcatga tcagaatcca ccagatgaac agcgagctgt ccgtgctggc | 420 |
| | caacttcagc cagcccgaga tcgtgcccat cagcaacatc accgagaacg tgtacatcaa | 480 |
| | cctgacctgc agcagcatcc acggctaccc cgagcccaag aaaatgagcg tgctgctgcg | 540 |
| | gaccaagaac agcaccatgc agtacgacgg cgtgatgcag aaaagccagg acaacgtgac | 600 |
| | cgagctgtac gacgtgagca tcagcctgag cgtgagcttc cccgacgtga ccagcaacat | 660 |
| | gaccatcttt tgcatcctgg aaaccgacaa gacccggctg ctgtccagcc ccttcagcat | 720 |
| | cgagctggaa gatccccagc ccctcccga ccacatcccc tggatcaccg ccgtgctgcc | 780 |
| | caccgtgatc atctgcgtga tggtgttctg cctgatcctg tggaagtgga agaagaagaa | 840 |
| | gcggcctagg aacagctaca agtgcggcac caacaccatg gaacgggagg aaagcgagca | 900 |
| | gaccaagaag cgggagaaga tccacatccc cgagcggagc gacgaggccc agcgggtgtt | 960 |
| | caagagcagc aagaccagca gctgcgacaa gagcgacacc tgcttctagg acccagcttt | 1020 |
| | cttgtacaaa gtggtcccc | 1039 |
| | | |
| SEQ ID NO: 21 (pDONR221 CD86 vector) | ctttcctgcg ttatcccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga aagcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcgggcgt cctgcccgcc accctccggg ccgttgcttc | 360 |
| | acaacgttca aatccgctcc ggcggatttg tcctactcag gagagcgtt caccgacaaa | 420 |
| | caacagataa aacgaaaggc ccagtcttcc gactgagcct ttcgttttat ttgatgcctg | 480 |
| | gcagttccct actctcgcgt taacgctagc atggatgttt tcccagtcac gacgttgtaa | 540 |
| | aacgacggcc agtcttaagc tcgggcccca ataatgatt ttattttgac tgatagtgac | 600 |
| | ctgttcgttg caacacattg atgagcaatg cttttttata atgcacaagt ttgtacaaaa | 660 |
| | aagcaggctt cgccaccatg ggcctgagca acatcctgtt cgtgatggcc ttcctgctgt | 720 |
| | ccggagccgc ccctctgaag atccaggcct acttcaacga gaccgccgac ctgccctgcc | 780 |
| | agttcgccaa cagccagaac cagagcctga gcgaactggt ggtgttctgg caggaccagg | 840 |
| | aaaacctggt cctgaacgag gtgtacctgg gcaaagaaaa gttcgacagc gtgcacagca | 900 |
| | agtacatggg ccggaccagc ttcgacagcg acagctggac cctgcggctg cacaacctgc | 960 |
| | agatcaagga caagggcctg taccagtgca tcatccacca caagaaaccc accggcatga | 1020 |
| | tcagaatcca ccagatgaac agcgagctgt ccgtgctggc caacttcagc cagcccgaga | 1080 |
| | tcgtgcccat cagcaacatc accgagaacg tgtacatcaa cctgacctgc agcagcatcc | 1140 |
| | acggctaccc cgagcccaag aaaatgagcg tgctgctgcg gaccaagaac agcaccatcc | 1200 |
| | agtacgacgg cgtgatgcag aaaagccagg acaacgtgac cgagctgtac gacgtgagca | 1260 |
| | tcagcctgag cgtgagcttc cccgacgtga ccagcaacat gaccatcttt tgcatcctgg | 1320 |
| | aaaccgacaa gacccggctg ctgtccagcc ccttcagcat cgagctggaa gatccccagc | 1380 |
| | cccctcccga ccacatcccc tggatcaccg ccgtgctgcc caccgtgatc atctgcgtga | 1440 |
| | tggtgttctg cctgatcctg tggaagtgga agaagaagaa gcggcctagg aacagctaca | 1500 |
| | agtgcggcac caacaccatg gaacgggagg aaagcgagca gaccaagaag cgggagaaga | 1560 |
| | tccacatccc cgagcggagc gacgaggccc agcgggtgtt caagagcagc aagaccagca | 1620 |
| | gctgcgacaa gagcgacacc tgcttctagg acccagcttt cttgtacaaa gtggtcatta | 1680 |
| | taagaaagca ttgcttatca atttgttgca acgaacaggt cactatcagt caaaataaaa | 1740 |
| | tcattatttg ccatccagct gatatccct atagtgagtc gtattacatg gtcatagctg | 1800 |
| | tttcctggca gctctggccc gtgtctcaaa atctctgatg ttacattgca caagataaaa | 1860 |
| | taatatcatc atgaacaata aaactgtctg cttacataaa cagtaataca aggggtgtta | 1920 |
| | tgagccatat tcaacgggaa acgtcgaggc cgcgattaaa ttccaacatg gatgctgatt | 1980 |
| | tatatgggta taaatgggct cgcgataatg tcgggcaatc aggtgcgaca atctatcgct | 2040 |
| | tgtatgggaa gcccgatgcg ccagagttgt ttctgaaaca tggcaaaggt agcgttgcca | 2100 |
| | atgatgttac agatgagatg gtcagactaa actggctgac ggaatttatg cctcttccga | 2160 |
| | ccatcaagca ttttatccgt actcctgatg atgcatggtt actcaccact gcgatccccg | 2220 |
| | gaaaaacagc attccaggta ttagaagaat atcctgattc aggtgaaaat attgttgatg | 2280 |
| | cgctggcagt gttcctgcgc cggttgcatt cgattcctgt ttgtaattgt ccttttaaca | 2340 |
| | gcgatcgcgt atttcgtctc gctcaggcgc aatcacgaat gaataacggt ttggttgatg | 2400 |
| | cgagtgattt tgatgacgag cgtaatggct ggcctgttga acaagtctgg aaagaaatgc | 2460 |
| | ataaactttt gccattctca ccggattcag tcgtcactca tggtgatttc tcacttgata | 2520 |
| | accttatttt tgacgagggg aaattaatag gttgtattga tgttggacga gtcggaatcg | 2580 |
| | cagaccgata ccaggatctt gccatcctat ggaactgcct cggtgagttt tctccttcat | 2640 |
| | tacagaaacg gctttttcaa aaatatggta ttgataatcc tgatatgaat aaattgcagt | 2700 |
| | ttcatttgat gctcgatgag tttttctaat cagaattggt taattggttg taacactggc | 2760 |
| | agagcattac gctgacttga cgggacggcg caagctcatg accaaaatcc cttaacgtga | 2820 |
| | gttacgcgtc gttccactga gcgtcagacc ccgtagaaaa gatcaaagga tcttcttgag | 2880 |
| | atcctttttt tctgcgcgta atctgctgct tgcaaacaaa aaaaccaccg ctaccagcgg | 2940 |
| | tggtttgttt gccggatcaa gagctaccaa ctcttttccc gaaggtaact ggcttcagca | 3000 |

TABLE 6-continued

Nucleotide sequences for preparation of lentivirus for transduction of aAPCs.

| Identifier (Description) | Sequence | |
|---|---|---|
| | gagcgcagat accaaatact gttcttctag tgtagccgta gttaggccac cacttcaaga | 3060 |
| | actctgtagc accgcctaca tacctcgctc tgctaatcct gttaccagtg gctgctgcca | 3120 |
| | gtggcgataa gtcgtgtctt accgggttgg actcaagacg atagttaccg gataaggcgc | 3180 |
| | agcggtcggg ctgaacgggg ggttcgtgca cacagcccag cttggagcga acgacctaca | 3240 |
| | ccgaactgag atacctacg cgtgagctat gagaaagcgc cacgcttccc gaagggagaa | 3300 |
| | aggcggacag gtatccggta agcggcaggg tcggaacagg agagcgcacg agggagcttc | 3360 |
| | caggggaaa cgcctggtat ctttatagtc ctgtcgggtt cgccacctc tgacttgagc | 3420 |
| | gtcgatttt gtgatgctcg tcaggggggc ggagcctatg gaaaaacgcc agcaacgcgg | 3480 |
| | ccttttacg gttcctggcc ttttgctggc cttttgctca catgtt | 3526 |
| SEQ ID NO: 22 (pDONR221 4- 1BBL vector) | ctttcctgcg ttatcccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga aagcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcggggcgt cctgcccgcc accctccggg ccgttgcttc | 360 |
| | acaacgttca aatccgctcc cggcggattt gtcctactca ggagagcgtt caccgacaaa | 420 |
| | caacagataa aacgaaaggc ccagtcttcc gactgagcct ttcgttttat ttgatgcctg | 480 |
| | gcagttccct actctcgcgt taacgctagc atggatgttt cccagtcac gacgttgtaa | 540 |
| | aacgacggcc agtcttaagc tcgggcccca aataatgatt ttattttgac tgatagtgac | 600 |
| | ctgttcgttg caacacattg atgagcaatg cttttttata atgcacaagt ttgtacaaaa | 660 |
| | aagcaggctt cgccaccatg aatacgcct ctgatgccag cctggacccc gaagctcctt | 720 |
| | ggcctcctgc ccctagagcc agagcctgta gagtgctgcc ttgggctctg gtggctggcc | 780 |
| | ttctccttct gctgctgctg gccgctgcct gcgctgtgtt tctggcttgt ccttgggccg | 840 |
| | tgtcaggcgc cagagcttct cctggatctg ccgccagccc cagactgaga gagggacctg | 900 |
| | agctgagccc cgatgatccc gccggactgc tggatctgag acagggcatg ttcgcccagc | 960 |
| | tggtggccca gaacgtgctg ctgatcgatg gcccctgag ctggtacagc gatcctggac | 1020 |
| | tggctggcgt gtcactgaca ggcggcctga gctacaaaga ggacaccaaa gaactggtgg | 1080 |
| | tggccaaggc cggcgtgtac tacgtgttct ttcagctgga actgcggaga gtggtggccg | 1140 |
| | gcgaaggatc cggctctgtg tctctggcac tgcatctgca gcccctgaga tctgctcag | 1200 |
| | gcgctgctgc actggccctg acagtggacc tgcctccagc ctctagcgag gccagaaact | 1260 |
| | ccgcattcgg gtttcaaggc agactgctgc acctgtctgc cggccagaga ctgggagtgc | 1320 |
| | atctgcacac agaggccaga gccagacacg cctggcacgt gacacagggc gctacagtgc | 1380 |
| | tgggcctgtt cagagtgacc cccgaaattc cagccggcct gcccagccct agaagcgagt | 1440 |
| | aggacccagc tttcttgtac aaagtggtca ttataagaaa gcattgctta tcaatttgtt | 1500 |
| | gcaacgaaca ggtcactatc agtcaaaata aaatcattat ttgccatcca gctgatatcc | 1560 |
| | cctatagtga gtcgtattac atggtcatag ctgtttcctg gcagctctgg cccgtgtcc | 1620 |
| | aaaatctctg atgttacatt gcacaagata aaataatatc atcatgaaca ataaaactgt | 1680 |
| | ctgcttacat aaacagtaat acaaggggtg ttatgagcca tattcaacgg gaaacgtcga | 1740 |
| | ggccgcgatt aaattccaac atggatgctg atttatatgg gtataaatgg gctcgcgata | 1800 |
| | atgtcgggca atcaggtgcg acaatctatc gcttgtatgg gaagcccgat gcgccagagt | 1860 |
| | tgtttctgaa acatggcaaa ggtagcgttg ccaatgatgt tacagatgag atggtcagac | 1920 |
| | taaactggct gacggaattt atgcctcttc cgaccatcaa gcattttatc cgtactcctg | 1980 |
| | atgatgcatg gttactcacc actgcgatcc ccggaaaaac agcattccag gtattagaag | 2040 |
| | aatatcctga ttcaggtgaa aatattgttg atgcgctggc agtgttcctg cgccggttgc | 2100 |
| | attcgattcc tgtttgtaat gtccttttta cagcgatcg cgtatttcgt ctcgctcagg | 2160 |
| | cgcaatcacg aatgaataac ggtttggttg atgcgagtga ttttgatgac gagcgtaatg | 2220 |
| | gctggcctgt tgaacaagtc tggaaagaaa tgcataaact tttgccattc tcaccggatt | 2280 |
| | cagtcgtcac tcatggtgat ttctcacttg ataaccttat ttttgacgag gggaaattaa | 2340 |
| | taggttgtat tgatgttgga cgagtcggaa tcgcagaccg ataccaggat cttgccatcc | 2400 |
| | tatggaactg cctcggtgag ttttctcctt cattacagaa acggctttt caaaaatatg | 2460 |
| | gtattgataa tcctgatatg aataaattgc agtttcattt gatgctcgat gagtttttct | 2520 |
| | aatcagaatt ggttaattgg ttgtaacact ggcagagcat tacgctgact tgacgggacg | 2580 |
| | gcgcaagctc atgaccaaaa tcccttaacg tgagttacgc gtcgttccac tgagcgtcag | 2640 |
| | accccgtaga aaagatcaaa ggatcttctt gagatccttt ttttctgcgc gtaatctgct | 2700 |
| | gcttgcaaac aaaaaaacca ccgctaccag cggtggtttg tttgccggat caagagctac | 2760 |
| | caactctttt tccgaaggta actggcttca gcagagcgca gataccaaat actgttcttc | 2820 |
| | tagtgtagcc gtagttaggc caccacttca agaactctgt agcaccgcct acatacctcg | 2880 |
| | ctctgctaat cctgttacca gtggctgctg ccagtggcga taagtcgtgt cttaccgggt | 2940 |
| | tggactcaag acgatagtta ccggataagg cgcagcggtc gggctgaacg ggggggttcgt | 3000 |
| | gcacacagcc cagcttggag cgaacgacct acaccgaact gagataccta cagcgtgagc | 3060 |
| | tatgagaaag cgccacgctt cccgaaggga aaaggcggac aggtatccgg taagcggcagg | 3120 |
| | gggtcggaac aggagagcgc acgagggagc ttccagggg aaacgcctgg tatctttata | 3180 |
| | gtcctgtcgg gtttcgccac ctctgacttg agcgtcgatt tttgtgatgc tcgtcagggg | 3240 |
| | ggcggagcct atggaaaaac gccagcaacg cggccttttt acggttcctg gccttttgct | 3300 |
| | ggccttttgc tcacatgtt | 3319 |
| SEQ ID NO: 23 (pLV430G vector) | cgataaccct aattcgatag catatgcttc ccgttgggta acatatgcta ttgaattagg | 60 |
| | gttagtctgg atagtatata ctactacccg ggaagcatat gctaccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |

TABLE 6-continued

Nucleotide sequences for preparation of lentivirus for transduction of aAPCs.

| Identifier (Description) | Sequence | |
|---|---|---|
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggga agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggtttta aaagaaaagg ggggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacagcaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaaccccct cactcggcgc gccagtcctc cgatagactg cgtcgcccgg gtaccgatat | 2700 |
| | cacaagtttg tacaaaaaag ctgaacgaga aacgtaaaat gatataaata tcaatatatt | 2760 |
| | aaaattagatt ttgcataaaa aacagactac ataatactgt aaaacacaac atatccagtc | 2820 |
| | actatggcgg ccgcattagg caccccaggc tttacacttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttc agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact cttcgccccc gttttcacc atggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcggggc gtaaacgcgt | 3600 |
| | ggatccggct tactaaaagc cagataacag tatgcgtatt tgcgcgctga ttttttgcggt | 3660 |
| | ataagaatat atactgatat gtatacccga agtatgtcaa aagaggtat gctatgaagc | 3720 |
| | agcgtattac agtgacagtt gacagcgaca gctatcagtt gctcaaggca tatatgatgt | 3780 |
| | caatatctcc ggtctggtaa gcacaaccat gcagaatgaa gcccgtcgtc tgcgtgccga | 3840 |
| | acgctggaaa gcggaaaatc aggaagggat ggctgaggtc gcccggttta ttgaaatgaa | 3900 |
| | cggctctttt gctgacgaga acaggggctg gtttaaggt tacacctata | 3960 |
| | aaagagagag ccgttatcgt ctgtttgtgg atgtacagag tgatattatt gacacgcccg | 4020 |
| | ggcgacggat ggtgatcccc ctggccagtg cacgtctgct gtcagataaa gtctcccgtg | 4080 |
| | aactttaccc ggtggtgcat atcggggatg aaagctggcg catgatgacc accgatatgg | 4140 |
| | ccagtgtgcc ggtctccgtt atcggggaag aagtggctga tctcagccac cgcgaaaatg | 4200 |
| | acatcaaaaa cgccattaac ctgatgttct ggggaatata aatgtcaggc tcccttatac | 4260 |
| | acagccagtc tgcaggtcga ccatagtgac tggatatgtt gtgttttaca gtattatgta | 4320 |
| | gtctgttttt tatgcaaaat ctaatttaat atattgatat ttatatcatt ttacgtttct | 4380 |
| | cgttcagctt tcttgtacaa agtggtgatt cgagttaatt aagctagct agtgccattt | 4440 |
| | gttcagtggt tcgtagggct ttcccccact gtttggcttt cagttatatg gatgatgtgg | 4500 |
| | tattgggggc caagtctgta cagcatcttg agtccctttt taccgctgtt accaattttc | 4560 |
| | ttttgtcttt gggtatacat ttaaaccta acaaacaaa gagatggggg tactctctaa | 4620 |
| | attttatggg ttatgtcatt ggatgttatg ggtccttgca acaagaacac atcatacaaa | 4680 |
| | aaatcaaaga atgttttaga aaatcaaaga ttaacaggcc tattgattgg aaagtatgtc | 4740 |
| | aacgaattgt gggtcttttg ggttttgctg ccccttttac acaatgtggt tatcctgcgt | 4800 |
| | tgatgccttt gtatgcatgt attcaatcta agcaggcttt cactttctcg ccaacttaca | 4860 |
| | aggcctttct gtgtaaacaa tacctgaacc tttaccccgt tgcccggcaa cggccaggtc | 4920 |
| | tgtgccaagt gtttgctgac gcaaccccca ctggctgggg cttggtcatg ggccatcagc | 4980 |

Nucleotide sequences for preparation of lentivirus for transduction of aAPCs.

| Identifier (Description) | Sequence | |
|---|---|---|
| | gcatgcgtgg aacctttcg gctcctctgc cgatccatac tgcggaactc ctagccgctt | 5040 |
| | gttttgctcg cagcaggtct ggagcaaaca ttatcgggac tgataactct gttgtcctat | 5100 |
| | cccgcaaata tacatcgttt ccatggctgc taggctgtgc tgccaactgg atcctgcgcg | 5160 |
| | ggacgtcctt tgtttacgtc ccgtcggcgc tgaatcctgc ggacgaccct tctcggggtc | 5220 |
| | gcttgggact ctctcgtccc cttctccgtc tgccgttccg accgaccacg gggcgcacct | 5280 |
| | ctctttacgc ggactccccg tctgtgcctt ctcatctgcc ggaccgtgtg cacttcgctt | 5340 |
| | cacctctgca cgtcgcatgg agaccaccgt gaacgcccac caaatattgc ccaaggtctt | 5400 |
| | acataagagg actcttggac tctcagcaat gtcaacgacc gaccttgagg catacttcaa | 5460 |
| | agactgtttg tttaaagact gggaggagtt gggggaggag attaggttaa aggtctttgt | 5520 |
| | actaggaggc tgtaggcata aattggtctg cgcaccagca ccatggcgca atcactagag | 5580 |
| | cggggtacct ttaagaccaa tgacttacaa ggcagctgta gatcttagcc acttttttaaa | 5640 |
| | agaaaagggg ggactggaag ggctaattca ctcccaacga agacaagatc tgctttttga | 5700 |
| | ttgtactggg tctctctggt tagaccagat ctgagcctgg gagctctctg gctaactagg | 5760 |
| | gaacccactg cttaagcctc aataaagctt gccttgagtg cttcaagtag tgtgtgcccg | 5820 |
| | tctgttgtgt gactctggta actagagatc cctcagaccc ttttagtcag tgtggaaaat | 5880 |
| | ctctagcagt agtagttcat gtcatcttat tattcagtat ttataacttg caaagaaatg | 5940 |
| | aatatcagag agtgagagga acttgtttat tgcagcttat aatggttaca aataaagcaa | 6000 |
| | tagcatcaca aatttcacaa ataaagcatt ttttcactg cattctagtt gtggtttgtc | 6060 |
| | caaactcatc aatgtatctt atcatgtctg gctctagcta tcccgcccct aactccgccc | 6120 |
| | atcccgcccc taactccgcc cagttccgcc cattctccgc cccatggctg actaattttt | 6180 |
| | tttatttatg cagaggccga ggccggatcc cttgagtggc tttcatcctg gagcagactt | 6240 |
| | tgcagtctgt ggactgcaac acaacattgc ctttatgtgt aactcttggc tgaagctctt | 6300 |
| | acaccaatgc tggggggacat gtacctccca ggggcccagg aagactacgg gaggctacac | 6360 |
| | caacgtcaat cagagggggc tgtgtagcta ccgataagcg gaccctcaag gggcattag | 6420 |
| | caatagtgtt tataaggccc ccttgttaat tcttgaagac gaaagggcct cgtgatacgc | 6480 |
| | ctatttttat aggttaatgt catgataata atggtttctt agacgtcagg tggcactttt | 6540 |
| | cggggaaatg tgcgcggaac ccctatttgt ttattttctt aaatacattc aaatatgtat | 6600 |
| | ccgctcatga gacaataacc ctgataaatg cttcaataat attgaaaaag gaagagtatg | 6660 |
| | agtattcaac atttccgtgt cgcccttatt ccctttttttg cggcattttg ccttcctgtt | 6720 |
| | tttgctcacc cagaaacgct ggtgaaagta aaagatgctg aagatcagtt gggtgcacga | 6780 |
| | gtgggttaca tcgaactgga tctcaacagc ggtaagatcc ttgagagttt tcgccccgaa | 6840 |
| | gaacgttttc caatgatgag cacttttaaa gttctgctat gtggcgcggt attatcccgt | 6900 |
| | gttgacgccg ggcaagagca actcggtcgc cgcatacact attctcagaa tgacttggtt | 6960 |
| | gagtactcac cagtcacaga aaagcatctt acggatggca tgacagtaag agaattatgc | 7020 |
| | agtgctgcca taaccatgag tgataacact gcggccaact tacttctgac aacgatcgga | 7080 |
| | ggaccgaagg agctaaccgc ttttttgcac aacatggggg atcatgtaac tcgccttgat | 7140 |
| | cgttgggaac cggagctgaa tgaagccata ccaaacgacg agcgtgacac cacgatgcct | 7200 |
| | gcagcaatgg caacaacgtt gcgcaaacta ttaactggcg aactacttac tctagcttcc | 7260 |
| | cggcaacaat taatagactg gatggaggcg gataaagttg caggaccact tctgcgctcg | 7320 |
| | gcccttccgg ctggctggtt tattgctgat aaatctggag ccggtgagcg tgggtctcgc | 7380 |
| | ggtatcattg cagcactggg gccagatggt aagccctccc gtatcgtagt tatctacacg | 7440 |
| | acggggagtc aggcaactat ggatgaacga aatagacaga tcgctgagat aggtgcctca | 7500 |
| | ctgattaagc attggtaact gtcagaccaa gtttactcat atatacttta gattgattta | 7560 |
| | aaacttcatt tttaatttaa aaggatctag gtgaagatcc tttttgataa tctcatgacc | 7620 |
| | aaaatccctt aacgtgagtt ttcgttccac tgagcgtcag accccgtaga aagatcaaa | 7680 |
| | ggatcttctt gagatccttt ttttctgcgc gtaatctgct gcttgcaaac aaaaaaacca | 7740 |
| | ccgctaccag cggtggtttg tttgccggat caagagctac caactctttt tccgaaggta | 7800 |
| | actggcttca gcagagcgca gataccaaat actgtccttc tagtgtagcc gtagttaggc | 7860 |
| | caccacttca agaactctgt agcaccgcct acatacctcg ctctgctaat cctgttacca | 7920 |
| | gtggctgctg ccagtggcga taagtcgtgt cttaccgggt tggactcaag acgatagtta | 7980 |
| | ccggataagg cgcagcggtc gggctgaacg gggggttcgt gcacacagcc cagcttggag | 8040 |
| | cgaacgacct acaccgaact gagatacctg cagcgtgagc attgagaaag cgccacgctt | 8100 |
| | cccgaaggga gaaaggcgga caggtatccg gtaagcggca gggtcggaac aggagagcgc | 8160 |
| | acgagggagc ttccaggggg aaacgcctgg tatctttata gtcctgtcgg gtttcgccac | 8220 |
| | ctctgacttg agcgtcgatt tttgtgatgc tcgtcagggg ggcggagcct atggaaaaac | 8280 |
| | gccagcaacg cggccttttt acggttcctg gccttttgct ggccttttgc tcacatgttc | 8340 |
| | tgatggtcgt catctacctg cctggacagc atggcctgca acgcgggcat cccgatgccg | 8400 |
| | ccgaagcga gaagaatcat aatggggaag gccatccagc ctcgcgtcg | 8449 |
| SEQ ID NO: 24 (pDONR221 vector) | ctttcctgcg ttatcccctg attctgtgga taaccgtatt accgcctttg agtgagctga | 60 |
| | taccgctcgc cgcagccgaa cgaccgagcg cagcgagtca gtgagcgagg aagcggaaga | 120 |
| | gcgcccaata cgcaaaccgc ctctccccgc gcgttggccg attcattaat gcagctggca | 180 |
| | cgacaggttt cccgactgga aagcgggcag tgagcgcaac gcaattaata cgcgtaccgc | 240 |
| | tagccaggaa gagtttgtag aaacgcaaaa aggccatccg tcaggatggc cttctgctta | 300 |
| | gtttgatgcc tggcagttta tggcgggcgt cctgcccgcc accctccggg ccgttgcttc | 360 |
| | acaacgttca aatccgctcc cggcggattt gtcctactca ggagagcgtt caccgacaaa | 420 |
| | caacagataa aacgaaaggc ccagtcttcc gactgagcct ttcgtttat ttgatgcctg | 480 |
| | gcagttccct actctcgcgt taacgctagc atggatgttt cccagtcac gacgttgtaa | 540 |
| | aacgacggcc agtcttaagc tcgggcccca ataatgatt ttattttgac tgatagtgac | 600 |
| | ctgttcgttg caacacattg atgagcaatg cttttttata atgccaactt tgtacaaaaa | 660 |
| | agctgaacga gaaacgtaaa atgatataaa tatcaatata ttaaattaga ttttgcataa | 720 |
| | aaaacagact acataatact gtaaaacaca acatatccag tcactatgaa tcaactactt | 780 |
| | agatggtatt agtgacctgt agtcgaccga cagccttcca atgttcttc gggtgatgct | 840 |
| | gccaacttag tcgaccgaca gccttccaaa tgttcttctc aaacggaatc gtcgtatcca | 900 |
| | gcctactcgc tattgtcctc aatgccgtat aaatcataa aaagaaataa gaaaaagagg | 960 |

TABLE 6-continued

Nucleotide sequences for preparation of lentivirus for transduction of aAPCs.

| Identifier (Description) | Sequence | |
|---|---|---|
| | tgcgagcctc ttttttgtgt gacaaaataa aaacatctac ctattcatat acgctagtgt | 1020 |
| | catagtcctg aaaatcatct gcatcaagaa caatttcaca actcttatac ttttctctta | 1080 |
| | caagtcgttc ggcttcatct ggattttcag cctctatact tactaaacgt gataaagttt | 1140 |
| | ctgtaatttc tactgtatcg acctgcagac tggctgtgta taagggagcc tgacatttat | 1200 |
| | attccccaga acatcaggtt aatggcgttt ttgatgtcat tttcgcggtg gctgagatca | 1260 |
| | gccacttctt ccccgataac ggagaccggc acactggcca tatcggtggt catcatgcgc | 1320 |
| | cagctttcat ccccgatatg caccaccggg taaagttcac gggagacttt atctgacagc | 1380 |
| | agacgtgcac tggccagggg gatcaccatc cgtccgcccgg gcgtgtcaat aatatcactc | 1440 |
| | tgtacatcca caaacagacg ataacggctc tctcttttat aggtgtaaac cttaaactgc | 1500 |
| | atttcaccag cccctgttct cgtcagcaaa agagccgttc atttcaataa accgggcgac | 1560 |
| | ctcagccatc ccttcctgat tttccgcttt ccagcgttcg gcacgcagac gacgggcttc | 1620 |
| | attctgcatg gttgtgctta ccagaccgga gatattgaca tcatatatgc cttgagcaac | 1680 |
| | tgatagctgt cgctgtcaac tgtcactgta atacgctgct tcatagcata cctctttttg | 1740 |
| | acatacttcg ggtatacata tcagtatata ttcttatacc gcaaaaatca gcgcgcaaat | 1800 |
| | acgcatactg ttatctggct tttagtaagc cggatccacg cggcgtttac gccccgccct | 1860 |
| | gccactcatc gcagtactgt tgtaattcat taagcattct gccgacatgg aagccatcac | 1920 |
| | agacggcatg atgaacctga atcgccagcg gcatcagcac cttgtcgcct tgcgtataat | 1980 |
| | atttgcccat ggtgaaaacg ggggcgaaga agttgtccat attggccacg tttaaatcaa | 2040 |
| | aactggtgaa actcacccag ggattggctg agacgaaaaa catattctca ataaaccctt | 2100 |
| | tagggaaata ggccaggttt tcaccgtaac acgccacatc ttgcgaatat atgtgtagaa | 2160 |
| | actgccggaa atcgtcgtgg tattcactcc agagcgatga aaacgtttca gtttgctcat | 2220 |
| | ggaaaacggt gtaacaaggg tgaacactat cccatatcac cagctcaccg tctttcattg | 2280 |
| | ccatacggaa ttccggatga gcattcatca ggcgggcaag aatgtgaata aaggccggat | 2340 |
| | aaaacttgtg cttatttttc tttacggtct ttaaaaaggc cgtaatatcc agctgaacgg | 2400 |
| | tctggttata ggtacattga gcaactgact gaaatgcctc aaaatgttct ttacgatgcc | 2460 |
| | attgggatat atcaacggtg gtatatccag tgattttttt ctccatttta gcttccttag | 2520 |
| | ctcctgaaaa tctcgataac tcaaaaaata cgcccggtag tgatcttatt tcattatggt | 2580 |
| | gaaagttgga acctcttacg tgccgatcaa cgtctcattt tcgccaaaag ttggcccagg | 2640 |
| | gcttcccggt atcaacaggg acaccagagt ttatttattc tgcgaagtga tcttccgtca | 2700 |
| | caggtattta ttcggcgcaa agtgcgtcgg gtgatgctgc caacttagtc gactacaggt | 2760 |
| | cactaatacc atctaagtag ttgattcata gtgactggat atgttgtgtt ttacagtatt | 2820 |
| | atgtagtctg ttttttatgc aaaatctaat ttaatatatt gatatttata tcattttacg | 2880 |
| | tttctcgttc agctttcttg tacaaagttg gcattataag aaagcattgc ttatcaattt | 2940 |
| | gttgcaacga acaggtcact atcagtcaaa ataaaatcat tatttgccat ccagctgata | 3000 |
| | tcccctatag tgagtcgtat tacatggtca tagctgtttc ctggcagctc tggcccgtgt | 3060 |
| | ctcaaaatct ctgatgttac attgcacaag ataaaataat atcatcatga caataaaac | 3120 |
| | tgtctgctta cataaacagt aatacaaggg gtgttatgag ccatattcaa cgggaaacgt | 3180 |
| | cgaggccgcg attaaattcc aacatggatg ctgatttata tgggtataaa tgggctcgcg | 3240 |
| | ataatgtcgg gcaatcaggt gcgacaatct atcgcttgta tgggaagccc gatgcgccag | 3300 |
| | agttgtttct gaaacatggc aaaggtagcg ttgccaatga tgttacagat gagatggtca | 3360 |
| | gactaaactg gctgacggaa tttatgcctc ttccgaccat caagcatttt atccgtactc | 3420 |
| | ctgatgatgc atggttactc accactgcga tccccggaaa aacagcattc caggtattag | 3480 |
| | aagaatatcc tgattcaggt gaaaatattg ttgatgcgct ggcagtgttc ctgcgccggt | 3540 |
| | tgcattcgat tcctgttttg aattgtcctt ttaacagcga tcgcgtattt cgtctcgctc | 3600 |
| | aggcgcaatc acgaatgaat aacggtttgg ttgatgcgct tgtttttgcc gatcagcgta | 3660 |
| | atggctggc tgttgaacaa gtctggaaag aaatgcataa acttttgcca ttctcaccgg | 3720 |
| | attcagtcgt cactcatggt gatttctcac ttgataacct tatttttgac gaggggaaat | 3780 |
| | taataggttg tattgatgtt ggacgagtcg gaatcgcaga ccgataccag gatcttgcca | 3840 |
| | tcctatggaa ctgcctcggt gagttttctc cttcattaca gaaacggctt tttcaaaaat | 3900 |
| | atggtattga taatcctgat atgaataaat tgcagtttca tttgatgctc gatgagtttt | 3960 |
| | tctaatcaga attggttaat tggttgtaac actggcagag cattacgctg acttgacggg | 4020 |
| | acggcgcaag ctcatgacca aaatccctta acgtgagtta cgcgtcgttc cactgagcgt | 4080 |
| | cagaccccgt agaaaagatc aaaggatctt cttgagatcc ttttttttctg cgcgtaatct | 4140 |
| | gctgcttgca aacaaaaaaa ccaccgctac cagcggtggt ttgtttgccg gatcaagagc | 4200 |
| | taccaactct ttttccgaag gtaactggct tcagcagagc gcagatacca aatactgttc | 4260 |
| | ttctagtgta gccgtagtta ggccaccact tcaagaactc tgtagcaccg cctacatacc | 4320 |
| | tcgctctgct aatcctgtta ccagtggctg ctgccagtgg cgataagtcg tgtcttaccg | 4380 |
| | ggttggactc aagacgatag ttaccggata aggcgcagcg gtcgggctga acggggggtt | 4440 |
| | cgtgcacaca gcccagcttg gagcgaacga cctacaccga actgagatac ctacagcgtg | 4500 |
| | agctatgaga aagcgccacg cttcccgaag ggagaaaggc ggacaggtat ccggtaagcg | 4560 |
| | gcagggtcgg aacaggagag cgcacgaggg agcttccagg gggaaacgcc tggtatcttt | 4620 |
| | atagtcctgt cgggtttcgc cacctctgac ttgagcgtcg atttttgtga tgctcgtcag | 4680 |
| | gggggcggag cctatggaaa aacgccagca acgcggcctt tttacggttc ctggcctttt | 4740 |
| | gctggccttt tgctcacatg t | 4761 |
| SEQ ID NO: 25 (psPAX2 plasmid) | aaaaggatct tcacctagat cctttttaaat taaaaatgaa gttttaaatc aatctaaagt | 60 |
| | atatatgagt aaacttggtc tgacagttac caatgcttaa tcagtgaggc acctatctca | 120 |
| | gcgatctgtc tatttcgttc atccatagtt gcctgactcc ccgtcgtgta gataactacg | 180 |
| | atacgggagg gcttaccatc tggccccagt gctgcaatga taccgcgaga cccacgctca | 240 |
| | ccggctccag atttatcagc aataaaccag ccagccggaa gggccgagcg cagaagtggt | 300 |
| | cctgcaactt tatccgcctc catccagtct attaattgtt gccgggaagc tagagtaagt | 360 |
| | agttcgccag ttaatagttt gcgcaacgtt gttgccattg ctacaggcat cgtggtgtca | 420 |
| | cgctcgtcgt ttggtatggc ttcattcagc tccggttccc aacgatcaag gcgagttaca | 480 |
| | tgatccccca tgttgtgcaa aaaagcggtt agctccttcg gtcctccgat cgttgtcaga | 540 |
| | agtaagttgg ccgcagtgtt atcactcatg gttatggcag cactgcataa ttctcttact | 600 |

TABLE 6-continued

Nucleotide sequences for preparation of lentivirus for transduction of aAPCs.

| Identifier<br>(Description) | Sequence | |
|---|---|---|
| | gtcatgccat ccgtaagatg cttttctgtg actggtgagt actcaaccaa gtcattctga | 660 |
| | gaatagtgta tgcggcgacc gagttgctct tgcccggcgt caatacggga taataccgcg | 720 |
| | ccacatagca gaactttaaa agtgctcatc attggaaaac gttcttcggg gcgaaaactc | 780 |
| | tcaaggatct taccgctgtt gagatccagt tcgatgtaac ccactcgtgc acccaactga | 840 |
| | tcttcagcat ctttttacttt caccagcgtt tctgggtgag caaaaacagg aaggcaaaat | 900 |
| | gccgcaaaaa agggaataag ggcgacacgg aaatgttgaa tactcatact cttccttttt | 960 |
| | caatattatt gaagcattta tcagggttat tgtctcatga gcggatacat atttgaatgt | 1020 |
| | atttagaaaa ataaacaaat aggggttccg cgcacatttc cccgaaaagt gccacctggt | 1080 |
| | cgacattgat tattgactag ttattaatag taatcaatta cggggtcatt agttcatagc | 1140 |
| | ccatatatgg agttccgcgt tacataactt acggtaaatg gcccgcctgg ctgaccgccc | 1200 |
| | aacgacccc gcccattgac gtcaataatg acgtatgttc ccatagtaac gccaataggg | 1260 |
| | actttccatt gacgtcaatg ggtggactat ttacggtaaa ctgcccactt ggcagtacat | 1320 |
| | caagtgtatc atatgccaag tacgccccct attgacgtca atgacggtaa atggcccgcc | 1380 |
| | tggcattatg cccagtacat gaccttatgg gactttccta cttggcagta catctacgta | 1440 |
| | ttagtcatcg ctattaccat gggtcgaggt gagccccacg ttctgcttca ctctccccat | 1500 |
| | ctcccccccc tcccacccc caattttgta tttatttatt ttttaattat tttgtgcagc | 1560 |
| | gatgggggcg ggggggggggg gggcgcgcgc caggcggggc ggggcggggc gaggggcggg | 1620 |
| | gcggggcgag gcggagaggt gcggcggcag ccaatcagag cggcgcgctc cgaaagtttc | 1680 |
| | cttttatggc gaggcggcgg cggcggcggc cctataaaaa gcgaagcgcg cggcgggcgg | 1740 |
| | gagtcgctgc gttgccttcg ccccgtgccc cgctccgcgc cgcctcgcgc cgcccgcccc | 1800 |
| | ggctctgact gaccgcgtta ctcccacagg tgagcgggcg ggacggccct tctcctccgg | 1860 |
| | gctgtaatta gcgcttggtt taatgacggc tcgtttcttt tctgtggctg cgtgaaagcc | 1920 |
| | ttaaagggct ccgggagggc cctttgtgcg ggggggagcg gctcggggggg tgcgtgcgtg | 1980 |
| | tgtgtgtgcg tggggagcgc cgcgtgcggc ccgcgctgcc cggcggctgt gagcgctgcg | 2040 |
| | ggcgcggcgc ggggctttgt gcgctccgcg tgtgcgcgag gggagcgcgg ccggggggcg | 2100 |
| | tgcccgcgcg tgcgggggggg ctgcgagggg aacaaaggct gcgtgcggggg tgtgtgcgtg | 2160 |
| | gggggggtgag caggggggtgt gggcgcggcg gtcgggctgt aacccccccc tgcaccccccc | 2220 |
| | tccccgagtt gctgagcacg gcccggcttc gggtgcgggg ctccgtgcgg ggcgtggcgc | 2280 |
| | ggggctcgcc gtgccggggcg gggggtggcg gcaggtgggg gtgccgggcg gggcggggcc | 2340 |
| | gcctcgggcc ggggagggct cggggggaggg gcgcggcggc cccggagcgc cggcggctgt | 2400 |
| | cgaggcgcgg cgagccgcag ccattgcctt ttatggtaat cgtgcgagag ggcgcaggga | 2460 |
| | cttcctttgt cccaaatctg gcggagccga aatctgggag gcgccgccgc accccctcta | 2520 |
| | gcgggcgcgg gcgaagcggt ggcgcgcggg caggaagcaa atgggcgggg agggccttcg | 2580 |
| | tgcgtcgccg cgccgccgtc cccttctcca tctccagcct cggggctgcc gcagggggac | 2640 |
| | ggctgccttc ggggggggacg gggcagggcg gggttcggct tctggcgtgt gaccggcggc | 2700 |
| | tctagagcct ctgctaacca tgttcatgcc ttcttctttt tcctacagct cctgggcaac | 2760 |
| | gtgctggtta ttgtgctgtc tcatcatttt ggcaaagaat tcggggtccgc cgcgttgacg | 2820 |
| | cgcacggcaa gaggcgaggg gcggcgactg gtgagagatg ggtgcgagag cgtcagtatt | 2880 |
| | aagcgggggga gaattagatc gatgggaaaa aattcggtta aggccagggg gaaagaaaaa | 2940 |
| | atataaatta aaacatatag tatgggcaag cagggagcta gaacgattcg cagttaatcc | 3000 |
| | tggcctgtta gaaacatcag aaggctgtag acaaatactg ggacagctac aaccatccct | 3060 |
| | tcagacagga tcagaagaac ttagatcatt atataataca gtagcaaccc tctattgtgt | 3120 |
| | gcatcaaagg atagagataa aagacaccaa ggaagcttta gacaagatag aggaagagca | 3180 |
| | aaacaaaagt aagaaaaaag cacagcaagc agcagctgac acaggacaca gcaatcaggt | 3240 |
| | cagccaaaat taccctatag tgcagaacat ccaggggcaa atggtacatc aggccatatc | 3300 |
| | acctagaact ttaaatgcat gggtaaaagt agtagaagag aaggctttca gcccagaagt | 3360 |
| | gatacccatg tttttcagcat tatcagaagg agccaccccca caagatttaa acaccatgct | 3420 |
| | aaacacagtg ggggggacatc aagcagccat gcaaatgtta aaagagacca tcaatgagga | 3480 |
| | agctgcagaa tgggatagag tgcatccagt gcatgcaggg cctattgcac caggccagat | 3540 |
| | gagagaacca aggggaagtg acatagcagg aactactagt acccttcagg aacaaatagg | 3600 |
| | atggatgaca cataatccac ctatcccagt aggagaaatc tataaaagat ggataatcct | 3660 |
| | gggattaaat aaaatagtaa gaatgtatag ccctaccagc attctggaca taagacaagg | 3720 |
| | accaaaggaa cccctttagag actatgtaga ccgattctat aaaactctaa gagccgagca | 3780 |
| | agcttcacaa gaggtaaaaa attggatgac agaaaccttg ttggtccaaa atgcgaaccc | 3840 |
| | agattgtaag actattttaa aagcattggg accaggagcg acactagaag aaatgatgac | 3900 |
| | agcatgtcag ggagtggggg gacccggcca taaagcaaga gttttggctg aagcaatgag | 3960 |
| | ccaagtaaca aatccagcta ccataatgat acagaaaggc aattttagga accaaagaaa | 4020 |
| | gactgttaag tgtttcaatt gtggcaaaga agggcacata gccaaaaatt gcagggcccc | 4080 |
| | taggaaaaag ggctgttgga aatgtggaaa ggaaggacac caaatgaaag attgtactga | 4140 |
| | gagacaggct aattttttag ggaagatctg gccttcccac aagggaaggc cagggaattt | 4200 |
| | tcttcagagc agaccagagc caacagcccc accagaagag agcttcaggt ttggggaaga | 4260 |
| | gacaacaact ccctctcaga agcaggagcc gatagacaag gaactgtatc ctttagcttc | 4320 |
| | cctcagatca ctctttggca gcgacccctc gtcacaataa agatagggggg gcaattaaag | 4380 |
| | gaagctctat tagatacagg agcagatgat acagtattag aagaaatgaa tttgccagga | 4440 |
| | agatggaaac caaaaatgat agggggaatt ggaggtttta tcaaagtagg acagtatgat | 4500 |
| | cagatactca tagaaatctg cggacataaa gctataggta cagtattagt aggacctaca | 4560 |
| | cctgtcaaca taattggaag aaatctgttg actcagattg gctgcacttt aaattttccc | 4620 |
| | attagtccta ttgagactgt accagtaaaa ttaaagccag gaatggatgg cccaaaagtt | 4680 |
| | aaacaatggc cattgacaga agaaaaaata aaagcattag tagaaatttg tacagaaatg | 4740 |
| | gaaaaggaag gaaaaatttc aaaaattggg cctgaaaatc catacaatac tccagtattt | 4800 |
| | gccataaaga aaaaagacag tactaaatgg agaaaattag tagatttcag agaacttaat | 4860 |
| | aagagaactc aagatttctg ggaagttcaa ttaggaatac cacatcctgc agggttaaaa | 4920 |
| | cagaaaaaat cagtaacagt actggatgtg ggcgatgcat attttttcagt tcccttagat | 4980 |
| | aaagacttca ggaagtatac tgcatttacc atacctagta taaacaatga gacaccaggg | 5040 |
| | attagatatc agtacaatgt gcttccacag ggatggaaag gatcaccagc aatattccag | 5100 |

TABLE 6-continued

Nucleotide sequences for preparation of lentivirus for transduction of aAPCs.

Identifier
(Description)                                    Sequence

```
tgtagcatga caaaaatctt agagcctttt agaaaacaaa atccagacat agtcatctat  5160
caatacatgg atgatttgta tgtaggatct gacttagaaa tagggcagca tagaacaaaa  5220
atagaggaac tgagacaaca tctgttgagg tggggattta ccacaccaga caaaaaacat  5280
cagaaagaac ctccattcct ttggatgggt tatgaactcc atcctgataa atggacagta  5340
cagcctatag tgctgccaga aaaggacagc tggactgtca atgacataca gaaattagtg  5400
ggaaaattga attgggcaag tcagatttat gcagggatta aagtaaggca attatgtaaa  5460
cttcttaggg gaaccaaagc actaacagaa gtagtaccac taacagaaga agcagagcta  5520
gaactggcag aaaacaggga gattctaaaa gaaccggtac atggagtgta ttatgaccca  5580
tcaaaagact taatagcaga aatacagaag caggggcaag gccaatggac atatcaaatt  5640
tatcaagagc catttaaaaa tctgaaaaca ggaaaatatg caagaatgaa gggtgcccac  5700
actaatgatg tgaaacaatt aacagaggca gtacaaaaaa tagccacaga aagcatagta  5760
atatggggaa agactcctaa atttaaatta cccatacaaa aggaaacatg ggaagcatgg  5820
tggacagagt attggcaagc cacctggatt cctgagtggg agtttgtcaa taccctctcc  5880
ttagtgaagt tatggtacca gttagagaaa gaacccataa taggagcaga aactttctat  5940
gtagatgggg cagccaatag ggaaactaaa ttaggaaaag caggatatgt aactgacaga  6000
ggaagacaaa aagttgtccc cctaacggac acaacaaatc agaagactga gttacaagca  6060
attcatctag ctttgcagga ttcgggatta gaagtaaaca tagtgacaga ctcacaatat  6120
gcattgggaa tcattcaagc acaaccagat aagagtgaat cagagttagt cagtcaaata  6180
atagagcagt taataaaaaa ggaaaaagtc tacctggcat gggtaccagc acacaaagga  6240
attggaggaa atgaacaagt agatgggttg gtcagtgctg gaatcaggaa agtactattt  6300
ttagatggaa tagataaggc ccaagaagaa catgagaaat atcacagtaa ttggagagca  6360
atggctagtg attttaacct accacctgta gtagcaaaag aaatagtagc cagctgtgat  6420
aaatgtcagc taaaagggga agccatgcat ggacaagtag actgtagccc aggaatatgg  6480
cagctagatt gtacacattt agaaggaaaa gttatcttgg tagcagttca tgtagccagt  6540
ggatatatag aagcagaagt aattccagca gagacagggc aagaaacagc atacttcctc  6600
ttaaaattag caggaagatg gccagtaaaa acagtacata cagacaatgg cagcaatttc  6660
accagtacta cagttaaggc cgcctgttgg tgggcgggga tcaagcagga atttggcatt  6720
ccctacaatc cccaaagtca aggagtaata gaatctatga ataaagaatt aaagaaaatt  6780
ataggacagg taagagatca ggctgaacat cttaagacag cagtacaaat ggcagtattc  6840
atccacaatt ttaaaagaaa aggggggatt gggggtaca gtgcagggga aagaatagta  6900
gacataatag caacagacat acaaactaaa gaattacaaa aacaaattac aaaaattcaa  6960
aattttcggg tttattacag ggacagcaga gatccagttt ggaaaggacc agcaaagctc  7020
ctctggaaag gtgaaggggc agtagtaata caagataata gtgacataaa agtagtgcca  7080
agaagaaaag caaagatcat cagggattat ggaaaacaga tggcaggtga tgattgtgtg  7140
gcaagtagac aggatgagga ttaacacatg gaattctgca caactgctg tttatccatt  7200
tcagaattgg gtgtcgacat agcagaatag gcgttactcg acagaggaga gcaagaaatg  7260
gagccagtag atcctagact agagccctgg aagcatccag gaagtcagcc taaaactgct  7320
tgtaccaatt gctattgtaa aaagtgttgc tttcattgcc aagtttgttt catgacaaaa  7380
gccttaggca tctcctatgg caggaagaag cggagacagc gacgaagagc tcatcagaac  7440
agtcagactc atcaagcttc tctatcaaag cagtaagtag tacatgtaat gcaacctata  7500
atagtagcaa tagtagcatt agtagtagca ataataatag caatagttgt gtggtccata  7560
gtaatcatag aatataggaa aatggccgct gatcttcaga cctggaggag gagatatgag  7620
ggacaattgg agaagtgaat tatataaata taaagtagta aaaattgaac cattaggagt  7680
agcacccacc aaggcaaaga gaagagtggt gcagagagaa aaaagagcag tgggaatagg  7740
agctttgttc cttgggttct tgggagcagc aggaagcact atgggcgcag cctcaatgac  7800
gctgacggta caggccagac aattattgtc tggtatagtg cagcagcaga acaatttgct  7860
gagggctatt gaggcgcaac agcatctgtt gcaactcaca gtctggggca tcaagcagct  7920
ccaagcaaga atcctagctg tggaaagata cctaaaggat caacagctcc tagggatttg  7980
gggttgctct ggaaaactca tttgcaccac tgctgtgcct tggaatgcta gttggagtaa  8040
taaatctctg gaacagatct ggaatcacac gacctggatg gagtgggaca gagaaattaa  8100
caattacaca agcttaaac actccttaat tgaagaatcg caaaaccagc aagaaaagaa  8160
tgaacaagaa ttattggaat tagataaatg ggcaagtttg tggaattggt ttaacataac  8220
aaattggctg tggtatataa aattattcat aatgatagta ggaggcttgg taggtttaag  8280
aatagttttt gctgtacttt ctatagtgaa tagagttagg cagggatatt caccattatc  8340
gtttcagacc cacctcccaa tcccgagggg acccgacagg cccgaaggaa tagaagaaga  8400
aggtggagag agagacagag acagatccat tcgattagtg aacggatcct ggcacttat  8460
ctgggacgat ctgcggagcc tgtgcctctt cagctaccac cgcttgagag acttactctt  8520
gattgtaacg aggattgtgg aacttctggg acgcaggggg tgggaagccc tcaaatattg  8580
gtggaatctc ctacaatatt ggagtcagga gctaaagaat agtgctgtta gcttgctcaa  8640
tgccacagcc atagcagtag ctgaggggac agatagggtt atagaagtag tacaaggagc  8700
ttgtagagct attcgccaca tacctagaag aataagacag ggcttggaaa ggattttgct  8760
ataagctcga aacaaccggt acctctagaa ctatagctag cagatctttt tccctctgcc  8820
aaaaattatg gggacatcat gaagcccctt gagcatctga cttctggcta taaaggaaa  8880
tttattttca ttgcaatagt gtgttggaat tttttgtgtc tctcactcgg aaggacatat  8940
gggagggcaa atcatttaaa acatcagaat gagtatttgg tttagagttt ggcaacatat  9000
gccatatgta ggctgccatg aacaaaggtg gctataaaga ggtcatcagt atatgaaaca  9060
gccccctgct gtccattcct tattccatag aaaagccttg acttgaggtt agatttttt  9120
tatattttgt tttgtgttat ttttttcttt aacatcccta aaattttcct tacatgtttt  9180
actagccaga ttttctctcc tctcctgact actcccagtc atagctgtcc ctcttctctt  9240
atgaagatcc ctcgacctgc agcccaagct tggcgtaatc atggtcatag ctgtttcctg  9300
tgtgaaattg ttatccgctc acaattccac acaacatacg agccggaagc ataaagtgta  9360
aagcctgggg tgcctaatga gtgagctaac tcacattaat tgcgttgcgc tcactgcccg  9420
ctttccagtc gggaaacctg tcgtgccagc ggatccgcat ctcaattagt cagcaaccat  9480
agtcccgccc ctaactccgc ccatcccgcc cctaactccg cccagttccg cccattctcc  9540
gccccatggc tgactaattt ttttttattta tgcagaggcc gaggccgcct cggcctctga  9600
```

TABLE 6-continued

Nucleotide sequences for preparation of lentivirus for transduction of aAPCs.

| Identifier (Description) | Sequence | |
|---|---|---|
| | gctattccag aagtagtgag gaggcttttt tggaggccta ggcttttgca aaaagctaac | 9660 |
| | ttgtttattg cagcttataa tggttacaaa taaagcaata gcatcacaaa tttcacaaat | 9720 |
| | aaaagcatttt tttcactgca ttctagttgt ggtttgtcca aactcatcaa tgtatcttat | 9780 |
| | catgtctgga tccgctgcat taatgaatcg gccaacgcgc ggggagaggc ggtttgcgta | 9840 |
| | ttgggcgctc ttccgcttcc tcgctcactg actcgctgcg ctcggtcgtt cggctgcggc | 9900 |
| | gagcggtatc agctcactca aaggcggtaa tacggttatc cacagaatca ggggataacg | 9960 |
| | caggaaagaa catgtgagca aaaggccagc aaaaggccag gaaccgtaaa aaggccgcgt | 10020 |
| | tgctggcgtt tttccatagg ctccgccccc ctgacgagca tcacaaaaat cgacgctcaa | 10080 |
| | gtcagaggtg gcgaaacccg acaggactat aaagatacca ggcgtttccc cctggaagct | 10140 |
| | ccctcgtgcg ctctcctgtt ccgaccctgc cgcttaccgg atacctgtcc gcctttctcc | 10200 |
| | cttcgggaag cgtggcgctt tctcaatgct cacgctgtag gtatctcagt tcggtgtagg | 10260 |
| | tcgttcgctc caagctgggc tgtgtgcacg aaccccccgt tcagcccgac cgctgcgcct | 10320 |
| | tatccggtaa ctatcgtctt gagtccaacc cggtaagaca cgacttatcg ccactggcag | 10380 |
| | cagccactgg taacaggatt agcagagcga ggtatgtagg cggtgctaca gagttcttga | 10440 |
| | agtggtggcc taactacggc tacactagaa ggacagtatt tggtatctgc gctctgctga | 10500 |
| | agccagttac cttcggaaaa agagttggta gctcttgatc cggcaaacaa accaccgctg | 10560 |
| | gtagcggtgg ttttttttgtt tgcaagcagc agattacgcg cagaaaaaaa ggatctcaag | 10620 |
| | aagatccttt gatcttttct acggggtctg acgctcagtg gaacgaaaac tcacgttaag | 10680 |
| | ggattttggt catgagatta tca | 10703 |
| SEQ ID NO: 26 (pCIGO-VSV.G plasmid) | gtcgaeggat egggagagatca attccggcac ctgtcctacg agttgcatga taaagaagac | 60 |
| | agtcataagt geggegaega tagtcatgee ccgcgcccac eggaaggage tgactgggtt | 120 |
| | gaaggctctc aagggcatcg gtcgatgcag gaaaaggaca ageagegaaa attcacgccc | 180 |
| | ccttgggagg tggeggcata tgcaaaggat agcactccca ctctactact gggtatcata | 240 |
| | tgctgactgt atatgeatga ggatagcata tgctacccgg atacagatta ggatagcata | 300 |
| | tactacccag atatagatta ggatagcata tgctacccag atatagatta ggatagecta | 360 |
| | tgctacccag atataaatta ggatagcata tactacccag atatagatta ggatagcata | 420 |
| | tgctacccag atatagatta ggatagecta tgctacccag atatagatta ggatagcata | 480 |
| | tgctacccag atatagatta ggatagcata tgctatccag atatttgggt agtatatget | 540 |
| | acccagatat aaattaggat agcatatact accctaatct ctattaggat ageatatget | 600 |
| | acccggatac agattaggat agcatatact acccagatat agattaggat ageatatget | 660 |
| | acccagatat agattaggat agectatget acccagatat aaattaggat agcatatact | 720 |
| | acccagatat agattaggat ageatatget acccagatat agattaggat agectatget | 780 |
| | acccagatat agattaggat ageatatget atccagatat ttgggtagta tatgctaccc | 840 |
| | atggcaacat tagcccaccg tgctctcagc gacctcgtga atatgaggac caacaaccct | 900 |
| | gtgcttggcg ctcaggcgca agtgtgtgta atttgtcctc cagatcgcag caatcgcgcc | 960 |
| | cctatcttgg cccgcccacc tacttatgea tgtattcccc ggggtgccat tagtggtttt | 1020 |
| | gtgggcaagt ggtttgaccg cagtggttag eggggttaca ateageaag ttattacacc | 1080 |
| | cttatttttac agtccaaaac egcagggegg cgtgtggggg ctgacgcgtg cccccactcc | 1140 |
| | acaatttcaa aaaaagagt ggccacttgt ctttgtttat gggccccatt ggcgtggagc | 1200 |
| | cccgtttaat tttcggggggt gttagagaca accagtgcag tccgctgctg tcggcgtcca | 1260 |
| | ctctctttcc ccttgttaca aatagagtgt aacaacatgg ttcacctgtc ttggtccctg | 1320 |
| | cctgggacac atcttaataa ccccagtatc atattgeact aggattatgt gttgeccata | 1380 |
| | gecataaatt cgtgtgagat ggacatccag tctttaegge ttgtccccac cccatggatt | 1440 |
| | tctattgtta aagatattca gaatgtttca ttcctacact agtatttatt geccaagggg | 1500 |
| | tttgtgaggg ttatattggt gtcatagcac aatgccacca ctgaacccc cgtccaaatt | 1560 |
| | ttattctggg ggcgtcacct gaaaccttgt tttcgagcac ctcacataca ccttactgtt | 1620 |
| | cacaactcag cagttattct attagctaaa cgaaggagaa tgaagaagca ggeagaagatt | 1680 |
| | caggagagtt cactgcccgc tccttgatct tcagccactg ccettgtgac taaaatggtt | 1740 |
| | cactaccctc gtggaatcct gaccccatgt aaaataaaacc gtgacagctc atggggtggg | 1800 |
| | agatatcgct gttccttagg acccttttac taaccctaat tcgatagcat atgcttcccg | 1860 |
| | ttgggtaaca tatgetattg aattagggtt agtctggata gtatatacta ctacccggga | 1920 |
| | ageatatget accegtttag ggttaacaag ggggecttat aaacactatt gctaatgecc | 1980 |
| | tcttgagggt ccgcttatcg gtagctacac aggcccctct gattgaegtt ggtgtagcct | 2040 |
| | cccgtagtct tcctgggccc ctgggaggta catgtccccc agcattggtg taagagcttc | 2100 |
| | agecaagagt tacacataaa ggcaatgttg tgttgcagtc cacagactgc aaagtctgct | 2160 |
| | ccaggatgaa agccactcaa gggatcttca atattggcca ttagecatat tattcattgg | 2220 |
| | ttatatagca taaatcaata ttggctattg gecattgaat acgttgtatc tatatcataa | 2280 |
| | tatgtacatt tatattggct catgtccaat atgacegcca tgttggcatt gattattgac | 2340 |
| | tagttattaa tagtaatcaa ttacggggtc attagttcat agcccatata tggagttccg | 2400 |
| | cgttacataa ettacggtaa atggcccgcc tggctgaccg cccaacgacc cccgcccatt | 2460 |
| | gacgtcaata atgacgtatg ttcccatagt aacgccaata gggactttcc attgacgtca | 2520 |
| | atgggtggag tatttacggt aaactgccca cttggcagta tcaagtgt atcatatgcc | 2580 |
| | aagtccgccc cctattgacg tcaatgacgg taaatggccc gcctggcatt atgcccagta | 2640 |
| | catgacctta cgggactttc ctacttggca gtacatctac gtattagtca tcgctattac | 2700 |
| | catggtgatg cggttttggc agtacaccaa tgggcgtgga tagcggtttg actcacgggg | 2760 |
| | atttccaagt ctccaccccca ttgacgtcaa tgggagtttg ttttggcacc aaaatcaacg | 2820 |
| | ggactttcca aaatgtcgta ataacccgc ccgttgacg caaatgggcg gtaggcgtgt | 2880 |
| | acggtgggag gtctatataa gcagagctcg tttagtgaac cgtcagatca ctagaagctt | 2940 |
| | tattgcggta gtttatcaca gttaaattgc tacaacagt ctcgaactta agctgcagaa | 3000 |
| | ctcgaactta agctgcagaa gttggtcgtg aggcactggg caggtaagta tcaaggttac | 3060 |
| | aagacaggtt taaggagacc aatagaaact gggcttgtcg agacagagaa gactcttgcg | 3120 |
| | tttctgatag gcacctattg gtcttactga catccacttt gcctttctct ccacaggtgt | 3180 |
| | ccactcccag ttcaattaca gctcttaagg ctagagtact aatacgact cactataggc | 3240 |
| | tagcggtacc gagctcggat ccactagtaa cggccgccag tgtgctggaa ttcaacagag | 3300 |

TABLE 6-continued

Nucleotide sequences for preparation of lentivirus for transduction of aAPCs.

| Identifier (Description) | Sequence | |
|---|---|---|
| | atcgatctgt ttccttgaca ctatgaagtg ccttttgtac ttagcctttt tattcattgg | 3360 |
| | ggtgaattgc aagttcacca tagttttttcc acacaaccaa aaaggaaact ggaaaaatgt | 3420 |
| | tccttctaat taccattatt gcccgtcaag ctcagattta aattggcata atgacttaat | 3480 |
| | aggcacagcc atacaagtca aaatgcccaa gagtcacaag gctattcaag cagacggttg | 3540 |
| | gatgtgtcat gcttccaaat gggtcactac ttgtgatttc cgctggtatg gaccgaagta | 3600 |
| | tataacacag tccatccgat ccttcactcc atctgtagaa caatgcaagg aaagcattga | 3660 |
| | acaaacgaaa caaggaactt ggctgaatcc aggcttccct cctcaaagtt gtggatatgc | 3720 |
| | aactgtgacg gatgccgaag cagtgattgt ccaggtgact cctcaccatg tgctggttga | 3780 |
| | tgaatacaca ggagaatggg ttgattcaca gttcatcaac ggaaaatgca gcaattacat | 3840 |
| | atgccccact gtccataact ctacaacctg gcattctgac tataaggtca aagggctatg | 3900 |
| | tgattctaac ctcatttcca tggacatcac cttcttctca gaggacggag agctatcatc | 3960 |
| | cctgggaaag gagggcacag ggttcagaag taactacttt gcttatgaaa ctggaggcaa | 4020 |
| | ggcctgcaaa atgcaatact gcaagcattg gggagtcaga ctcccatcag gtgtctggtt | 4080 |
| | cgagatggct gataaggatc tctttgctgc agccagattc cctgaatgcc cagaagggtc | 4140 |
| | aagtatctct gctccatctc agacctcagt ggatgtaagt ctaattcagg acgttgagag | 4200 |
| | gatcttggat tattccctct gccaagaaac ggagcaaa atcagagcgg gtcttccaat | 4260 |
| | ctctccagtg gatctcagct atcttgctcc taaaaaccca ggaaccggtc ctgctttcac | 4320 |
| | cataatcaat ggtaccctaa aatactttga gaccagatac atcagagtcg atattgctgc | 4380 |
| | tccaatcctc tcaagaatgg tcggaatgat cagtggaact accacagaaa gggaactgtg | 4440 |
| | ggatgactgg gcaccatatg aagacgtgga aattggaccc aatggagttc tgaggaccag | 4500 |
| | ttcaggatat aagtttcctt tatacatgat tggacatggt atgttggact ccgatcttca | 4560 |
| | tcttagctca aaggctcagg tgttcgaaca tcctcacatt caagacgctg cttcgcaact | 4620 |
| | tcctgatgat gagagtttat tttttggtga tactgggcta tccaaaaatc caatcgagct | 4680 |
| | tgtagaaggt tggttcagta gttggaaaag ctctattgcc tctttttttct ttatcatagg | 4740 |
| | gttaatcatt ggactattct tggttctccg agttggtatc catctttgca ttaaattaaa | 4800 |
| | gcacaccaag aaaagacaga tttatacaga catagagatg aaccgacttg gaaagtaact | 4860 |
| | caaatcctgc acaacagatt cttcatgttt ggaccaaatc aacttgtgat accatgctca | 4920 |
| | aagaggcctc aattatattt gagtttttaa tttttatgga attctgcaga tatccatcac | 4980 |
| | actggcggcc gctcgagcat gcatctagag ggccctattc tatagtgtca cctaaatgct | 5040 |
| | agagctcgct gatcagcctc gactgtgcct tctagttgcc agccatctgt tgtttgcccc | 5100 |
| | tccccccgtgc cttccttgac cctggaaggt gccactccca ctgtcctttc ctaataaaat | 5160 |
| | gaggaaattg catcgcattg tctgagtagg tgtcattcta ttctgggggg tggggtgggg | 5220 |
| | caggacagca aggggggagga ttgggaagac aatagcaggc atgctgggga tgcggtgggc | 5280 |
| | tctatggctt ctgaggcgga aagaaccagc tgcattaatg aatcggccaa cgcgcgggga | 5340 |
| | gaggcggttt gcgtattggg cgctcttccg cttcctcgct cactgactcg ctgcgctcgg | 5400 |
| | tcgttcggct gcggcgagcg gtatcagctc actcaaaggc ggtaatacgg ttatccacag | 5460 |
| | aatcagggga taacgcagga aagaacatgt gagcaaaagg ccagcaaaag gccaggaacc | 5520 |
| | gtaaaaaggc cgcgttgctg gcgtttttcc ataggctccg cccccctgac gagcatcaca | 5580 |
| | aaaatcgacg ctcaagtcag aggtggcgaa acccgacagg actataaaga taccaggcgt | 5640 |
| | ttccccctgg aagctccctc gtgcgctctc ctgttccgac cctgccgctt accggatacc | 5700 |
| | tgtccgcctt tctcccttcg ggaagcgtgg cgctttctca atgctcacgc tgtaggtatc | 5760 |
| | tcagttcggt gtaggtcgtt cgctccaagc tgggctgtgt gcacgaaccc cccgttcagc | 5820 |
| | ccgaccgctg cgccttatcc ggtaactatc gtcttgagtc caacccggta agacacgact | 5880 |
| | tatcgccact ggcagcagcc actggtaaca ggattagcag agcgaggtat gtaggcggtg | 5940 |
| | ctacagagtt cttgaagtgg tggcctaact acggctacac tagaaggaca gtatttggta | 6000 |
| | tctgcgctct gctgaagcca gttaccttcg gaaaaagagt tggtagctct tgatccggca | 6060 |
| | aacaaaccac cgctggtagc ggtggttttt ttgtttgcaa gcagcagatt acgcgcagaa | 6120 |
| | aaaaaggatc tcaagaagat cctttgatct tttctacggg gtctgacgct cagtggaacg | 6180 |
| | aaaactcacg ttaagggatt ttggtcatga gattatcaaa aaggatcttc acctagatcc | 6240 |
| | ttttaaatta aaaatgaagt tttaaatcaa tctaaagtat atatgagtaa acttggtctg | 6300 |
| | acagttacca atgcttaatc agtgaggcac ctatctcagc gatctgtcta tttcgttcat | 6360 |
| | ccatagttgc ctgactcccc gtcgtgtaga taactacgat acgggagggc ttaccatctg | 6420 |
| | gccccagtgc tgcaatgata ccgcgagacc cacgctcacc ggctccagat ttatcagcaa | 6480 |
| | taaaccagcc agccggaagg gccgagcgca gaagtggtcc tgcaacttta tccgcctcca | 6540 |
| | tccagtctat taattgttgc cgggaagcta gagtaagtag ttcgccagtt aatagtttgc | 6600 |
| | gcaacgttgt tgccattgct acaggcatcg tggtgtcacg ctcgtcgttt ggtatggctt | 6660 |
| | cattcagctc cggttcccaa cgatcaaggc gagttacatg atcccccatg ttgtgcaaaa | 6720 |
| | aagcggttag ctccttcggt cctccgatcg ttgtcagaag taagttggcc gcagtgttat | 6780 |
| | cactcatggt tatggcagca ctgcataatt ctcttactgt catgccatcc gtaagatgct | 6840 |
| | tttctgtgac tggtgagtac tcaaccaagt cattctgaga atagtgtatg cggcgaccga | 6900 |
| | gttgctcttg cccggcgtca tacgggata ataccgcgcc acatagcaga actttaaaag | 6960 |
| | tgctcatcat tggaaaacgt tcttcggggc gaaaactctc aaggatctta ccgctgttga | 7020 |
| | gatccagttc gatgtaaccc actcgtgcac ccaactgatc ttcagcatct tttactttca | 7080 |
| | ccagcgtttc tgggtgagca aaaacaggaa ggcaaaatgc cgcaaaaaag ggaataagag | 7140 |
| | cgacacggaa atgttgaata ctcatactct tcctttttca atattattga agcatttatc | 7200 |
| | agggttattg tctcatgagc ggatacatat ttgaatgtat ttagaaaaat aaacaaatag | 7260 |
| | gggttccgcg cacatttccc cgaaaagtgc cacctgac | 7298 |

Figure 12:
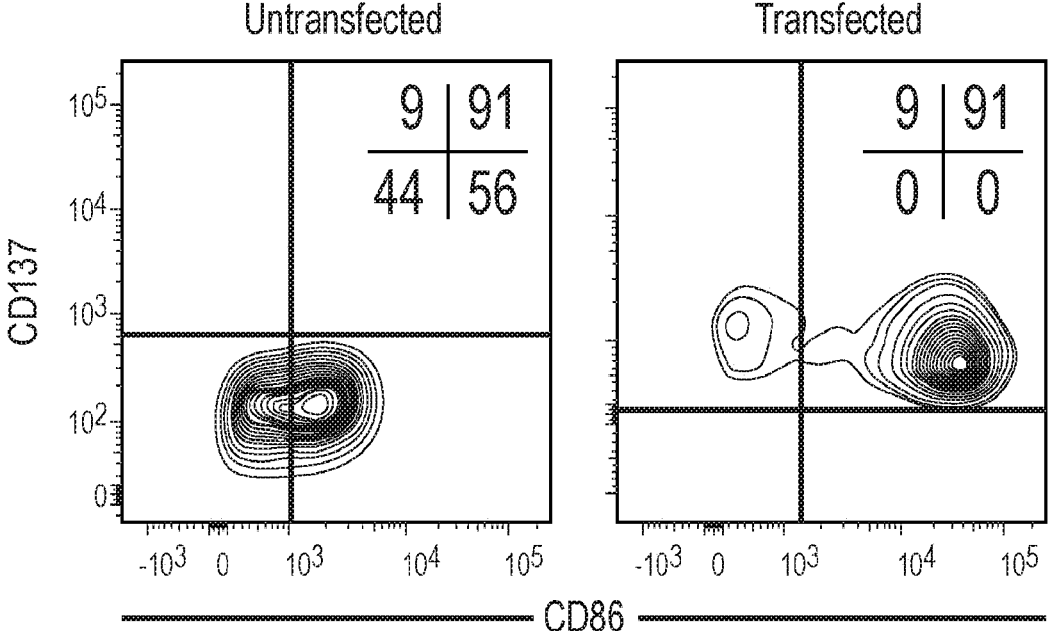
FIG. 12 illustrates the results of flow cytometry experiments on MOLM-14 cells before lentiviral transfection ("Untransfected") and after transfection ("Transfected"), confirming the expression of CD137 and CD86 on engineered MOLM-14 cells.
Figure 13:
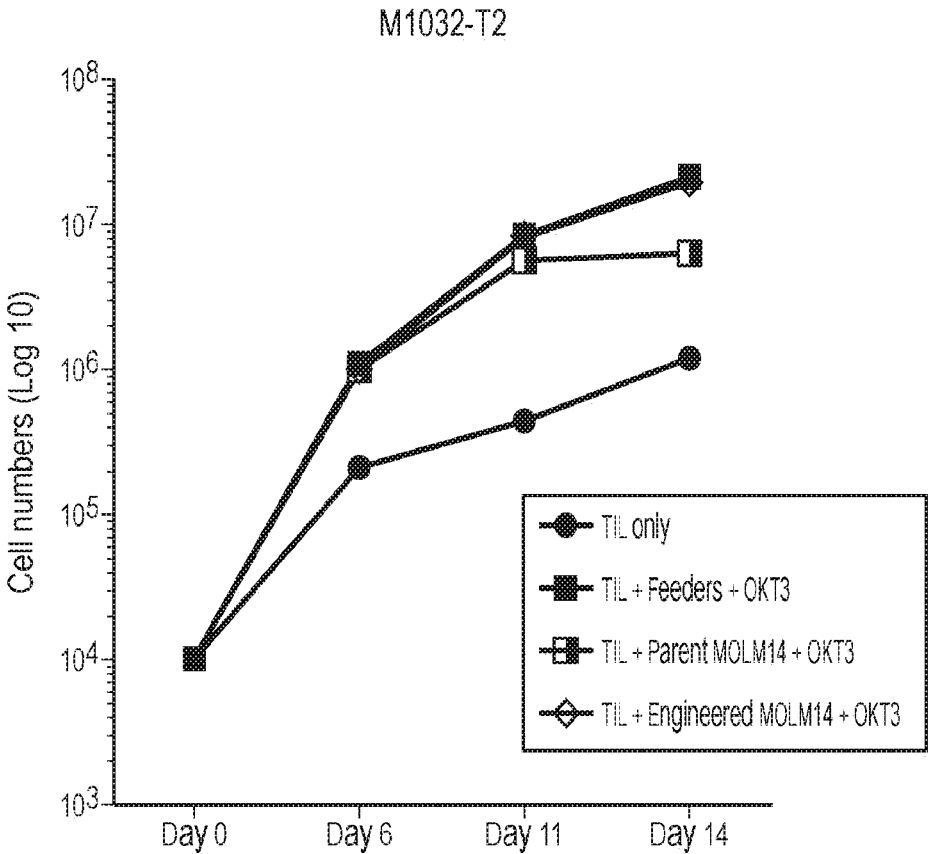
FIG. 13 illustrates the results of rapid expansion of TILs using irradiated parental unmodified MOLM-14 cells ("Parent MOLM14"), engineered MOLM-14 cells (CD86/4-1BBL, "Engineered MOLM14"), or PBMC feeders ("Feeders") for TIL lot M1032-T2. TIL were co-cultured with PBMC feeders or parental or engineered MOLM14 cells at 1:100 ratios with OKT-3 (30 ng/mL) and IL-2 (3000 IU/mL). Cells were counted and split on Day 6 and 11. Each dot represents cell numbers determined on Day 0, 6, 11 and 14 respectively. A logarithmic scale is used.
Figure 14:
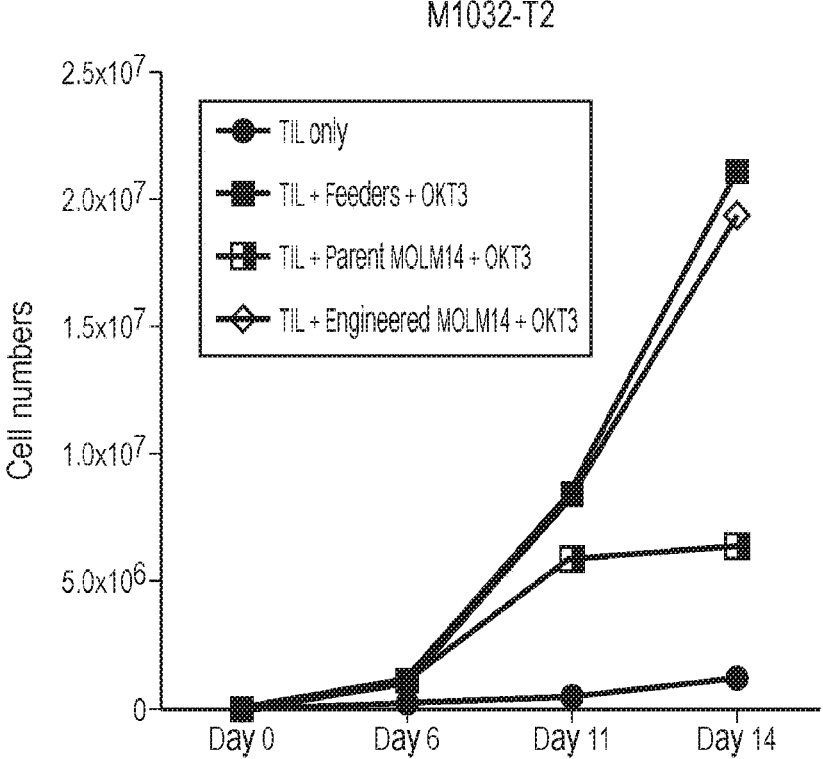
FIG. 14 illustrates results as shown in FIG. 13, depicted using a linear scale.
Figure 15:
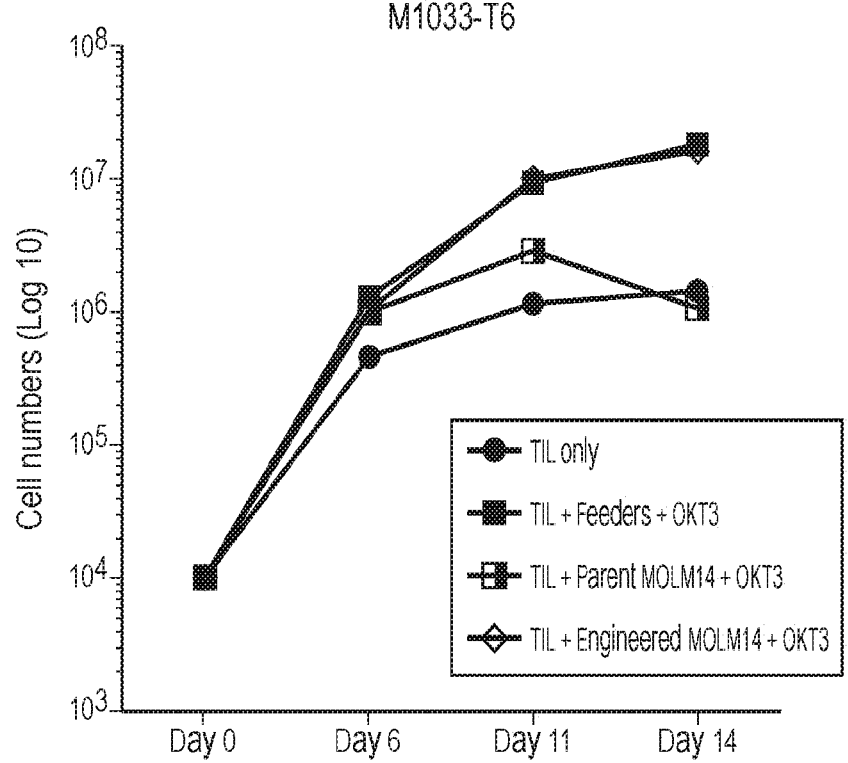
FIG. 15 illustrates results for TIL lot M1033-T6 with other parameters as given in FIG. 13, using a logarithmic scale.
Figure 16:
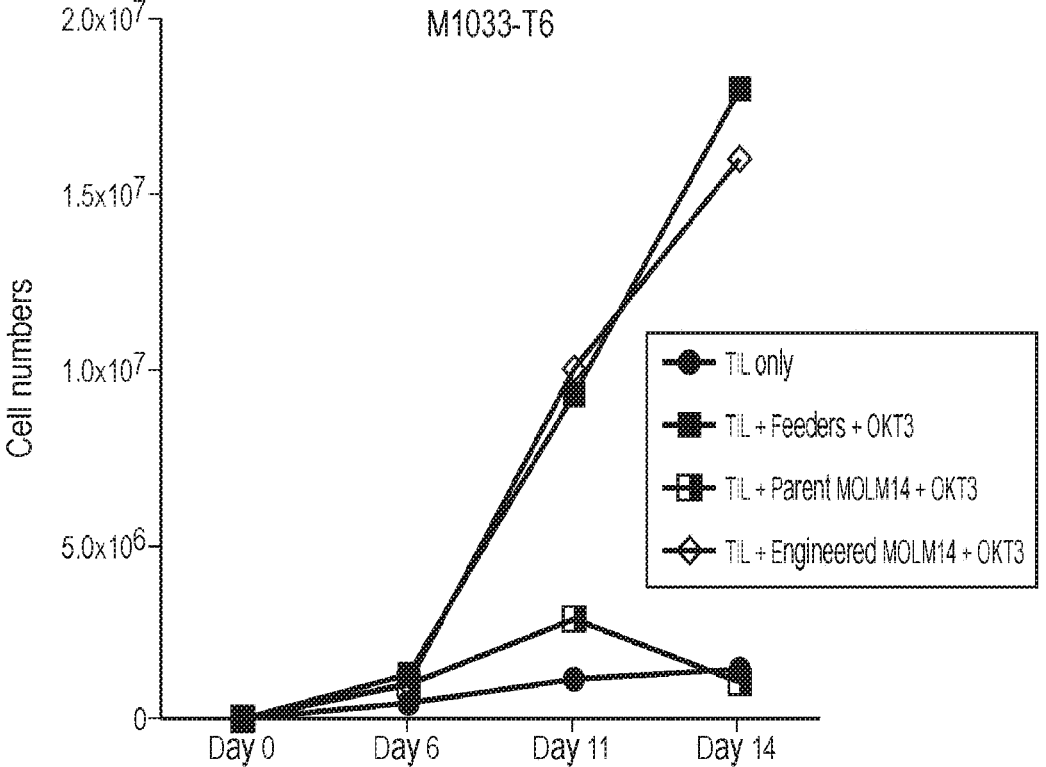
FIG. 16 illustrates results as shown in FIG. 14, depicted using a linear scale.

Expression of CD86 and 4-1BBL on engineered MOLM-14 aAPCs (also referred to herein as aMOLM14 aAPCs) was confirmed using flow cytometry (Canto II flow cytometer, Becton, Dickinson, and Co., Franklin Lakes, NJ, USA), with results shown in FIG. 12. aMOLM-14 aAPCs were γ-irradiated at 100 Gy and frozen.

Example 4—Expansion of Tumor Infiltrating Lymphocytes Using MOLM-14 Artificial Antigen Presenting Cells Engineered MOLM-14 cells were gamma-irradiated at 100 Gy before co-culturing with TILs. REPs were initiated by culturing TILs with irradiated, engineered MOLM-14 cells at 1:100 ratios in CM2 media containing OKT-3 (30 ng/mL) and IL-2 (3000 IU/mL) for 14 days. At REP harvest, the TIL expansion rates, phenotype for activation and differentiation stage markers, metabolism rate, cytotoxicity and re-rapid expansion protocol (re-REP) assay were measured.

The results are shown in FIG. 13, FIG. 14, FIG. 15, and FIG. 16, where two expansions for two sets of patient TILs are compared. The results with the CD86/4-1BBL modified MOLM-14 cells (labeled "TIL+Engineered MOLM14+OKT3") are comparable to the PBMC feeders (labeled "TIL+Feeders+OKT3").

Figure 17:
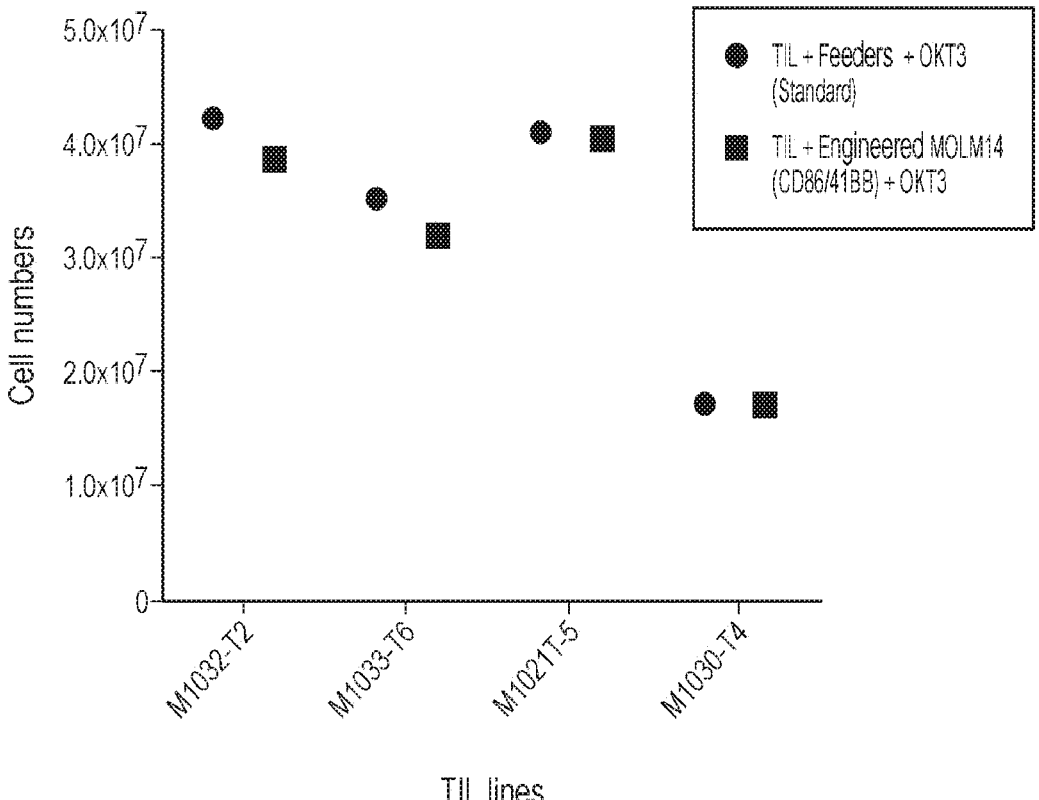
FIG. 17 illustrates the results of rapid expansions of TILs using engineered MOLM-14 cells expressing CD86 and 4-1BBL ("TIL+Engineered MOLM14 (CD86/41BB)+ OKT3") or irradiated PBMC feeders ("TIL+Feeders+ OKT3"). TIL were co-cultured with PBMC feeders or engineered MOLM-14 cells (aMOLM14) at 1:100 ratios plus OKT-3 (30 ng/mL) and IL-2 (3000 IU/mL). Cells were counted and split on Day 6 and 11. Each point represents cell numbers determined on Day 14.

The results at day 14 are compared in FIG. 17, where results from two additional patient TILs are shown. The results indicate that MOLM-14 cells that were engineered with CD86 and 4-1BBL showed similar TIL expansion in the rapid expansion protocol when compared with allogeneic feeder cells. However, TILs cultured with parental MOLM-14 did not expand.

In addition, TILs expanded against MOLM-14 maintained a TIL phenotype and showed potency to kill P815 cells as measured using BRLA, which is described in detail in Example 9. Briefly, luciferin-transduced P815 target cells and TILs of interest were co-cultured with and without anti-CD3 to determine whether tumor reactivity of TILs is through TCR activation (specific killing) or non-specific killing. Following 4 hours of incubation, luciferin was added to the wells and incubated for 5 minutes. After the incubation, bioluminescence intensity was read using a luminometer. The percentage cytotoxicity and percentage survival were calculated using the following formula: % Survival= (experimental survival-minimum)/(maximum signal-minimum signal)×100 or % Cytotoxicity=100−(% Survival).

Figure 18:
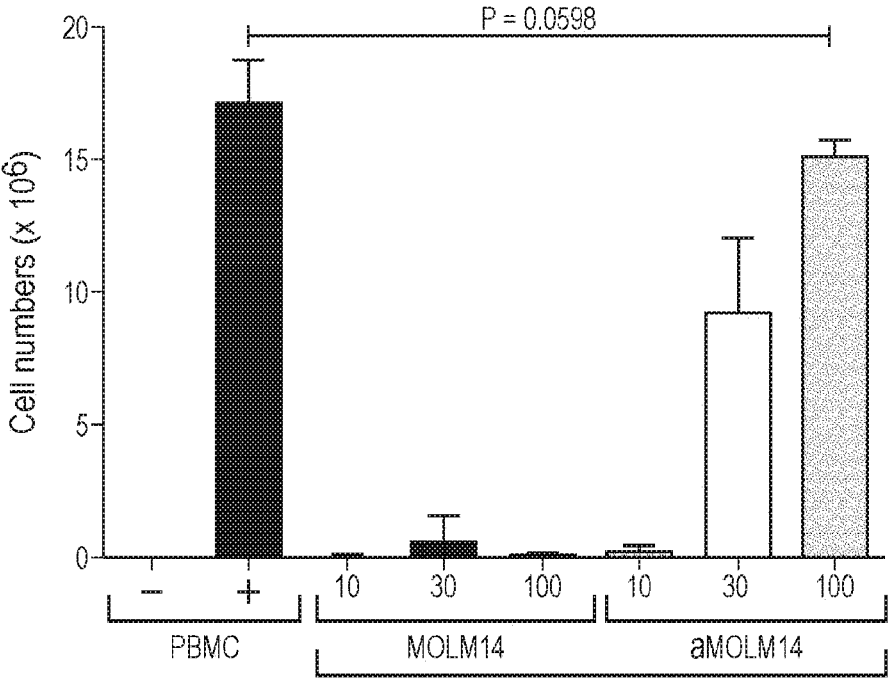
FIG. 18 illustrates the results of experiments in which TILs ($2 \times 10^4$) were cultured with different ratios (1:10, 1:30, and 1:100, denoted "10", "30", and "100", respectively) of parental MOLM-14 ("MOLM14") cells, MOLM-14 cells transduced to express CD86 and 4-1BBL ("aMOLM14"), or PBMC feeders ("PBMC+"), each with OKT-3 (30 ng/mL) and IL-2 (3000 IU/mL) in wells of a 24-well G-Rex plate. A control was performed using only OKT-3 (30 ng/mL) and IL-2 (3000 IU/mL) ("PBMC-"). Each condition was cultured in triplicate. Cultures were fed with fresh media and IL-2 on Day 4 and 7. Viable cells were counted on Day 7. The bar graph represented here shows the mean plus standard deviation (SD) of viable cell numbers counted on Day 11. The p-value was calculated by the student 't.' test.

In FIG. 18, the results of expansions performed with low ratios of TILs to MOLM-14 aAPCs are shown in comparison to the results of expansions with PBMC feeders. TILs ($2 \times 10^4$) were cultured at different TIL to aAPC or PBMC ratios (1:10, 1:30, and 1:100, denoted "10", "30", and "100", respectively) with parental MOLM-14 ("MOLM14") cells, MOLM-14 cells transduced to express CD86 and 4-1BBL ("aMOLM14"), or PBMC feeders ("PBMC+"), each with OKT-3 (30 ng/mL) and IL-2 (3000 IU/mL) in a 24-well G-Rex plate. A control was performed using only OKT-3 (30 ng/mL) and IL-2 (3000 IU/mL) ("PBMC-"). Each condition was cultured in triplicate. Cultures were fed with fresh media and IL-2 on Day 4 and 7. Viable cells were counted on Day 7. FIG. 18 shows the mean plus standard deviation (SD) of viable cell numbers counted on Day 11, with a p-va\ue calculated by the student I-test. Additional control experiments were performed using TILs alone, PBMCs alone, and aMOLM-14 cells alone, all of which resulted in undetectable cell numbers (data not shown). The results show that a ratio of 1:100 (TIL:aMOLM14) with OKT-3 and IL-2 yields a similar expansion when compared to PBMC feeders with OKT-3 and IL-2 (p=0.0598).

Figure 19:
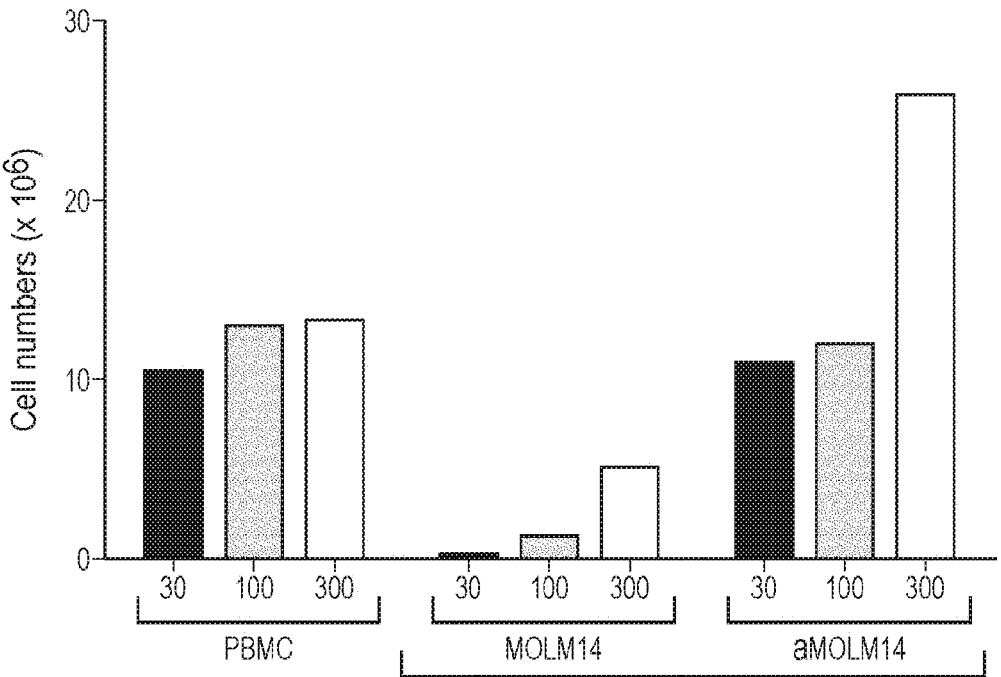
FIG. 19 illustrates the results of TILs cultured with different ratios (1:30, 1:100, and 1:300, denoted "30", "100", and "300", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Viable cells were counted on day 11 and plotted. Other conditions are as in FIG. 18.
Figure 20:
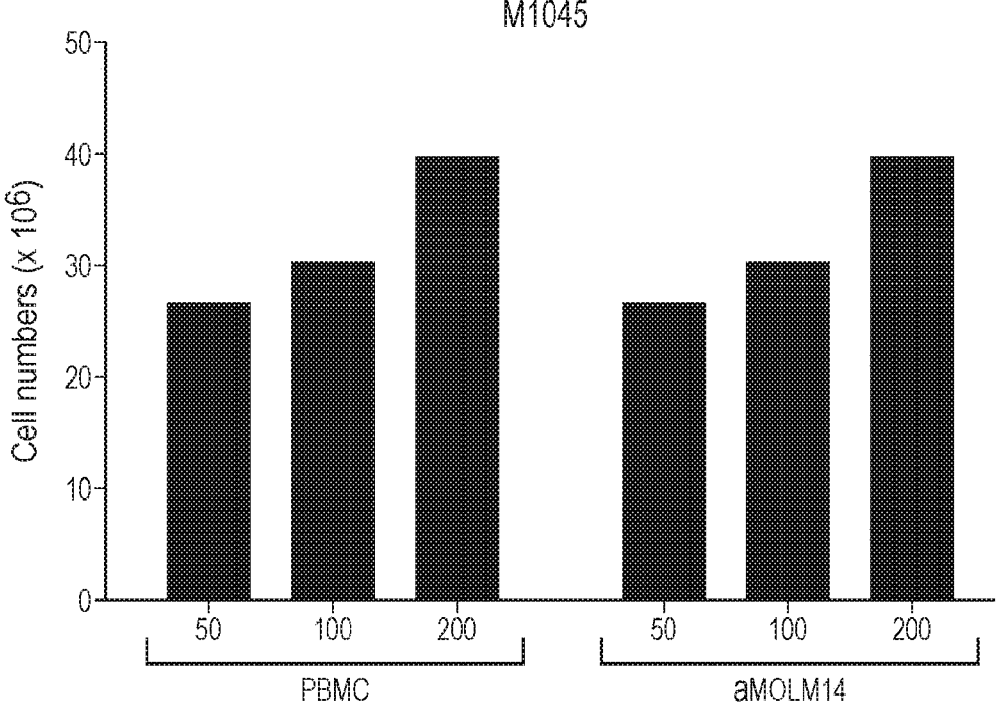
FIG. 20 illustrates the results of TILs cultured with different ratios (1:50, 1:100, and 1:200, denoted "50", "100", and "200", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Cells were counted on day 14. Other conditions are as in FIG. 18.
Figure 21:
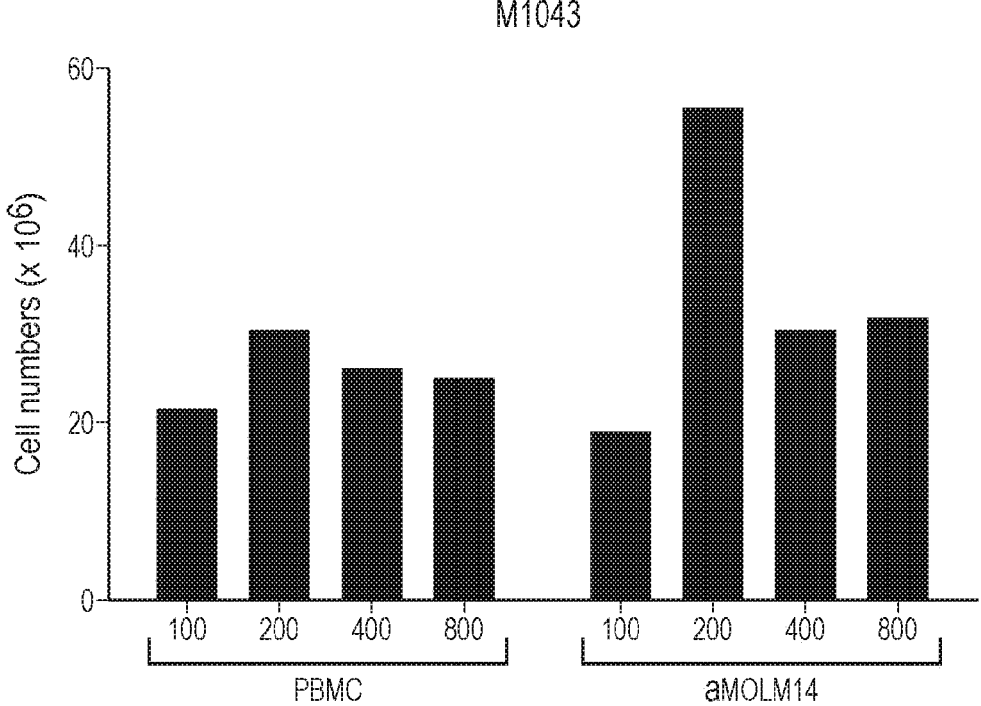
FIG. 21 illustrates the results of TILs cultured with different ratios (1:100, 1:200, 1:400, and 1:800, denoted "100", "200", "400", and "800", respectively) of PBMC feeders ("PBMC"), parental MOLM-14 cells ("MOLM14"), or MOLM-14 cells transduced to express CD86 and 4-1BBL ("aMOLM14"), each with OKT-3 (30 ng/mL) and IL-2 (3000 IU/mL) in the single 24 well G-Rex culture plates. Cells were counted on day 14. Other conditions are as in FIG. 18.

In FIG. 19, the results of expansions performed with higher ratios of TILs to MOLM-14 aAPCs, and otherwise performed as described above for FIG. 18, are shown in comparison to the results of expansions with PBMC feeders. At a ratio of 1:300, the CD86/4-1BBL modified MOLM-14 aAPCs with OKT-3 and IL-2 significantly outperform PBMC feeders with OKT-3 and IL-2. These results were verified using different TIL batches in repeat experiments shown in FIG. 20 and FIG. 21. In particular, as seen in FIG. 21, TIL to aMOLM14 ratios of 1:200 show enhanced TIL expansion compared to PBMC feeders under the same conditions. These results confirm that aMOLM14 aAPCs are unexpectedly superior in terms of expanding the TIL numbers than PBMCs particularly when using TIL:aMOLM14 ratios of 1:200 to 1:300.

Figure 24:
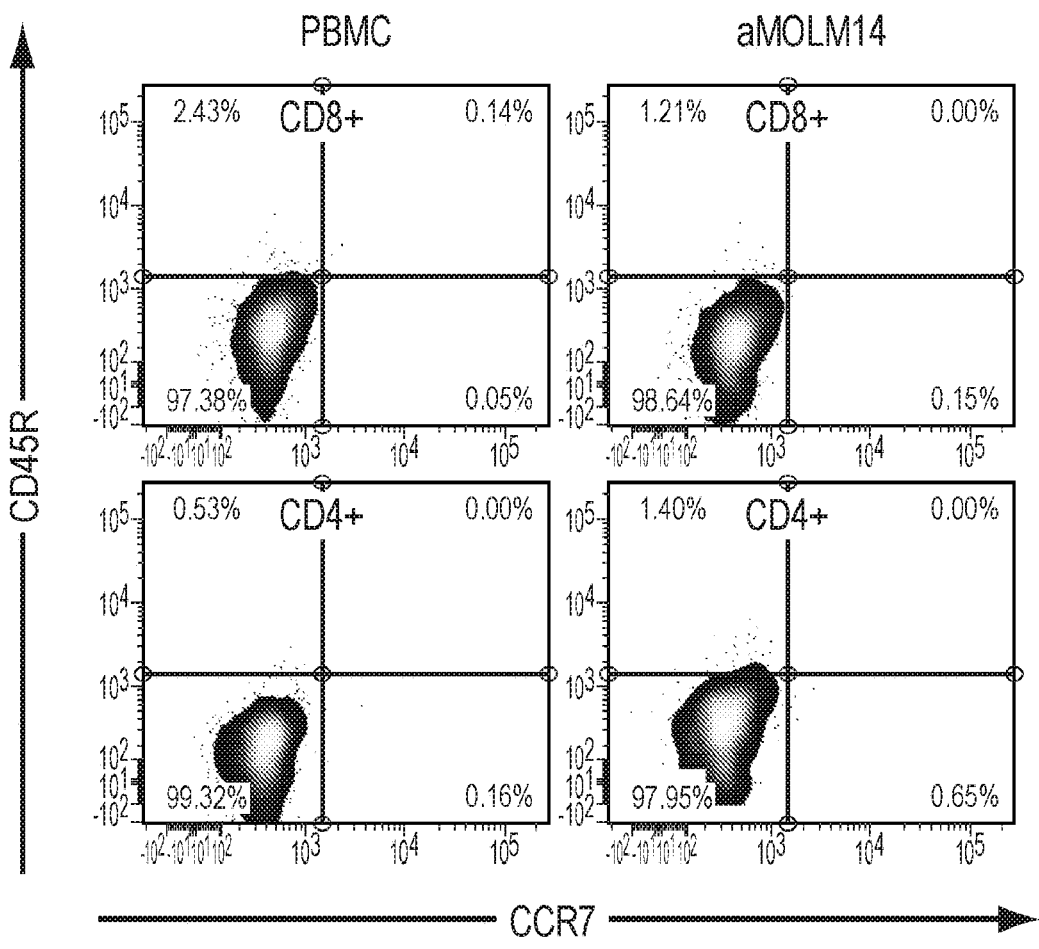
FIG. 24 depicts a flow cytometry contour plot showing memory subset (CD45RA+/−, CCR7+/−) gated on Live, TCR α/β+, CD4+, or CD8+ TILs.

In FIG. 22 and FIG. 23, TILs expanded with aMOLM14 or PBMC were compared by flow cytometry analysis to confirm that the TILs exhibited a similar phenotype and would be expected to perform similarly upon reinfusion into a patient. Briefly, TILs were first stained with L/D Aqua to determine viability. Next, cells were surface stained with TCR α/β PE-Cy7, CD4 FITC, CD8 PB, CD56 APC, CD28PE, CD27 APC-C7, and CD57-PerCP-Cy5.5. Phenotype analysis was done by gating 10,000 to 100,000 cells according to forward light scattering (FSC)/side light scattering (SSC) using a Canto II flow cytometer (Becton, Dickinson, and Co., Franklin Lakes, NJ, USA). Data was analyzed by Cytobank software to create sunburst diagrams and SPADE (Spanning Tree Progression of Density Normalized Event) analyses. Gates were set based on fluorescence minus one (FMO) controls. TILs expanded against aMOLM14 increases $CD8^+$ TILs when compared to PBMC feeders. Without being bound by theory, this enhanced $CD8^+$ TIL percentage may be due to the presence of 4-1BBL engineered to MOLM14. There is no difference in the expression of CD28, CD57, and CD27 differentiation markers. Additional flow cytometry data is shown in FIG. 24, and depicts a flow cytometry contour plot showing a memory subset (CD45RA+/−, CCR7+/−) gated on Live, TCR α/β+, $CD4^+$ or $CD8^+$ TILs, indicating that the memory subset obtained with PBMC feeders is replicated by the aMOLM14 aAPCs.

Figure 25:
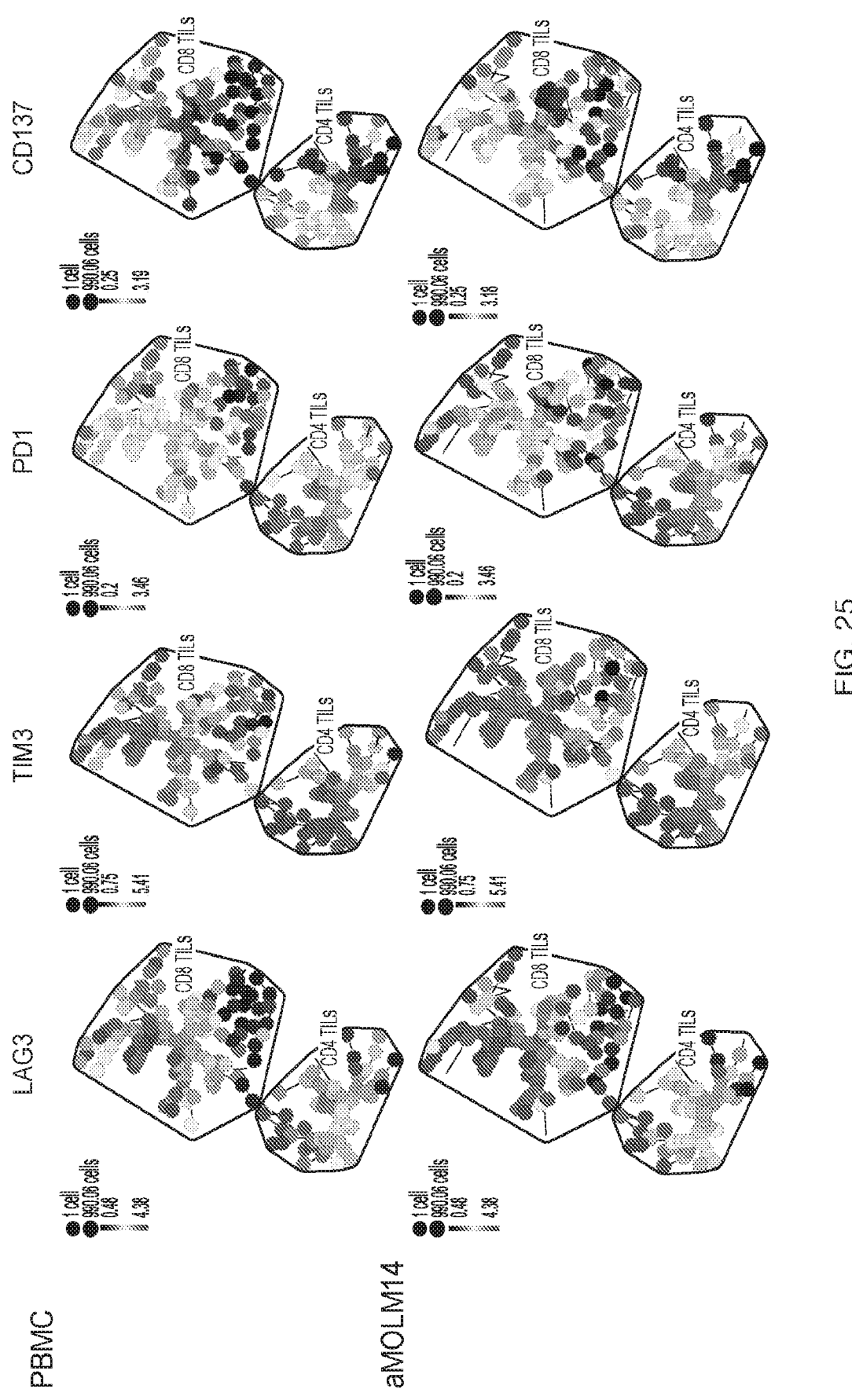
FIG. 25 illustrates phenotypic characterization of the T cell subset, CD4+ and CD8+ post-REP TILs (expanded with aMOLM14 aAPCs) gated on CD3+ cells using a SPADE tree. The color gradient is proportional to the mean fluorescence intensity (MFI) of LAGS, TEVI3, PD1, and CD137.
Figure 26:
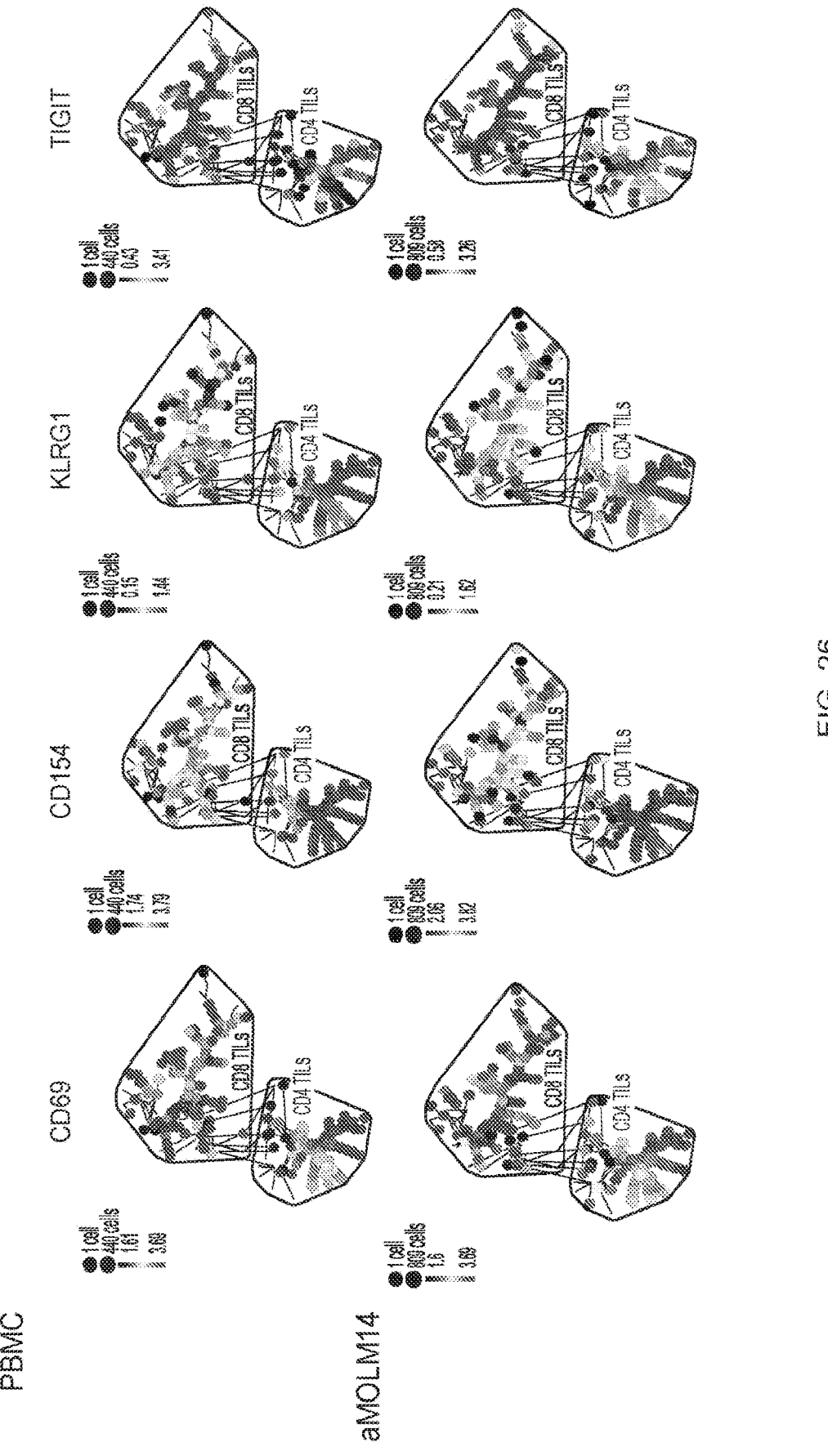
FIG. 26 illustrates phenotypic characterization of the T cell subset, CD4+ and CD8+ post-REP TILs (expanded with aMOLM14 aAPCs) gated on CD3+ cells using a SPADE tree. The color gradient is proportional to the MFI CD69, CD 154, KLRG1, and TIGIT

The CD4 and CD8 SPADE tree of TILs expanded with aMOLM14 aAPCs or PBMC feeders using CD3+ cells is shown in FIG. 25 and FIG. 26. The color gradient is proportional to the mean fluorescence intensity (MFI) of LAG3, TIL3, PD1 and CD 137 or CD69, CD 154, KLRG1 and TIGIT. Without being bound by theory, the results show that two batches of TILs expanded against aMOLM14 had undergone activation, but there was no difference in MFI between the aMOLM14 aAPCs and PBMC feeders, indicating that the aMOLM14 aAPCs effectively replicate the TIL phenotypic results obtained with PBMC feeders.

TILs expanded against aMOLM14 or PBMC were also analyzed for metabolic profiles. Oxygen consumption rate (OCR) and extracellular acidification rate (ECAR) of TILs after expansion with irradiated PBMC feeders or aMOLM14 aAPCs were measured using a dual mitochondrial-glycolytic stress test. Briefly, cells were washed in assay medium (XF Assay Medium, Agilent Technologies, Santa Clara, CA, USA), supplemented with 10 mM glucose, 1 mM sodium pyruvate, and 2 mM L-glutamine, at pH 7.4, and then $1 \times 10^5$ viable cells were plated onto an adhesive-coated (Cell-Tak™, Corning) XFp cell culture microplate. Plates were spun to adhere the cells to the plate, then equilibrated at 37°

C. in a humidified, non-CO$_2$ incubator prior to analysis of cellular metabolism. Mitochondrial and glycolytic stress test experiments were performed using a Seahorse XFp Analyzer (Agilent Technologies, Santa Clara, CA, USA), sequentially lentiviral system and sorted using eGFP. EM37C12CD86CD137L and EM38B3CD86CD137L were regularly assessed for the consistent expression of each transduced molecule by flow cytometry.

TABLE 7

Amino acid sequences of scFv clones 7C12 and 8B3.

Figure 27:
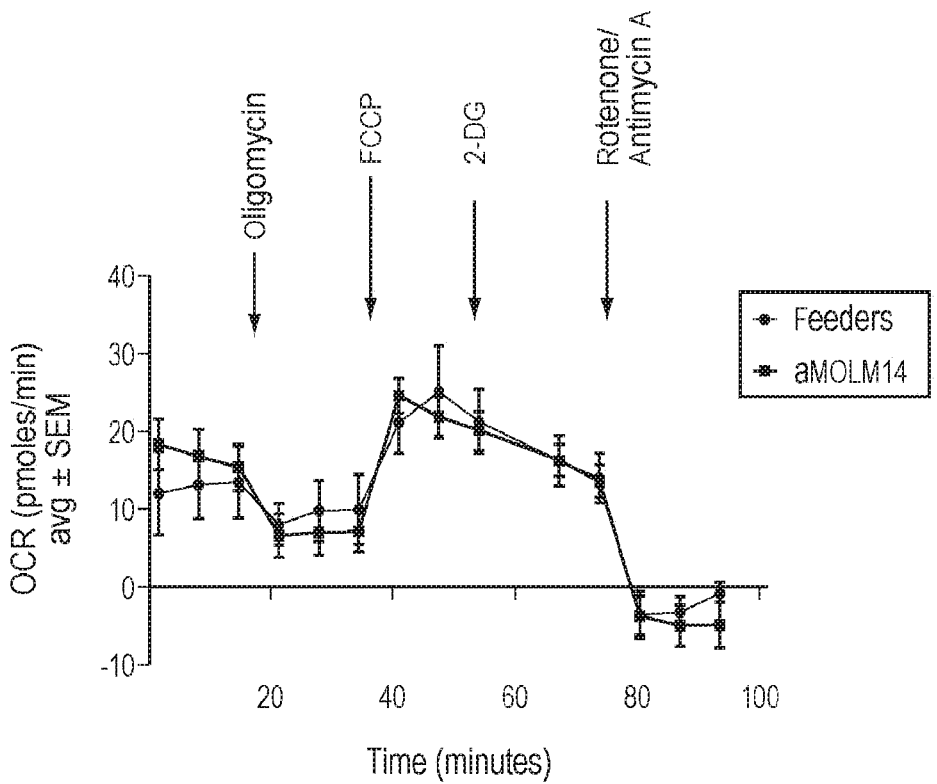
FIG. 27 illustrates oxygen consumption rate (OCR) of TIL after expansion with Feeders or aMOLM14 measured during a mitochondrial stress test. Each data point represents mean±standard error of the mean (SEM) measured in triplicate.
Figure 28:
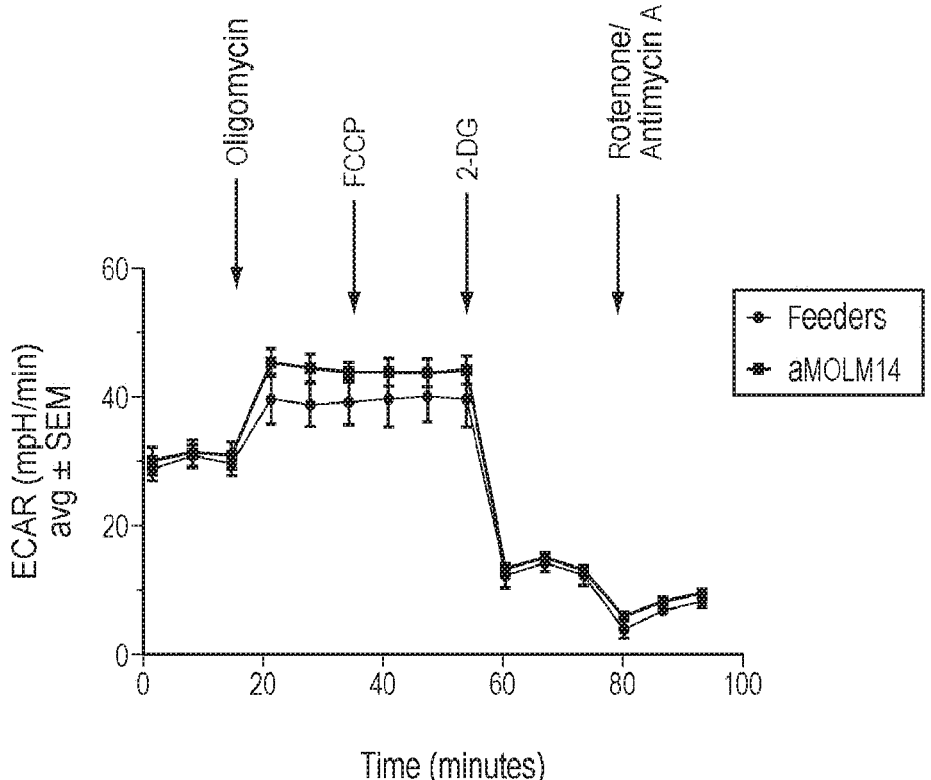
FIG. 28 illustrates extracellular acidification rate (ECAR) of TIL after expansion with Feeders or aMOLM14 measured during a mitochondrial stress test. Each data point represents mean±SEM measured in triplicate.
Figure 29:
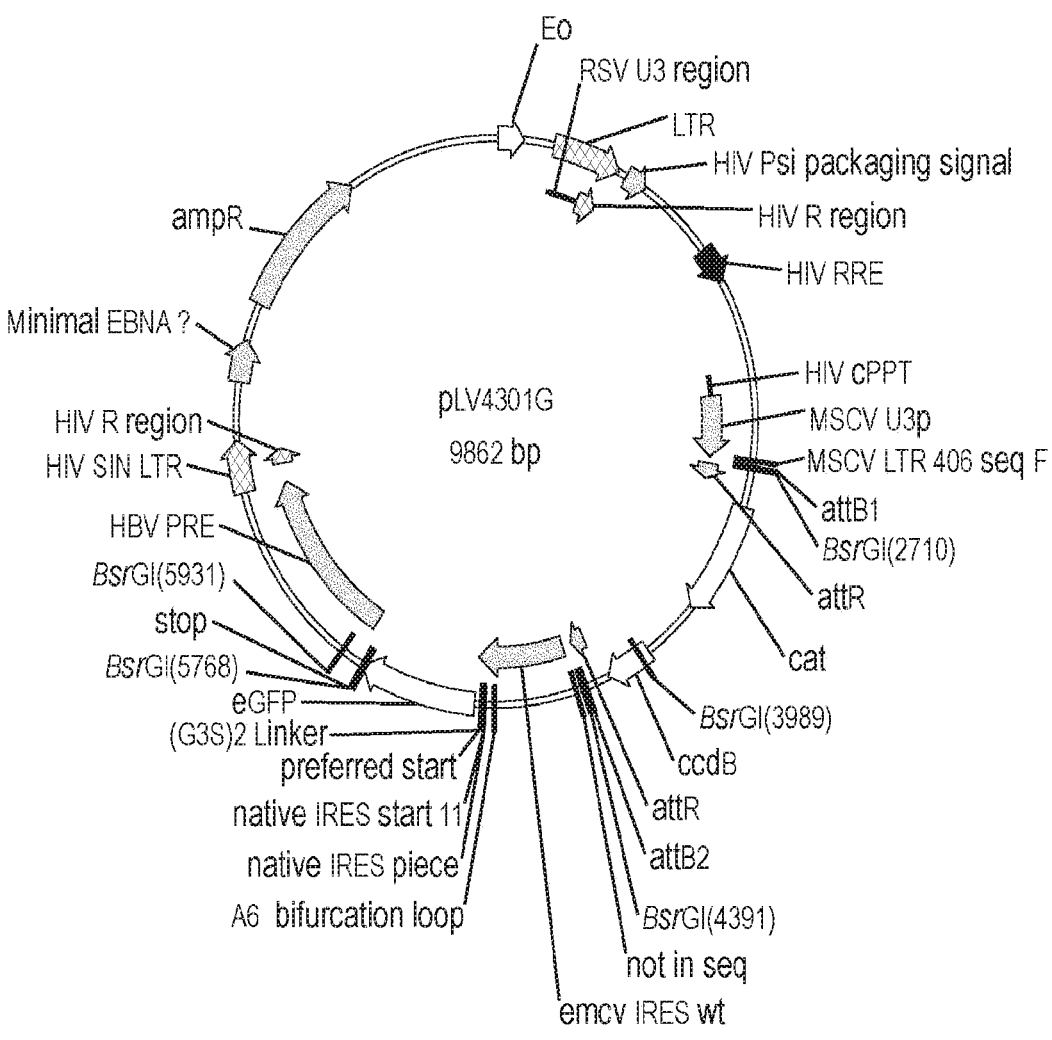
FIG. 29 illustrates a vector diagram of the destination vector pLV4301G.
Figure 30:
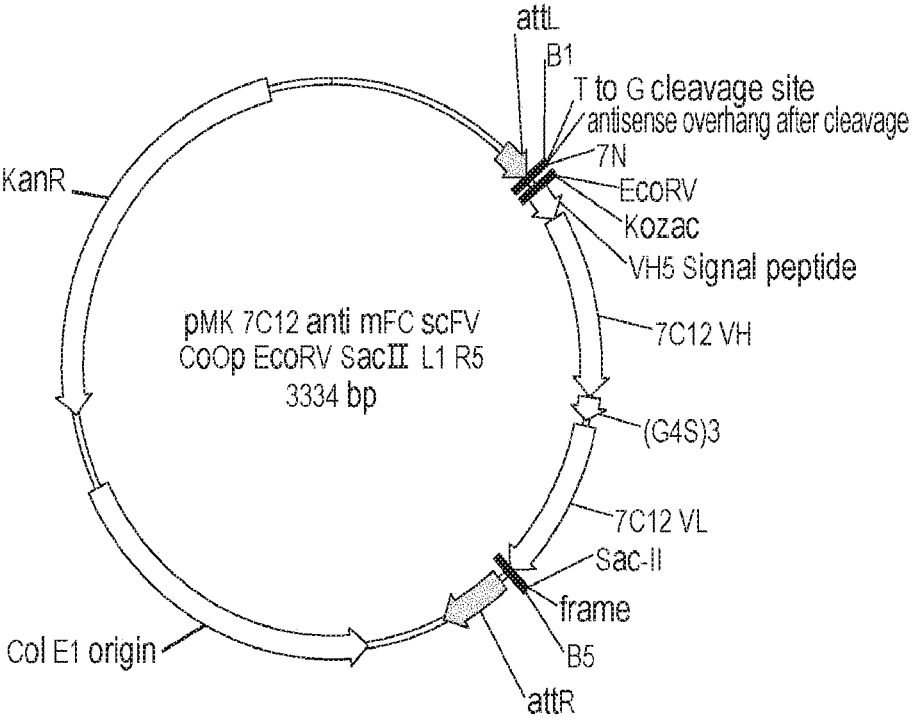
FIG. 30 illustrates a vector diagram of donor vector 1, pMK 7c12 anti mFC scFv CoOp ECORV SacII L1R5.
Figure 31:
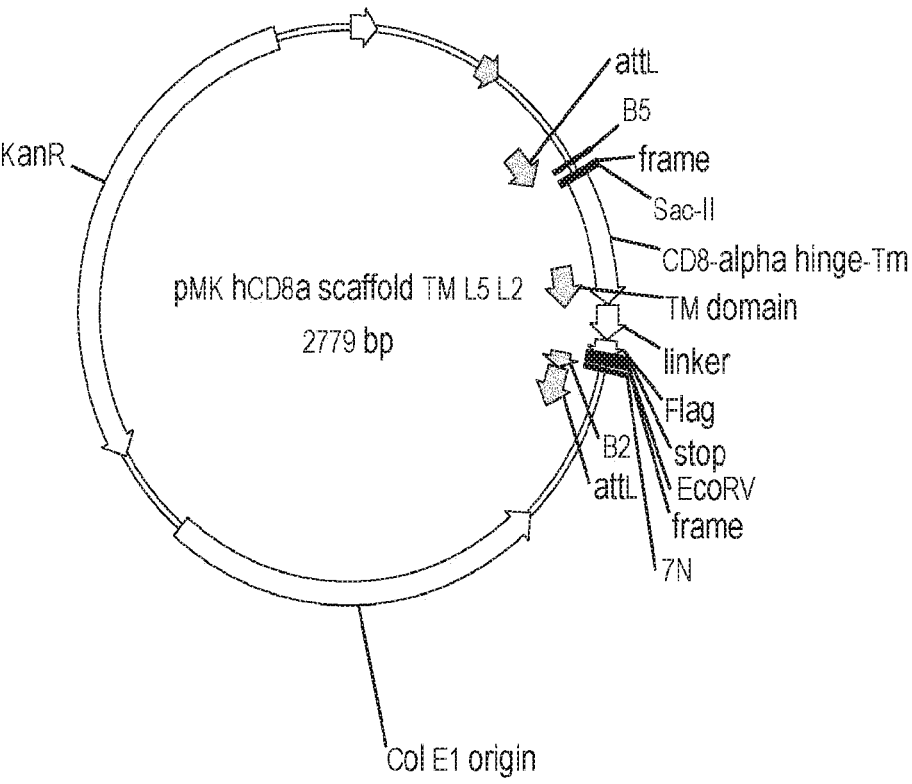
FIG. 31 illustrates a vector diagram of donor vector 2, pMK hCD8a scaffold TN L5 L2.
Figure 32:
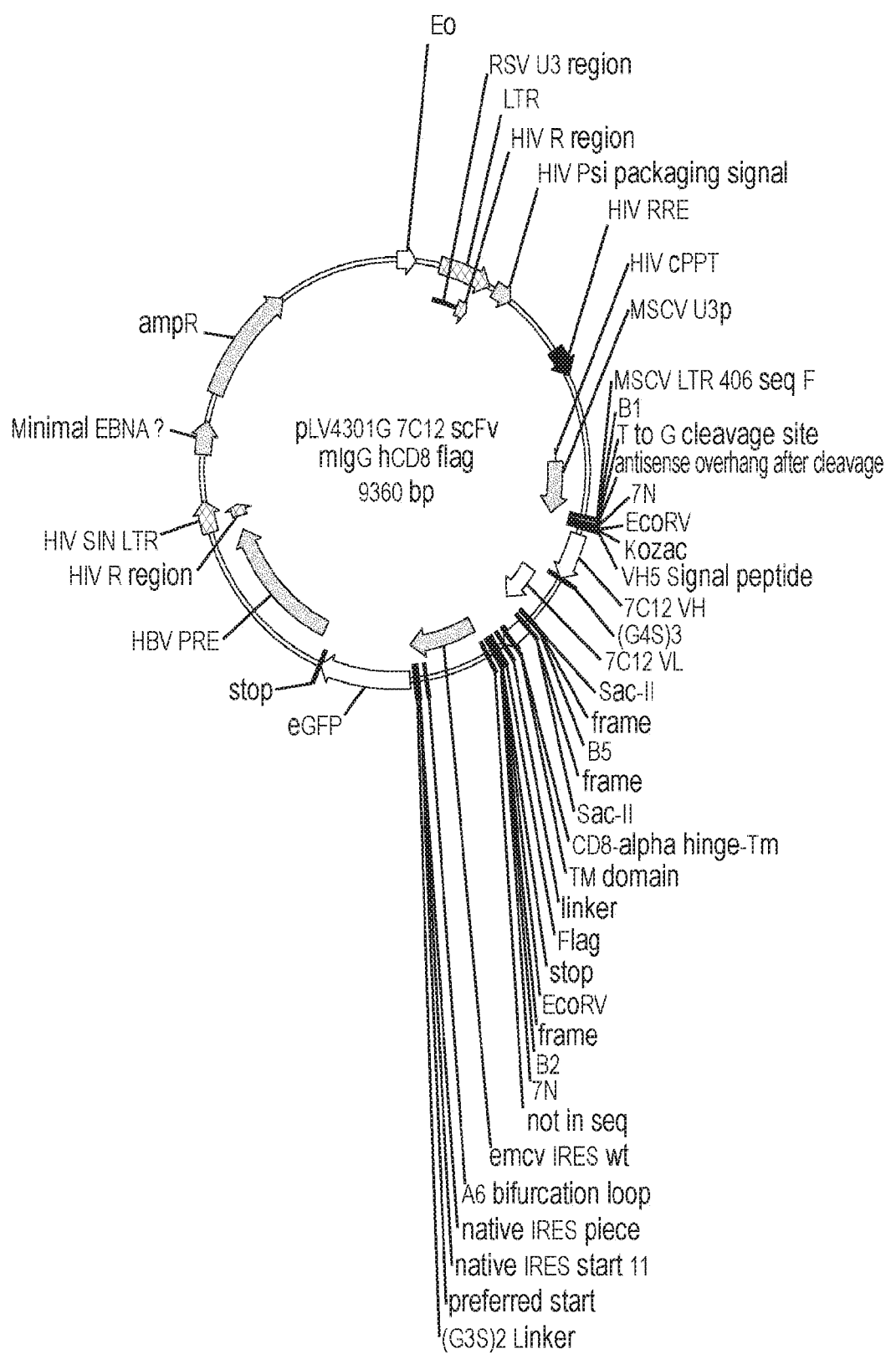
FIG. 32 illustrates a vector diagram of final vector used for lentiviral production, pLV4301G 7C12 scFv mlgG hCD8 flag.
Figure 33:
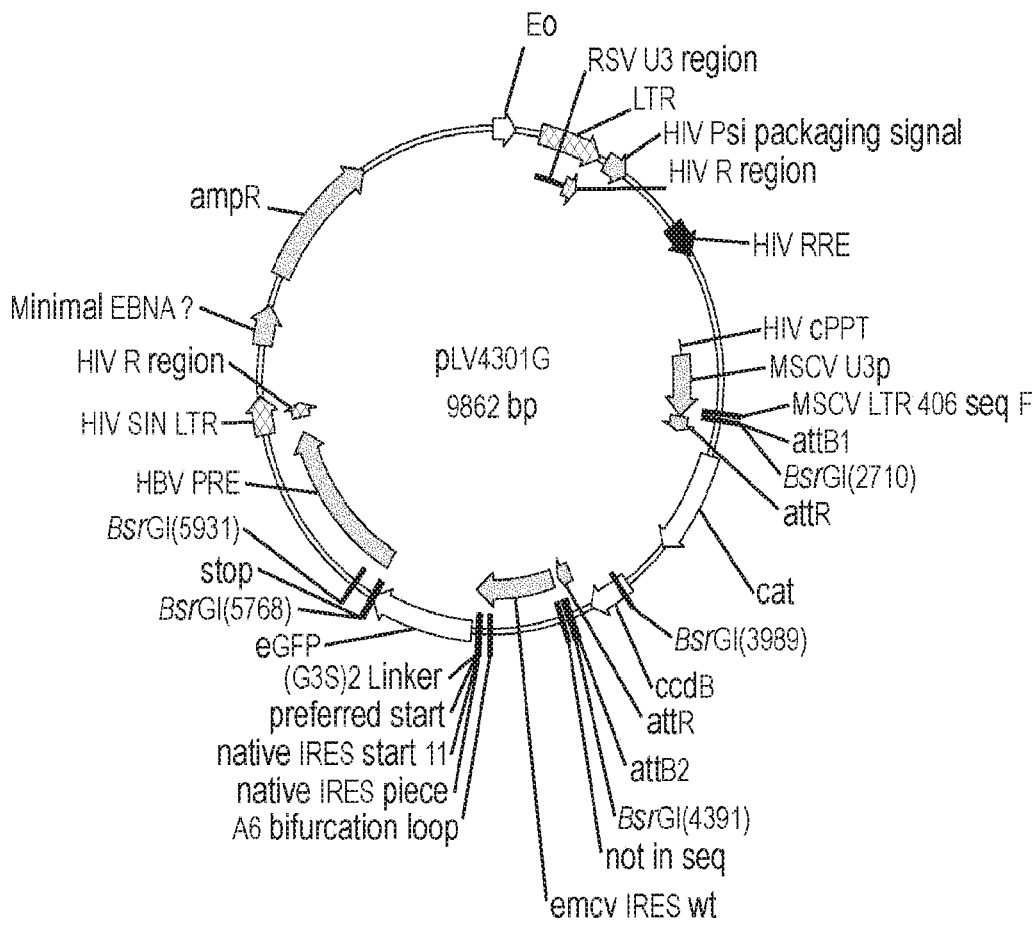
FIG. 33 illustrates a vector diagram of the destination vector pLV4301G.
Figure 34:
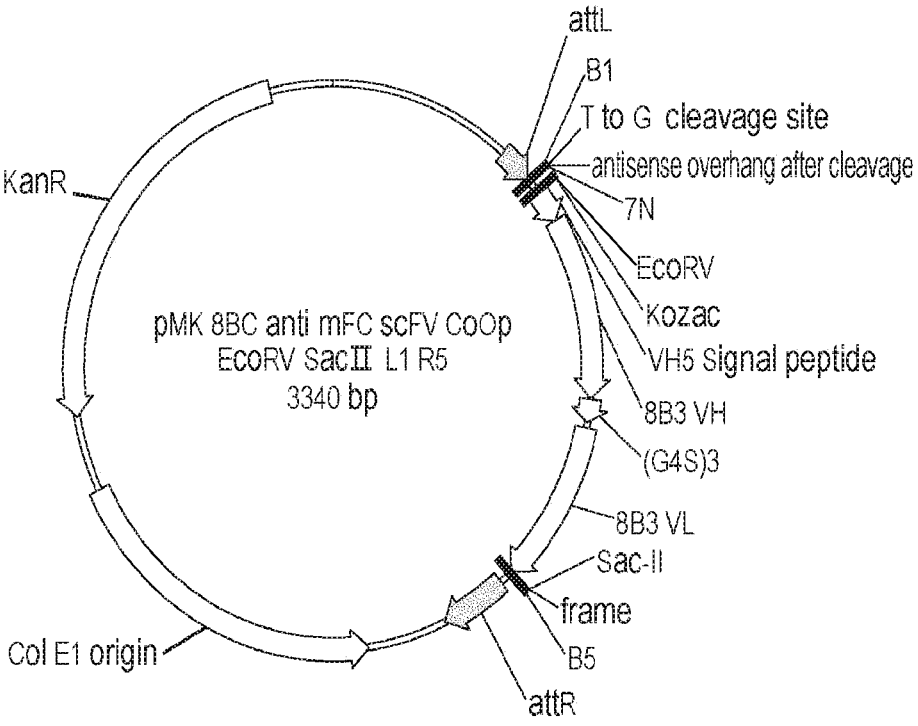
FIG. 34 illustrates a vector diagram of donor vector 1, pMK 8B3 anti mFC scFv CoOp ECORV SacII L1R5.
Figure 35:
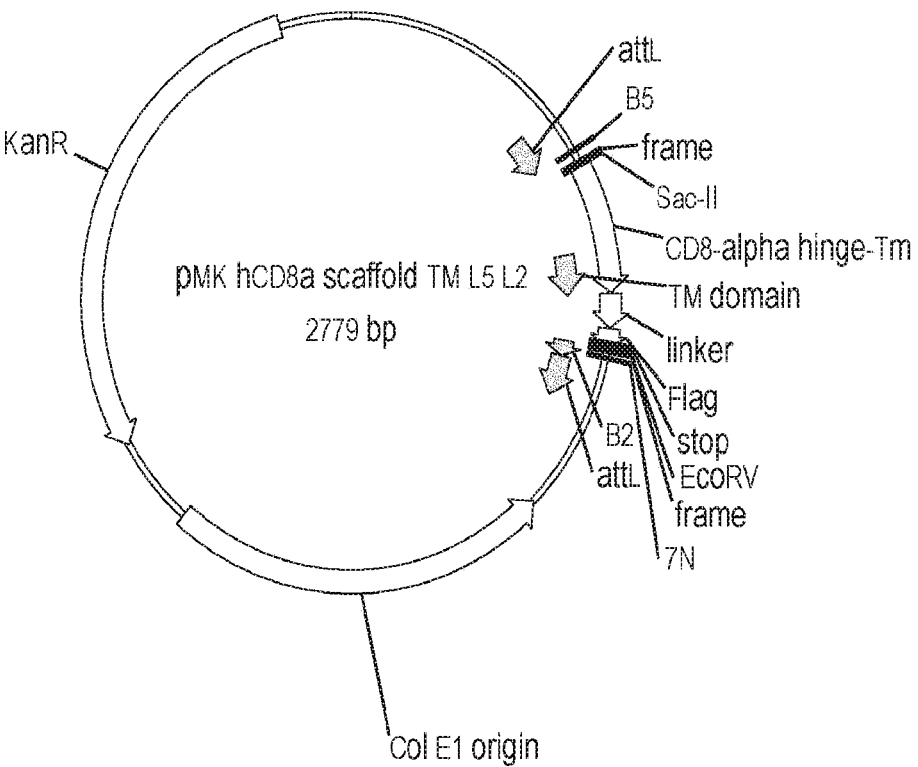
FIG. 35 illustrates a vector diagram of donor vector 2, pMK hCD8a scaffold TN L5 L2.
Figure 36:
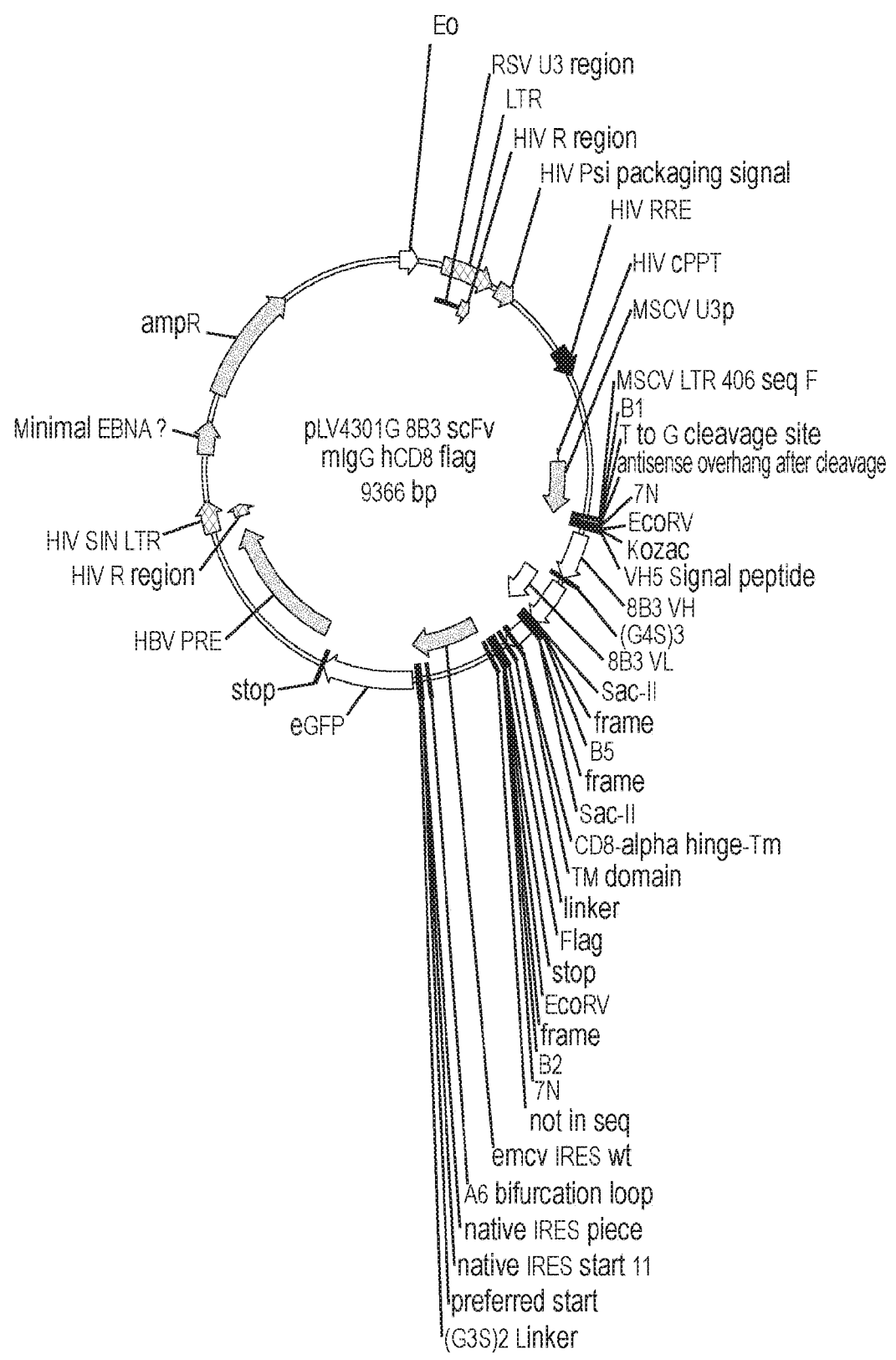
FIG. 36 illustrates a vector diagram of final vector used for lentiviral production, pLV4301G 8B3 scFv mlgG hCD8 flag.

| Identifier (Description) | Sequence (One-Letter Amino Acid Symbols) | | | | | |
|---|---|---|---|---|---|---|
| SEQ ID NO: 27 | QVQLVQSGGG | LVKPGGSLRL | SCAASGFNFN | DQYMSWIRQA | PGKGLEWVSF | ISGSGGTTYY | 60 |
| (mFC-7C12 | TDSVKGRFTI | SRDNTKDSLY | LQMNSLTVED | TAVYYCARGG | NYYTSVGRGT | LVTVSAGGGG | 120 |
| scFv) | SGAPDIQMTQ | SPGTLSLSPG | ERAILSCRAS | QSVSGYLAWY | QQKPGQAPRL | LIYGASSRAT | 180 |
| | GIPDRFSGSG | SGTDFTLTIS | SLRPEDIGTY | YCKQYINAPF | TEGGGTKVEI | K | 231 |
| SEQ ID NO: 28 | QVQLQQSGAE | VKKPGSSVKV | SCKASGGTFS | SYAISWVRQA | PGQGLEWMGW | ISPYNGNTDY | 60 |
| (mFC-8B3 scFv) | AQKVQGRVTL | TTDTSTSTAY | MELRSLRSDD | TAVYYCATGG | GTWYSDLWGR | GTLVTVSAGG | 120 |
| | GGSGGGGSGG | GGSGAPEIVL | TQSPSTLSAS | VGDRVSITCR | ASQSIGGSLA | WYQQKPGKAP | 180 |
| | KLLISEASTL | ERGVPSRFSG | SGSGTDFTLT | ISSLQPEDVA | TYYCQKYNSV | PLTFGPGTKV | 240 |
| | EIK | | | | | | 243 | injecting the following compounds at specified intervals for simultaneous analysis of mitochondrial and glycolytic respiration of the cells: 1 µM oligomycin; 0.5 µM FCCP; 50 mM 2-deoxyglucose; and 0.5 µM each of rotenone and antimycin A. Results were analyzed using WAVE v2.3.0 software (Agilent Technologies, Santa Clara, CA, USA) and GraphPad Prism v6.07 graphing software and are shown in FIG. 27 and FIG. 28, where points represent mean±SEM measured in triplicate. Both TILs grown with aMOLM14 aAPCs and PBMC feeders show similar oxphos and glycolysis behavior. This data suggests that aMOLM14 does not alter the metabolic programming of TILs when compared with PBMC feeders.

Example 5—Preparation of EM-3 Artificial Antigen Presenting Cells (aEM3 aAPCs)

EM-3 cells were obtained from Creative Bioarray, Inc. (Shirley, NY, USA). To develop an EM-3 based artificial APC, EM-3 cell lines were engineered with CD86, 4-1BBL, and antibody against IgG Fc region (Clone 7C12 or Clone 8B3). Human CD86 and human 4-1BBL/CD137 genes were cloned into commercially-available PLV430G and co-transfected with PDONR221 vectors (Invitrogen) using a lentiviral transduction method. The gateway cloning method was used as described in Katzen, *Expert Opin. Drug Disc.* 2007, 4, 571-589, to clone hCD86 and hCD137L genes onto the PLV430G and PDONR221 vectors. The 293T cell line was used for lentiviral production, and transduced to EM-3 cell lines. The transfected cells were sorted (S3e Cell Sorter, BioRad, Hercules, CA, USA) using APC-conjugated CD86 and PE-conjugated CD137L to isolate and enrich the cells. The enriched cells were checked for purity by flow cytometry. Single-chain Fv (scFv) antibody clones designated 7C12 and 8B3 were generated against Fc of mouse IgG1, IgG2a and IgG2b (Viva Biotech Ltd., Chicago, IL, USA). The amino acid sequences of these scFv clones are given in Table 7 (SEQ ID NO:27 and SEQ ID NO:28). The generated scFv clones were screened for Fc binding efficiency against OKT-3, engineered towards pLV4301G containing eGFP as co-reporter to produce lentivirus. The 293T cell line was used for packaging and lentiviral production. Engineered EM-3 (CD86/CD137L) cells were transduced using the A non-limiting protocol for preparation of aEM3 aAPCs, which may also be adapted for use with aMOLM14 aAPCs, is described in the following paragraphs.

Molecular cloning of plasmids of interest may be performed as follows. To generate DONR vector the following cocktail may be used: B site flanked PCR product or destination vector (e.g., Gateway-adapted lentivector) 50-100 µg; DONR vector (e.g., pDONR222) 50-100 µg; BR Clonase II (Life Technologies) 1 µL; and TE buffer ((1 mM Tris, 0.1 mM EDTA, pH 8.0, q.s. to bring volume to 5 µL). Incubate at room temperature for at least 1 hour. After incubation perform bacterial transformation either by heat shock method or electroporation. To generate destination vector, the following cocktail may be used: recombined pDONR vector (e.g., pDON222-geneX) 50-100 µg, destination vector (e.g., Gateway adapted lentivector) 50-100 µg, LR Clonase II (Life Technologies) 1 µL, and TE buffer ((1 mM Tris, 0.1 mM EDTA, pH 8.0, q.s. to bring volume to 5 µL). Incubate at room temperature for at least 1 hour. After incubation, perform bacterial transformation either by chemical competent transformation/heat shock method.

Transformation and selection of the cloned plasmid may be performed as follows. The chemical competent transformation method may be performed as follows. Prepare nutrient agar plates (LB-Lennox or YT) with antibiotic for selection. Ensure that Recovery Medium (supplied by Lucigen, Middleton, WI, USA) is readily available at room temperature. Optionally, sterile culture tubes may be chilled on ice (e.g., 17 mm×100 mm tubes (14 mL tube)), one tube for each transformation reaction). Remove E. cloni cells (Lucigen) from an −80° C. freezer and thaw completely on wet ice (5-15 minutes). Optionally add 40 µL, of E. cloni cells to the chilled culture tube. Add 1-4 µL of DNA sample to the 40 µL of cells. Flick with finger (do not pipet up and down to mix, which can introduce air bubbles and warm the cells). Incubate the cell/DNA mixture on ice for 30 minutes. Heat shock cells by placing the culture tubes in a 42° C. water bath for 45 seconds. Return the 1.7 mL tube or culture tubes to ice for 2 minutes. Add 350 µL room temperature Recovery Medium to the cells or 960 µL of room temperature Recovery Medium to the cells in the culture tube. Place the tubes in a shaking incubator at 250 rpm for 1 hour at 37° C. Plate up to 100% of the transformation mixture on LB-Lennox or YT agar plates containing the appropriate antibiotic. The plating volume may need to be optimized depending on DNA. Incubate the plates overnight at 37° C. Transformed clones can be further grown in any rich culture medium (e.g., LB or TB).

Colonies for Miniprep (Qiagen, Inc., Valencia, CA, USA) may be grown as follows. After colonies have formed from plating recovered transformation reaction of DNA manipulation (e.g. LR reaction), add 1 mL desired TB/antibiotics into desired number of 2 mL Eppendorf microtubes with punctured caps. Pick desired number of colonies using ART LTS 20 µL soft pipette tip (VWR 8903 1-352) or \0 µL Denville tip. Place tip in 2 mL Eppendorf microtube with punctured cap. Cut the tip so that it fits in tube, close cap, and place tubes on shaker (purple 15 mL tube holder with VWR brand 15 mL tubes). Shake overnight (for no more than 16 hours) at 225 rpm/37° C. After overnight incubation, place each tip in a 1 mL tube in a ClavePak 96 plate from Denville with sterile water in it (to save the tip for making bacterial stock production after the plasmids are screened and selected). Perform Miniprep according to the Qiagen Mini prep kit protocol (Qiagen, Inc., Valencia, CA, USA). Once the plasmids are eluted, restriction digestion is performed to select the right clones. After selecting the plasmids, use the tips saved from the same plasmids clone to grow the *E. coli* with the plasmid to make bacterial stock.

Lentiviral production may be performed as follows. The following media composition is prepared: 500 mL DMEM/F12 (Sigma); 25 mL FBS Heat Inactivated (HI) (Hyclone); 10 mM HEPES (Life Technologies); IX Primocin (Invivogen); IX Plasmocin (Invivogen); and 1×2-mermactoethanol (Life Technologies). Harvest T75 flasks (Thermo Fisher Scientific) containing 90% confluent 293T cells. Aspirate media. Add 10 ml PBS, rinse gently and aspirate off. Add 2 mL TrypLE Express (Life Technologies) and evenly distribute it over the cell layer, let sit for 3-5 minutes at 37° C. (cell culture incubator). Add 10 mL media and disperse cells by pipetting up and down. Combine if there are multiple flasks. Count cells. If using a hemacytometer to determine concentration, cells/mL=(# counted cells$_\chi$dilution factor$_\chi 10^4$). To split back into T75 flasks, determine the time at which the cells will need to be fully confluent and dilute accordingly. (Cells double every 16-18 hours, so 3 days=1/27 dilution). Generally, a multiplication factor of 2.5 per day may be used where confluence is $2\times10^5$ cells/cm$^2$. Bring volume up to 25 mL of media. To plate for titration of stocks, each well of the assay requires 5×10$^4$ cells in 0.4 mL of media. Adjust 293T cells to 2×l0$^4$/mL in media. Plate 1 mL per well in a 24 well plate. For example, cells plated Monday may be infected on Tuesday and run on the flow cytometer on Friday, and cells plated Thursday are infected Friday and run on the flow cytometer on Monday. To plate for packaging transfections, seed T75 flasks with 6.8$_\chi 10^6$ cells one day before transfection or 1.7×10$^6$ cells on the morning of transfection. (Seeding on the day of transfection may reduce the variation in transfection efficiency). Bring volume in flask up to 25 mL with media. For example, flasks set up Monday are transfected Tuesday, and virus is collected on Thursday and Friday. In some cases (e.g., high titering constructs), the second collection can be omitted. To package lentiviral vectors, each T75 flask transfection requires 2 µs Baculo p35 plasmid (optional; only necessary if packaging a death gene), 2 µg VSV.G env plasmid (e.g., pMD2.G or PCIGO VSV-G); 4.7 µs Gag/polymerase plasmid (e.g., psPAX2 or pCMV-deltaR8.91), and 2.3 µs of the lentiviral vector described above. Determine the amount of VSV and R8.2/9.1 (+/–Baculo) plasmids needed for all samples (make a mixture of these DNAs if preparing many samples). Each T75 transfection requires 90 µL LipofectAmine 2000

(Thermo Fisher Scientific) in 2 mL Opti-MEM medium (Thermo Fisher Scientific). Make a mix containing enough Opti-Mem and LipofectAmine 2000 for all samples. Mix gently and let sit for 5 minutes at room temp, and label as tube A. For each transfection, add packaging DNA and specific lentiviral vector DNA to 500 µL room temperature Opti-MEM medium to a microtube and mix, and label as tube B. Add the 500 µL of DNA from tube B to the 2 mL of the LipofectAmine 2000 mix in tube A and mix gently, and incubate for 20-30 minutes at room temperature. Aspirate media from packaging flasks. Add the 2.5 mL of DNA/Lipofectamine complexes to 5 mL Opti-MEM medium and add to cells (do not pipet directly on cells since 293T cells are only semi adherent). Process plates in small groups to avoid drying. Incubate overnight and change media the next day in the morning. Collect the supernatant after 24 hours of media change. Supernatants can be harvested in a single collection, 48 hours after transfection or as 2 collections, 48 and 72 hours after transfection (in which case, harvests are pooled). If double collection is desired, collect supernatants by pipet on the first day, and replace with 20 mL of fresh media. To avoid flasks drying, work with only 5 flasks at a time. Keep collected supernatants at 4° C. until pooling the next day. Cool supernatants again on the following day and pool as appropriate. Spin the supernatants at 2000 rpm for 5 minutes to sediment any contaminating 293T cells. Filter harvested supernatants through a 0.45 µm or 0.8 µm filter unit containing a pre-filter disc. Use a large enough filtration unit so that the filtration speed is relatively fast. Store at 4° C. until ready to concentrate.

Virus may be concentrated using the PEG-it method (System Biosciences, Inc., Palo Alto, CA 94303) for longer-term storage at –80° C. Collect the supernatant from the transfection plates. Spin down the cell debris in the supernatant. The supernatant may also be filtered to completely remove any packaging cells. Add an amount of PEG-it solution equal to a quarter of the volume of supernatant to the supernatant. Incubate the suspension at 4° C. for overnight. Centrifuge at 3500 rpm (1500 g) at 4° C. for 30 minutes. Remove supernatant and centrifuge at 3500 rpm at 4° C. for 5 minutes. Remove remaining supernatant. Resuspend virus in desired amount of phosphate-buffered saline (PBS) and freeze aliquots at –80° C.

Transduction of cell line using lentivirus may be performed as follows. Adjust cells to be transduced to either: 1$\chi 10^6$ suspension cells per well in 24 well plate (1 well per transduction) or 50% confluence for adherent cells (1 well per transduction) in 24 well plate. For suspended cells, adjust concentration of cells to 1$\chi 10^7$/mL and plate 100 µL per well in 24 well plate (1 well per transduction). For adherent cells, plate to achieve 50% confluence on day of transduction based on cells/cm$^2$ (e.g., for 293T cells, confluence=2$\chi 10^5$/cm$^2$). Total volume of transduction per well should be approximately 500 µL with 3-10 µg/mL Polybrene (Hexadimethrine bromide, Sigma-Aldrich Co., St. Louis, MO, USA). The amount of concentrated virus added will depend on the MOI (multiplicity of infection) desired. A typical MOI is 10:1 but this may vary depending on cell type. The transfection well should contain 100 µL of standard media containing either 1×10$^6$ suspension cells or 50% confluent cells. For a MOI of 10:1 (e.g., virus activity is 1×10$^8$ IU/mL and the target is to infect 1×10$^6$ cells, then 1×10$^7$ virions or 100 µL of virus is needed). Add standard media to 500 µL. Add Polybrene to 3 µg/mL (primary cells) to 10 µg/mL (tumor cell lines). Spin plate(s) at 1800 rpm for 1.5 to 2 hours at 30° C. Incubate plate(s) at 37° C./5% CO$_2$ using a Tissue Culture incubator for 5 hours to overnight.

Change media. After 72 hours of transduction, if enough cells are available, perform flow cytometric analysis to test the transduction efficiency.

Sorting of aAPCs may be performed as follows. Culture the cells in the media described above until the cell count reaches a minimum of 10-20 million. Take $1\chi10^6$ cells for each condition and stain with the antibodies for the proteins transduced. Wash the cells and analyze by flow cytometry to test the stability of transduction. Once the expression of protein of interest has been analyzed and confirmed, prepare the rest of the cells for sorting. Sort the cells in an S3 sorter by gating on markers of interest. Culture the sorted cells using the media mentioned above. Before freezing the vial, test the stability of the protein expression of interest. Use Recovery cell culture Freezing media (Invitrogen), to make the cell bank of the same cells. Cells may be banked after each transduction and sorting procedure.

Nucleotide sequence information for the 7C12 and 8B3 scFv clones (SEQ ID NO:29 and SEQ ID NO: 30) and their lentiviral vectors are given in Table 8. Sequences used for generation of the pLV4301G 7C12 scFv mIgG hCD8 flag vector are provided as SED IQ NO: 31 to SEQ ID NO:34 and are depicted in FIG. 29 to FIG. 32. Sequences used for generation of the pLV4301G 8B3 scFv mIgG hCD8 flag vector are provided as SEQ ID NO:35 to SEQ ID NO:38 and are depicted in FIG. 33 to FIG. 36.

TABLE 8

Nucleotide sequences for preparation of lentivirus for transduction of aAPCs.

| Identifier (Description) | Sequence | |
|---|---|---|
| SEQ ID NO: 29 (mFC-7C12 scFv) | caggtgcagc tggtgcagtc tggggggaggc ttggtcaagc ctggagggtc cctgagactc | 60 |
| | tcctgtgcag cctctggatt caatttcaat gaccagtaca tgagttggat ccgccaggct | 120 |
| | ccagggaagg ggctgggagtg ggtttcattc attagtggta gtggtggtac cacatactac | 180 |
| | acagactctg tgaagggccg gttcaccatc tccagggaca acaccaagga ctcattgtat | 240 |
| | ttgcaaatga acagcctgac agtcgaggac acggccgtgt actactgtgc gagaggaggg | 300 |
| | aattattata cttcggtggg ccggggcacc ctggtcaccg tctcggccgg tggcggcgga | 360 |
| | tctggcgcgc cagacatcca gatgacccag tctccaggca ccctgtcttt gtctccaggg | 420 |
| | gaaagagcca tcctctcctg cagggccagt cagagtgtta gcggctacct agcctggtat | 480 |
| | caacagaaac ctggccaggc tcccaggctc ctcatctatg gtgcatccag cagggccact | 540 |
| | ggcatcccag acaggttcag tggcagtggg tctgggacag acttcactct caccatcagc | 600 |
| | agcctgcggc ctgaagatat tggaacatat tactgtaaac agtacattaa tgccccattc | 660 |
| | actttcggcg gcgggaccaa ggtggagatc aaa | 693 |
| SEQ ID NO: 30 (mFC-8B3 scFv) | caggtacagc tgcagcagtc aggggctgag gtgaagaagc ctgggtcctc ggtgaaggtc | 60 |
| | tcctgcaagg cttctggagg caccttcagc agctatgcta tcagctgggt gcgacaggcc | 120 |
| | cctggacaag ggcttgagtg gatgggatgg atcagccctt acaatggtaa cacagattat | 180 |
| | gcacagaagg tccagggcag agtcaccttg accacagaca catccacgag cacagcctac | 240 |
| | atggagctga ggagcctgag atccgacgac acggccgtgt attactgtgc gacaggtggc | 300 |
| | gggacctggt actccgatct ctggggccgt ggcaccctgg tcaccgtctc ggccggtggc | 360 |
| | ggtggcagcg gcggtggtgg gtccggtggc ggcggatctg gcgcgccaga aattgtgctg | 420 |
| | actcagtctc cctccaccct gtctgcatct gtaggagaca gagtcagcat cacttgccgg | 480 |
| | gccagtcaga gtattggtgg gtcgttggcc tggtatcaac aaaagccagg gaaagcccct | 540 |
| | aagctcctga tctctgaggc gtctacttta gagaggggcg tcccatcaag attcagcggc | 600 |
| | agtggatctg ggacagattt cactctcacc atcagcagcc tgcagcctga agatgttgca | 660 |
| | acttattact gtcaaaaata taacagtgtc ccgctcactt tcggccctgg gaccaaggtg | 720 |
| | gagatcaaa | 729 |
| SEQ ID NO: 31 (destination vector pLV4301G) | cgataaccct aattcgatag catatgcttc ccgttgggta acatatgcta ttgaattagg | 60 |
| | gttagtctgg atagtatata ctactacccg ggaagcatat gctaccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctc caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag agctctctcg acgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggaa agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |

TABLE 8-continued

Nucleotide sequences for preparation of lentivirus for transduction of aAPCs.

| Identifier (Description) | Sequence | |
|---|---|---|
| | aatgggcaag tttgtggaat tggtttaaca taacaaattg gctgtggtat ataaaattat | 1920 |
| | tcataatgat agtaggaggc ttggtaggtt taagaatagt ttttgctgta ctttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac aggacagat | 2100 |
| | ccattcgatt agtgaacgga tctcgacggt atcggtttta aaagaaaagg ggggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacagcaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | cacaagtttg tacaaaaaag ctgaacgaga aacgtaaaat gatataaata tcaatatatt | 2760 |
| | aaattagatt ttgcataaaa aacagactac ataatactgt aaaacacaac atatccagtc | 2820 |
| | actatggcgg ccgcattagg caccccaggc tttacacttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttc agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact tcttcgcccc cgtttctacc atgggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcggggc gtaaatggat | 3600 |
| | ccggcttact aaaagccaga taacagtatg cgtatttgcg cgctgatttt tgcggtataa | 3660 |
| | gaatatatac tgatatgtat acccgaagta tgtcaaaaag aggtatgcta tgaagcagcg | 3720 |
| | tattacagtg acagttgaca gcgacagcta tcagttgctc aaggcatata tgatgtcaat | 3780 |
| | atctccggtc tggtaagcac aaccatgcag aatgaagccc gtcgtctgcg tgccgaacgc | 3840 |
| | tggaaagcgg aaaatcagga agggatggct gaggtcgccc ggtttattga aatgaacggc | 3900 |
| | tcttttgctg acgagaacag gggctggtga aatgcagttt aaggtttaca cctataaaag | 3960 |
| | agagagccgt tatcgtctgt ttgtggatgt acagagtgat attattgaca cgcccgggcg | 4020 |
| | acggatggtg atccccctgg ccagtgcacg tctgctgtca gataaagtct cccgtgaact | 4080 |
| | ttacccggtg gtgcatatcg gggatgaaag ctggcgcatg atgaccaccg atatggccag | 4140 |
| | tgtgccggtc tccgttatcg gggaagaagt ggctgatctc agccaccgcg aaaatgacat | 4200 |
| | caaaaacgcc attaacctga tgttctgggg aatataaatg tcaggctccc ttatacacag | 4260 |
| | ccagtctgca ggtcgaccat agtgactgga tttacagtat tatgtagtct | 4320 |
| | gtttttttatg caaaatctaa tttaatatat tgatatttat atcattttac gtttctcgtt | 4380 |
| | cagctttctt gtacaaagtg gtgattcgag ttaattaagt taacgaattc ccccctctc | 4440 |
| | cctccccccc ccctaacgtt actggccgaa gccgcttgga ataaggccgg tgtgcgtttg | 4500 |
| | tctatatgtt attttccacc atattgccgt cttttggcaa tgtgagggcc cggaaacctg | 4560 |
| | gccctgtctt cttgacgagc attcctaggg gtctttcccc tctcgccaaa ggaatgcaag | 4620 |
| | gtctgttgaa tgtcgtgaag gaagcagttc ctctggaagc ttcttgaaga caaacaacgt | 4680 |
| | ctgtagcgac cctttgcagg cagcggaacc ccccacctgg cgacaggtgc ctctgcggcc | 4740 |
| | aaaagccacg tgtataagat acacctgcaa aggcggcaca accccagtgc cacgttgtga | 4800 |
| | gttggatagt tgtggaaaga gtcaaatggc tctcctcaag cgtattcaac aaggggctga | 4860 |
| | aggatgccca gaaggtaccc cattgtatgg gatctgatct ggggcctcgg tgcacatgct | 4920 |
| | ttacatgtgt ttagtcgagg ttaaaaaacg tctaggcccc ccgaaccacg gggacgtggt | 4980 |
| | tttcctttga aaaacacgat gataatatgg ccacaaccat gggaggcgga agcggcggag | 5040 |
| | gctccctctcg aggcaccatg gtgagcaagg gcgaggagct gttcaccggg gtggtgccca | 5100 |
| | tcctggtcga gctggacggc gacgtaaacg gccacaagtt cagcgtgtcc ggcgagggcga | 5160 |
| | agggcgatgc cacctacggc aagctgaccc tgaagttcat ctgcaccacc ggcaagctgc | 5220 |
| | ccgtgccctg gcccaccctc gtgaccaccc tgacctacgg cgtgcagtgc ttcagccgct | 5280 |
| | acccccgacca catgaagcag cacgacttct tcaagtccgc catgcccgaa ggctacgtcc | 5340 |
| | aggagcgcac catcttcttc aaggacgacg gcaactacaa gacccgcgcc gaggtgaagt | 5400 |
| | tcgagggcga caccctggtg aaccgcatcg agctgaaggg catcgacttc aaggaggacg | 5460 |
| | gcaacatcct ggggcacaag ctggagtaca actacaacag ccacaacgtc tatatcatgg | 5520 |
| | ccgacaagca gaagaacggc atcaaggtga acttcaagat ccgccacaac atcgaggacg | 5580 |
| | gcagcgtgca gctcgccgac cactaccagc agaacacccc catcggcgac ggccccgtgc | 5640 |
| | tgctgcccga caaccactac ctgagcaccc agtccgccct gagcaaagac cccaacgaga | 5700 |
| | agcgcgatca catggtcctg ctggagttcg tgaccgccgc cgggatcact ctcggcatgg | 5760 |
| | acgagctgta caagtaacgc gtcccgggtc tagagctgac ggtaccatgc attacgtagt | 5820 |
| | cgacgactta attaagctag cctagtgcca tttgttcagt ggttcgtagg gctttccccc | 5880 |
| | actgtttggc tttcagttat atggatgatg tggtattggg ggcaagtct gtacagcatc | 5940 |
| | ttgagtccct ttttaccgct gttaccaatt ttcttttgtc tttgggtata catttaaacc | 6000 |
| | ctaacaaaac aaagagatgg ggttactctc taaattttat gggttatgtc attggatgtt | 6060 |
| | atgggtcctt gccacaagaa cacatcatac aaaaaatcaa agaatgtttt agaaaacttc | 6120 |
| | ctattaacag gcctattgat tggaaagtat gtcaacgaat tgtgggtctt ttgggttttg | 6180 |
| | ctgccccttt tacacaatgt ggttatcctg cgttgatgcc tttgtatgca tgtattcaat | 6240 |
| | ctaagcaggc tttcactttc tcgccaactt acaaggcctt tctgtgtaaa caatacctga | 6300 |
| | acctttacccc cgttgcccgg caacggccag gtctgtgcca agtgtttgct gacgcaaccc | 6360 |

TABLE 8-continued

Nucleotide sequences for preparation of lentivirus for transduction of aAPCs.

| Identifier (Description) | Sequence | |
|---|---|---|
| | ccactggctg gggcttggtc atgggccatc agcgcatgcg tggaacctttt tcggctcctc | 6420 |
| | tgccgatcca tactgcggaa ctcctagccg cttgtttttgc tcgcagcagg tctggagcaa | 6480 |
| | acattatcgg gactgataac tctgttgtcc tatcccgcaa atatacatcg tttccatggc | 6540 |
| | tgctaggctg tgctgccaac tggatcctgc gcgggacgtc ctttgtttac gtcccgtcgg | 6600 |
| | cgctgaatcc tgcggacgac ccttctcggg gtcgcttggg actctctcgt ccccttctcc | 6660 |
| | gtctgccgtt ccgaccgacc acggggcgca cctctcttta cgcggactcc ccgtctgtgc | 6720 |
| | cttctcatct gccggaccgt gtgcacttcg cttcacctct gcacgtcgca tggagaccac | 6780 |
| | cgtgaacgcc caccaaatat tgcccaaggt cttacataag aggactcttg gactctcagc | 6840 |
| | aatgtcaacg accgaccttg aggcatactt caaagactgt ttgtttaaag actgggagga | 6900 |
| | gttgggggag gagattaggt taaaggtctt tgtactagga ggctgtaggc ataaattggt | 6960 |
| | ctgcgcacca gcaccatggc gcaatcacta gagcggggta cctttaagac caatgactta | 7020 |
| | caaggcagct gtagatctta gccacttttt aaaagaaaag gggggactgg aagggctaat | 7080 |
| | tcactcccaa cgaagacaag atctgctttt tgcttgtact gggtctctct ggttagacca | 7140 |
| | gatctgagcc tgggagctct ctggctaact agggaaccca ctgcttaagc ctcaataaag | 7200 |
| | cttgccttga gtgcttcaag tagtgtgtgc ccgtctgttg tgtgactctg gtaactagag | 7260 |
| | atccctcaga cccttttagt cagtgtggaa aatctctagc agtagtagtt catgtcatct | 7320 |
| | tattattcag tatttataac ttgcaaagaa atgaatatca gagagtgaga ggaacttgtt | 7380 |
| | tattgcagct tataatggtt acaaataaag caatagcatc acaaatttca caaataaagc | 7440 |
| | atttttttca ctgcattcta gttgtggttt gtccaaactc atcaatgtat cttatcatgt | 7500 |
| | ctggctctag ctatcccgcc cctaactccg cccatccgac ccctaactcc gcccagttcc | 7560 |
| | gcccattctc cgccccatgg ctgactaatt ttttttattt atgcagaggc cgaggccgga | 7620 |
| | tcccttgagt ggctttcatc ctggagcaga ctttgcagtc tgtggactgc aacacaacat | 7680 |
| | tgcctttatg tgtaactctt ggctgaagct cttacaccaa tgctggggga catgtacctc | 7740 |
| | ccaggggccc aggaagacta cgggagggcta caccaacgtc aatcagaggg gcctgtgtag | 7800 |
| | ctaccgataa gcggaccctc aagagggcat tagcaatagt gtttataagg ccccttgtt | 7860 |
| | aattcttgaa gacgaaaggg cctcgtgata cgcctatttt tataggttaa tgtcatgata | 7920 |
| | ataatggttt cttagacgtc aggtggcact tttcggggaa atgtgcgcgg aacccctatt | 7980 |
| | tgtttatttt tctaaataca ttcaaatatg tatccgctca tgagacaata accctgataa | 8040 |
| | atgcttcaat aatattgaaa aaggaagagt atgagtattc aacatttccg tgtcgccctt | 8100 |
| | attccctttt ttgcggcatt ttgccttcct gtttttgctc acccagaaac gctggtgaaa | 8160 |
| | gtaaaagatg ctgaagatca gttgggtgca cgagtgggtt acatcgaact ggatctcaac | 8220 |
| | agcggtaaga tccttgagag ttttcgcccc gaagaacgtt ttccaatgat gagcactttt | 8280 |
| | aaagttctgc tatgtggcgc ggtattatcc cgtgttgacg ccgggcaaga gcaactcggt | 8340 |
| | cgccgcatac actattctca gaatgacttg gttgagtact caccagtcac agaaaagcat | 8400 |
| | cttacggatg gcatgacagt aagagaatta tgcagtgctg ccataaccat gagtgataac | 8460 |
| | actgcggcca acttacttct gacaacgatc ggaggaccga aggagctaac cgctttttg | 8520 |
| | cacaacatgg gggatcatgt aactcgcctt gatcgttggg aaccggagct gaatgaagcc | 8580 |
| | ataccaaacg acgagcgtga caccacgatg cctgcagcaa tggcaacaac gttgcgcaaa | 8640 |
| | ctattaactg gcgaactact tactctagct tcccggcaac aattaataga ctggatggag | 8700 |
| | gcggataaag ttgcaggacc acttctgcgc tcggcccttc cggctggctg gtttattgct | 8760 |
| | gataaatctg gagccggtga gcgtgggtct cgcggtatca ttgcagcact ggggccagat | 8820 |
| | ggtaagccct cccgtatcgt agttatctac acgacgggga gtcaggcaac tatggatgaa | 8880 |
| | cgaaatagac agatcgctga gataggtgcc tcactgatta agcattggta actgtcagac | 8940 |
| | caagtttact catatatact ttagattgat ttaaaacttc atttttaatt taaaaggatc | 9000 |
| | taggtgaaga tcctttttga taatctcatg accaaaatcc cttaacgtga gttttcgttc | 9060 |
| | cactgagcgt cagacccccg agaaaagatc aaaggatctt cttgagatcc tttttttctg | 9120 |
| | cgcgtaatct gctgcttgca aacaaaaaaa ccaccgctac cagcggtggt ttgtttgccg | 9180 |
| | gatcaagagc taccaactct ttttccgaag gtaactggct tcagcagagc gcagatacca | 9240 |
| | aatactgtcc ttctagtgta gccgtagtta ggccaccact tcaagaactc tgtagcaccg | 9300 |
| | cctacatacc tcgctctgct aatcctgtta ccagtggctg ctgccagtgg cgataagtcg | 9360 |
| | tgtcttaccg ggttggactc aagacgatag ttaccggata aggcgcagcg tcgggctga | 9420 |
| | acggggggtt cgtgcacaca gcccagcttg gagcgaacga cctacaccga actgagatac | 9480 |
| | ctacagcgtg agcattgaga aagcgccacg cttcccgaag ggagaaaggc ggacaggtat | 9540 |
| | ccggtaagcg gcagggtcgg aacaggagag cgcacgaggg agcttccagg gggaaacgcc | 9600 |
| | tggtatcttt atagtcctgt cgggtttcgc cacctctgac ttgagcgtcg attttttgtga | 9660 |
| | tgctcgtcag ggggggcggag cctatggaaa aacgccagca acgcggcctt tttacggttc | 9720 |
| | ctggcctttt gctggccttt ttgaagctgt ccctgatggt cgtcatctac ctgcctggac | 9780 |
| | agcatgcct gcaacgcggg catcccgatg ccgccggaag cgagaagaat cataatgggg | 9840 |
| | aaggccatcc agcctcgcgt cg | 9862 |
| SEQ ID NO: 32 (donor vector 1, pMK 7c12 anti mFC scFV CoOp ECORV SacII L1R5) | ctaaattgta agcgttaata ttttgttaaa attcgcgtta aattttgtt aaatcagctc | 60 |
| | attttttaac caataggccg aaatcgcctt aaatcaaaag aatagaccga | 120 |
| | gatagggttg agtggccgct acaggcgcgt cccattcgcc attcaggctg cgcaactgtt | 180 |
| | gggaagggcg tttcggtgcg ggcctcttcg ctattacgcc agctggcgaa aggggggatgt | 240 |
| | gctgcaaggc gattaagttg ggtaacgcca gggttttccc agtcacgacg ttgtaaaacg | 300 |
| | acggccagtg agcgcgacgt aatacgactc actatagtgc gaattgaagg aaggccgtca | 360 |
| | aggccgcata ataatgatt ttattttgac tgatagtgac ctgttcgttg caacaaattg | 420 |
| | atgagcaatg ctttttttata atgccaactt tgtacaaaaa agctgaacga tatcgccacc | 480 |
| | atgggcagca cagccattcc ggccctgctg ctggcagtgc tgcaggcgt gtcagctcag | 540 |
| | gtgcagctgg tgcagtctgg cggcggactc gtgaaacctg gcggaggctc gagactgagc | 600 |
| | tgtgccgcca gcggcttcaa cttcaacgac cagtacatga gctgggatcc gcaggcccct | 660 |
| | ggcaagggac tggaatgggt gtccttcatc agcggcagcg gcggcaccac ctactacacc | 720 |
| | gatagcgtga agggccggtt caccatcagc cgggacaaca ccaaggacag cctgtacctg | 780 |
| | cagatgaaca gcctgaccgt ggaagatacc gccgtgtact actgcgccag aggcggcaat | 840 |
| | tactacacca gcgtgggcag aggcaccctc gtgacagtgt ctgctgcgg aggcggatca | 900 |

TABLE 8-continued

Nucleotide sequences for preparation of lentivirus for transduction of aAPCs.

| Identifier (Description) | Sequence | | | | | |
|---|---|---|---|---|---|---|
| | ggcggcggag | gatcaggggg | aggcggaagc | ggagcacccg | atatccagat | gacacagagc | 960 |
| | cccggcaccc | tgtctctgag | ccctggcgaa | agagccatcc | tgagctgcag | agccagccag | 1020 |
| | agcgtgtccg | gatacctggc | ttggtatcag | cagaagcccg | gccaggcccc | cagactgctg | 1080 |
| | atctatggcg | ccagcagcag | agccacaggc | atccccgata | gattcagcgg | ctctggcagc | 1140 |
| | ggcaccgact | tcaccctgac | aatcagctcc | ctgcggcccg | aggacatcgg | cacctactat | 1200 |
| | tgcaagcagt | acatcaacgc | ccccttcacc | tteggcggag | gcaccaaggt | ggaaatcaag | 1260 |
| | ccgcgggcca | actttgtata | caaaagtgga | acgagaaacg | taaaatgata | taaatatcaa | 1320 |
| | tatattaaat | tagattttgc | ataaaaaaca | gactacataa | tactgtaaaa | cacaacatat | 1380 |
| | ccagtcacta | tgaatcaact | acttagatgg | tattagtgac | ctgtactggg | cctcatgggc | 1440 |
| | cttcctttca | ctgcccgctt | tccagtcggg | aaacctgtcg | tgccagctgc | attaacatgg | 1500 |
| | tcatagctgt | ttccttgcgt | attgggcgct | ctccgcttcc | tcgctcactg | actcgctgcg | 1560 |
| | ctcggtcgtt | cgggtaaagc | ctggggtgcc | taatgagcaa | aaggccagca | aaaggccagg | 1620 |
| | aaccgtaaaa | aggccgcgtt | gctggcgttt | ttccataggc | tccgcccccc | tgacgagcat | 1680 |
| | cacaaaaatc | gacgctcaag | tcagaggtgg | cgaaacccga | caggactata | aagataccag | 1740 |
| | gcgtttcccc | ctggaagctc | cctcgtgcgc | tctcctgttc | cgaccctgcc | gcttaccgga | 1800 |
| | tacctgtccg | cctttctccc | ttcgggaagc | gtggcgcttt | ctcatagctc | acgctgtagg | 1860 |
| | tatctcagtt | cggtgtaggt | cgttcgctcc | aagctgggct | gtgtgcacga | accccccgtt | 1920 |
| | cagcccgacc | gctgcgcctt | atccggtaac | tatcgtcttg | agtccaaccc | ggtaagacac | 1980 |
| | gacttatcgc | cactggcagc | agccactggt | aacaggatta | gcagagcgag | gtatgtaggc | 2040 |
| | ggtgctacag | agttcttgaa | gtggtggcct | aactacggct | acactagaag | aacagtattt | 2100 |
| | ggtatctgcg | ctctgctgaa | gccagttacc | ttcggaaaaa | gagttggtag | ctcttgatcc | 2160 |
| | ggcaaacaaa | ccaccgctgg | tagcggtggt | ttttttgttt | gcaagcagca | gattacgcgc | 2220 |
| | agaaaaaaag | gatctcaaga | agatcctttg | atcttttcta | cggggtctga | cgctcagtgg | 2280 |
| | aacgaaaact | cacgttaagg | gattttggtc | atgagattat | caaaaaggat | cttcacctag | 2340 |
| | atccttttaa | attaaaaatg | aagttttaaa | tcaatctaaa | gtatatatga | gtaaacttgg | 2400 |
| | tctgacagtt | attagaaaaa | ttcatccagc | agacgataaa | acgcaatacg | ctggctatcc | 2460 |
| | ggtgccgcaa | tgccatacag | caccagaaaa | cgatccgccc | attcgccgcc | cagttcttcc | 2520 |
| | gcaatatcac | gggtggccag | cgcaatatcc | tgataacgat | ccgccacgcc | cagacggccg | 2580 |
| | caatcaataa | agccgctaaa | acggccattt | tccaccataa | tgttcggcag | gcacgcatca | 2640 |
| | ccatgggtca | ccaccagatc | ttcgccatcc | ggcatgctcg | ctttcagacg | cgcaaacagc | 2700 |
| | tctgccggtg | ccaggccctg | atgttcttca | tccagatcat | cctgatccac | caggcccgct | 2760 |
| | tccatacggg | tacgcgcacg | ttcaatacga | tgtttcgcct | gatgatcaaa | cggacaggtc | 2820 |
| | gccgggtcca | gggtatgcag | acgacgcatg | gcatccgcca | taatgctcac | tttttctgcc | 2880 |
| | ggcgccagat | ggctagacag | cagatcctga | cccggcactt | cgcccagcag | cagccaatca | 2940 |
| | cggcccgctt | cggtcaccac | atccagcacc | gccgcacacg | gaacaccggt | ggtggccagc | 3000 |
| | cagctcagac | gcgccgcttc | atcctgcagc | tcgttcagcg | caccgctcag | atcggttttc | 3060 |
| | acaaacagca | ccggacgacc | ctgcgcgctc | agacgaaaca | ccgccgcatc | agagcagcca | 3120 |
| | atggtctgct | gcgcccaatc | atagccaaac | agacgttcca | cccacgctgc | cgggctaccc | 3180 |
| | gcatgcaggc | catcctgttc | aatcatactc | ttcctttttc | aatattattg | aagcatttat | 3240 |
| | cagggttatt | gtctcatgag | cggatacata | tttgaatgta | tttagaaaaa | taaacaaata | 3300 |
| | ggggttccgc | gcacatttcc | ccgaaaagtg | ccac | | | 3334 |
| SEQ ID NO: 33 (donor vector 2, pMK hCD8a scaffold TN L5 L2 ) | ctaaattgta | agcgttaata | ttttgttaaa | attcgcgtta | aattttttgtt | aaatcagctc | 60 |
| | atttttttaac | caataggccg | aaatcggcaa | aatccccttat | aaatcaaaag | aatagaccga | 120 |
| | gataggggttg | agtggccgct | acaggggcgct | cccattcgcc | attcaggctg | cgcaactgtt | 180 |
| | gggaaggggc | tttcggtgcg | ggcctcttcg | ctattacggc | agctggcgaa | aggggggatgt | 240 |
| | gctgcaaggc | gattaagttg | ggtaacgcca | gggttttccc | agtcacgacg | ttgtaaaacg | 300 |
| | acggccagtg | agcgcgacgt | aatacgactc | actatagggc | gaattgaagg | aaggccgtca | 360 |
| | aggccgcata | aataatgatt | ttattttgac | tgataatgac | ctgttcgttg | caacaaattg | 420 |
| | atgagcaatg | cttttttata | atgcccaact | ttgtatacaa | aagtggcccg | cggacaacaa | 480 |
| | cccctgcccc | cagacctcct | accccagccc | ctacaattgc | cagccagcct | ctgagcctga | 540 |
| | ggcccgaggc | ttgtagacct | gctgctggcg | gagccgtgca | caccagagga | ctggatttcg | 600 |
| | cctgcgacat | ctacatctgt | gcccctctgg | ccggcacatg | tggcgtgctg | ctgctgagcc | 660 |
| | tcgtgatcac | cctgtactgc | ggctccacca | tcgggctccg | caagcccggc | tctggcgagg | 720 |
| | gctccaccag | cggcgactac | aaggacgacg | atgacaagta | ataggatatc | ggttcagctt | 780 |
| | tcttgtacaa | agttggcatt | ataagaaagc | attgcttatc | aatttgttgc | aacgaacagg | 840 |
| | tcactatcag | tcaaaataaa | atcattattt | ctgggcctca | tgggccttcc | tttcactgcc | 900 |
| | cgctttccag | tcgggaaacc | tgtcgtgcca | gctgcattaa | catggtcata | gctgtttcct | 960 |
| | tgcgtattgg | gcgctctccg | cttcctcgct | cactgactcg | ctgcgctcgg | tcgttcgggt | 1020 |
| | aaagcctggg | gtgcctaatg | agcaaaaggc | cagcaaaagg | ccaggaaccg | taaaaaggcc | 1080 |
| | gcgttgctgg | cgttttttcca | taggctccgc | cccccctgacg | agcatcacaa | aaatcgacgc | 1140 |
| | tcaagtcaga | ggtggcgaaa | cccgacagga | ctataaagat | accaggcgtt | tcccccctgga | 1200 |
| | agctccctcg | tgcgctctcc | tgttccgacc | ctgccgctta | ccggatacct | gtccgccttt | 1260 |
| | ctcccttcgg | gaagcgtggc | gctttctcat | agctcacgct | gtaggtatct | cagttcggtg | 1320 |
| | taggtcgttc | gctccaagct | gggctgtgtg | cacgaacccc | ccgttcagcc | cgaccgctgc | 1380 |
| | gccttatccg | gtaactatcg | tcttgagtcc | aacccggtaa | gacacgactt | atcgccactg | 1440 |
| | gcagcagcca | ctggtaacag | gattagcaga | gcgaggtatg | taggcggtgc | tacagagttc | 1500 |
| | ttgaagtggt | ggcctaacta | cggctacact | agaagaacag | tatttggtat | ctgcgctctg | 1560 |
| | ctgaagccag | ttaccttcgg | aaaaagagtt | ggtagctctt | gatccggcaa | acaaaccacc | 1620 |
| | gctggtagcg | gtggtttttt | tgtttgcaag | cagcagatta | cgcgcagaaa | aaaaggatct | 1680 |
| | caagaagatc | ctttgatctt | ttctacgggg | tctgacgctc | agtggaacga | aaactcacgt | 1740 |
| | taagggattt | tggtcatgag | attatcaaaa | aggatcttca | cctagatcct | tttaaattaa | 1800 |
| | aaatgaagtt | ttaaatcaat | ctaaagtata | tatgagtaaa | cttggtctga | cagttattag | 1860 |
| | aaaaattcat | ccagcagacg | ataaaacgca | atacgctggc | tatccggtgc | cgcaatgcca | 1920 |
| | tacagcacca | gaaaacgatc | cgcccattcg | ccgcccagtt | cttccgcaat | atcacgggtg | 1980 |

TABLE 8-continued

Nucleotide sequences for preparation of lentivirus for transduction of aAPCs.

| Identifier (Description) | Sequence | |
|---|---|---|
| | gccagcgcaa tatcctgata acgatccgcc acgcccagac ggccgcaatc aataaagccg | 2040 |
| | ctaaaacggc cattttccac cataatgttc ggcaggcacg catcaccatg ggtcaccacc | 2100 |
| | agatcttcgc catccggcat gctcgctttc agacgcgcaa acagctctgc cggtgccagg | 2160 |
| | ccctgatgtt cttcatccag atcatcctga tccaccaggc ccgcttccat acgggtacgc | 2220 |
| | gcacgttcaa tacgatgttt cgcctgatga tcaaacggac aggtcgccgg gtccagggta | 2280 |
| | tgcagacgac gcatggcatc cgccataatg ctcacttttt ctgccggcgc cagatggcta | 2340 |
| | gacagcagat cctgaccccgg cacttcgccc agcagcagcc aatcacggcc cgcttcggtc | 2400 |
| | accacatcca gcaccgccgc acacggaaca ccggtggtgg ccagccagct cagacgcgcc | 2460 |
| | gcttcatcct gcagctcgtt cagcgcaccg ctcagatcgg ttttcacaaa cagcaccgga | 2520 |
| | cgaccctgcg cgctcagacg aaacaccgcc gcatcagagc agccaatggt ctgctgcgcc | 2580 |
| | caatcatagc caaacagacg ttccacccac gctgccgggc tacccgcatg caggccatcc | 2640 |
| | tgttcaatca tactcttcct ttttcaatat tattgaagca tttatcaggg ttattgtctc | 2700 |
| | atgagcggat acatatttga atgtatttag aaaaataaac aaataggggg tccgcgcaca | 2760 |
| | tttccccgaa aagtgccac | 2779 |
| SEQ ID NO: 34 (Final vector used for lentiviral production, pLV4301G 7C12 scFV mIgG hCD8 flag) | cgataaccct aattcgatag catatgcttc ccgtttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggaa agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccaggc aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta cttttctatag | 1980 |
| | tgaatagagt taggcaggga tattcaccat tatcgtttca gacccacctc ccaacccccga | 2040 |
| | ggggacccga caggcccgaa ggaatagaag aagaaggtgg agagagagac agagacagat | 2100 |
| | ccattcgatt agtgaacgga tctcgacggt atcggtttta aagaaaaggg ggggattggg | 2160 |
| | gggtacagtg caggggaaag aatagtagac ataatagcaa cagacataca aactaaagaa | 2220 |
| | ttacaaaaac aaattacaaa aattcaaaat tttatcgatt ttatttagtc tccagaaaaa | 2280 |
| | gggggggaatg aaagacccca cctgtaggtt tggcaagcta gcttaagtaa cgccattttg | 2340 |
| | caaggcatgg aaaatacata actgagaata gagaagttca gatcaaggtt aggaacagag | 2400 |
| | agacagcaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga aatgaccctg tgccttattt gaactaacca | 2580 |
| | atcagttcgc ttctcgcttc tgttcgcgcg cttctgctcc ccgagctcaa taaaagagcc | 2640 |
| | cacaacccct cactcggcgc gccagtcctc cgatagactg cgtcgcccgg gtaccgatat | 2700 |
| | caccaacttt gtacaaaaaa gctgaacgat atcgccacca tgggcagcac agccattctg | 2760 |
| | gccctgctgc tggcagtgct gcagggcgtg tcagctctgg tgcagctggt gcagtctgga | 2820 |
| | ggcggactcg tgaaacctgg cggcagcctg agactgagct gtgccgccag cggcttcaac | 2880 |
| | ttcaacgacc agtacatgag ctggatccgg caggcccctg gcaagggact ggaatgggtg | 2940 |
| | tccttcatca gcggcagcgg cggcaccacc tactacaccg atagcgtgaa gggccggttc | 3000 |
| | accatcagcc gggacaacac caaggacaac ctgtacctgc agatgaacag cctgaccgtg | 3060 |
| | gaagataccg ccgtgtacta ctgcgccaga ggcggcaatt actacaccag cgtgggcaga | 3120 |
| | ggcaccctcg tgacagtgtc tgctgcggga ggcggatcag gcggcggagg atcaggggga | 3180 |
| | ggcggaagcg gagcacccga tatccagatg acacagagcc cggcaccct gtctctgagc | 3240 |
| | cctggcgaaa gagccatcct gagctgcaga gccagccaga gcgtgtccgg ataactggct | 3300 |
| | tggtatcagc agaagcccgg ccaggccccc agactgctga tctatggcgc cagcagcaga | 3360 |
| | gccacaggca tccccgatag attcagcggc tctggcagcg gcaccgactt caccctgaca | 3420 |
| | atcagctccc tgcggcccga ggacatcggc acctactatt gcaagcagta catcaacgcc | 3480 |
| | cccttcacct tcggcggagg caccaaggtg gaaatcaagc gcgggccaa ctttgtatac | 3540 |
| | aaaagtggcc gcgcgacaac aaccccctgcc cccagacctc ctaccccagc ccctacaatt | 3600 |

TABLE 8-continued

Nucleotide sequences for preparation of lentivirus for transduction of aAPCs.

| Identifier (Description) | Sequence | |
|---|---|---|
| | gccagccagc ctctgagcct gaggcccgag gcttgtagac ctgctgctgg cggagccgtg | 3660 |
| | cacaccagag gactggattt cgcctgcgac atctacatct gggcccctct ggccggcaca | 3720 |
| | tgtggcgtgc tgctgctgag cctcgtgatc accctgtact gcggctccac cagcggctcc | 3780 |
| | ggcaagcccg gctctggcga gggctccacc agcggcgact acaaggacga cgatgacaag | 3840 |
| | taataggata tcggttcagc tttcttgtac aaagttggga ttcgagttaa ttaagttaac | 3900 |
| | gaattccccc cctctccctc cccccccct aacgttactg gccgaagccg cttggaataa | 3960 |
| | ggccggtgtg cgtttgtcta tatgttattt tccaccatat tgccgtcttt tggcaatgtg | 4020 |
| | agggcccgga aacctggccc tgtcttcttg acgagcattc ctaggggtct ttcccctctc | 4080 |
| | gccaaaggaa tgcaaggtct gttgaatgtc gtgaaggaag cagttcctct ggaagcttct | 4140 |
| | tgaagacaaa caacgtctgt agcgaccctt gcaggcagc ggaacccccc acctggcgac | 4200 |
| | aggtgcctct gcggccaaaa gccacgtgta taagatacac ctgcaaaggc ggcacaaccc | 4260 |
| | cagtgccacg ttgtgagttg gatagttgtg gaaagagtca aatggctctc ctcaagcgta | 4320 |
| | ttcaacaagg ggctgaagga tgcccagaag gtaccccatt gtatgggatc tgatctgggg | 4380 |
| | cctcggtgca catgctttac atgtgtttag tcgaggttaa aaaacgtcta ggccccccga | 4440 |
| | accacgggga cgtggttttc ctttgaaaaa cacgatgata atatggccac aaccatggga | 4500 |
| | ggcggaagcg gcggaggctc ccctcgaggc accatggtga gcaagggcga ggagctgttc | 4560 |
| | accgggggtgg tgcccatcct ggtcgagctg gacggcgacg taaacggcca caagttcagc | 4620 |
| | gtgtccggcg agggcgaggg cgatgccacc tacggcaagc tgaccctgaa gttcatctgc | 4680 |
| | accaccggca agctgcccgt gccctggccc accctcgtga ccaccctgac ctacggcgtg | 4740 |
| | cagtgcttca gccgctaccc cgaccacatg aagcagcacg acttcttcaa gtccgccatg | 4800 |
| | cccgaaggct acgtccagga gcgcaccatc ttcttcaagg acgacggcaa ctacaagacc | 4860 |
| | cgcgccgagg tgaagttcga gggcgacacc ctggtgaacc gcatcgagct gaagggcatc | 4920 |
| | gacttcaagg aggacggcaa catcctgggg cacaagctgg agtacaacta caacagccac | 4980 |
| | aacgtctata tcatggccga caagcagaag aacggcatca aggtgaactt caagatccgc | 5040 |
| | cacaacatcg aggacggcag cgtgcagctc gccgaccact accagcagaa cacccccatc | 5100 |
| | ggcgacggcc ccgtgctgct gcccgacaac cactacctga gcacccagtc cgccctgagc | 5160 |
| | aaagacccca cgagaagcg cgatcacatg gtcctgctgg agttcgtgac cgccgccggg | 5220 |
| | atcactctcg gcatggacga gctgtacaag taacgcgtcc cgggtctaga gctagcggta | 5280 |
| | ccatgcatta cgtagtcgac gacttaatta agctagccta gtgccatttg ttcagtggtt | 5340 |
| | cgtagggctt tcccccactg tttggctttc agttatatgg atgatgtggt attgggggcc | 5400 |
| | aagtctgtac agcatcttga gtccctttt accgctgtta ccaattttct tttgtctttg | 5460 |
| | ggtatacatt taaacccta caaaacaaag agatggggtt actctctaaa ttttatgggt | 5520 |
| | tatgtcattg gatgttatgg gtccttgcca caagaacaca tcatacaaaa aatcaaagaa | 5580 |
| | tgtttttagaa aacttcctat taacaggcct attgattgga aagtatgtca acgaattgtg | 5640 |
| | ggtcttttgg gttttgctgc ccctttttaca caatgtggtt atcctgcgtt gatgcctttg | 5700 |
| | tatgcatgta ttcaatctaa gcaggctttc actttctcgc caacttacaa ggcctttctg | 5760 |
| | tgtaaacaat acctgaacct ttaccccgtt gcccggcaac ggccaggtct gtgccaagtg | 5820 |
| | tttgctgacg caaccccac tggctggggc ttggtcatgg gccatcagcg catgcgtgga | 5880 |
| | accttttcgg ctcctctgcc gatccatact gcggaactcc tagccgcttg ttttgctcgc | 5940 |
| | agcaggtctg gagcaaacat tatcgggact gataactctg ttgtcctatc ccgcaaatat | 6000 |
| | acatcgtttc catggctgct aggctgtgct gccaactgga tcctgcgcgg gacgtccttt | 6060 |
| | gtttacgtcc cgtcggcgct gaatcctgcg gacgacccct ctcggggtcg cttgggactc | 6120 |
| | tctcgtcccc ttctccgtct gccgttccga ccgaccacgg ggcgcacctc tctttacgcg | 6180 |
| | gactccccgt ctgtgccttc tcatctgccg gaccgtgtgc acttcgcttc acctctgcac | 6240 |
| | gtcgcatgga gaccaccgtg aacgcccacc aaatattgcc caaggtctta cataagagga | 6300 |
| | ctcttggact ctcagcaatg tcaacgaccg accttgaggc atacttcaaa gactgtttgt | 6360 |
| | ttaaagactg ggaggagttg ggggaggaga ttaggttaaa ggtctttgta ctaggaggct | 6420 |
| | gtaggcataa attggtctgc gcaccagcac catggcgcaa tcactagagc ggggtacctt | 6480 |
| | taagaccaat gacttacaag gcagctgtag atcttagcca ctttttaaaa gaaaaggggg | 6540 |
| | gactggaagg gctaattcac tcccaacgaa gacaagatct gctttttgct tgtactgggt | 6600 |
| | ctctctggtt agaccagatc tgagcctggg agctctctgg ctaactaggg aacccactgc | 6660 |
| | ttaagcctca ataaagcttg ccttgagtgc ttcaagtagt gtgtgcccgt ctgttgtgtg | 6720 |
| | actctggtaa ctagagatcc ctcagaccct tttagtcagt gtggaaaatc tctagcagta | 6780 |
| | gtagttcatg tcatcttatt attcagtatt tataacttgc aaagaaatga atatcagaga | 6840 |
| | gtgagaggaa cttgtttatt gcagcttata atggttacaa ataaagcaat agcatcacaa | 6900 |
| | atttcacaaa taaagcattt ttttcactgc attctagttg tggtttgtcc aaactcatca | 6960 |
| | atgtatctta tcatgtctgg ctctagctat cccgcccta actccgccca tcccgcccct | 7020 |
| | aactccgccc agttccgccc attctccgcc ccatggctga ctaatttttt ttatttatgc | 7080 |
| | agaggccgag gccggatccc ttgagtggct ttcatcctgg agcagacttt gcagtctgtg | 7140 |
| | gactgcaaca caacattgcc tttatgtgta actcttggct gaagctctta caccaatgct | 7200 |
| | gggggacatg tacctcccag gggcccagga agactacggg aggctacacc aacgtcaatc | 7260 |
| | agaggggcct gtgtagctac cgataagcgg accctcaaga gggcattagc aatagtgttt | 7320 |
| | ataaggcccc cttgttaatt cttgaagacg aaagggcctc gtgatacgcc tatttttata | 7380 |
| | ggttaatgtc atgataataa tggtttctta gacgtcaggt ggcactttc ggggaaatgt | 7440 |
| | gcgcggaacc cctatttgtt tattttttcta aatacattca aatatgtatc cgctcatgag | 7500 |
| | acaataaccc tgataaatgc ttcaataata ttgaaaaagg aagagtatga gtattcaaca | 7560 |
| | tttccgtgtc gcccttattc cctttttgc ggcattttgc cttcctgttt ttgctcaccc | 7620 |
| | agaaacgctg gtgaaagtaa aagatgctga agatcagttg ggtgcacgag tgggttacat | 7680 |
| | cgaactggat ctcaacagcg gtaagatcct tgagagtttt cgccccgaag aacgttttcc | 7740 |
| | aatgatgagc acttttaaag ttctgctatg tggcgcggta ttatcccgt ttgacgccgg | 7800 |
| | gcaagagcaa ctcggtcgcc gcatacacta ttctcagaat gacttggttg agtactcacc | 7860 |
| | agtcacagaa aagcatctta cggatggcat gacagtaaga gaattatgca gtgctgccat | 7920 |
| | aaccatgagt gataacactg cggccaactt acttctgaca acgatcggag gaccgaagga | 7980 |
| | gctaaccgct tttttgcaca acatggggga tcatgtaact cgccttgatc gttgggaacc | 8040 |
| | ggagctgaat gaagccatac caaacgacga gcgtgacacc acgatgcctg cagcaatggc | 8100 |

TABLE 8-continued

Nucleotide sequences for preparation of lentivirus for transduction of aAPCs.

| Identifier (Description) | Sequence | |
|---|---|---|
| | aacaacgttg cgcaaactat taactggcga actacttact ctagcttccc ggcaacaatt | 8160 |
| | aatagactgg atggaggcgg ataaagttgc aggaccactt ctgcgctcgg cccttccggc | 8220 |
| | tggctggttt attgctgata aatctggagc cggtgagcgt gggtctcgcg gtatcattgc | 8280 |
| | agcactgggg ccagatggta agccctcccg tatcgtagtt atctacacga cggggagtca | 8340 |
| | ggcaactatg gatgaacgaa atagacagat cgctgagata ggtgcctcac tgattaagca | 8400 |
| | ttggtaactg tcagaccaag tttactcata tatactttag attgatttaa aacttcattt | 8460 |
| | ttaatttaaa aggatctagg tgaagatcct ttttgataat ctcatgacca aaatccctta | 8520 |
| | acgtgagttt tcgttccact gagcgtcaga ccccgtagaa aagatcaaag gatcttcttg | 8580 |
| | agatcctttt tttctgcgcg taatctgctg cttgcaaaca aaaaaaccac cgctaccagc | 8640 |
| | ggtggtttgt ttgccggatc aagagctacc aactcttttt ccgaaggtaa ctggcttcag | 8700 |
| | cagagcgcag ataccaaata ctgtccttct agtgtagccg tagttaggcc accacttcaa | 8760 |
| | gaactctgta gcaccgccta catacctcgc tctgctaatc ctgttaccag tggctgctgc | 8820 |
| | cagtggcgat aagtcgtgtc ttaccgggtt ggactcaaga cgatagttac cggataaggc | 8880 |
| | gcagcggtcg ggctgaacgg ggggttcgtg cacacagccc agcttggagc gaacgaccta | 8940 |
| | caccgaactg agatacctac agcgtgagca ttgagaaagc gccacgcttc ccgaagggag | 9000 |
| | aaaggcggac aggtatccgg taagcggcag ggtcggaaca ggagagcgca cgagggagct | 9060 |
| | tccaggggga aacgcctggt atctttatag tcctgtcggg tttcgccacc tctgacttga | 9120 |
| | gcgtcgattt ttgtgatgct cgtcaggggg gcggagccta tggaaaaacg ccagcaacgc | 9180 |
| | ggcctttttta cggttcctgg ccttttgctg gccttttttga agctgtccct gatggtcgtc | 9240 |
| | atctacctgc ctggacagca tggcctgcaa cgcgggcatc ccgatgccgc cggaagcgag | 9300 |
| | aagaatcata tgggggaagg ccatccagcc tcgcgtcg | 9338 |
| SEQ ID NO: 35 (destination vector, pLV4301G) | cgataaccct aattcgatag catatgcttc ccgttgggta acatatgcta ttgaattagg | 60 |
| | gttagtctgg atagtatata ctactacccg ggaagcatat gctacccgtt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |
| | tgtagtcttg caacatggta acgatgagtt agcaacatgc cttacaagga gagaaaaagc | 420 |
| | accgtgcatg ccgattggtg gaagtaaggt ggtacgatcg tgccttatta ggaaggcaac | 480 |
| | agacgggtct gacatggatt ggacgaacca ctgaattgcc gcattgcaga gatattgtat | 540 |
| | ttaagtgcct agctcgatac ataaacgggt ctctctggtt agaccagatc tgagcctggg | 600 |
| | agctctctgg ctaactaggg aacccactgc ttaagcctca ataaagcttg ccttgagtgc | 660 |
| | ttcaagtagt gtgtgcccgt ctgttgtgtg actctggtaa ctagagatcc ctcagaccct | 720 |
| | tttagtcagt gtggaaaatc tctagcagtg gcgcccgaac agggacttga aagcgaaagg | 780 |
| | gaaaccagag gagctctctc gacgcaggac tcggcttgct gaagcgcgca cggcaagagg | 840 |
| | cgaggggcgg cgactggtga gtacgccaaa aattttgact agcggaggct agaaggagag | 900 |
| | agatgggtgc gagagcgtca gtattaagcg ggggagaatt agatcgcgat gggaaaaaat | 960 |
| | tcggttaagg ccagggggaa agaaaaaata taaattaaaa catatagtat gggcaagcag | 1020 |
| | ggagctagaa cgattcgcag ttaatcctgg cctgttagaa acatcagaag gctgtagaca | 1080 |
| | aatactggga cagctacaac catcccttca gacaggatca gaagaactta gatcattata | 1140 |
| | taatacagta gcaaccctct attgtgtgca tcaaaggata gagataaaag acaccaagga | 1200 |
| | agctttagac aagatagagg aagagcaaaa caaaagtaag accaccgcac agcaagcggc | 1260 |
| | cgctgatctt cagacctgga ggaggagata tgagggacaa ttggagaagt gaattatata | 1320 |
| | aatataaagt agtaaaaatt gaaccattag gagtagcacc caccaaggca aagagaagag | 1380 |
| | tggtgcagag agaaaaaaga gcagtgggaa taggagcttt gttccttggg ttcttgggag | 1440 |
| | cagcaggaag cactatgggc gcagcgtcaa tgacgctgac ggtacaggcc agacaattat | 1500 |
| | tgtctggtat agtgcagcag cagaacaatt tgctgagggc tattgaggcg caacagcatc | 1560 |
| | tgttgcaact cacagtctgg ggcatcaagc agctccagac aagaatcctg gctgtggaaa | 1620 |
| | gatacctaaa ggatcaacag ctcctgggga tttggggttg ctctggaaaa ctcatttgca | 1680 |
| | ccactgctgt gccttggaat gctagttgga gtaataaatc tctggaacag atttggaatc | 1740 |
| | acacgacctg gatggagtgg gacagagaaa ttaacaatta cacaagctta atacactcct | 1800 |
| | taattgaaga atcgcaaaac cagcaagaaa agaatgaaca agaattattg gaattagata | 1860 |
| | aatgggcaag tttgtggaat tggtttaaca taacaaattg gctgtggtat ataaaattat | 1920 |
| | tcataatgat agtaggaggc ttggtaggtt taagaatagt ttttgctgta cttttctatag | 1980 |
| | tgaatagagt taggcaggga tattcaccat tatcgtttca gacccacctc ccaaccccga | 2040 |
| | ggggacccga caggcccgaa ggaatagaag aagaaggtgg agagagagac agagacagat | 2100 |
| | ccattcgatt agtgaacgga tctcgacggt atcggttcta aagaaaaagg gggattggg | 2160 |
| | gggtacagtg caggggaaag aatagtagac ataatagcaa cagacatca aactaaagaa | 2220 |
| | ttacaaaaac aaattacaaa aattcaaaat tttatcgatt ttatttagtc tccagaaaaa | 2280 |
| | gggggaatg aaagacccca cctgtaggtt tggcaagcta gcttaagtaa cgccatttttg | 2340 |
| | caaggcatgg aaaatacata actgagaata aggaagttaa gatcaaggtt aggaacagag | 2400 |
| | agacagcaga atatgggcca aacaggatat ctgtggtaag cagttcctgc cccggctcag | 2460 |
| | ggccaagaac agatggtccc cagatgcggt cccgccctca gcagtttcta gagaaccatc | 2520 |
| | agatgtttcc agggtgcccc aaggacctga atgaccctg tgccttattt gaactaacca | 2580 |
| | atcagttcgc ttctcgcttc tgttccgcgc cttctgctcc ccgagctcaa taaaagagcc | 2640 |
| | cacaacccct cactcggcgc gccagtcctc cgatagactg cgtcgcccgg gtaccgatat | 2700 |
| | cacaagtttg tacaaaaaag ctgaacgaga acgtaaaat gatataaata tcaatatatt | 2760 |
| | aaattagatt ttgcataaaa aacagactac ataatactgt aaaacacaac atatccagtc | 2820 |
| | actatggcgg ccgcattagg caccccaggc tttacacttt atgcttccgg ctcgtataat | 2880 |
| | gtgtggattt tgagttagga tccgtcgaga ttttcaggag ctaaggaagc taaaatggag | 2940 |
| | aaaaaaatca ctggatatac caccgttgat atatcccaat ggcatcgtaa agaacatttt | 3000 |
| | gaggcatttt agtcagttgc tcaatgtacc tataaccaga ccgttcagct ggatattacg | 3060 |
| | gcctttttaa agaccgtaaa gaaaaataag cacaagtttt atccggcctt tattcacatt | 3120 |
| | cttgcccgcc tgatgaatgc tcatccggaa ttccgtatgg caatgaaaga cggtgagctg | 3180 |

TABLE 8-continued

Nucleotide sequences for preparation of lentivirus for transduction of aAPCs.

| Identifier (Description) | Sequence | |
|---|---|---|
| | gtgatatggg atagtgttca cccttgttac accgttttcc atgagcaaac tgaaacgttt | 3240 |
| | tcatcgctct ggagtgaata ccacgacgat ttccggcagt ttctacacat atattcgcaa | 3300 |
| | gatgtggcgt gttacggtga aaacctggcc tatttcccta aagggtttat tgagaatatg | 3360 |
| | tttttcgtct cagccaatcc ctgggtgagt ttcaccagtt ttgatttaaa cgtggccaat | 3420 |
| | atggacaact tcttcgcccc cgttttcacc atgggcaaat attatacgca aggcgacaag | 3480 |
| | gtgctgatgc cgctggcgat tcaggttcat catgccgttt gtgatggctt ccatgtcggc | 3540 |
| | agaatgctta atgaattaca acagtactgc gatgagtggc agggcggggc gtaaatggat | 3600 |
| | ccggcttact aaaagccaga taacagtatg cgtatttgcg cgctgatttt tgcggtataa | 3660 |
| | gaatatatac tgatatgtat acccgaagta tgtcaaaaag aggtatgcta tgaagcagcg | 3720 |
| | tattacagtg acagttgaca gcgacagcta tcagttgctc aaggcatata tgatgtcaat | 3780 |
| | atctccggtc tggtaagcac aaccatgcag aatgaagccc gtcgtctgcg tgccgaacgc | 3840 |
| | tggaaagcgg aaaatcagga agggatggct gaggtcgccc ggtttattga aatgaacggc | 3900 |
| | tcttttgctg acgagaacag gggctggtga aatgcagttt aaggtttaca cctataaaag | 3960 |
| | agagagccgt tatcgtctgt ttgtggatgt acagagtgat attattgaca cgcccgggcg | 4020 |
| | acggatggtg atccccctgg ccagtgcacg tctgctgtca gataaagtct cccgtgaact | 4080 |
| | ttacccggtg gtgcatatcg gggatgaaag ggctcgcata atgaccaccg atatgcccag | 4140 |
| | tgtgccggtc tccgttatcg gggaagaagt ggctgatctc agccaccgcg aaaatgacat | 4200 |
| | caaaaacgcc attaacctga tgttctgggg aatataaatg tcaggctccc ttatacacag | 4260 |
| | ccagtctgca ggtcgaccat agtgactgga tatgttgtgt tttacagtat tatgtagtct | 4320 |
| | gttttttatg caaaatctaa tttaatatat tgatatttat atcattttac gtttctcgtt | 4380 |
| | cagctttctt gtacaaagtg gtgattcgag ttaattaagt taacgaattc ccccctctc | 4440 |
| | cctcccccc ccctaacgtt actggccgaa gccgcttgga ataaggccgg tgtgcgtttg | 4500 |
| | tctatatgtt attttccacc atattgccgt cttttggcaa tgtgagggcc cggaaacctg | 4560 |
| | gccctgtctt cttgacgagc attcctaggg gtctttcccc tctcgccaaa ggaatgcaag | 4620 |
| | gtctgttgaa tgtcgtgaag gaagcagttc ctctggaagc ttcttgaaga caaacaacgt | 4680 |
| | ctgtagcgac cctttgcagg cagcggaacc ccccacctgg cgacaggtgc ctctgcggcc | 4740 |
| | aaaagccacg tgtataagat acacctgcaa aggcggcaca accccagtgc cacgttgtga | 4800 |
| | gttggatagt tgtggaaaga gtcaaatggc tctcctcaag cgtattcaac aaggggctga | 4860 |
| | aggatgccca gaaggtaccc cattgtatgg gatctgatct ggggcctcgg tgcacatgct | 4920 |
| | ttacatgtgt ttagtcgagg ttaaaaaacg tctaggcccc ccgaaccacg gggacgtggt | 4980 |
| | tttcctttga aaaacacgat gataatatgg ccacaaccat gggaggcgga agcggcggag | 5040 |
| | gctcccctcg aggcaccatg gtgagcaagg gcgaggagct gttcaccggg gtggtgccca | 5100 |
| | tcctggtcga gctggacggc gacgtaaacg gccacaagtt cagcgtgtcc ggcgagggcg | 5160 |
| | agggcgatgc cacctacggc aagctgaccc tgaagttcat ctgcaccacc ggcaagctgc | 5220 |
| | ccgtgccctg gcccaccctc gtgaccaccc tgacctacgg cgtgcagtgc ttcagccgct | 5280 |
| | accccgacca catgaagcag cacgacttct tcaagtccgc catgcccgaa ggctacgtcc | 5340 |
| | aggagcgcac catcttcttc aaggacgacg gcaactacaa gacccgcgcc gaggtgaagt | 5400 |
| | tcgagggcga caccctggtg aaccgcatcg agctgaaggg catcgacttc aaggaggacg | 5460 |
| | gcaacatcct ggggcacaag ctggagtaca actacaacag ccacaacgtc tatatcatgg | 5520 |
| | ccgacaagca gaagaacggc atcaaggtga acttcaagat ccgccacaac atcgaggacg | 5580 |
| | gcagcgtgca gctcgccgac cactaccagc agaacacccc catcggcgac ggccccgtgc | 5640 |
| | tgctgcccga caaccactac ctgagcaccc agtccgccct gagcaaagac cccaacgaga | 5700 |
| | agcgcgatca catggtcctg ctggagttcg tgaccgccgc cgggatcact ctcggcatgg | 5760 |
| | acgagctgta caagtaacgc gtcccgggtc tagagctagc ggtaccatgc attacgtagt | 5820 |
| | cgacgactta attaagctag cctagtgcca tttgttcagt ggttcgtagg gctttcccc | 5880 |
| | actgtttggc tttcagttat atggatgatg tggtattggg ggccaagtct gtacagcatc | 5940 |
| | ttgagtccct tttaccgct gttaccaatt ttcttttgtc tttgggtata catttaaacc | 6000 |
| | ctaacaaaac aaagagatgg ggttactctc taaattttat gggttatgtc attggatgtt | 6060 |
| | atgggtcctt gccacaagaa cacatcatac aaaaaatcaa agaatgtttt agaaaactca | 6120 |
| | ctattaacag gcctattgat tggaaagtat gtcaacgaat tgtgggtctt ttgggttttg | 6180 |
| | ctgccccttt tacacaatgt ggttatcctg cgttgatgcc tttgtatgca tgtattcaat | 6240 |
| | ctaagcaggc tttcactttc tcgccaactt acaaggcctt tctgtgtaaa caatacctga | 6300 |
| | acctttaccc cgttgcccgg caacggccag gtctgtgcca agtgtttgct gacgcaaccc | 6360 |
| | ccactggctg gggcttggtc atgggccatc agcgcatgcg tggaaccttt tcggctcctc | 6420 |
| | tgccgatcca tactgcggaa ctcctagccg cttgttttgc tcgcagcagg tctggagcaa | 6480 |
| | acattatcgg gactgataac tctgttgtcc tatcccgcaa atatacatcg tttccatggc | 6540 |
| | tgctaggctg tgctgccaac tggatcctgc gcgggacgtc ctttgtttac gtcccgtcgg | 6600 |
| | cgctgaatcc tgcggacgac ccttctcggg gtcgcttggg actctctcgt cccttctcgt | 6660 |
| | gtctgccgtt ccgaccgacc acggggcgca cctctcttta cgcggactcc ccgtctgtgc | 6720 |
| | cttctcatct gccggaccgt gtgcacttcg cttcacctct gcacgtcgca tggagaccac | 6780 |
| | cgtgaacgcc caccaaatat tgcccaaggt cttacataag gagactcttg gactctcagc | 6840 |
| | aatgtcaacg accgacctg aggcatactt caaagactgt ttgtttaaag actgggagga | 6900 |
| | gttggggggag gagattaggt taaaggtctt tgtactagga ggctgtaggc ataaattggt | 6960 |
| | ctgcgcacca gcaccatggc gcaatcacta gagcggggta ccttttaagac caatgactta | 7020 |
| | caaggcagct gtagatctta gccactttt aaaagaaaag ggggactgg aagggctaat | 7080 |
| | tcactcccaa cgaagacaag atctgctttt tgcttgtact gggtctctct ggttagacca | 7140 |
| | gatctgagcc tgggagctct ctggctaact agggaaccca ctgcttaagc ctcaataaag | 7200 |
| | cttgccttga gtgcttcaag tagtgtgtgc ccgtctgttg tgtgactctg gtaactagag | 7260 |
| | atccctcaga cccttttagt cagtgtggaa aatctctagc agtagtagtt catgtcatct | 7320 |
| | tattattcag tatttataac ttgcaaagaa atgaatatca gagagtgaga ggaacttgtt | 7380 |
| | tattgcagct tataatggtt acaaataaag caatagcatc acaaatttca caaataaagc | 7440 |
| | atttttttca ctgcattcta gttgtggttt gtccaaactc atcaatgtat cttatcatgt | 7500 |
| | ctggctctag ctatcccgcc cctaactccg cccatcccgc ccctaactcc gcccagttcc | 7560 |
| | gcccattctc cgccccatgc ctgactaatt tttttattt atgcagaggc cgaggccgga | 7620 |
| | tcccttgagt ggctttcatc ctggagcaga ctttgcagtc tgtggactgc aacacaacat | 7680 |

TABLE 8-continued

Nucleotide sequences for preparation of lentivirus for transduction of aAPCs.

| Identifier (Description) | Sequence | |
|---|---|---|
| | tgcctttatg tgtaactctt ggctgaagct cttacaccaa tgctggggga catgtacctc | 7740 |
| | ccaggggccc aggaagacta cgggaggcta caccaacgtc aatcagaggg gcctgtgtag | 7800 |
| | ctaccgataa gcggaccctc aagagggcat tagcaatagt gtttataagg cccccttgtt | 7860 |
| | aattcttgaa gacgaaaggg cctcgtgata cgcctatttt tataggttaa tgtcatgata | 7920 |
| | ataatggttt cttagacgtc aggtggcact tttcggggaa atgtgcgcgg aacccctatt | 7980 |
| | tgtttatttt tctaaataca ttcaaatatg tatccgctca tgagacaata accctgataa | 8040 |
| | atgcttcaat aatattgaaa aaggaagagt atgagtattc aacatttccg tgtcgccctt | 8100 |
| | attccctttt ttgcggcatt ttgccttcct gtttttgctc acccagaaac gctggtgaaa | 8160 |
| | gtaaaagatg ctgaagatca gttgggtgca cgagtgggtt acatcgaact ggatctcaac | 8220 |
| | agcggtaaga tccttgagag ttttcgcccc gaagaacgtt ttccaatgat gagcacttt | 8280 |
| | aaagttctgc tatgtggcgc ggtattatcc cgtgttgacg ccgggcaaga gcaactcggt | 8340 |
| | cgccgcatac actattctca gaatgacttg gttgagtact caccagtcac agaaaagcat | 8400 |
| | cttacggatg gcatgacagt aagagaatta tgcagtgctg ccataaccat gagtgataac | 8460 |
| | actgcggcca acttacttct gacaacgatc ggaggaccga aggagctaac cgcttttttg | 8520 |
| | cacaacatgg gggatcatgt aactcgcctt gatcgttggg aaccggagct gaatgaagcc | 8580 |
| | ataccaaacg acgagcgtga ccacgatg cctgcagcaa tggcaacaac gttgcgcaaa | 8640 |
| | ctattaactg gcgaactact tactctagct tcccggcaac aattaataga ctggatggag | 8700 |
| | gcggataaag ttgcaggacc acttctgcgc tcggcccttc cggctggctg gtttattgct | 8760 |
| | gataaatctg gagccggtga gcgtgggtct cgcggtatca ttgcagcact ggggccagat | 8820 |
| | ggtaagccct cccgtatcgt agttatctac gacgcgggga gtcaggcaac tatggatgaa | 8880 |
| | cgaaatagac agatcgctga gataggtgcc tcactgatta gcattggta actgtcagac | 8940 |
| | caagtttact catatatact ttagattgat ttaaaacttc attttttaatt taaaaggatc | 9000 |
| | taggtgaaga tcctttttga taatctcatg accaaaatcc cttaacgtga gttttcgttc | 9060 |
| | cactgagcgt cagaccccgt agaaaagatc aaaggatctt cttgagatcc ttttttttctg | 9120 |
| | cgcgtaatct gctgcttgca aacaaaaaa ccaccgctac cagcggtggt ttgtttgccg | 9180 |
| | gatcaagagc taccaactct ttttccgaag gtaactggct tcagcagagc gcagatacca | 9240 |
| | aatactgtcc ttctagtgta gccgtagtta ggccaccact tcaagaactc tgtagcaccg | 9300 |
| | cctacatacc tcgctctgct aatcctgtta ccagtggctg ctgccagtgg cgataagtcg | 9360 |
| | tgtcttaccg ggttggactc aagacgatag ttaccggata aggcgcagcg gtcgggctga | 9420 |
| | acggggggtt cgtgcacaca gcccagcttg gagcgaacga cctacaccga actgagatac | 9480 |
| | ctacagcgtg agcattgaga aagcgccacg cttcccgaag ggagaaaggc ggacaggtat | 9540 |
| | ccggtaagcg gcagggtcgg aacaggagag cgcacgaggg agcttccagg gggaaacgcc | 9600 |
| | tggtatcttt atagtcctgt cgggtttcgc cacctctgac ttgagcgtcg atttttgtga | 9660 |
| | tgctcgtcag ggggggcggag cctatggaaa aacgccagca acgcggcctt tttacggttc | 9720 |
| | ctggcctttt gctggccttt tgaagctgt ccctgatggt cgtcatctac ctgcctgac | 9780 |
| | agcatggcct gcaacgcggg catcccgatg ccgccggaag cgagaagaat cataatgggg | 9840 |
| | aaggccatcc agcctcgcgt cg | 9862 |
| SEQ ID NO: 36 (donor vector 1, pMK 8B3 anti mFC scFV CoOp ECORV SacII L1R5) | ctaaattgta agcgttaata ttttgttaaa attcgcgtta aatttttgtt aaatcagctc | 60 |
| | attttttaac caataggccg aaatcggcaa aatcccttat aaatcaaaag aatagaccga | 120 |
| | gatagggttg agtggccgca acagggget cccattcgcc attcaggctg cgcaactgtt | 180 |
| | gggaagggcg tttcggtgcg ggcctcttcg ctattacgcc agctggcgaa agggggatgt | 240 |
| | gctgcaagge gattaagttg ggtaacgcca gggttttccc agtcacgacg ttgtaaaacg | 300 |
| | acggccagtg agcgcgaagt aatacgactc actatagggc gaattgaagg aaggccgtca | 360 |
| | aggccgcata aataatgatt ttattttgac tgataatgac ctgttcgttg caacaaattg | 420 |
| | atgagcaatg ctttttttata atgccaaett tgtacaaaaa agctgaacga tatcgccacc | 480 |
| | atgggcagca cagccattct ggccctgctg ctggcagtgc tgcagggcgt gtcagctcag | 540 |
| | gtgcagctgc agcagtctgg cgccgaagtg aagaaacccg gcagcagt gaaggtgtcc | 600 |
| | tgcaaggcta gcggcggcac cttcagcagc tacgccattt cttgggtgcg ccaggcccct | 660 |
| | ggacaggggc tggaatggat gggctggatc agccctaca acggcaacac cgactacgcc | 720 |
| | cagaaagtgc agggcagagt gaccctgacc accgacacca gcacctccac cgcctacatg | 780 |
| | gaactgcgga gctgagaag cgacgacacc gccgtgtact actgtgccac aggcggggga | 840 |
| | acctggtaca gcgatctgtg gggccagaggc accctcgtga cagtgtctgc tggcggcgga | 900 |
| | ggatctggcg gaggcggaag tggcgggga ggaagcgagac cacctgagat cgtgctgacc | 960 |
| | cagagcccta gcacactgag cgccagcgtg ggcgacagag tgtccatcac ctgtagagcc | 1020 |
| | agcagagca tcggaggcag cctggcctgg tatcagcaga agcctggcaa ggccccaag | 1080 |
| | ctgctgatct ctgaggccac caccctggaa agaggcgtgc ccagcagatt ttccggcagc | 1140 |
| | ggctctggca ccgacttcac cctgacaatc agcagcctgc agccggagga cgtggccacc | 1200 |
| | tactactgcc agaagtacaa cagcgtgccc ctgaccttcg gccctggcac caaggtggaa | 1260 |
| | atcaagccgc gggccaactt tgtatacaaa agtggaacga gaaacgtaaa atgatataaa | 1320 |
| | tatcaatata ttaaattaga ttttgcataa aaaacagact acataatact gtaaaacaca | 1380 |
| | acatatccag tcactatgaa tcaactactt agatggtatt agtgacctgt actgggcctc | 1440 |
| | atgggccttc ctttcactgc ccgctttcca gtcgggaaac ctgtcgtgcc agctgcatta | 1500 |
| | acatggtcat agctgtttcc ttgcgtattg ggcgctctcc gcttcctcgc tcactgactc | 1560 |
| | gctgcgctcg gtcgttcggg taaagcctgg ggtgcctaat gagcaaaagg ccagcaaaag | 1620 |
| | gccaggaacc gtaaaaaggc cgcgttgctg gcgtttttcc ataggctccg cccccctgac | 1680 |
| | gagcatcaca aaaatcgacg ctcaagtcag aggtggcgaa acccgacagg actataaaga | 1740 |
| | taccaggcgt ttccccctgg aagctccctc gtgcgctctc ctgttccgac cctgccgctt | 1800 |
| | accggatacc tgtccgcctt tctcccttcg ggaagcgtgg cgctttctca tagctcacgc | 1860 |
| | tgtaggtatc tcagttcggt gtaggtcgtt cgctccaagc tgggctgtgt gcacgaaccc | 1920 |
| | cccgttcagc ccgaccgctg cgccttatcc ggtaactatc gtcttgagtc caacccggta | 1980 |
| | agacacgact tatcgccact ggcagcagcc actggtaaca ggattagcag agcgaggtat | 2040 |
| | gtaggcggtg ctacagagtt cttgaagtgg tggcctaact acggctacac tagaagaaca | 2100 |
| | gtatttggta tctgcgctct gctgaagcca gttaccttcg gaaaaagagt tggtagctct | 2160 |
| | tgatccggca aacaaaccac cgctggtagc ggtggttttt ttgtttgcaa gcagcagatt | 2220 |

TABLE 8-continued

Nucleotide sequences for preparation of lentivirus for transduction of aAPCs.

| Identifier (Description) | Sequence | |
|---|---|---|
| | acgcgcagaa aaaaaggatc tcaagaagat cctttgatct tttctacggg gtctgacgct | 2280 |
| | cagtggaacg aaaactcacg ttaagggatt ttggtcatga gattatcaaa aaggatcttc | 2340 |
| | acctagatcc ttttaaatta aaaatgaagt tttaaatcaa tctaaagtat atatgagtaa | 2400 |
| | acttggtctg acagttatta gaaaaattca tccagcagac gataaaacgc aatacgctgg | 2460 |
| | ctatccggtg ccgcaatgcc atacagcacc agaaaacgat ccgcccattc gccgcccagt | 2520 |
| | tcttccgcaa tatcacgggt ggccagcgca atatcctgat aacgatccgc cacgcccaga | 2580 |
| | cggccgcaat caataaagcc gctaaaacgg ccattttcca ccataatgtt cggcaggcac | 2640 |
| | gcatcaccat gggtcaccac cagatcttcg ccatccggca tgctcgcttt cagacgcgca | 2700 |
| | aacagctctg ccggtgccag gccctgatgt tcttcatcca gatcatcctg atccaccagg | 2760 |
| | cccgcttcca tacgggtacg cgcacgttca atacgatgtt tcgcctgatg atcaaacgga | 2820 |
| | caggtcgccg ggtccagggt atgcagacga cgcatggcat ccgccctaat gctcacttt | 2880 |
| | tctgccggcg ccagatggct agacagcaga tcctgacccg gcacttcgcc cagcagcagc | 2940 |
| | caatcacggc ccgcttcggt caccacatcc agcaccgccg cacacggaac accggtggtg | 3000 |
| | gccagccagc tcagacgcgc cgcttcatcc tgcagctcgt tcagcgcacc gctcagatcg | 3060 |
| | gtttttcacaa acagcaccgg acgaccctgc gcgctcagac gaaacaccgc cgcatcagag | 3120 |
| | cagccaatgg tctgctgcgc ccaatcatag ccaaacagac gttccaccca cgctgccggg | 3180 |
| | ctacccgcat gcaggccatc ctgttcaatc atactcttcc tttttcaata ttattgaagc | 3240 |
| | atttatcagg gttattgtct catgagcgga tacatatttg aatgtattta gaaaaataaa | 3300 |
| | caaatagggg ttccgcgcac atttccccga aaagtgccac | 3340 |
| | | |
| SEQ ID NO: 37 (donor vector 2, pMK hCD8a scaffold TN L5 L2 ) | ctaaattgta agcgttaata ttttgttaaa attcgcgtta aatttttgtt aaatcagctc | 60 |
| | attttttaac caataggccg aaatcggcaa aatccccttat aaatcaaaag aatagaccga | 120 |
| | gatagggttg agtggccgct acagggcgct cccattcgcc attcaggctg cgcaactgtt | 180 |
| | gggaagggcg tttcggtgcg ggcctcttcg ctattacgcc agctggcgaa aggggggatgt | 240 |
| | gctgcaaggc gattaagttg ggtaacgcca gggtttttccc agtcacgacg ttgtaaaacg | 300 |
| | acggccagtg agcgcgacgt aatacgactc actatagggc gaattgaagg aaggccgtca | 360 |
| | aggccgcata aataatgatt ttattttgac tgatagtgac ctgttcgttg caacaaattg | 420 |
| | atgagcaatg cttttttata atgcccaact ttgtatacaa aagtggcccg cggacaacaa | 480 |
| | cccctgcccc cagacctcct accccagccc ctacaattgc cagccagcct ctgagcctga | 540 |
| | ggcccgaggc ttgtagacct gctgctggcg gagccgtgca caccagagga ctggatttcg | 600 |
| | cctgcgacat ctacatctgg gcccctctgg ccggcacatg tggcgtgctg ctgctgagcc | 660 |
| | tcgtgatcac cctgactgc ggctccacca gcggctccgg caagcccggc tctggcgagg | 720 |
| | gctccaccag cggcgactac aaggacgacg atgacaagta ataggatatc ggttcagctt | 780 |
| | tcttgtacaa agttggcatt ataagaaagc attgcttatc aatttgttgc aacgaacagg | 840 |
| | tcactatcag tcaaaataaa atcattattt ctgggcctca tgggccttcc tttcactgcc | 900 |
| | cgctttccag tcgggaaacc tgtcgtgcca gctgcattaa catggtcata gctgtttcct | 960 |
| | tgcgtattgg gcgctctccg cttcctcgct cactgactcg ctgcgctcgg tcgttcgggt | 1020 |
| | aaagcctggg gtgcctaatg agcaaaaggc cagcaaaagg ccaggaaccg taaaaaggcc | 1080 |
| | gcgttgctgg cgttttttcca taggctccgc cccctgacg agcatcacaa aaatcgacgc | 1140 |
| | tcaagtcaga ggtggcgaaa cccgacagga ctataaagat accaggcgtt tccccctgga | 1200 |
| | agctccctcg tgcgctctcc tgttccgacc ctgccgctta ccggatacct gtccgccttt | 1260 |
| | ctcccttcgg gaagcgtggc gctttctcat agctcacgct gtaggtatct cagttcggtg | 1320 |
| | taggtcgttc gctccaagct gggctgtgtg cacgaacccc ccgttcagcc cgaccgctgc | 1380 |
| | gccttatccg gtaactatcg tcttgagtcc aacccggtaa gacacgactt atcgccactg | 1440 |
| | gcagcagcca ctggtaacag gattagcaga gcgaggtatg taggcggtgc tacagagttc | 1500 |
| | ttgaagtggt ggcctaacta cggctacact agaagaacag tatttggtat ctgcgctctg | 1560 |
| | ctgaagccag ttaccttcgg aaaaagagtt ggtagctctt gatccggcaa acaaaccacc | 1620 |
| | gctggtagcg gtggtttttt tgtttgcaag cagcagatta cgcgcagaaa aaaaggatct | 1680 |
| | caagaagatc ctttgatctt ttctacgggg tctgacgctc agtggaacga aaactcacg | 1740 |
| | taagggattt tggtcatgag attatcaaaa aggatcttca cctagatcct tttaaattaa | 1800 |
| | aaatgaagtt ttaaatcaat ctaaagtata tatgagtaaa cttggtctga cagttattag | 1860 |
| | aaaaattcat ccagcagacg ataaaacgca atacgctggc tatccggtgc cgcaatgcca | 1920 |
| | tacagcacca gaaaacgatc cgcccattcg ccgcccagtt cttccgcaat atcacgggtg | 1980 |
| | gccagcgcaa tatcctgata acgatccgcc acgcccagtt ggccagcgcaa tatcctgata | 2040 |
| | ctaaaacggc cattttccac cataatgttc ggcaggcacg catcaccatg ggtcaccacc | 2100 |
| | agatcttcgc catccggcat gctcgctttc agacgcgcaa acagctctgc cggtgccagg | 2160 |
| | ccctgatgtt cttcatccag atcatcctga tccaccagcc ccgcttccat acgggtacgc | 2220 |
| | gcacgttcaa tacgatgttt cgcctgatga tcaaacggac aggtcgccgg gtccagggta | 2280 |
| | tgcagacgac gcatggcatc cgccataatg ctcactttt ctgccggcgc cagatggcta | 2340 |
| | gacagcagat cctgacccgg cacttcgccc agcagcagcc aatcacggcc cgcttcggtc | 2400 |
| | accacatcca gcaccgccgc acacggaaca ccggtggtgg ccagccagct cagacgcgcc | 2460 |
| | gcttcatcct gcagctcgtt cagcgcaccg ctcagatcgg ttttcacaaa cagcaccgga | 2520 |
| | cgaccctgcg cgctcagacg aaacaccgcc gcatcagagc agccaatggt ctgctgcgcc | 2580 |
| | caatcatagc caaacagacg ttccaccca gctgccgggc tacccgcatg caggccatcc | 2640 |
| | tgttcaatca tactcttcct ttttcaatat tattgaagca tttatcaggg ttattgtctc | 2700 |
| | atgagcggat acatatttga atgtatttag aaaaataaac aaataggggt tccgcgcaca | 2760 |
| | tttccccgaa aagtgccac | 2779 |
| | | |
| SEQ ID NO: 38 (Final vector used for lentiviral production, pLV4301G 8B3 | cgataaccct aattcgatag catatgcttc ccgttgggta acatatgcta ttgaattagg | 60 |
| | gttagtctgg atagtatata ctactacccg ggaagcatat gctaccgttt tagggttcac | 120 |
| | cggtgatgcc ggccacgatg cgtccggcgt agaggatcta atgtgagtta gctcactcat | 180 |
| | taggcacccc aggctttaca ctttatgctt ccggctcgta tgttgtgtgg aattgtgagc | 240 |
| | ggataacaat ttcacacagg aaacagctat gaccatgatt acgccaagcg cgcaattaac | 300 |
| | cctcactaaa gggaacaaaa gctggagctg caagcttaat gtagtcttat gcaatactct | 360 |

TABLE 8-continued

Nucleotide sequences for preparation of lentivirus for transduction of aAPCs.

| Identifier (Description) | Sequence |
|---|---|
| scFV mIgG hCD8 flag) | tgtagtcttg caacatggta acgatgagtt agcaacatgc cttacaagga gagaaaaagc  420 |
| | accgtgcatg ccgattggtg gaagtaaggt ggtacgatcg tgccttatta ggaaggcaac  480 |
| | agacgggtct gacatggatt ggacgaacca ctgaattgcc gcattgcaga gatattgtat  540 |
| | ttaagtgcct agctcgatac ataaacgggt ctctctggtt agaccagatc tgagcctggg  600 |
| | agctctctgg ctaactaggg aacccactgc ttaagcctca ataaagcttg ccttgagtgc  660 |
| | ttcaagtagt gtgtgcccgt ctgttgtgtg actctggtaa ctagagatcc ctcagaccct  720 |
| | tttagtcagt gtggaaaatc tctagcagtg gcgcccgaac agggacttga aagcgaaagg  780 |
| | gaaaccagag gagctctctc gacgcaggac tcggcttgct gaagcgcgca cggcaagagg  840 |
| | cgaggggcgg cgactggtga gtacgccaaa aattttgact agcggaggct agaaggagag  900 |
| | agatgggtgc gagagcgtca gtattaagcg ggggagaatt agatcgcgat gggaaaaaat  960 |
| | tcggttaagg ccagggggaa agaaaaaata taaattaaaa catatagtat gggcaagcag 1020 |
| | ggagctagaa cgattcgcag ttaatcctgg cctgttagaa acatcagaag gctgtagaca 1080 |
| | aatactggga cagctacaac catcccttca gacaggatca gaagaactta gatcattata 1140 |
| | taatacagta gcaaccctct attgtgtgca tcaaaggata gagataaaag acaccaagga 1200 |
| | agctttagac aagatagagg aagagcaaaa caaaagtaag accaccgcac agcaagcggc 1260 |
| | cgctgatctt cagacctgga ggaggagata tgagggacaa ttggagaagt gaattatata 1320 |
| | aatataaagt agtaaaaatt gaaccattag gagtagcacc caccaaggca aagagaagag 1380 |
| | tggtgcagag agaaaaaaga gcagtgggaa taggagcttt gttccttggg ttcttgggag 1440 |
| | cagcaggaag cactatgggc gcagcgtcaa tgacgctgac ggtacaggcc agacaattat 1500 |
| | tgtctggtat agtgcagcag cagaacaatt tgctgagggc tattgaggcg caacagcatc 1560 |
| | tgttgcaact cacagtctgg ggcatcaagc agctccaggc aagaatcctg gctgtggaaa 1620 |
| | gatacctaaa ggatcaacag ctcctgggga tttggggttg ctctggaaaa ctcatttgca 1680 |
| | ccactgctgt gccttggaat gctagttgga gtaataaatc tctggaacag atttggaatc 1740 |
| | acacgacctg gatggagtgg gacagaagaa ttaacaatta cacaagctta atacactcct 1800 |
| | taattgaaga atcgcaaaac cagcaagaaa agaatgaaca agaattattg gaattagata 1860 |
| | aatgggcaag tttgtggaat tggtttaaca taacaaattg gctgtggtat ataaaattat 1920 |
| | tcataatgat agtaggaggc ttggtaggtt taagaatagt ttttgctgta ctttctatag 1980 |
| | tgaatagagt taggcaggga tattcaccat tatcgtttca gacccacctc ccaaccccga 2040 |
| | ggggacccga caggcccgaa ggaatagaag aagaaggtgg agagagagac agagacagat 2100 |
| | ccattcgatt agtgaacgga tctcgacggt atcggtttta aaagaaaagg ggggattggg 2160 |
| | gggtacagtg caggggaaag aatagtagac ataatagcaa cagacataca aactaaagaa 2220 |
| | ttacaaaaac aaaattacaa aattcaaaat tttatcgatt ttatttagtc tccagaaaaa 2280 |
| | gggggaatg aaagacccca cctgtaggtt tggcaagcta gcttaagtaa cgccattttg 2340 |
| | caaggcatgg aaaatacata actgagaata gagaagttca gatcaaggtt aggaacagag 2400 |
| | agacagcaga atatgggcca aacaggatat ctgtggtaag cagttcctgc cccggctcag 2460 |
| | ggccaagaac agatggtccc cagatgcggt cccgccctca gcagtttcta gagaaccatc 2520 |
| | agatgtttcc agggtgcccc aaggacctga aatgaccctg tgccttattt gaactaacca 2580 |
| | atcagttcgc ttctcgcttc tgttcgcgcg cttctgctcc ccgagctcaa taaaagagcc 2640 |
| | cacaacccct cactcggcgc gccagtcctc cgatagactg cgtcgcccgg gtaccgatat 2700 |
| | caccaacttt gtacaaaaaa gctgaacgat atcgccacca tgggcagcac agccattctg 2760 |
| | gccctgctgc tggcagtgct gcagggcgtg tcagctcagg tgcagctgca gcagtctgga 2820 |
| | gccgaagtga agaaacccgg cagcagcgtg aaggtgtcct gcaaggctag cggcggcacc 2880 |
| | ttcagcagct acgccatttc ttgggtgcgc caggcccctg gacagggcct ggaatggatg 2940 |
| | ggctggatca gcccctacaa cggcaacacc gactacgccc agaaagtgca gggcagagtg 3000 |
| | accctgacca ccgacaccag cacctccacc gcctacatgg aactgcggag cctggacagc 3060 |
| | gacgacaccg ccgtgtacta ctgtgccaca ggcggcggaa cctggtacag cgatctgtgg 3120 |
| | ggcagaggca ccctcgtgac agtgtctgct ggcggcggag gatctggcgg aggcggaagt 3180 |
| | ggcgggggag gaagcggagc acctgagatc gtgctgaccc agagccctag cacactgagc 3240 |
| | gccagcgtgg gcgacagagt gtccatcacc tgtagagcca gccagagcat cggaggcgagc 3300 |
| | ctggcctggt atcagcagaa gcctggcaag gcccccaagc tgctgatctc tgaggccagc 3360 |
| | accctggaaa gaggcgtgcc cagcagattt tccggcagcg gctctggcac cgacttcacc 3420 |
| | ctgacaatca gcagcctgca gcccgaggac gtggccacct actactgcca gaagtacaac 3480 |
| | agcgtgcccc tgaccttcgg ccctggcacc aaggtggaaa tcaagccgcg ggccaacttt 3540 |
| | gtatacaaaa gtggcccgcg gacaacaacc cctgccccca gacctcctac cccagcccct 3600 |
| | acaattgcca gccagcctct gagcctgagg cccgaggctt gtagacctgc tgctggcgga 3660 |
| | gccgtgcaca ccagaggact ggatttcgcc tgcgacatct acatctgggc ccctctggcc 3720 |
| | ggcacatgtg gcgtgctgct gctgagcctc gtgatcaccc tgtactgcgg ctccaccagc 3780 |
| | ggctccggca agcccggctc tggcgagggc tccaccaagg gcgactacaa ggacgacgat 3840 |
| | gacaagtaat aggatatcgg ttcagctttc ttgtacaaag ttgggattcg agttaattaa 3900 |
| | gttaacgaat ccccccctc tccctcccc ccccctaacg ttactggccg aagccgcttg 3960 |
| | gaataaggcc ggtgtgcgtt tgtctatatg ttattttcca ccatattgcc gtcttttggc 4020 |
| | aatgtgaggg cccggaaacc tggccctgtc ttcttgacga gcattcctag gggtcttttgc 4080 |
| | cctctcgcca aaggaatgca aggtctgttg aatgtcgtga aggaagcagt tcctctggaa 4140 |
| | gcttcttgaa gacaaacaac gtctgtagcg acccctttgca ggcagcggaa ccccccacct 4200 |
| | ggcgacaggt gcctctgcgg ccaaaagcca cgtgtataag atacacctgc aaaggcggca 4260 |
| | caacccccagt gccacgttgt gagttggata gttgtggaaa gagtcaaatg gctctcctca 4320 |
| | agcgtattca acaaggggct gaaggatgcc cagaaggtac cccattgtat gggatctgat 4380 |
| | ctggggcctc ggtgcacatg ctttacatgt gtttagtcga ggttaaaaaa cgtctaggcc 4440 |
| | ccccgaacca cggggacgtg gttttccttt gaaaaacacg atgataatat ggccacaacc 4500 |
| | atgggaggag gaagcgcgg aggctccct cgaggcacca tggtgagcaa gggcgaggag 4560 |
| | ctgttcaccg gggtggtgcc catcctggtc gagctggacg gcgacgtaaa cggccacaag 4620 |
| | ttcagcgtgt ccggcgaggg cgagggcgat gccacctacg gcaagctgac cctgaagttc 4680 |
| | atctgcacca ccggcaagct gcccgtgccc tggcccaccc tcgtgaccac cctgacctac 4740 |
| | ggcgtgcagt gcttcagccg ctaccccgac cacatgaagc agcacgactt cttcaagtcc 4800 |
| | gccatgcccg aaggctacgt ccaggagcgc accatcttct tcaaggacga cggcaactac 4860 |

TABLE 8-continued

Nucleotide sequences for preparation of lentivirus for transduction of aAPCs.

Identifier
(Description)          Sequence

```
aagacccgcg ccgaggtgaa gttcgagggc gacaccctgg tgaaccgcat cgagctgaag    4920
ggcatcgact tcaaggagga cggcaacatc ctggggcaca agctggagta caactacaac    4980
agccacaacg tctatatcat ggccgacaag cagaagaacg gcatcaaggt gaacttcaag    5040
atccgccaca acatcgagga cggcagcgtg cagctcgccg accactacca gcagaacacc    5100
cccatcggcg acggccccgt gctgctgccc gacaaccact acctgagcac ccagtccgcc    5160
ctgagcaaag accccaacga gaagcgcgat cacatggtcc tgctggagtt cgtgaccgcc    5220
gccgggatca ctctcggcat ggacgagctg tacaagtaac gcgtcccggg tctagagcta    5280
gcggtaccat gcattacgta gtcgacgact taattaagct agcctagtgc catttgttca    5340
gtggttcgta gggctttccc ccactgtttg gctttcagtt atatggatga tgtggtattg    5400
ggggccaagt ctgtacagca tcttgagtcc cttttaccg ctgttaccaa ttttcttttg     5460
tctttgggta tacatttaaa ccctaacaaa acaaagagat ggggttactc tctaaatttt    5520
atgggttatg tcattggatg ttatgggtcc ttgccacaag aacacatcat acaaaaaatc    5580
aaagaatgtt ttagaaaact tcctattaac aggcctattg attggaaagt atgtcaacga    5640
attgtgggtc ttttgggttt tgctgcccct tttacacaat gtggttatcc tgcgttgatg    5700
cctttgtatg catgtattca atctaagcag gctttcactt tctcgccaac ttacaaggcc    5760
tttctgtgta aacaatacct gaacctttac cccgttgccc ggcaacggcc aggtctgtgc    5820
caagtgtttg ctgacgcaac ccccactggc tggggcttgg tcatgggcca tcagcgcatg    5880
cgtggaacct tttcggctcc tctgccgatc catactgcgg aactcctagc cgcttgtttt    5940
gctcgcagca ggtctggagc aaacattatc gggactgata actctgttgt cctatcccgc    6000
aaatatacat cgttccatg gctgctaggc tgtgctgcca actggatcct gcgcgggacg     6060
tcctttgttt acgtcccgtc ggcgctgaat cctgcggacg acccttctcg gggtcgcttg     6120
ggactctctc gtccccttct ccgtctgccg ttccgaccga ccacggggcg cacctctctt    6180
tacgcggact ccccgtctgt gccttctcat ctgccggacc gtgtgcactt cgcttcacct    6240
ctgcacgtcg catggagacc accgtgaacg cccaccaaat attgcccaag gtcttacata    6300
agaggactct tggactctca gcaatgtcaa cgaccgacct tgaggcatac ttcaaagact    6360
gtttgtttaa agactgggag gagttggggg aggagattag gttaaaggtc tttgtactag    6420
gaggctgtag gcataaaattg gtctgcgcac cagcaccatg gcgcaatcac tagagcgggg    6480
tacctttaag accaatgact tacaaggcag ctgtagatct tagccacttt ttaaaagaaa    6540
agggggggact ggaagggcta attcactccc aacgaagaca agatctgctt tttgcttgta    6600
ctgggtctct ctggttagac cagatctgag cctgggagct ctctggctaa ctagggaacc    6660
cactgcttaa gcctcaataa agcttgcctt gagtgcttca agtagtgtgt gcccgtctgt    6720
tgtgtgactc tggtaactag agatccctca gacccttta gtcagtgtgg aaaatctcta     6780
gcagtagtag ttcatgtcat cttattattc agtatttata acttgcaaag aaatgaatat    6840
cagagagtga gaggaacttg tttattgcag cttataatgg ttacaaataa agcaatagca    6900
tcacaaattt cacaaataaa gcatttttttt cactgcattc tagttgtggt ttgtccaaac    6960
tcatcaatgt atcttatcat gtctggctct agctatcccg cccctaactc cgcccatccc    7020
gcccctaact ccgcccagtt ccgcccattc tccgccccat ggctgactaa ttttttttatt   7080
ttatgcagag gccgaggccg gatcccttga gtggctttca tcctggagca gactttgcag    7140
tctgtggact gcaacacaac attgccttta tgtgtaactc ttggctgaag ctcttacacc    7200
aatgctgggg gacatgtacc tcccagggggc ccaggaagac tacgggaggc tacaccaacg    7260
tcaatcagag gggcctgtgt agctaccgat aagcggaccc tcaagaggcc attagcaata    7320
gtgtttataa ggcccccttg ttaattcttg aagacgaaag ggcctcgtga tacgcctatt     7380
tttataggtt aatgtcatga taataatggt ttcttagacg tcaggtggca cttttcgggg    7440
aaatgtgcgc ggaacccta tttgtttatt tttctaaata cattcaaata tgtatccgct     7500
catgagacaa taaccctgat aaatgcttca ataatattga aaaaggaaga gtatgagtat    7560
tcaacatttc cgtgtcgccc ttattccctt ttttgcggca ttttgccttc ctgttttttgc   7620
tcacccagaa acgctggtga aagtaaaaga tgctgaagat cagttgggtg cacgagtggg    7680
ttacatcgaa ctggatctca acagcggtaa gatccttgag agttttcgcc ccgaagaacg    7740
ttttccaatg atgagcactt ttaaagttct gctatgtggc gcggtattat cccgtgttga    7800
cgccgggcaa gagcaactcg gtcgccgcat acactattct cagaatgact tggttgagta    7860
ctcaccagtc acagaaaagc atcttacgga tggcatgaca gtaagagaat tatgcagtgc    7920
tgccataacc atgagtgata acactgcggc caacttactt ctgacaacga tcggaggacc    7980
gaaggagcta accgcttttt tgcacaacat gggggatcat gtaactcgcc ttgatcgttg    8040
ggaaccggag ctgaatgaag ccataccaaa cgacgagcgt gacaccacga tgcctgcagc    8100
aatggcaaca acgttgcgca aactattaac tggcgaacta cttactctag cttcccggca    8160
acaattaata gactggatgg aggcggataa agttgcagga ccacttctgc gctcggccct    8220
tccggctggc tggtttattg ctgataaatc tggagccggt gagcgtgggt ctcgcggtat    8280
cattgcagca ctggggccag atggtaagcc ctcccgtatc gtagttatct acacgacggg    8340
gagtcaggca actatggatg aacgaaatag acagatcgct gagataggtg cctcactgat    8400
taagcattgg taactgtcag accaagttta ctcatatata ctttagattg atttaaaact    8460
tcattttttaa tttaaaagga tctaggtgaa gatcctttt gataatctca tgaccaaaat    8520
cccttaacgt gagttttcgt tccactgagc gtcagacccc gtagaaaaga tcaaaggatc    8580
ttcttgagat cctttttttc tgcgcgtaat ctgctgcttg caaacaaaaa aaccaccgct    8640
accagcggtg tttgtttgc cggatcaaga gctaccaact ctttttccga aggtaactgg     8700
cttcagcaga gcgcagatac caaatactgt ccttctagtg tagccgtagt taggccacca    8760
cttcaagaac tctgtagcac cgcctacata cctcgctctg ctaatcctgt taccagtggc    8820
tgctgccagt ggcgataagt cgtgtcttac cgggttggac tcaagacgat agttaccgga    8880
taaggcgcag cggtcgggct gaacgggggg ttcgtgcaca gcccagct tggagcgaac      8940
gacctacacc gaactgagat acctacagcg tgagcattga gaaagcgcca cgcttcccga    9000
agggagaaag gcggacaggt atccggtaag cggcagggtc ggaacaggag agcgcacgag    9060
ggagcttcca gggggaaacg cctggtatct ttatagtcct gtcgggtttc gccacctctg    9120
acttgagcgt cgatttttgt gatgctcgtc agggggggcgg agcctatgga aaaacgccag    9180
caacgcggcc ttttttacggt tcctggcctt ttgctggcct ttttgaagct gtccctgatg    9240
gtcgtcatct acctgcctga cagcatggc ctgcaacgcg ggcatcccga tgccgccgga     9300
agcgagaaga atcataatgg ggaaggccat ccagcctcgc gtcg                     9344
```

TABLE 8-continued

Nucleotide sequences for preparation of lentivirus for transduction of aAPCs.

| Identifier (Description) | Sequence | | | | | |
|---|---|---|---|---|---|---|
| SEQ ID NO: 39 (pLenti-C-Myc-DDK OX40L) | gtcgacggat | cggggagatct | cccgatcccc | tatggtgcac | tctcagtaca | atctgctctg | 60 |
| | atgccgcata | gttaagccag | tatctgctcc | ctgcttgtgt | gttggaggtc | gctgagtagt | 120 |
| | gcgcgagcaa | aatttaagct | acaacaaggc | aaggcttgac | cgacaattgc | atgaagaatc | 180 |
| | tgcttagggt | taggcgtttt | gcgctgcttc | gcgatgtacg | ggccagatat | cgcgttgaca | 240 |
| | ttgattattg | actagttatt | aatagtaatc | aattacgggg | tcattagttc | atagcccata | 300 |
| | tatggagttc | cgcgttacat | aacttacggt | aaatggcccg | cctggctgac | cgcccaacga | 360 |
| | cccccgccca | ttgacgtcaa | taatgacgta | tgttcccata | gtaacgccaa | tagggacttt | 420 |
| | ccattgacgt | caatgggtgg | agtatttacg | gtaaactgcc | cacttggcag | tacatcaagt | 480 |
| | gtatcatatg | ccaagtacgc | ccctattga | cgtcaatgac | ggtaaatggc | ccgcctggca | 540 |
| | ttatgcccag | tacatgacct | tatgggactt | tcctacttgg | cagtacatct | acgtattagt | 600 |
| | catcgctatt | accatggtga | tgcggttttg | gcagtacatc | aatgggcgtg | gatagcggtt | 660 |
| | tgactcacgg | ggatttccaa | gtctccaccc | cattgacgtc | aatgggagtt | tgttttggca | 720 |
| | ccaaaatcaa | cgggactttc | caaaatgtcg | taacaactcc | gccccattga | cgcaaatggg | 780 |
| | cggtaggcgt | gtacggtggg | aggtctatat | aagcagcgcg | ttttgcctgt | actgggtctc | 840 |
| | tctggttaga | ccagatctga | gcctgggagc | tctctggcta | actagggaac | ccactgctta | 900 |
| | agcctcaata | aagcttgcct | tgagtgcttc | aagtagtgtg | tgcccgtctg | ttgtgtgact | 960 |
| | ctggtaacta | gagatccctc | agacccttt | agtcagtgtg | gaaaatctct | agcagtggcg | 1020 |
| | cccgaacagg | gacttgaaag | cgaaagggaa | accagaggag | ctctctcgac | gcaggactcg | 1080 |
| | gcttgctgaa | gcgcgcacgg | caagaggcga | ggggcggcga | ctggtgagta | cgccaaaaat | 1140 |
| | tttgactagc | ggaggctaga | aggagagaga | tgggtgcgag | agcgtcagta | ttaagcgggg | 1200 |
| | gagaattaga | tcgcgatggg | aaaaaattcg | gttaaggcca | gggggaaaga | aaaaatataa | 1260 |
| | attaaaacat | atagtatggg | caagcaggga | gctagaacga | ttcgcagtta | atcctggcct | 1320 |
| | gttagaaaca | tcagaaggct | gtagacaaat | actgggacag | ctacaaccat | cccttcagac | 1380 |
| | aggatcagaa | gaacttagat | cattatataa | tacagtagca | accctctatt | gtgtgcatca | 1440 |
| | aaggatagag | ataaaagaca | ccaaggaagc | tttagacaag | atagaggaag | agcaaaacaa | 1500 |
| | aagtaagacc | accgcacagc | aagcggccgg | ccgctgatct | tcagacctgg | aggaggagat | 1560 |
| | atgagggaca | attggagaag | tgaattatat | aaatataaag | tagtaaaaat | tgaaccatta | 1620 |
| | ggagtagcac | ccaccaaggc | aaagagaaga | gtggtgcaga | gagaaaaaag | agcagtggga | 1680 |
| | ataggagctt | tgttccttgg | gttcttggga | gcagcaggaa | gcactatggg | cgcagcgtca | 1740 |
| | atgacgctga | cggtacaggc | cagacaatta | ttgtctggta | tagtgcagca | gcagaacaat | 1800 |
| | ttgctgaggg | ctattgaggc | gcaacagcat | ctgttgcaac | tcacagtctg | gggcatcaag | 1860 |
| | cagctccagg | caagaatcct | ggctgtggaa | agatacctaa | aggatcaaca | gctcctgggg | 1920 |
| | atttgggggt | gctctggaaa | actcatttgc | accactgctg | tgccttggaa | tgctagttgg | 1980 |
| | agtaataaat | ctctggaaca | gatttggaat | cacacgacct | ggatggagtg | ggacagagaa | 2040 |
| | attaacaatt | acacaagctt | aatacactcc | ttaattgaag | aatcgcaaaa | ccagcaagaa | 2100 |
| | aagaatgaac | aagaattatt | ggaattagat | aaatgggcaa | gtttgtggaa | ttggtttaac | 2160 |
| | ataacaaatt | ggctgtggta | tataaaatta | ttcataatga | tagtaggagg | cttggtaggt | 2220 |
| | ttaagaatag | tttttgctgt | actttctata | gtgaatagag | ttaggcaggg | atattcacca | 2280 |
| | ttatcgtttc | agacccacct | cccaaccccg | aggggacccg | acaggcccga | aggaatagaa | 2340 |
| | gaagaaggtg | gagagagaga | cagagacaga | tccattcgat | tagtgaacgg | atcggcactg | 2400 |
| | cgtgcgccaa | ttctgcagac | aaatggcagt | attcatccac | aattttaaaa | gaaaaggggg | 2460 |
| | gattggggggg | tacagtgcag | gggaaagaat | agtagacata | atagcaacag | acatacaaac | 2520 |
| | taaagaatta | caaaaacaaa | ttacaaaaat | tcaaaatttt | cgggtttatt | acagggacag | 2580 |
| | cagagatcca | gtttggttag | taccgggccc | gctctagaca | tgtccaatat | gaccgccatg | 2640 |
| | ttgacattga | ttattgacta | gttattaata | gtaatcaatt | acggggtcat | tagttcatag | 2700 |
| | cccatatatg | gagttccgcg | ttacataact | tacggtaaat | ggcccgcctg | gctgaccgcc | 2760 |
| | caacgacccc | cgcccattga | cgtcaataat | gacgtatgtt | cccatagtaa | cgccaatagg | 2820 |
| | gactttccat | tgacgtcaat | gggtggagta | tttacggtaa | actgcccact | tggcagtaca | 2880 |
| | tcaagtgtat | catatgccaa | gtccgcccc | tattgacgtc | aatgacggta | aatggcccgc | 2940 |
| | ctggcattat | gcccagtaca | tgaccttacg | gactttcct | acttggcagt | acatctacgt | 3000 |
| | attagtcatc | gctattacca | tggtgatgcg | gttttggcag | tacaccaatg | ggcgtggata | 3060 |
| | gcggtttgac | tcacggggat | ttccaagtct | ccacccattt | gacgtcaatg | ggagtttgtt | 3120 |
| | ttggcaccaa | aatcaacggg | actttccaaa | atgtcgtaac | aacccgccc | cgttgacgca | 3180 |
| | aatgggcggt | aggcgtgtac | ggtgggaggt | ctatataagc | agagctcgtt | tagtgaaccg | 3240 |
| | tcagaatttt | gtaatacgac | tcactatagg | gcggccggga | attcgtcgac | tggatccggt | 3300 |
| | accgaggaga | tctgccgccg | cgatcgccat | ggaaagggtc | caaccctgg | aagagaatgt | 3360 |
| | gggaaatgca | gccaggccaa | gattcgagag | gaacaagcta | ttgctggtgg | cctctgtaat | 3420 |
| | tcaggggactg | gggctgctcc | tgtgcttcac | ctacatctgc | ctgcacttct | ctgctcttca | 3480 |
| | ggtatcacat | cggtatcctc | gaattcaaag | tatcaaagta | caatttaccg | aatataagaa | 3540 |
| | ggagaaaggt | ttcatcctca | cttcccaaaa | ggaggatgaa | atcatgaagg | tgcagaacaa | 3600 |
| | ctcagtcatc | atcaactgtg | atgggtttta | tctcatctcc | ctgaagggct | acttctccca | 3660 |
| | ggaagtcaac | attagccttc | attaccagaa | ggatgaggag | cccctcttcc | aactgaagaa | 3720 |
| | ggtcaggtct | gtcaactcct | tgatggtggc | ctctctgact | tacaaagaca | aagtctactt | 3780 |
| | gaatgtgacc | actgacaata | cctccctgga | tgacttccat | gtgaatggcg | gagaactgat | 3840 |
| | tcttatccat | caaaatcctg | gtgaattctg | tgtccttacg | cgtacgcggc | cgctcgagca | 3900 |
| | gaaactcatc | tcagaagagg | atctggcagc | aaatgatatc | ctggattaca | aggatgacga | 3960 |
| | cgataaggtt | taaacggccg | gcgcgcggtct | gtacaagtag | gattcgtcga | gggacctaat | 4020 |
| | aacttcgtat | agcatacatt | atacgaagtt | atacatgttt | aagggttccg | gttccactag | 4080 |
| | gtacaattcg | atatcaagct | tatcgataat | caacctctgg | attacaaaat | ttgtgaaaga | 4140 |
| | ttgactggta | ttcttaacta | tgttgctcct | tttacgctat | gtggatacgc | tgctttaatg | 4200 |
| | cctttgtatc | atgctattgc | ttcccgtatg | gctttcattt | tctcctcctt | gtataaatcc | 4260 |
| | tggttgctgt | ctctttatga | ggagttgtgg | cccgttgtca | ggcaacgtgg | cgtggtgtgc | 4320 |
| | actgtgtttg | ctgacgcaac | ccccactggt | tggggcattg | ccaccacctg | tcagctcctt | 4380 |
| | tccgggactt | tcgctttccc | cctccctatt | gccacggcgg | aactcatcgc | cgcctgcctt | 4440 |

TABLE 8-continued

Nucleotide sequences for preparation of lentivirus for transduction of aAPCs.

Identifier
(Description)      Sequence

```
gcccgctgct ggacaggggc tcggctgttg ggcactgaca attccgtggt gttgtcgggg  4500
aaatcatcgt cctttccttg gctgctcgcc tgtgttgcca cctggattct gcgcgggacg  4560
tccttctgct acgtcccttc ggccctcaat ccagcggacc ttccttcccg cggcctgctg  4620
ccggctctgc ggcctcttcc gcgtcttcgc cttcgccctc agacgagtcg gatctccctt  4680
tgggccgcct ccccgcatcg ataccgtcga cctcgatcga gacctagaaa aacatggagc  4740
aatcacaagt agcaatacag cagctaccaa tgctgattgt gcctggctag aagcacaaga  4800
ggaggaggag gtgggttttc cagtcacacc tcaggtacct ttaagaccaa tgacttacaa  4860
ggcagctgta gatcttagcc acttttaaa agaaaagggg ggactggaag ggctaattca  4920
ctcccaacga agacaagata tccttgatct gtggatctac cacacacaag gctacttccc  4980
tgattggcag aactacacac cagggccagg gatcagatat ccactgacct ttggatggtg  5040
ctacaagcta gtaccagttg agcaagagaa ggtagaagaa gccaatgaag gagagaacac  5100
ccgcttgtta caccctgtga gcctgcatgg gatgactggc cggagagag aagtattaga  5160
gtggaggttt gacagccgcc tagcatttca tcacatggcc cgagagctgc atccggactg  5220
tactgggtct ctctggttag accagatctg agcctgggag ctctctggct aactagggaa  5280
cccactgctt aagcctcaat aaagcttgcc ttgagtgctt caagtagtgt gtgcccgtct  5340
gttgtgtgac tctggtaact agagatccct cgaccctttt agtcagtgt ggaaaatctc  5400
tagcagcatg tgagcaaaag gccagcaaaa ggccaggaac cgtaaaaagg ccgcgttgct  5460
ggcgtttttc cataggctcc gcccccctga cgagcatcac aaaaatcgac gctcaagtca  5520
gaggtggcga aacccgacag gactataaag ataccaggcg tttcccctg gaagctccct  5580
cgtgcgctct cctgttccga ccctgccgct taccggatac ctgtccgcct ttctcccttc  5640
gggaagcgtg gcgctttctc atagctcacg ctgtaggtat ctcagttcgg tgtaggtcgt  5700
tcgctccaag ctgggctgtg tgcacgaacc ccccgttcag cccgaccgct gcgccttatc  5760
cggtaactat cgtcttgagt ccaacccggt aagacacgac ttatcgccac tggcagcagc  5820
cactggtaac aggattagca gagcgaggta tgtaggcggt gctacagagt tcttgaagtg  5880
gtggcctaac tacggctaca ctagaagaac agtatttggt atctgcgctc tgctgaagcc  5940
agttaccttc ggaaaaagag ttggtagctc ttgatccggc aaacaaacca ccgctggtag  6000
cggtggtttt tttgtttgca agcagcagat tacgcgcaga aaaaaggat ctcaagaaga  6060
tcctttgatc ttttctacgg ggtctgacgc tcagtggaac gaaaactcac gttaagggat  6120
tttggtcatg attacgcccc gccctgccac tcatggtgat actgttgtaa ttcattaagc  6180
attctgccga catggaagcc atcacaaacg gcatgatgaa cctgaatcgc cagcggcatc  6240
agcaccttgt cgccttgcgt ataatatttg cccatggtga aaacgggggc gaagaagttg  6300
tccatattgg ccacgtttaa atcaaaactg gtgaaactca cccagggatt ggctgagacg  6360
aaaaacatat tctcaataaa ccctttaggg aaataggcca ggtttcacc gtaacacgcc  6420
acatcttgcg aatatatgtg tagaaactgc cggaaatcgt cgtggtattc actccagagc  6480
gatgaaaacg tttcagtttg ctcatggaaa acggtgtaac aagggtgaac actatcccat  6540
atcaccagct caccgtcttt cattgccata cggaactccg gatgagcatt catcaggcgg  6600
gcaagaatgt gaataaaggc cggataaaac ttgtgcttat ttttctttac ggtctttaaa  6660
aaggccgtaa tatccagctg aacggtctgg ttataggtac attgagcaac tgactgaaat  6720
gcctcaaaat gttctttacg atgccattgg gatatatcaa cggtggtata tccagtgatt  6780
tttttctcca tactcttcct ttttcaatat tattgaagca tttatcaggg ttattgtctc  6840
atgagcggat acatatttga atgtatttag aaaaataaac aaatagggt cccgcgcaca  6900
tttccccgaa aagtgccacc tgac                                         6924
```

Figure 37:
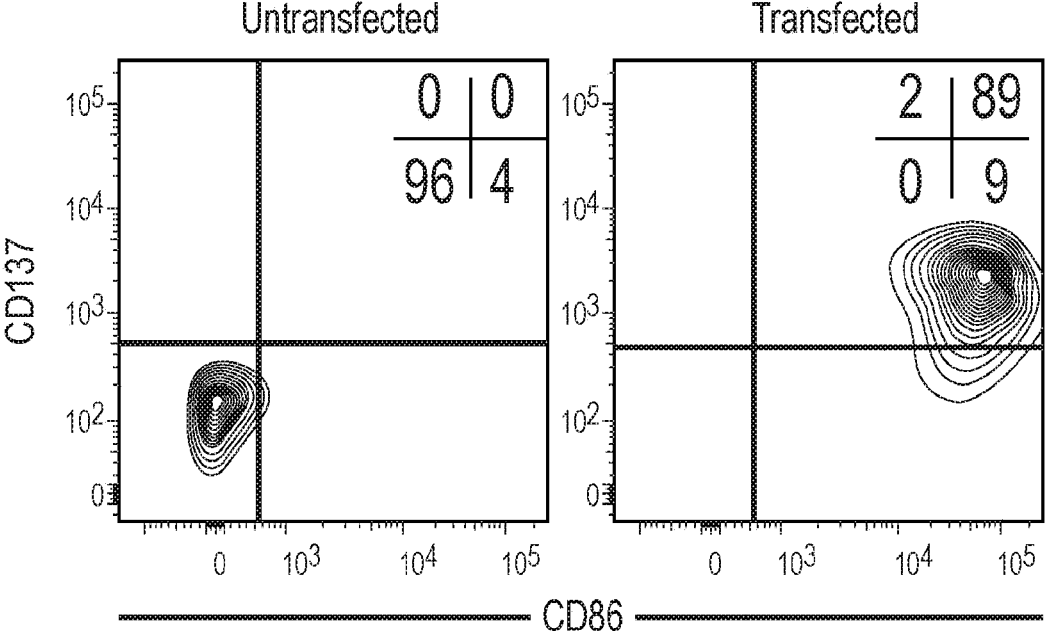
FIG. 37 illustrates the results of flow cytometry experiments on EM-3 cells before lentiviral transfection ("Untransfected") and after transfection ("Transfected"), confirming the expression of CD137 and CD86 on engineered EM-3 cells.
Figure 90:
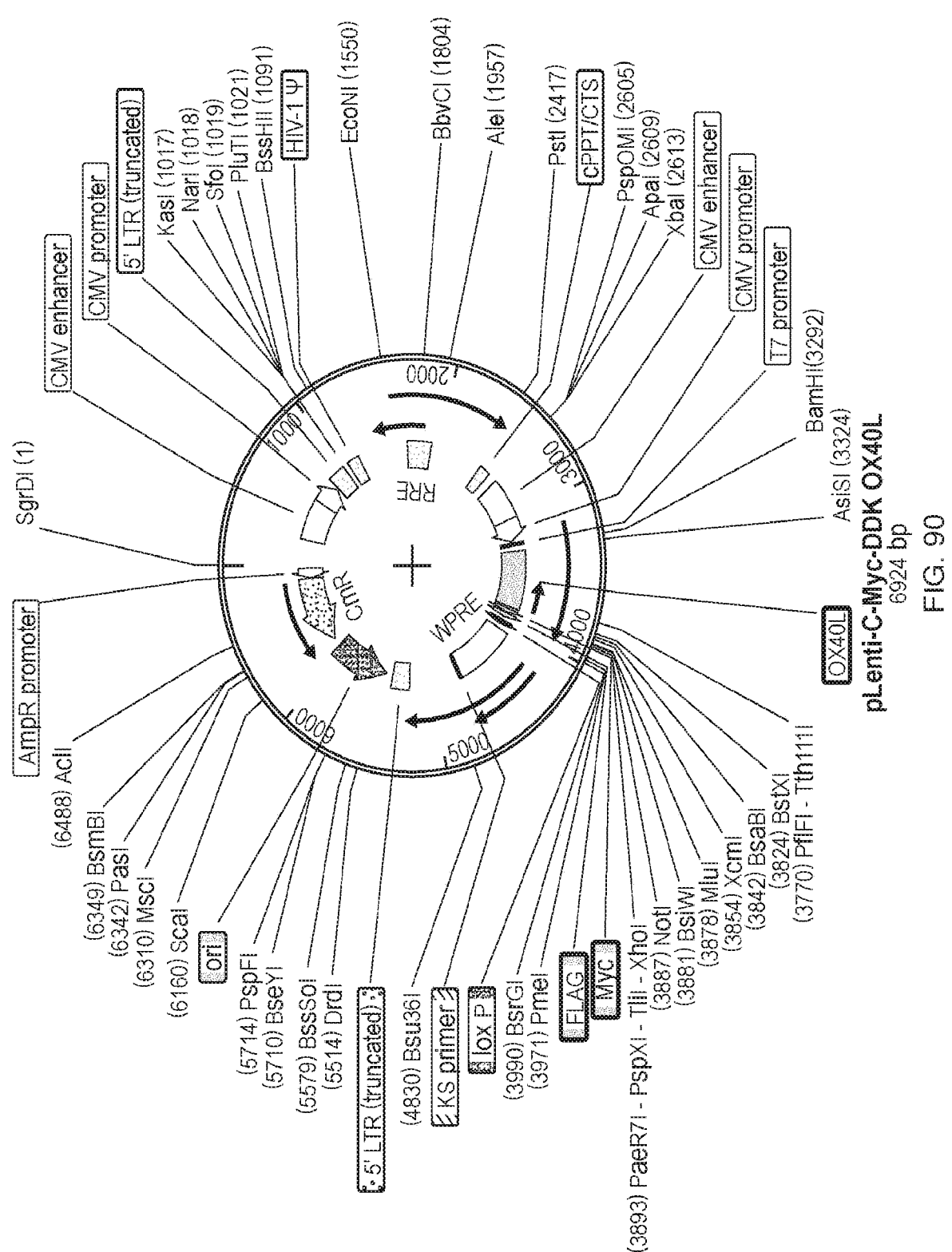
FIG. 90 illustrates a vector diagram of the pLenti-C-Myc-DDK human OX40L vector.

In the preparations of engineered EM-3 aAPCs (also referred to herein as aEM3 aAPCs) used for the experiments described herein, expression of CD86 and 4-1BBL was confirmed using flow cytometry (Canto II flow cytometer, Becton, Dickinson, and Co., Franklin Lakes, NJ, USA), with results shown in FIG. 37. aEM3 aAPCs were γ-irradiated at 100 Gy and frozen.

aEM-3 cells previously transduced to express CD86, antibody against IgG Fc region, and 4-1BBL (or optionally without 4-1BBL), as described above, were genetically engineered with a co-stimulatory human OX-40L using a similar lentiviral transduction approach. To generate lentivirus containing human OX-40L, pLenti-C-Myc-DDK OX40L (PS 100064, Origene, SEQ ID NO: 39, FIG. 90) vector together with the VSV-G envelope plasmid (pCIGO-VSV.G) were co-transfected into a Phoenix-GP (ATCC CRL-3215) cell line using PolyJet (Signagen Laboratories, Rockville, MD, USA). The supernatants were harvested 60 hours later and concentrated using Amicon Ultra-15 Centrifugal Filter Unit with Ultracel-100 membrane. aEM-3 cells were then infected with concentrated lentivirus and further expanded for five days. The cells were stained with PE-conjugated anti-human OX40L, Brilliant Violet 421-conjugated anti-human CD137L (if 4-1BBL is included in the prior aEM-3 cells), and PE/Cy7 conjugated anti-human CD86 and sorted based on the expression of GFP, OX40L, CD137L (when included), and CD86 using a S3e Cell Sorter (Bio-Rad, Inc., Hercules, CA, USA). The purity of sorted cells was further validated using flow cytometry. The enriched cells were checked for purity by flow cytometry.

Figure 38:
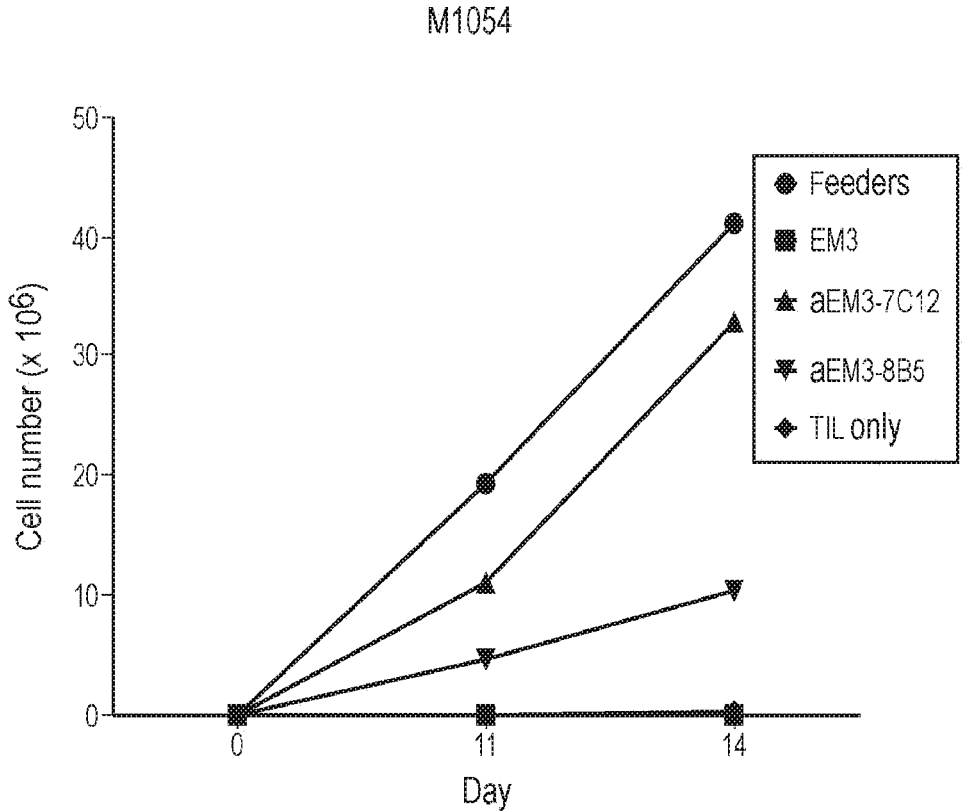
FIG. 38 illustrates the results of experiments wherein TILs were co-cultured with aEM3 (7C12 or 8B3) at a ratio of 1:100 plus OKT-3 (30 ng/mL) and IL-2 (3000 IU/mL). Cells were counted on Day 11 and 14.
Figure 39:
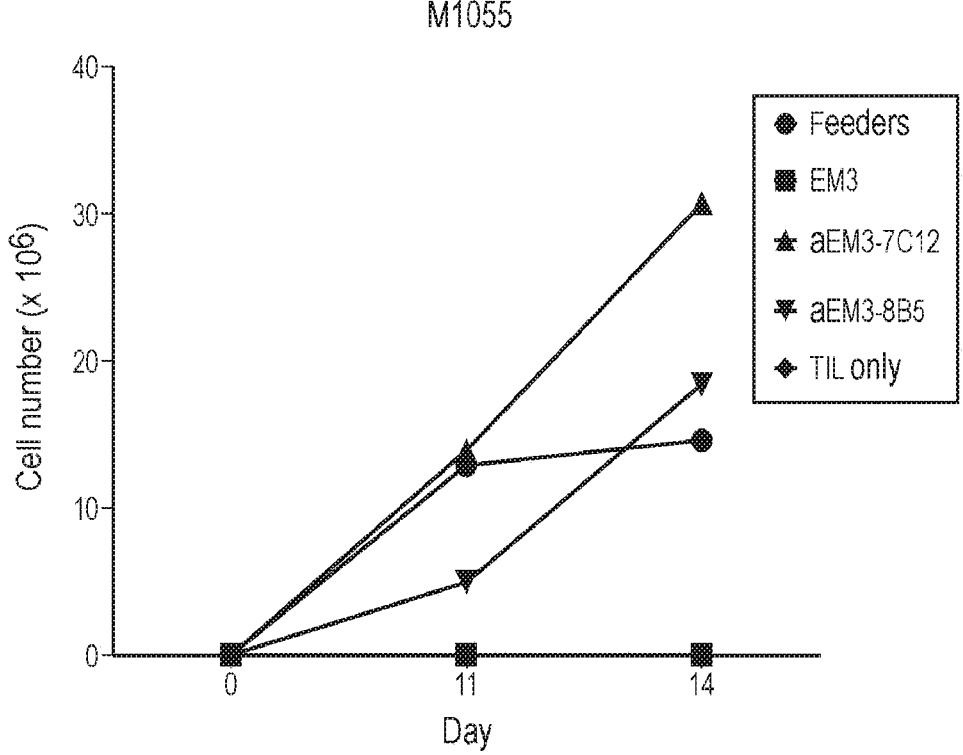
FIG. 39 illustrates the results of experiments wherein TILs were co-cultured with aEM3 (7C12 or 8B3) at a ratio of 1:100 plus OKT-3 (30 ng/mL) and IL-2 (3000 IU/mL). Cells were counted on Day 11 and 14.
Figure 40:
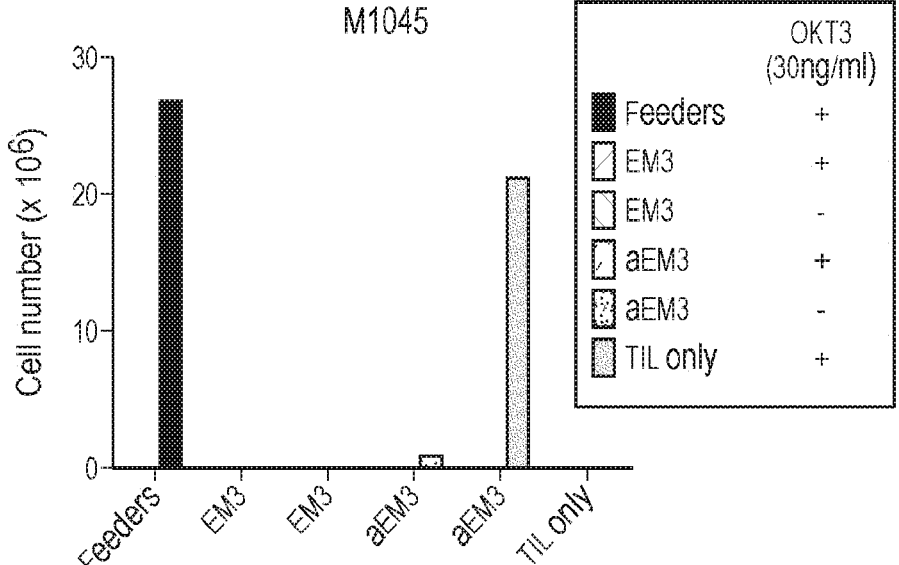
FIG. 40 illustrates the results of experiments wherein TILs were co-cultured with aEM3 or PBMC feeders at a 1:100 ratio with IL-2 (3000 IU/mL), with or without OKT-3 (30 ng/mL). The bar graph shows cell numbers determined on Day 11.

Example 6—Expansion of Tumor Infiltrating Lymphocytes Using EM-3 Artificial Antigen Presenting Cells Experiments were performed to test the ability of EM-3 aAPCs (aEM3) to expand TILs. TIL were co-cultured with aEM3 (7C12 or 8B3) at a ratio of 1:100 ratio plus OKT-3 (30 mg/mL) and IL-2 (3000 R7/mL). Cells were counted on Day 11 and 14. The results are plotted for two batches of TILs in FIG. 38 and FIG. 39. In addition, TILs were co-cultured with aEM3 or PBMC feeders at a 1:100 ratio with IL-2 (3000 IU/mL) with or without OKT-3 (30 mg/mL). The results are plotted in FIG. 40, where the bar graph shows cell numbers determined on Day 11.

Figure 41:
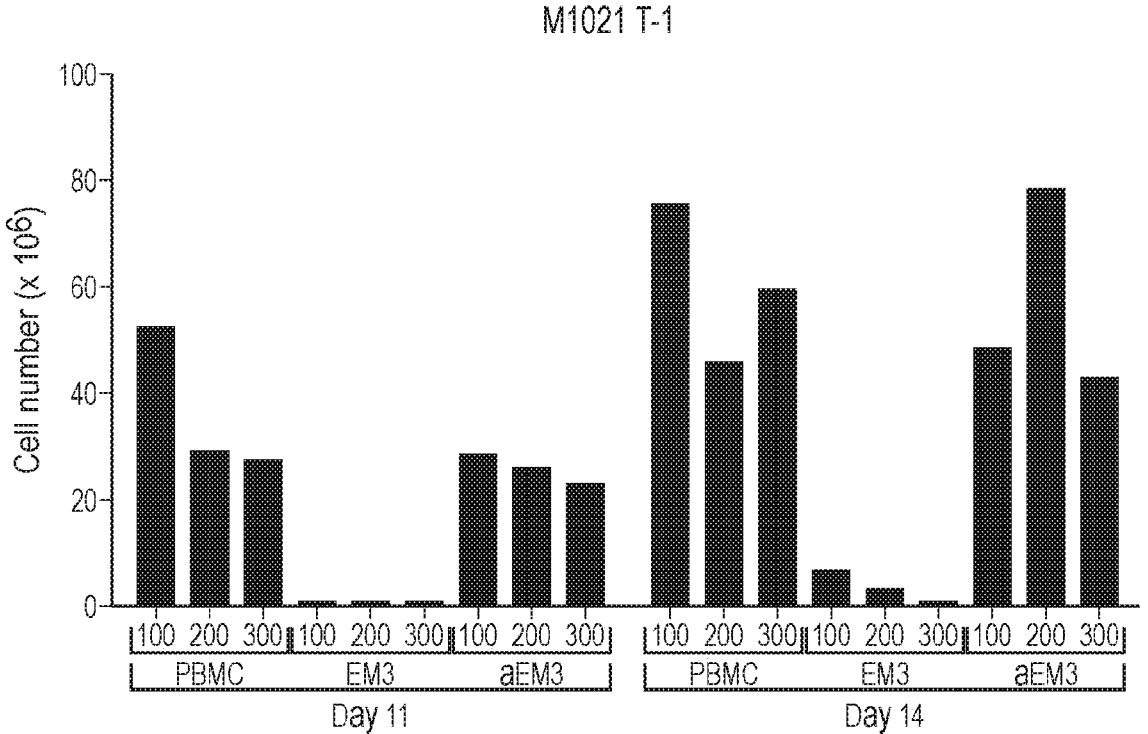
FIG. 41 illustrates the results of TIL expansions with EM-3 aAPCs at different TIL:aAPC ratios.

FIG. 41 illustrates the results of TIL expansions with EM-3 aAPCs (aEM3) at different TIL:aAPC ratios. The results show that aEM3 aAPCs perform comparably to and in some cases better than PBMCs, particularly at ratios of 1:200 at longer culture times (14 days).

Figure 42:
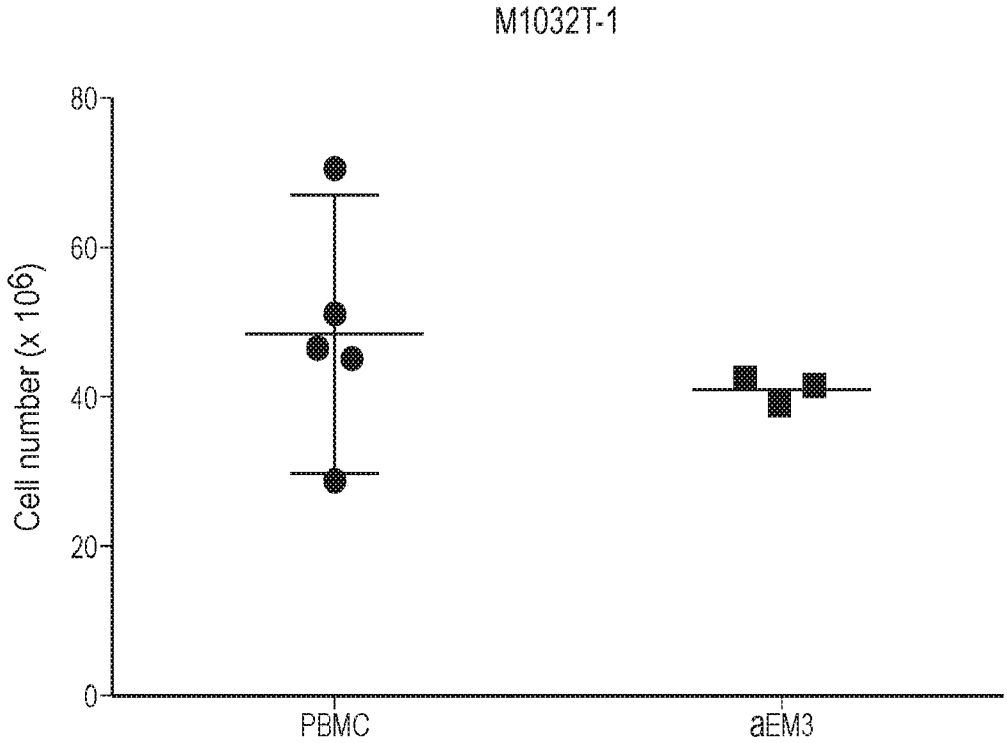
FIG. 42 illustrates the results of TIL expansions with EM-3 aAPCs. TILs ($2 \times 10^4$) were co-cultured with five different PBMC feeder lots or aEM3 (in triplicate) at a 1:100 ratio with IL-2 (3000 IU/mL) in a G-Rex 24 well plate. Viable cells were counted on Day 14. The graph shows viable cell numbers (mean) with 95% confidence interval counted on Day 14.
Figure 43:
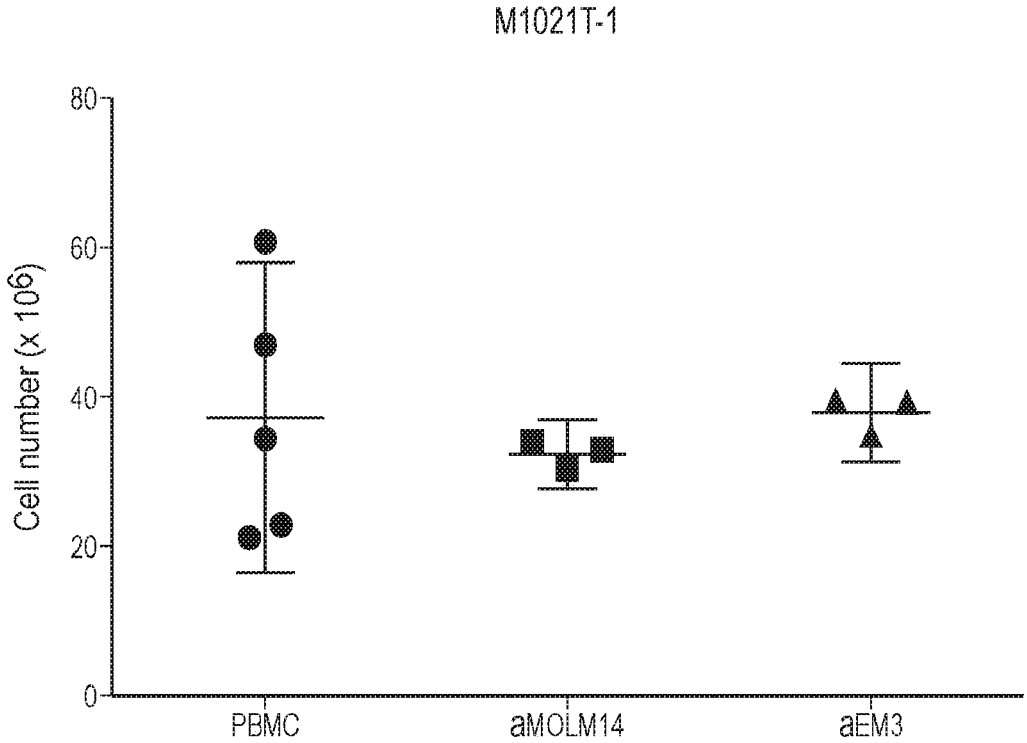
FIG. 43 illustrates the results of TIL expansions with EM-3 aAPCs and MOLM-14 aAPCs. TILs ($2 \times 10^4$) were co-cultured with five different PBMC feeder lots or aMOLM14 (in triplicate) or aEM3 (also in triplicate) at 1:100 ratio with IL-2 (3000 IU/mL) in a G-Rex 24 well plate. The graph shows viable cell numbers (mean) with 95% confidence interval counted on Day 14.

FIG. 42 illustrates the low variability in cell counts from TIL expansions with EM-3 aAPCs (aEM3) in comparison to PBMC feeders. TILs ($2\chi10^4$) were co-cultured with five different PBMC feeder lots or aEM3 (in triplicate) at 1:100 ratio with IL-2 (3000 IU/mL) in a G-Rex 24 well plate. The graph shows viable cell numbers (mean) with 95% confidence interval counted on Day 14. FIG. 43 compares the results of TIL expansions with EM-3 aAPCs and MOLM-14 aAPCs, to illustrate variability in cell counts for both aEM3 and aMOLM14 in comparison to TILs ($2\chi10^4$) were co-cultured with five different PBMC feeder lots or aMOLM14 (in triplicate) or aEM3 (also in triplicate) at 1:100 ratio with IL-2 (3000 IU/mL) in a G-Rex 24 well plate. Viable cells were counted on day 14, and the graph shows viable cell numbers (mean) with 95% confidence interval. The aEM3 and aMOLM14 results indicate that much greater consistency can be obtained with both aAPCs compared to the PBMC feeder approach preferred in the prior art.

TILs expanded against aEM3 or PBMC feeders were used for flow cytometry analysis using 4 different panels (differentiation panels 1 and 2, T cell activation panels 1 and 2). Briefly, TILs were first stained with L/D Aqua to determine viability. Next, cells were surface stained with TCR α/β PE-Cy7, CD4 FITC, CD8 PB, CD56 APC, CD28 PE, CD27 APC-Cy7, and CD57-PerCP-Cy5.5 for differentiation panel 1; CD45RA PE-Cy7, CD8a PerCP/Cy5, CCR7 PE, CD4 FITC, CD3 APC-Cy7, CD38 APC, and HLA-DR PB, for differentiation panel 2; CD 137 PE-Cy7, CD8a PerCP-Cy5.5, Lag3 PE, CD4 FITC, CD3 APC-Cy7, PD1 APC, and Tim-3 BV421 for T cell activation panel 1; or CD69 PE-Cy7, CD8a PerCP/Cy5.5, TIGIT PE, CD4 FITC, CD3 APC-Cy7, KLRG1 ALEXA 647, and CD 154 BV421 for T cell activation panel 2. Phenotype analysis was done by gating 10,000 to 100,000 cells according to FSC/SSC using the Canto II flow cytometer. Data was analyzed using Cytobank software (Cytobank, Inc., Santa Clara, CA, USA) to create sunburst diagrams and SPADE (Spanning-tree Progression Analysis of Density-normalized Events) plots. Gates were set based on fluorescence minus one (FMO) controls. SPADE plots were generated with the group of cells, characterized in a form of related nodes based on the expression level of surface markers. CD4$^+$ and CD8$^+$ TIL subsets were determined based on CD3$^+$ gating, and trees were generated. Sunburst visualizations are shown in FIG. 44 and FIG. 45. FIG. 44 shows that TILs expanded against aEM3 aAPCs maintained the CD8$^+$ phenotype when compared to the same TILs expanded against PBMC feeders. FIG. 45 shows the results of a second batch of TILs from a different patient expanded against aEM3 aAPCs, where a clear increase of CD8$^+$ cells (65.6%) is seen in comparison to the results from expansion using PBMC feeders (25%).

Figure 46:
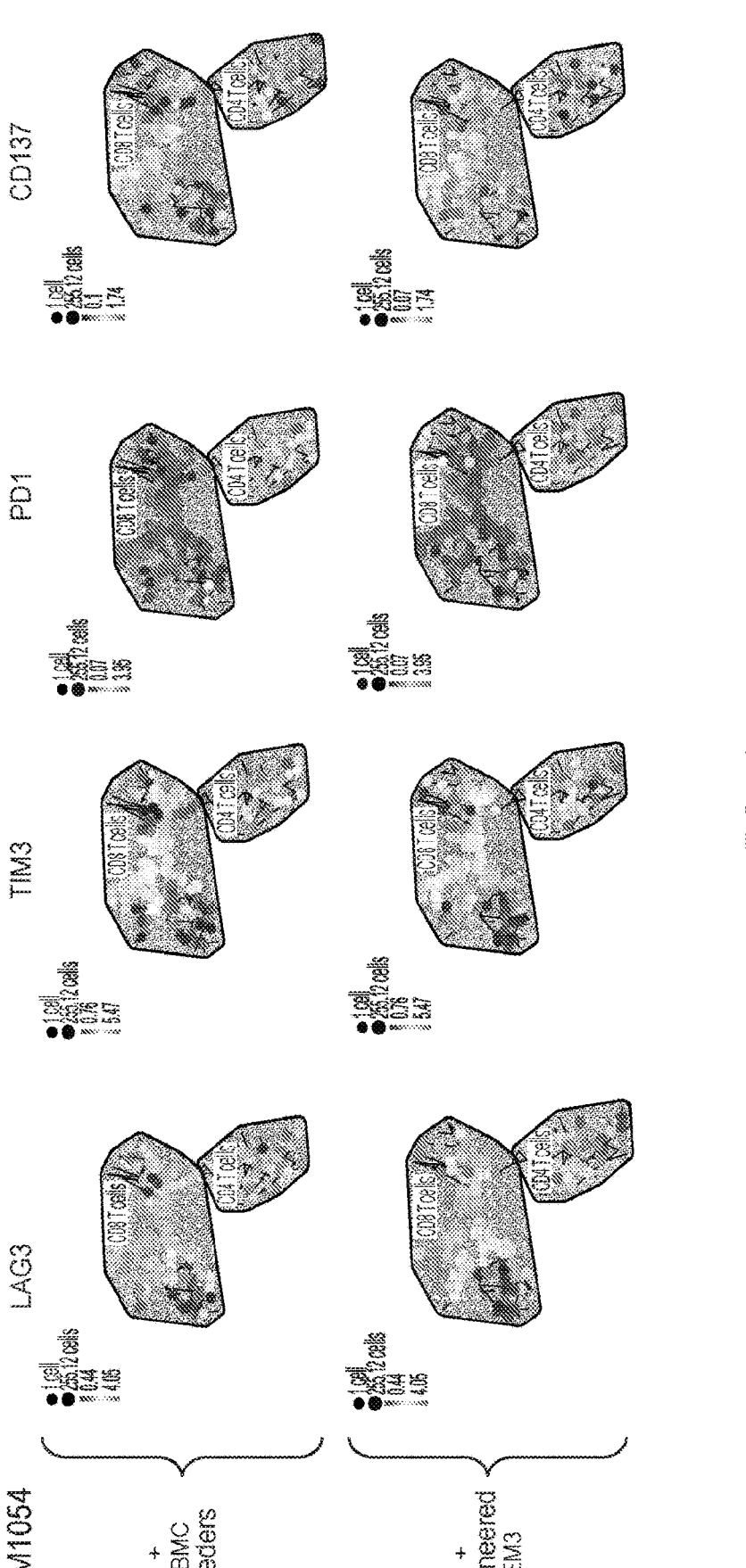
FIG. 46 illustrates the CD4+ and CD8+ SPADE tree of TILs expanded with aEM3 aAPCs or PBMC feeders using CD3+ cells. The color gradient is proportional to the MFI of LAG-3, TIM-3, PD-1, and CD137.
Figure 47:
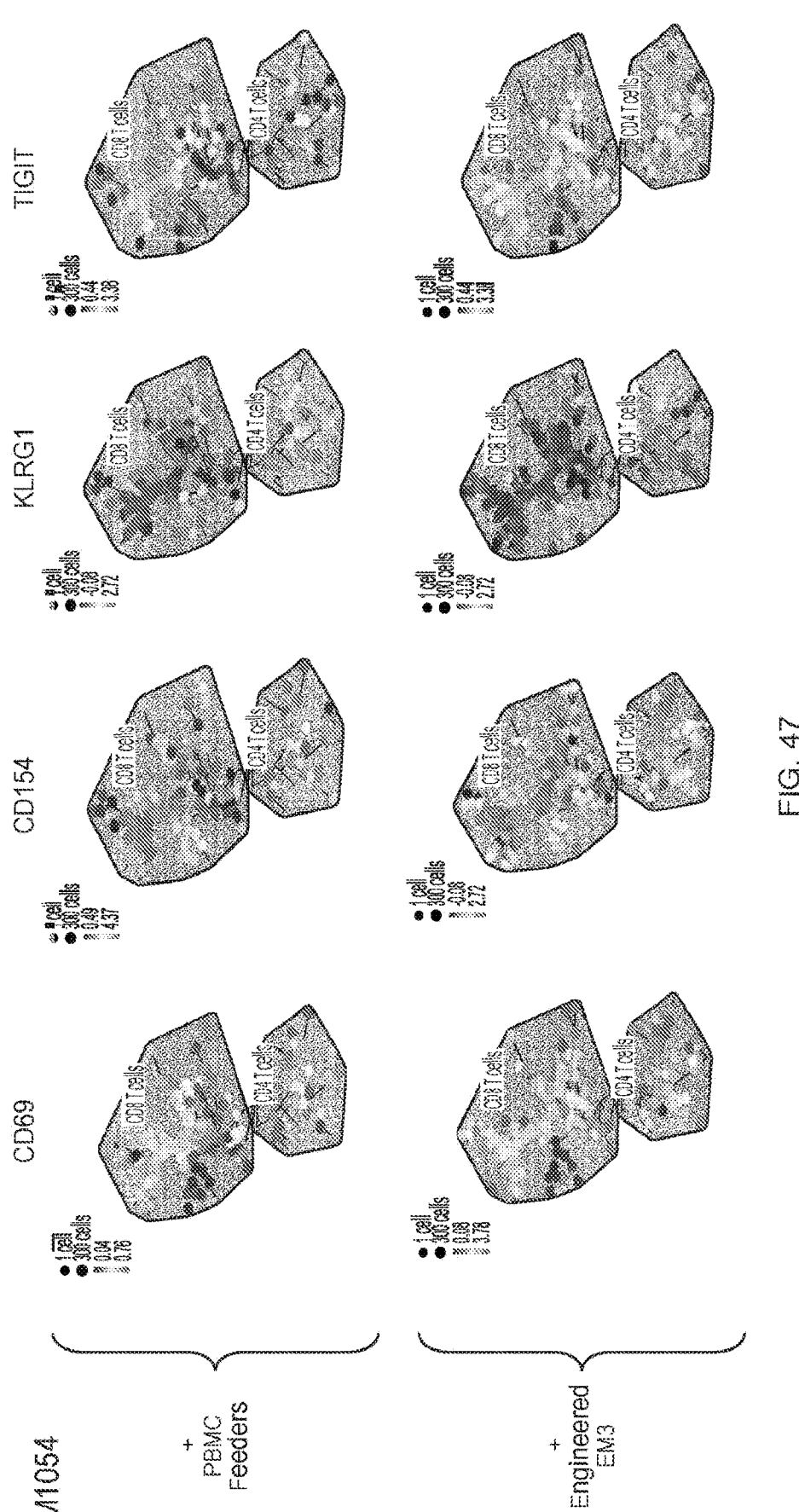
FIG. 47 illustrates the CD4+ and CD8+ SPADE tree of TILs expanded with aEM3 aAPCs or PBMC feeders using CD3+ cells. The color gradient is proportional to the MFI of CD69, CD 154, KLRG1, and TIGIT.

The CD4 and CD8 SPADE tree of TILs expanded with aEM3 aAPCs or PBMC feeders using CD3$^+$ cells is shown in FIG. 46 and FIG. 47. The color gradient is proportional to the mean fluorescence intensity (MFI) of LAG3, TIL3, PD1 and CD 137 or CD69, CD 154, KLRG1 and TIGIT. Without being bound by theory, the results show that TILs expanded with aEM3 aAPCs had undergone activation, but there was no difference in MFI between the aEM3 aAPCs and PBMC feeders, indicating that the aEM3 aAPCs effectively replicate the phenotypic results obtained with PBMC feeders.

Figure 48:
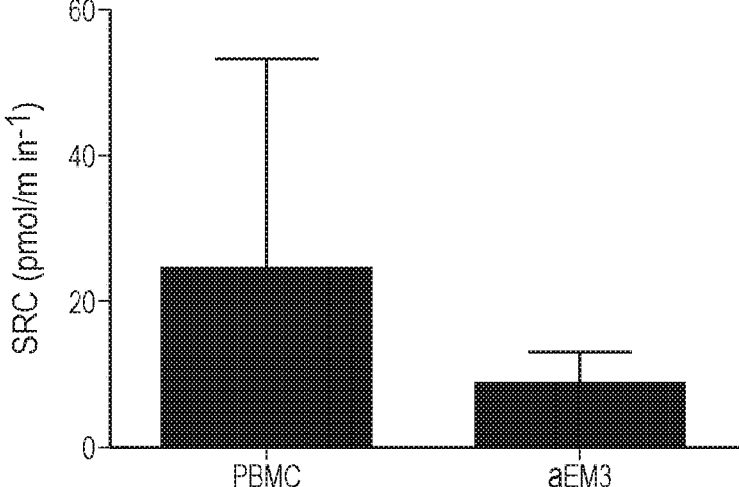
FIG. 48 illustrates a summary of spare respiratory capacity measured by the Seahorse XF Mito stress test.
Figure 49:
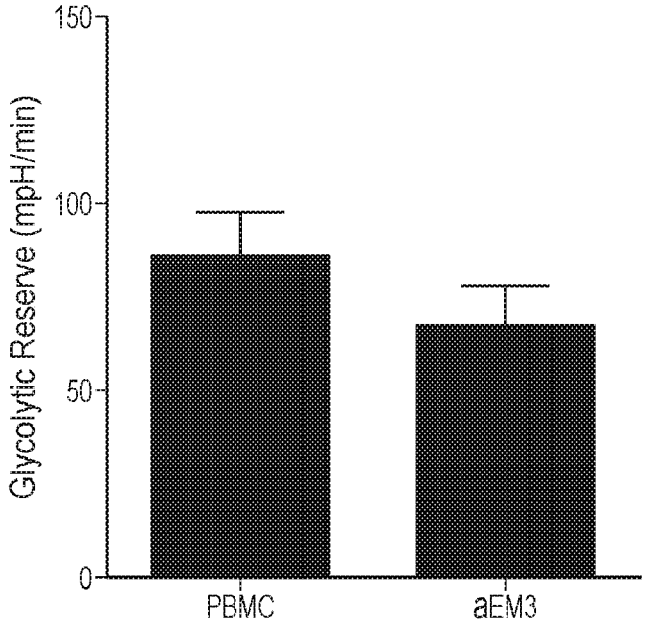
FIG. 49 illustrates a summary of glycolytic reserve measured by the Seahorse XF Mito stress test.

Spare respiratory capacity (SRC) and glycolytic reserve were also evaluated for TILs expanded with aEM3 aAPCs in comparison to PBMC feeders, with results shown in FIG. 48 and FIG. 49. The Seahorse XF Cell Mito Stress Test measures mitochondrial function by directly measuring the oxygen consumption rate (OCR) of cells, using modulators of respiration that target components of the electron transport chain in the mitochondria. The test compounds (oligomycin, FCCP, and a mix of rotenone and antimycin A, described below) are serially injected to measure ATP production, maximal respiration, and non-mitochondrial respiration, respectively. Proton leak and spare respiratory capacity are then calculated using these parameters and basal respiration. Each modulator targets a specific component of the electron transport chain. Oligomycin inhibits ATP synthase (complex V) and the decrease in OCR following injection of oligomycin correlates to the mitochondrial respiration associated with cellular ATP production. Carbonyl cyanide-4 (trifluoromethoxy) phenylhydrazone (FCCP) is an uncoupling agent that collapses the proton gradient and disrupts the mitochondrial membrane potential. As a result, electron flow through the electron transport chain is uninhibited and oxygen is maximally consumed by complex IV. The FCCP-stimulated OCR can then be used to calculate spare respiratory capacity, defined as the difference between maximal respiration and basal respiration. Spare respiratory capacity (SRC) is a measure of the ability of the cell to respond to increased energy demand. The third injection is a mix of rotenone, a complex I inhibitor, and antimycin A, a complex III inhibitor. This combination shuts down mitochondrial respiration and enables the calculation of nonmitochondrial respiration driven by processes outside the mitochondria.

Figure 50:
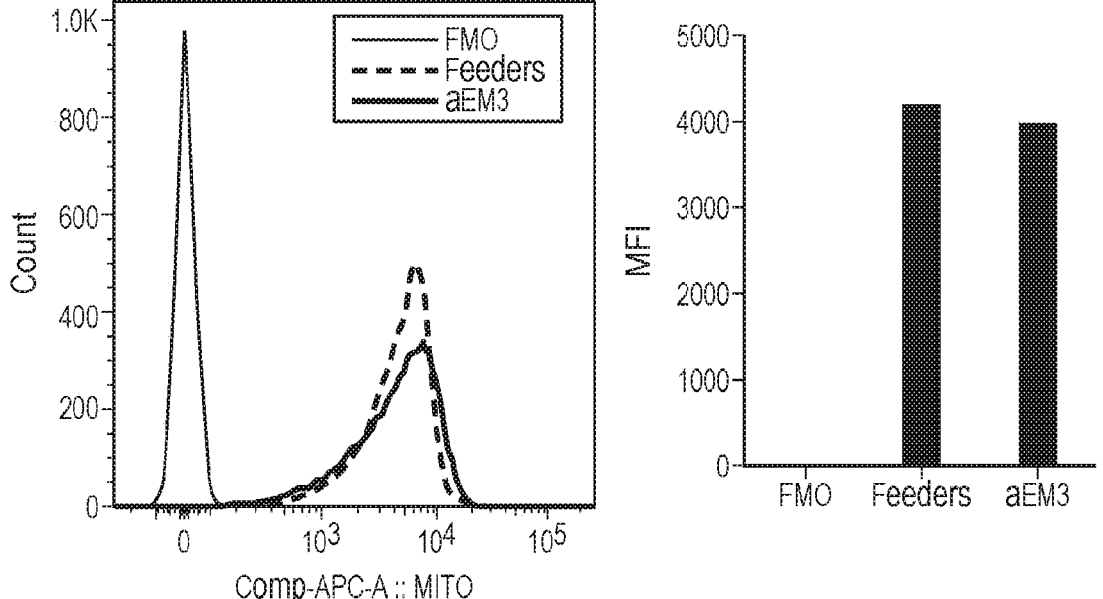
FIG. 50 illustrates a mitochondrial stain of live TILs expanded against PBMC or aEM3 using MitoTracker dye, which stains mitochondria in live cells and for which accumulation is dependent upon membrane potential. TILs expanded against PBMC or aEM3 were stained L/D Aqua followed by MitoTracker red dye. Data shown are MitoTracker positive (MFI) cells gated on live population.

FIG. 50 illustrates a mitochondrial stain of Live TILs expanded against PBMC feeders or aEM3 aAPCs. MitoTracker dye stains mitochondria in live cells and its accumulation is dependent upon membrane potential. TILs expanded against PBMC feeders or aEM3 were stained L/D Aqua followed by MitoTracker red dye. The data show MitoTracker positive (MFI) cells gated on live population,

Example 7—Comparison of Engineered MOLM-14 (aMOLM14) and EM-3 (aEM3) aAPCs

Figure 51:
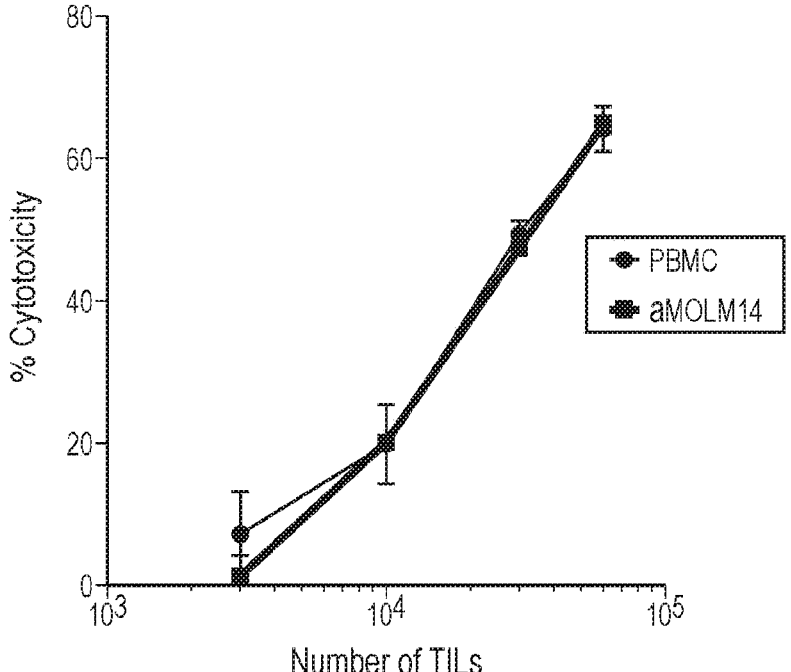
FIG. 51 illustrates results of a P815 BRLA for cytotoxic potency and functional activity, comparing TILs expanded with PBMC feeders to TILs expanded using aMOLM14 aAPCs.
Figure 52:
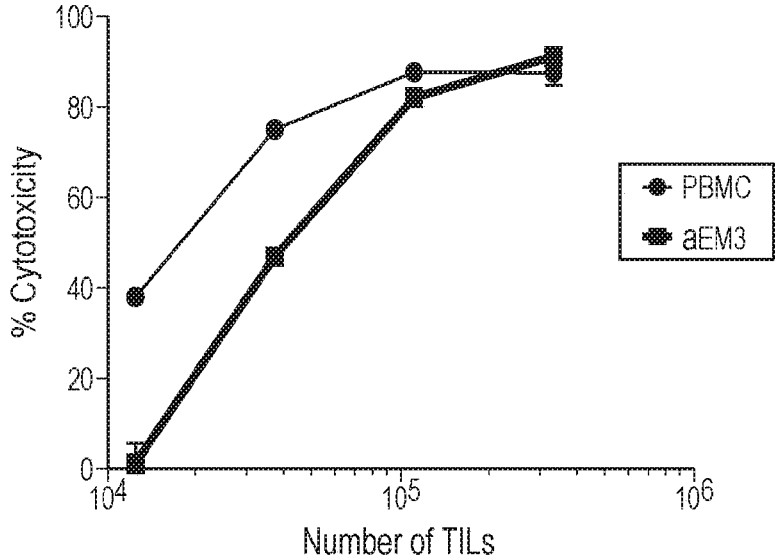
FIG. 52 illustrates results of a P815 BRLA for cytotoxic potency and functional activity, comparing TILs expanded with PBMC feeders to TILs expanded using aEM3 aAPCs.

TILs expanded with PBMC feeders and aMOLM14 and aEM3 aAPCs, as described in the previous examples, were assessed for functional activity using the BRLA for cytotoxic potency. The P815 BRLA is described in detail in Example 9. The results are shown in FIG. 51 and FIG. 52, and show that TILs expanded with aAPCs have similar functional properties (and expected clinical efficacy) to those expanded with PBMC feeders.

Figure 53:
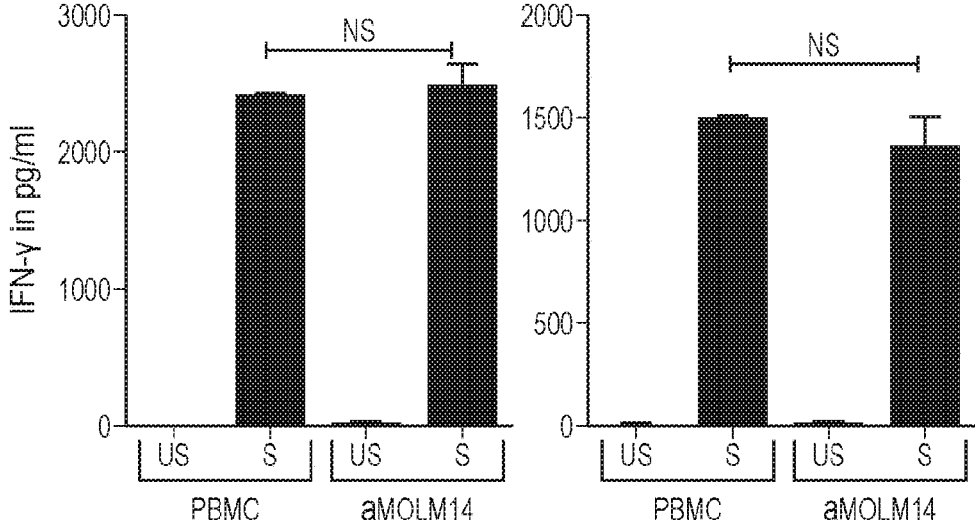
FIG. 53 illustrates IFN-γ release for two batches of TILs following overnight stimulation ("S") with microbeads coated with anti-CD3/CD28/4-1BB in comparison to unstimulated ("US") TILs, comparing TILs expanded with PBMC feeders to TILs expanded using aMOLM14 aAPCs. * p<0.05,  p<0.005, * pO.001, ns=not significant.
Figure 54:
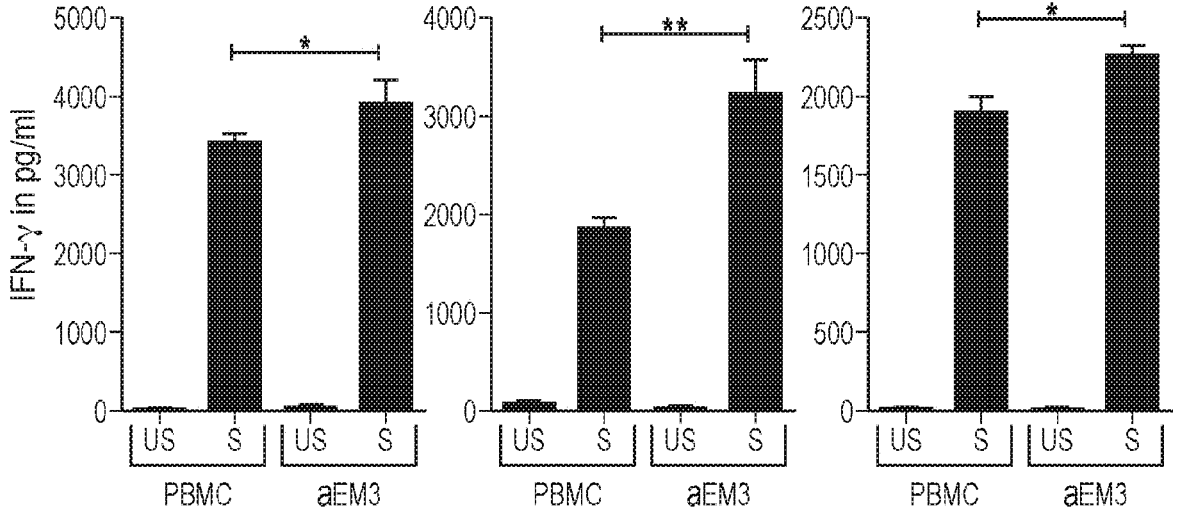
FIG. 54 illustrates IFN-γ release for three batches of TILs following overnight stimulation ("S") with microbeads coated with anti-CD3/CD28/4-1BB in comparison to unstimulated ("US") TILs, comparing TILs expanded with PBMC feeders to TILs expanded using aEM3 aAPCs. * p<0.05,  p<0.005, * pO.001, ns=not significant.
Figure 55:
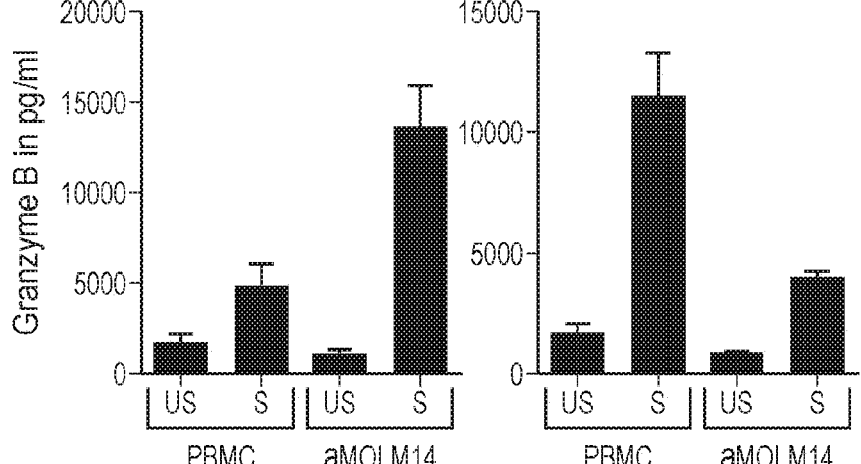
FIG. 55 illustrates Granzyme B release for two batches of TILs following overnight stimulation ("S") with microbeads coated with anti-CD3/CD28/4-1BB in comparison to unstimulated ("US") TILs, comparing TILs expanded with PBMC feeders to TILs expanded using aMOLM14 aAPCs. * p<0.05,  p<0.005, * pO.001, ns=not significant.
Figure 56:
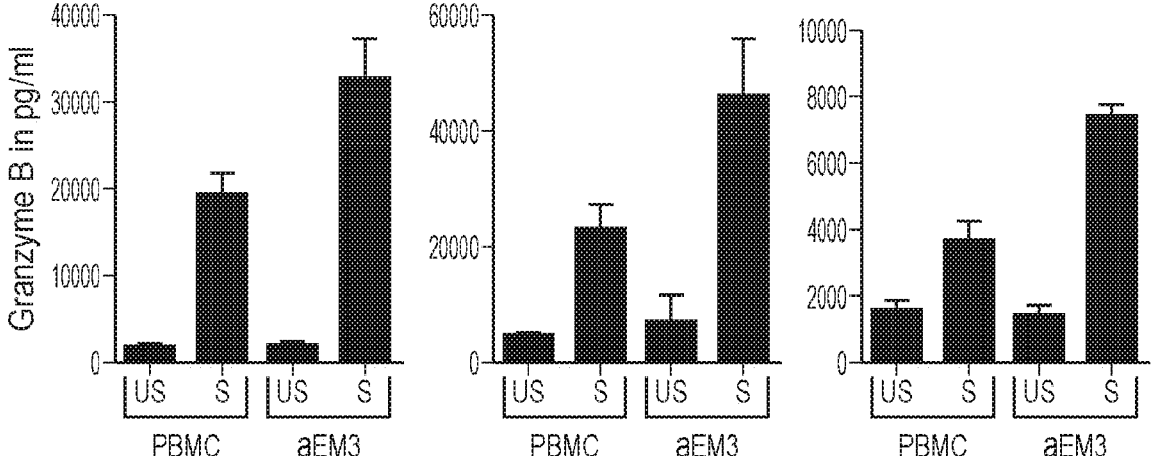
FIG. 56 illustrates Granzyme B release for three batches of TILs following overnight stimulation ("S") with microbeads coated with anti-CD3/CD28/4-1BB in comparison to unstimulated ("US") TILs, comparing TILs expanded with PBMC feeders to TILs expanded using aEM3 aAPCs. * p<0.05,  p<0.005, * pO.001, ns=not significant.

IFN-γ release and Granzyme B release from TILs expanded with PBMC feeders and aMOLM14 and aEM3 aAPCs as described above was also assessed following overnight stimulation with microbeads coated with anti-CD3/CD28/4-1BB. The IFN-γ release results are shown in FIG. 53 and FIG. 54, and the Granzyme B release results are shown in FIG. 55 and FIG. 56. Significant and surprising increases in IFN-γ release and Granzyme B release were observed for TILs expanded with aEM3 aAPCs relative to those expanded with PBMC feeders, but not for TILs expanded by aMOLM14 aAPCs. Without being bound by theory, this suggests that TILs cultured with aEM3 aAPCs may be more active in vivo as a cancer therapy. Most other differences observed were not statistically significant.

The results of TIL expansions with aEM3 and aMOLM14 aAPCs are summarized in Table 9.

TABLE 9

| aAPC | TIL# | Fold Expansion | | Relative expansion | CD8 (%) | | CD4 (%) | | Relative CD8 | Relative CD4 |
|---|---|---|---|---|---|---|---|---|---|---|
| | | PBMC | aAPC | | PBMC | aAPC | PBMC | aAPC | | |
| aMOLM14 | M1032-T2 | 2112 | 1936 | 0.92 | 53 | 65 | 44 | 27 | 1.226 | 0.614 |
| | M1033-T6 | 1761 | 1598 | 0.91 | 50 | 57 | 36 | 40 | 1.140 | 1.111 |
| | M1021T-5 | 2053 | 2024 | 0.99 | 91 | 82 | 8 | 17 | 0.901 | 2.125 |
| | M1030T-4 | 860 | 853 | 0.99 | 46 | 78 | 51 | 12 | 1.696 | 0.235 |
| | M1045 | 858* | 758* | 0.88 | — | — | — | — | — | — |
| | M1021T-1 | 1866 | 1620 | 0.87 | — | — | — | — | — | — |
| | M1032T-1 | 2423 | 2049 | 0.85 | — | — | — | — | — | — |
| | M1042 | 1278 | 1704 | 1.33 | 8 | 8 | 88 | 89 | 0.919 | 1.015 |
| | M1043 | 1601 | 1587 | 0.99 | 90 | 87 | 5 | 5 | 0.968 | 0.947 |
| aEM3 | M1054 | 2058 | 1647 | 0.80 | 98 | 96 | 2 | 2 | 0.981 | 1.400 |
| | M1055 | 729 | 1533 | 2.10 | 25 | 66 | 70 | 31 | 2.694 | 0.441 |
| | M1021T-1 | 2985 | 2805 | 0.94 | 87 | 75 | 10 | 20 | 0.862 | 2.000 |
| | M1045 | 1336 | 1047 | 0.78 | — | — | — | — | — | — |

Example 8—Preparation of Master Cell Banks for aEM3 and aMOLM14 aAPCs aEM3 and aMOLM14 aAPCs may be grown in the following media compositions to produce master cell banks, which may be further grown in this media for supply of aAPCs: 500 mL of Dulbecco's Modified Eagle Medium DMEM/F12 (Sigma-Aldrich, St. Louis, MO, USA), 50 mL fetal bovine serum (FBS) Heat Inactivated (HI) (Hyclone); 10 mM 4-(2-hydroxyethyl)-1-piperazineethanesulfonic acid (HEPES buffer) (Life Technologies); IX Primocin (Invivogen); IX Plasmocin (Invivogen), and IX 2-mercaptoethanol (Life Technologies).

The aAPCs described herein, including aEM3 and aMOLM14 aAPCs, may also be grown from a master cell bank using any suitable method known in the art for the growth of cells. In an embodiment, aAPCs are thawed and are then expanded in a medium of 80-90% RPMI 1640+10-20% h.i. FBS (fetal bovine serum) by splitting saturated culture 1:2 to 1:3 every 2-3 days, seeding out at about $0.5-1 \times 10^6$ cells/mL in 24-well plates, and maintaining at about $0.5-1.5 \times 10^6$ cells/mL, with incubation at 37° C. and 5% $CO_2$.

Further steps that may be employed to use the aAPCs of certain embodiments of the present invention in the production of human therapies are known in the art and include cell line characterization (HLA high resolution typing); cytokine release testing; testing of human serum to replace FBS to grow aAPC; testing freezing media to freeze aAPCs; master cell banking (including raw material testing and stability testing); standardization of irradiation (including irradiation dose (1000, 3000, 5000, 10000, 15000 rad), fresh versus frozen aAPCs, and with/without TILs); stability of aAPC; development of a panel to evaluate the contamination of aAPCs; development of molecular biology assays (qPCR, DNA sequencing); testing of TIL expansions from different tumor types, including melanoma, cervical, and head and neck cancer (using a G-Rex 5M); potency, purity, and identity testing; *mycoplasma* and sterility assays; microbiological testing (USP/EP sterility, bioburden and endotoxin assays); and adventitious viral agent testing.

Example 9—Methods of Expanding TILs and Treating Cancer with Expanded TILs

Figure 57:
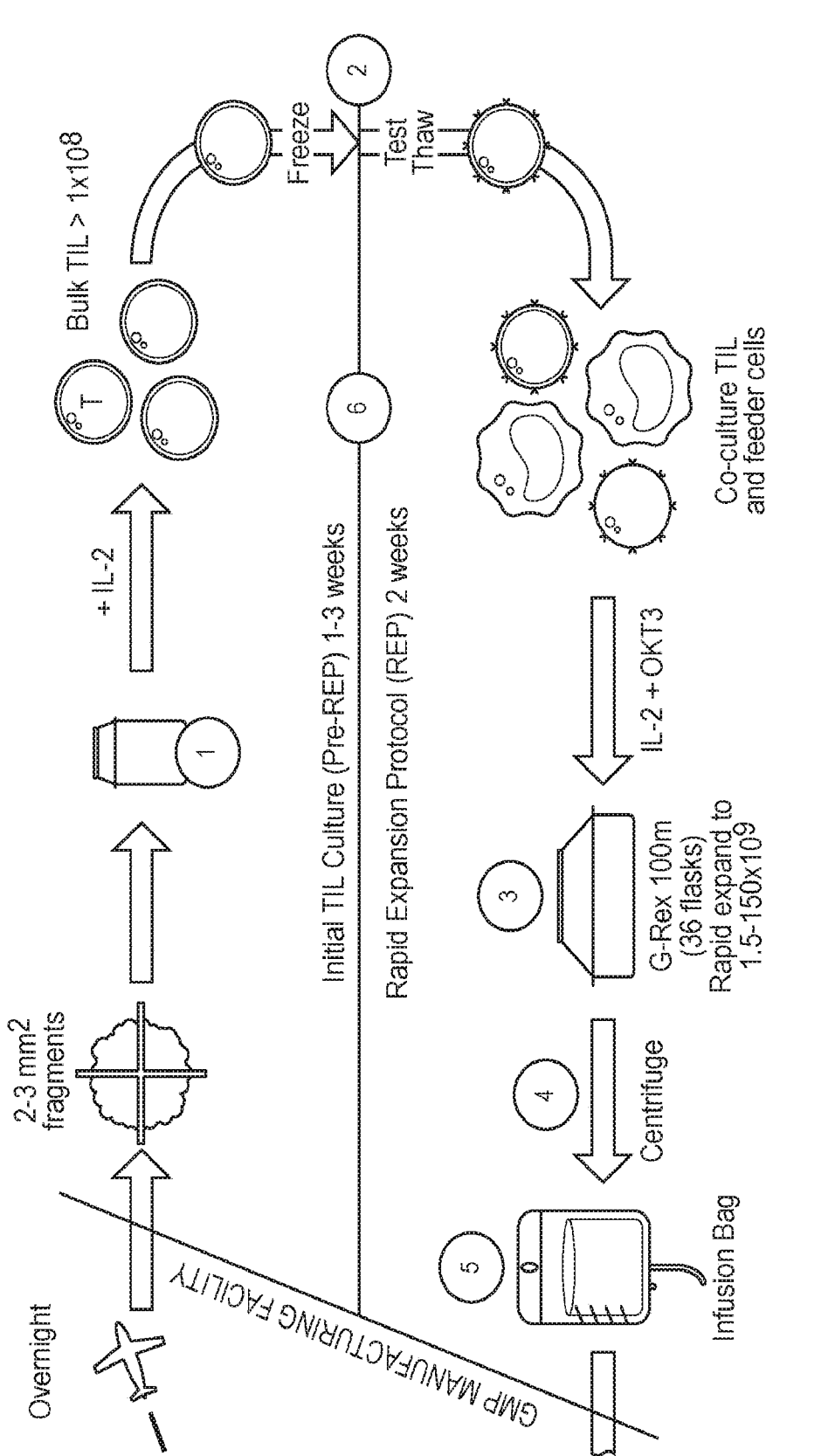
FIG. 57 illustrates a TIL expansion and treatment process. aAPCs of the present invention may be used in both the pre-REP stage (top half of figure) or REP stage (bottom half of figure) and may be added when IL-2 is added to each cell culture. Step 1 refers to the addition of 4 tumor fragments into 10 G-Rex 10 flasks. At step 2, approximately $40 \times 10^6$ TILs or greater are obtained. At step 3, a split occurs into 36 G-Rex 100 flasks for REP. TILs are harvested by centrifugation at step 4. Fresh TIL product is obtained at step 5 after a total process time of approximate 43 days, at which point TILs may be infused into a patient.
Figure 58:
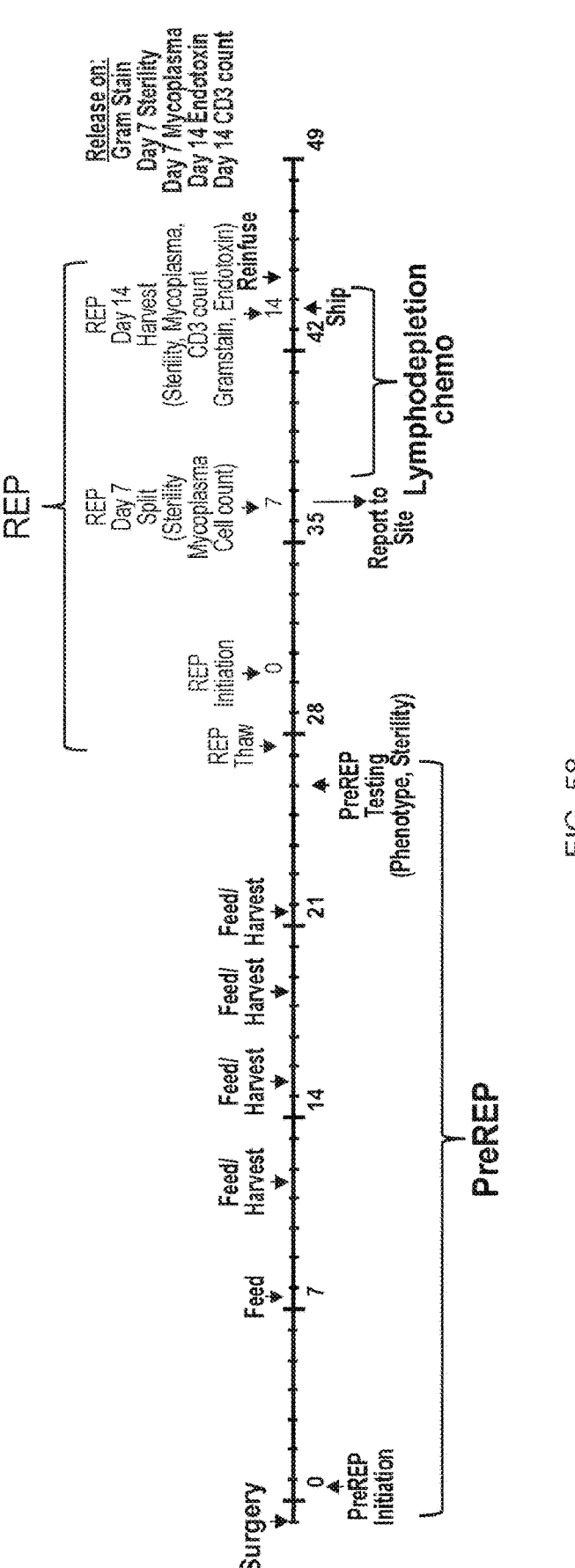
FIG. 58 illustrates a treatment protocol for use with TILs expanded with aAPCs. Surgery (and tumor resection) occurs at the start, and lymphodepletion chemo refers to non-myeloablative lymphodepletion with chemotherapy as described elsewhere herein.

TILs may be expanded using the aAPCs of certain embodiments of the present invention, such as aEM3 and aMOLM14 aAPCs, using any of the expansion methods described herein. For example, a method for expanding TILs is depicted in FIG. 57. The expansion of TILs using aAPCs may be further combined with any method of treating cancer in a patient described herein. A method for expanding TILs and treating a patient with expanded TILs, wherein the expansion makes use of aAPCs (including aEM3 and aMOLM14 aAPCs), is shown in FIG. 58.

Example 10—P815 Bioluminescent Redirected Lysis Assay

In this example, the development of a surrogate target cell line to evaluate the lytic potential of TILs in a Bioluminescent Redirected Lysis Assay (BRLA) is described. The BRLA enables assessment of T cell mediated killing in the absence of autologous tumor cells. Cytolytic activity can be assessed with and without engaging the T cell receptor in one to four hours, assessing T cell killing engaging the T cell receptor and without so-called lymphokine activated killer activities (LAK).

Mouse mastocytoma P815 cells expressing the endogenous CD 16 Fc receptor can bind anti-CD38 (OKT-3), providing a potent TCR activation signal as a target cell line. The P815 Clone G6 was transduced with a lentiviral vector based on eGFP and firefly luciferase, sorted and cloned using the BD FACSAria II. Clone G6 was selected based on eGFP intensity analyzed using an Intellicyt iQue Screener. Target cells and TILs of interest were co-cultured+/−OKT-3 to assess TCR activation (specific killing) or non-specific (lymphokine activated killing, LAK) respectively. Following 4 hours of incubation, firefly luciferin ((4S)-2-(6-hydroxy-1, 3-benzothiazol-2-yl)-4,5-dihydrothiazole-4-carboxylic acid, commercially available from multiple sources) was added to the wells and incubated for 5 minutes. Bioluminescence intensity was read using a luminometer. Percent cytotoxicity and survival were calculated using the following formula: % Survival=(experimental survival−minimum)/(maximum signal−minimum signal)×100; % Cytotoxicity=100−(% Survival). Interferon gamma release in the media supernatant of co-cultured TILs was analyzed by ELISA, and LAMP1 (CD107a, clone eBioH4A3) expression on TILs was analyzed on a flow cytometer to evaluate the cytotoxic potency of TILs.

Figure 59:
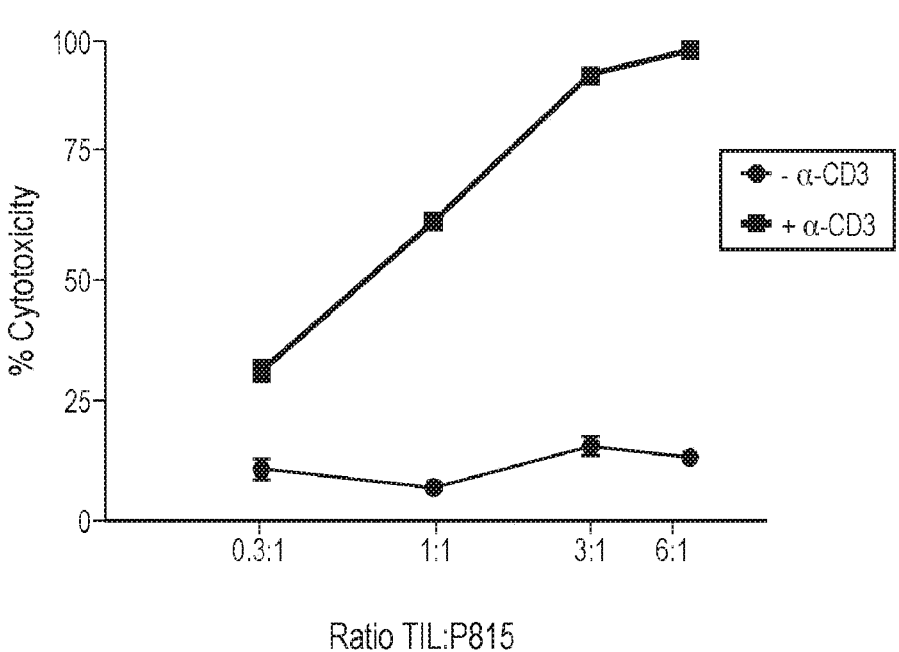
FIG. 59 illustrates Bioluminescent Redirected Lysis Assay (BRLA) results, showing percentage cytotoxicity of TIL batch M1033T-1 when co-cultured with P815 Clone G6 (with and without anti-CD3) at individual effector:target ratios.
Figure 60:
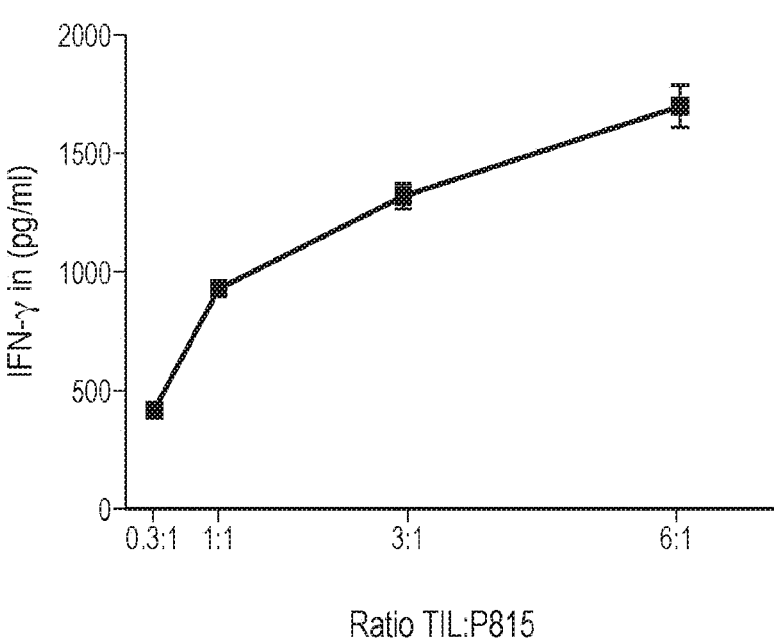
FIG. 60 illustrates enzyme-linked immunosorbent assay (ELISA) data showing amount of IFN-γ released against different ratios of effector to target cells.
Figure 61:
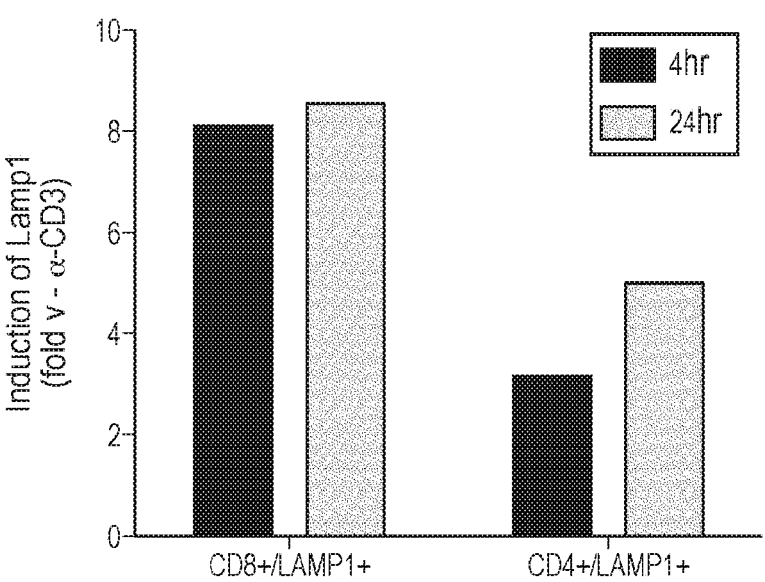
FIG. 61 illustrates LAMP1(%) expressed by TIL batch M1033T-1 when co-cultured with P815 Clone G6 in the presence of anti-CD3 at a ratio of 1:1 effector to target cells for 4 hr and 24 hr co-culture.

Results are shown in FIG. 59 to FIG. 75. FIG. 59 illustrates percent toxicity of TIL batch M1033T-1 co-cultured with P815 Clone G6 (with and without anti-CD3)

at individual effectontarget ratios by BRLA. FIG. 60 illustrates enzyme-linked immunosorbent assay (ELISA) data showing the amount of IFN-γ released against different ratios of effector to target cells. FIG. 61 illustrates LAMP1 (%) expressed by TIL batch M1033T-1 when co-cultured with P815 Clone G6 in the presence of anti-CD3 at a ratio of 1:1 effector to target cells for 4 hours and 24 hours co-culture.

Figure 62:
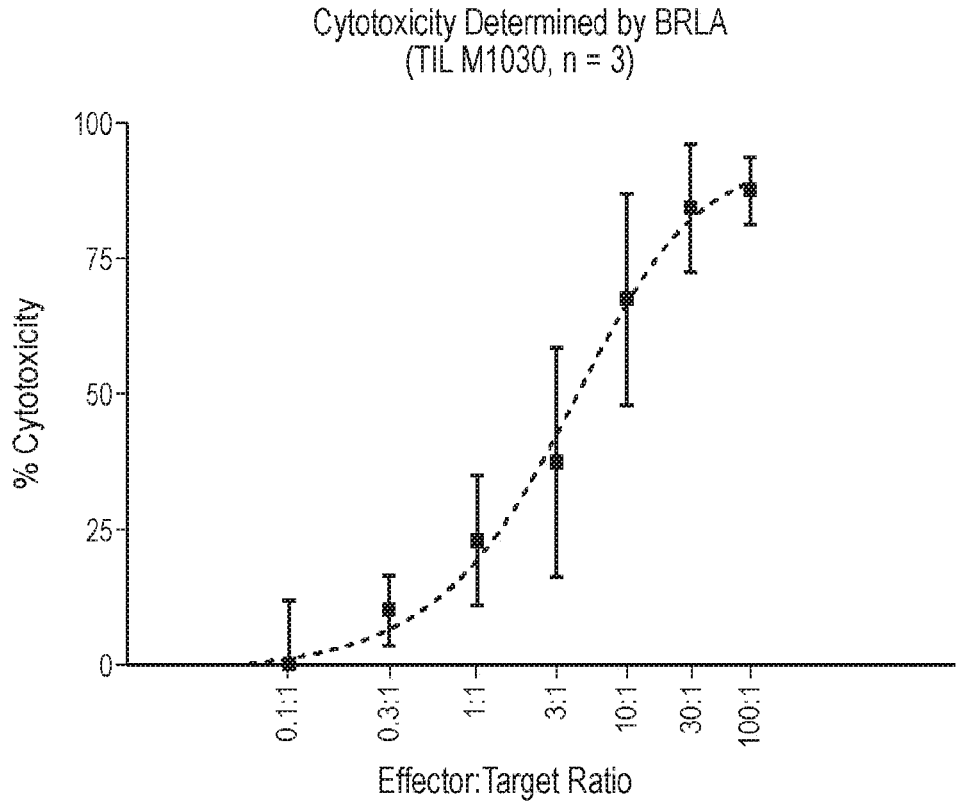
FIG. 62 illustrates BRLA results for TIL batch M1030. Cytotoxicity (measured as LUso/lx$10^6$ TIL) by BRLA is 26±16.
Figure 63:
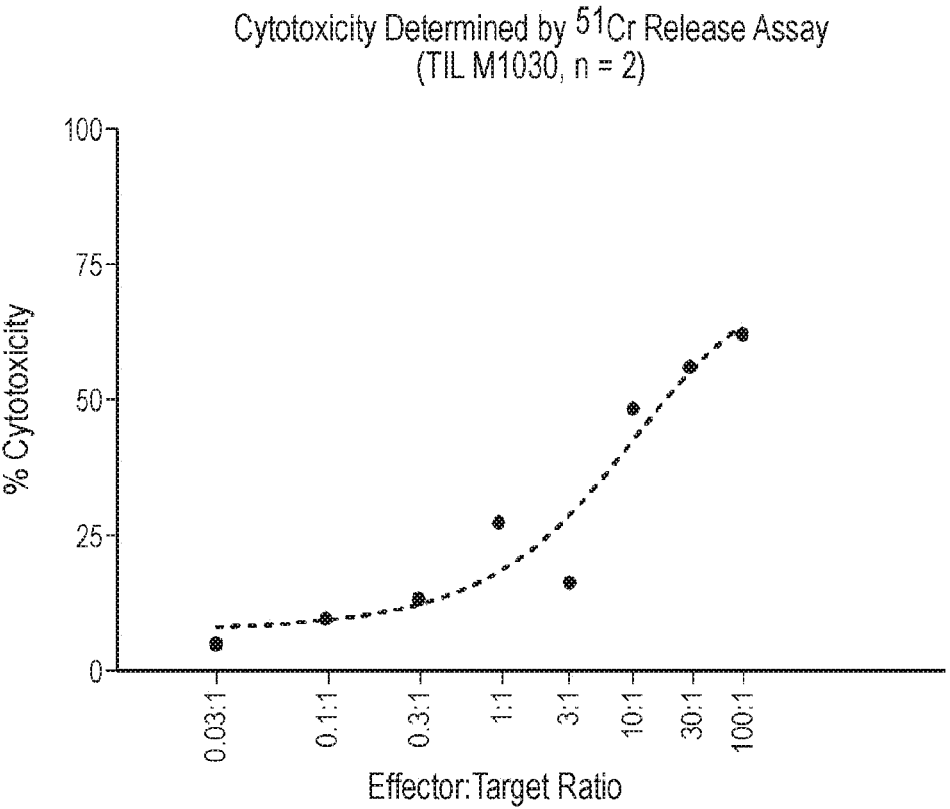
FIG. 63 illustrates standard chromium release assay for TIL batch M1030. Cytotoxicity (measured as $LU_{5_0}/1 \times 10^6$ TIL) by the chromium release assay is 22.

The results were confirmed using a second TIL batch as shown in FIG. 62, which illustrates BRLA for TIL batch M1030. The cytotoxicity (measured as $LD_{50}/1\times10^6$ TIL) by BRLA is 26±16. FIG. 63 illustrates the results of a standard chromium release assay for TIL batch M1030. The cytotoxicity (measured as $LD_{50}/1\times10^6$ TIL) by chromium release assay is 22.

Figure 64:
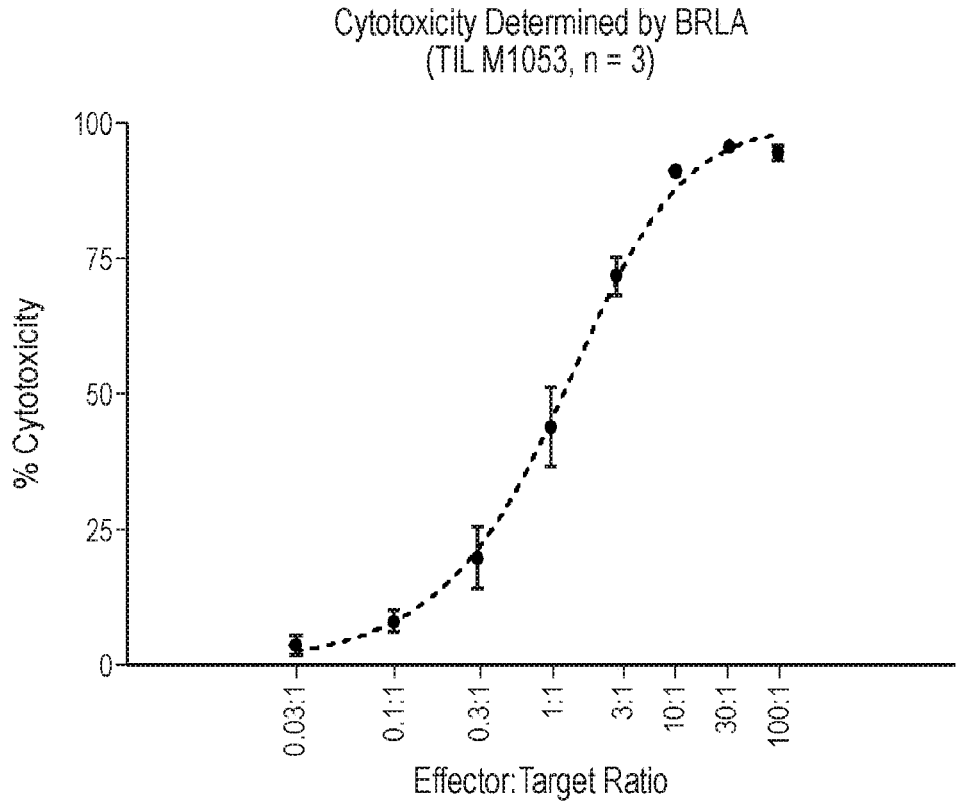
FIG. 64 illustrates BRLA results for TIL batch M1053, showing the lytic units of the TILs by BRLA as 70±17.
Figure 65:
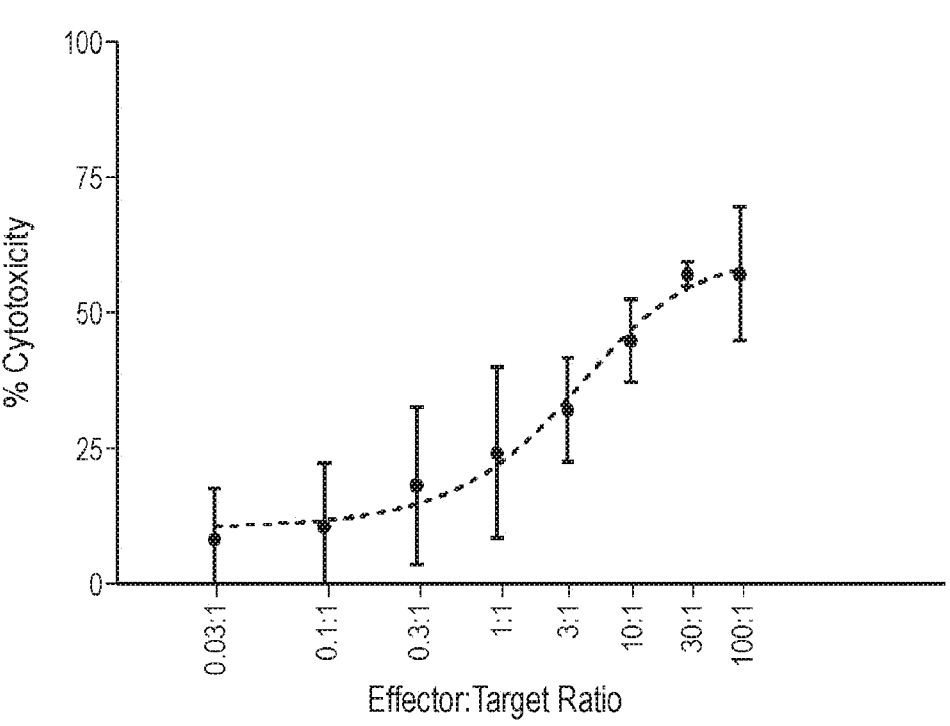
FIG. 65 illustrates standard chromium release assay results for TIL batch M1053, also showing lytic unit of the TILs by chromium assay as 14±5. Comparison of this result with FIG. 64 shows the comparable performance of the BRLA and chromium release assay.

Results were further confirmed using a third TIL batch. FIG. 64 illustrates BRLA results for TIL batch M1053, showing lytic units of the TILs by BRLA as 70±17. FIG. 65 illustrates the results of a standard chromium release assay for TIL batch M1053, showing lytic unit of the TILs by chromium assay as 14±5. Comparison of two assay results shows the comparable performance of the BRLA result to the chromium release assay result.

Figure 66:
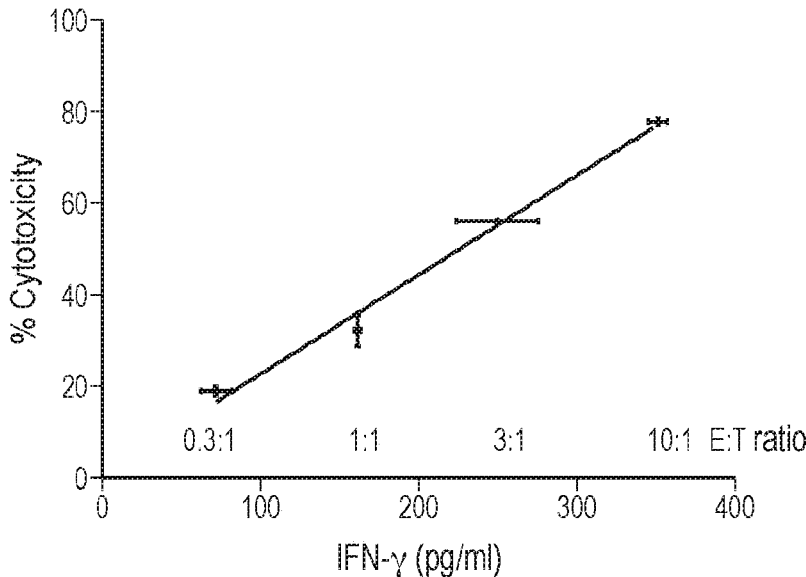
FIG. 66 illustrates the linear relationship between IFN-γ release and cytotoxic potential of TILs.
Figure 67:
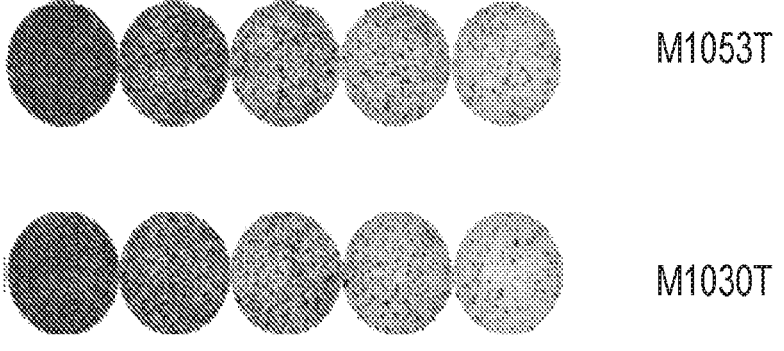
FIG. 67 illustrates ELISpot results for IFN-γ.
Figure 68:
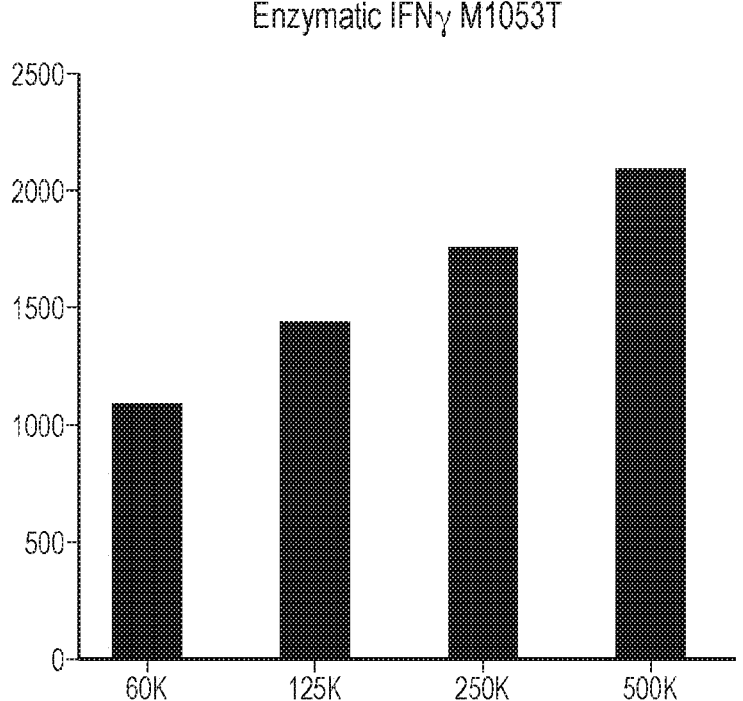
FIG. 68 illustrates enzymatic IFN-γ release for TIL batch M1053.
Figure 69:
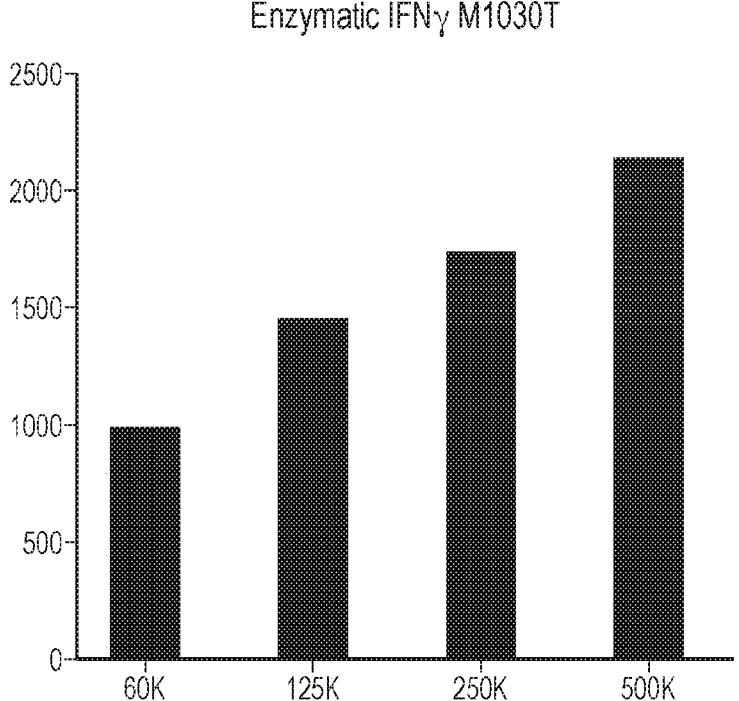
FIG. 69 illustrates enzymatic IFN-γ release for TIL batch M1030.
Figure 70:
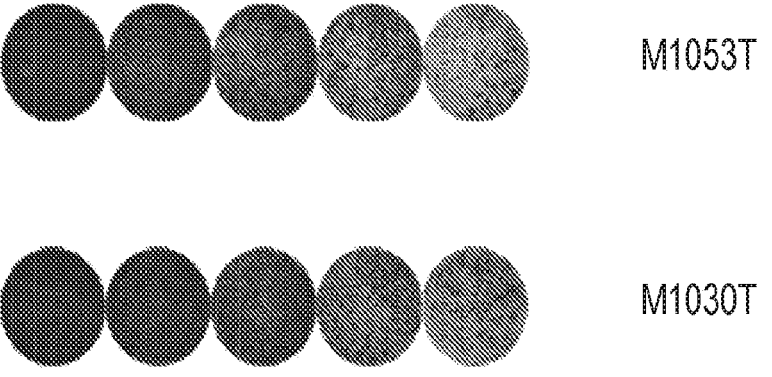
FIG. 70 illustrates ELISpot data showing Granzyme B release by M1053T and M1030T. This data confirms the potency of the TILs shown by the BRLA.
Figure 71:
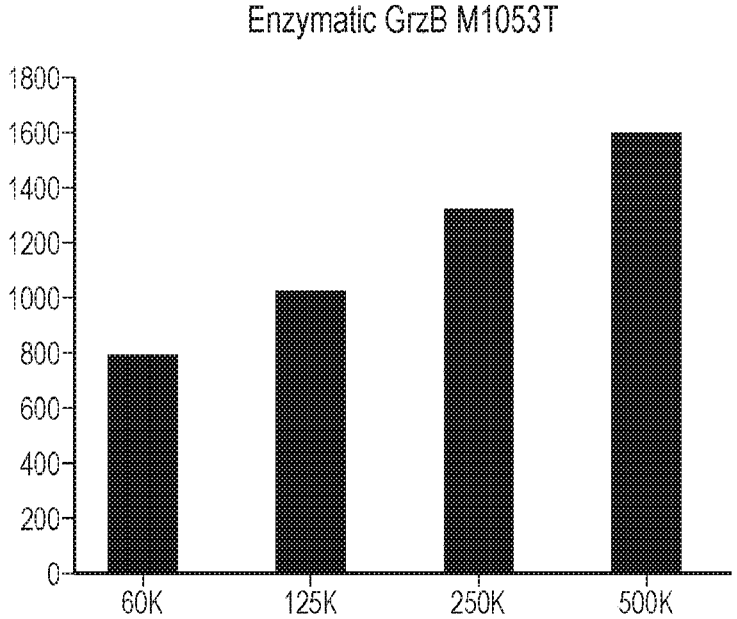
FIG. 71 illustrates enzymatic Granzyme B release for TIL batch M1053.
Figure 72:
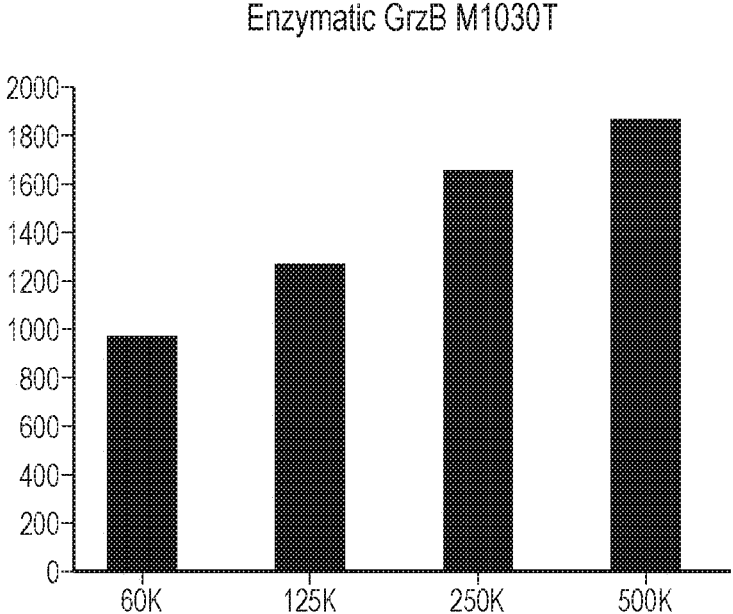
FIG. 72 illustrates enzymatic Granzyme B release for TIL batch M1030.
Figure 73:
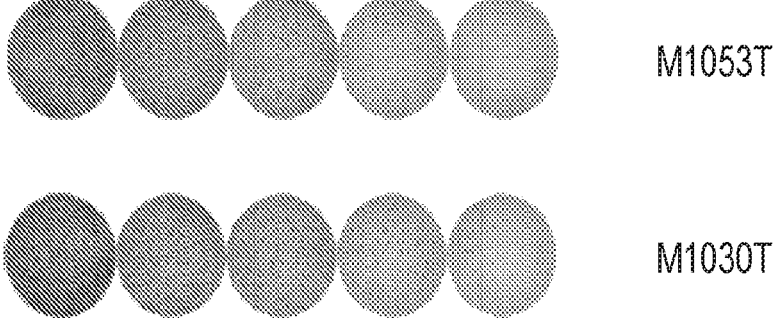
FIG. 73 illustrates ELISpot data showing TNF-α release by M1053T and M1030T. This data confirms the potency of the TILs shown by the BRLA.
Figure 74:
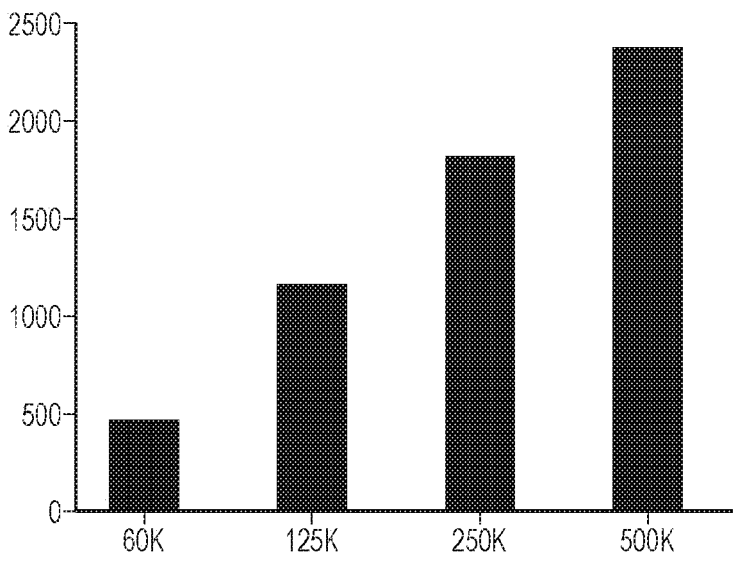
FIG. 74 illustrates enzymatic TNF-α release for TIL batch M1053.
Figure 75:
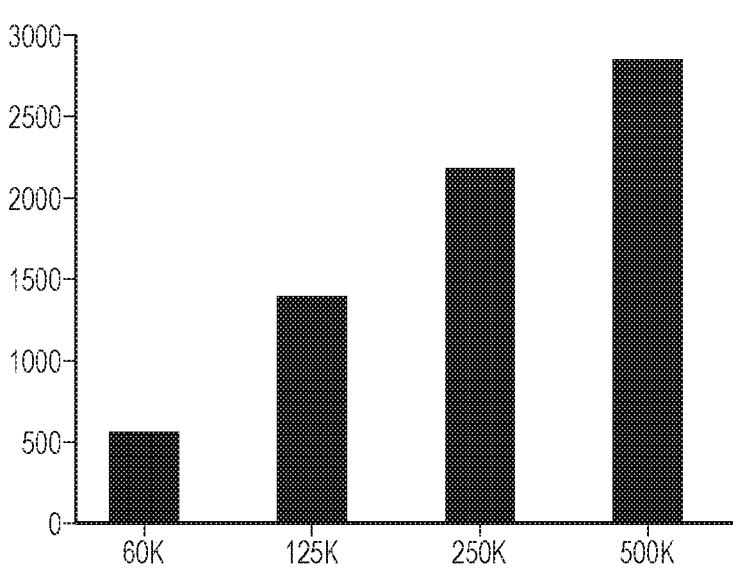
FIG. 75 illustrates enzymatic TNF-α release for TIL batch M1030.

FIG. 66 illustrates the linear relationship between IFN-γ release and cytotoxic potential of TILs. FIG. 67 illustrates ELISpot results for IFN-γ. FIG. 68 illustrates enzymatic IFN-γ release for TIL batch M1053. FIG. 69 illustrates enzymatic IFN-γ release for TIL batch M1030. FIG. 70 illustrates ELISpot data showing Granzyme B release by M1053T and M1030T. FIG. 71 illustrates enzymatic Granzyme B release for TIL batch M1053. FIG. 72 illustrates enzymatic Granzyme B release for TIL batch M1030. FIG. 73 illustrates ELISpot data showing TNF-α release by M1053T and M1030T. FIG. 74 illustrates enzymatic TNF-α release for TIL batch M1053. FIG. 75 illustrates enzymatic TNF-α release for TIL batch M1030. The data in FIG. 66 to FIG. 76 confirms the potency of these batches of TILs as also shown by the BRLA.

In conclusion, the BRLA requires no radionuclides and is as efficient and sensitive as traditional cytotoxicity assays. Flow cytometric assessment of Lamp 1 expression on TILs at individual time points demonstrates degranulation of cytotoxic T cells relative to the potency shown by BRLA. The BRLA demonstrates similar to better potency than standard chromium release assay. BRLA also enables evaluation of the potency of TIL lytic activity. Comparison of BRLA with chromium release assay shows the efficiency and reliability of BRLA. BRLA has a linear relationship with IFNγ release by TILs. Release assay of IFN-γ, TNFa and Granzyme B by ELISpot is consistent with the cytotoxic efficiency of the TILs evaluated by BRLA.

Example 11—Process for Weaning EM3 Cells from FBS to hAB Serum

Figure 76:
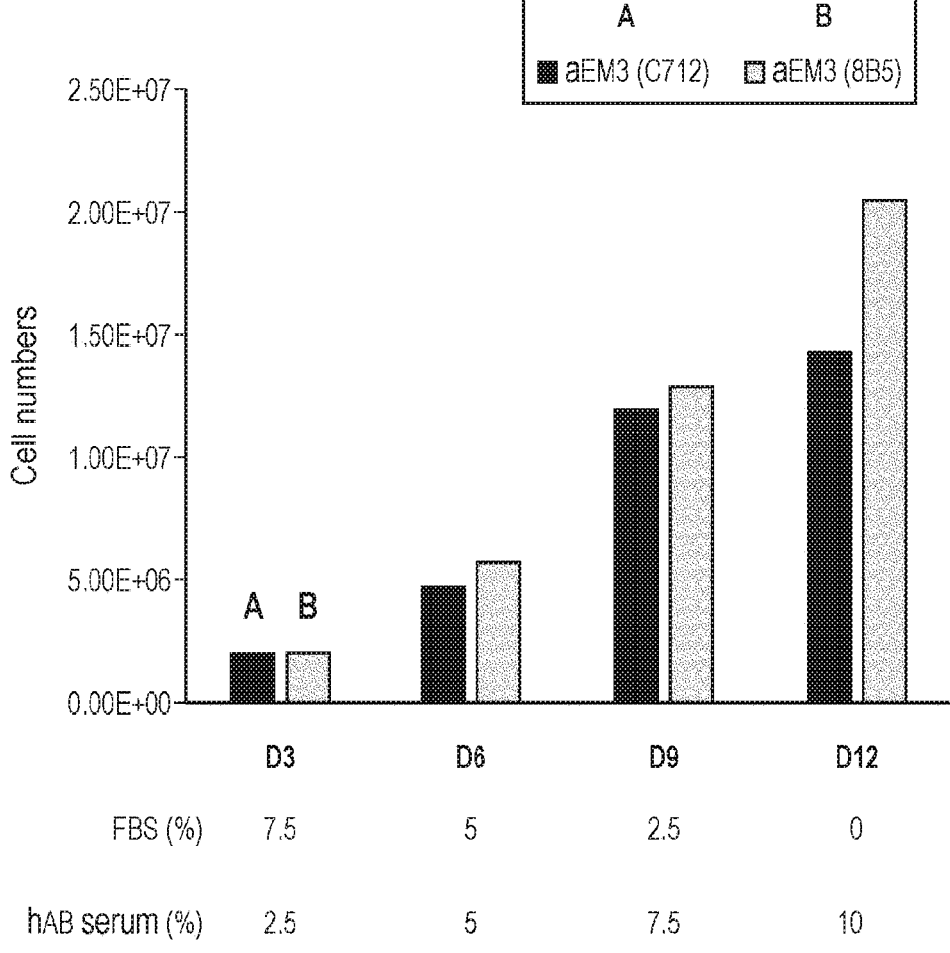
FIG. 76 illustrates changes in cell populations of aEM3 cells (C712 (A) and 8B5 (B)) when weaning such cell populations off of FBS to hAB serum media.

In order to avoid reactivity, some cell lines may need to be weaned from one medium to another. Here, EM3 cells are weaned from FBS to hAB serum to avoid reactivity. As shown in FIG. 76, aEM3 cells were successfully weaned off of FBS to hAB serum.

Example 12—Freezing Media Formulation Optimization

Figure 77:
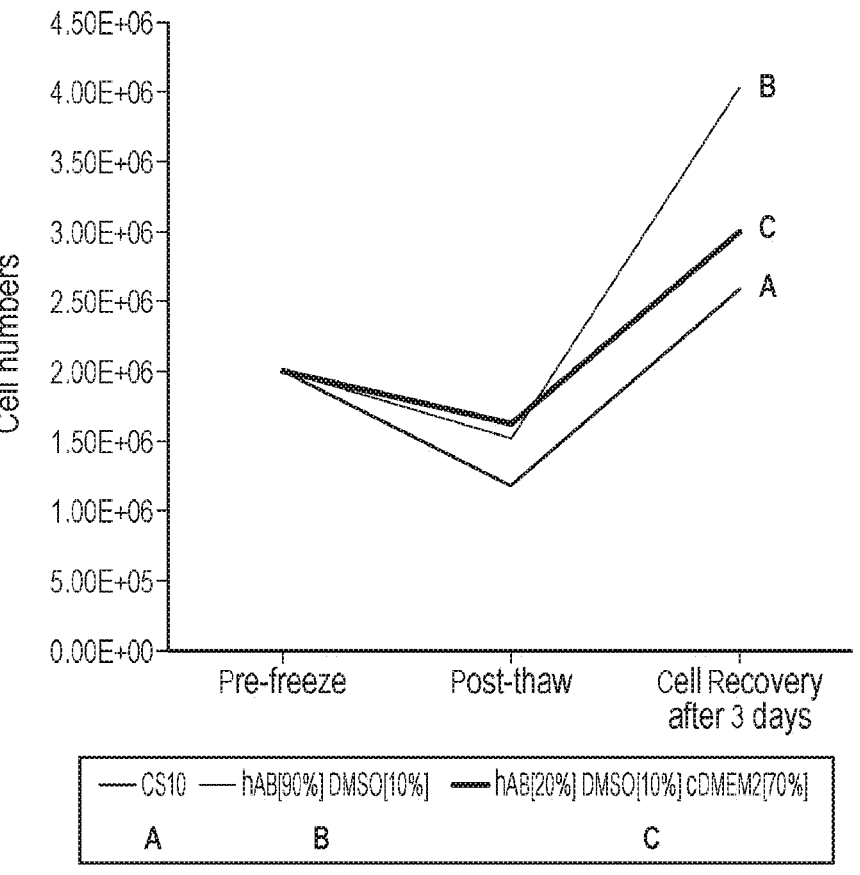
FIG. 77 illustrates changes in cell populations of during freeze-thaw-recovery cycles with aEM3 cell populations suspended in various freezing media.

To cryobank EM3 cells cultured as described herein, methods were freezing media formulation were optimized. As shown in FIG. 77, three freezing media were used and their effect on cell numbers were counted. The cell media utilized included CryStor 10 (Biolife Solutions (CS10)) (A), hAB [90%] and DMSO [10%] (B), and hAB [20%] with DMSO [10%] and cDMEM2 [70%] (C). FIG. 77 demonstrates that the formulation of human AB serum (90%) and DMSO (10%) provided for unexpectedly increased EM3 cell numbers after 3 days of recovery.

Figure 78:
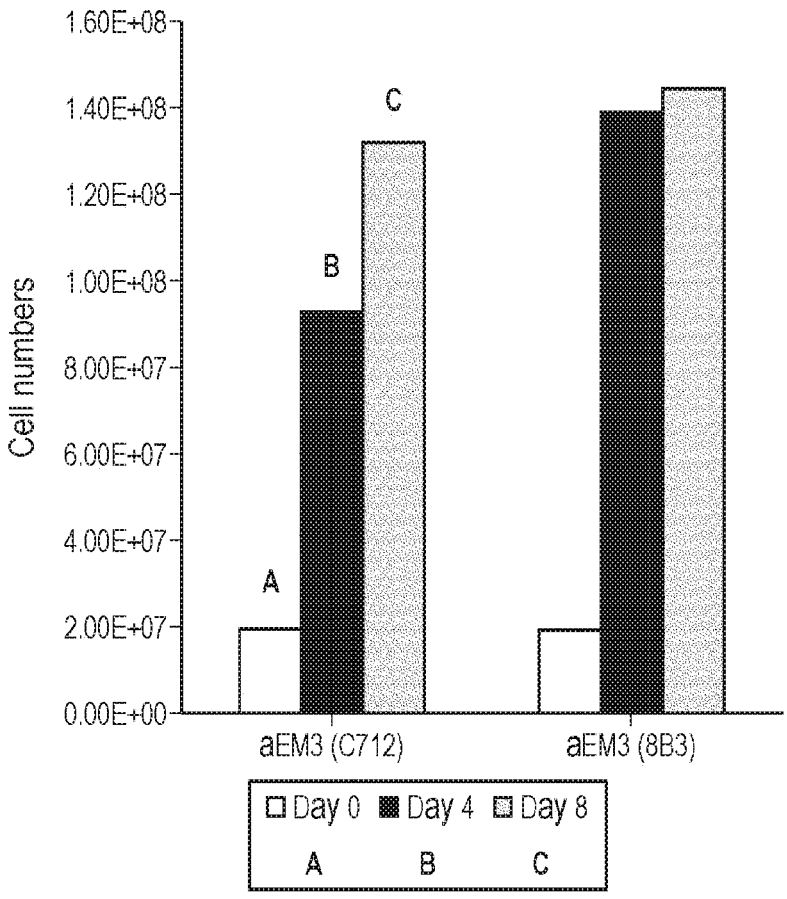
FIG. 78 illustrates the growth of aEM3 cells in gas permeable cell culture flasks over an eight-day time course.

Example 13—Growth of aEM3 Cells in GREX Flasks aEM3 cells were cultured in gas permeable cell culture flasks (i.e., GREX flasks (Wilson Wolf Manufacturing)) and the effect on cell doubling time was observed over an 8 day time course. As shown in FIG. 78, the GREX flasks provided for rapid growth of aEM3 cells.

Example 14—Flow Panel Analysis to Determine aEM3 Cell Purity

Figure 79:
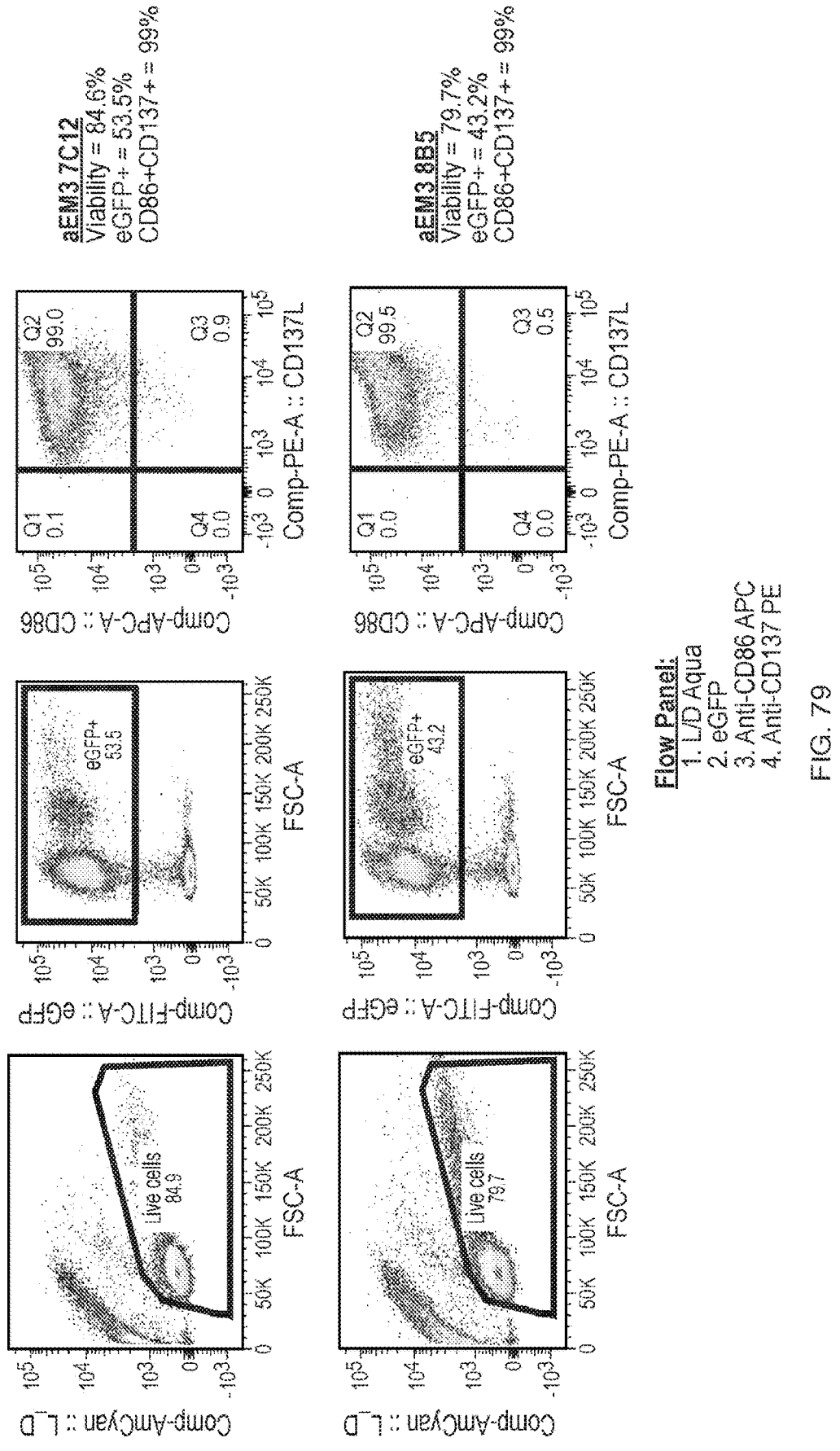
FIG. 79 illustrates a flow panel analysis to determine the purity of aEM3 cells.

To determine the purity of cells cultured according to the processes described herein, a flow panel analysis was used to determine the purity of aEM3 aAPCs. The results of such analysis are described in FIGS. 79 and 80. As shown in FIG. 80, before sorting aEM3 cell populations were 53.5% and 43.2% eGFP+ for aEM3 7C12 and aEM3 8B5 cells, respectively. Postsorting, cell populations was improved to 96.8% and 96.3% eGFP+ for aEM3 7C12 and aEM3 8B5 cells, respectively (FIG. 80).

Example 15—aEM3 Feeder Cells as an Alternative to PBMC Feeders

Figure 81:
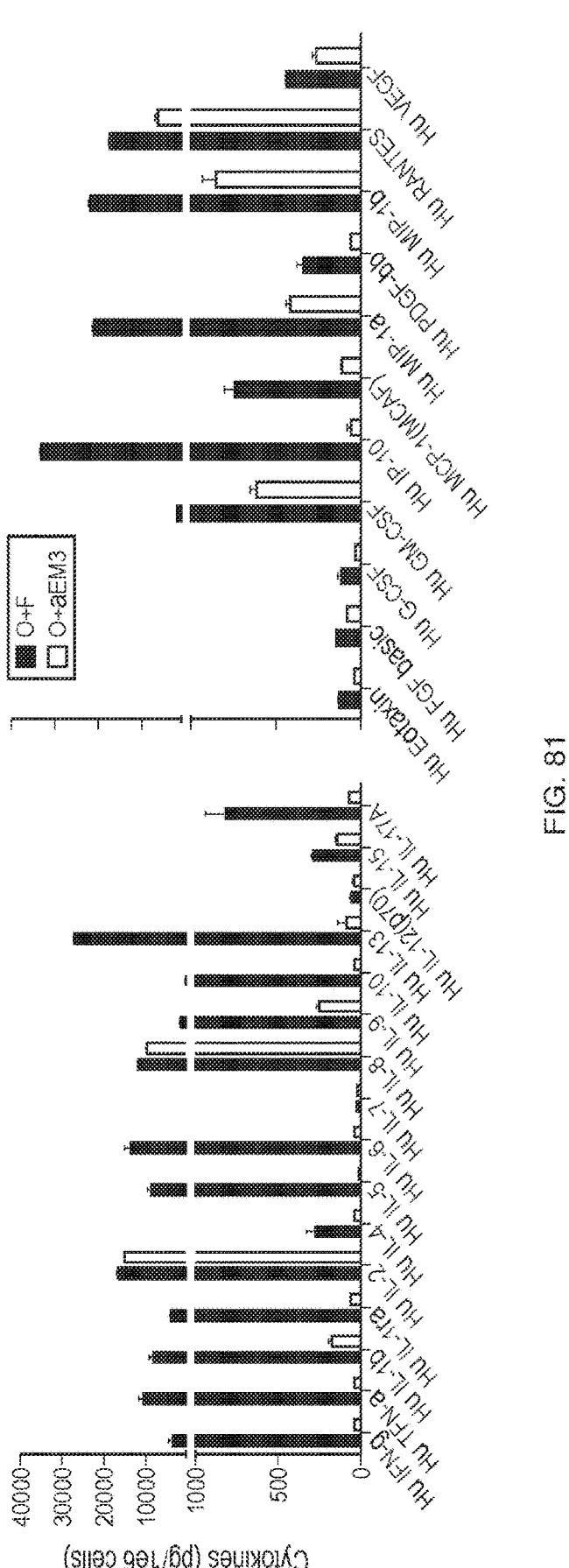
FIG. 81 illustrates the differences in cytokine expression between aEM3 feeder cells and PBMC feeders stimulated by OKT3.

As described herein, aEM3 cells may be used as an alternative for PBMC feeders, resulting in unexpectedly different properties for both TIL expansion process and the resulting TILs. To compare differences in cytokine expression, PBMCs and aEM3 cells were stimulated by treatment with OKT-3. As shown in FIG. 81, aEM3 cells displayed a comparatively different cytokine expression profile as compared to PBMCs. Surprisingly, the aEM3 cells of the present invention provide efficacious TILs (as shown herein) without reproducing the same cytokine secretion properties of TILs expanded with conventional PBMCs.

Example 16—Comparison Between Complete Media and Serum Free Media TIL Expansion In order to optimize the TIL expansion protocols, several TIL expansion experiments were performed as described herein, but with serum free media rather than complete media (CMl).

Figure 82:
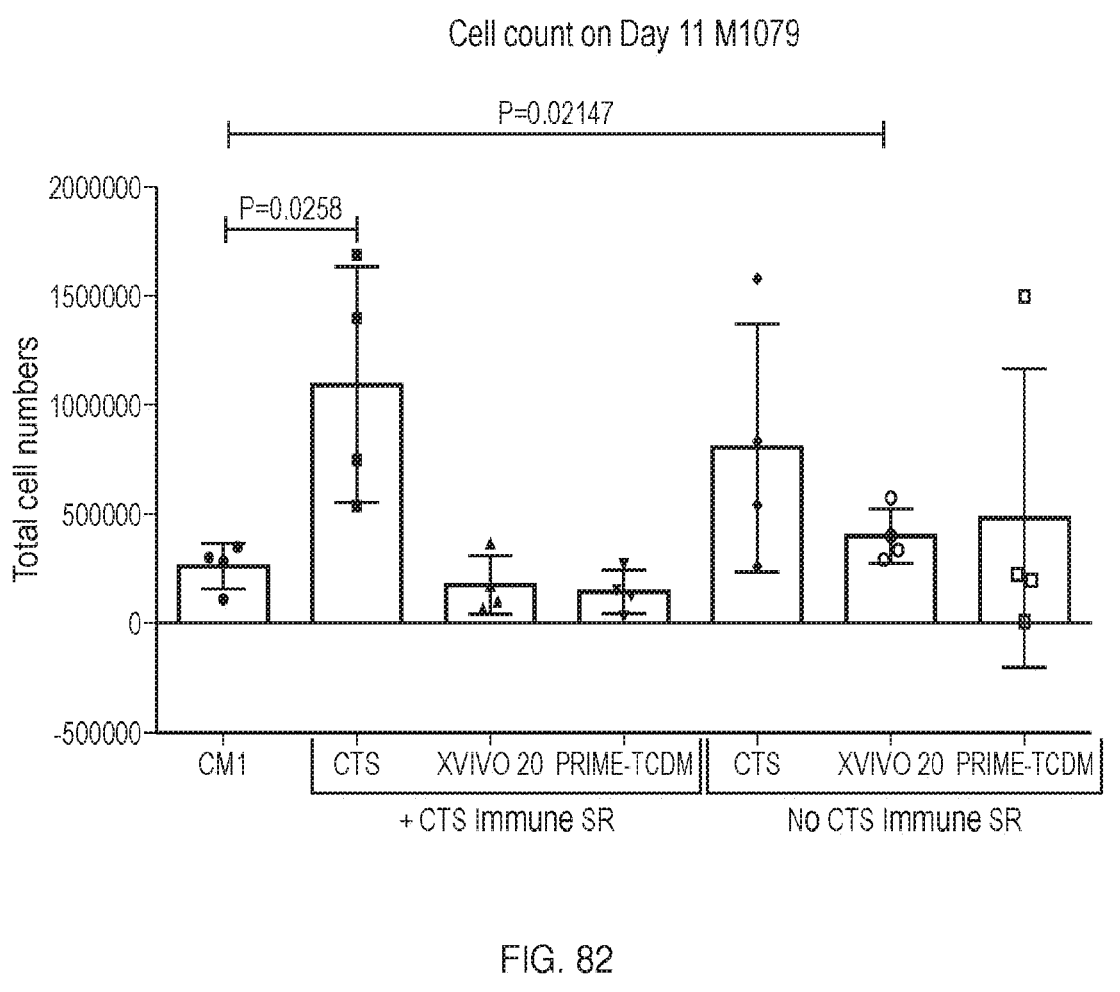

In one experiment, tissue fragments were cultured in a single well with CMl or various serum free media with 300 IU/mL of IL-2. Cells were then counted on Day 11 before initiating REP. The various serum free media used included Prime CDM (Irvine), CTS Optimizer (ThermoFisher), and Xvivo-20 (Lonza). As shown in FIG. 82, TIL expansion (PreREP) with CTS provided increased cell numbers as compared to CMl.

Figure 83:
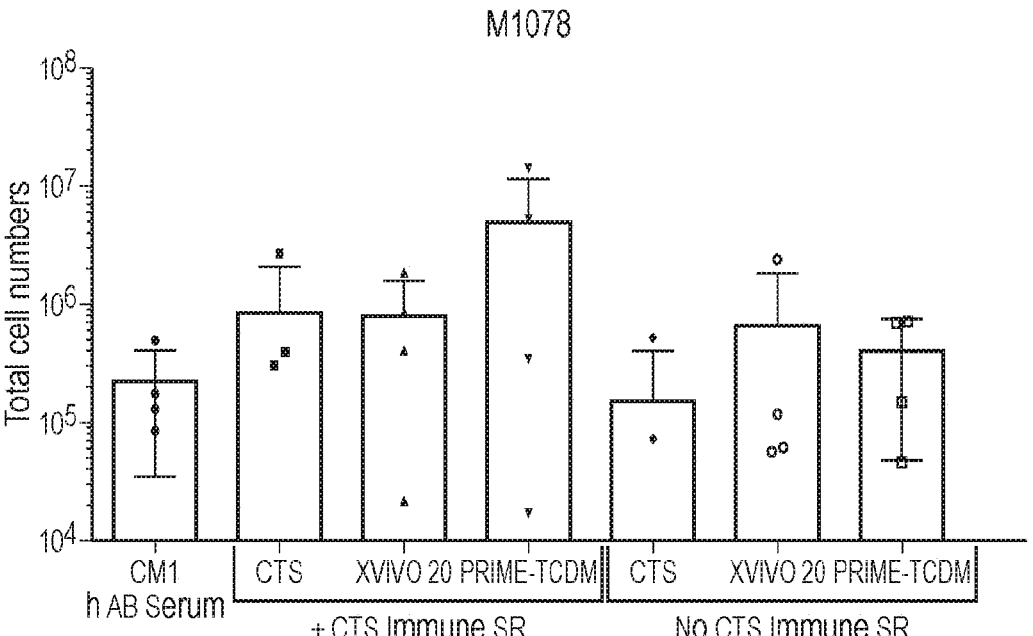
FIG. 83 and FIG. 84 illustrate that TIL may advantageously expanded with serum free media (i.e., CTS Optmizer) to provide increased cell numbers as compared to CM1 at Day 11 (PreREP) (FIG. 83) and Day 22 (Pre- and Post-REP) (FIG. 84).
Figure 84:
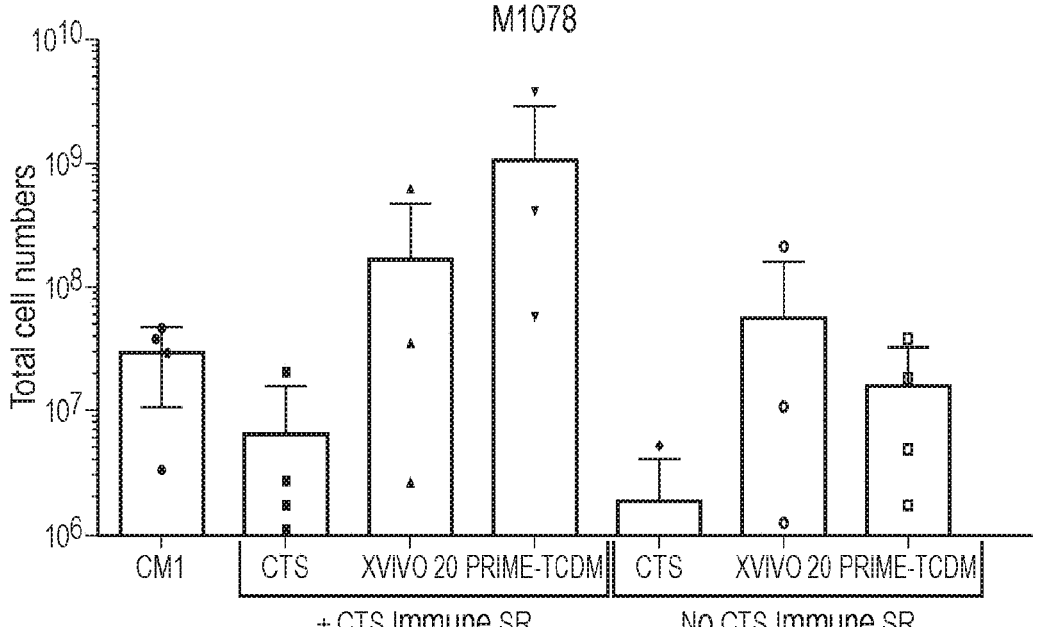

Additionally, tissue fragments were cultured with CM1 or various serum free media with 6000 IU/mL of IL-2 until Day 11. REP was then initiated on Day 11 using PBMC feeders, OKT-3, and IL-2, and culture was split on Day 16. Cultures were then terminated at the end of Day 22. The various serum free media used included Prime CDM (Irvine), CTS Optimizer (ThermoFisher), and Xvivo-20 (Lonza). As shown in FIG. 83 and FIG. 84, when counting cells at Days 11 and Day 22, respectively, TIL expansion (PreREP) with Prime CDM provided increased cell numbers as compared to CM1.

Example 17—Growth of aAPCs in Serum Free Media as Compared to Serum-Based Media In order to optimize aAPC growth and maintenance protocols in the absence of serum, aEM3 cells were cultured using various serum free media.

aEM3 cells were cultured in 24 well plates at $1\times10^6$ cells per well for 3 days using general cell culture protocols as described herein, with the exception that that one group of cells were provided with serum-based media (cDMEM (10% hSerum) and the other groups of cells were provided with serum free media. The serum free media utilized for the study included CTS OpTmizer (ThermoFisher), Xvivo 20 (Lonza), Prime-TCDM (Irvine), and XFSM (MesenCult) media. Cells were then counted on Day 3.

Figure 85:
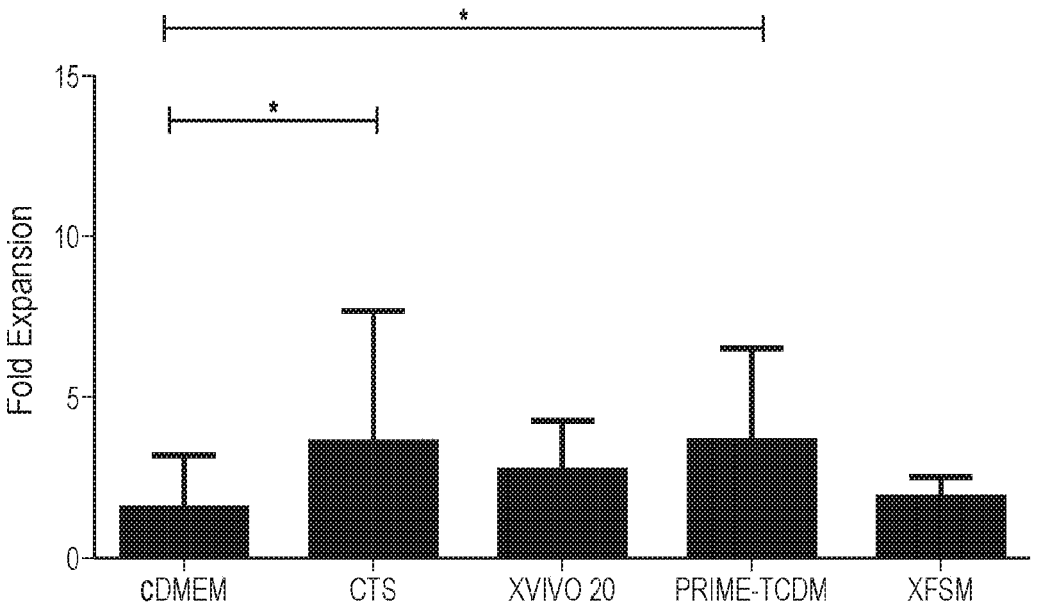
FIG. 85 illustrates that aAPC cells (i.e., aEM3 cells) can be grown and using serum free media. Specifically, CTS OpTimizer and Prime-TCDM were found to be effective in growing aEM3 as compared to cDMEM (10% hSerum). Data shown were mean±SD of five separate experiments. The p value was calculated by the student t-test. *P<0.05.

As shown in FIG. 85, CTS OpTmizer and Prime-TCDM serum free media provided cell growth that was comparable to serum-based media (i.e., cDMEM (10% hSerum). Therefore, serum free media is an effective alternative for growing and maintaining aAPCs as compared to serum-based media.

Example 18—Propagation, Maintenance, and Cryopreservation of aAPCs

In this example, procedures are provided for the preparation and preservation of aAPCs. Specifically, aEM3 cells from a cell line designated TIL-Rs3 were propagated and cryopreserved.

Thawing and recovery of aEM3 cells may be accomplished using the following non-limiting procedure. Cyropreserved aEM3 cells are warmed slowly in pre-warmed media (37° C.) that is prepared from CTS OpTmizer Basal Media (Thermo Fisher), CTS OpTmizer Cell Supplement (Thermo Fisher), Gentamicin (Lonza), and Glutamax (Life Technologies). The suspended cells are then centrifuged at 1500 rpm for 5 minutes at 4° C. The resulting supernatant is discarded and the remaining aEM3 cells are resuspended in the foregoing media and plated ($5\times10^6$ cells/10 mL per well of a 6 well plate).

Propagation of aEM3 cells may be accomplished using the following non-limiting procedure. Aliquots of the foregoing media are prepared in gas permeable cell culture flasks (i.e., GREX 10 flasks (Wilson Wolf Manufacturing)). The plated aEM3 cells are washed by centrifugation (i.e., 1500 rpm for 5 minutes at 4° C.), resuspended in media, and added to the GREX flasks at cell density of $1\text{-}2\times10^6$ cells/mL. The aEM3 cell suspension was diluted with 30 mL of media and the GREX flasks were then incubated for 3-4 days at 37° C. under $CO_2$. After 3-4 days, the GREX flasks were removed from the incubator and placed in a biological safety cabinet (BSC). The cultured aEM3 cells are carefully extracted from the GREX flasks by pipette and the resulting extraction is centrifuged to provide the increased number of aEM3 cells, which may be resuspended at a cell density of $10\text{-}20\times10^6$ cells per GREX 10 flask.

An alternative cryopreservation of aEM3 cells may be accomplished using the following non-limiting procedure. The foregoing GREX 10 flasks containing the aEM3 cells are removed from the incubator and placed in a BSC. The cultured aEM3 cells are carefully extracted from the GREX flasks by pipette and the resulting extraction is centrifuged to provide the increased number of aEM3 cells, which is resuspended in a volume of CryStor 10 (Biolife Solutions) to provide a concentration of $10\text{-}100\times10^6$ cells/vial in cryovials. The aEM3 cell suspensions may be placed in a freezing container and transferred to a −80° C. freezer.

Figure 86:
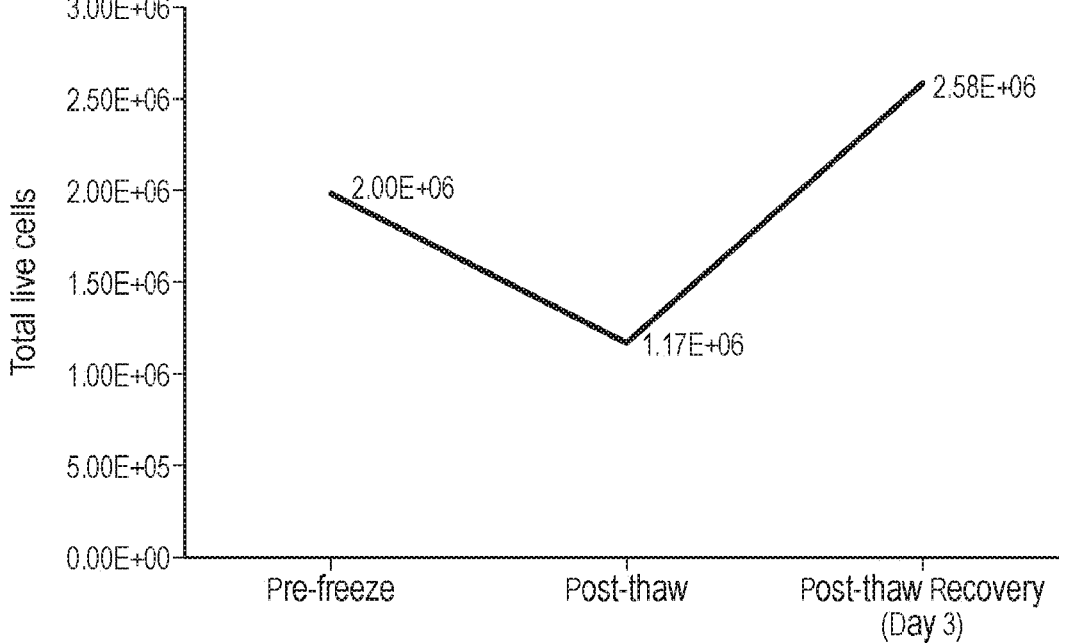
FIG. 86 and FIG. 87 illustrate the results of two experiments that demonstrate the rapid recovery of aEM3 cells from the TIL-R3 cell line on day 3 following cryopreservation.
Figure 87:
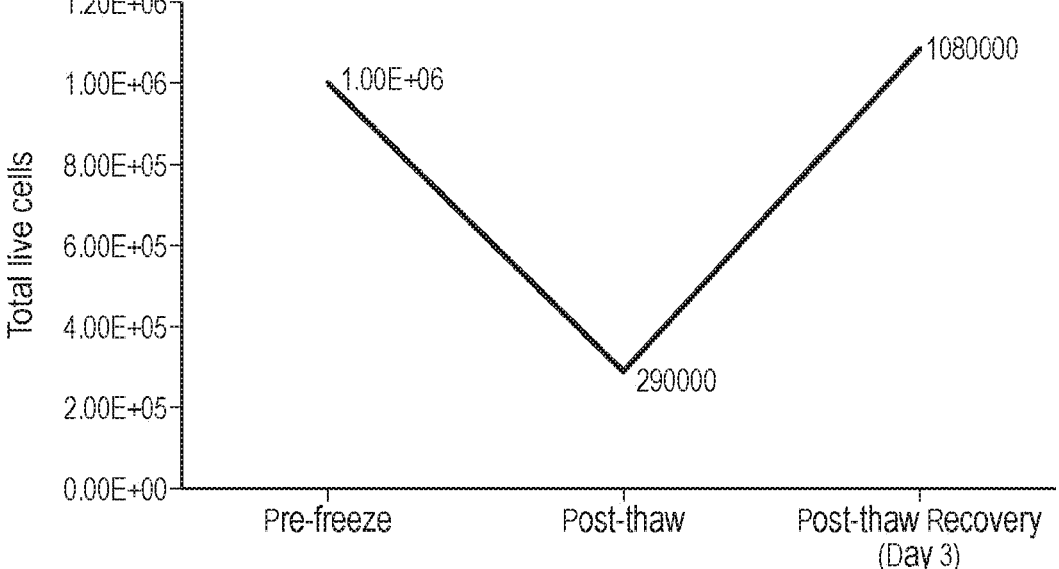

Example 19—Demonstration of Rapid Recovery of aEM3 Cells Following Cryopreservation aEM3 cells from the TIL-R3 cell line ($1\text{-}2\times10^6$ cells) were cryopreserved according to the procedure set forth in Example 18 using CS-10 cryopreservation media. Vials of such cells were then thawed and the cells were counted. Cell counts were taken pre-freeze, post-thaw, and 3 days after thaw (i.e., Post-Thaw Recovery). As shown in FIG. 86 and FIG. 87, the total live cell counts recovered rapidly post thaw in two separate experiments.

Figure 88:
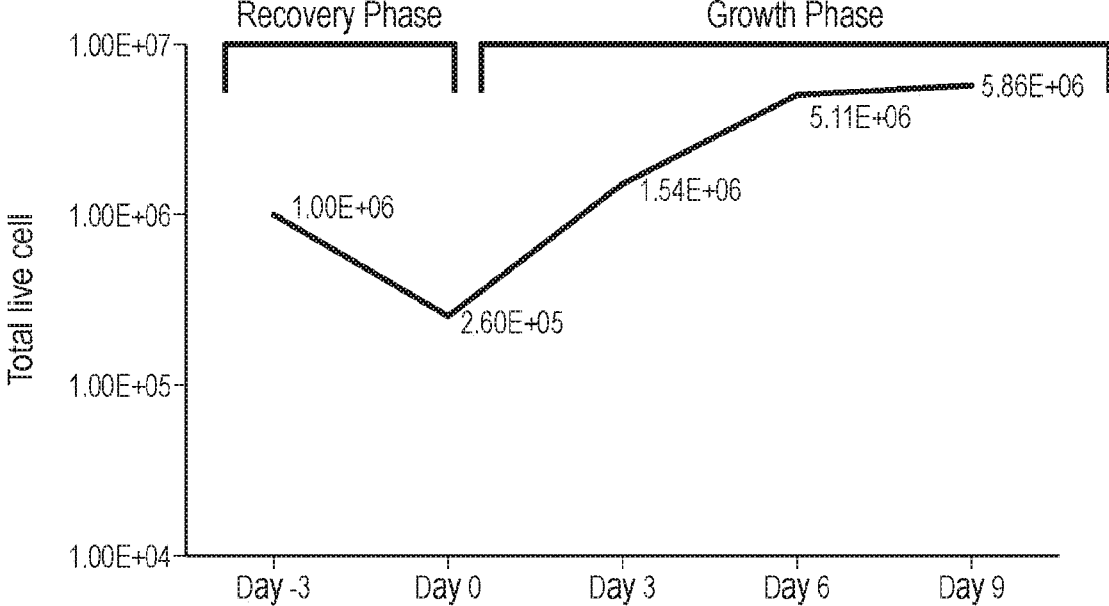
FIG. 88 illustrates the growth of aEM3 cells from the TIL-R3 cell line following cryopreservation where the cells were plated and grown for 9 days. Cell counts were measured every three days post thaw.

TIL-R3 cells ($1\times10^6$ cells) were thawed (Day 3 post-thaw) and plated at a density of $0.5\times10^6/cm^2$ in each well of a 24 well plate. On day 0 and 3, viable cells were counted and recorded. On the first passage (Day 6), cells were split at the density of $2\times10^6$ cells/$cm^2$ or $0.5\times10^6$ cells/$cm^2$. At the end of the first passage, a cell count was performed. The resulting cell counts are shown in FIG. 88, which demonstrate both a recovery phase post-thaw and a growth phase.

Figure 89:
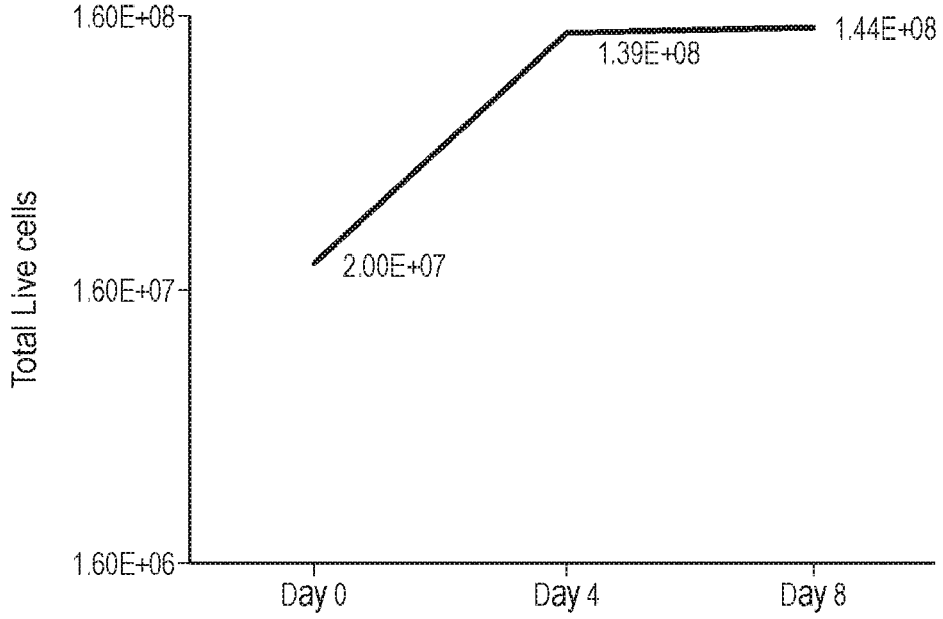
FIG. 89 illustrates the growth of aEM3 cells from the TIL-R3 cell line following cryopreservation where the cells were plated in GREX 10 flasks and grown for 8 days. Cell counts were measured every four days post thaw.

Furthermore, TIL-R3 cells ($20\times10^6$ cells) were cultured at a density of $2\times10^6/cm^2$ in GREX 10 flasks according to the procedure described in Example 18. On days 4 and 8, live cells were counted and recorded. The resulting cell counts are shown in FIG. 89, which demonstrates a growth phase for the cells following cryopreservation that reaches a plateau between days 4 and 8 when the cells reached a density of $13.9\times10^6$ cells/$cm^2$.

Figure 91:
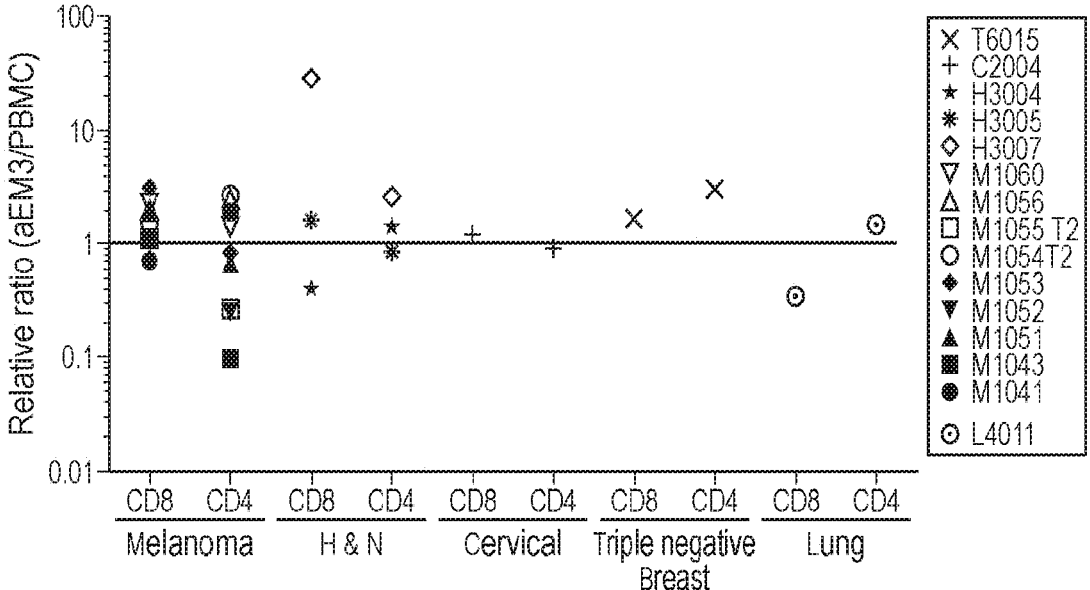
FIG. 91 illustrates the results of flow cytometry analysis of TILs expanded in a REP with the aEM3 cell line and PBMC feeders, showing that TILs cultured with aEM3 promotes CD8$^+$ TIL skewness.
Figure 92:
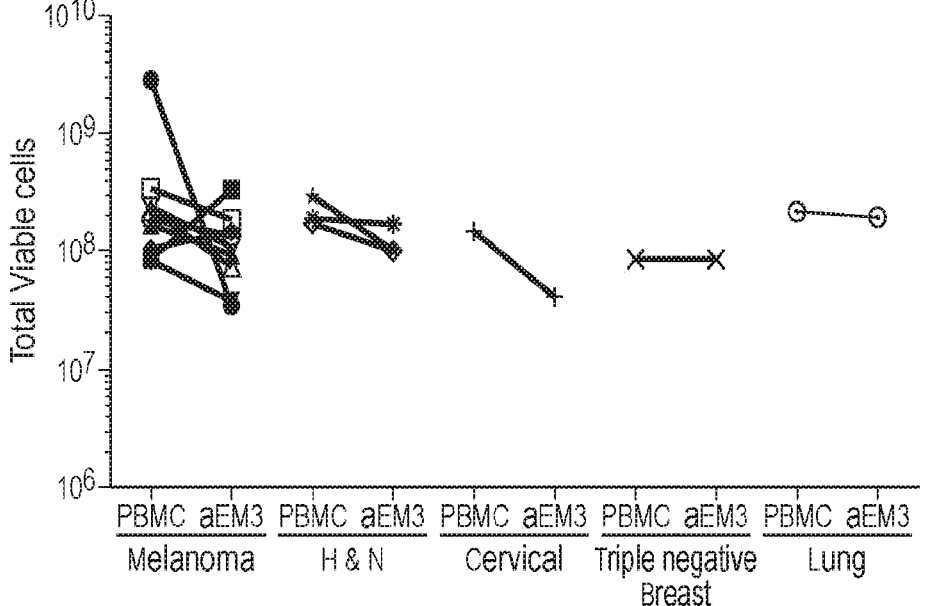
FIG. 92 illustrates the numbers of viable cells obtained from experiments wherein TILs were expanded in a REP with the aEM3 cell line and PBMC feeders.
Figure 93:
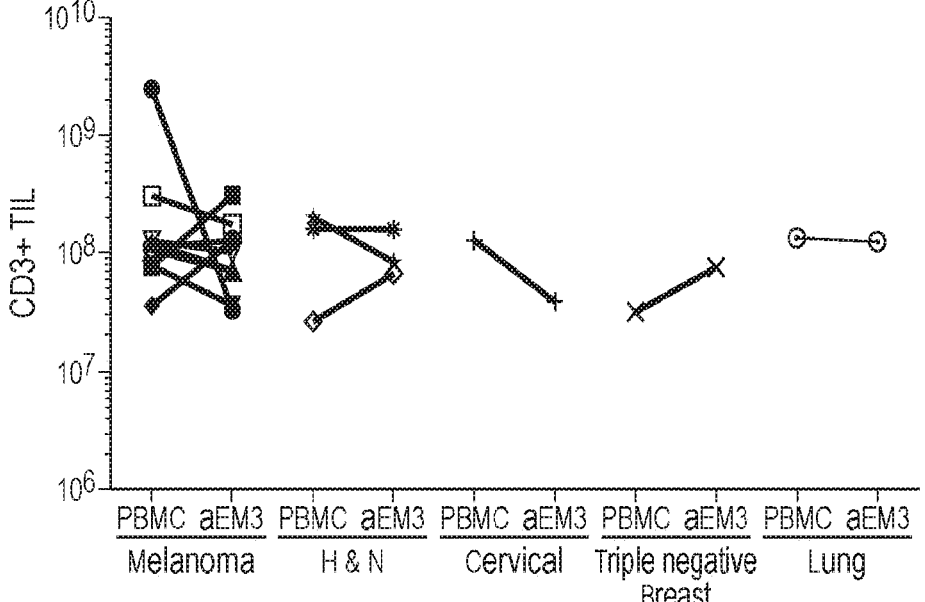
FIG. 93 illustrates the numbers of CD3$^+$ cells obtained from experiments wherein TILs were expanded in a REP with the aEM3 cell line and PBMC feeders.
Figure 94:
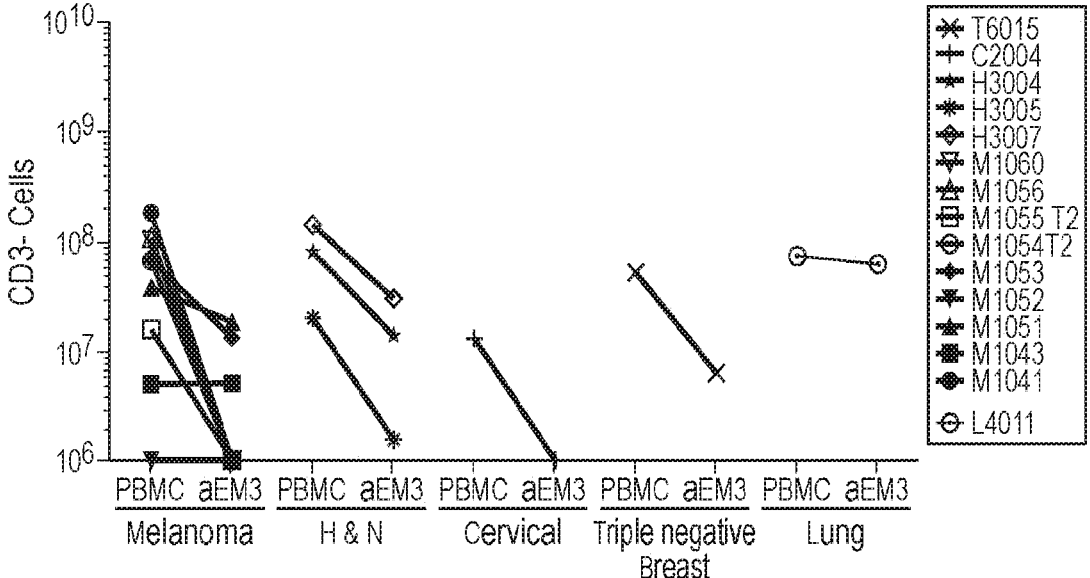
FIG. 94 illustrates the numbers of CD3$^-$ cells obtained from experiments wherein TILs were expanded in a REP with the aEM3 cell line and PBMC feeders.

Example 20—CD8 Skewness, Expansion Performance, and CD3 Contamination of TILs Cultured with aEM3 aAPCs Fifteen different PreREP TIL lines ($0.4\times10^5$ cells) were co-cultured with either aEM3 aAPCs (as described herein) or PBMC feeders ($10\times10^6$), OKT3 (30 ng/mL) and IL-2 (3000 IU/mL) and cultures were split on Day 5 using 6 well Grex plates. Cultures were sampled at day 11 and analyzed by flow cytometry. The relative ratio of CD8$^+$ cells was calculated by the formula (CD8% aEM3)/(CD8% PBMC). The results shown in FIG. 91 indicate that TILs cultured with aEM3 cells surprisingly promote CD8$^+$ skewing and and an improved TIL product. Additional results of these experiments are shown in FIG. 92, FIG. 93, and FIG. 94, where the results shown that TILs cultured with aEM3 aAPCs displayed comparable expansion and less non-CD3+ cell contamination in comparison to TILs cultured with PBMC feeders.

Example 21—Telomere Length Measurement

Genomic DNA was isolated from pre-REP or post-REP (magnetic bead sorted for CD3±) TILs for a qPCR (quantitative polymerase chain reaction) assay to measure telomere length. The real time qPCR method is described in Cawthon, *Nucleic Acids Res.* 2002, 30(10), e47; and Yang, et al., *Leukemia,* 2013, 27, 897-906. Briefly, the telomere repeat copy number to single gene copy number (T/S) ratio was determined using an PCR thermal cycler (Bio-Rad Laboratories, Inc.) in a 96-well format. Ten ng of genomic DNA was used for either the telomere or hemoglobin (hgb) PCR reaction and the primers used were as follows:

Tel-1b primer
(SEQ ID NO: 40)
(CGG TTT GTT TGG GTT TGG GTT TGG GTT TGG GTT TGG

GTT);

Tel-2b primer
(SEQ ID NO: 41)
(GGC TTG CCT TAC CCT TAC CCT TAC CCT TAC CCT TAC

CCT);

hgb1 primer
(SEQ ID NO: 42)
(GCT TCT GAC ACA ACT GTG TTC ACT AGC);
and hgb2 primer
(SEQ ID NO: 43)
(CAC CAA CTT CAT CCA CGT TCA CC).

All samples were analyzed by both the telomere and hemoglobin reactions, and the analysis was performed in triplicate on the same plate. In addition to the test samples, each 96-well plate contained a five-point standard curve from 0.08 ng to 250 ng using genomic DNA isolated from the 1301 human T-cell leukemia cell line (available from Sigma and ATCC). The T/S ratio (–dCt) for each sample was calculated by subtracting the median hemoglobin threshold cycle (Ct) value from the median telomere Ct value. The relative T/S ratio (–ddCt) was determined by subtracting the T/S ratio of the 10.0 ng standard curve point from the T/S ratio of each unknown sample.

Figure 95:
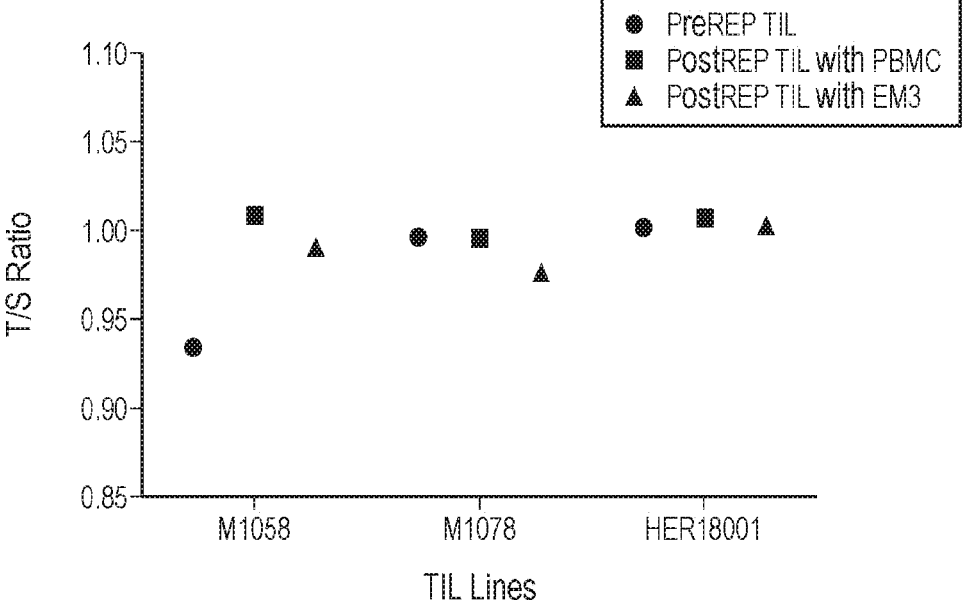
FIG. 95 illustrates the results of telomere length analysis using a qPCR method.

Results are shown in FIG. 95. Each data point shown is the median measurement of relative T/S ratio. The results indicate that TILs cultured with aEM3 maintain their telomere length.

---

We claim:

1. A method of expanding a population of lymphocytes, the method comprising:
(i) transducing a population of myeloid cells with one or more viral vectors comprising (a) a nucleic acid encoding CD86, (b) one or more nucleic acids encoding one or more costimulatory molecules, and (c) a nucleic acid encoding an anti-OKT-3 antibody scFv binding domain, to obtain a population of artificial antigen presenting cells (aAPCs) expressing a protein encoded by each of the nucleic acids of (a), (b), and (c); and (ii) contacting the population of lymphocytes with the population of aAPCs in a cell culture medium for a period of time to obtain an expanded population of lymphocytes.

2. The method of claim 1, wherein the population of lymphocytes comprises tumor-infiltrating lymphocytes (TILs).

3. The method of claim 1, wherein the cell culture medium comprises IL-2.

4. The method of claim 3, wherein the IL-2 is at an initial concentration of about 3000 IU/mL.

5. The method of claim 1, wherein the cell culture medium comprises OKT-3 antibody.

6. The method of claim 5, wherein the OKT-3 antibody is at an initial concentration of about 30 ng/mL.

7. The method of claim 1, wherein the population of lymphocytes is expanded by at least 50-fold over a period of about 7 days.

8. The method of claim 1, wherein the population of aAPCs endogenously expresses HLA-A/B/C, ICOS-L, and CD58.

9. The method of claim 1, wherein the anti-OKT-3 antibody scFv binding domain comprises the peptide sequence of SEQ ID NO:27 or SEQ ID NO:28.

10. The method of claim 1, wherein the one or more costimulatory molecules are independently selected from the group consisting of 4-1BB (CD137), OX40 (CD134), CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79a, CD79B, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD114, CD115, CD116, CD117, CD118, CD119, CD120a, CD120b, CD121a, CD121b, CD122, CD123, CDw124, CD125, CD126, CDw127, CDw128a, CDw128b, CDw130, CDw131, CD132, CD133, CD135, CD136, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCRζ.

11. The method of claim 10, wherein the one or more costimulatory molecules are independently selected from the group consisting of CD28, 4-1BB (CD137), and OX40 (CD134).

12. The method of claim 1, wherein the expansion is performed using a gas permeable container.

13. The method of claim 1, wherein the ratio of the population of lymphocytes to the population of APCs is between about 1 to 200 and about 1 to 400.

14. The method of claim 13, wherein the ratio of the population of lymphocytes to the population of APCs is about 1 to 300.

15. The method of claim 1, wherein the one or more viral vectors comprise a lentiviral vector.

16. The method of claim 1, wherein the expanded population of lymphocytes is cryopreserved.

17. The method of claim 2, wherein the expanded population of TILs is cryopreserved.

18. The method of claim 1, wherein the population of myeloid cells comprises a MOLM-14 cell, an EM-3 cell, a K562 cell, a MOLM-13 cell, a KG1-246 cell, aKG1-8031 cell, or an EM-2 cell.

19. The method of claim 1, wherein the CD86 protein comprises a sequence selected from the group consisting of SEQ ID NO:8 and SEQ ID NO:19, or a sequence comprising one or more conservative amino acid substitutions thereof.

20. The method of claim 1, wherein the one or more costimulatory molecules comprises 4-1BBL protein.

21. The method of claim 20, wherein the 4-1BBL protein comprises a sequence as set forth in SEQ ID NO:9 or SEQ ID NO:16, or a sequence comprising one or more conservative amino acid substitutions thereof.

22. The method of claim 1, wherein the one or more costimulatory molecules comprises OX40L protein.

23. The method of claim 21, wherein the OX40L protein comprises a sequence as set forth in SEQ ID NO: 10, or a sequence comprising one or more conservative amino acid substitutions thereof.

* * * * *